(12) United States Patent
SunSpiral et al.

(10) Patent No.: US 11,242,524 B2
(45) Date of Patent: Feb. 8, 2022

(54) HTP GENOMIC ENGINEERING PLATFORM FOR IMPROVING FUNGAL STRAINS

(71) Applicant: Zymergen Inc., Emeryville, CA (US)

(72) Inventors: Vytas SunSpiral, Oakland, CA (US); Jennifer Fredlund, Emeryville, CA (US); Hassan Abdulla, Oakland, CA (US); Paolo Boccazzi, Emeryville, CA (US); Sean Poust, El Cerrito, CA (US); Sara da Luz Areosa Cleto, Emeryville, CA (US); Brian Chaikind, Oakland, CA (US); Dylan Vaughan, Oakland, CA (US); Kenneth S. Bruno, Walnut Creek, CA (US); Patrick Westfall, Walnut Creek, CA (US); Edyta Szewczyk, Walnut Creek, CA (US); Kyle Rothschild-Mancinelli, Woodside, CA (US); Arthur Muir Fong, III, Sacramento, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 17/207,376

(22) Filed: Mar. 19, 2021

(65) Prior Publication Data
US 2021/0284993 A1 Sep. 16, 2021

Related U.S. Application Data

(60) Division of application No. 16/600,062, filed on Oct. 11, 2019, now Pat. No. 10,954,511, which is a continuation of application No. PCT/US2018/036360, filed on Jun. 6, 2018.

(60) Provisional application No. 62/515,907, filed on Jun. 6, 2017.

(51) Int. Cl.
| | |
|---|---|
| *C12N 15/10* | (2006.01) |
| *C12N 1/14* | (2006.01) |
| *C12N 9/22* | (2006.01) |
| *C12N 15/11* | (2006.01) |
| *C12N 15/80* | (2006.01) |

(52) U.S. Cl.
CPC .......... *C12N 15/1079* (2013.01); *C12N 1/14* (2013.01); *C12N 9/22* (2013.01); *C12N 15/1058* (2013.01); *C12N 15/11* (2013.01); *C12N 15/80* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 4,935,349 A | 6/1990 | Mcknight et al. | |
| 5,198,345 A | 3/1993 | Gwynne et al. | |
| 5,252,726 A | 10/1993 | Woldike | |
| 5,516,670 A | 5/1996 | Kuehnle et al. | |
| 5,578,463 A | 11/1996 | Berke et al. | |
| 5,605,793 A | 2/1997 | Stemmer | |
| 5,705,358 A | 1/1998 | Gouka et al. | |
| 5,741,665 A | 4/1998 | Kato et al. | |
| 5,753,477 A | 5/1998 | Chan | |
| 5,837,458 A | 11/1998 | Minshull et al. | |
| 5,876,988 A | 3/1999 | Selten et al. | |
| 5,965,384 A | 10/1999 | Boel et al. | |
| 6,040,439 A | 3/2000 | Hayakawa | |
| 9,744,533 B2 | 8/2017 | Breinlinger et al. | |
| 9,815,056 B2 | 11/2017 | Wu et al. | |
| 9,857,333 B2 | 1/2018 | Chapman et al. | |
| 9,889,445 B2 | 2/2018 | Chapman et al. | |
| 9,895,699 B2 | 2/2018 | Short et al. | |
| 9,908,115 B2 | 3/2018 | Hobbs et al. | |
| 9,988,624 B2 | 6/2018 | Serber et al. | |
| 9,996,920 B2 | 6/2018 | Du et al. | |
| 10,010,882 B2 | 7/2018 | White et al. | |
| 10,047,358 B1 | 8/2018 | Serber et al. | |
| 10,058,865 B2 | 8/2018 | Breinlinger et al. | |
| 10,101,250 B2 | 10/2018 | White et al. | |
| 10,239,058 B2 | 3/2019 | Lavieu et al. | |
| D844,471 S | 4/2019 | Stone et al. | |
| 10,245,588 B2 | 4/2019 | Khandros et al. | |
| 10,252,907 B2 | 4/2019 | Breinlinger et al. | |
| 10,336,998 B2 | 7/2019 | Serber et al. | |
| 10,350,594 B2 | 7/2019 | Hobbs et al. | |
| 10,384,204 B2 | 8/2019 | Mcfarland et al. | |

(Continued)

FOREIGN PATENT DOCUMENTS

| | | |
|---|---|---|
| EP | 0238023 A2 | 9/1987 |
| EP | 0635574 B1 | 4/2003 |

(Continued)

OTHER PUBLICATIONS

Aoyama, et al., "Spy1, a Histidine-Containing Phosphotransfer Signaling Protein, Regulates the Fission Yeast Cell Cycle through the Mcs4 Response Regulator." Journal of Bacteriology (Sep. 2000); 182(17): 4868-4874.

(Continued)

*Primary Examiner* — Nancy J Leith

(74) *Attorney, Agent, or Firm* — Cooley LLP

(57) ABSTRACT

A HTP genomic engineering platform for improving filamentous fungal cells that is computationally driven and integrates molecular biology, automation, and advanced machine learning protocols is provided. This integrative platform utilizes a suite of HTP molecular tool sets to create HTP genetic design libraries, which are derived from, inter alia, scientific insight and iterative pattern recognition. Methods for isolating clonal populations derived from individual fungal spores are also provided.

18 Claims, 80 Drawing Sheets

Specification includes a Sequence Listing.

(56) References Cited

U.S. PATENT DOCUMENTS

| | | |
|---|---|---|
| 10,407,658 B2 | 9/2019 | Newstrom et al. |
| 10,457,933 B2 | 10/2019 | Serber et al. |
| 10,569,271 B2 | 2/2020 | Wu et al. |
| 10,578,630 B2 | 3/2020 | Du |
| 10,646,871 B2 | 5/2020 | White et al. |
| D887,296 S | 6/2020 | Stone et al. |
| 10,675,625 B2 | 6/2020 | Lionberger et al. |
| 10,690,628 B2 | 6/2020 | Chapman et al. |
| 10,705,082 B2 | 7/2020 | Beaumont et al. |
| 10,712,344 B2 | 7/2020 | Chapman et al. |
| 10,723,988 B2 | 7/2020 | Lowe, Jr. et al. |
| 10,751,715 B1 | 8/2020 | Guan et al. |
| 10,954,511 B2 | 3/2021 | SunSpiral et al. |
| 10,973,227 B2 | 4/2021 | White et al. |
| 11,007,520 B2 | 5/2021 | Lowe, Jr. et al. |
| 11,028,401 B2 | 6/2021 | Bruno et al. |
| 2009/0280529 A1 | 11/2009 | Berg et al. |
| 2009/0317798 A1 | 12/2009 | Heid et al. |
| 2010/0216648 A1 | 8/2010 | Staehler et al. |
| 2011/0272127 A1 | 7/2011 | Jacobson et al. |
| 2011/0223671 A1 | 9/2011 | Yoder et al. |
| 2013/0149742 A1 | 6/2013 | Bower et al. |
| 2013/0319861 A1 | 12/2013 | Khandros et al. |
| 2014/0017791 A1 | 1/2014 | Chapman et al. |
| 2014/0116881 A1 | 5/2014 | Chapman et al. |
| 2014/0120558 A1 | 5/2014 | Chapman |
| 2014/0124370 A1 | 5/2014 | Short et al. |
| 2014/0220689 A1 | 8/2014 | Bodie et al. |
| 2015/0111784 A1 | 4/2015 | Chapman |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0166326 A1 | 6/2015 | Chapman et al. |
| 2015/0211013 A1 | 7/2015 | Emalfarb et al. |
| 2015/0306598 A1 | 10/2015 | Khandros et al. |
| 2015/0306599 A1 | 10/2015 | Khandros et al. |
| 2015/0352547 A1 | 12/2015 | Breinlinger et al. |
| 2016/0158748 A1 | 6/2016 | Wu et al. |
| 2016/0158757 A1 | 6/2016 | Breinlinger et al. |
| 2016/0160259 A1 | 6/2016 | Du |
| 2016/0171686 A1 | 6/2016 | Du et al. |
| 2016/0184821 A1 | 6/2016 | Hobbs et al. |
| 2016/0193604 A1 | 7/2016 | Mcfarland et al. |
| 2016/0199837 A1 | 7/2016 | Breinlinger et al. |
| 2016/0257918 A1 | 9/2016 | Chapman et al. |
| 2016/0304905 A1 | 10/2016 | Hansen et al. |
| 2016/0312165 A1 | 10/2016 | Lowe, Jr. et al. |
| 2016/0318038 A1 | 11/2016 | Short et al. |
| 2016/0338347 A1 | 11/2016 | White et al. |
| 2016/0340632 A1 | 11/2016 | Breinlinger et al. |
| 2016/0370266 A1 | 12/2016 | White et al. |
| 2017/0021366 A1 | 1/2017 | Chapman et al. |
| 2017/0043343 A1 | 2/2017 | Khandros et al. |
| 2017/0113231 A9 | 4/2017 | Breinlinger et al. |
| 2017/0114316 A1 | 4/2017 | Newstrom et al. |
| 2017/0159045 A1 | 6/2017 | Serber et al. |
| 2017/0165667 A1 | 6/2017 | Beaumont et al. |
| 2017/0173580 A1 | 6/2017 | Lowe, Jr. et al. |
| 2017/0184583 A1 | 6/2017 | Beaumont et al. |
| 2017/0224734 A1 | 8/2017 | Chapman et al. |
| 2017/0276679 A1 | 9/2017 | Chapman et al. |
| 2017/0316353 A1 | 11/2017 | Frewen et al. |
| 2017/0354969 A1 | 12/2017 | Lionberger et al. |
| 2017/0355595 A1 | 12/2017 | Breinlinger et al. |
| 2018/0037919 A1 | 2/2018 | Bodie et al. |
| 2018/0099282 A1 | 4/2018 | Breinlinger et al. |
| 2018/0126380 A1 | 5/2018 | Khandros et al. |
| 2018/0135011 A1 | 5/2018 | Bronevetsky et al. |
| 2018/0147576 A1 | 5/2018 | Lavieu et al. |
| 2018/0193835 A1 | 7/2018 | Hobbs et al. |
| 2018/0259482 A1 | 9/2018 | Chapman et al. |
| 2018/0272350 A1 | 9/2018 | Chapman et al. |
| 2018/0298318 A1 | 10/2018 | Kurz et al. |
| 2018/0362991 A1 | 12/2018 | Serber et al. |
| 2019/0060900 A1 | 2/2019 | Breinlinger et al. |
| 2019/0060907 A1 | 2/2019 | Bao et al. |
| 2019/0064038 A1 | 2/2019 | White et al. |
| 2019/0083983 A1 | 3/2019 | Breinlinger et al. |
| 2019/0085375 A1 | 3/2019 | Mcewen |
| 2019/0134630 A1 | 5/2019 | White |
| 2019/0152771 A1 | 5/2019 | Breinlinger et al. |
| 2019/0172196 A1 | 6/2019 | Du et al. |
| 2019/0194692 A1 | 6/2019 | Meijrink et al. |
| 2019/0217297 A1 | 7/2019 | Lavieu et al. |
| 2019/0240665 A1 | 8/2019 | Lionberger et al. |
| 2019/0275516 A1 | 9/2019 | Lowe, Jr. et al. |
| 2019/0283026 A1 | 9/2019 | Loutherback et al. |
| 2019/0323036 A1 | 10/2019 | Bruno et al. |
| 2019/0345488 A1 | 11/2019 | Soumillon et al. |
| 2019/0374944 A1 | 12/2019 | Lundquist et al. |
| 2019/0376070 A1 | 12/2019 | Bruno et al. |
| 2019/0384963 A1 | 12/2019 | Kim et al. |
| 2020/0017817 A1 | 1/2020 | Kelly-greene et al. |
| 2020/0032193 A1 | 1/2020 | Newstrom et al. |
| 2020/0038857 A1 | 2/2020 | Mcfarland et al. |
| 2020/0064337 A1 | 2/2020 | Park et al. |
| 2020/0071693 A1 | 3/2020 | SunSpiral et al. |
| 2020/0078785 A1 | 3/2020 | Hobbs et al. |
| 2020/0078788 A1 | 3/2020 | Chapman et al. |
| 2020/0115680 A1 | 4/2020 | Bronevetsky et al. |
| 2020/0123491 A1 | 4/2020 | Beemiller et al. |
| 2020/0123535 A1 | 4/2020 | SunSpiral et al. |
| 2020/0139362 A1 | 5/2020 | Beemiller et al. |
| 2020/0171501 A1 | 6/2020 | Mcewen et al. |
| 2020/0230601 A1 | 7/2020 | White et al. |
| 2021/0102150 A1 | 4/2021 | Kurz et al. |
| 2021/0114020 A1 | 4/2021 | Lowe, Jr. et al. |
| 2021/0115436 A1 | 4/2021 | Ramenani et al. |
| 2021/0129142 A1 | 5/2021 | Hobbs et al. |
| 2021/0254080 A1 | 8/2021 | Bruno et al. |

FOREIGN PATENT DOCUMENTS

| | | |
|---|---|---|
| JP | H11304666 A | 11/1999 |
| JP | 2012504390 A | 2/2012 |
| JP | 2013017408 A | 1/2013 |
| JP | 2013533737 A | 8/2013 |
| WO | WO 1993/007277 A1 | 4/1993 |
| WO | WO 1993/025663 A1 | 12/1993 |
| WO | WO 1997/006261 A2 | 2/1997 |
| WO | WO 1997/008332 A1 | 3/1997 |
| WO | WO 2000/020555 A1 | 4/2000 |
| WO | WO 2000/020555 A2 | 4/2000 |
| WO | WO 2005/021772 A1 | 3/2005 |
| WO | WO 2005/095624 A2 | 10/2005 |
| WO | WO 2008/113847 A2 | 9/2008 |
| WO | WO 2009/085135 A2 | 7/2009 |
| WO | WO-2010039889 A2 | 4/2010 |
| WO | WO 2011/154147 A1 | 12/2011 |
| WO | WO-2012142591 A2 | 10/2012 |
| WO | WO 2013/135729 A1 | 9/2013 |
| WO | WO 2015/082535 A1 | 6/2015 |
| WO | WO 2015/168184 A1 | 11/2015 |
| WO | WO 2016/073990 A2 | 5/2016 |
| WO | WO 2016/100272 A1 | 6/2016 |
| WO | WO 2016/100568 A1 | 6/2016 |
| WO | WO 2016/100571 A1 | 6/2016 |
| WO | WO 2017/100376 A2 | 6/2017 |
| WO | WO 2017/100377 A1 | 6/2017 |
| WO | WO 2017/189784 A1 | 11/2017 |
| WO | WO 2018/126207 A1 | 12/2017 |
| WO | WO 2018/009372 A1 | 1/2018 |
| WO | WO 2018/050666 A1 | 3/2018 |
| WO | WO 2018/226900 A2 | 6/2018 |
| WO | WO 2018/123134 A1 | 7/2018 |
| WO | WO 2019/236848 A1 | 12/2019 |
| WO | WO 2021/081432 A1 | 4/2021 |
| WO | WO 2021/097449 A1 | 5/2021 |

OTHER PUBLICATIONS

Arentshorst, et al., "Efficient Generation of Aspergillus niger Knock Out Strains by Combining NHEJ Mutants and a Split Marker

(56) References Cited

OTHER PUBLICATIONS

Approach". In: van den Berg M., Maruthachalam K. (eds) Genetic Transformation Systems in Fungi (2014), vol. 1. Fungal Biology, pp. 263-272, 10 pages.
Arras and Fraser, "Chemical Inhibitors of Non-Homologous End Joining Increase Targeted Construct Integration in Cryptococcus neoformans". PLoS One (Sep. 2016); 11(9): e0163049.
Barcellos, et al. "Genetic analysis of Aspergillus nidulans unstable transformants obtained by the biolistic process." Canadian Journal of Microbiology (1998); 44(12): 1137-1141.
Basu, et al., "Purification of specific cell population by fluorescence activated cell sorting (FACS)". J Vis Exp. (2010); (41):1546. Published Jul. 10, 2010.
Becker and Guarente, "[12] High-efficiency transformation of yeast by electroporation." Methods in Enzymology (1991); 194: 182-187.
Bégueret, et al., "Cloning gene ura5 for the orotidylic acid pyrophosphorylase of the filamentous fungus Podospora anserina: transformation of protoplasts". Gene (Dec. 1984); 32(3): 487-492.
Beydon, et al., "Microbiological High Throughput Screening: An Opportunity for the Lead Discovery Process". Journal of Biomolecular Screening (2000); 5(1): 13-22.
Bischof, et al., "A versatile platform for creating a comprehensive UAS-ORFeome library in *Drosophila*", Development (Jun. 2013); 140(11): 2434-2442. Epub May 1, 2013.
Blumhoff, et al., "Targeting enzymes to the right compartment: metabolic engineering for itaconic acid production by Aspergillus niger". Metab Eng. (2013); 19: 26-32.
Brown, et al., "Yeast Skn7p functions in a eukaryotic two-component regulatory pathway." The EMBO Journal (1994); 13(21): 5186-5194.
Casqueiro, et al., "Gene Targeting in Penicillium chrysogenum: Disruption of the lys2 Gene Leads to Penicillin Overproduction". Journal of Bacteriology (Feb. 1999); 181(4): 1181-1188.
Catlett, et al., "Split-Marker Recombination for Efficient Targeted Deletion of Fungal Genes". Fungal Genetics Reports (2003); 50(Article 4): 9-11.
Chakraborty and Kapoor, "Transformation of filamentous fungi by electroporation." Nucleic Acids Research (1990); 18(22): 6737.
Cheng and Bélanger, "Protoplast preparation and regeneration from spores of the biocontrol fungus Pseudozyma flocculosa". FEMS Microbiology Letters (Sep. 2000); 190(2): 287-291.
Choi, et al., "Single spore isolation of fungi". Fungal Diversity (Oct. 1999); 3: 29-38.
Christiansen, et al.,"Biolistic transformation of the obligate plant pathogenic fungus, *Erysiphe graminis* f. sp. *hordei*." Current Genetics (1995); 29(1): 100-102.
Christie and Gordon, "The Agrobacterium Ti plasmids." Microbiology Spectrum (2014); 2(6): 10.1128.
Collado, et al., "High-throughput culturing of fungi from plant litter by a dilution-to-extinction technique". FEMS Microbiol Ecol. (2007); 60(3): 521-533.
Crameri, et al. "DNA shuffling of a family of genes from diverse species accelerates directed evolution." Nature (1998); 391(6664): 288-291.
Crameri, et al. "Molecular evolution of an arsenate detoxification pathway by DNA shuffling." Nature Biotechnology (1997); 15(5): 436-438.
Dai, et al., "Impact of alg3 gene deletion on growth, development, pigment production, protein secretion, and functions of recombinant Trichoderma reesei cellobiohydrolases in Aspergillus niger". Fungal Genetics and Biology (Dec. 2013); 61: 120-132. Epub Sep. 25, 2013.
Dai, et al., "Identification of Genes Associated with Morphology in Aspergillus niger by Using Suppression Subtractive Hybridization". Applied and Environmental Microbiology (Apr. 2004); 70(4): 2474-2485.
De Almeida, et al. "Transgenic expression of two marker genes under the control of an *Arabidopsis* rbcS promoter: Sequences encoding the Rubisco transit peptide increase expression levels." Molecular and General Genetics MGG (1989); 218(1): 78-86.
De Boer, et al., "Highly efficient gene targeting in Penicillium chrysogenum using the bi-partite approach in Δlig4 or Δku70 mutants". Fungal Genet Biol. (Oct. 2010); 47(10): 839-846. Epub Jul. 24, 2010.
Durand, et al. "Transient expression of the β-glucuronidase gene after biolistic transformation of the anaerobic fungus Neocallimastix frontalis." Current Genetics (1997); 31(2): 158-161.
Extended European Search Report for European Patent Application No. EP 17886439.3, dated Jul. 3, 2020, 12 pages.
Eyini, et al., "Isolation, Regeneration and PEG-Induced Fusion of Protoplasts of Pleurotus pulmonarius and Pleurotus florida." Mycobiology (Jun. 2006); 34(2): 73-78.
Fincham, J.R., "Transformation in fungi." Microbiological Reviews (Mar. 1989); 53(1): 148-170.
Goosen, et al., "Transformation of Aspergillus niger using the homologous orotidine-5'-phosphate-decarboxylase gene". Current Genetics (Mar. 1987); 11(6-7): 499-503.
Ho and Ko, "A simple method for obtaining single-spore isolates of fungi", Bot. Bull. Acad. Sin. (1997); 38(1): 41-43.
Huang, et al., "Microfluidic screening and whole-genome sequencing identifies mutations associated with improved protein secretion by yeast". PNAS (Aug. 25, 2015); 112 (34): E4689-E4696. Epub Aug. 10, 2015.
Hynes, M.J., "Genetic transformation of filamentous fungi". J. Genet. (Dec. 1996); 75(3): 297-311.
Ito, et al., "Transformation of intact yeast cells treated with alkali cations." Journal of Bacteriology (1983); 153(1): 163-168.
Ji, et al., "Iterative combinatorial mutagenesis as an effective strategy for generation of deacetoxycephalosporin C synthase with improved activity toward penicillin". G. Appl Environ Microbiol. (2012); 78(21): 7809-7812.
Jiang, et al., "Molecular tools for functional genomics in filamentous fungi: Recent advances and new strategies". Biotechnol Adv. (Dec. 2013); 31(8): 1562-1574. Epub Aug. 26, 2013.
Jones, et al., "High level expression of introduced chimaeric genes in regenerated transformed plants." The EMBO Journal (1985); 4(10): 2411-2418.
Khanna, N.C., et al. "Identification of the template binding polypeptide in the pea chloroplast transcriptional complex." Nucleic Acids Research (1992); 20.1: 69-74.
Krijgsheld, et al., "Development in Aspergillus". Studies in Mycology (Mar. 2013); 74: 1-29. Epub Sep. 12, 2012.
Li, et al., "Methods for genetic transformation of filamentous fungi". Microb Cell Fact. (Oct. 3, 2017); 16(1): 168, pp. 1-13.
Li, et al., "The yeast histidine protein kinase, Sln1p, mediates phosphotransfer to two response regulators, Ssk1p and Skn7p". The EMBO Journal (1998); 17(23): 6952-6962.
Liu, et al., "Improved Production of a Heterologous Amylase in *Saccharomyces cerevisiae* by Inverse Metabolic Engineering". Appl Environ Microbiol (Sep. 2014); 80(17): 5542-5550. Epub Jun. 27, 2014.
Liu, et al., "Efficient genome editing in filamentous fungus *Trichoderma reesei* using the CRISPR/Cas9 system". Cell Discov (2015); 1, 15007, 11 pages.
Loske, et al., "Tandem shock waves to enhance genetic transformation of Aspergillus niger". Ultrasonics (Aug. 2014); 54(6): 1656-1662.
Magaña-Ortíz, et al., "A novel and highly efficient method for genetic transformation of fungi employing shock waves". Fungal Genetics and Biology (Jul. 2013); 56: 9-16.
Moore, et al. "Strategies for the in vitro evolution of protein function: enzyme evolution by random recombination of improved sequences." Journal of Molecular Biology (1997); 272(3): 336-347.
Nakashima, et al., "Bacterial cellular engineering by genome editing and gene silencing." International Journal of Molecular Sciences (2014); 15(2): 2773-2793.
Nakasone, et al., "Preservation and distribution of fungal cultures". Biodiversity of Fungi, G.M. Mueller et al., (ED), (2004), Ch. 3, pp. 37-47, 13 pages.

(56) References Cited

OTHER PUBLICATIONS

Nielsen, et al., "Efficient PCR-based gene targeting with a recyclable marker for Aspergillus nidulans". Fungal Genet Biol. (Jan. 2006); 43(1): 54-64. Epub Nov. 11, 2005.
Nielsen, et al., "Transient disruption of non-homologous end-joining facilitates targeted genome manipulations in the filamentous fungus Aspergillus nidulans". Fungal Genet Biol. (Mar. 2008); 45(3): 165-170. Epub Jul. 20, 2007.
Nielsen, et al., "Transient Marker System for Iterative Gene Targeting of a Prototrophic Fungus". Appl Environ Microbiol. (Nov. 2007); 73(22): 7240-7245. Epub Oct. 5, 2007.
Nódvig, et al., "A CRISPR-Cas9 System for Genetic Engineering of Filamentous Fungi". PLoS One (Jul. 2015); 10(7): e0133085.
Park, et al., "High-throughput production of gene replacement mutants in Neurospora crassa". Methods Mol Biol. (2011); Ch. 13, 722: 179-189.
PCT/US2017/069086, International Preliminary Report on Patentability, dated Jul. 2, 2019, 10 pages.
PCT/US2017/069086, International Search Report and Written Opinion dated May 14, 2018, 13 pages.
PCT/US2017/069086, Invitation to Pay Additional Fees, dated Mar. 12, 2018, 2 pages.
PCT/US2018/036360, International Preliminary Report on Patentability dated Dec. 10, 2019, 20 pages.
PCT/US2018/036360, International Search Report and Written Opinion dated Nov. 23, 2018, 39 pages.
PCT/US2018/036360, Invitation to Pay Additional Fees, dated Sep. 21, 2018, 28 pages.
PCT/US2019/035793, Invitation to Pay Additional Fees, dated Aug. 22, 2019, 4 pages.
PCT/US2019/035793, International Search Report and Written Opinion dated Nov. 8, 2019, 16 pages.
PCT/US2019/035793, International Preliminary Report on Patentability dated Dec. 8, 2020, 9 pages.
Pohl, et al., "CRISPR/Cas9 Based Genome Editing of Penicillium chrysogenum". ACS Synth Biol. (Jul. 15, 2016); 5(7): 754-764. Epub May 3, 2016.
Ricciardelli, et al., "Development and characterization of primary cultures of smooth muscle cells from the fibromuscular stroma of the guinea pig prostate." In Vitro Cellular & Developmental Biology (1989); 25(11): 1016-1024.
Roncero, et al., "Mutagenesis in multinucleate cells: the effects of N-methyl-N'-nitro-N-nitrosoguanidine on phycomyces sporres". Mutation Research/Fundamental and Molecular Mechanisms of Mutagenesis (Feb. 1984); 125(2): 195-204.
Ruiz-Díez, B., "Strategies for the transformation of filamentous fungi". J. Appl. Microbiology (Jan. 2002); 92(2): 189-195.
Stemmer, Willem P.C., "Rapid evolution of a protein in vitro by DNA shuffling." Nature (1994); 370(6488): 389-391.
Stemmer, Willem P.C., "DNA shuffling by random fragmentation and reassembly: In vitro recombination for molecular evolution." Proceedings of the National Academy of Sciences (1994); 91(22): 10747-10751.
Szewczyk, et al., "Fusion PCR and gene targeting in Aspergillus nidulans". Nat Protoc. (Jan. 1, 2006); 1(6): 3111-3120.
Tear, et al., "Excision of Unstable Artificial Gene-Specific Inverted Repeats Mediates Scar-Free Gene Deletions in Escherichia coli." Applied Biochemistry and Biotechnology (2014); 175(4): 1858-1867.
Wyatt, et al., "Essential Roles for Polymerase θ-Mediated End Joining in the Repair of Chromosome Breaks". Molecular Cell (Aug. 2016); 63(4): 662-673.
Yabuki, et al., "Rapid method for converting fungal cells into protoplasts with a high regeneration frequency". Experimental Mycology (Dec. 1984); 8(4): 386-390.
Yelton, et al., "Transformation of Aspergillus nidulans by using a trpC plasmid." Proceedings of the National Academy of Sciences (1984); 81(5): 1470-1474.
Zhang, et al., "Directed evolution of a fucosidase from a galactosidase by DNA shuffling and screening." Proceedings of the National Academy of Sciences (1997); 94 (9): 4504-4509.
Zhang, et al., "An Optimized Protocol of Single Spore Isolation for Fungi". Cryptogamie, Mycologie (Dec. 2013); 34(4): 349-356.
U.S. Appl. No. 17/207,376, filed Mar. 19, 2021, SunSpiral, et al.
U.S. Appl. No. 17/387,634, filed Jul. 28, 2021, Knox, et al.
Aslanidis, et al., "Ligation-independent cloning of PCR products (LIC-PCR)." Nucleic Acids Research 18.20 (1990): 6069-6074.
Azhayev, et al., "Amide group assisted 3'-dephosphorylation of oligonucleotides synthesized on universal A-supports." Tetrahedron 57.23 (2001): 4977-4986.
Czar, et al. "Gene synthesis demystified" Trends in Biotechnology 27.2 (2009): 63-72.
Damha, et al., "An improved procedure for derivatization of controlled-pore glass beads for solid-phase oligonucleotide synthesis." Nucleic Acids Research 18.13 (1990): 3813-3821.
Engler, et al., "A one pot, one step, precision cloning method with high throughput capability." PLoS One 3.11 (2008): e3647.
Farrow and Arnold, "High Throughput Screening of Fungal Endoglucanase Activity in Escherichia coli". J. Vis. Exp. (54), e2942. Epub Aug. 13, 2011.
Gibson, et al., "Enzymatic assembly of DNA molecules up to several hundred kilobases." Nature Methods 6.5 (2009): 343-345.
Hagiwara, et al., "Characterization of NikA histidine kinase and two response regulators with special reference to osmotic adaptation and asexual development in Aspergillus nidulans". Bioscience, Biotechnology, and Biochemistry (Jul. 23, 2009); 73(7): 1566-1571.
Kotera, et al., "A high-throughput and single-tube recombination of crude PCR products using a DNA polymerase inhibitor and type IIS restriction enzyme." Journal of Biotechnology 137.1-4 (2008): 1-7.
Kozlov, et al., "Significant improvement of quality for long oligonucleotides by using controlled pore glass with large pores." Nucleosides, Nucleotides and Nucleic Acids 24.5-7 (2005): 1037-1041.
Reyrat, et al., "Counterselectable markers: untapped tools for bacterial genetics and pathogenesis." Infection and Immunity 66.9 (1998): 4011-4017.
Sierzchala, et al., "Solid-phase oligodeoxynucleotide synthesis: a two-step cycle using peroxy anion deprotection." Journal of the American Chemical Society 125.44 (2003): 13427-13444.
Tian, et al., "Advancing high-throughput gene synthesis technology." Molecular BioSystems 5.7 (2009): 714-722.
Weber, et al., "Assembly of designer TAL effectors by Golden Gate cloning." PLoS One 6.5 (2011): e19722.
Yu, et al., "Double-joint PCR: a PCR-based molecular tool for gene manipulations in filamentous fungi." Fungal Genetics and Biology 41.11 (2004): 973-981.
PCT/US2021/043704, Invitation to Pay Additional Fees, dated Oct. 13, 2021, 2 pages.

FIG. 6A

Acquire and Build DNA | Assemble Vectors

- Source DNA fragments from vendors or internal storage.
- Alternatively synthesize DNA fragments in house.
- Join smaller DNA fragments into larger inserts for vector cloning.
- Evaluate joined DNA inserts prior to cloning.

- Stitch together DNA inserts into vectors for genomic insertion into host organisms.
- Evaluate vectors prior to transformation.

Transform Vectors into Host Cell | Remove Selection Markers

- Transform host cell with DNA Vectors.
- Select for transformed cells and evaluate cassette insertion into genomic DNA.

- Loop out selection markers through counter selection.
- Evaluate insertion site to confirm deletion of loop out regions.

Transformation, propagation, heterokaryon elimination w/volumes

Repeated to purify transformed nuclei away from parental

Consolidation for NGS screen and Test Tech Dev w/volumes

FIG. 21
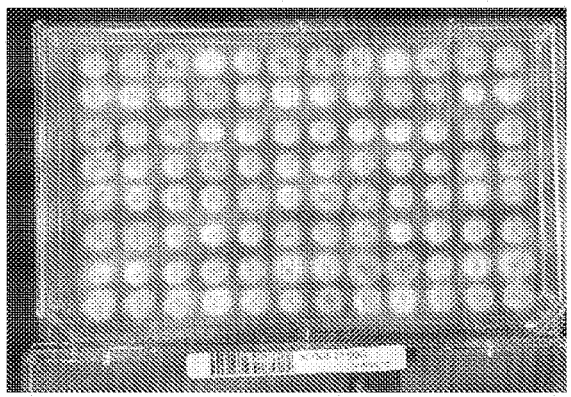
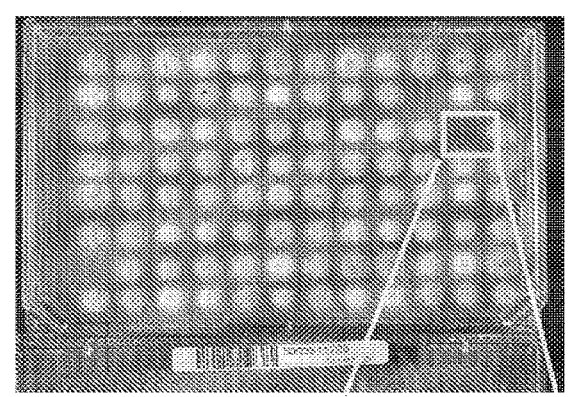
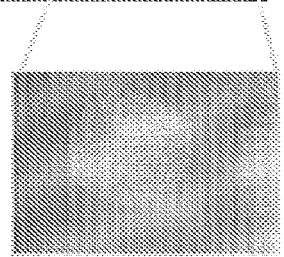

FIG. 23A

The DNA placed in each well
- Transformed 4 different types of small changes to aygA gene
- Transformants become pyrG+, met3-
- %? Will take up SNP

Round outs prior to counterselection
- 8 pure yellow strains
- Likely many more Heterokaryons
- Screening by NGS at each step
- Can score phenotype readily and Genotype

FIG. 23B

Strain Build - Delta/Epsilon/DARPA Cg

BB10: Protoplast Prep

| Workflow | Inoculate Cultures | Incubate | Collect Hyphae | Inoculate Cultures | Incubate | LTP OD |
|---|---|---|---|---|---|---|
| | | | ◇ OD | | | |
| 5. Parameters | •Plate Type<br>•# of Plates<br>•Flask Type<br>•# of Flasks<br>•Volume Media<br>•Volume Inoculum<br>•Media<br>•Time/Date | •Instrument<br>•Time/Date<br>•Duration<br>•Temp<br>•Humidity<br>•Speed<br>•Media<br>•Volume<br>•Labware | •Miracloth<br>•Buchner Funnel<br>•Water Rinse Vol<br>•Time/Date<br>•<br>•Tip Type<br>•Tip Type | •Plate Type<br>•# of Plates<br>•Flask Type<br>•# of Flasks<br>•Volume Media<br>•Volume Inoculum<br>•Media<br>•Time/Date | •Instrument<br>•Time/Date<br>•Duration<br>•Temp<br>•Humidity<br>•Speed<br>•Media<br>•Volume<br>•Labware | •Dilution Factor<br>•# Cuvettes<br>•Media<br>•Time/Date<br>•Microscopy<br>•Tip Type<br>•Tip Type |
| | Null<br>Null<br>250mL baffle flask<br>2<br>50mL<br>100-500uL<br>BHI<br>Time Stamp | Innova Shaker<br>Time Stamp<br>14-16 hours<br>30C<br>80%<br>175 RPM<br>Complete Media<br>100mL<br>250mL Baffled Flask | 1:10<br>2-3<br>BHI Blank<br>Time stamp<br>Microscopy<br>Labware<br>P1000<br>Serological | Null<br>Null<br>2.8L Baffled Flask<br>2<br>500mL<br>10ul-20mL (variable)<br>BHI<br>Time Stamp | Innova Shaker<br>Time Stamp<br>6-18 hours<br>30C, 18C<br>80%<br>200 RPM<br>BHI+culture<br>500mL<br>2.8L Baffled Flask | 1:10, 1:100, 1:1000<br>2-5<br>BHI Blank<br>Time stamp<br>Microscopy<br>Labware<br>P1000, p100<br>Serological |

FIG. 28

Integrate
- Yellow spores
- Loop-outs yellow
- 2 copies of SNP

Ectopic
- Black
- 2 SNPs, 1 wt

Integrate
- Yellow spores
- Loop-outs yellow? Black?
- 1 SNP, 1 wt

Ectopic
- Black
- 1 SNP, 2 wt

Integrate
- Yellow spores
- Loop-outs Black
- 2 copies wt

Ectopic
- Black
- 3 wt

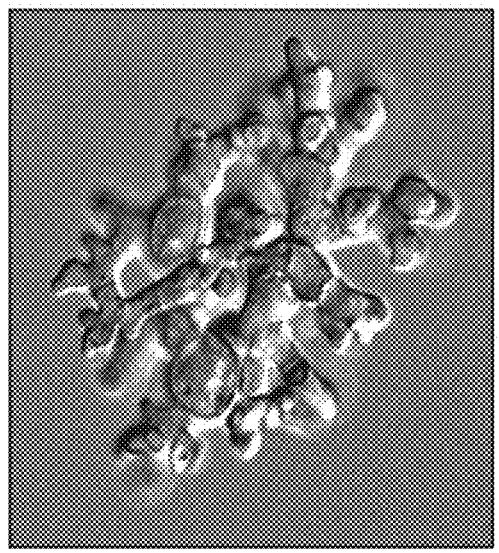
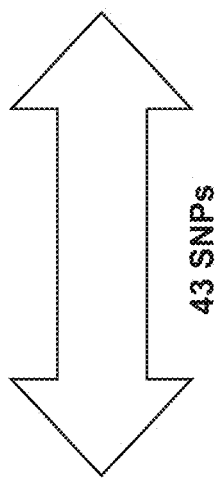
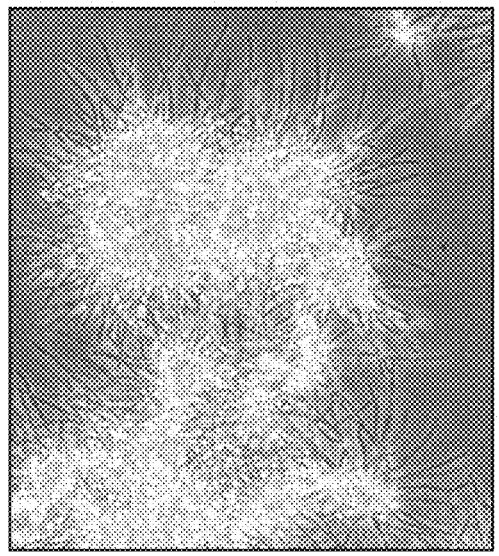
FIG. 44

```
LOCUS       arg_01    1734116bp DNA    UNK 16-FEB-2016
DEFINITION mutant of chr_102;change: c > A at 871418
ACCESSION Z13000142126
VERSION   Z13000142126
KEYWORDS  [;;].
SOURCE    .
ORGANISM ..
          [;].
FEATURES         Location/Qualifiers
     engineered_inse 871418
                     /description="change: C>A"
                     /old_value="C"
                     /annotationName="introduced mutation"
                     /label="introduced mutation"
                     /createTimestamp=1455662143073
                     /creatorId=39
ORIGIN
    1 gtataaatta tatattatta atattacata tatatittac ttctgaagag cttcattacc
   61 tacttaatat tatattata attttcata tttataitc tatctatgag actaagaatt agtttgagaa
  121 acttactag attttcata taatttacta attttttct gaacaatctt ctgattatta
  181 gttctctgtt taatgaaaca atagatatt attataaaaa ttttatataa aataaatcta
```

(SEQ ID NO: 27)

Genomic sequence uploaded into LIMS

FIG. 44 (Cont. 1)

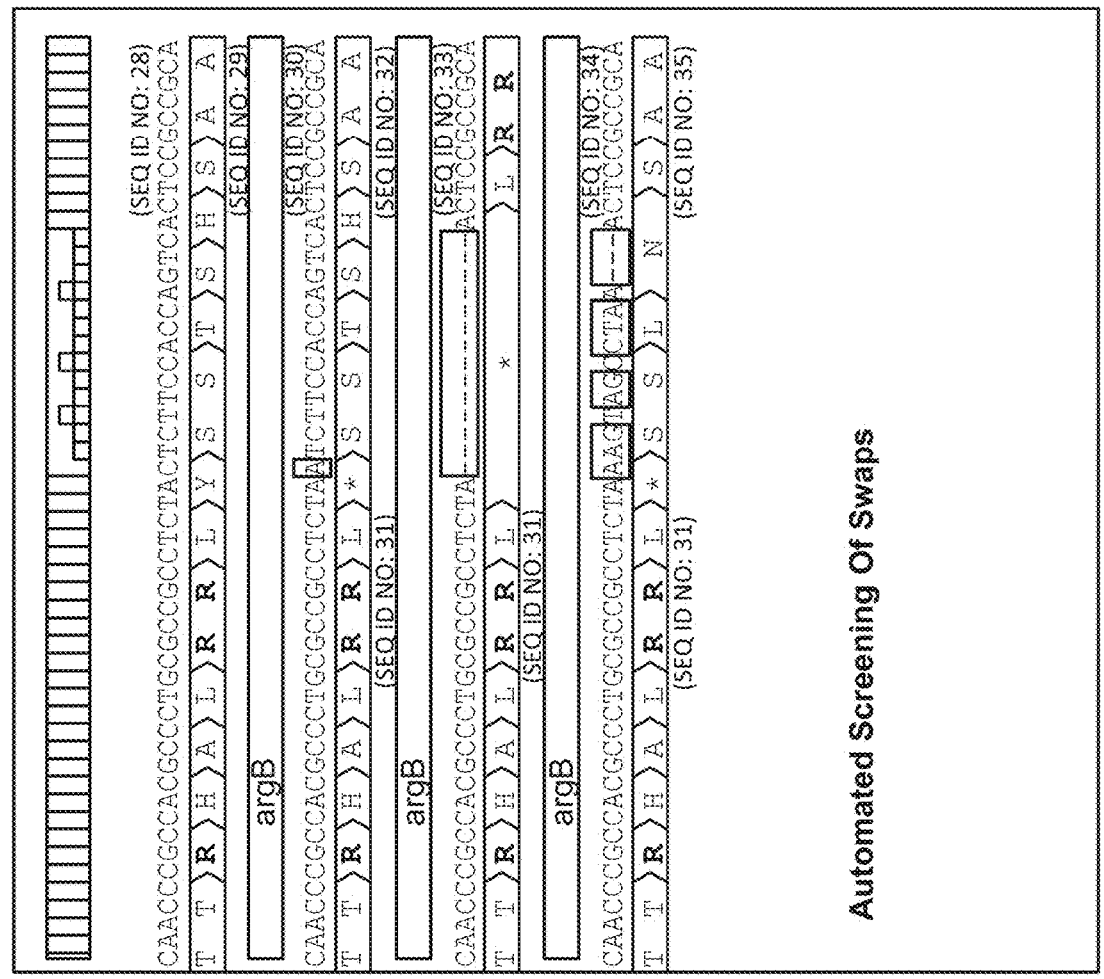
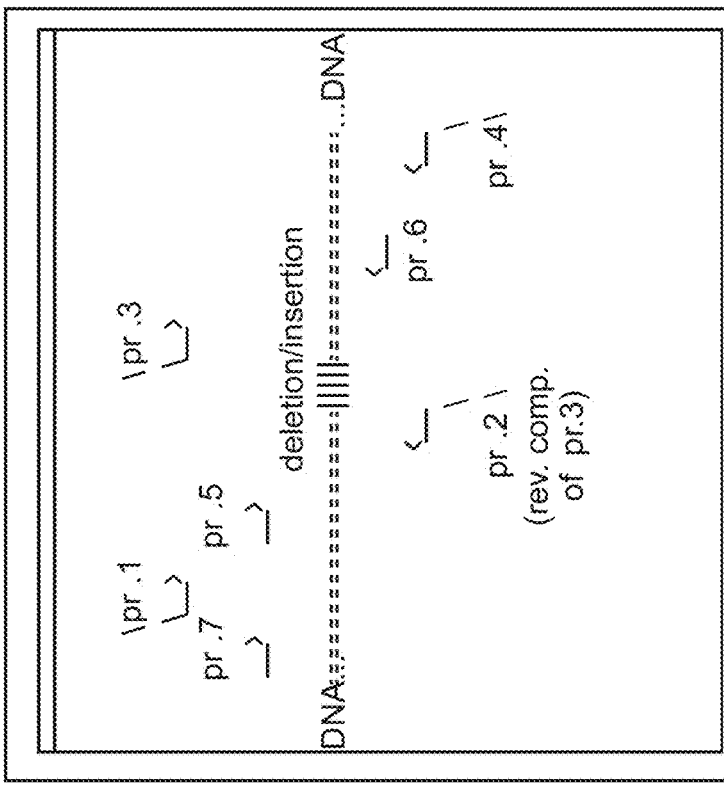
FIG. 44 (Cont. 2)

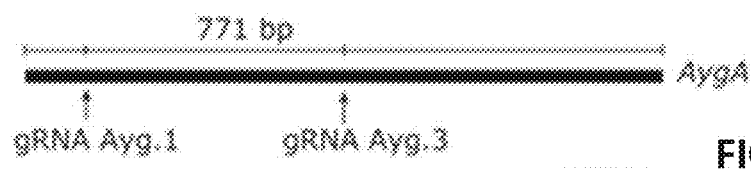
FIG. 49A
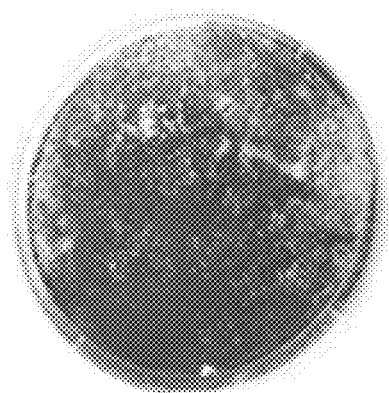
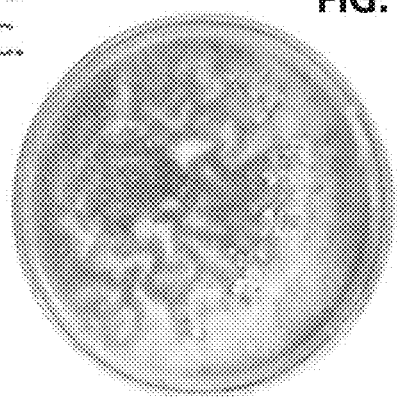
FIG. 49B — Cas9 + control crRNA/trRNA + plasmid
FIG. 49C — Cas9 + Ayg.1 crRNA/trRNA + plasmid
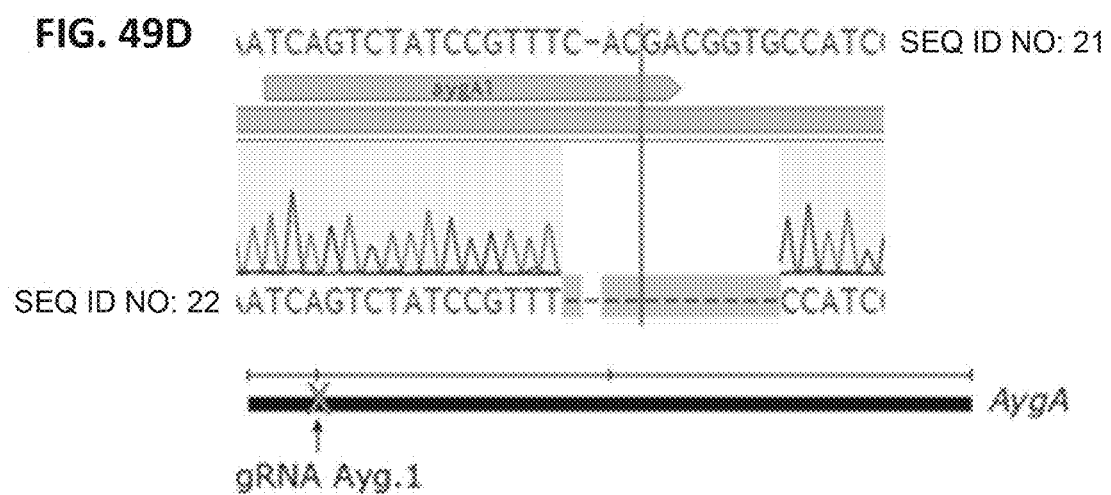
FIG. 49D

FIG. 51

GAGACCCGAGACAGACAGTGACGCCCCTTGTTCCCTCAGCGGCCGTGGATTGGTCAGCCCCCTGCGTTTGTAGCC
CTAAGTACTCTCAATGGTGGTTGTGATGTCACAAGGTTTGGAGGAGAGTTCATGTGCAACCCAGTCGGCAAGTTTC
GCCGTGAGTACCTTACATTGAATGGGCTACGTTTAAAAAGGGTCCTTCAATGCTGTCTCCCGCCTGAACTGTAAAT
CTTCACATTGTCTACTCACAGACTGGACGACGCGAACAAGCAAGCAAACACAATGGCTCCTTGGATCCTCGGCGAG
AAGTTCAACACCGTTTACCCCCACAAGGGCTCTATCAAAGCTCTCTGGGAAACGAACTGGAAGTTTGCAGTAAGTT
TTCACTGGTGGTCGGCATCACCACCCCTTGCTCAGTGGTTGGCCAACCGCTCAGCCAGGTCTTATCTAACGTAGCAT
GCACTGTCAAAAATCAGTCTATCCGTTTCAgggtcgcagtgcttgtacggcagcttctacttgcttgcacagggagctctctgggcttg
agtcttttggagttgcgaggagttgattcctacttctaagtttggactgaatcgtggtgtgattgaggtgattggcgatgcttagctataccagctat
atgtaatactctactgtatactactattcaacgcatttactatgcgtgctgctagggtcggcaatgcaatctgactgacggggtctctttct
ccatgtgcagcaggaatacgagctcaatggactggagagtggcacagtcaatggcaaggaaactccgccttgcaggtgtggctgaacccacg
ggtcggcagcggagcaatccccgacgtggctgctcggaggagcctcgcgatgatttactgagctgattctgtcgacatgaacattgtc
ctggtcttcattcagattaagggtcagtcactgctacattctcaglagtatcgcgcacgtctctggattacgaataggtcaaccagtcgaaact
tcgaactactcttattatacaatcctctttccattccgcgatttaaccctccatcaacacactgctcacagtcgcaactgactacactgcgtgca
gcaagcatcccaaatgctctggcgaagaggctgtcgagattgcgagggccaagaagaccaatgtgactgtctcggctgacgtaccacacataaggc
gctactagatctctgctgaccgtaggccgaccgtactctgcctgattatgctgcatgcaaacttattaacggtgatccggctgcaggctcggtccc
tacattgccgtgatccaaacccaaacactagtactctctgattcagcaacgagaccattgagggccttaaggctcacgagcgagaagcacaacttctc
atctcgaggacgcaagttcattgacattggccaacacggtccagaagcatatcacggcggaaccctccgtatctcggaataggcccacatcatcaaa
ctgcagccattctcctggtgaggcgatcgtcgaggctctgctccagaacggggtctgcaccaggacttgcctcacggccccgaacgcggtctgttgatcttg
gcagagatgacctctaagggctccttggctacaggccagtacactactcctcggctcgattatgccggaaataccagaactcgttatggggatcgtgt
cgacagccgcgttgggtgaagtgcagtcaggaagtcagctctccttggatgaaggaggactttgtggtcttcacgactggtgtgaacatttcttccaagg
gagataaggttggccagccagtaccagacgccgagaatcggtatggagaaggtctgacttcattacgagggtcgggtatctacgcgcgcggt
ccggtgccaggctgcgcaacagtatcagaaggaggggtaggaagcctaccggccgtgtcggcggaaactaatactataaaaggaggatcgaagtt
ctgatggtatgaatgatatagaaatgcaacttgccgcaacggatacggagcggaaacggaccaatgtcgagcacgggctatgctgagcatc
gggatccaaaaggctatgatcctgccaggctactatggtgtggcacaaggatcaatgcggtacgacgtttgatgcagtaagcaggctcggaggtag
taactctgcgtagagaaatggcgacgggtgctgataaggcccggtgataagcttaattgcatcgcagataagcactgcgtcttCGACGGTGC
CATCGAAGACTTTCGACCTATCTTCCAAAAGCTTATCGATGTAGGTTATCATAATCTTGCCATGTGCGCCTTACGAG
CGCAAGGGTAAAATACTCACTTCTAGATAGGAAAAATATCAACGATGCCTACACCGATGCCTACACGCAGGCTTTCT
TCCCGGTTGCTGAGGCACTCGAAAATAAGGCCGTCAGCTGCTTTGAACAACAACAATGTGGAGATGGCATCTGACT
TGCTCCGAAGAGCTGCTGTGGTCTACCGTATCTCCCGCTTCCCATATGTCGACCCGACCAGAGAAGACATCAAAAA
AGAGGCCTTCAACCGCCAGAAGAAGGTCTATCTGAAGGCAGCATCCTTCTGGAAGCCCACCATCCAGGAGGTCAT
CATCCCGCACAAGCATAAGTCGGCCACCGACGGAGCCTATGTTCCCCTTT    (SEQ ID NO: 9)

FIG. 52

(SEQ ID NO: 10)

FIG. 56A
SEQ ID NO: 24

FIG. 56B
SEQ ID NO: 25

SEQ ID NO: 25

SEQ ID NO: 26

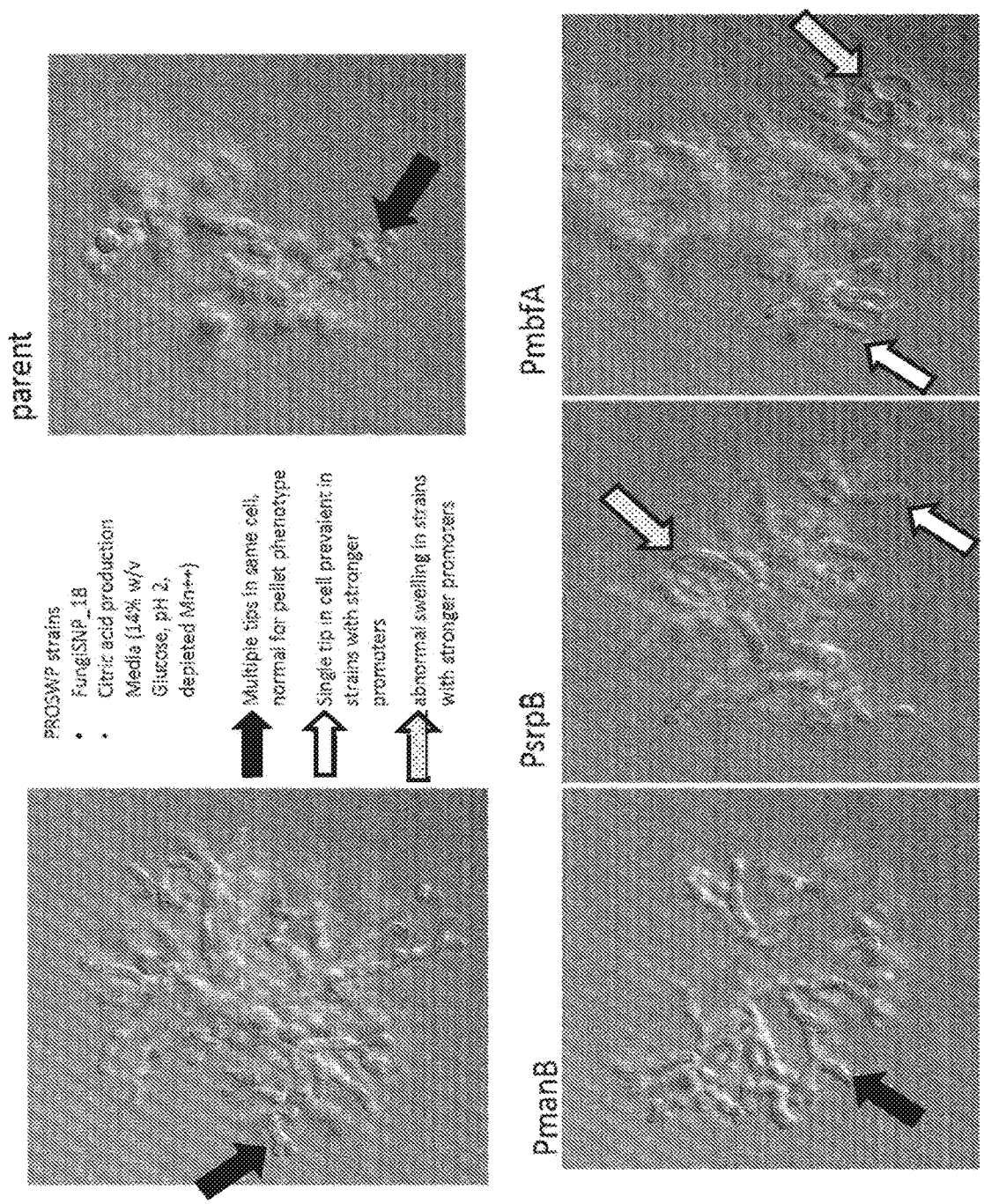

FIG. 62
Minimal MediapH2.0
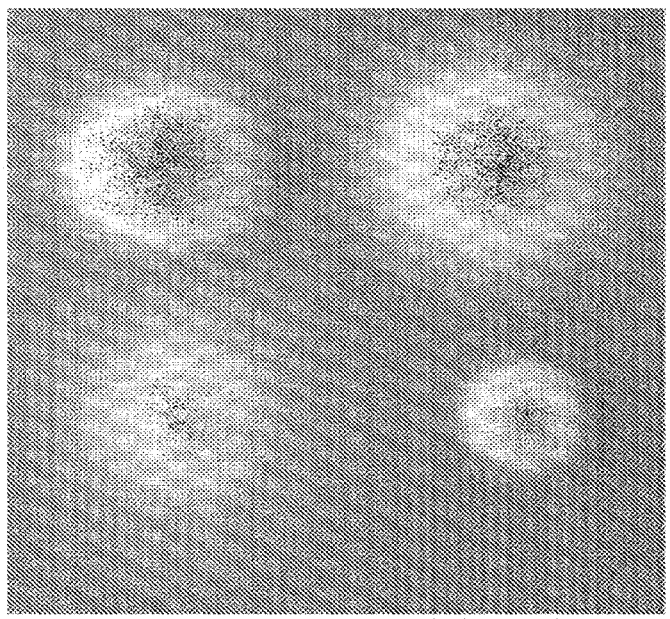
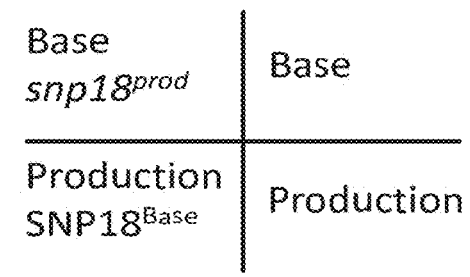

FIG. 64
Base Parent
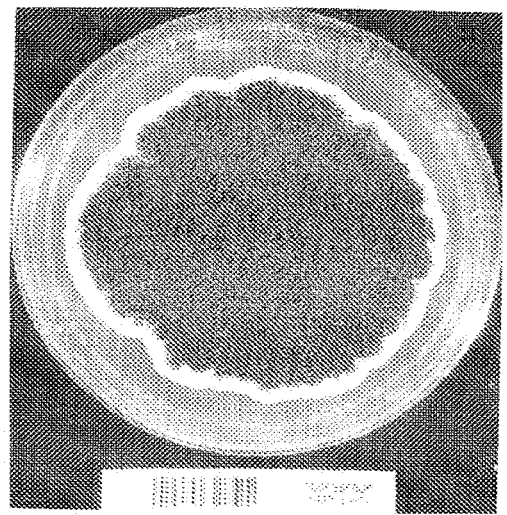
Base snp18<sup>prod</sup>
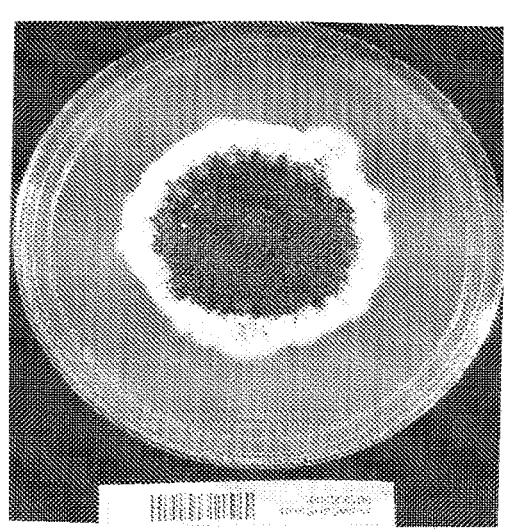
Production parent
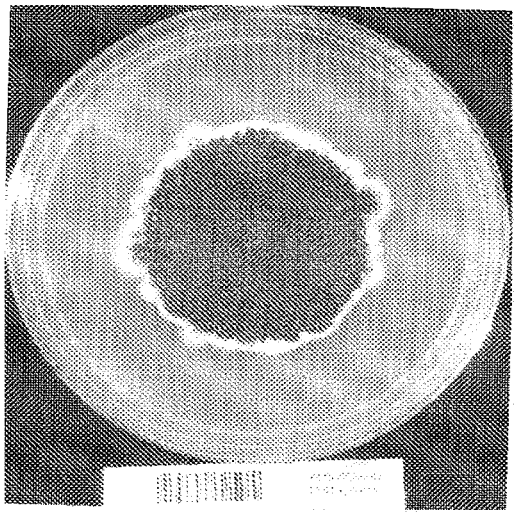
Production SNP18<sup>Base</sup>
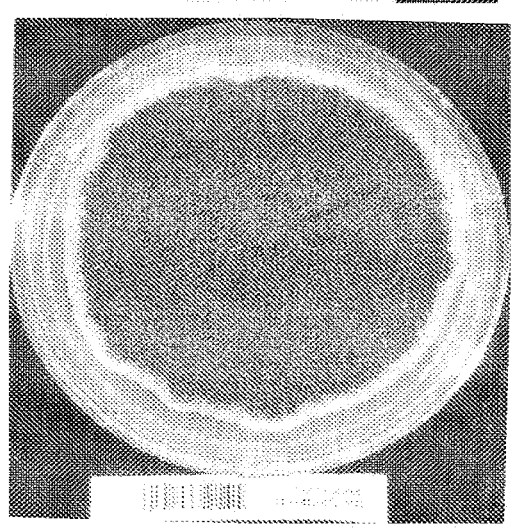

FIG. 70
Base strain dense tight colonies
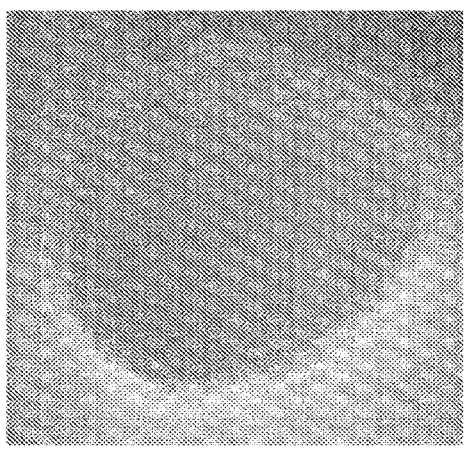
Production strain less dense. More straight hyphae
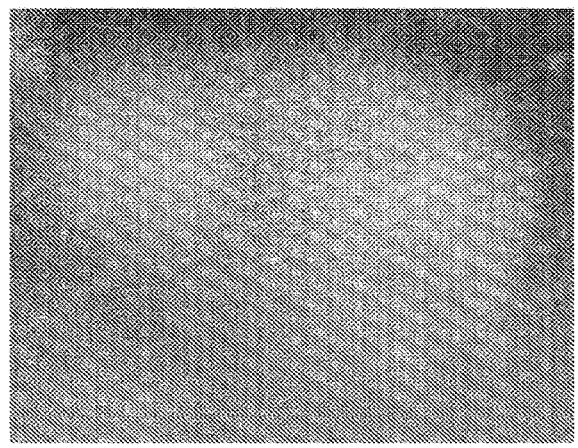

HTP GENOMIC ENGINEERING PLATFORM FOR IMPROVING FUNGAL STRAINS

CROSS-REFERENCE TO RELATED APPLICATIONS

This application is a Divisional of U.S. application Ser. No. 16/600,062, filed Oct. 11, 2019, (issued as U.S. Pat. No. 10,954,511 on Mar. 23, 2021), which is a Continuation of International PCT Application No. PCT/US2018/036360, filed Jun. 6, 2018, which claims the benefit of priority to U.S. Provisional Application No. 62/515,907, filed on Jun. 6, 2017, each of which is hereby incorporated by reference in its entirety for all purposes.

FIELD

The present disclosure is directed to automated fungal genomic engineering. The disclosed automated genomic engineering platform entails the genetic manipulation of filamentous fungi to generate fungal production strains as well as facilitate purification thereof. The resultant fungal production strains are well-suited for growth in sub-merged cultures, e.g., for the large-scale production of products of interest (e.g., antibiotics, metabolites, proteins, etc.) for commercial applications.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_008_05US_SubSeqList_ST25.txt. The text file is 52,485 bytes, was created on Mar. 19, 2021, and is being submitted electronically via EFS-Web.

BACKGROUND

Eukaryotic cells are preferred organisms for the production of polypeptides and secondary metabolites. In fact, filamentous fungi are capable of expressing native and heterologous proteins to high levels, making them well-suited for the large-scale production of enzymes and other proteins for industrial, pharmaceutical, animal health and food and beverage applications. However, use of filamentous fungi for large-scale production of products of interest often requires genetic manipulation of said fungi as well as use of automated machinery and equipment and certain aspects of the filamentous fungal life cycle can make genetic manipulation and handling difficult.

For example, DNA introduced into a fungus integrates randomly within a genome, resulting in mostly random integrated DNA fragments, which quite often can be integrated as multiple tandem repeats (see for example Casqueiro et al., 1999, J. Bacteriol. 181:1181-1188). This uncontrolled "at random multiple integration" of an expression cassette can be a potentially detrimental process, which can lead to unwanted modification of the genome of the host.

Additionally, present transfection systems for filamentous fungi can be very laborious (see for review Fincham, 1989, Microbiol. Rev. 53:148-170) and relatively small scale in nature. This can involve protoplast formation, viscous liquid handling (i.e. polyethylene glycol solutions), one-by-one swirling of glass tubes and subsequent selective plating. Further, conditions for protoplasting can be difficult to determine and yields can often be quite low. Moreover, the protoplasts can contain multiple nuclei such that introduction of a desired genetic manipulation can lead to the formation of heterokaryotic protoplasts that can be difficult to separate from homokaryotic protoplasts.

Further, typical filamentous fungal cells, including those derived from protoplasts, grow as long fibers called hyphae that can form dense networks of hyphae called mycelium. These hyphae can contain multiple nuclei that can differ from one another in genotype. The hyphae can differentiate and form asexual spores that can be easily dispersed in the air. If the hyphae contain nuclei of different genotypes, the spores will also contain a mixture of nuclei. Due to this aspect of fungal growth, genetic manipulation inherently results in a mixed population that must be purified to homogeneity in order to assess any effect of the genetic changes made. Further, in an automated environment, the spores can cause contamination of equipment that could negatively impact the ability to purify strains and may contaminate any other work performed on the equipment.

To mitigate the aerial dispersal of spores, the filamentous fungi can be grown in submerged cultures. However, the mycelium formed by hyphal filamentous fungi growth in submerged cultures can affect the rheological properties of the broth. Generally, the higher the viscosity of the broth, the less uniform the distribution of oxygen and nutrients, and the more energy required to agitate the culture. In some cases, the viscosity of the broth due to hyphal filamentous fungal growth becomes sufficiently high to significantly interfere with the dissolution of oxygen and nutrients, thereby adversely affecting the growth of the fungi and ultimately the yield and productivity of any desired product of interest.

Thus, there is a great need in the art for new methods of engineering filamentous fungi, which do not suffer from the aforementioned drawbacks inherent with traditional strain building programs in fungi and greatly accelerate the process of discovering and consolidating beneficial mutations.

SUMMARY OF THE DISCLOSURE

The present disclosure provides a high-throughput (HTP) genomic engineering platform for coenocytic organisms such as, for example filamentous fungi that does not suffer from the myriad of problems associated with traditional microbial strain improvement programs. While the methods provided herein are tested in filamentous fungi, it is contemplated that said methods can be applied to and/or utilized in other coenocytic organisms. In one embodiment, the filamentous fungus is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. Further to this embodiment, the filamentous fungus useful for the methods and HTP genomic engineering platform is *Aspergillus niger*.

Further, the HTP platform taught herein is able to rehabilitate filamentous fungal strains that have accumulated non-beneficial mutations through decades of random mutagenesis-based strain improvement programs.

The disclosure also provides for unique genomic engineering toolsets and procedures, which undergird the HTP platform's functionality in a filamentous fungal system. The filamentous fungus can be an *Aspergillus* species. The *Aspergillus* can be *A. niger*.

The disclosed HTP genomic engineering platform is computationally driven and integrates molecular biology, automation, and advanced machine learning protocols. This integrative platform utilizes a suite of HTP molecular tool sets to create HTP genetic design libraries, which are derived from, inter alia, scientific insight and iterative pattern recognition.

The taught HTP genetic design libraries function as drivers of the genomic engineering process, by providing libraries of particular genomic alterations for testing in filamentous fungal The microbes engineered utilizing a particular library, or combination of libraries, are efficiently screened in a HTP manner for a resultant outcome, e.g. production of a product of interest. This process of utilizing the HTP genetic design libraries to define particular genomic alterations for testing in a microbe and then subsequently screening host microbial genomes harboring the alterations is implemented in an efficient and iterative manner. In some aspects, the iterative cycle or "rounds" of genomic engineering campaigns can be at least 1, 2, 3, 4, 5, 6, 7, 8, 9, 10, 20, 30, 40, 50, 60, 70, 80, 90, 100, or more iterations/cycles/rounds.

Thus, in some aspects, the present disclosure teaches methods of conducting at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 or more "rounds" of HTP genetic engineering (e.g., rounds of SNP swap, PRO swap, Terminator (STOP) swap, or combinations thereof) in an filamentous fungal host system.

In some embodiments, the present disclosure teaches a linear approach, in which each subsequent HTP genetic engineering round is based on genetic variation identified in the previous round of genetic engineering. In other embodiments the present disclosure teaches a non-linear approach, in which each subsequent HTP genetic engineering round is based on genetic variation identified in any previous round of genetic engineering, including previously conducted analysis, and separate HTP genetic engineering branches.

The data from these iterative cycles enables large scale data analytics and pattern recognition, which is utilized by the integrative platform to inform subsequent rounds of HTP genetic design library implementation. Consequently, the HTP genetic design libraries utilized in the taught platform are highly dynamic tools that benefit from large scale data pattern recognition algorithms and become more informative through each iterative round of microbial engineering. Such a system has never been developed for filamentous fungal and is desperately needed in the art.

In some embodiments, the genetic design libraries of the present disclosure comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 or more individual genetic changes (e.g., at least X number of promoter:gene combinations in the PRO swap library).

In some embodiments, the present disclosure teaches a high-throughput (HTP) method of genomic engineering to evolve an filamentous fungal strain to acquire a desired phenotype, comprising: a) perturbing the genomes of an initial plurality of filamentous fungal strains having the same strain background, to thereby create an initial HTP genetic design filamentous fungal strain library comprising individual strains with unique genetic variations; b) screening and selecting individual strains of the initial HTP genetic design filamentous fungal strain library for the desired phenotype; c) providing a subsequent plurality of filamentous fungal microbes that each comprise a unique combination of genetic variation, said genetic variation selected from the genetic variation present in at least two individual filamentous fungal strains screened in the preceding step, to thereby create a subsequent HTP genetic design filamentous fungal strain library; d) screening and selecting individual filamentous fungal strains of the subsequent HTP genetic design filamentous fungal strain library for the desired phenotype; e) repeating steps c)-d) one or more times, in a linear or non-linear fashion, until an filamentous fungal strain has acquired the desired phenotype, wherein each subsequent iteration creates a new HTP genetic design filamentous fungal strain library comprising individual Filamentous fungal strains harboring unique genetic variations that are a combination of genetic variation selected from amongst at least two individual filamentous fungal strains of a preceding HTP genetic design filamentous fungal strain library.

In some embodiments, the present disclosure teaches that the initial HTP genetic design filamentous fungi strain library is at least one selected from the group consisting of a promoter swap microbial strain library, SNP swap microbial strain library, start/stop codon microbial strain library, optimized sequence microbial strain library, a terminator swap microbial strain library, or any combination thereof.

In some embodiments, the present disclosure teaches methods of making a subsequent plurality of filamentous fungi strains that each comprise a unique combination of genetic variations, wherein each of the combined genetic variations is derived from the initial HTP genetic design filamentous fungi strain library or the HTP genetic design filamentous fungi strain library of the preceding step.

In some embodiments, the combination of genetic variations in the subsequent plurality of filamentous fungi strains will comprise a subset of all the possible combinations of the genetic variations in the initial HTP genetic design filamentous fungi strain library or the HTP genetic design filamentous fungi strain library of the preceding step.

In some embodiments, the present disclosure teaches that the subsequent HTP genetic design filamentous fungi strain library is a full combinatorial strain library derived from the genetic variations in the initial HTP genetic design filamentous fungi strain library or the HTP genetic design filamentous fungi strain library of the preceding step.

For example, if the prior HTP genetic design filamentous fungi strain library only had genetic variations A, B, C, and D, then a partial combinatorial of said variations could include a subsequent HTP genetic design filamentous fungi strain library comprising three strains with each comprising either the AB, AC, or AD unique combinations of genetic variations (order in which the mutations are represented is unimportant). A full combinatorial filamentous fungi strain library derived from the genetic variations of the HTP genetic design library of the preceding step would include six microbes, each comprising either AB, AC, AD, BC, BD, or CD unique combinations of genetic variations.

In some embodiments, the methods of the present disclosure teach perturbing the genome of filamentous fungi utilizing at least one method selected from the group consisting of: random mutagenesis, targeted sequence insertions, targeted sequence deletions, targeted sequence replacements, or any combination thereof.

In some embodiments of the presently disclosed methods, the initial plurality of filamentous fungi unique genetic variations derived from an industrial production filamentous fungi strain.

In some embodiments of the presently disclosed methods, the initial plurality of filamentous fungi comprise industrial production filamentous fungi strains denoted $S_1Gen_1$ and any number of subsequent microbial generations derived therefrom denoted $S_nGen_n$.

In some embodiments, the present disclosure teaches a method for generating a SNP swap filamentous fungi strain library, comprising the steps of: a) providing a reference filamentous fungi strain and a second filamentous fungi strain, wherein the second filamentous fungi strain comprises a plurality of identified genetic variations selected from single nucleotide polymorphisms, DNA insertions, and DNA deletions, which are not present in the reference strain; b) perturbing the genome of either the reference strain, or the second strain, to thereby create an initial SNP swap filamentous fungi strain library comprising a plurality of individual filamentous fungi strains with unique genetic variations found within each strain of said plurality of individual strains, wherein each of said unique genetic variations corresponds to a single genetic variation selected from the plurality of identified genetic variations between the reference strain and the second strain.

In some embodiments of a SNP swap library, the genome of the reference filamentous fungi strain is perturbed to add one or more of the identified single nucleotide polymorphisms, DNA insertions, or DNA deletions, which are found in the second filamentous fungi strain.

In some embodiments of a SNP swap library, the genome of the second filamentous fungi strain is perturbed to remove one or more of the identified single nucleotide polymorphisms, DNA insertions, or DNA deletions, which are not found in the reference filamentous fungi strain.

In some embodiments, the genetic variations of the SNP swap library will comprise a subset of all the genetic variations identified between the reference filamentous fungi strain and the second filamentous fungi strain.

In some embodiments, the genetic variations of the SNP swap library will comprise all of the identified genetic variations identified between the reference filamentous fungi strain and the second filamentous fungi strain.

In some embodiments, the present disclosure teaches a method for rehabilitating and improving the phenotypic performance of an industrial filamentous fungi strain, comprising the steps of: a) providing a parental lineage filamentous fungi strain and an industrial filamentous fungi strain derived therefrom, wherein the industrial strain comprises a plurality of identified genetic variations selected from single nucleotide polymorphisms, DNA insertions, and DNA deletions, not present in the parental lineage strain; b) perturbing the genome of either the parental lineage strain, or the industrial strain, to thereby create an initial SNP swap filamentous fungi strain library comprising a plurality of individual strains with unique genetic variations found within each strain of said plurality of individual strains, wherein each of said unique genetic variations corresponds to a single genetic variation selected from the plurality of identified genetic variations between the parental lineage strain and the industrial strain; c) screening and selecting individual strains of the initial SNP swap filamentous fungi strain library for phenotype performance improvements over a reference filamentous fungi strain, thereby identifying unique genetic variations that confer said filamentous fungi strains with phenotype performance improvements; d) providing a subsequent plurality of filamentous fungi strains that each comprise a unique combination of genetic variation, said genetic variation selected from the genetic variation present in at least two individual strains screened in the preceding step, to thereby create a subsequent SNP swap filamentous fungi strain library; e) screening and selecting individual strains of the subsequent SNP swap filamentous fungi strain library for phenotype performance improvements over the reference strain, thereby identifying unique combinations of genetic variation that confer said filamentous fungi strains with additional phenotype performance improvements; and f) repeating steps d)-e) one or more times, in a linear or non-linear fashion, until a strain exhibits a desired level of improved phenotype performance compared to the phenotype performance of the industrial filamentous fungi strain, wherein each subsequent iteration creates a new SNP swap filamentous fungi strain library comprising individual microbial strains harboring unique genetic variations that are a combination of genetic variation selected from amongst at least two individual microbial strains of a preceding SNP swap filamentous fungi strain library.

In some embodiments, the present disclosure teaches methods for rehabilitating and improving the phenotypic performance of an industrial filamentous fungi strain, wherein the genome of the parental lineage filamentous fungi strain is perturbed to add one or more of the identified single nucleotide polymorphisms, DNA insertions, or DNA deletions, which are found in the industrial filamentous fungi strain.

In some embodiments, the present disclosure teaches methods for rehabilitating and improving the phenotypic performance of an industrial filamentous fungi strain, wherein the genome of the industrial filamentous fungi strain is perturbed to remove one or more of the identified single nucleotide polymorphisms, DNA insertions, or DNA deletions, which are not found in the parental lineage filamentous fungi strain.

In some embodiments, the present disclosure teaches a method for generating a promoter swap filamentous fungi strain library, said method comprising the steps of: a) providing a plurality of target genes endogenous to a base filamentous fungi strain, and a promoter ladder, wherein said promoter ladder comprises a plurality of promoters exhibiting different expression profiles in the base filamentous fungi strain; b) engineering the genome of the base filamentous fungi strain, to thereby create an initial promoter swap filamentous fungi strain library comprising a plurality of individual filamentous fungi strains with unique genetic variations found within each strain of said plurality of individual strains, wherein each of said unique genetic variations comprises one of the promoters from the promoter ladder operably linked to one of the target genes endogenous to the base filamentous fungi strain.

In some embodiments, the present disclosure teaches a promoter swap method of genomic engineering to evolve an filamentous fungi strain to acquire a desired phenotype, said method comprising the steps of: a) providing a plurality of target genes endogenous to a base filamentous fungi strain, and a promoter ladder, wherein said promoter ladder comprises a plurality of promoters exhibiting different expression profiles in the base filamentous fungi strain; b) engineering the genome of the base filamentous fungi strain, to thereby create an initial promoter swap filamentous fungi strain library comprising a plurality of individual filamentous fungi strains with unique genetic variations found within each strain of said plurality of individual strains, wherein each of said unique genetic variations comprises one of the promoters from the promoter ladder operably linked to one of the target genes endogenous to the base filamentous fungi strain; c) screening and selecting individual strains of the initial promoter swap filamentous fungi strain library for the desired phenotype; d) providing a subsequent plurality of filamentous fungi strains that each comprise a unique combination of genetic variation, said genetic variation selected from the genetic variation present in at least two individual strains screened in the preceding step, to thereby create a subsequent promoter swap filamentous fungi strain library; e) screening and selecting individual strains of the subsequent promoter swap filamentous fungi strain library for the desired phenotype; f) repeating steps d)-e) one or more times, in a linear or non-linear fashion, until a microbe has acquired the desired phenotype, wherein each subsequent iteration creates a new promoter swap filamentous fungi strain library comprising individual strains harboring unique genetic variations that are a combination of genetic variation selected from amongst at least two individual strains of a preceding promoter swap filamentous fungi strain library.

In some embodiments, the present disclosure teaches a method for generating a terminator swap filamentous fungi strain library, said method comprising the steps of: a) providing a plurality of target genes endogenous to a base filamentous fungi strain, and a terminator ladder, wherein said terminator ladder comprises a plurality of terminators exhibiting different expression profiles in the base filamentous fungi strain; b) engineering the genome of the base filamentous fungi strain, to thereby create an initial terminator swap filamentous fungi strain library comprising a plurality of individual strains with unique genetic variations found within each strain of said plurality of individual strains, wherein each of said unique genetic variations comprises one of the target genes endogenous to the base filamentous fungi strain operably linked to one or more of the terminators from the terminator ladder.

In some embodiments, the present disclosure teaches a terminator swap method of genomic engineering to evolve an filamentous fungi strain to acquire a desired phenotype, said method comprising the steps of; a) providing a plurality of target genes endogenous to a base filamentous fungi strain, and a terminator ladder, wherein said terminator ladder comprises a plurality of terminators exhibiting different expression profiles in the base filamentous fungi strain; b) engineering the genome of the base filamentous fungi strain, to thereby create an initial terminator swap filamentous fungi strain library comprising a plurality of individual filamentous fungi strains with unique genetic variations found within each strain of said plurality of individual strains, wherein each of said unique genetic variations comprises one of the target genes endogenous to the base filamentous fungi strain operably linked to one or more of the terminators from the terminator ladder; c) screening and selecting individual microbial strains of the initial terminator swap filamentous fungi strain library for the desired phenotype; d) providing a subsequent plurality of filamentous fungi strains that each comprise a unique combination of genetic variation, said genetic variation selected from the genetic variation present in at least two individual strains screened in the preceding step, to thereby create a subsequent terminator swap filamentous fungi strain library; e) screening and selecting individual strains of the subsequent terminator swap filamentous fungi strain library for the desired phenotype; f) repeating steps d)-e) one or more times, in a linear or non-linear fashion, until a microbe has acquired the desired phenotype, wherein each subsequent iteration creates a new terminator swap filamentous fungi strain library comprising individual strains harboring unique genetic variations that are a combination of genetic variation selected from amongst at least two individual strains of a preceding terminator swap filamentous fungi strain library.

In some embodiments, the present disclosure teaches iteratively improving the design of candidate filamentous fungi strains by (a) accessing a predictive model populated with a training set comprising (1) inputs representing genetic changes to one or more background filamentous fungi strains and (2) corresponding performance measures; (b) applying test inputs to the predictive model that represent genetic changes, the test inputs corresponding to candidate filamentous fungi strains incorporating those genetic changes; (c) predicting phenotypic performance of the candidate filamentous fungi strains based at least in part upon the predictive model; (d) selecting a first subset of the candidate filamentous fungi strains based at least in part upon their predicted performance; (e) obtaining measured phenotypic performance of the first subset of the candidate filamentous fungi strains; (f) obtaining a selection of a second subset of the candidate filamentous fungi strains based at least in part upon their measured phenotypic performance; (g) adding to the training set of the predictive model (1) inputs corresponding to the selected second subset of candidate filamentous fungi strains, along with (2) corresponding measured performance of the selected second subset of candidate filamentous fungi strains; and (h) repeating (b)-(g) until measured phenotypic performance of at least one candidate filamentous fungi strain satisfies a performance metric. In some cases, during a first application of test inputs to the predictive model, the genetic changes represented by the test inputs comprise genetic changes to the one or more background filamentous fungi strains; and during subsequent applications of test inputs, the genetic changes represented by the test inputs comprise genetic changes to candidate filamentous fungi strains within a previously selected second subset of candidate filamentous fungi strains.

In some embodiments, selection of the first subset may be based on epistatic effects. This may be achieved by: during a first selection of the first subset: determining degrees of dissimilarity between performance measures of the one or more background filamentous fungi strains in response to application of a plurality of respective inputs representing genetic changes to the one or more background filamentous fungi strains; and selecting for inclusion in the first subset at least two candidate filamentous fungi strains based at least in part upon the degrees of dissimilarity in the performance measures of the one or more background filamentous fungi strains in response to application of genetic changes incorporated into the at least two candidate filamentous fungi strains.

In some embodiments, the present disclosure teaches applying epistatic effects in the iterative improvement of candidate filamentous fungi strains, the method comprising: obtaining data representing measured performance in response to corresponding genetic changes made to at least one filamentous fungi background strain; obtaining a selection of at least two genetic changes based at least in part upon a degree of dissimilarity between the corresponding responsive performance measures of the at least two genetic changes, wherein the degree of dissimilarity relates to the degree to which the at least two genetic changes affect their corresponding responsive performance measures through different biological pathways; and designing genetic changes to an filamentous fungi background strain that include the selected genetic changes. In some cases, the filamentous fungi background strain for which the at least two selected genetic changes are designed is the same as the at least one filamentous fungi background strain for which data representing measured responsive performance was obtained.

In some embodiments, the present disclosure teaches HTP filamentous fungi strain improvement methods utilizing only a single type of genetic library. For example, in some embodiments, the present disclosure teaches HTP filamentous fungi strain improvement methods utilizing only SNP swap libraries. In other embodiments, the present disclosure teaches HTP filamentous fungi strain improvement methods utilizing only PRO swap libraries. In some embodiments, the present disclosure teaches HTP filamentous fungi strain improvement methods utilizing only STOP swap libraries. In some embodiments, the present disclosure teaches HTP filamentous fungi strain improvement methods utilizing only Start/Stop Codon swap libraries.

In other embodiments, the present disclosure teaches HTP filamentous fungi strain improvement methods utilizing two or more types of genetic libraries. For example, in some embodiments, the present disclosure teaches HTP filamentous fungi strain improvement methods combining SNP swap and PRO swap libraries. In some embodiments, the present disclosure teaches HTP filamentous fungi strain improvement methods combining SNP swap and STOP swap libraries. In some embodiments, the present disclosure teaches HTP filamentous fungi strain improvement methods combining PRO swap and STOP swap libraries.

In other embodiments, the present disclosure teaches HTP filamentous fungi strain improvement methods utilizing multiple types of genetic libraries. In some embodiments, the genetic libraries are combined to produce combination mutations (e.g., promoter/terminator combination ladders applied to one or more genes). In yet other embodiments, the HTP filamentous fungi strain improvement methods of the present disclosure can be combined with one or more traditional strain improvement methods.

In some embodiments, the HTP filamentous fungi strain improvement methods of the present disclosure result in an improved filamentous fungi host cell. That is, the present disclosure teaches methods of improving one or more filamentous fungi host cell properties. In some embodiments the improved filamentous fungi host cell property is selected from the group consisting of: volumetric productivity, specific productivity, yield or titre, of a product of interest produced by the filamentous fungi host cell. In some embodiments, the improved filamentous fungi host cell property is volumetric productivity. In some embodiments, the improved filamentous fungi host cell property is specific productivity. In some embodiments, the improved filamentous fungi host cell property is yield.

In some embodiments, the HTP filamentous fungi strain improvement methods of the present disclosure result in an filamentous fungi host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one filamentous fungi host cell property over a control filamentous fungi host cell that is not subjected to the HTP strain improvements methods (e.g, an X % improvement in yield or productivity of a biomolecule of interest, incorporating any ranges and subranges therebetween). In some embodiments, the HTP filamentous fungi strain improvement methods of the present disclosure are selected from the group consisting of SNP swap, PRO swap, STOP swap, and combinations thereof.

Thus, in some embodiments, the SNP swap methods of the present disclosure result in an filamentous fungi host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one filamentous fungi host cell property over a control filamentous fungi host cell that is not subjected to the SNP swap methods (e.g., an X % improvement in yield or productivity of a biomolecule of interest, incorporating any ranges and subranges therebetween).

Thus, in some embodiments, the PRO swap methods of the present disclosure result in an filamentous fungi host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one filamentous fungi host cell property over a control filamentous fungi host cell that is not subjected to the PRO swap methods (e.g., an X % improvement in yield or productivity of a biomolecule of interest, incorporating any ranges and subranges therebetween).

Thus, in some embodiments, the Terminator (STOP) swap methods of the present disclosure result in an filamentous fungi host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one filamentous fungi host cell property over a control filamentous fungi host cell that is not subjected to the Terminator (STOP) swap methods (e.g, an X % improvement in yield or productivity of a biomolecule of interest, incorporating any ranges and subranges therebetween).

In one aspect, provided herein is a method for producing a filamentous fungal strain, the method comprising: a.) providing a plurality of protoplasts, wherein the protoplasts were prepared from a culture of filamentous fungal cells; b.) transforming the plurality of protoplasts with a first construct and a second construct, wherein the first construct comprises a first polynucleotide flanked on both sides by nucleotides homologous to a first locus in the genome of the protoplast and the second construct comprises a second polynucleotide flanked on both sides by nucleotides homologous to a second locus in the genome of the protoplast, wherein transformation results in integration of the first construct into the first locus and the second construct into the second locus by homologous recombination, wherein at least the second locus is a first selectable marker gene in the protoplast genome, and wherein the first polynucleotide comprises mutation and/or a genetic control element; c.) purifying homokaryotic transformants by performing selection and counter-selection; and d.) growing the purified transformants in media conducive to regeneration of the filamentous fungal cells. In some cases, the first construct is split into construct A and construct B, wherein construct A comprises a first portion of the first polynucleotide and nucleotides homologous to the first locus 5' to the first portion of the first polynucleotide, and wherein construct B comprises a second portion of the first polynucleotide and nucleotides homologous to the first locus 3' to the second portion of the first polynucleotide, wherein the first portion and the second portion of the first polynucleotide comprises overlapping complementary sequence. In some cases, the second construct is split into construct A and construct B, wherein construct A comprises a first portion of the second polynucleotide and nucleotides homologous to the first locus 5' to the first portion of the second polynucleotide, and wherein construct B comprises a second portion of the second polynucleotide and nucleotides homologous to the first locus 3' to the second portion of the second polynucleotide, wherein the first portion and the second portion of the second polynucleotide comprises overlapping complementary sequence. In some cases, each protoplast from the plurality of protoplasts is transformed with a single first construct from a plurality of first constructs and a single second construct from a plurality of second constructs, wherein the first polynucleotide in each first construct from the plurality of first constructs comprises a different mutation and/or genetic control element; and wherein the second polynucleotide in each second construct from the plurality of second constructs is identical. In some cases, the method further comprises repeating steps a-d to generate a library of filamentous fungal cells, wherein each filamentous fungal cell in the library comprises a first polynucleotide with a different mutation and/or genetic control element. In some cases, the first polynucleotide encodes a target filamentous fungal gene or a heterologous gene. In some cases, the mutation is a single nucleotide polymorphism. In some cases, the genetic control is a promoter sequence and/or a terminator sequence. In some cases, the genetic control element is a promoter sequence, wherein the promoter sequence is selected from the promoter sequences listed in Table 1. In some cases, the plurality of protoplasts are distributed in wells of a microtiter plate. In some cases, steps a-d are performed in wells of a microtiter plate. In some cases, the microtiter plate is a 96 well, 384 well or 1536 well microtiter plate. In some cases, the filamentous fungal cells are selected from *Achlya, Acrenonium, Aspergillus, Aureobasidium, Bjerkandera, Ceriporiopsis. Cephalosporium, Chrysosporium, Cochliohohns, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penticillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal cells are *Aspergillus niger*. In some cases, the filamentous fungal cells possess a non-mycelium forming phenotype. In some cases, wherein the fungal cell possesses a non-functional non-homologous end joining (NHEJ) pathway. In some cases, the NHEJ pathway is made non-functional by exposing the cell to an antibody, a chemical inhibitor, a protein inhibitor, a physical inhibitor, a peptide inhibitor, or an anti-sense or RNAi molecule directed against a component of the NHEJ pathway. In some cases, the chemical inhibitor is W-7. In some cases, the first locus is for the target filamentous fungal gene. In some cases, the first locus is for a second selectable marker gene in the protoplast genome. In some cases, the second selectable marker gene is selected from an auxotrophic marker gene, a colorimetric marker gene or a directional marker gene. In some cases, the first selectable marker gene is selected from an auxotrophic marker gene, a colorimetric marker gene or a directional marker gene. In some cases, the second polynucleotide is selected from an auxotrophic marker gene, a directional marker gene or an antibiotic resistance gene. In some cases, the colorimetric marker gene is an aygA gene. In some cases, the auxotrophic marker gene is selected from an argB gene, a trpC gene, a pyrG gene, or a met3 gene. In some cases, the directional marker gene is selected from an acetamidase (amdS) gene, a nitrate reductase gene (niaD), or a sulphate permease (Sut B) gene. In some cases, the antibiotic resistance gene is a ble gene, wherein the ble gene confers resistance to pheomycin. In some cases, the first selectable marker gene is an aygA gene and the second polynucleotide is a pyrG gene. In some cases, the first selectable marker gene is a met3 gene, the second selectable marker gene is an aygA gene and the second polynucleotide is a pyrG gene. In some cases, the plurality of protoplasts are prepared by removing cell walls from the filamentous fungal cells in the culture of filamentous fungal cells, isolating the plurality of protoplasts; and resuspending the isolated plurality of protoplasts in a mixture comprising dimethyl sulfoxide (DMSO), wherein the final concentration of DMSO is 7% v/v or less. In some cases, the mixture is stored at at least −20° C. or −80° C. prior to performing steps a-d. In some cases, the culture is at least 1 liter in volume. In some cases, the culture is grown for at least 12 hours prior to preparation of the protoplasts. In some cases, the fungal culture is grown under conditions whereby at least 70% of the protoplasts are smaller and contain fewer nuclei. In some cases, removing the cell walls is performed by enzymatic digestion. In some cases, the enzymatic digestion is performed with mixture of enzymes comprising a beta-glucanase and a polygalacturonase. In some cases, the method further comprises adding 40% v/v polyethylene glycol (PEG) to the mixture comprising DMSO prior to storing the protoplasts. In some cases, the PEG is added to a final concentration of 8% v/v or less. In some cases, steps a-d are automated.

In another aspect, provided herein is a method for preparing filamentous fungal cells for storage, the method comprising: preparing protoplasts from a fungal culture comprising filamentous fungal cells, wherein the preparing the protoplasts comprises removing cell walls from the filamentous fungal cells in the fungal culture; isolating the protoplasts; and resuspending the isolated protoplasts in a mixture comprising dimethyl sulfoxide (DMSO) at a final concentration of 7% v/v or less. In some cases, the mixture is stored at at least −20° C. or −80° C. In some cases, the fungal culture is at least 1 liter in volume. In some cases, the fungal culture is grown for at least 12 hours prior to preparation of the protoplasts. In some cases, the fungal culture is grown under conditions whereby at least 70% of the protoplasts are smaller and have fewer nuclei. In some cases, removing the cell walls is performed by enzymatic digestion. In some cases, the enzymatic digestion is performed with mixture of enzymes comprising a beta-glucanase and a polygalacturonase. In some cases, the method further comprises adding 40% v/v polyethylene glycol (PEG) to the mixture comprising DMSO prior to storing the protoplasts. In some cases, the PEG is added to a final concentration of 8% v/v or less. In some cases, the method further comprises distributing the protoplasts into microtiter plates prior to storing the protoplasts. In some cases, the filamentous fungal cells in the fungal culture possess a non-mycelium forming phenotype. In some cases, the filamentous fungal cells in the fungal culture are selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus. Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scylalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal cells in the fungal culture are *Aspergillus niger* or teleomorphs or anamorphs thereof.

In yet another aspect, provided herein is a system for generating a fungal production strain, the system comprising: one or more processors; and one or more memories operatively coupled to at least one of the one or more processors and having instructions stored thereon that, when executed by at least one of the one or more processors, cause the system to: a.) transform a plurality of protoplasts derived from culture of filamentous fungal cells with a first construct and a second construct, wherein the first construct comprises a first polynucleotide flanked on both sides by nucleotides homologous to a first locus in the genome of the protoplast and the second construct comprises a second polynucleotide flanked on both sides by nucleotides homologous to a second locus in the genome of the protoplast, wherein transformation results in integration of the first construct into the first locus and the second construct into the second locus by homologous recombination, wherein at least the second locus is a first selectable marker gene in the protoplast genome, and wherein the first polynucleotide comprises a mutation and/or a genetic control element; b.) purifying homokaryotic transformants by performing selection and counter-selection; and c.) growing the purified transformants in media conducive to regeneration of the filamentous fungal cells. In some cases, the first construct is split into construct A and construct B, wherein construct A comprises a first portion of the first polynucleotide and nucleotides homologous to the first locus 5' to the first portion of the first polynucleotide, and wherein construct B comprises a second portion of the first polynucleotide and nucleotides homologous to the first locus 3' to the second portion of the first polynucleotide, wherein the first portion and the second portion of the first polynucleotide comprises overlapping complementary sequence. In some cases, the second construct is split into construct A and construct B, wherein construct A comprises a first portion of the second polynucleotide and nucleotides homologous to the first locus 5' to the first portion of the second polynucleotide, and wherein construct B comprises a second portion of the second polynucleotide and nucleotides homologous to the first locus 3' to the second portion of the second polynucleotide, wherein the first portion and the second portion of the second polynucleotide comprises overlapping complementary sequence. In some cases, each protoplast from the plurality of protoplasts is transformed with a single first construct from a plurality of first constructs and a single second construct from a plurality of second constructs, wherein the first polynucleotide in each first construct from the plurality of first constructs comprises a different mutation and/or genetic control element; and wherein the second polynucleotide in each second construct from the plurality of second constructs is identical. In some cases, the system further comprises repeating steps a-c to generate a library of filamentous fungal cells, wherein each filamentous fungal cell in the library comprises a first polynucleotide with a different mutation and/or genetic control element. In some cases, the mutation is a single nucleotide polymorphism. In some cases, the genetic control is a promoter sequence and/or a terminator sequence. In some cases, the genetic control element is a promoter sequence, wherein the promoter sequence is selected from the promoter sequences listed in Table 1. In some cases, steps a-c are performed in wells of a microtiter plate. In some cases, the microtiter plate is a 96 well, 384 well or 1536 well microtiter plate. In some cases, the filamentous fungal cells are selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal cells are *Aspergillus niger*. In some cases, the filamentous fungal cells possess a non-mycelium forming phenotype. In some cases, the fungal cell possesses a non-functional non-homologous end joining pathway. In some cases, the NHEJ pathway is made non-functional by exposing the cell to an antibody, a chemical inhibitor, a protein inhibitor, a physical inhibitor, a peptide inhibitor, or an anti-sense or RNAi molecule directed against a component of the NHEJ pathway. In some cases, the chemical inhibitor is W-7. In some cases, the first locus is for the target filamentous fungal gene. In some cases, the first locus is for a second selectable marker gene in the protoplast genome. In some cases, the second selectable marker gene is selected from an auxotrophic marker gene, a colorimetric marker gene or a directional marker gene. In some cases, the first selectable marker gene is selected from an auxotrophic marker gene, a colorimetric marker gene or a directional marker gene. In some cases, the second polynucleotide is selected from an auxotrophic marker gene, a directional marker gene or an antibiotic resistance gene. In some cases, the colorimetric marker gene is an aygA gene. In some cases, the auxotrophic marker gene is selected from an argB gene, a trpC gene, a pyrG gene, or a met3 gene. In some cases, the directional marker gene is selected from an acetamidase (amdS) gene, a nitrate reductase gene (nlaD), or a sulphate permease (Sut B) gene. In some cases, the antibiotic resistance gene is a ble gene, wherein the ble gene confers resistance to pheomycin. In some cases, the first selectable marker gene is an aygA gene and the second polynucleotide is a pyrG gene. In some cases, the first selectable marker gene is a met3 gene, the second selectable marker gene is an aygA gene and the second polynucleotide is a pyrG gene. In some cases, the plurality of protoplasts are prepared by removing cell walls from the filamentous fungal cells in the culture of filamentous fungal cells; isolating the plurality of protoplasts; and resuspending the isolated plurality of protoplasts in a mixture comprising dimethyl sulfoxide (DMSO) at a final concentration of 7% v/v or less. In some cases, the mixture is stored at at least −20° C. or −80° C. prior to performing steps a-c. In some cases, the culture is at least 1 liter in volume. In some cases, the culture is grown for at least 12 hours prior to preparation of the protoplasts. In some cases, the fungal culture is grown under conditions whereby at least 70% of the protoplasts are smaller and have fewer nuclei. In some cases, removing the cell walls is performed by enzymatic digestion. In some cases, the enzymatic digestion is performed with mixture of enzymes comprising a beta-glucanase and a polygalacturonase. In some cases, the system further comprises adding 40% v/v polyethylene glycol (PEG) to the mixture comprising DMSO prior to storing the protoplasts. In some cases, the PEG is added to a final concentration of 8% v/v or less.

In yet another aspect, provided herein is a method for isolating clonal populations derived from single fungal spores, the method comprising: (a) providing a plurality of fungal spores in a liquid suspension, wherein the plurality of fungal spores were derived from a fungal strain; (b) dispensing a discrete volume of the liquid suspension to an individual reaction area in a substrate comprising a plurality of reaction areas, wherein each reaction area in the plurality of reaction areas comprises growth media, wherein the dispensing results in a probability that at least 75% of the individual reaction areas contain no more than a single viable fungal spore from the plurality of fungal spores; (c) culturing the dispensed single viable fungal spores in the reaction areas comprising growth media; and (d) selecting clonal populations growing in the reaction areas, thereby isolating clonal populations derived from single fungal spores. In some cases, the method further comprises screening the discrete volumes for the presence or absence of a single fungal spore in the discrete volumes, wherein only the discrete volumes containing a single fungal spore are selected for step (b). In some cases, the dispensing results in a probability that at least 80% of the individual reaction areas contain no more than a single viable fungal spore from the plurality of fungal spores. In some cases, the dispensing results in a probability that at least 90% of the individual reaction areas contain no more than a single viable fungal spore from the plurality of fungal spores. In some cases, the dispensing results in a probability that at least 95% of the individual reaction areas contain no more than a single viable fungal spore from the plurality of fungal spores. In some cases, the dispensing results in a probability that at least 99/o of the individual reaction areas contain no more than a single viable fungal spore from the plurality of fungal spores. In some cases, the dispensing results in a probability that substantially all of the individual reaction areas contain no more than a single viable fungal spore from the plurality of fungal spores. In some cases, the screening the discrete volumes entails optically distinguishing the presence or absence of a single fungal spore in the discrete volumes. In some cases, the screening is performed using a microfluidic device capable of optically distinguishing the presence or absence of a single fungal spore in the discrete volumes. In some cases, the reaction areas are present in a microtiter plate. In some cases, the microtiter plate contains 96 wells, 384 wells or 1536 wells. In some cases, the fungal strain is a filamentous fungal strain. In some cases, the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal strain is *Aspergillus niger* or teleomorphs or anamorphs thereof. In some cases, the filamentous fungal strain possess a non-mycelium, pellet morphology. In some cases, the filamentous fungal strain expresses a mutant form of an ortholog of the *S. cerevisiae* SLN1 gene. In some cases, the filamentous fungal strain is *A. niger* and a nucleic sequence of the mutant form of the *A. niger* ortholog of the *S. cerevisiae* SLN1 gene is SEQ ID NO: 13. In some cases, the mutant form of the orthologue of the *S. cerevisiae* SLN1 gene (e.g., the *A. niger* orthologue) is operably linked to a promoter sequence selected from SEQ ID NO: 1 or 2. In some cases, the fungal strain possesses a genetic perturbation. In some cases, the genetic perturbation is selected from single nucleotide polymorphisms, DNA insertions, DNA deletions or any combination thereof. In some cases, the genetic perturbation is introduced into protoplasts derived from the fungal strain via transforming the protoplasts with a ribonucleoprotein complex (RNP-complex). In some cases, the RNP-complex comprises an RNA guided endonuclease complexed with a guide RNA (gRNA). In some cases, the RNA guided endonuclease is a Class 2 CRISPR-Cas System RNA guided endonuclease. In some cases, the Class 2 CRISPR-Cas system RNA guided endonuclease is a Type II, Type V or Type VI RNA guided endonuclease. In some cases, the Class 2 CRISPR-Cas system RNA guided endonuclease is selected from Cas9, Cas12a, Cas12b, Cas12c, Cas12d, Cas12e, Cas13a, Cas13b, Cas13c or homologs, orthologs, mutants, variants or modified versions thereof. In some cases, the Class 2 CRISPR-Cas system RNA guided endonuclease is Cas9 or homologs, orthologs or paralogs thereof. In some cases, the gRNA is a CRISPR RNA (crRNA) alone or annealed to a transactivating CRISPR RNA (tracrRNA). In some cases, the gRNA is a single guide RNA (sgRNA)

comprising a tracrRNA and a crRNA. In some cases, the crRNA comprises a guide sequence complementary to a target gene within the genome of the fungal strain, wherein introduction of the RNP-complex into the protoplasts facilitates introduction of the genetic perturbation into the target gene. In some cases, the genetic perturbation of the target gene is facilitated by cleavage of the target gene by the RNP-complex to generate DNA ends in the target gene followed by non-homologous end joining of the DNA ends in the target gene by the non-homologous end joining (NHEJ) pathway. In some cases, the method further comprises co-transforming a donor DNA comprising a mutated version of the target gene, wherein the mutated version of the target gene is flanked on both sides by nucleotides homologous to the target gene locus. In some cases, the genetic perturbation of the target gene is facilitated by cleavage of the target gene by the RNP-complex to generate DNA ends in the target gene followed by replacement of the target gene with the donor DNA via homologous recombination. In some cases, step (b) further comprises co-transforming a vector comprising a selectable marker. In some cases, the selectable marker is used during step (d) to select clonal populations derived from transformation competent fungal strains. In some cases, the genetic perturbation is introduced into protoplasts derived from the fungal strain by transforming the plurality of protoplasts with a first construct and a second construct, wherein the first construct comprises a first polynucleotide flanked on both sides by nucleotides homologous to a first locus in the genome of the protoplast and the second construct comprises a second polynucleotide flanked on both sides by nucleotides homologous to a second locus in the genome of the protoplast, wherein the transformation results in integration of the first construct into the first locus and the second construct into the second locus by homologous recombination, wherein at least the second locus is a first selectable marker gene in the protoplast genome, and wherein the first polynucleotide comprises the genetic perturbation. In some cases, the selectable marker gene is used during step (d) to facilitate selection of clonal populations derived from fungal strains comprising the genetic perturbation. In some cases, the fungal strain possesses a non-functional non-homologous end joining (NHEJ) pathway. In some cases, the NHEJ pathway is made non-functional by exposing the fungal strain to an antibody, a chemical inhibitor, a protein inhibitor, a physical inhibitor, a peptide inhibitor, or an anti-sense or RNAi molecule directed against a component of the NHEJ pathway. In some cases, the chemical inhibitor is W-7.

In another aspect, provided herein is a method for isolating clonal populations derived from single fungal spores, the method comprising. (a) providing a plurality of fungal spores in a liquid suspension, wherein the plurality of fungal spores were derived from a fungal strain; (b) diluting the liquid suspension, wherein the dilution is a limiting dilution; (c) dispensing a discrete volume of the dilution to an individual reaction area in a substrate comprising a plurality of reaction areas, wherein each reaction area in the plurality of reaction areas comprises growth media, wherein the limiting dilution results in a probability that the discrete volume of the dilution dispensed to each reaction area contains either one or no viable spore follows a Poisson Distribution, whereby greater than 90% b of the reaction areas in the plurality of reaction areas contain no viable spores and greater than 90% of reaction areas that contain one or more viable spores contain only a single viable spore; (d) culturing the dispensed single viable fungal spores in the reaction areas comprising growth media; and (e) selecting clonal populations growing in the reaction areas, thereby isolating clonal populations derived from single fungal spores. In some cases, the reaction areas are present in a microtiter plate. In some cases, the microtiter plate contains 96 wells, 384 wells or 1536 wells. In some cases, the fungal strain is a filamentous fungal strain. In some cases, the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal strain is *Aspergillus niger* or teleomorphs or anamorphs thereof. In some cases, the filamentous fungal strain possess a non-mycelium, pellet morphology. In some cases, the filamentous fungal strain expresses a mutant form of an ortholog of the *S. cerevisiae* SLN1 gene. In some cases, the filamentous fungal strain is *A. niger* and a nucleic sequence of the mutant form of the *A. niger* orthologue of the *S. cerevisiae* SLN1 gene is SEQ ID NO: 13. In some cases, the mutant form of the orthologue of the *S. cerevisiae* SLN1 gene (e.g., the *A. niger* orthologue) is operably linked to a promoter sequence selected from SEQ ID NO: 1 or 2. In some cases, the fungal strain possesses a genetic perturbation. In some cases, the genetic perturbation is selected from single nucleotide polymorphisms, DNA insertions, DNA deletions or any combination thereof. In some cases, the genetic perturbation is introduced into protoplasts derived from the fungal strain via transforming the protoplasts with a ribonucleoprotein complex (RNP-complex). In some cases, the RNP-complex comprises an RNA guided endonuclease complexed with a guide RNA (gRNA). In some cases, the RNA guided endonuclease is a Class 2 CRISPR-Cas System RNA guided endonuclease. In some cases, the Class 2 CRISPR-Cas system RNA guided endonuclease is a Type II, Type V or Type VI RNA guided endonuclease. In some cases, the Class 2 CRISPR-Cas system RNA guided endonuclease is selected from Cas9, Cas12a, Cas12b, Cas12c, Cas12d, Cas12e, Cas13a, Cas13b, Cas13c or homologs, orthologs, mutants, variants or modified versions thereof. In some cases, the Class 2 CRISPR-Cas system RNA guided endonuclease is Cas9 or homologs, orthologs or paralogs thereof. In some cases, the gRNA is a CRISPR RNA (crRNA) alone or annealed to a transactivating CRISPR RNA (tracrRNA). In some cases, the gRNA is a single guide RNA (sgRNA) comprising a tracrRNA and a crRNA. In some cases, the crRNA comprises a guide sequence complementary to a target gene within the genome of the fungal strain, wherein introduction of the RNP-complex into the protoplasts facilitates introduction of the genetic perturbation into the target gene. In some cases, the genetic perturbation of the target gene is facilitated by cleavage of the target gene by the RNP-complex to generate DNA ends in the target gene followed by non-homologous end joining of the DNA ends in the target gene by the non-homologous end joining (NHEJ) pathway. In some cases, the method further comprises co-transforming a donor DNA comprising a mutated version of the target gene, wherein the mutated version of the target gene is flanked on both sides by nucleotides homologous to the target gene locus. In some cases, the genetic perturbation of the target gene is facilitated by cleavage of the target gene by the RNP-complex to generate DNA ends in the target gene followed by replacement of the target gene with the donor DNA via homologous recombination. In some cases, step (b) further comprises co-transforming a vector comprising a selectable marker. In some cases, the selectable marker is used during step (d) to select clonal populations derived from transformation competent fungal strains. In some cases, the genetic perturbation is introduced into protoplasts derived from the fungal strain by transforming the plurality of protoplasts with a first construct and a second construct, wherein the first construct comprises a first polynucleotide flanked on both sides by nucleotides homologous to a first locus in the genome of the protoplast and the second construct comprises a second polynucleotide flanked on both sides by nucleotides homologous to a second locus in the genome of the protoplast, wherein the transformation results in integration of the first construct into the first locus and the second construct into the second locus by homologous recombination, wherein at least the second locus is a first selectable marker gene in the protoplast genome, and wherein the first polynucleotide comprises the genetic perturbation. In some cases, the selectable marker gene is used during step (d) to facilitate selection of clonal populations derived from fungal strains comprising the genetic perturbation. In some cases, the fungal strain possesses a non-functional non-homologous end joining (NHEJ) pathway. In some cases, the NHEJ pathway is made non-functional by exposing the fungal strain to an antibody, a chemical inhibitor, a protein inhibitor, a physical inhibitor, a peptide inhibitor, or an anti-sense or RNAi molecule directed against a component of the NHEJ pathway. In some cases, the chemical inhibitor is W-7.

In one aspect, provided herein is a method for producing a filamentous fungal strain, the method comprising: a.) providing a plurality of protoplasts, wherein the plurality of protoplasts were prepared from a culture of a parent filamentous fungal strain; b.) transforming each protoplast from the plurality of protoplasts with a ribonucleoprotein complex (RNP-complex); and c.) selecting and screening individual filamentous fungal strains derived from the transformed protoplasts for phenotypic performance improvements over the parent filamentous fungal strain, thereby identifying genetic perturbations in the genome of the selected individual filamentous fungal strains that confer phenotypic performance improvements. In some cases, the genetic perturbations are selected from single nucleotide polymorphisms, DNA insertions, DNA deletions or any combination thereof. In some cases, the RNP-complex comprises an RNA guided endonuclease complexed with a guide RNA (gRNA). In some cases, the RNA guided endonuclease is a Class 2 CRISPR-Cas System RNA guided endonuclease. In some cases, the Class 2 CRISPR-Cas system RNA guided endonuclease is a Type II, Type V or Type VI RNA guided endonuclease. In some cases, the Class 2 CRISPR-Cas system RNA guided endonuclease is selected from Cas9, Cas12a, Cas12b, Cas12c, Cas12d, Cas12e, Cas13a, Cas13b, Cas13c or homologs, orthologs, mutants, variants or modified versions thereof. In some cases, the Class 2 CRISPR-Cas system RNA guided endonuclease is Cas9 or homologs, orthologs or paralogs thereof. In some cases, the gRNA is a CRISPR RNA (crRNA) alone or annealed to a transactivating CRISPR RNA (tracrRNA). In some cases, the gRNA is a single guide RNA (sgRNA) comprising a tracrRNA and a crRNA. In some cases, the crRNA comprises a guide sequence that is complementary to a target gene within the genome of the parent filamentous fungal strain, wherein introduction of the RNP-complex perturbs the target gene in the protoplasts. In some cases, the perturbation of the target gene is facilitated by cleavage of the target gene by the RNP-complex to generate DNA ends in the target gene followed by non-homologous end joining of the DNA ends in the target gene by the non-homologous end joining (NHEJ) pathway. In some cases, step (b) further comprises co-transforming a donor DNA comprising a mutated version of the target gene, wherein the mutated version of the target gene is flanked on both sides by nucleotides homologous to the target gene locus. In some cases, the perturbation of the target gene is facilitated by cleavage of the target gene by the RNP-complex to generate DNA ends in the target gene followed by replacement of the target gene with the donor DNA via homologous recombination. In some cases, step (b) further comprises co-transforming a vector comprising a selectable marker. In some cases, the selectable marker is used during step (c) to select transformation competent individual filamentous fungal strains for subsequent screening for phenotypic performance improvements over the parent filamentous fungal strain. In some cases, the parent filamentous fungal strain possesses a non-functional non-homologous end joining (NHEJ) pathway. In some cases, the NHEJ pathway is made non-functional by exposing the cell to an antibody, a chemical inhibitor, a protein inhibitor, a physical inhibitor, a peptide inhibitor, or an anti-sense or RNAi molecule directed against a component of the NHEJ pathway. In some cases, the chemical inhibitor is W-7. In some cases, the phenotypic performance improvement of the filamentous fungal strain comprises at least a 10% increase in a measured phenotypic variable for a product of interest compared to the phenotypic performance of the parent filamentous fungal strain. In some cases, the phenotypic performance improvement of the filamentous fungal strain comprises at least a one-fold increase in a measured phenotypic variable for a product of interest compared to the phenotypic performance of the parent filamentous fungal strain. In some cases, the measured phenotypic variable is selected from the group consisting of: volumetric productivity of the product of interest, specific productivity of the product of interest, yield of the product of interest, titer of the product of interest, and combinations thereof. In some cases, the measured phenotypic variable is increased or more efficient production of the product of interest. In some cases, the product of interest is selected from the group consisting of: a small molecule, enzyme, peptide, amino acid, organic acid, synthetic compound, fuel, alcohol, primary extracellular metabolite, secondary extracellular metabolite, intracellular component molecule, and combinations thereof. In some cases, the parent filamentous fungal strain is selected from *Achlya, Acremonium, Aspergillus, Aureobasidium, Bjerkandera, Ceriporiopsis, Cephalosporium, Chrysosporium. Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal strain is *Aspergillus niger* or teleomorphs or anamorphs thereof. In some cases, the filamentous fungal strain possess a non-mycelium, pellet morphology. In some cases, the filamentous fungal strain expresses a mutant form of an orthologue of the *S. cerevisiae* SLN1 gene. In some cases, the filamentous fungal strain is *A. niger* and a nucleic sequence of the mutant form of the *A. niger* orthologue of the *S. cerevisiae* SLN1 gene is SEQ ID NO: 13. In some cases, the mutant form of the orthologue of the *S. cerevisiae* SLN1 gene (e.g., the *A. niger* orthologue) is operably linked to a promoter sequence selected from SEQ ID NO: 1 or 2. In some cases, the method further comprises generating isolated clonal populations derived from the individual filamentous fungal strains prior to step (c). In some cases, the isolating comprises: (i) inducing the transformed protoplasts to produce a plurality of fungal spores, wherein each fungal spore form the plurality is derived from a single transformed protoplast; (ii) resuspending the plurality of fungal spores derived from a single transformed protoplast in a liquid to generate a liquid suspension; (iii) dispensing a discrete volume of the liquid suspension to an individual reaction area in a substrate comprising a plurality of reaction areas, wherein each reaction area in the plurality of reaction areas comprises growth media, wherein the dispensing results in a probability that at least 75% of the individual reaction areas contain no more than a single viable fungal spore from the plurality of fungal spores; and (iv) culturing the dispensed single viable fungal spores in the reaction areas comprising growth media, thereby generating isolated clonal populations derived from the individual filamentous fungal strains. In some cases, the method further comprises screening the discrete volumes for the presence or absence of a single fungal spore in the discrete volumes, wherein only the discrete volumes containing a single fungal spore are selected for step (iii). In some cases, the screening the discrete volumes entails optically distinguishing the presence or absence of a single fungal spore in the discrete volumes. In some cases, the screening is performed using a microfluidic device capable of optically distinguishing the presence or absence of a single fungal spore in the discrete volumes. In some cases, the dispensing results in a probability that at least 80% of the individual reaction areas contain no more than an single viable fungal spore from the plurality of fungal spores. In some cases, the dispensing results in a probability that at least 90% of the individual reaction areas contain no more than a single viable fungal spore from the plurality of fungal spores. In some cases, the dispensing results in a probability that at least 95% of the individual reaction areas contain no more than a single viable fungal spore from the plurality of fungal spores. In some cases, the dispensing results in a probability that at least 99% of the individual reaction areas contain no more than a single viable fungal spore from the plurality of fungal spores. In some cases, the dispensing results in a probability that substantially all of the individual reaction areas contain no more than a single viable fungal spore from the plurality of fungal spores In some cases, the isolating comprises: (i) inducing the transformed protoplasts to produce a plurality of fungal spores, wherein each fungal spore form the plurality is derived from a single transformed protoplast; (ii) resuspending the plurality of fungal spores derived from a single transformed protoplast in a liquid to generate a liquid suspension; (iii) diluting the liquid suspension, wherein the dilution is a limiting dilution; (iv) dispensing a discrete volume of the dilution to an individual reaction area in a substrate comprising a plurality of reaction areas, wherein each reaction area in the plurality of reaction areas comprises growth media, wherein the limiting dilution results in a probability that the discrete volume of the dilution dispensed to each reaction area contains either one or no viable spore follows a Poisson Distribution, whereby greater than 90% of the reaction areas in the plurality of reaction areas contain no viable spores and greater than 90% of reaction areas that contain one or more viable spores contain only a single viable spore; (v) culturing the dispensed single viable fungal spores in the reaction areas comprising growth media; and (vi) selecting clonal populations growing in the reaction areas, thereby isolating clonal populations derived from single fungal spores. In some cases, the reaction areas are present in a microtiter plate. In some cases, the microtiter plate contains 96 wells, 384 wells or 1536 wells.

BRIEF DESCRIPTION OF THE FIGURES

FIG. 6A-6B depicts the DNA assembly, transformation, and filamentous fungal strain screening steps of one of the embodiments of the present disclosure. FIG. 6A depicts the steps for building DNA fragments, cloning said DNA fragments, transforming said fragments into host filamentous fungal strains, and looping out selection sequences through counter selection. FIG. 6B depicts the steps for high-throughput culturing, screening, and evaluation of selected filamentous fungal host strains. This figure also depicts the optional steps of culturing, screening, and evaluating selected filamentous fungal strains in culture tanks.

FIG. 21 depicts screening of A. niger mutant strain cotransformants utilizing the argB marker by observing growth of A. niger mutant strains on minimal media with and without arginine following automated transformation and screening as described in Example 2. Successful co-transformation resulted in disruption of the argB gene and no growth on minimal media.

FIG. 23A-B depicts the results of *A. niger* transformation and validation according to the methods of the present disclosure. FIG. 23A is a picture of a 96-well media plate of *A. niger* transformants. Transformed cultures comprise a mutation in the aygA, which causes the cells to appear lighter yellow instead of black (transformed wells are circled in white). FIG. 23B depicts the results of next generation sequencing of transformed *A. niger* mutants. The X-axis represents the target DNA's sequence identity with the untransformed parent strain. The Y-axis represents the target DNA's sequence identity with the expected mutation. Data points towards the bottom right of the chart exhibit high similarity with the parent strain, and low similarity with the expected transformed sequences. Data points towards the top left of the chart exhibit high similarity to expected transformed sequences and low identity with parent strain. Data points in the middle likely represent heterokaryons with multiple nuclei.

FIG. 44 illustrates an empirical design strategy to systematically and comprehensively explore the genome independent of defined gene functions. Depicted in this figure are 2 strains that differ in their genome by 43 SNPs. Using the SNPSWP methods provided throughout the present disclosure, the role of each of these SNP alone or in combination can be examined with automation.

FIG. 49A-49F illustrates the non-homologous end joining (NHEJ) repair of the Cas9 RNP cleavage at the AygA locus. The AygA gene is targeted by one or two crRNA sequences complexed to tracrRNA and Cas9 (FIG. 49A). Indels result in a change in conidia color from (FIG. 49B) black to (FIG. 49C) yellow, enabling a phenotypic screen for successful RNP transformation. An example of a trace file from amplified genomic DNA isolated from protoplasts transformed with a single crRNA complexed to a tracrRNA and Cas9 protein demonstrates that an indel has formed proximal to the target site (FIG. 49D; see SEQ ID NOs 21 and 22). A trace file of amplified genomic DNA isolated from transformations with RNPs targeting two sites 771 bp apart suggests that both RNPs can co-transform into a single protoplast and mediate a large internal deletion between two target sites (FIG. 49E; see SEQ ID NO: 23). Number of colony forming units (CFUs) of a transformation experiment and the estimated percent of those colonies containing indels when transformed with 1, 2 or control crRNA/tracrRNA sequences (FIG. 49F). The CFUs are counted after a 10× dilution of the total transformation.

FIG. 51 illustrates the DJV_03_pyrG_insertion_in_AygA shows pyrG with promoter and terminator (lowercase) flanked by 5' and 3' regions of homology (uppercase) to the AygA gene. This figure corresponds to SEQ ID NO:9.

FIG. 52 illustrates the DJV_07_4 bp_insertion_in_AygA contains a 4 bp insertion (lowercase) flanked by 5' and 3' regions of homology (uppercase) to the AygA gene. This figure corresponds to SEQ ID NO:10.

FIG. 56A-B illustrate that two annealed oligos can create a SNP without altering the PAM or seed region of the protospacer site. A double stranded donor was cotransformed with RNP and a plasmid as described in Example 11. FIG. 56A shows the donor contains a nonsense mutation (shown in lower case in SEQ ID NO: 24) flanked on the 5' and 3' sides by 50 bp homology to the AygA gene. FIG. 56B shows two trace files of isolated colonies sequenced with Sanger technology. The first aligns to the wildtype sequence (see SEQ ID NO: 25) and the second trace file contains the intended mutation (indicated by an asterisk; see SEQ ID NO: 26).

FIG. 57 illustrates promoter swapping of morphology gene (i.e., FungiSNP_18; SEQ ID NO: 13). Different promoters controlling expression of this gene impact morphology. The strains containing the manB fusion and the amyB fusion retain the multiple tips vs. the 11414 parent strain, whereas those with higher expression srpB and mbfA lack the multiple tip phenotype. The strains were grown in citric acid production media (14% w/v Glucose, pH 2, depleted Mn++) at 30° C. for 48 hours. When allowed to incubate for 168 hours, the strains with higher expression promoters as well as the parent control all contained long filamentous hyphae. The strains with the lower level of expression from the promoter fusion, amyB and manB, remained pelleted.

FIG. 62 illustrates that strains that contain the Base SNP18 grow faster on low pH media.

FIG. 64 illustrates that exchanging FungiSNP_18 between the base and production strains has an impact on sporulation and radial growth rate.

FIG. 70 illustrates that when driven by weaker promoters, FungiSNP_18 (snp_18) has more severe morphological phenotype in the base strain than in the production strain.

DETAILED DESCRIPTION

Figure 1:
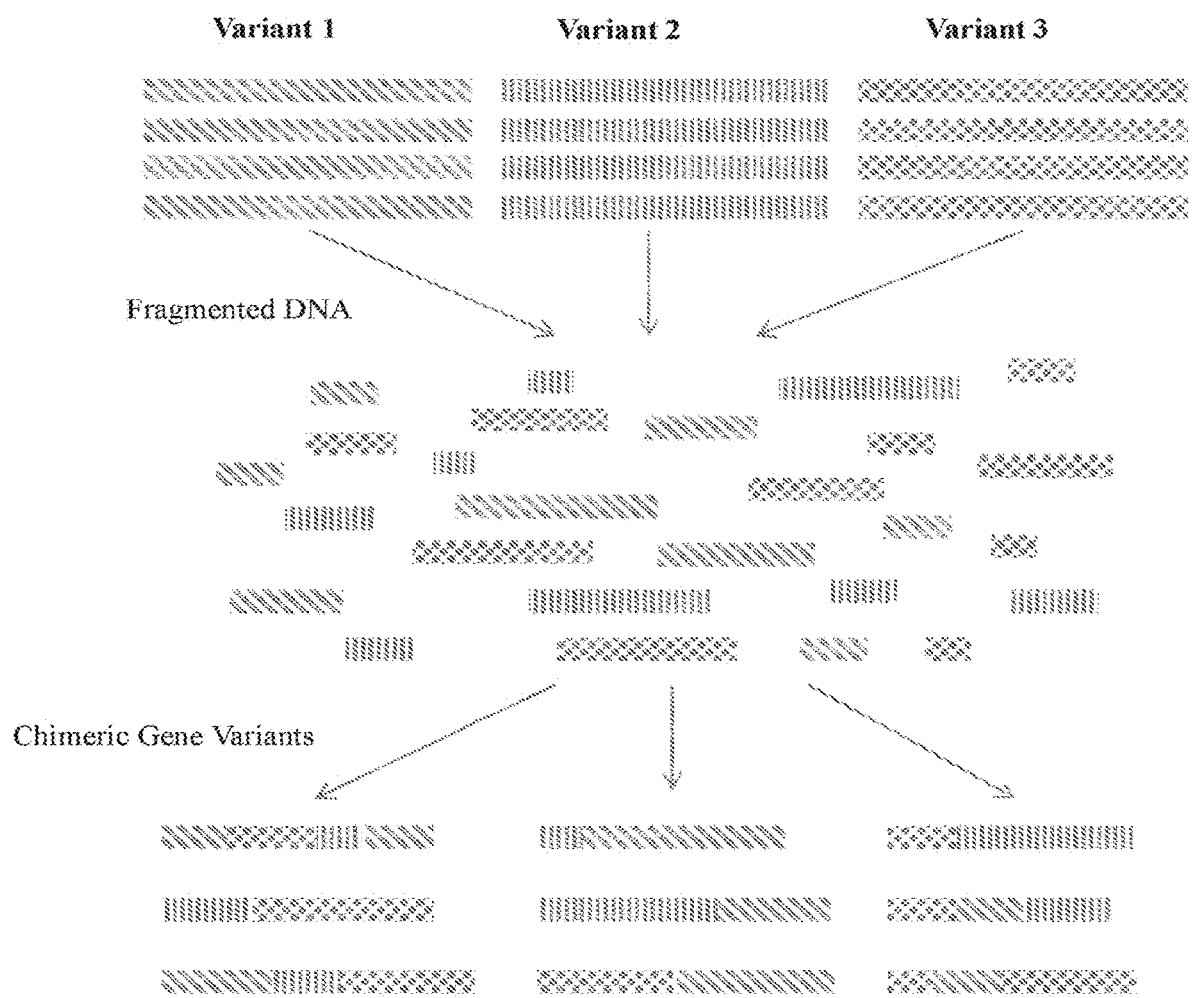
FIG. 1 depicts a DNA recombination method of the present disclosure for increasing variation in diversity pools. DNA sections, such as genome regions from related species, can be cut via physical or enzymatic/chemical means. The cut DNA regions are melted and allowed to reanneal, such that overlapping genetic regions prime polymerase extension reactions. Subsequent melting/extension reactions are carried out until products are reassembled into chimeric DNA, comprising elements from one or more starting sequences.

The current disclosure overcomes many of the challenges inherent in genetically manipulating filamentous fungi in an automated, high-throughput platform. The methods provided herein are designed to generate fungal production strains by incorporating genetic changes using automated co-transformation combined with automated screening of transformants thereby allowing exchange of genetic traits between two strains without going through a sexual cross. This disclosure also includes a procedure for generating large numbers of protoplasts and a means to store them for later use. Large batches of readily available competent cells can greatly facilitate automation.

Definitions

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi (e.g., filamentous fungi described herein) and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "coenocyte" or "coenocytic organism" as used herein can refer to a multinucleate cell or an organism comprising a multinucleate cell. The multinucleate cell can result from multiple nuclear divisions without their accompanying cytokinesis, in contrast to a syncytium, which results from cellular aggregation followed by dissolution of the cell membranes inside the mass. Examples of coenocytic organisms as it pertains to the methods, compositions and systems provided herein can include protists (e.g., algae, protozoa, myxogastrids (slime molds), alveolates, plants, fungi (e.g., filamentous fungi), and/or metazoans (e.g., *Drosophila* spp).

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) thermophilus (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified.

The term "parent strain" or "parental strain" or "parent" may refer to a host cell from which mutant strains are derived. Accordingly, the "parent strain" or "parental strain" is a host cell or cell whose genome is perturbed by any manner known in the art and/or provided herein to generate one or more mutant strains. The "parent strain" or "parental strain" may or may not have a genome identical to that of a wild-type strain.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell. In some embodiments, the present disclosure teaches the use of parent strains as control host cells (e.g., the $S_1$ strain that was used as the basis for the strain improvement program). In other embodiments, a host cell may be a genetically identical cell that lacks a specific promoter or SNP being tested in the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype".

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment. The term "recombinant" refers to an organism having a new genetic makeup arising as a result of a recombination event.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "DNA scaffold" or "nucleic acid scaffold" refers to a nucleic acid scaffold that is either artificially produced or a naturally occurring sequence that is repurposed as a scaffold. In one embodiment of the present disclosure, the nucleic acid scaffold is a synthetic deoxyribonucleic acid scaffold. The deoxyribonucleotides of the synthetic scaffold may comprise purine and pyrimidine bases or other natural, chemically or biochemically modified, non-natural, or derivatized deoxyribonucleotide bases.

As described in more detail herein, the nucleic acid scaffold of the present disclosure is utilized to spatially and temporally assemble and immobilize two or more proteins involved in a biological pathway, i.e. biosynthetic enzymes, to create a functional complex. The assembly and immobilization of each biological pathway protein on the scaffold occurs via the binding interaction between one of the protein-binding sequences, i.e., protein docking sites, of the scaffold and a corresponding DNA-binding portion of a chimeric biosynthetic enzyme. Accordingly, the nucleic acid scaffold comprises one or more subunits, each subunit comprising two or more protein-binding sequences to accommodate the binding of two or more different chimeric biological pathway proteins.

As used herein, a "DNA binding sequence" or "DNA binding site" refers to a specific nucleic acid sequence that is recognized and bound by a DNA-binding domain portion of a chimeric biosynthetic genes of the present disclosure. Many DNA-binding protein domains and their cognate binding partner recognition sites (i.e., protein binding sites) are well known in the art. For example, numerous zinc finger binding domains and their corresponding DNA protein binding target sites are known in the art and suitable for use in the present disclosure. Other DNA binding domains include, without limitation, leucine zipper binding domains and their corresponding DNA protein binding sites, winged helix binding domains and their corresponding DNA protein binding sites, winged helix-turn-helix binding domains and their corresponding DNA protein binding sites, HMG-box binding domains and their corresponding DNA protein binding sequences, helix-loop-helix binding domains and their corresponding DNA protein binding sequences, and helix-turn-helix binding domains and their corresponding DNA protein binding sequences. Other known DNA binding domains with known DNA protein binding sequences include the immunoglobulin DNA domain, B3 DNA binding domain, and TAL effector DNA binding domain. Nucleic acid scaffold subunits of the present disclosure may comprises any two or more of the aforementioned protein binding sites.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "heterologous modification" can refer to a modification coming from a source other than a source native to a particular biological system (e.g., a host cell as provided herein), or a modification from a source that is native to the particular biological system, but which is found in a non-native context/position/location. Thus, the modification is non-native or not naturally occurring in reference to a biological system (e.g., a host cell as provided herein, or non-native context/position/location within a host cell), in which said modification has been or will be introduced. The heterologous modification can therefore be considered artificially introduced to the biological system (e.g., a host cell as provided herein, or heterologous context/position/location within a host). The modification can be a genetic or epigenetic variation, disruption or perturbation. A genetic variation, disruption or perturbation can be, for example, replacement of a native promoter and/or terminator of a gene with a promoter and/or terminator that is not native to said host, or it can be a promoter and/or terminator from within the host organism that has been moved to a non-native heterologous context/position/location. A genetic variation, disruption or perturbation can be replacement of a native or naturally occurring gene with a non-native or naturally occurring gene such as, for example a selectable marker gene. Or, a genetic variation, disruption or perturbation can be replacement, or swapping, of a native or naturally occurring gene, with another native gene (e.g. promoter) from within the host genome, which is placed into a non-natural context/position/location. A genetic variation, disruption or perturbation can be replacement of a native or naturally occurring gene with a non-native or naturally occurring form of the gene. The non-native or naturally occurring form of the gene can be a mutant form of the gene not naturally found in a particular host cell and/or a mutant form of the gene not naturally found in a particular host cell operably linked to a heterologous promoter and/or terminator.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang el al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, N.Y.). See also Innis el al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. A promoter for use in the methods and systems described herein can be inducible such that expression of a gene or genes under control of said promoter is regulated by the presence and/or absence of a specific agent. The inducible promoters can be any promoter whose transcriptional activity is regulated by the presence or absence of a chemical or a physical condition such as for example, alcohol, tetracycline, steroids, metal or other compounds known in the art or by the presence or absence of light or low or high temperatures. It is further recognized that since in most cases the exact boundaries of regulatory sequences have not been completely defined, DNA fragments of some variation may have identical promoter activity.

As used herein, "terminator" generally refers to a section of DNA sequence that marks the end of a gene in genomic DNA and is capable of stopping transcription. Terminators may be derived in their entirety from a native gene, or be composed of different elements derived from different terminators found in nature, or even comprise synthetic DNA segments. It is understood by those skilled in the art that different terminators may direct the expression of a gene in different tissues or cell types, or at different stages of development, or in response to different environmental conditions.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others. The product of interest may also refer to a "protein of interest".

The term "protein of interest" generally refers to any polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be encoded by an endogenous gene or a heterologous gene relative to the variant strain and/or the parental strain. The protein of interest can be expressed intracellularly or as a secreted protein. If the protein of interest is not naturally secreted, the polynucleotide encoding the protein may be modified to have a signal sequence in accordance with techniques known in the art. The proteins, which are secreted may be endogenous proteins which are expressed naturally, but can also be heterologous. Heterologous means that the gene encoded by the protein is not produced under native condition in the filamentous fungal host cell. Examples of enzymes which may be produced by the filamentous fungi of the disclosure are carbohydrases, e.g. cellulases such as endoglucanases, beta-glucanases, cellobiohydrolases or beta-glucosidases, hemicellulases or pectinolytic enzymes such as xylanases, xylosidases, mannanases, galactanases, galactosidases, rhamnogalacturonases, arabanases, galacturonases, lyases, or amylolytic enzymes; phosphatases such as phytases, esterases such as lipases, proteolytic enzymes, oxidoreductases such as oxidases, transferases, or isomerases.

The term "carbon source" generally refers to a substance suitable to be used as a source of carbon for cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product of interest (e.g. small molecule, peptide, synthetic compound, fuel, alcohol, etc.) in a fermentation process. However, a feedstock may contain nutrients other than a carbon source.

The term "volumetric productivity" or "production rate" is defined as the amount of product formed per volume of medium per unit of time. Volumetric productivity can be reported in gram per liter per hour (g/L/h).

The term "specific productivity" is defined as the rate of formation of the product. Specific productivity is herein further defined as the specific productivity in gram product per gram of cell dry weight (CDW) per hour (g/g CDW/h). Using the relation of CDW to $OD_{600}$ for the given microorganism specific productivity can also be expressed as gram product per liter culture medium per optical density of the culture broth at 600 nm (OD) per hour (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" is defined as the strength of a solution or the concentration of a substance in solution. For example, the titre of a product of interest (e.g. small molecule, peptide, synthetic compound, fuel, alcohol, etc.) in a fermentation broth is described as g of product of interest in solution per liter of fermentation broth (g/L).

The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process As used herein, the term "HTP genetic design library" or "library" refers to collections of genetic perturbations according to the present disclosure. In some embodiments, the libraries of the present disclosure may manifest as i) a collection of sequence information in a database or other computer file, ii) a collection of genetic constructs encoding for the aforementioned series of genetic elements, or iii) host cell strains comprising said genetic elements. In some embodiments, the libraries of the present disclosure may refer to collections of individual elements (e.g., collections of promoters for PRO swap libraries, or collections of terminators for STOP swap libraries). In other embodiments, the libraries of the present disclosure may also refer to combinations of genetic elements, such as combinations of promoter::genes, gene:terminator, or even promoter:gene: terminators. In some embodiments, the libraries of the present disclosure further comprise meta data associated with the effects of applying each member of the library in host organisms. For example, a library as used herein can include a collection of promoter::gene sequence combinations, together with the resulting effect of those combinations on one or more phenotypes in a particular species, thus improving the future predictive value of using said combination in future promoter swaps.

As used herein, the term "SNP" can refer to Small Nuclear Polymorphism(s). In some embodiments, SNPs of the present disclosure should be construed broadly, and include single nucleotide polymorphisms, sequence insertions, deletions, inversions, and other sequence replacements. As used herein, the term "non-synonymous" or non-synonymous SNPs" can refer to mutations that lead to coding changes in host cell proteins A "high-throughput (HTP)" method of genomic engineering may involve the utilization of at least one piece of automated equipment (e.g. a liquid handler or plate handler machine) to carry out at least one step of said method.

The CRISPR/Cas system is a prokaryotic immune system that confers resistance to foreign genetic elements such as those present within plasmids and phages and that provides a form of acquired immunity. CRISPR stands for Clustered Regularly Interspaced Short Palindromic Repeat, and cas stands for CRISPR-associated system, and refers to the small cas genes associated with the CRISPR complex.

CRISPR-Cas systems are most broadly characterized as either Class 1 or Class 2 systems. The main distinguishing feature between these two systems is the nature of the Cas-effector module. Class 1 systems require assembly of multiple Cas proteins in a complex (referred to as a "Cascade complex") to mediate interference, while Class 2 systems use a large single Cas enzyme to mediate interference. Each of the Class 1 and Class 2 systems are further divided into multiple CRISPR-Cas types based on the presence of a specific Cas protein. For example, the Class 1 system is divided into the following three types: Type I systems, which contain the Cas3 protein; Type III systems, which contain the Cas10 protein; and the putative Type IV systems, which contain the Csf1 protein, a Cas8-like protein. Class 2 systems are generally less common than Class 1 systems and are further divided into the following three types: Type II systems, which contain the Cas9 protein; Type V systems, which contain Cas12a protein (previously known as Cpf1, and referred to as Cpf1 herein), Cas12b (previously known as C2c1), Cas12c (previously known as C2c3), Cas12d (previously known as CasY), and Cas12e (previously known as CasX); and Type VI systems, which contain Cas13a (previously known as C2c2), Cas13b, and Cas13c. Pyzocha et al., ACS Chemical Biology, Vol. 13 (2), pgs. 347-356. In one embodiment, the CRISPR-Cas system for use in the methods provided herein is a Class 2 system. In one embodiment, the CRISPR-Cas system for use in the methods provided herein is a Type II, Type V or Type VI Class 2 system. In one embodiment, the CRISPR-Cas system for use in the methods provided herein is selected from Cas9, Cas12a, Cas12b, Cas12c, Cas12d, Cas12e, Cas13a, Cas13b, Cas13c or homologs, orthologs or paralogs thereof.

CRISPR systems used in methods disclosed herein comprise a Cas effector module comprising one or more nucleic acid guided CRISPR-associated (Cas) nucleases, referred to herein as Cas effector proteins. In some embodiments, the Cas proteins can comprise one or multiple nuclease domains. A Cas effector protein can target single stranded or double stranded nucleic acid molecules (e.g. DNA or RNA nucleic acids) and can generate double strand or single strand breaks. In some embodiments, the Cas effector proteins are wild-type or naturally occurring Cas proteins. In some embodiments, the Cas effector proteins are mutant Cas proteins, wherein one or more mutations, insertions, or deletions are made in a WT or naturally occurring Cas protein (e.g., a parental Cas protein) to produce a Cas protein with one or more altered characteristics compared to the parental Cas protein.

In some instances, the Cas protein is a wild-type (WT) nuclease. Non-limiting examples of suitable Cas proteins for use in the present disclosure include C2c1, C2c2, C2c3, Cas1, Cas1B, Cas2, Cas3, Cas4, Cas5, Cas6, Cas7, Cas8, Cas9 (also known as Csn1 and Csx12), Cas10, Cpf1, Csy1, Csy2, Csy3, Cse1, Cse2, Csc1, Csc2, Csa5, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx100, Csx16, CsaX, Csx3, Csx1, Csx15, Csf1, Csf2, Csf3, Csf4, MAD1-20, SmCsm1, homologes thereof, orthologes thereof, variants thereof, mutants thereof, or modified versions thereof. Suitable nucleic acid guided nucleases (e.g., Cas 9) can be from an organism from a genus, which includes but is not limited to: *Thiomicrospira, Succinivibrio, Candidatus, Porphyromonas, Acidomonococcus, Prevotella, Smithella, Moraxella, Synergistes, Francisella, Leptospira, Catenibacterium, Kandleria, Clostridium, Dorea, Coprococcus, Enterococcus, Fructobacillus, Weissella, Pediococcus, Corynebacter, Sutterella, Legionella, Treponema, Roseburia, Filfactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitralifractor, Mycoplasma, Alicyclobacillus, Brevibacilus, Bacillus, Bacteroidetes, Brevibacilus, Carnobacterium, Clostridiaridium, Clostridium, Desulfonatronum, Desulfovibrio, Helcococcus, Leptotrichia, Listeria, Methanomethyophilus, Methylobacterium, Opitutaceae, Paludibacter, Rhodobacter, Sphaerochaeta, Tuberibacillus,* and *Campylobacter*. Species of organism of such a genus can be as otherwise herein discussed.

Suitable nucleic acid guided nucleases (e.g., Cas9) can be from an organism from a phylum, which includes but is not limited to: Firmicute, Actinobacteria, Bacteroidetes, Proteobacteria, Spirochates, and Tenericutes. Suitable nucleic acid guided nucleases can be from an organism from a class, which includes but is not limited to: Erysipelotrichia, Clostridia, Bacilli, Actinobacteria, Bacteroidetes, Flavobacteria, Alphaproteobacteria, Betaproteobacteria, Gammaproteobacteria, Deltaproteobacteria, Epsilonproteobacteria, Spirochaetes, and Mollicutes. Suitable nucleic acid guided nucleases can be from an organism from an order, which includes but is not limited to: Clostridiales, Lactobacillales, Actinomycetales, Bacteroidales, Flavobacteriales, Rhizobiales, Rhodospirillales, Burkholderiales, Neisseriales, Legionellales, Nautiliales, Campylobacterales, Spirochaetales, Mycoplasmatales, and Thiotrichales. Suitable nucleic acid guided nucleases can be from an organism from within a family, which includes but is not limited to: Lachnospiraceae, Enterococcaceae, Leuconostocaceae, Lactobacillaceae, Streptococcaceae, Peptostreptococcaceae, Staphylococcaceae, Eubacteriaceae, Corynebacterineae, Bacteroidaceae, *Flavobacterium*, Cryomoorphaceae, Rhodobiaceae, Rhodospirillaceae, Acetobacteraceae, Sutterellaceae, Neisseriaceae, Legionellaceae, Nautiliaceae, Campylobacteraceae, Spirochaetaceae, Mycoplasmataceae, and Francisellaceae.

Other nucleic acid guided nucleases (e.g., Cas9) suitable for use in the methods, systems, and compositions of the present disclosure include those derived from an organism such as, but not limited to: *Thiomicrospira* sp. XS5, *Eubacterium rectale, Succinivibrio dextrinosolvens, Caandidatus Methanoplasma termitum, Candidatus Methanomethylophilus alvus, Porphyromonas crevioricanis, Flavobacterium branchiophilum, Acidomonococcus* sp., Lachnospiraceae bacterium COE1, *Prevotella brevis* ATCC 19188, *Smithella* sp. SCADC, *Moraxella bovoculi, Synergistes jonesii*, Bacteroidetes oral taxon 274, *Francisella tularensis, Leptospira inadai* serovar Lyme str. 10, *Acidomonococcus* sp. crystal structure (5B43) *S. mutans, S. agalactiae, S. equisimilis, S. sanguinis, S. pneumonia; C. jejuni, C. coli; N. salsuginis, N. tergarcus; S. auricularis, S. carnosus; N. meningitides. N. gonorrhoeae; L. monocytogenes, L. ivanovii; C. botulinum, C. difficile, C. tetani, C. sordellii; Francisella tularensis* 1. *Prevotella albensis*, Lachnospiraceae bacterium MC2017 1, *Butyrivibrio proteoclasticus*, Peregrinibacteria bacterium GW2011_GWA2_33_10, *Parcubacteria bacterium* GW2011_GWC2_44_17, *Smithella* sp. SCADC, *Microgenomates, Acidaminococcus* sp. BV3L6, Lachnospiraceae bacterium MA2020, *candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens, Porphvromonas macacae, Catenibacterium* sp. CAG:290, *Kandleria vitulina*, Clostridiales bacterium KA00274, Lachnospiraceae bacterium 3-2, *Dorea longicatena, Coprococcus catus* GD/7, *Enterococcus columbae* DSM 7374, *Fructobacillius* sp. EFB-N1, *Weissella halotolerans, Pediococcus acidilactici, Lactobacillus curvatus, Streptococcus pyogenes, Lactobacillus versmoldensis*, and *Filifactor alocis* ATCC 35896. See, U.S. Pat. Nos. 8,697,359; 8,771,945; 8,795,965; 8,865,406; 8,871,445; 8,889,356; 8,895,308; 8,906,616; 8,932,814; 8,945,839; 8,993,233; 8,999,641; 9,822,372; 9,840,713; U.S. patent application Ser. No. 13/842,859 (US 2014/0068797 A1); U.S. Pat. Nos. 9,260,723; 9,023,649; 9,834,791; 9,637,739; U.S. patent application Ser. No. 14/683,443 (US 2015/0240261 A1); U.S. patent application Ser. No. 14/743,764 (US 2015/0291961 A1); U.S. Pat. Nos. 9,790,490; 9,688,972; 9,580,701; 9,745,562; 9,816,081; 9,677,090; 9,738,687; U.S. application Ser. No. 15/632,222 (US 2017/0369879 A1); U.S. application Ser. No. 15/631, 989; U.S. application Ser. No. 15/632,001; and U.S. Pat. No. 9,896,696, each of which is herein incorporated by reference.

In some embodiments, a Cas effector protein comprises one or more of the following activities:

a nickase activity, i.e., the ability to cleave a single strand of a nucleic acid molecule;

a double stranded nuclease activity, i.e., the ability to cleave both strands of a double stranded nucleic acid and create a double stranded break;

an endonuclease activity;

an exonuclease activity; and/or a helicase activity, i.e., the ability to unwind the helical structure of a double stranded nucleic acid.

In aspects of the disclosure the term "guide nucleic acid" refers to a polynucleotide comprising 1) a guide sequence capable of hybridizing to a target sequence (referred to herein as a "targeting segment") and 2) a scaffold sequence capable of interacting with (either alone or in combination with a tracrRNA molecule) a nucleic acid guided nuclease as described herein (referred to herein as a "scaffold segment"). A guide nucleic acid can be DNA. A guide nucleic acid can be RNA. A guide nucleic acid can comprise both DNA and RNA. A guide nucleic acid can comprise modified non-naturally occurring nucleotides. In cases where the guide nucleic acid comprises RNA, the RNA guide nucleic acid can be encoded by a DNA sequence on a polynucleotide molecule such as a plasmid, linear construct, or editing cassette as disclosed herein.

In some embodiments, the guide nucleic acids described herein are RNA guide nucleic acids ("guide RNAs" or "gRNAs") and comprise a targeting segment and a scaffold segment. In some embodiments, the scaffold segment of a gRNA is comprised in one RNA molecule and the targeting segment is comprised in another separate RNA molecule. Such embodiments are referred to herein as "double-molecule gRNAs" or "two-molecule gRNA" or "dual gRNAs." In some embodiments, the gRNA is a single RNA molecule and is referred to herein as a "single-guide RNA" or an "sgRNA." The term "guide RNA" or "gRNA" is inclusive, referring both to two-molecule guide RNAs and sgRNAs.

The DNA-targeting segment of a gRNA comprises a nucleotide sequence that is complementary to a sequence in a target nucleic acid sequence. As such, the targeting segment of a gRNA interacts with a target nucleic acid in a sequence-specific manner via hybridization (i.e., base pairing), and the nucleotide sequence of the targeting segment determines the location within the target DNA that the gRNA will bind. The degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 75, or more nucleotides in length. In some embodiments, a guide sequence is less than about 75, 50, 45, 40, 35, 30, 25, 20 nucleotides in length. In aspects, the guide sequence is 10-30 nucleotides long. The guide sequence can be 15-20 nucleotides in length. The guide sequence can be 15 nucleotides in length. The guide sequence can be 16 nucleotides in length. The guide sequence can be 17 nucleotides in length. The guide sequence can be 18 nucleotides in length. The guide sequence can be 19 nucleotides in length. The guide sequence can be 20 nucleotides in length.

The scaffold segment of a guide RNA interacts with a one or more Cas effector proteins to form a ribonucleoprotein complex (referred to herein as a CRISPR-RNP or a RNP-complex). The guide RNA directs the bound polypeptide to a specific nucleotide sequence within a target nucleic acid sequence via the above-described targeting segment. The scaffold segment of a guide RNA comprises two stretches of nucleotides that are complementary to one another and which form a double stranded RNA duplex. Sufficient sequence within the scaffold sequence to promote formation of a targetable nuclease complex may include a degree of complementarity along the length of two sequence regions within the scaffold sequence, such as one or two sequence regions involved in forming a secondary structure. In some cases, the one or two sequence regions are comprised or encoded on the same polynucleotide. In some cases, the one or two sequence regions are comprised or encoded on separate polynucleotides. Optimal alignment may be determined by any suitable alignment algorithm, and may further account for secondary structures, such as self-complementarity within either the one or two sequence regions. In some embodiments, the degree of complementarity between the one or two sequence regions along the length of the shorter of the two when optimally aligned is about or more than about 25%, 30%, 40%, 50%, 60%, 70%, 80%, 90%, 95%, 97.5%, 99%, or higher. In some embodiments, at least one of the two sequence regions is about or more than about 5, 6, 7, 8, 9, 10, 11, 12, 13, 14, 15, 16, 17, 18, 19, 20, 25, 30, 40, 50, or more nucleotides in length.

A scaffold sequence of a subject gRNA can comprise a secondary structure. A secondary structure can comprise a pseudoknot region or stem-loop structure. In some examples, the compatibility of a guide nucleic acid and nucleic acid guided nuclease is at least partially determined by sequence within or adjacent to the secondary structure region of the guide RNA. In some cases, binding kinetics of a guide nucleic acid to a nucleic acid guided nuclease is determined in part by secondary structures within the scaffold sequence. In some cases, binding kinetics of a guide nucleic acid to a nucleic acid guided nuclease is determined in part by nucleic acid sequence with the scaffold sequence.

A compatible scaffold sequence for a gRNA-Cas effector protein combination can be found by scanning sequences adjacent to a native Cas nuclease loci. In other words, native Cas nucleases can be encoded on a genome within proximity to a corresponding compatible guide nucleic acid or scaffold sequence.

Nucleic acid guided nucleases can be compatible with guide nucleic acids that are not found within the nucleases endogenous host. Such orthogonal guide nucleic acids can be determined by empirical testing. Orthogonal guide nucleic acids can come from different bacterial species or be synthetic or otherwise engineered to be non-naturally occurring. Orthogonal guide nucleic acids that are compatible with a common nucleic acid-guided nuclease can comprise one or more common features. Common features can include sequence outside a pseudoknot region. Common features can include a pseudoknot region. Common features can include a primary sequence or secondary structure A guide nucleic acid can be engineered to target a desired target sequence by altering the guide sequence such that the guide sequence is complementary to the target sequence, thereby allowing hybridization between the guide sequence and the target sequence. A guide nucleic acid with an engineered guide sequence can be referred to as an engineered guide nucleic acid. Engineered guide nucleic acids are often non-naturally occurring and are not found in nature.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector.

In some embodiments, the present disclosure provides a gRNA complexed with a site-directed modifying polypeptide to form an RNP-complex that is capable of being introduced into a host cell comprising a target nucleic acid sequence for which the targeting segment of the gRNA comprising sequence that is complementary thereto. The site-directed modifying polypeptide can be a nucleic acid guided nuclease. The nucleic acid guided nuclease can be any nucleic acid guided nuclease as known in the art and/or provided herein (e.g., Cas9). The nucleic acid guided nuclease can be guided by and RNA (e.g., gRNA) and thus be referred to as an RNA guided nuclease or RNA guided endonuclease.

Traditional Methods of Strain Improvement

Traditional approaches to strain improvement can be broadly categorized into two types of approaches: directed strain engineering, and random mutagenesis.

Directed engineering methods of strain improvement involve the planned perturbation of a handful of genetic elements of a specific organism. These approaches are typically focused on modulating specific biosynthetic or developmental programs, and rely on prior knowledge of the genetic and metabolic factors affecting said pathways. In its simplest embodiments, directed engineering involves the transfer of a characterized trait (e.g., gene, promoter, or other genetic element capable of producing a measurable phenotype) from one organism to another organism of the same, or different species.

Random approaches to strain engineering involve the random mutagenesis of parent strains, coupled with extensive screening designed to identify performance improvements. Approaches to generating these random mutations include exposure to ultraviolet radiation, or mutagenic chemicals such as Ethyl methanesulfonate. Though random and largely unpredictable, this traditional approach to strain improvement had several advantages compared to more directed genetic manipulations. First, many industrial organisms were (and remain) poorly characterized in terms of their genetic and metabolic repertoires, rendering alternative directed improvement approaches difficult, if not impossible.

Second, even in relatively well characterized systems, genotypic changes that result in industrial performance improvements are difficult to predict, and sometimes only manifest themselves as epistatic phenotypes requiring cumulative mutations in many genes of known and unknown function.

Additionally, for many years, the genetic tools required for making directed genomic mutations in a given industrial organism were unavailable, or very slow and/or difficult to use.

The extended application of the traditional strain improvement programs, however, yield progressively reduced gains in a given strain lineage, and ultimately lead to exhausted possibilities for further strain efficiencies. Beneficial random mutations are relatively rare events, and require large screening pools and high mutation rates. This inevitably results in the inadvertent accumulation of many neutral and/or detrimental (or partly detrimental) mutations in "improved" strains, which ultimately create a drag on future efficiency gains.

Another limitation of traditional cumulative improvement approaches is that little to no information is known about any particular mutation's effect on any strain metric. This fundamentally limits a researcher's ability to combine and consolidate beneficial mutations, or to remove neutral or detrimental mutagenic "baggage."

Other approaches and technologies exist to randomly recombine mutations between strains within a mutagenic lineage. For example, some formats and examples for iterative sequence recombination, sometimes referred to as DNA shuffling, evolution, or molecular breeding, have been described in U.S. patent application Ser. No. 08/198,431, filed Feb. 17, 1994, Serial No. PCT/US95/02126, filed, Feb. 17, 1995, Ser. No. 08/425,684, filed Apr. 18, 1995, Ser. No. 08/537,874, filed Oct. 30, 1995, Ser. No. 08/564,955, filed Nov. 30, 1995, Ser. No. 08/621,859, filed. Mar. 25, 1996, Ser. No. 08/621,430, filed Mar. 25, 1996, Serial No. PCT/US96/05480, filed Apr. 18, 1996, Ser. No. 08/650,400, filed May 20, 1996, Ser. No. 08/675,502, filed Jul. 3, 1996, Ser. No. 08/721,824, filed Sep. 27, 1996, and Ser. No. 08/722, 660 filed Sep. 27, 1996; Stemmer, Science 270:1510 (1995); Stemmer et al., Gene 164:49-53 (1995); Stemmer, Bio/Technology 13:549-553 (1995); Stemmer, Proc. Natl. Acad. Sci. U.S.A. 91:10747-10751 (1994); Stemmer, Nature 370: 389-391 (1994); Crameri et al., Nature Medicine 2(1):1-3 (1996); Crameri et al., Nature Biotechnology 14:315-319 (1996), each of which is incorporated herein by reference in its entirety for all purposes.

These include techniques such as protoplast fusion and whole genome shuffling that facilitate genomic recombination across mutated strains. For some industrial microorganisms such as yeast and filamentous fungi, natural mating cycles can also be exploited for pairwise genomic recombination. In this way, detrimental mutations can be removed by 'back-crossing' mutants with parental strains and beneficial mutations consolidated. Moreover, beneficial mutations from two different strain lineages can potentially be combined, which creates additional improvement possibilities over what might be available from mutating a single strain lineage on its own. However, these approaches are subject to many limitations that are circumvented using the methods of the present disclosure.

For example, traditional recombinant approaches as described above are slow and rely on a relatively small number of random recombination crossover events to swap mutations, and are therefore limited in the number of combinations that can be attempted in any given cycle, or time period. In addition, although the natural recombination events in the prior art are essentially random, they are also subject to genome positional bias.

Most importantly, the traditional approaches also provide little information about the influence of individual mutations and due to the random distribution of recombined mutations many specific combinations cannot be generated and evaluated.

To overcome many of the aforementioned problems associated with traditional strain improvement programs, the present disclosure sets forth a unique HTP genomic engineering platform that is computationally driven and integrates molecular biology, automation, data analytics, and machine learning protocols. This integrative platform utilizes a suite of HTP molecular tool sets that are used to construct HTP genetic design libraries. These genetic design libraries will be elaborated upon below.

The presently disclosed HTP platform and its unique microbial genetic design libraries fundamentally shift the paradigm of microbial strain development and evolution. For example, traditional mutagenesis-based methods of developing an industrial microbial strain will eventually lead to microbes burdened with a heavy mutagenic load that has been accumulated over years of random mutagenesis.

The ability to solve this issue (i.e. remove the genetic baggage accumulated by these microbes) has eluded microbial researchers for decades. However, utilizing the HTP platform disclosed herein, these industrial strains can be "rehabilitated," and the genetic mutations that are deleterious can be identified and removed. Congruently, the genetic mutations that are identified as beneficial can be kept, and in some cases improved upon. The resulting microbial strains demonstrate superior phenotypic traits (e.g., improved production of a compound of interest), as compared to their parental strains.

Furthermore, the HTP platform taught herein is able to identify, characterize, and quantify the effect that individual mutations have on microbial strain performance. This information, i.e. what effect does a given genetic change x have on host cell phenotype y (e.g., production of a compound or product of interest), is able to be generated and then stored in the microbial HTP genetic design libraries discussed below. That is, sequence information for each genetic permutation, and its effect on the host cell phenotype are stored in one or more databases, and are available for subsequent analysis (e.g., epistasis mapping, as discussed below). The present disclosure also teaches methods of physically saving/storing valuable genetic permutations in the form of genetic insertion constructs, or in the form of one or more host cell organisms containing said genetic permutation (e.g., see libraries discussed below.)

When one couples these HTP genetic design libraries into an iterative process that is integrated with a sophisticated data analytics and machine learning process a dramatically different methodology for improving host cells emerges. The taught platform is therefore fundamentally different from the previously discussed traditional methods of developing host cell strains. The taught HTP platform does not suffer from many of the drawbacks associated with the previous methods. These and other advantages will become apparent with reference to the HTP molecular tool sets and the derived genetic design libraries discussed below.

Overview

It is an object of the present disclosure to circumvent all the limitations described above by providing a high-throughput method for transforming filamentous fungal cells or protoplasts derived therefrom, purifying homokaryotic transformants and screening purified transformants. In general, the methods and systems described herein entail preparation of protoplasts from filamentous fungal cells, transformation of the prepared protoplasts, purification of protoplasts containing a single nucleus by altering the growth conditions used to prepare mycelia for protoplast preparation. Strain purification is achieved through selection and counter-selection, and, optionally, screening purified transformants possessing the correct phenotype and/or producing products of interest. The products of interest can be produced at a desired yield, productivity or titer. Preferably, protoplasts are used, but the method is applicable to other fungal cell types. In some cases, the methods and systems provided herein are high-throughput. In some cases, the methods and systems provided herein comprise steps that are semi-automated (e.g., transformation or selection, counterselection). In some cases, the methods and systems provided herein comprise steps that are fully automated. In some cases, the methods and systems provided herein are high-throughput and the steps therein are semi-automated (e.g., transformation or selection, counterselection) or fully automated. As used herein, high-throughput can refer to any partially—or fully-automated method provided herein that is capable of evaluating about 1,000 or more transformants per day, and particularly to those methods capable of evaluating 5,000 or more transformants per day, and most particularly to methods capable of evaluating 10,000 or more transformants per day. Moreover, suitable volumes in which the method is performed are those of commercially available (deep well) microtiter plates, i.e. smaller than 1 ml, preferably smaller than 500 ul, more preferably smaller than 250 ul, most preferably from 1.5 ul to 250 ul, still most preferably from 10 ul to 100 ul.

The filamentous fungal cells used to prepare the protoplasts can be any filamentous fungus strains known in the art or described herein including holomorphs, teleomorphs or anamorphs thereof. The preparation of the protoplasts can be performed using those described herein or any known method in the art for preparing protoplasts.

Transformation of the protoplasts can be with at least one polynucleotide designed to integrate into a pre-determined locus in the filamentous fungal genome as provided herein. In a preferred embodiment, the protoplasts are co-transformed with at least two polynucleotides as provided herein such that each polynucleotide construct is designed to integrate into a different pre-determined locus in the filamentous fungal genome. A pre-determined locus can be for a target filamentous fungal gene (e.g., a gene whose protein product is involved in citric acid production) or a selectable marker gene present in the filamentous fungal genome. A polynucleotide for use in transforming or co-transforming protoplasts using the methods or systems provided herein can comprise sequence of a target filamentous fungal gene (e.g., a gene whose protein product is involved in citric acid production) comprising or containing a mutation and/or a genetic control element(s). The mutation can be a small nuclear polymorphism(s) such as a single nucleotide polymorphism, sequence insertions, deletions, inversions, and other sequence replacements. The genetic control element can be a promoter sequence (endogenous or heterologous) and/or a terminator sequence (endogenous or heterologous). The promoter can be inducible. A polynucleotide for use in transforming or co-transforming protoplasts using the methods or systems provided herein can comprise sequence of a selectable marker gene. A polynucleotide for use in transforming or co-transforming protoplasts using the methods or systems provided herein can be separated into two or more portions such that integration of the whole polynucleotide in a transformed protoplast occurs only if each separate portion of the polynucleotide integrates at the same target site in the transformed protoplast's genome. Each portion of the polynucleotide can comprise a mutation and/or genetic control element as provided herein. In one embodiment, the methods and systems provided herein entail co-transformation of protoplasts provided herein with two polynucleotides such that a first polynucleotide comprise sequence of a target filamentous fungal gene (e.g., a gene whose protein product is involved in citric acid production) comprising or containing a mutation and/or a genetic control element(s), while a second polynucleotide comprises sequence of a selectable marker gene. Further to this embodiment, the second polynucleotide can be designed to integrate into an additional selectable marker gene in the protoplast genome, while the first polynucleotide can be designed to integrate into the locus for the target filamentous fungal gene or, alternatively, into the locus of yet a further selectable marker gene. A selectable marker gene in any of the embodiments provided herein can be any of the selectable marker genes described herein.

It is also the object of this disclosure to provide a method for preparing and storing a plurality of protoplasts from filamentous fungal cells. The method can entail removing cell walls from the filamentous fungal cells in the fungal culture, isolating the protoplasts, and resuspending the isolated protoplasts in a mixture comprising at least dimethyl sulfoxide (DMSO) and storing the isolated protoplasts. Storage can be for at least 1, 2, 3, 4, 5, 6, 7, 8, 9, 10, 11, 12 or 24 hours. Storage can be for at least 1, 7, 14, 30 or more days. Storage can be for at least 3, 6, 12, or more months. Storage can be at 4, −20 or −80° C. The fungal culture can be a culture with a volume of at least 500 ml, 1 liter, 2 liters, 3 liters, 4 liters or 5 liters. The filamentous fungal cells can be any filamentous fungus provided herein or known in the art. Prior to preparation of the protoplasts the fungal culture can be grown for at least 6, 8, 10, 12, 14, 16, 18, 20, 22 or 24 hours. In one embodiment, the fungal culture is grown under conditions whereby at least 70% of the protoplasts are homokaryotic following preparation of the protoplasts. In another embodiment, removing the cell walls is performed by enzymatic digestion. The enzymatic digestion can be performed with mixture of enzymes comprising a beta-glucanase and a polygalacturonase. The enzymatic digestion can be performed with VinoTaste concentrate. In yet another embodiment, the method further comprises adding polyethylene glycol (PEG) to the mixture comprising DMSO prior to storing the protoplasts. The PEG can be added to a final concentration of 50%, 40%, 30%, 20%, 15%, 10%, 5% or less. In still another embodiment, the method further comprises distributing the protoplasts into microtiter plates prior to storing the protoplasts. The microtiter plate can be a 6 well, 12 well, 24 well, 96 well, 384 well or 1536 well plate.

Genetic Design & Microbial Engineering: A Systematic Combinatorial Approach to Strain Improvement Utilizing a Suite of HTP Molecular Tools and HTP Genetic Design Libraries As aforementioned, the present disclosure provides a novel HTP platform and genetic design strategy for engineering microbial organisms through iterative systematic introduction and removal of genetic changes across strains. The platform is supported by a suite of molecular tools, which enable the creation of HTP genetic design libraries and allow for the efficient implementation of genetic alterations into a given host strain.

The HTP genetic design libraries of the disclosure serve as sources of possible genetic alterations that may be introduced into a particular microbial (e.g., filamentous fungal) strain background. In this way, the HTP genetic design libraries are repositories of genetic diversity, or collections of genetic perturbations, which can be applied to the initial or further engineering of a given microbial strain. Techniques for programming genetic designs for implementation to host strains are described in pending U.S. patent application Ser. No. 15/140,296 and pending International Application Serial No. PCT/US17/29725, entitled "Microbial Strain Design System and Methods for Improved Large Scale Production of Engineered Nucleotide Sequences," each of which is incorporated by reference in its entirety herein.

The HTP molecular tool sets utilized in this platform may include, inter alia: (1) Promoter swaps (PRO Swap), (2) SNP swaps, (3) Start/Stop codon exchanges, (4) STOP swaps, and (5) Sequence optimization. The HTP methods of the present disclosure also teach methods for directing the consolidation/combinatorial use of HTP tool sets, including (6) Epistasis mapping protocols. As aforementioned, this suite of molecular tools, either in isolation or combination, enables the creation of HTP genetic design host cell libraries.

As will be demonstrated, utilization of the aforementioned HTP genetic design libraries in the context of the taught HTP microbial engineering platform enables the identification and consolidation of beneficial "causative" mutations or gene sections and also the identification and removal of passive or detrimental mutations or gene sections. This new approach allows rapid improvements in strain performance that could not be achieved by traditional random mutagenesis or directed genetic engineering. The removal of genetic burden or consolidation of beneficial changes into a strain with no genetic burden also provides a new, robust starting point for additional random mutagenesis that may enable further improvements.

In some embodiments, the present disclosure teaches that as orthogonal beneficial changes are identified across various discrete branches of a mutagenic strain lineage, they can also be rapidly consolidated into better performing strains. These mutations can also be consolidated into strains that are not part of mutagenic lineages, such as strains with improvements gained by directed genetic engineering.

In some embodiments, the present disclosure differs from known strain improvement approaches in that it analyzes the genome-wide combinatorial effect of mutations across multiple disparate genomic regions, including expressed and non-expressed genetic elements, and uses gathered information (e.g., experimental results) to predict mutation combinations expected to produce strain enhancements.

In some embodiments, the present disclosure teaches: i) industrial microorganisms, and other host cells amenable to improvement via the disclosed disclosures, ii) generating diversity pools for downstream analysis, iii) methods and hardware for high-throughput screening and sequencing of large variant pools, iv) methods and hardware for machine learning computational analysis and prediction of synergistic effects of genome-wide mutations, and v) methods for high-throughput strain engineering.

The following molecular tools and libraries are discussed in terms of illustrative microbial examples. Persons having skill in the art will recognize that the HTP molecular tools of the present disclosure are compatible with any host cell, including eukaryotic cellular, and higher life forms such as, for example, the same principles and process can be deployed in filamentous fungal cells (e.g., *Aspergillus niger*).

Each of the identified HTP molecular tool sets-which enable the creation of the various HTP genetic design libraries utilized in the microbial engineering platform-will now be discussed.

1. Promoter Swaps: A Molecular Tool for the Derivation of Promoter Swap Microbial Strain Libraries In some embodiments, the present disclosure teaches methods of selecting promoters with optimal expression properties to produce beneficial effects on overall-host strain phenotype (e.g., yield or productivity).

For example, in some embodiments, the present disclosure teaches methods of identifying one or more promoters and/or generating variants of one or more promoters within a host cell, which exhibit a range of expression strengths (e.g. promoter ladders discussed infra), or superior regulatory properties (e.g., tighter regulatory control for selected genes). A particular combination of these identified and/or generated promoters can be grouped together as a promoter ladder, which is explained in more detail below.

The promoter ladder in question is then associated with a given gene of interest. Thus, if one has promoters $P_1$-$P_8$ (representing eight promoters that have been identified and/or generated to exhibit a range of expression strengths) and associates the promoter ladder with a single gene of interest in a microbe (i.e. genetically engineer a microbe with a given promoter operably linked to a given target gene), then the effect of each combination of the eight promoters can be ascertained by characterizing each of the engineered strains resulting from each combinatorial effort, given that the engineered microbes have an otherwise identical genetic background except the particular promoter(s) associated with the target gene.

The resultant microbes that are engineered via this process form HTP genetic design libraries.

In a specific embodiment, the promoter swapping (PRO Swap) methods provided herein entail systematically associating each promoter from the promoter ladder depicted in Table 1 with a gene shown to or suspected to play a role or affect morphology of filamentous fungal cells when grown under specific conditions (referred to as target morphological genes). The perturbation of the gene can cause a desired morphological phenotype. The desired phenotype can be a non-mycelium, pellet morphology when grown in submerged cultures of a production media (e.g., CAP media). Thus, if one has promoters $P_1$-$P_4$ (representing the four promoters from Table 1 that have been identified and/or generated to exhibit a range of expression strengths) and associates the promoter ladder with a single target morphological gene of interest in a microbe (i.e. genetically engineer a microbe with a given promoter operably linked to a given target morphological gene), then the effect of each combination of the four promoters can be ascertained by characterizing each of the engineered strains resulting from each combinatorial effort, given that the engineered microbes have an otherwise identical genetic background except the particular promoter(s) associated with the specific target morphological gene. The resultant microbes that are engineered via this process can form HTP morphological genetic design libraries. The gene shown to or suspected to play a role or affect morphology of filamentous fungal cells can be any such gene known in the art and/or provided herein.

The HTP genetic design library can refer to the actual physical microbial strain collection that is formed via this process, with each member strain being representative of a given promoter operably linked to a particular target gene, in an otherwise identical genetic background, said library being termed a "promoter swap microbial strain library." In the specific context of filamentous fungi (e.g., *A. niger*), the library can be termed a "promoter swap filamentous fungal strain library," or "promoter swap *A. niger* strain library," but the terms can be used synonymously, as filamentous fungus or *A. niger* are specific examples of a microbe or coenocytic organism.

Furthermore, the HTP genetic design library can refer to the collection of genetic perturbations—in this case a given promoter x operably linked to a given gene y—said collection being termed a "promoter swap library."

Further, one can utilize the same promoter ladder comprising promoters $P_1$-$P_8$ to engineer microbes, wherein each of the 8 promoters is operably linked to 10 different gene targets. The result of this procedure would be 80 microbes that are otherwise assumed genetically identical, except for the particular promoters operably linked to a target gene of interest. These 80 microbes could be appropriately screened and characterized and give rise to another HTP genetic design library. The characterization of the microbial strains in the HTP genetic design library produces information and data that can be stored in any data storage construct, including a relational database, an object-oriented database or a highly distributed NoSQL database. This data/information could be, for example, a given promoter's (e.g. $P_1$-$P_8$) effect when operably linked to a given gene target. This data/information can also be the broader set of combinatorial effects that result from operably linking two or more of promoters $P_1$-$P_8$ to a given gene target.

The aforementioned examples of eight promoters and 10 target genes is merely illustrative, as the concept can be applied with any given number of promoters that have been grouped together based upon exhibition of a range of expression strengths and any given number of target genes. Persons having skill in the art will also recognize the ability to operably link two or more promoters in front of any gene target. Thus, in some embodiments, the present disclosure teaches promoter swap libraries in which 1, 2, 3 or more promoters from a promoter ladder are operably linked to one or more genes.

In summary, utilizing various promoters to drive expression of various genes in an organism is a powerful tool to optimize a trait of interest. The molecular tool of promoter swapping, developed by the inventors, uses a ladder of promoter sequences (e.g., Table 1) that have been demonstrated to vary expression of at least one locus under at least one condition. This ladder is then systematically applied to a group of genes (e.g., within the same pathway as FungiSNP_18 as provided herein) in the organism using high-throughput genome engineering. This group of genes is determined to have a high likelihood of impacting the trait of interest based on any one of a number of methods. These could include selection based on known function, or impact on the trait of interest, or algorithmic selection based on previously determined beneficial genetic diversity. In some embodiments, the selection of genes can include all the genes in a given host. In other embodiments, the selection of genes can be a subset of all genes in a given host, chosen randomly.

The resultant HTP genetic design microbial strain library of organisms containing a promoter sequence linked to a gene is then assessed for performance in a high-throughput screening model, and promoter-gene linkages which lead to increased performance are determined and the information stored in a database. The collection of genetic perturbations (i.e. given promoter x operably linked to a given gene y) form a "promoter swap library," which can be utilized as a source of potential genetic alterations to be utilized in microbial engineering processing. Over time, as a greater set of genetic perturbations is implemented against a greater diversity of host cell backgrounds, each library becomes more powerful as a corpus of experimentally confirmed data that can be used to more precisely and predictably design targeted changes against any background of interest.

Transcription levels of genes in an organism are a key point of control for affecting organism behavior. Transcription is tightly coupled to translation (protein expression), and which proteins are expressed in what quantities determines organism behavior. Cells express thousands of different types of proteins, and these proteins interact in numerous complex ways to create function. By varying the expression levels of a set of proteins systematically, function can be altered in ways that, because of complexity, are difficult to predict. Some alterations may increase performance, and so, coupled to a mechanism for assessing performance, this technique allows for the generation of organisms with improved function.

In the context of a small molecule synthesis pathway, enzymes interact through their small molecule substrates and products in a linear or branched chain, starting with a substrate and ending with a small molecule of interest. Because these interactions are sequentially linked, this system exhibits distributed control, and increasing the expression of one enzyme can only increase pathway flux until another enzyme becomes rate limiting.

Metabolic Control Analysis (MCA) is a method for determining, from experimental data and first principles, which enzyme or enzymes are rate limiting. MCA is limited however, because it requires extensive experimentation after each expression level change to determine the new rate limiting enzyme. Promoter swapping is advantageous in this context, because through the application of a promoter ladder to each enzyme in a pathway, the limiting enzyme is found, and the same thing can be done in subsequent rounds to find new enzymes that become rate limiting. Further, because the read-out on function is better production of the small molecule of interest, the experiment to determine which enzyme is limiting is the same as the engineering to increase production, thus shortening development time. In some embodiments the present disclosure teaches the application of PRO swap to genes encoding individual subunits of multi-unit enzymes. In yet other embodiments, the present disclosure teaches methods of applying PRO swap techniques to genes responsible for regulating individual enzymes, or whole biosynthetic pathways.

In some embodiments, the promoter swap tool of the present disclosure is used to identify optimum expression of a selected gene target. In some embodiments, the goal of the promoter swap may be to increase expression of a target gene to reduce bottlenecks in a metabolic or genetic pathway. In other embodiments, the goal of the promoter swap may be to reduce the expression of the target gene to avoid unnecessary energy expenditures in the host cell, when expression of said target gene is not required.

In the context of other cellular systems like transcription, transport, or signaling, various rational methods can be used to try and find out, apriori, which proteins are targets for expression change and what that change should be. These rational methods reduce the number of perturbations that must be tested to find one that improves performance, but they do so at significant cost. Gene deletion studies identify proteins whose presence is critical for a particular function, and important genes can then be over-expressed. Due to the complexity of protein interactions, this is often ineffective at increasing performance. Different types of models have been developed that attempt to describe, from first principles, transcription or signaling behavior as a function of protein levels in the cell. These models often suggest targets where expression changes might lead to different or improved function. The assumptions that underlie these models are simplistic and the parameters difficult to measure, so the predictions they make are often incorrect, especially for non-model organisms. With both gene deletion and modeling, the experiments required to determine how to affect a certain gene are different than the subsequent work to make the change that improves performance. Promoter swapping sidesteps these challenges, because the constructed strain that highlights the importance of a particular perturbation is also, already, the improved strain.

Thus, in particular embodiments, promoter swapping is a multi-step process comprising:

1. Selecting a set of "x" promoters to act as a "ladder." Ideally these promoters have been shown to lead to highly variable expression across multiple genomic loci, but the only requirement is that they perturb gene expression in some way.

2. Selecting a set of "n" genes to target. This set can be every open reading frame (ORF) in a genome, or a subset of ORFs. The subset can be chosen using annotations on ORFs related to function, by relation to previously demonstrated beneficial perturbations (previous promoter swaps or previous SNP swaps), by algorithmic selection based on epistatic interactions between previously generated perturbations, other selection criteria based on hypotheses regarding beneficial ORF to target, or through random selection. In other embodiments, the "n" targeted genes can comprise non-protein coding genes, including non-coding RNAs. In one embodiment, the set of "n" genes can be orthologues of the S. cerevisiae SLN1 gene and orthologues of one or more genes that are part of the same pathway. The orthologues of the S. cerevisiae SLN1 gene and one or more genes that are part of the same pathway can be wild-type are mutant forms of said genes. In one embodiment, the filamentous fungal strain or host cell is *A. niger*, and the set of "n" genes selected is the SNPs in Table 4. In another embodiment wherein *A. niger* is the host cell, the set of "n" genes selected is the non-SNPs or wildtype versions of the SNP containing genes in Table 4. When *A. niger* is the host cell, the set of "n" genes can be the gene for FungiSNP_9 found in Table 4 in addition to one or more genes that are part of the same pathway. When *A. niger* is the host cell, the set of "n" genes can be the gene for FungiSNP_12 found in Table 4 in addition to one or more genes that are part of the same pathway. When *A. niger* is the host cell, the set of "n" genes can be the gene for FungiSNP_40 found in Table 4 in addition to one or more genes that are part of the same pathway. In a preferred embodiment, when *A. niger* is the host cell, the set of "n" genes can be the gene for FungiSNP_18 (i.e., a mutant form of the *A. niger* orthologue of the *S. cerevisiae* SLN1 gene) from Table 4 in addition to one or more genes that are part of the same pathway. The *A. niger* orthologue of the *S. cerevisiae* SLN1 gene and/or the one or more genes in the same pathway can be wild-type or mutant forms of the gene. A mutant form of the *A. niger* orthologue of the *S. cerevisiae* SLN1 gene can be the form with SEQ ID NO: 13. The one or more genes in the pathway can be an *A. niger* orthologue of the *S. cerevisiae* Ypd1, Skn7, Ssk1 and Ssk2 genes or any combination thereof. The one or more genes that are part of the same pathway can be selected from the nucleic acid sequences represented by SEQ ID NOs: 15, 16, 17, 18, 19 or any combination thereof.

Figure 10:
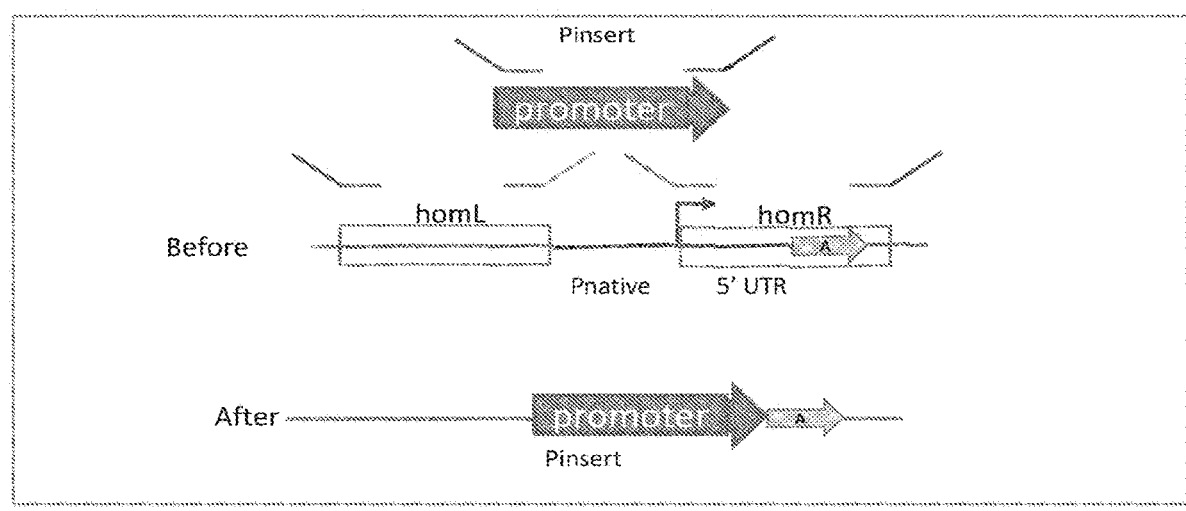
FIG. 10 depicts the different available approaches to promoter swapping. In particular, a promoter swap design for a gene with an annotated promoter is shown.

3. High-throughput strain engineering to rapidly—and in some embodiments, in parallel-carry out the following genetic modifications: When a native promoter exists in front of target gene n and its sequence is known, replace the native promoter with each of the x promoters in the ladder. When the native promoter does not exist, or its sequence is unknown, insert each of the x promoters in the ladder in front of gene n (see e.g., FIG. 10). In this way a "library" (also referred to as a HTP genetic design library) of strains is constructed, wherein each member of the library is an instance of x promoter operably linked to n target, in an otherwise identical genetic context. As previously described combinations of promoters can be inserted, extending the range of combinatorial possibilities upon which the library is constructed.

4. High-throughput screening of the library of strains in a context where their performance against one or more metrics is indicative of the performance that is being optimized.

This foundational process can be extended to provide further improvements in strain performance by, inter alia: (1) Consolidating multiple beneficial perturbations into a single strain background, either one at a time in an interactive process, or as multiple changes in a single step. Multiple perturbations can be either a specific set of defined changes or a partly randomized, combinatorial library of changes. For example, if the set of targets is every gene in a pathway, then sequential regeneration of the library of perturbations into an improved member or members of the previous library of strains can optimize the expression level of each gene in a pathway regardless of which genes are rate limiting at any given iteration; (2) Feeding the performance data resulting from the individual and combinatorial generation of the library into an algorithm that uses that data to predict an optimum set of perturbations based on the interaction of each perturbation; and (3) Implementing a combination of the above two approaches.

The molecular tool, or technique, discussed above is characterized as promoter swapping, but is not limited to promoters and can include other sequence changes that systematically vary the expression level of a set of targets. Other methods for varying the expression level of a set of genes could include: a) a ladder of ribosome binding sites (or Kozak sequences in eukaryotes); b) replacing the start codon of each target with each of the other start codons (i.e start/stop codon exchanges discussed infra); c) attachment of various mRNA stabilizing or destabilizing sequences to the 5' or 3' end, or at any other location, of a transcript, d) attachment of various protein stabilizing or destabilizing sequences at any location in the protein.

The approach is exemplified in the present disclosure with industrial microorganisms, but is applicable to any organism where desired traits can be identified in a population of genetic mutants. For example, this could be used for improving the performance of CHO cells, yeast, insect cells, algae, as well as multi-cellular organisms, such as plants.

Figure 9:
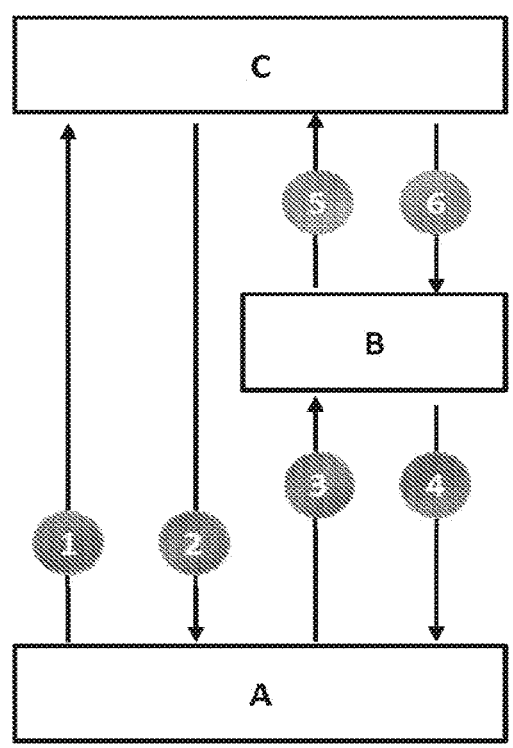
FIG. 9 depicts a first-round SNP swapping experiment according to the methods of the present disclosure. (1) all the SNPs from C will be individually and/or combinatorially cloned into the base A strain ("wave up" A to C). (2) all the SNPs from C will be individually and/or combinatorially removed from the commercial strain C ("wave down" C to A). (3) all the SNPs from B will be individually and/or combinatorially cloned into the base A strain (wave up A to B). (4) all the SNPs from B will be individually and/or combinatorially removed from the commercial strain B (wave down B to A). (5) all the SNPs unique to C will be individually and/or combinatorially cloned into the commercial B strain (wave up B to C). (6) all the SNPs unique to C will be individually and/or combinatorially removed from the commercial strain C (wave down C to B).
Figure 42:
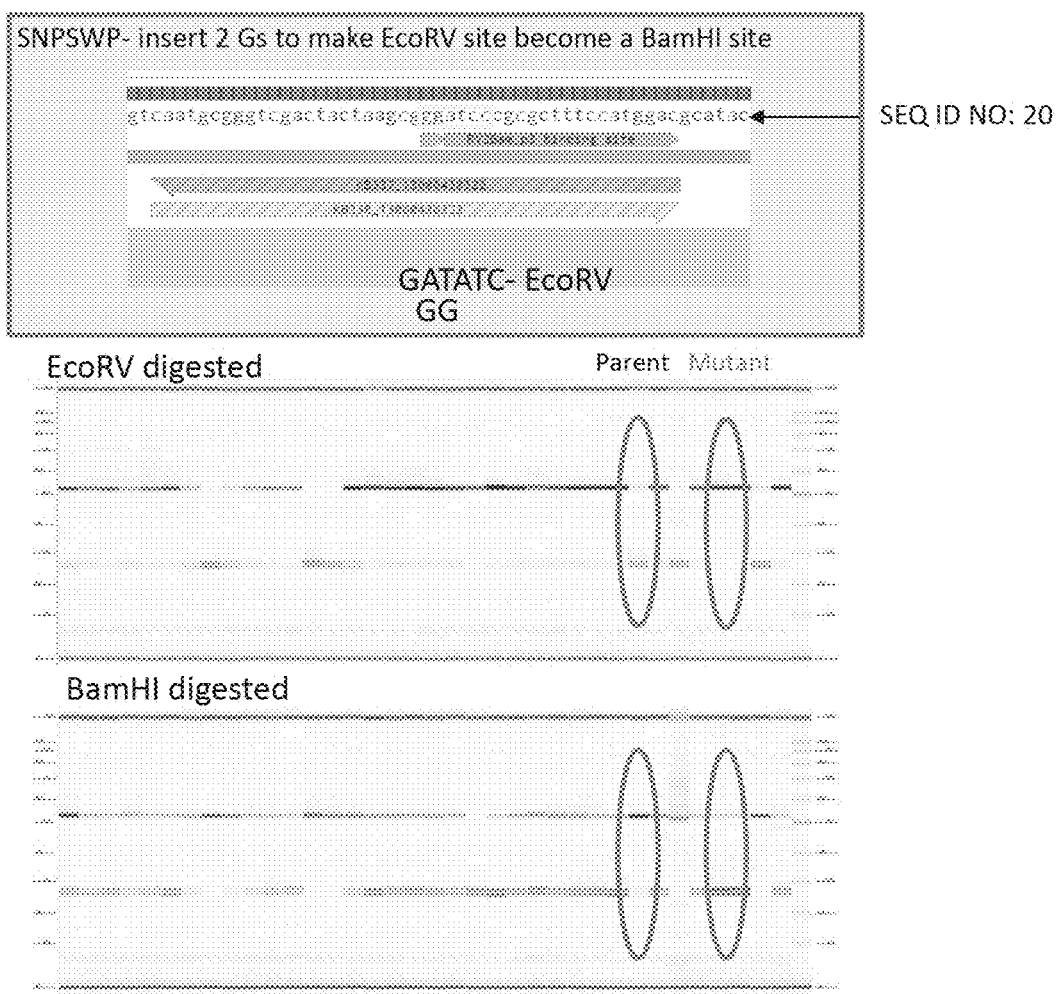
FIG. 42 illustrates the use of SNP SWP to integrate two BP changes as demonstrated by restriction analysis of amplicons. The results depicted in this figure are for an experiment whereby a SNPSWP was performed in a kusA+ strain. Here, an EcoRV restriction site was targeted via SNPSWP in order to add two bp SNP that change the EcoRV site to a BamHI restriction site (see SEQ ID NO: 20). The pyrG gene was targeted to the aygA locus in order to allow for colorimetric selection (i.e., pick yellow colonies) and amplification was followed by restriction digestion to screen for integration of the SNP. Of the 36 yellow transformants picked, 24/36 contained a BamHI site in the amplicon. Thus, SNPSWP co-transformation works without kusA.

2. SNP Swaps: A Molecular Tool for the Derivation of SNP Swap Microbial Strain Libraries In certain embodiments, SNP swapping is not a random mutagenic approach to improving a microbial strain, but rather involves the systematic introduction or removal of individual Small Nuclear Polymorphism nucleotide mutations (i.e. SNPs) (hence the name "SNP swapping") across strains. FIG. 9 conceptually depicts a round of SNP Swapping in the filamentous fungal cells of the present invention. The demonstration of the utility of SNP swapping in filamentous fungal cells is shown in FIG. 42.

Figure 37:
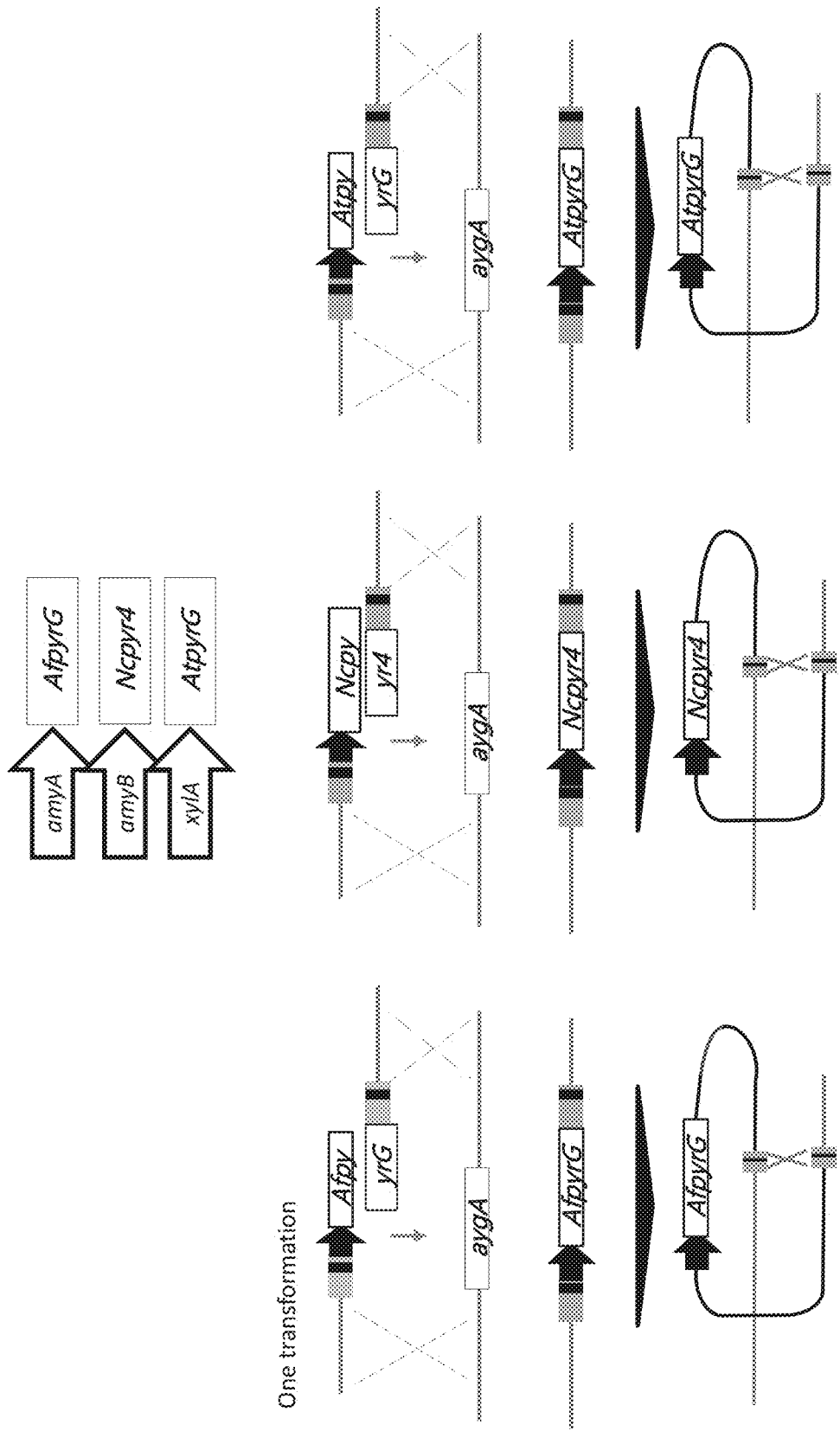
FIG. 37 depicts an embodiment utilizing bipartite marker transformation for performing combinatorial SNPSWP in a coenocytic organism such as a filamentous fungi. This figure depicts a tool for combinatorial SNPSWP in fungi that can combine various inducible promoters with divergent pyrG genes and promoters that can be catabolite repressed by glucose, Transformants can be selected on glucose such that multiple integrations of weakly expressed genes will be favored and transformants can be plated on induction media with FOA to get loop-outs.

In one embodiment, the methods and systems provided herein are utilized for SNP swapping in order to generate filamentous fungal libraries comprising filamentous fungi with individual SNPs or combinations of SNPs. Combinatorial SNP swapping can be achieved using bipartite transformation as illustrated in FIG. 37.

The resultant microbes that are engineered via this process form HTP genetic design libraries.

The HTP genetic design library can refer to the actual physical microbial strain collection that is formed via this process, with each member strain being representative of the presence or absence of a given SNP, in an otherwise identical genetic background, said library being termed a "SNP swap microbial strain library." In the specific context of filamentous fungus (e.g., *A. niger*), the library can be termed a "SNP swap filamentous fungal strain library," or "SNP swap *A. niger* strain library," but the terms can be used synonymously, as filamentous fungus is a specific example of a microbe or coenocytic organism.

Furthermore, the HTP genetic design library can refer to the collection of genetic perturbations—in this case a given SNP being present or a given SNP being absent-said collection being termed a "SNP swap library."

In some embodiments, SNP swapping involves the reconstruction of host organisms with optimal combinations of target SNP "building blocks" with identified beneficial performance effects. Thus, in some embodiments, SNP swapping involves consolidating multiple beneficial mutations into a single strain background, either one at a time in an iterative process, or as multiple changes in a single step. Multiple changes can be either a specific set of defined changes or a partly randomized, combinatorial library of mutations.

In other embodiments, SNP swapping also involves removing multiple mutations identified as detrimental from a strain, either one at a time in an iterative process, or as multiple changes in a single step. Multiple changes can be either a specific set of defined changes or a partly randomized, combinatorial library of mutations. In some embodiments, the SNP swapping methods of the present disclosure include both the addition of beneficial SNPs, and removing detrimental and/or neutral mutations.

SNP swapping is a powerful tool to identify and exploit both beneficial and detrimental mutations in a lineage of strains subjected to mutagenesis and selection for an improved trait of interest. SNP swapping utilizes high-throughput genome engineering techniques to systematically determine the influence of individual mutations in a mutagenic lineage. Genome sequences are determined for strains across one or more generations of a mutagenic lineage with known performance improvements. High-throughput genome engineering is then used systematically to recapitulate mutations from improved strains in earlier lineage strains, and/or revert mutations in later strains to earlier strain sequences. The performance of these strains is then evaluated and the contribution of each individual mutation on the improved phenotype of interest can be determined. As aforementioned, the microbial strains that result from this process are analyzed/characterized and form the basis for the SNP swap genetic design libraries that can inform microbial strain improvement across host strains.

Removal of detrimental mutations can provide immediate performance improvements, and consolidation of beneficial mutations in a strain background not subject to mutagenic burden can rapidly and greatly improve strain performance. The various microbial strains produced via the SNP swapping process form the HTP genetic design SNP swapping libraries, which are microbial strains comprising the various added/deleted/or consolidated SNPs, but with otherwise identical genetic backgrounds.

As discussed previously, random mutagenesis and subsequent screening for performance improvements is a commonly used technique for industrial strain improvement, and many strains currently used for large scale manufacturing have been developed using this process iteratively over a period of many years, sometimes decades. Random approaches to generating genomic mutations such as exposure to UV radiation or chemical mutagens such as ethyl methanesulfonate were a preferred method for industrial strain improvements because: 1) industrial organisms may be poorly characterized genetically or metabolically, rendering target selection for directed improvement approaches difficult or impossible; 2) even in relatively well characterized systems, changes that result in industrial performance improvements are difficult to predict and may require perturbation of genes that have no known function, and 3) genetic tools for making directed genomic mutations in a given industrial organism may not be available or very slow and/or difficult to use.

However, despite the aforementioned benefits of this process, there are also a number of known disadvantages. Beneficial mutations are relatively rare events, and in order to find these mutations with a fixed screening capacity, mutations rates must be sufficiently high. This often results in unwanted neutral and partly detrimental mutations being incorporated into strains along with beneficial changes. Over time this 'mutagenic burden' builds up, resulting in strains with deficiencies in overall robustness and key traits such as growth rates. Eventually 'mutagenic burden' renders further improvements in performance through random mutagenesis increasingly difficult or impossible to obtain. Without suitable tools, it is impossible to consolidate beneficial mutations found in discrete and parallel branches of strain lineages.

SNP swapping is an approach to overcome these limitations by systematically recapitulating or reverting some or all mutations observed when comparing strains within a mutagenic lineage. In this way, both beneficial ('causative') mutations can be identified and consolidated, and/or detrimental mutations can be identified and removed. This allows rapid improvements in strain performance that could not be achieved by further random mutagenesis or targeted genetic engineering.

Removal of genetic burden or consolidation of beneficial changes into a strain with no genetic burden also provides a new, robust starting point for additional random mutagenesis that may enable further improvements.

In addition, as orthogonal beneficial changes are identified across various, discrete branches of a mutagenic strain lineage, they can be rapidly consolidated into better performing strains. These mutations can also be consolidated into strains that are not part of mutagenic lineages, such as strains with improvements gained by directed genetic engineering.

Other approaches and technologies exist to randomly recombine mutations between strains within a mutagenic lineage. These include techniques such as protoplast fusion and whole genome shuffling that facilitate genomic recombination across mutated strains. For some industrial microorganisms such as yeast and filamentous fungi, natural mating cycles can also be exploited for pairwise genomic recombination. In this way, detrimental mutations can be removed by 'back-crossing' mutants with parental strains and beneficial mutations consolidated. However, these approaches are subject to many limitations that are circumvented using the SNP swapping methods of the present disclosure.

For example, as these approaches rely on a relatively small number of random recombination crossover events to swap mutations, it may take many cycles of recombination and screening to optimize strain performance. In addition, although natural recombination events are essentially random, they are also subject to genome positional bias and some mutations may be difficult to address. These approaches also provide little information about the influence of individual mutations without additional genome sequencing and analysis. SNP swapping overcomes these fundamental limitations as it is not a random approach, but rather the systematic introduction or removal of individual mutations across strains.

In some embodiments, the present disclosure teaches methods for identifying the SNP sequence diversity present among the organisms of a diversity pool. A diversity pool can be a given number in of microbes utilized for analysis, with said microbes' genomes representing the "diversity pool."

In particular aspects, a diversity pool may be an original parent strain ($S_1$) with a "baseline" or "reference" genetic sequence at a particular time point ($S_1Gen_1$) and then any number of subsequent offspring strains ($S_{2-n}$) that were derived/developed from said $S_1$ strain and that have a different genome ($S_{2-n}Gen_{2-n}$), in relation to the baseline genome of $S_1$.

For example, in some embodiments, the present disclosure teaches sequencing the microbial genomes in a diversity pool to identify the SNPs present in each strain. In one embodiment, the strains of the diversity pool are historical microbial production strains. Thus, a diversity pool of the present disclosure can include for example, an industrial reference strain, and one or more mutated industrial strains produced via traditional strain improvement programs.

In some embodiments, the SNPs within a diversity pool are determined with reference to a "reference strain." In some embodiments, the reference strain is a wild-type strain. In other embodiments, the reference strain is an original industrial strain prior to being subjected to any mutagenesis. The reference strain can be defined by the practitioner and does not have to be an original wild-type strain or original industrial strain. The base strain is merely representative of what will be considered the "base," "reference" or original genetic background, by which subsequent strains that were derived, or were developed from said reference strain, are to be compared.

Once all SNPS in the diversity pool are identified, the present disclosure teaches methods of SNP swapping and screening methods to delineate (i.e. quantify and characterize) the effects (e.g. creation of a phenotype of interest) of SNPs individually and/or in groups.

In some embodiments, the SNP swapping methods of the present disclosure comprise the step of introducing one or more SNPs identified in a mutated strain (e.g., a strain from amongst $S_{2-n}Gen_{2-n}$) to a reference strain ($S_1Gen_1$) or wild-type strain ("wave up").

In other embodiments, the SNP swapping methods of the present disclosure comprise the step of removing one or more SNPs identified in a mutated strain (e.g., a strain from amongst $S_{2-n}Gen_{2-n}$) ("wave down").

In some embodiments, each generated strain comprising one or more SNP changes (either introducing or removing) is cultured and analyzed under one or more criteria of the present disclosure (e.g., production of a chemical or product of interest). Data from each of the analyzed host strains is associated, or correlated, with the particular SNP, or group of SNPs present in the host strain, and is recorded for future use. Thus, the present disclosure enables the creation of large and highly annotated HTP genetic design microbial strain libraries that are able to identify the effect of a given SNP on any number of microbial genetic or phenotypic traits of interest. The information stored in these HTP genetic design libraries informs the machine learning algorithms of the HTP genomic engineering platform and directs future iterations of the process, which ultimately leads to evolved microbial organisms that possess highly desirable properties/traits.

3. Start/Stop Codon Exchanges: A Molecular Tool for the Derivation of Start/Stop Codon Microbial Strain Libraries In some embodiments, the present disclosure teaches methods of swapping start and stop codon variants. For example, typical stop codons for *S. cerevisiae* and mammals are TAA (UAA) and TGA (UGA), respectively. The typical stop codon for monocotyledonous plants is TGA (UGA), whereas insects and *E. coli* commonly use TAA (UAA) as the stop codon (Dalphin et al. (1996) Nucl. Acids Res. 24: 216-218). In other embodiments, the present disclosure teaches use of the TAG (UAG) stop codons.

The present disclosure similarly teaches swapping start codons. In some embodiments, the present disclosure teaches use of the ATG (AUG) start codon utilized by most organisms (especially eukaryotes). In some embodiments, the present disclosure teaches that prokaryotes use ATG (AUG) the most, followed by GTG (GUG) and TTG (UUG).

In other embodiments, the present disclosure teaches replacing ATG start codons with TTG. In some embodiments, the present disclosure teaches replacing ATG start codons with GTG. In some embodiments, the present disclosure teaches replacing GTG start codons with ATG. In some embodiments, the present disclosure teaches replacing GTG start codons with TTG. In some embodiments, the present disclosure teaches replacing TTG start codons with ATG. In some embodiments, the present disclosure teaches replacing TTG start codons with GTG.

In other embodiments, the present disclosure teaches replacing TAA stop codons with TAG. In some embodiments, the present disclosure teaches replacing TAA stop codons with TGA. In some embodiments, the present disclosure teaches replacing TGA stop codons with TAA. In some embodiments, the present disclosure teaches replacing TGA stop codons with TAG. In some embodiments, the present disclosure teaches replacing TAG stop codons with TAA. In some embodiments, the present disclosure teaches replacing TAG stop codons with TGA.

4. Stop Swap: A Molecular Tool for the Derivation of STOP Swap Microbial Strain Libraries In some embodiments, the present disclosure teaches methods of improving host cell productivity through the optimization of cellular gene transcription. Gene transcription is the result of several distinct biological phenomena, including transcriptional initiation (RNAp recruitment and transcriptional complex formation), elongation (strand synthesis/extension), and transcriptional termination (RNAp detachment and termination). Although much attention has been devoted to the control of gene expression through the transcriptional modulation of genes (e.g., by changing promoters, or inducing regulatory transcription factors), comparatively few efforts have been made towards the modulation of transcription via the modulation of gene terminator sequences.

The most obvious way that transcription impacts on gene expression levels is through the rate of Pol II initiation, which can be modulated by combinations of promoter or enhancer strength and trans-activating factors (Kadonaga, J T. 2004 "Regulation of RNA polymerase II transcription by sequence-specific DNA binding factors" Cell. 2004 Jan. 23; 116(2):247-57). In eukaryotes, elongation rate may also determine gene expression patterns by influencing alternative splicing (Cramer P. et al., 1997 "Functional association between promoter structure and transcript alternative splicing." Proc Natl Acad Sci USA. 1997 Oct. 14; 94(21):11456-60). Failed termination on a gene can impair the expression of downstream genes by reducing the accessibility of the promoter to Pol II (Greger IH. et al., 2000 "Balancing transcriptional interference and initiation on the GAL7 promoter of *Saccharomyces cerevisiae*." Proc Natl Acad Sci USA. 2000 Jul. 18; 97(15):8415-20). This process, known as transcriptional interference, is particularly relevant in lower eukaryotes, as they often have closely spaced genes.

Termination sequences can also affect the expression of the genes to which the sequences belong. For example, studies show that inefficient transcriptional termination in eukaryotes results in an accumulation of unspliced pre-mRNA (see West, S., and Proudfoot, N.J., 2009 "Transcriptional Termination Enhances Protein Expression in Human Cells" Mol Cell. 2009 Feb. 13; 33(3-9); 354-364). Other studies have also shown that 3' end processing, can be delayed by inefficient termination (West, S et al., 2008 "Molecular dissection of mammalian RNA polymerase II transcriptional termination." Mol Cell. 2008 Mar. 14; 29(5): 600-10). Transcriptional termination can also affect mRNA stability by releasing transcripts from sites of synthesis.

Termination of Transcription Mechanism in Eukaryotes

Transcriptional termination in eukaryotes operates through terminator signals that are recognized by protein factors associated with the RNA polymerase II. In some embodiments, the cleavage and polyadenylation specificity factor (CPSF) and cleavage stimulation factor (CstF) transfer from the carboxyl terminal domain of RNA polymerase II to the poly-A signal. In some embodiments, the CPSF and CstF factors also recruit other proteins to the termination site, which then cleave the transcript and free the mRNA from the transcription complex. Termination also triggers polyadenylation of mRNA transcripts. Illustrative examples of validated eukaryotic termination factors, and their conserved structures are discussed in later portions of this document.

Terminator sequences or signals can be operably linked to the 3' termini of sequences to be expressed. A variety of known fungal terminators are likely to be functional in the host strains of the disclosure. Examples are the *A. nidulans* trpC terminator, *A. niger* alpha-glucosidase terminator, *A. niger* glucoamylase terminator, *Mucor miehei* carboxyl protease terminator (see U.S. Pat. No. 5,578,463), *Chrysosporium* terminator sequences, e.g. the EG6 terminator, and the *Trichoderma reesei* cellobiohydrolase terminator. In one embodiment, the terminator sequences are direct repeats (DRs). In one embodiment, the terminator sequence is the native *A. niger* pyrG terminator. The native *A. niger* pyrG sequence can have the sequence of SEQ ID NO. 5

Terminator Swapping (STOP Swap)

In some embodiments, the present disclosure teaches methods of selecting termination sequences ("terminators") with optimal expression properties to produce beneficial effects on overall-host strain productivity.

For example, in some embodiments, the present disclosure teaches methods of identifying one or more terminators and/or generating variants of one or more terminators within a host cell, which exhibit a range of expression strengths (e.g. terminator ladders discussed infra). A particular combination of these identified and/or generated terminators can be grouped together as a terminator ladder, which is explained in more detail below.

The terminator ladder in question is then associated with a given gene of interest. Thus, if one has terminators $T_1$-$T_8$ (representing eight terminators that have been identified and/or generated to exhibit a range of expression strengths when combined with one or more promoters) and associates the terminator ladder with a single gene of interest in a host cell (i.e. genetically engineer a host cell with a given terminator operably linked to the 3' end of to a given target gene), then the effect of each combination of the terminators can be ascertained by characterizing each of the engineered strains resulting from each combinatorial effort, given that the engineered host cells have an otherwise identical genetic background except the particular terminator(s) associated with the target gene. The resultant host cells that are engineered via this process form HTP genetic design libraries.

The HTP genetic design library can refer to the actual physical microbial strain collection that is formed via this process, with each member strain being representative of a given terminator operably linked to a particular target gene, in an otherwise identical genetic background, said library being termed a "terminator swap microbial strain library" or "STOP swap microbial strain library." In the specific context of filamentous fungus (e.g., *A. niger*), the library can be termed a "terminator swap filamentous fungal strain library," "terminator swap filamentous *A. niger* library", "STOP swap filamentous fungal strain library," or "STOP swap *A. niger* strain library," but the terms can be used synonymously, as filamentous fungus or *A. niger* are specific examples of a microbe.

Furthermore, the HTP genetic design library can refer to the collection of genetic perturbations—in this case a given terminator x operably linked to a given gene y—said collection being termed a "terminator swap library" or "STOP swap library."

Further, one can utilize the same terminator ladder comprising terminators $T_1$-$T_8$ to engineer microbes, wherein each of the eight terminators is operably linked to 10 different gene targets. The result of this procedure would be 80 host cell strains that are otherwise assumed genetically identical, except for the particular terminators operably linked to a target gene of interest. These 80 host cell strains could be appropriately screened and characterized and give rise to another HTP genetic design library. The characterization of the microbial strains in the HTP genetic design library produces information and data that can be stored in any database, including without limitation, a relational database, an object-oriented database or a highly distributed NoSQL database. This data/information could include, for example, a given terminators' (e.g., $T_1$-$T_8$) effect when operably linked to a given gene target. This data/information can also be the broader set of combinatorial effects that result from operably linking two or more of promoters $T_1$-$T_8$ to a given gene target.

The aforementioned examples of eight terminators and 10 target genes is merely illustrative, as the concept can be applied with any given number of promoters that have been grouped together based upon exhibition of a range of expression strengths and any given number of target genes.

In summary, utilizing various terminators to modulate expression of various genes in an organism is a powerful tool to optimize a trait of interest. The molecular tool of terminator swapping, developed by the inventors, uses a ladder of terminator sequences that have been demonstrated to vary expression of at least one locus under at least one condition. This ladder is then systematically applied to a group of genes in the organism using high-throughput genome engineering. This group of genes is determined to have a high likelihood of impacting the trait of interest based on any one of a number of methods. These could include selection based on known function, or impact on the trait of interest, or algorithmic selection based on previously determined beneficial genetic diversity.

The resultant HTP genetic design microbial library of organisms containing a terminator sequence linked to a gene is then assessed for performance in a high-throughput screening model, and promoter-gene linkages which lead to increased performance are determined and the information stored in a database. The collection of genetic perturbations (i.e. given terminator x linked to a given gene y) form a "terminator swap library," which can be utilized as a source of potential genetic alterations to be utilized in microbial engineering processing. Over time, as a greater set of genetic perturbations is implemented against a greater diversity of microbial backgrounds, each library becomes more powerful as a corpus of experimentally confirmed data that can be used to more precisely and predictably design targeted changes against any background of interest. That is in some embodiments, the present disclosures teaches introduction of one or more genetic changes into a host cell based on previous experimental results embedded within the meta data associated with any of the genetic design libraries of the disclosure.

Thus, in particular embodiments, terminator swapping is a multi-step process comprising:

1. Selecting a set of "x" terminators to act as a "ladder." Ideally these terminators have been shown to lead to highly variable expression across multiple genomic loci, but the only requirement is that they perturb gene expression in some way.

2. Selecting a set of "n" genes to target. This set can be every ORF in a genome, or a subset of ORFs. The subset can be chosen using annotations on ORFs related to function, by relation to previously demonstrated beneficial perturbations (previous promoter swaps, STOP swaps, or SNP swaps), by algorithmic selection based on epistatic interactions between previously generated perturbations, other selection criteria based on hypotheses regarding beneficial ORF to target, or through random selection. In other embodiments, the "n" targeted genes can comprise non-protein coding genes, including non-coding RNAs.

3. High-throughput strain engineering to rapidly and in parallel carry out the following genetic modifications: When a native terminator exists at the 3' end of target gene n and its sequence is known, replace the native terminator with each of the x terminators in the ladder. When the native terminator does not exist, or its sequence is unknown, insert each of the x terminators in the ladder after the gene stop codon.

In this way a "library" (also referred to as a HTP genetic design library) of strains is constructed, wherein each member of the library is an instance of x terminator linked to n target, in an otherwise identical genetic context. As previously described, combinations of terminators can be inserted, extending the range of combinatorial possibilities upon which the library is constructed.

4. High-throughput screening of the library of strains in a context where their performance against one or more metrics is indicative of the performance that is being optimized.

This foundational process can be extended to provide further improvements in strain performance by, inter alia: (1) Consolidating multiple beneficial perturbations into a single strain background, either one at a time in an interactive process, or as multiple changes in a single step. Multiple perturbations can be either a specific set of defined changes or a partly randomized, combinatorial library of changes. For example, if the set of targets is every gene in a pathway, then sequential regeneration of the library of perturbations into an improved member or members of the previous library of strains can optimize the expression level of each gene in a pathway regardless of which genes are rate limiting at any given iteration; (2) Feeding the performance data resulting from the individual and combinatorial generation of the library into an algorithm that uses that data to predict an optimum set of perturbations based on the interaction of each perturbation; and (3) Implementing a combination of the above two approaches.

The approach is exemplified in the present disclosure with industrial microorganisms, but is applicable to any organism where desired traits can be identified in a population of genetic mutants. For example, this could be used for improving the performance of CHO cells, yeast, insect cells, algae, as well as multi-cellular organisms, such as plants.

5. Sequence Optimization: A Molecular Tool for the Derivation of Optimized Sequence Microbial Strain Libraries In one embodiment, the methods of the disclosure comprise codon optimizing one or more genes expressed by the host organism. Methods for optimizing codons to improve expression in various hosts are known in the art and are described in the literature (see U.S. Pat. App. Pub. No. 2007/0292918, incorporated herein by reference in its entirety). Optimized coding sequences containing codons preferred by a particular prokaryotic or eukaryotic host (see also, Murray el al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence.

Protein expression is governed by a host of factors including those that affect transcription, mRNA processing, and stability and initiation of translation. Optimization can thus address any of a number of sequence features of any particular gene. As a specific example, a rare codon induced translational pause can result in reduced protein expression. A rare codon induced translational pause includes the presence of codons in the polynucleotide of interest that are rarely used in the host organism may have a negative effect on protein translation due to their scarcity in the available tRNA pool.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stem-loop structures can also be involved in transcriptional pausing and attenuation. An optimized polynucleotide sequence can contain minimal secondary structures in the RBS and gene coding regions of the nucleotide sequence to allow for improved transcription and translation.

For example, the optimization process can begin by identifying the desired amino acid sequence to be expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures.

6. Epistasis Mapping—A Predictive Analytical Tool Enabling Beneficial Genetic Consolidations In some embodiments, the present disclosure teaches epistasis mapping methods for predicting and combining beneficial genetic alterations into a host cell. The genetic alterations may be created by any of the aforementioned HTP molecular tool sets (e.g., promoter swaps, SNP swaps, start/stop codon exchanges, sequence optimization, and STOP swaps) and the effect of those genetic alterations would be known from the characterization of the derived HTP genetic design microbial strain libraries. Thus, as used herein, the term epistasis mapping includes methods of identifying combinations of genetic alterations (e.g., beneficial SNPs or beneficial promoter/target gene associations) that are likely to yield increases in host performance.

In embodiments, the epistasis mapping methods of the present disclosure are based on the idea that the combination of beneficial mutations from two different functional groups is more likely to improve host performance, as compared to a combination of mutations from the same functional group. See, e.g., Costanzo, The Genetic Landscape of a Cell, Science, Vol. 327, Issue 5964, Jan. 22, 2010, pp. 425-431 (incorporated by reference herein in its entirety).

Mutations from the same functional group are more likely to operate by the same mechanism, and are thus more likely to exhibit negative or neutral epistasis on overall host performance. In contrast, mutations from different functional groups are more likely to operate by independent mechanisms, which can lead to improved host performance and in some instances synergistic effects.

Thus, in some embodiments, the present disclosure teaches methods of analyzing SNP mutations to identify SNPs predicted to belong to different functional groups. In some embodiments, SNP functional group similarity is determined by computing the cosine similarity of mutation interaction profiles. The present disclosure also illustrates comparing SNPs via a mutation similarity matrix or dendrogram.

Thus, the epistasis mapping procedure provides a method for grouping and/or ranking a diversity of genetic mutations applied in one or more genetic backgrounds for the purposes of efficient and effective consolidations of said mutations into one or more genetic backgrounds.

In aspects, consolidation is performed with the objective of creating novel strains which are optimized for the production of target biomolecules. Through the taught epistasis mapping procedure, it is possible to identify functional groupings of mutations, and such functional groupings enable a consolidation strategy that minimizes undesirable epistatic effects.

As previously explained, the optimization of microbes for use in industrial fermentation is an important and difficult problem, with broad implications for the economy, society, and the natural world. Traditionally, microbial engineering has been performed through a slow and uncertain process of random mutagenesis. Such approaches leverage the natural evolutionary capacity of cells to adapt to artificially imposed selection pressure. Such approaches are also limited by the rarity of beneficial mutations, the ruggedness of the underlying fitness landscape, and more generally underutilize the state of the art in cellular and molecular biology.

Modern approaches leverage new understanding of cellular function at the mechanistic level and new molecular biology tools to perform targeted genetic manipulations to specific phenotypic ends. In practice, such rational approaches are confounded by the underlying complexity of biology. Causal mechanisms are poorly understood, particularly when attempting to combine two or more changes that each has an observed beneficial effect. Sometimes such consolidations of genetic changes yield positive outcomes (measured by increases in desired phenotypic activity), although the net positive outcome may be lower than expected and in some cases higher than expected. In other instances, such combinations produce either net neutral effect or a net negative effect. This phenomenon is referred to as epistasis, and is one of the fundamental challenges to microbial engineering (and genetic engineering generally).

As aforementioned, the present HTP genomic engineering platform solves many of the problems associated with traditional microbial engineering approaches. The present HTP platform uses automation technologies to perform hundreds or thousands of genetic mutations at once. In particular aspects, unlike the rational approaches described above, the disclosed HTP platform enables the parallel construction of thousands of mutants to more effectively explore large subsets of the relevant genomic space, as disclosed in U.S. application Ser. No. 15/140,296, entitled Microbial Strain Design System And Methods For Improved Large-Scale Production Of Engineered Nucleotide Sequences, incorporated by reference herein in its entirety. By trying "everything," the present HTP platform sidesteps the difficulties induced by our limited biological understanding.

However, at the same time, the present HTP platform faces the problem of being fundamentally limited by the combinatorial explosive size of genomic space, and the effectiveness of computational techniques to interpret the generated data sets given the complexity of genetic interactions. Techniques are needed to explore subsets of vast combinatorial spaces in ways that maximize non-random selection of combinations that yield desired outcomes.

Somewhat similar HTP approaches have proved effective in the case of enzyme optimization. In this niche problem, a genomic sequence of interest (on the order of 1000 bases), encodes a protein chain with some complicated physical configuration. The precise configuration is determined by the collective electromagnetic interactions between its constituent atomic components. This combination of short genomic sequence and physically constrained folding problem lends itself specifically to greedy optimization strategies. That is, it is possible to individually mutate the sequence at every residue and shuffle the resulting mutants to effectively sample local sequence space at a resolution compatible with the Sequence Activity Response modeling.

However, for full genomic optimizations for biomolecules, such residue-centric approaches are insufficient for some important reasons. First, because of the exponential increase in relevant sequence space associated with genomic optimizations for biomolecules. Second, because of the added complexity of regulation, expression, and metabolic interactions in biomolecule synthesis. The present inventors have solved these problems via the taught epistasis mapping procedure.

The taught method for modeling epistatic interactions, between a collection of mutations for the purposes of more efficient and effective consolidation of said mutations into one or more genetic backgrounds, is groundbreaking and highly needed in the art.

When describing the epistasis mapping procedure, the terms "more efficient" and "more effective" refers to the avoidance of undesirable epistatic interactions among consolidation strains with respect to particular phenotypic objectives.

As the process has been generally elaborated upon above, a more specific workflow example will now be described.

First, one begins with a library of M mutations and one or more genetic backgrounds (e.g., parent filamentous fungal strains). Neither the choice of library nor the choice of genetic backgrounds is specific to the method described here. But in a particular implementation, a library of mutations may include exclusively, or in combination: SNP swap libraries, Promoter swap libraries, or any other mutation library described herein.

In one implementation, only a single genetic background is provided. In this case, a collection of distinct genetic backgrounds (microbial mutants) will first be generated from this single background. This may be achieved by applying the primary library of mutations (or some subset thereof) to the given background for example, application of a HTP genetic design library of particular SNPs or a HTP genetic design library of particular promoters to the given genetic background, to create a population (perhaps 100's or 1,000's) of microbial mutants with an identical genetic background except for the particular genetic alteration from the given HTP genetic design library incorporated therein. As detailed below, this embodiment can lead to a combinatorial library or pairwise library.

In another implementation, a collection of distinct known genetic backgrounds may simply be given. As detailed below, this embodiment can lead to a subset of a combinatorial library.

In a particular implementation, the number of genetic backgrounds and genetic diversity between these backgrounds (measured in number of mutations or sequence edit distance or the like) is determined to maximize the effectiveness of this method.

A genetic background may be a natural, native or wild-type strain or a mutated, engineered strain. N distinct background strains may be represented by a vector b. In one example, the background b may represent engineered backgrounds formed by applying N primary mutations $m_0=(m_1, m_2, \ldots m_N)$ to a wild-type background strain $b_0$ to form the N mutated background strains $b=m_0 b_0=(m_1 b_0, m_2 b_0, \ldots m_N b_0)$, where $m_i b_0$ represents the application of mutation $m_i$ to background strain $b_0$.

In either case (i.e. a single provided genetic background or a collection of genetic backgrounds), the result is a collection of N genetically distinct backgrounds. Relevant phenotypes are measured for each background.

Figure 14:
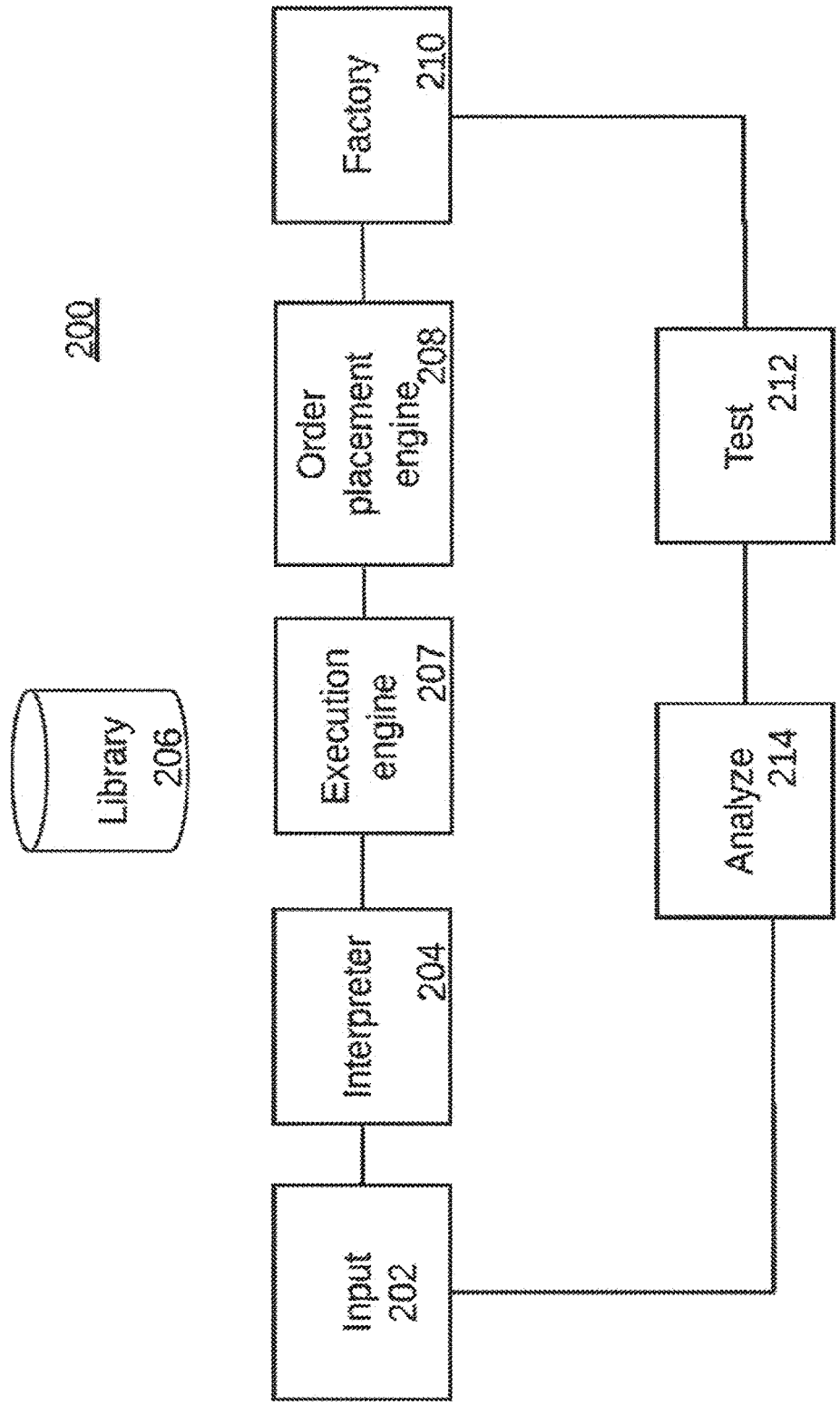
FIG. 14 diagrams an embodiment of LIMS system of the present disclosure for filamentous fungal strain improvement.

Second, each mutation in a collection of M mutations $m_1$ is applied to each background within the collection of N background strains b to form a collection of M×N mutants. In the implementation where the N backgrounds were themselves obtained by applying the primary set of mutations $m_0$ (as described above), the resulting set of mutants will sometimes be referred to as a combinatorial library or a pairwise library. In another implementation, in which a collection of known backgrounds has been provided explicitly, the resulting set of mutants may be referred to as a subset of a combinatorial library. Similar to generation of engineered background vectors, in embodiments, the input interface 202 (see, FIG. 14) receives the mutation vector $m_1$ and the background vector b, and a specified operation such as cross product.

Continuing with the engineered background example above, forming the M×N combinatorial library may be represented by the matrix formed by $m_1 \times m_0 b_0$, the cross product of $m_1$ applied to the N backgrounds of $b=m_0 b_0$, where each mutation in $m_1$ is applied to each background strain within b. Each ith row of the resulting M×N matrix represents the application of the ith mutation within $m_1$ to all the strains within background collection b. In one embodiment, $m_1=m_0$ and the matrix represents the pairwise application of the same mutations to starting strain $b_0$. In that case, the matrix is symmetric about its diagonal (M=N), and the diagonal may be ignored in any analysis since it represents the application of the same mutation twice.

In embodiments, forming the M×N matrix may be achieved by inputting into the input interface 202 (see, FIG. 14) the compound expression $m_1 \times m_0 b_0$. The component vectors of the expression may be input directly with their elements explicitly specified, via one or more DNA specifications, or as calls to the library 206 to enable retrieval of the vectors during interpretation by interpreter 204. As described in U.S. patent application Ser. No. 15/140,296, entitled "Microbial Strain Design System and Methods for Improved Large Scale Production of Engineered Nucleotide Sequences," via the interpreter 204, execution engine 207, order placement engine 208, and factory 210, the LIMS system 200 generates the microbial strains specified by the input expression.

Figure 19:
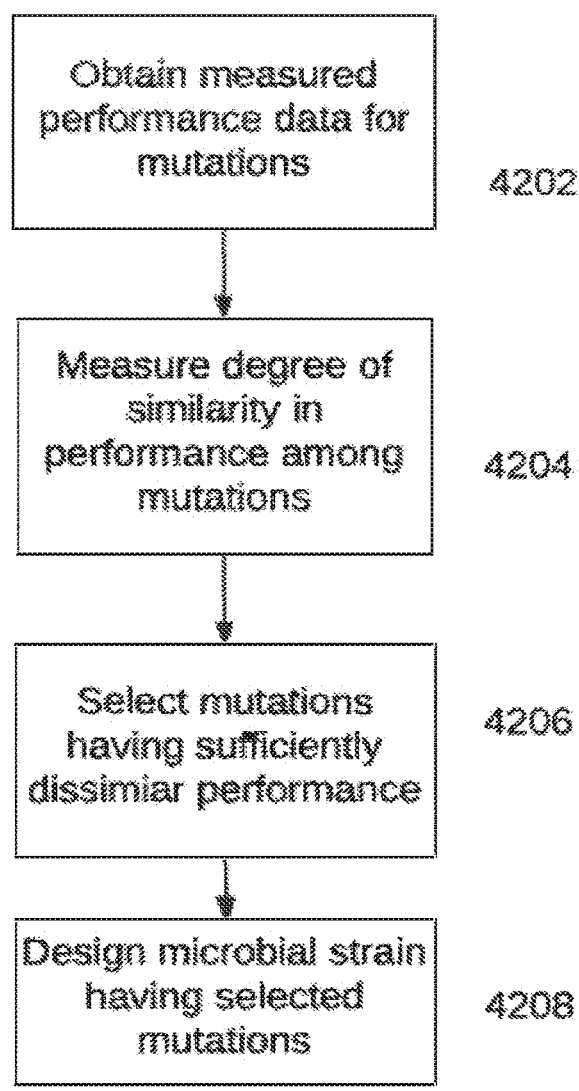
FIG. 19 is a flowchart illustrating the consideration of epistatic effects in the selection of mutations for the design of a microbial strain, according to embodiments of the disclosure.

Third, with reference to FIG. 19, the analysis equipment 214 (see, FIG. 14) measures phenotypic responses for each mutant within the M×N combinatorial library matrix (4202). As such, the collection of responses can be construed as an M×N Response Matrix R. Each element of R may be represented as $r_{ij}=y(m_i, m_j)$, where y represents the response (performance) of background strain $b_j$ within engineered collection b as mutated by mutation $m_i$. For simplicity, and practicality, we assume pairwise mutations where $m_1=m_0$. Where, as here, the set of mutations represents a pairwise mutation library, the resulting matrix may also be referred to as a gene interaction matrix or, more particularly, as a mutation interaction matrix.

Those skilled in the art will recognize that, in some embodiments, operations related to epistatic effects and predictive strain design may be performed entirely through automated means of the LIMS system 200, e.g., by the analysis equipment 214 (see, FIG. 14), or by human implementation, or through a combination of automated and manual means. When an operation is not fully automated, the elements of the LIMS system 200, e.g., analysis equipment 214, may, for example, receive the results of the human performance of the operations rather than generate results through its own operational capabilities. As described elsewhere herein, components of the LIMS system 200, such as the analysis equipment 214, may be implemented wholly or partially by one or more computer systems. In some embodiments, in particular where operations related to predictive strain design are performed by a combination of automated and manual means, the analysis equipment 214 may include not only computer hardware, software or firmware (or a combination thereof), but also equipment operated by a human operator such as that listed in Table 3 below, e.g., the equipment listed under the category of "Evaluate performance."

Fourth, the analysis equipment 214 (see, FIG. 14) normalizes the response matrix. Normalization consists of a manual and/or, in this embodiment, automated processes of adjusting measured response values for the purpose of removing bias and/or isolating the relevant portions of the effect specific to this method. With respect to FIG. 19, the first step 4202 may include obtaining normalized measured data. In general, in the claims directed to predictive strain design and epistasis mapping, the terms "performance measure" or "measured performance" or the like may be used to describe a metric that reflects measured data, whether raw or processed in some manner, e.g., normalized data. In a particular implementation, normalization may be performed by subtracting a previously measured background response from the measured response value. In that implementation, the resulting response elements may be formed as $r_{ij}=y(m_i, m_j)-y(m_j)$, where $y(m_j)$ is the response of the engineered background strain $b_j$ within engineered collection b caused by application of primary mutation $m_j$ to parent strain $b_0$. Note that each row of the normalized response matrix is treated as a response profile for its corresponding mutation. That is, the ith row describes the relative effect of the corresponding mutation mi applied to all the background strains $b_j$ for j=1 to N.

With respect to the example of pairwise mutations, the combined performance/response of strains resulting from two mutations may be greater than, less than, or equal to the performance/response of the strain to each of the mutations individually. This effect is known as "epistasis," and may, in some embodiments, be represented as $e_{ij}=y(m_i, m_j)-(y(m_i)+y(m_j))$. Variations of this mathematical representation are possible, and may depend upon, for example, how the individual changes biologically interact. As noted above, mutations from the same functional group are more likely to operate by the same mechanism, and are thus more likely to exhibit negative or neutral epistasis on overall host performance. In contrast, mutations from different functional groups are more likely to operate by independent mechanisms, which can lead to improved host performance by reducing redundant mutative effects, for example. Thus, mutations that yield dissimilar responses are more likely to combine in an additive manner than mutations that yield similar responses. This leads to the computation of similarity in the next step.

Fifth, the analysis equipment 214 measures the similarity among the responses—in the pairwise mutation example, the similarity between the effects of the ith mutation and jth (e.g., primary) mutation within the response matrix (4204). Recall that the ith row of R represents the performance effects of the ith mutation $m_i$ on the N background strains, each of which may be itself the result of engineered mutations as described above. Thus, the similarity between the effects of the ith and jth mutations may be represented by the similarity $s_{ij}$ between the ith and jth rows, $\rho_i$ and $\rho_j$, respectively, to form a similarity matrix S. Similarity may be measured using many known techniques, such as cross-correlation or absolute cosine similarity, e.g., $s_{ij}=abs(\cos(\rho_i, \rho_j))$.

As an alternative or supplement to a metric like cosine similarity, response profiles may be clustered to determine degree of similarity. Clustering may be performed by use of a distance-based clustering algorithms (e.g. k-mean, hierarchical agglomerative, etc.) in conjunction with suitable distance measure (e.g. Euclidean, Hamming, etc). Alternatively, clustering may be performed using similarity based clustering algorithms (e.g. spectral, min-cut, etc.) with a suitable similarity measure (e.g. cosine, correlation, etc). Of course, distance measures may be mapped to similarity measures and vice-versa via any number of standard functional operations (e.g., the exponential function). In one implementation, hierarchical agglomerative clustering may be used in conjunction absolute cosine similarity.

As an example of clustering, let C be a clustering of mutations $m_i$ into k distinct clusters. Let C be the cluster membership matrix, where $c_{ij}$ is the degree to which mutation i belongs to cluster j, a value between 0 and 1. The cluster-based similarity between mutations i and j is then given by $C_i \times C_j$ (the dot product of the ith and jth rows of C). In general, the cluster-based similarity matrix is given by $CC^T$ (that is, C times C-transpose). In the case of hard-clustering (a mutation belongs to exactly one cluster), the similarity between two mutations is 1 if they belong to the same cluster and 0 if not.

As is described in Costanzo, The Genetic Landscape of a Cell, *Science*, Vol. 327, Issue 5964, Jan. 22, 2010, pp. 425-431 (incorporated by reference herein in its entirety), such a clustering of mutation response profiles relates to an approximate mapping of a cell's underlying functional organization. That is, mutations that cluster together tend to be related by an underlying biological process or metabolic pathway. Such mutations are referred to herein as a "functional group." The key observation of this method is that if two mutations operate by the same biological process or pathway, then observed effects (and notably observed benefits) may be redundant. Conversely, if two mutations operate by distant mechanism, then it is less likely that beneficial effects will be redundant.

Sixth, based on the epistatic effect, the analysis equipment 214 selects pairs of mutations that lead to dissimilar responses, e.g., their cosine similarity metric falls below a similarity threshold, or their responses fall within sufficiently separated clusters, as shown in FIG. 19 (4206). Based on their dissimilarity, the selected pairs of mutations should consolidate into background strains better than similar pairs.

Based upon the selected pairs of mutations that lead to sufficiently dissimilar responses, the LIMS system (e.g., all of or some combination of interpreter 204, execution engine 207, order placer 208, and factory 210) may be used to design microbial strains having those selected mutations (4208). In embodiments, as described below and elsewhere herein, epistatic effects may be built into, or used in conjunction with the predictive model to weight or filter strain selection.

It is assumed that it is possible to estimate the performance (a.k.a. score) of a hypothetical strain obtained by consolidating a collection of mutations from the library into a particular background via some preferred predictive model. A representative predictive model utilized in the taught methods is provided in the below section entitled "Predictive Strain Design" that is found in the larger section of: "Computational Analysis and Prediction of Effects of Genome-Wide Genetic Design Criteria."

When employing a predictive strain design technique such as linear regression, the analysis equipment 214 may restrict the model to mutations having low similarity measures by, e.g., filtering the regression results to keep only sufficiently dissimilar mutations. Alternatively, the predictive model may be weighted with the similarity matrix. For example, some embodiments may employ a weighted least squares regression using the similarity matrix to characterize the interdependencies of the proposed mutations. As an example, weighting may be performed by applying the "kernel" trick to the regression model. (To the extent that the "kernel trick" is general to many machine learning modeling approaches, this re-weighting strategy is not restricted to linear regression.)

Such methods are known to one skilled in the art. In embodiments, the kernel is a matrix having elements $1-w^*s_{ij}$ where 1 is an element of the identity matrix, and w is a real value between 0 and 1. When w=0, this reduces to a standard regression model. In practice, the value of w will be tied to the accuracy ($r^2$ value or root mean square error (RMSE)) of the predictive model when evaluated against the pairwise combinatorial constructs and their associate effects $y(m_i, m_j)$. In one simple implementation, w is defined as $w=1-r^2$. In this case, when the model is fully predictive, $w=1-r^2=0$ and consolidation is based solely on the predictive model and epistatic mapping procedure plays no role. On the other hand, when the predictive model is not predictive at all, $w=1-r^2=1$ and consolidation is based solely on the epistatic mapping procedure. During each iteration, the accuracy can be assessed to determine whether model performance is improving.

It should be clear that the epistatic mapping procedure described herein does not depend on which model is used by the analysis equipment 214. Given such a predictive model, it is possible to score and rank all hypothetical strains accessible to the mutation library via combinatorial consolidation.

In some embodiments, to account for epistatic effects, the dissimilar mutation response profiles may be used by the analysis equipment 214 to augment the score and rank associated with each hypothetical strain from the predictive model. This procedure may be thought of broadly as a re-weighting of scores, so as to favor candidate strains with dissimilar response profiles (e.g., strains drawn from a diversity of clusters). In one simple implementation, a strain may have its score reduced by the number of constituent mutations that do not satisfy the dissimilarity threshold or that are drawn from the same cluster (with suitable weighting). In a particular implementation, a hypothetical strain's performance estimate may be reduced by the sum of terms in the similarity matrix associated with all pairs of constituent mutations associated with the hypothetical strain (again with suitable weighting). Hypothetical strains may be re-ranked using these augmented scores. In practice, such re-weighting calculations may be performed in conjunction with the initial scoring estimation.

The result is a collection of hypothetical strains with score and rank augmented to more effectively avoid confounding epistatic interactions. Hypothetical strains may be constructed at this time, or they may be passed to another computational method for subsequent analysis or use.

Those skilled in the art will recognize that epistasis mapping and iterative predictive strain design as described herein are not limited to employing only pairwise mutations, but may be expanded to the simultaneous application of many more mutations to a background strain. In another embodiment, additional mutations may be applied sequentially to strains that have already been mutated using mutations selected according to the predictive methods described herein. In another embodiment, epistatic effects are imputed by applying the same genetic mutation to a number of strain backgrounds that differ slightly from each other, and noting any significant differences in positive response profiles among the modified strain backgrounds.

Genetic Design & Microbial Engineering: Directed Genome Editing with Targeted Nucleases Metabolic engineering relies heavily on the alteration of key genes involved, both directly and indirectly, in the metabolism, regulation, and catabolism of molecules. It is often useful to precisely introduce small and large changes such as single nucleotide polymorphisms, insertions, or deletions into the genome to alter metabolic pathways. Such changes can also be used to introduce, delete or replace larger regions of genetic material such as promoters, terminators, genes, or even gene clusters.

Through sequence homology, these crRNAs guide a Cas nuclease to the specified exogenous genetic material, which must also contain a nuclease-specific sequence known as a protospacer adjacent motif (PAM). The CRISPR complex binds to the foreign DNA and cleaves it.

In one aspect provided herein, a host or parental strain of fungi (e.g., filamentous fungi as provided herein) that contains a metabolic pathway of interest that produces a molecule or biologic of interest can be modified by CRISPR. In one embodiment, a protoplast capable of being transformed is generated from the host or parental strain using the protoplasting methods provided herein and is transformed with a ribonucleoprotein complex (RNP-complex or CRISPR RNP). The RNP-complex comprises a nucleic acid guided nuclease as provided herein (e.g., Cas9) that is complexed with a guide nucleic acid as provided herein (e.g., guide RNA (gRNA)). When guided by an RNA, the nucleic acid guided nuclease can be referred to herein as an RNA guided nuclease or an RNA guided endonuclease. The guide nucleic acid (e.g., gRNA) can comprise a targeting segment that is a guide sequence that is complementary to a portion of a target gene or nucleic acid sequence present in the host or parental strain of fungi (e.g., filamentous fungi as provided herein). In one embodiment, a protoplast can be transformed with 2 or more RNP-complexes such that each RNP-complex comprises a nucleic acid guided endonuclease (e.g., Cas9) complexed with a guide nucleic acid (e.g., gRNA). In some cases, each guide nucleic acid (e.g., gRNA) in the 2 or more RNP-complexes can comprise guide sequence complementary to a different target gene or nucleic acid sequence. In some cases, each guide nucleic acid (e.g., gRNA) in the 2 or more RNP-complexes can comprise guide sequences to the same target gene or nucleic acid sequence. In cases where there are 3 or more RNP-complexes, there can be a subset of the RNP-complexes that can comprise guide sequences complementary to the same target gene or nucleic acid sequence and a subset or subsets of the RNP-complexes that can comprise guide sequence complementary to a different target gene or nucleic acid. In cases where 2 or more RNP-complexes are directed to the same target nucleic acid sequence via their respective targeting segment, each of the RNP-complexes can comprise a guide sequence or targeting segment that is complementary to a different or separate portion of said target gene or nucleic acid. Further to these embodiments, multiple gRNAs targeting multiple loci can be expressed in the same cell or organism (multiplex expression of gRNAs). Pooled gRNA libraries can be used to identify genes that are important to a given phenotype. Current libraries are available for gene knockout, as well as transcriptional activation or repression. Combined with the power of next-generation sequencing, CRISPR can be a robust system for genome-wide screening. Each gRNA can comprise a CRISPR RNA (crRNA) annealed to a transactivating crRNA (tracrRNA) or can comprise a single gRNA (sgRNA) that comprises a single transcript comprising a crRNA and a tracrRNA.

In one embodiment, the host or parental fungi has a functioning NHEJ pathway. Further to this embodiment, transformation of protoplasts derived from the host or parental fungi with a single RNP-complex or multiple RNP-complexes generates strand break(s) within the target gene(s) in the genome that are repaired via the NHEJ pathway. Repair using the NHEJ pathway can lead to indels within the target gene(s). The indels in the target gene(s) can result in amino acid deletions, insertions, or frameshift mutations leading to premature stop codons within the open reading frame (ORF) of the targeted gene(s). In a further embodiment, the strand breaks within the target gene(s) can be repaired by using homology directed repair (HDR). HDR mediated repair can be facilitated by co-transforming the protoplasts derived from the host or parental fungi with a donor DNA sequence. The donor DNA sequence can comprise a desired genetic perturbation (e.g., deletion, insertion, and/or single nucleotide polymorphism). In this embodiment, the RNP cleaves the target gene specified by the one or more gRNAs. The donor DNA can then be used as a template for the homologous recombination machinery to incorporate the desired genetic perturbation for modification of the metabolic pathway or molecule/biologic of interest. The donor DNA can be single-stranded, double-stranded or a double-stranded plasmid. The donor DNA can lack a PAM sequence or comprise a scrambled, altered or non-functional PAM in order to prevent re-cleavage. In some cases, the donor DNA can contain a functional or non-altered PAM site (see FIGS. 56A-B). The mutated or edited sequence in the donor DNA (also flanked by the regions of homology) prevents re-cleavage by the RNP after the mutation(s) has/have been incorporated into the genome. In some embodiments, the HDR pathway can be favored by performing the transformations in protoplasts derived from host or parental fungi that do not possess a functioning NHEJ pathway. Disabling the NHEJ pathway can be achieved using any of the methods provided herein.

Figure 53:
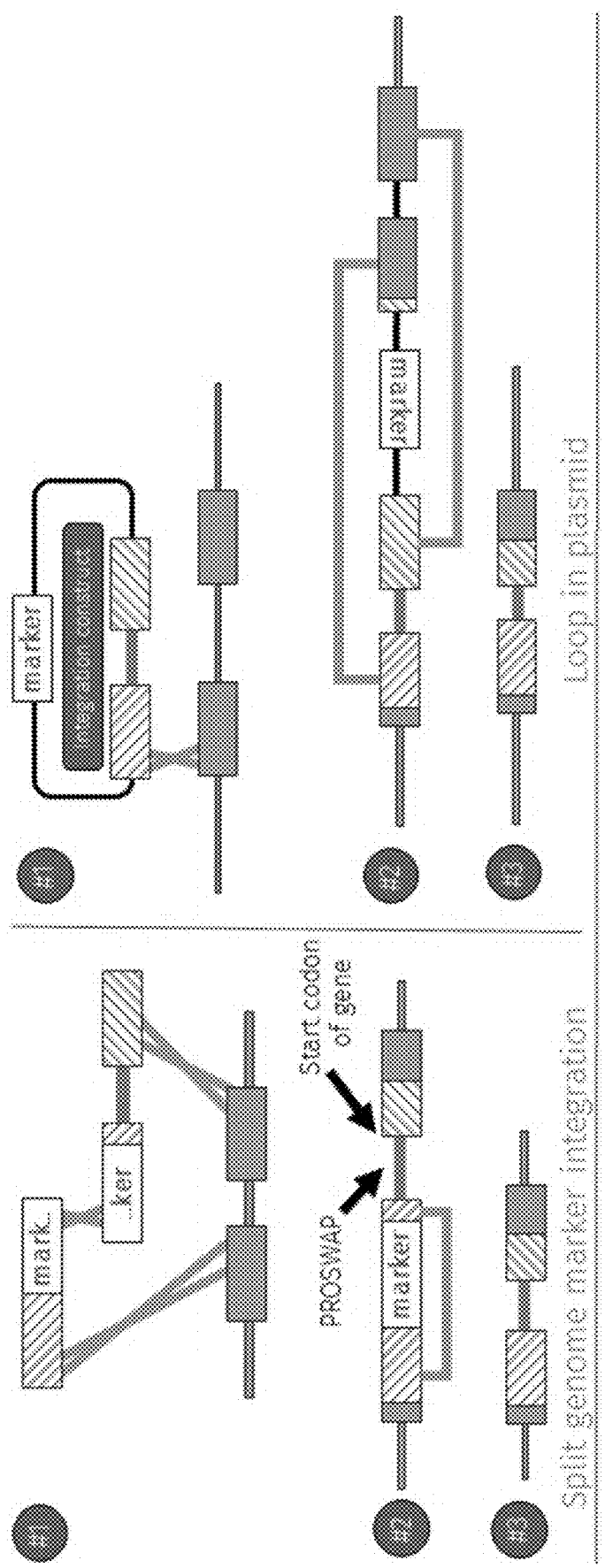
FIG. 53 illustrates traditional strategies for introducing or changing sequences in a genome. A split gene marker (left) or integration construct (right) can be used to incorporate new genetic material via three or one cross-over event(s) respectively. Regions of homology, surrounding the marker and mutation target the integration to a desired locus. Later, the marker can be used to select for the loop-in event and a counterselectable marker can then be used to select for the loop-out event. The integrants may loop out producing the wild type sequence shown in (1) or the new mutation shown in (3).

In some embodiments, the protoplasts can be co-transformed with the RNP complex, the donor DNA and a vector comprising a selectable marker. The vector can interact with the other components by enabling identification and/or survival of only transformationally competent protoplasts. This can facilitate identification of transformed and correctly edited strains. Iterative rounds of editing are possible because the plasmid can be cured. See FIG. 53.

Further to the above embodiments, the nucleic acid guided nuclease for use in the methods provided herein can be any of the nucleic acid guided nucleases known in the art and/or provided herein. In one embodiment, the nucleic acid guided nuclease is a Class 2 CRISPR-Cas System nucleic acid guided nuclease. The Class 2 CRISPR-Cas system nucleic acid guided nuclease can be selected from any one or more of the following: Type II, Type IIA, Type IIB, Type IIC, Type V, and Type VI nucleic acid guided nuclease as described herein. The Class 2 CRISPR-Cas system nucleic acid guided nuclease can be any one or more of the following: Cas9, Cas12a, Cas12b, Cas12c, Cas12d, Cas12e, Cas13a, Cas13b, Cas13c or homologs, orthologs, mutants, variants or modified versions thereof.

Organisms Amenable to Genetic Design

The disclosed HTP genomic engineering platform is exemplified with industrial microbial cell cultures (e.g., *A. niger*), but is applicable to any coenocytic host cell organism where desired traits can be identified in a population of genetic mutants.

Further, as set forth in the introduction, the current disclosure provides for a HTP genomic engineering platform to improve host cell characteristics in filamentous fungal systems and solves many problems that have previously prevented the development of such a system infilamentous fungus Thus, as used herein, the term "microorganism" should be taken broadly. It includes, but is not limited to, the two prokaryotic domains, Bacteria and Archaea, as well as certain eukaryotic fungi and protists. However, in certain aspects, "higher" eukaryotic organisms such as insects, plants, and animals can be utilized in the methods taught herein.

Suitable host cells include, but are not limited to: bacterial cells, algal cells, plant cells, fungal cells, insect cells, and mammalian cells. In one illustrative embodiment, suitable host cells include *A. niger*.

In one embodiment, the methods and systems provided herein use fungal elements derived from filamentous fungus that are capable of being readily separated from other such elements in a culture medium, and are capable of reproducing itself. For example, the fungal elements can be a spore, propagule, hyphal fragment, protoplast or micropellet. In a preferred embodiment, the systems and methods provided herein utilize protoplasts derived from filamentous fungus. Suitable filamentous fungi host cells include, for example, any filamentous forms of the division Ascomycota, Deuteromycota, Zygomycota or Fungi imperfecti. Suitable filamentous fungi host cells include, for example, any filamentous forms of the subdivision Eumycotina. (see, e.g., Hawksworth et al., In Ainsworth and Bisby's Dictionary of The Fungi, $8^{th}$ edition, 1995, CAB International, University Press, Cambridge, UK, which is incorporated herein by reference). In certain illustrative, but non-limiting embodiments, the filamentous fungal host cell may be a cell of a species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Filibasidium, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella*, or teleomorphs, or anamorphs, and synonyms or taxonomic equivalents thereof. In one embodiment, the filamentous fungus is selected from the group consisting of *A. nidulans, A. oryzae, A. sojae*, and *Aspergilli* of the *A. niger* Group. In a preferred embodiment, the filamentous fungus is *Aspergillus niger*.

In one embodiment, the filamentous fungus is a production strain selected from *Aspergillus foetidus* ACM 3996 (=FRR 3558), *Magnaporthe grisea* Guy-II or *Phanerochaete chrysosporium* RP78. In a separate embodiment, the filamentous fungus is an *A. niger* production strain known in the art. Examples of *A. niger* production strains for use in the methods provided herein can include *A. niger* ATCC 11414, ATCC 1015, ACM 4992 (=ATCC 9142), ACM 4993 (=ATCC 10577), ACM 4994 (=ATCC 12846), ATCC26550, ATCC 11414, N402, CBS 513.88 or NRRL3 (ATCC 9029, CBS 120.49).

In another embodiment of the present disclosure, specific mutants of the fungal species are used for the methods and systems provided herein. In one embodiment, specific mutants of the fungal species are used which are suitable for the high-throughput and/or automated methods and systems provided herein. Examples of such mutants can be strains that protoplast very well; strains that produce mainly or, more preferably, only protoplasts with a single nucleus; strains that regenerate efficiently in microtiter plates, strains that regenerate faster and/or strains that take up polynucleotide (e.g., DNA) molecules efficiently, strains that produce cultures of low viscosity such as, for example, cells that produce hyphae in culture that are not so entangled as to prevent isolation of single clones and/or raise the viscosity of the culture, strains that have reduced random integration (e.g., disabled non-homologous end joining pathway) or combinations thereof. In yet another embodiment, a specific mutant strain for use in the methods and systems provided herein can be strains lacking a selectable marker gene such as, for example, uridine-requiring mutant strains. These mutant strains can be either deficient in orotidine 5 phosphate decarboxylase (OMPD) or rotate p-ribosyl transferase (OPRT) encoded by the pyrG or pyrE gene, respectively (T. Goosen et al., Curr Genet. 1987, 11:499 503; J. Begueret et al., Gene. 1984 32:487 92.

In one embodiment, specific mutant strains for use in the methods and systems provided herein are strains that possess a compact cellular morphology characterized by shorter hyphae and a more yeast-like appearance. Examples of such mutants can be filamentous fungal cells with altered gas1 expression as described in US20140220689.

In still another embodiment, mutant strains for use in the methods and systems provided herein are modified in their DNA repair system in such a way that they are extremely efficient in homologous recombination and/or extremely inefficient in random integration. The efficiency of targeted integration of a nucleic acid construct into the genome of the host cell by homologous recombination, i.e. integration in a predetermined target locus, can be increased by augmented homologous recombination abilities and/or diminished non-homologous recombination abilities of the host cell. Augmentation of homologous recombination can be achieved by overexpressing one or more genes involved in homologous recombination (e.g., Rad51 and/or Rad52 protein). Removal, disruption or reduction in non-homologous recombination or the non-homologous end joining (NHEJ) pathway in the host cells of the present disclosure can be achieved by any method known in that art such as, for example, by use of an antibody, a chemical inhibitor, a protein inhibitor, a physical inhibitor, a peptide inhibitor, or an anti-sense or RNAi molecule directed against a component of the non-homologous recombination (NHR) or NHEJ pathway (e.g., yeast KU70, yeast KU80 or homologues thereof). Inhibition of the NHEJ pathway can be achieved using chemical inhibitors such as described in Arras S M D, Fraser J A (2016), "Chemical Inhibitors of Non-Homologous End Joining Increase Targeted Construct Integration in *Cryptococcus neoformans*" PloS ONE 11 (9): e0163049, the contents of which are hereby incorporated by reference. Treatment with the chemical inhibitor(s) to facilitate disabling or reducing the NHEJ pathway can be before and/or during generation of protoplasts. Alternatively, a host-cell for use in the methods provided herein can be deficient in one or more genes (e.g., yeast ku70, ku80 or homologues thereof) of the NHR pathway. Examples of such mutants are cells with a deficient hdfA or hdfB gene as described in WO 05/95624. Examples of chemical inhibitors for use in inhibiting NHR in host cells for use in the methods provided herein can be W-7, chlorpromazine, vanillin, Nu7026, Nu7441, mirin, SCR7, AG14361 or a combination thereof as described in Arras SDM et al (2016) Chemical Inhibitors of Non-Homologous End Joining Increase Targeted Construct Integration in *Cryptococcus neoformans*. PloS One 11(9).

In one embodiment, a mutant strain of filamentous fungal cell for use in the methods and systems provided herein have a disabled or reduced non-homologous end-joining (NHEJ) pathway and possess a yeast-like, non-mycelium forming phenotype when grown in culture (e.g., submerged culture).

Figure 29:
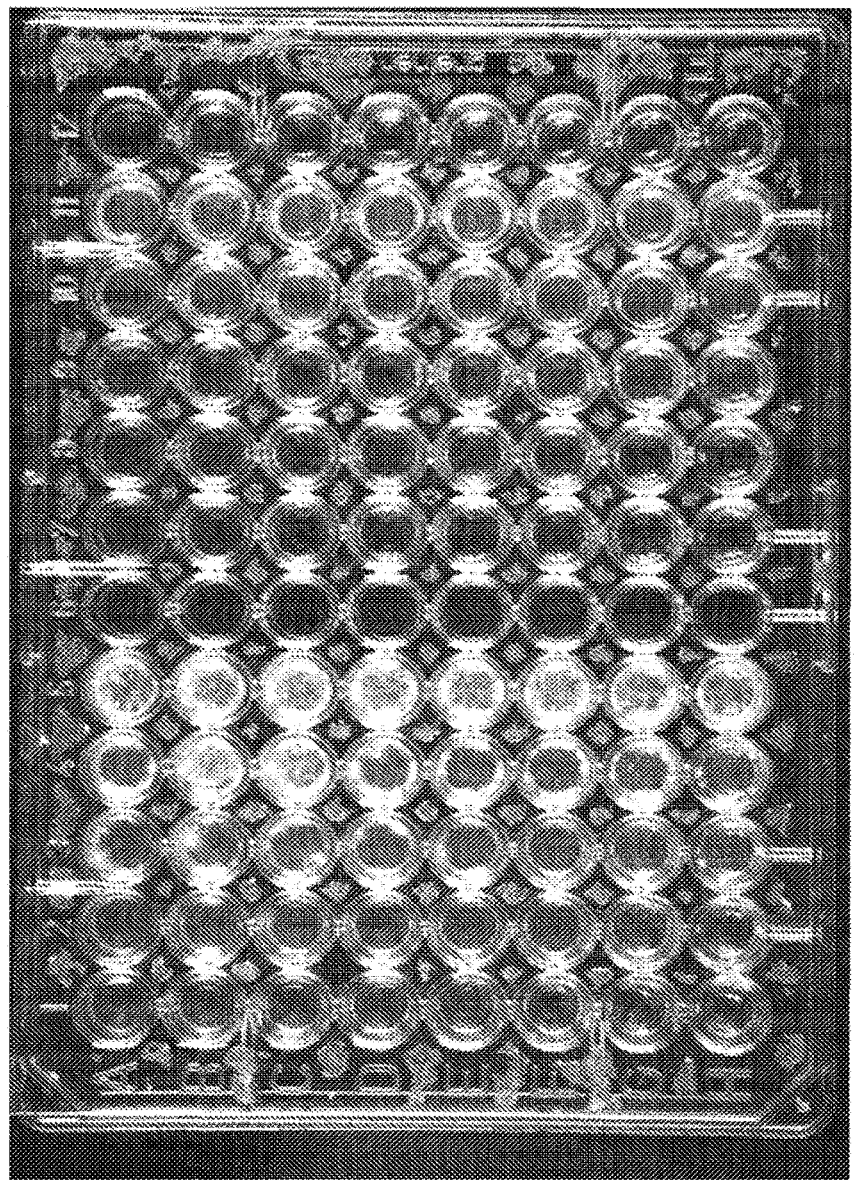
FIG. 29 depicts the minimum inhibitory concentration (MIC) of the chemical inhibitor W-7 on two strains (1015; 11414) of *Aspergillus niger* (*A. niger*).

In another embodiment, filamentous fungal cells for use in the methods and systems provided herein have a disabled or reduced NHEJ pathway due to treatment with a chemical inhibitor (e.g., W-7, chlorpromazine, vanillin, Nu7026, Nu7441, mirin, SCR7, AG14361 or any combination thereof) and possess a yeast-like, non-mycelium forming phenotype when grown in culture (e.g., submerged culture). In one embodiment, the chemical inhibitor is W-7. As reflected in FIG. 29, a filamentous fungal host cell (e.g., *A. niger*) can be treated with a minimum inhibitory concentration (MIC) of W-7 that can be host strain dependent.

Figure 54A:
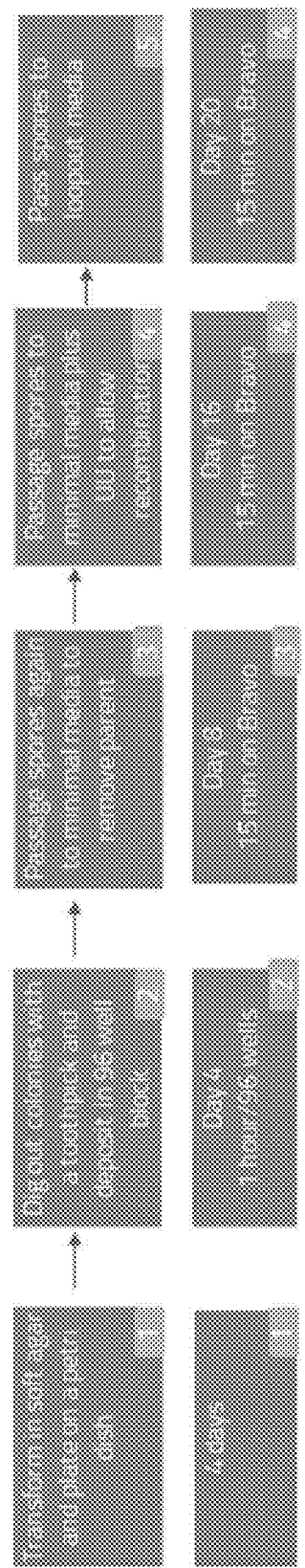
FIG. 54A-54B illustrate a workflows for modifying *Aspergillus niger* utilizing traditional and new methods. The traditional workflow takes 20 days and clonal populations are not explicitly achieved (FIG. 54A). Growth on minimal media inhibits parental strain from growing, but does not inhibit heterokaryons, which contain both transformed and untransformed nuclei in the same cell. The new protocol results in parent death and pure-clonal populations at step 2 and takes only 12 days (FIG. 54B).
Figure 54B:
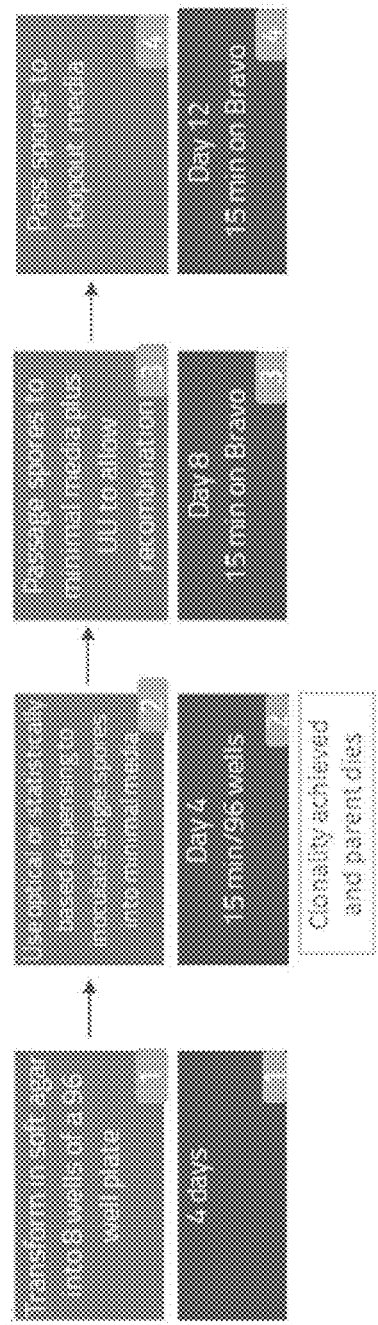

In some embodiments, the spore, propagule, hyphal fragment, protoplast, or micropellet are isolated to a clonal population. In some embodiments, the spore, propagule, hyphal fragment, protoplast, or micropellet are transformed prior to isolation. In some embodiments, the spore, propagule, hyphal fragment, protoplast, or micropellet are isolated to a clonal population in a microtiter plate or a microtiter well. Further to the above embodiments, the clonal populations are derived from a single spore, propagule, hyphal fragment, protoplast, or micropellet. In some embodiments, the spore, propagule, hyphal fragment, protoplast, or micropellet is in a diluted solution, and only a single spore, propagule, hyphal fragment, protoplast, or micropellet is transferred to a microtiter plate or well. In some embodiments, the spore, propagule, hyphal fragment, protoplast, or micropellet are diluted to a concentration to which it can be optically distinguished as a single spore, propagule, hyphal fragment, protoplast, or micropellet, which is then singly transferred to a microtiter plate or well. In some embodiments, the spore, propagule, hyphal fragment, protoplast, or micropellet are diluted using the Poisson distribution where there is a statistical probability of transferring only one spore, propagule, hyphal fragment, protoplast, or micropellet to the microtiter plate or well. In some embodiments, the spore, propagule, hyphal fragment, protoplast, or micropellet are transferred to any container, including a microtiter plate or well. In some embodiments, the optical distinguishment is performed by CellenONE, Berkeley Lights Beacon instrument, FACS machine, Cytena, or other like instrument. An example of a workflow for isolating a singular spore, propagule, hyphal fragment, protoplast, or micropellet for use in the methods provided herein can be seen in FIG. 54B. Further to any of the above embodiments, the spore, propagule, hyphal fragment, protoplast, or micropellet can be from any fungal cell provided herein. In one embodiment, the fungal cell is a filamentous fungal cell. The filamentous fungal cell can be filamentous fungal cell provided herein such as, for example, *A. niger*.

Generating Genetic Diversity Pools for Utilization in the Genetic Design & HTP Microbial Engineering Platform In some embodiments, the methods of the present disclosure are characterized as genetic design. As used herein, the term genetic design refers to the reconstruction or alteration of a host organism's genome through the identification and selection of the most optimum variants of a particular gene, portion of a gene, promoter, stop codon, 5'UTR, 3'UTR, or other DNA sequence to design and create new superior host cells.

In some embodiments, a first step in the genetic design methods of the present disclosure is to obtain an initial genetic diversity pool population with a plurality of sequence variations from which a new host genome may be reconstructed.

In some embodiments, a subsequent step in the genetic design methods taught herein is to use one or more of the aforementioned HTP molecular tool sets (e.g. SNP swapping or promoter swapping) to construct HTP genetic design libraries, which then function as drivers of the genomic engineering process, by providing libraries of particular genomic alterations for testing in a host cell.

Harnessing Diversity Pools from Existing Wild-Type Strains

In some embodiments, the present disclosure teaches methods for identifying the sequence diversity present among microbes of a given wild-type population. Therefore, a diversity pool can be a given number n of wild-type microbes utilized for analysis, with said microbes' genomes representing the "diversity pool."

In some embodiments, the diversity pools can be the result of existing diversity present in the natural genetic variation among said wild-type microbes. This variation may result from strain variants of a given host cell or may be the result of the microbes being different species entirely. Genetic variations can include any differences in the genetic sequence of the strains, whether naturally occurring or not. In some embodiments, genetic variations can include SNPs swaps, PRO swaps, Start/Stop Codon swaps, or STOP swaps, among others.

Harnessing Diversity Pools from Existing Industrial Strain Variants

In other embodiments of the present disclosure, diversity pools are strain variants created during traditional strain improvement processes (e.g., one or more host organism strains generated via random mutation and selected for improved yields over the years). Thus, in some embodiments, the diversity pool or host organisms can comprise a collection of historical production strains.

In particular aspects, a diversity pool may be an original parent microbial strain ($S_1$) with a "baseline" genetic sequence at a particular time point ($S_1Gen_1$) and then any number of subsequent offspring strains ($S_2$, $S_3$, $S_4$, $S_5$, etc., generalizable to $S_{2-n}$) that were derived/developed from said $S_1$ strain and that have a different genome ($S_{2-n}Gen_{2-n}$), in relation to the baseline genome of $S_1$.

For example, in some embodiments, the present disclosure teaches sequencing the microbial genomes in a diversity pool to identify the SNP's present in each strain. In one embodiment, the strains of the diversity pool are historical microbial production strains. Thus, a diversity pool of the present disclosure can include for example, an industrial base strain, and one or more mutated industrial strains produced via traditional strain improvement programs.

Once all SNPs in the diversity pool are identified, the present disclosure teaches methods of SNP swapping and screening methods to delineate (i.e. quantify and characterize) the effects (e.g. creation of a phenotype of interest) of SNPs individually and in groups. Thus, as aforementioned, an initial step in the taught platform can be to obtain an initial genetic diversity pool population with a plurality of sequence variations, e.g. SNPs. Then, a subsequent step in the taught platform can be to use one or more of the aforementioned HTP molecular tool sets (e.g. SNP swapping) to construct HTP genetic design libraries, which then function as drivers of the genomic engineering process, by providing libraries of particular genomic alterations for testing in a microbe.

In some embodiments, the SNP swapping methods of the present disclosure comprise the step of introducing one or more SNPs identified in a mutated strain (e.g., a strain from amongst $S_{2-n}Gen_{2-n}$) to a base strain ($S_1Gen_1$) or wild-type strain.

In other embodiments, the SNP swapping methods of the present disclosure comprise the step of removing one or more SNPs identified in a mutated strain (e.g., a strain from amongst $S_{2-n}Gen_{2-n}$).

Creating Diversity Pools Via Mutagenesis

In some embodiments, the mutations of interest in a given diversity pool population of cells can be artificially generated by any means for mutating strains, including mutagenic chemicals, or radiation. The term "mutagenizing" is used herein to refer to a method for inducing one or more genetic modifications in cellular nucleic acid material.

The term "genetic modification" refers to any alteration of DNA. Representative gene modifications include nucleotide insertions, deletions, substitutions, and combinations thereof, and can be as small as a single base or as large as tens of thousands of bases. Thus, the term "genetic modification" encompasses inversions of a nucleotide sequence and other chromosomal rearrangements, whereby the position or orientation of DNA comprising a region of a chromosome is altered. A chromosomal rearrangement can comprise an intrachromosomal rearrangement or an interchromosomal rearrangement.

In one embodiment, the mutagenizing methods employed in the presently claimed subject matter are substantially random such that a genetic modification can occur at any available nucleotide position within the nucleic acid material to be mutagenized. Stated another way, in one embodiment, the mutagenizing does not show a preference or increased frequency of occurrence at particular nucleotide sequences.

The methods of the disclosure can employ any mutagenic agent including, but not limited to: ultraviolet light, X-ray radiation, gamma radiation, N-ethyl-N-nitrosourea (ENU), methyinitrosourea (MNU), procarbazine (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6-MP), mitomycin-C (MMC), N-methyl-N'-nitro-N-nitrosoguanidine (MNNG), $^3H_2O$, and urethane (UR) (See e.g., Rinchik, 1991; Marker el al., 1997; and Russell, 1990). Additional mutagenic agents are well known to persons having skill in the art, including those described in www.iephb.nw.ru/~spirov/hazard/mutagen_1st.html.

The term "mutagenizing" also encompasses a method for altering (e.g., by targeted mutation) or modulating a cell function, to thereby enhance a rate, quality, or extent of mutagenesis. For example, a cell can be altered or modulated to thereby be dysfunctional or deficient in DNA repair, mutagen metabolism, mutagen sensitivity, genomic stability, or combinations thereof. Thus, disruption of gene functions that normally maintain genomic stability can be used to enhance mutagenesis. Representative targets of disruption include, but are not limited to DNA ligase I (Bentley et al., 2002) and casein kinase I (U.S. Pat. No. 6,060,296).

In some embodiments, site-specific mutagenesis (e.g., primer-directed mutagenesis using a commercially available kit such as the Transformer Site Directed mutagenesis kit (Clontech)) is used to make a plurality of changes throughout a nucleic acid sequence in order to generate nucleic acid encoding a cleavage enzyme of the present disclosure.

The frequency of genetic modification upon exposure to one or more mutagenic agents can be modulated by varying dose and/or repetition of treatment, and can be tailored for a particular application.

Thus, in some embodiments, "mutagenesis" as used herein comprises all techniques known in the art for inducing mutations, including error-prone PCR mutagenesis, oligonucleotide-directed mutagenesis, site-directed mutagenesis, and iterative sequence recombination by any of the techniques described herein.

Single Locus Mutations to Generate Diversity

In some embodiments, the present disclosure teaches mutating cell populations by introducing, deleting, or replacing selected portions of genomic DNA. Thus, in some embodiments, the present disclosure teaches methods for targeting mutations to a specific locus. In other embodiments, the present disclosure teaches the use of gene editing technologies such as ZFNs, TALENS, or CRISPR, to selectively edit target DNA regions.

In other embodiments, the present disclosure teaches mutating selected DNA regions outside of the host organism, and then inserting the mutated sequence back into the host organism. For example, in some embodiments, the present disclosure teaches mutating native or synthetic promoters to produce a range of promoter variants with various expression properties (see promoter ladder infra). In other embodiments, the present disclosure is compatible with single gene optimization techniques, such as ProSAR (Fox et al. 2007. "Improving catalytic function by ProSAR-driven enzyme evolution." Nature Biotechnology Vol 25 (3) 338-343, incorporated by reference herein).

In some embodiments, the selected regions of DNA are produced in vitro via gene shuffling of natural variants, or shuffling with synthetic oligos, plasmid-plasmid recombination, virus plasmid recombination, virus-virus recombination. In other embodiments, the genomic regions are produced via error-prone PCR.

In some embodiments, generating mutations in selected genetic regions is accomplished by "reassembly PCR." Briefly, oligonucleotide primers (oligos) are synthesized for PCR amplification of segments of a nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols. In brief, in an assembly protocol, the PCR products are first purified away from the primers, by, for example, gel electrophoresis or size exclusion chromatography. Purified products are mixed together and subjected to about 1-10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments of the disclosure, mutated DNA regions, such as those discussed above, are enriched for mutant sequences so that the multiple mutant spectrum, i.e. possible combinations of mutations, is more efficiently sampled. In some embodiments, mutated sequences are identified via a mutS protein affinity matrix (Wagner et al., Nucleic Acids Res. 23(19):3944-3948 (1995); Su et al., Proc. Natl. Acad. Sci. (U.S.A.), 83:5057-5061(1986)) with a preferred step of amplifying the affinity-purified material in vitro prior to an assembly reaction. This amplified material is then put into an assembly or reassembly PCR reaction as described in later portions of this application.

Promoter Ladders

Promoters regulate the rate at which genes are transcribed and can influence transcription in a variety of ways. Constitutive promoters, for example, direct the transcription of their associated genes at a constant rate regardless of the internal or external cellular conditions, while regulatable, tunable or inducible promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

Promoter sequences can be operably linked to the 5' termini of any sequences provided herein to be expressed in a filamentous fungal host cell as provided herein. A variety of known fungal promoters are likely to be functional in the host strains of the disclosure such as, for example, the promoter sequences of C1 endoglucanases, the 55 kDa cellobiohydrolase (CBH1), glyceraldehyde-3-phosphate dehydrogenase A, C. lucknowense GARG 27K and the 30 kDa xylanase (Xy1F) promoters from Chrysosporium, as well as the Aspergillus promoters described in, e.g. U.S. Pat. Nos. 4,935,349; 5,198,345; 5,252,726; 5,705,358; and 5,965,384; and PCT application WO 93/07277. In one embodiment, the promoters for use in the methods and systems provided herein are inducible promoters. The inducible promoters can be any promoter whose transcriptional activity is regulated by the presence or absence of a chemical such as for example, alcohol, tetracycline, steroids, metal or other compounds known in the art. The inducible promoters can be any promoter whose transcriptional activity is regulated by the presence or absence of light or low or high temperatures. In one embodiment, the inducible promoters are selected from filamentous fungal genes such as the srpB gene, the amyB gene, the manB gene or the mbfA gene. In one embodiment, the inducible promoter is selected form the promoters listed in Table 1. In one embodiment, the inducible promoter is catabolite repressed by glucose. The catabolite repressed by glucose can be the amyB promoter from A. oryzae (see FIG. 37).

In some embodiments, the present disclosure teaches methods for producing promoter ladder libraries for use in downstream genetic design methods. For example, in some embodiments, the present disclosure teaches methods of identifying one or more promoters and/or generating variants of one or more promoters within a host cell, which exhibit a range of expression strengths, or superior regulatory properties. A particular combination of these identified and/or generated promoters can be grouped together as a promoter ladder, which is explained in more detail below.

Figure 13:
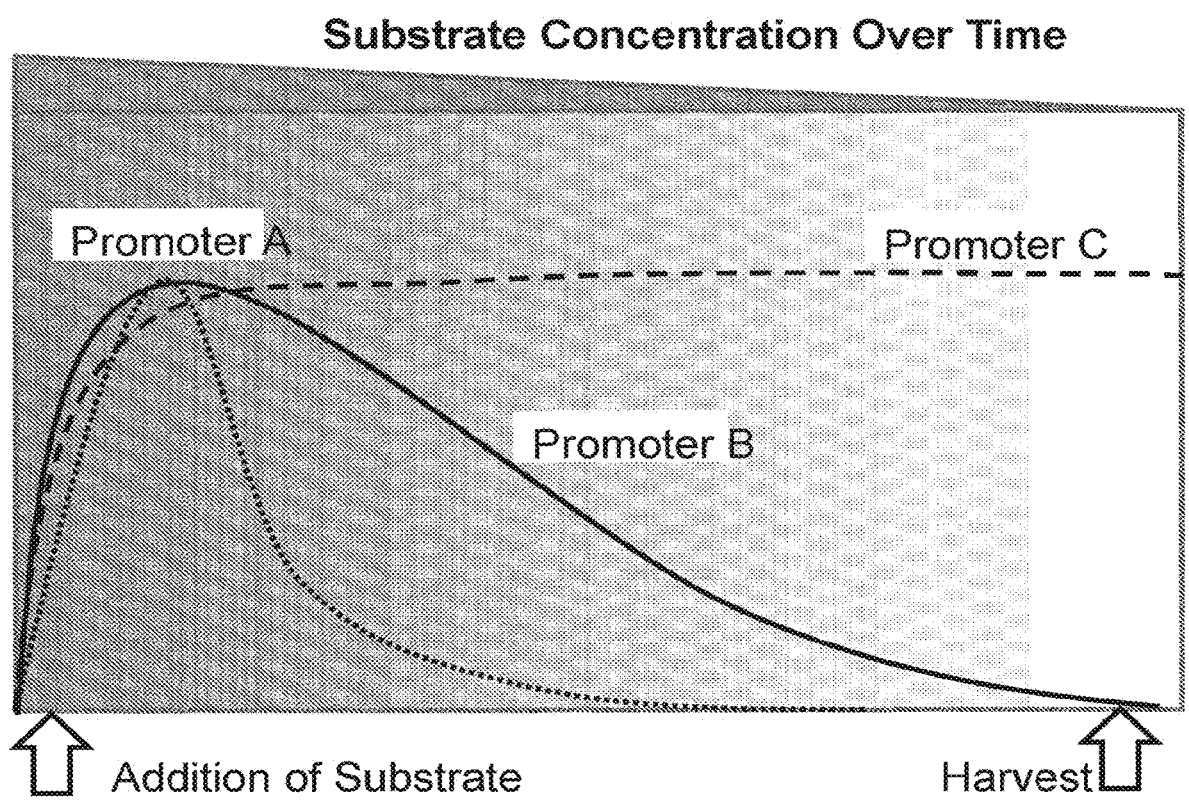
FIG. 13 depicts expression profiles of illustrative promoters exhibiting a range of regulatory expression, according to the promoter ladders of the present disclosure. Promoter A expression peaks immediately upon addition of a selected substrate, but quickly returns to undetectable levels as the concentration of the substrate is reduced. Promoter B expression peaks immediately upon addition of the selected substrate and lowers slowly back to undetectable levels together with the corresponding reduction in substrate. Promoter C expression peaks upon addition of the selected substrate, and remains highly expressed throughout the culture, even after the substrate has dissipated.

In some embodiments, the present disclosure teaches the use of promoter ladders. In some embodiments, the promoter ladders of the present disclosure comprise promoters exhibiting a continuous range of expression profiles. For example, in some embodiments, promoter ladders are created by: identifying natural, native, or wild-type promoters that exhibit a range of expression strengths in response to a stimuli, or through constitutive expression (see e.g., FIG. 13). These identified promoters can be grouped together as a promoter ladder.

In other embodiments, the present disclosure teaches the creation of promoter ladders exhibiting a range of expression profiles across different conditions. For example, in some embodiments, the present disclosure teaches creating a ladder of promoters with expression peaks spread throughout the different stages of a fermentation. In other embodiments, the present disclosure teaches creating a ladder of promoters with different expression peak dynamics in response to a specific stimulus (see e.g., FIG. 13). Persons skilled in the art will recognize that the regulatory promoter ladders of the present disclosure can be representative of any one or more regulatory profiles.

In some embodiments, the promoter ladders of the present disclosure are designed to perturb gene expression in a predictable manner across a continuous range of responses. In some embodiments, the continuous nature of a promoter ladder confers strain improvement programs with additional predictive power. For example, in some embodiments, swapping promoters or termination sequences of a selected metabolic or signaling pathway can produce a host cell performance curve, which identifies the most optimum expression ratio or profile; producing a strain in which the targeted gene is no longer a limiting factor for a particular reaction or genetic cascade, while also avoiding unnecessary over expression or misexpression under inappropriate circumstances. An example signaling pathway that can be selected can be a signaling pathway that has been identified to or is suspected of playing a role in controlling or affecting host cell morphology. Accordingly, in some embodiments, swapping promoters for a gene shown to or suspected of controlling or affecting morphology can produce a host cell performance curve with respect to morphology, which identifies the most optimum expression ratio or profile of a specific gene for producing a strain or host cell with a desired pellet morphology under the desired growth condition; producing a strain in which the targeted gene is no longer a limiting factor for a particular reaction or genetic cascade, while also avoiding unnecessary over expression or misexpression under inappropriate circumstances. Examples of genes shown to or suspected of controlling or affecting morphology can be any such genes known in the art or provided herein. In some embodiments, promoter ladders are created by: identifying natural, native, or wild-type promoters exhibiting the desired profiles. In other embodiments, the promoter ladders are created by mutating naturally occurring promoters to derive multiple mutated promoter sequences. Each of these mutated promoters is tested for effect on target gene expression. In some embodiments, the edited promoters are tested for expression activity across a variety of conditions, such that each promoter variant's activity is documented/characterized/annotated and stored in a database. The resulting edited promoter variants are subsequently organized into promoter ladders arranged based on the strength of their expression (e.g., with highly expressing variants near the top, and attenuated expression near the bottom, therefore leading to the term "ladder").

In some embodiments, the present disclosure teaches promoter ladders that are a combination of identified naturally occurring promoters and mutated variant promoters.

In some embodiments, the present disclosure teaches methods of identifying natural, native, or wild-type promoters that satisfied both of the following criteria: 1) represented a ladder of constitutive promoters; and 2) could be encoded by short DNA sequences, ideally less than 100 base pairs. In some embodiments, constitutive promoters of the present disclosure exhibit constant gene expression across two selected growth conditions (typically compared among conditions experienced during industrial cultivation). In some embodiments, the promoters of the present disclosure will consist of a ~60 base pair core promoter, and a 5' UTR between 26- and 40 base pairs in length.

In some embodiments, one or more of the aforementioned identified naturally occurring promoter sequences are chosen for gene editing. In some embodiments, the natural promoters are edited via any of the mutation methods described supra. In other embodiments, the promoters of the present disclosure are edited by synthesizing new promoter variants with the desired sequence.

The entire disclosures of U.S. Patent Application No. 62/264,232, filed on Dec. 7, 2015, and International Application No. PCT/US2016/06564, filed on Dec. 7, 2016, are hereby incorporated by reference in its entirety for all purposes A non-exhaustive list of the promoters of the present disclosure is provided in the below Table 1. Each of the promoter sequences can be referred to as a heterologous promoter or heterologous promoter polynucleotide.

TABLE 1

Selected promoter sequences of the present disclosure.

| SEQ ID NO: | Promoter Short Name | Promoter Name |
|---|---|---|
| 1 | manBp | manB promoter from Aspergillus niger |

TABLE 1-continued

Selected promoter sequences of the present disclosure.

| SEQ ID NO: | Promoter Short Name | Promoter Name |
|---|---|---|
| 2 | amyBp | amyB gene from Aspergillus oryzae |
| 3 | srpBp | srpB promoter from Aspergillus niger |
| 4 | mbfAp | mbfA promoter from Aspergillus niger |

In some embodiments, the promoters of the present disclosure exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter from the above table 1.

Terminator Ladders

In some embodiments, the present disclosure teaches methods of improving genetically engineered host strains by providing one or more transcriptional termination sequences at a position 3' to the end of the RNA encoding element. In some embodiments, the present disclosure teaches that the addition of termination sequences improves the efficiency of RNA transcription of a selected gene in the genetically engineered host. In other embodiments, the present disclosure teaches that the addition of termination sequences reduces the efficiency of RNA transcription of a selected gene in the genetically engineered host. Thus in some embodiments, the terminator ladders of the present disclosure comprises a series of terminator sequences exhibiting a range of transcription efficiencies (e.g., one weak terminator, one average terminator, and one strong promoter).

A transcriptional termination sequence may be any nucleotide sequence, which when placed transcriptionally downstream of a nucleotide sequence encoding an open reading frame, causes the end of transcription of the open reading frame. Such sequences are known in the art and may be of prokaryotic, eukaryotic or phage origin. Examples of terminator sequences include, but are not limited to, PTH-terminator, pET-T7 terminator, T3-Tφ terminator, pBR322-P4 terminator, vesicular stomatitus virus terminator, rrnB-T1 terminator, rrnC terminator, TTadc transcriptional terminator, and yeast-recognized termination sequences, such as Matα (α-factor) transcription terminator, native α-factor transcription termination sequence, ADR1transcription termination sequence, ADH2transcription termination sequence, and GAPD transcription termination sequence. A non-exhaustive listing of transcriptional terminator sequences may be found in the iGEM registry, which is available at: partsregistry.org/Terminators/Catalog.

In some embodiments, transcriptional termination sequences may be polymerase-specific or nonspecific, however, transcriptional terminators selected for use in the present embodiments should form a 'functional combination' with the selected promoter, meaning that the terminator sequence should be capable of terminating transcription by the type of RNA polymerase initiating at the promoter. For example, in some embodiments, the present disclosure teaches a eukaryotic RNA pol II promoter and eukaryotic RNA pol II terminators, a T7 promoter and T7 terminators, a T3 promoter and T3 terminators, a yeast-recognized promoter and yeast-recognized termination sequences, etc., would generally form a functional combination. The identity of the transcriptional termination sequences used may also be selected based on the efficiency with which transcription is terminated from a given promoter. For example, a heterologous transcriptional terminator sequence may be provided transcriptionally downstream of the RNA encoding element to achieve a termination efficiency of at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% from a given promoter.

In some embodiments, efficiency of RNA transcription from the engineered expression construct can be improved by providing nucleic acid sequence forms a secondary structure comprising two or more hairpins at a position 3' to the end of the RNA encoding element. Not wishing to be bound by a particular theory, the secondary structure destabilizes the transcription elongation complex and leads to the polymerase becoming dissociated from the DNA template, thereby minimizing unproductive transcription of non-functional sequence and increasing transcription of the desired RNA. Accordingly, a termination sequence may be provided that forms a secondary structure comprising two or more adjacent hairpins. Generally, a hairpin can be formed by a palindromic nucleotide sequence that can fold back on itself to form a paired stem region whose arms are connected by a single stranded loop. In some embodiments, the termination sequence comprises 2, 3, 4, 5, 6, 7, 8, 9, 10 or more adjacent hairpins. In some embodiments, the adjacent hairpins are separated by 0, 1, 2, 3, 4, 5, 6, 7, 8, 9, 10, 11, 12, 13, 14, or 15 unpaired nucleotides. In some embodiments, a hairpin stem comprises 4, 5, 6, 7, 8, 9, 10, 11, 12, 13, 14, 15, 16, 17, 18, 19, 20, 21, 22, 23, 24, 25, 26, 27, 28, 29, 30 or more base pairs in length. In certain embodiments, a hairpin stem is 12 to 30 base pairs in length. In certain embodiments, the termination sequence comprises two or more medium-sized hairpins having stem region comprising about 9 to 25 base pairs. In some embodiments, the hairpin comprises a loop-forming region of 1, 2, 3, 4, 5, 6, 7, 8, 9, or 10 nucleotides. In some embodiments, the loop-forming region comprises 4-8 nucleotides. Not wishing to be bound by a particular theory, stability of the secondary structure can be correlated with termination efficiency. Hairpin stability is determined by its length, the number of mismatches or bulges it contains and the base composition of the paired region. Pairings between guanine and cytosine have three hydrogen bonds and are more stable compared to adenine-thymine pairings, which have only two. The G/C content of a hairpin-forming palindromic nucleotide sequence can be at least 60%, at least 65%, at least 70%, at least 75%, at least 80%, at least 85%, at least 90% or more. In some embodiments, the G/C content of a hairpin-forming palindromic nucleotide sequence is at least 80%. In some embodiments, the termination sequence is derived from one or more transcriptional terminator sequences of prokaryotic, eukaryotic or phage origin. In some embodiments, a nucleotide sequence encoding a series of 4, 5, 6, 7, 8, 9, 10 or more adenines (A) are provided 3' to the termination sequence.

In some embodiments, the present disclosure teaches the use of a series of tandem termination sequences. In some embodiments, the first transcriptional terminator sequence of a series of 2, 3, 4, 5, 6, 7, or more may be placed directly 3' to the final nucleotide of the dsRNA encoding element or at a distance of at least 1-5, 5-10, 10-15, 15-20, 20-25, 25-30, 30-35, 35-40, 40-45, 45-50, 50-100, 100-150, 150-200, 200-300, 300-400, 400-500, 500-1,000 or more nucleotides 3' to the final nucleotide of the dsRNA encoding element. The number of nucleotides between tandem transcriptional terminator sequences may be varied, for example, transcriptional terminator sequences may be separated by 0, 1, 2, 3, 4, 5, 6, 7, 8, 9, 10, 10-15, 15-20, 20-25, 25-30, 30-35, 35-40, 40-45, 45-50 or more nucleotides. In some embodiments, the transcriptional terminator sequences may be selected based on their predicted secondary structure as determined by a structure prediction algorithm. Structural prediction programs are well known in the art and include, for example, CLC Main Workbench.

Persons having skill in the art will recognize that the methods of the present disclosure are compatible with any termination sequence. A non-exhaustive listing of transcriptional terminator sequences of the present disclosure is provided in Table 1.1 below. In one embodiment, a transcriptional terminator of the present disclosure can be an orthologue of a termination sequence provided in Table 1.1. For example, if the host cell is an *Aspergillus*, the termination sequence can be an orthologue of a non-*Aspergillus* termination sequence selected from Table 1.1.

TABLE 1.1

Non-exhaustive list of termination sequences of the present disclosure.
Yeast and other Eukaryotes

| Name | Description | Direction | Length |
| --- | --- | --- | --- |
| BBa_J63002 | ADH1 terminator from *S. cerevisiae* | Forward | 225 |
| BBa_K110012 | STE2 terminator | Forward | 123 |
| BBa_K1462070 | cyc1 | | 250 |
| BBa_K1486025 | ADH1 Terminator | Forward | 188 |
| BBa_K392003 | yeast ADH1 terminator | | 129 |
| BBa_K801011 | TEF1 yeast terminator | | 507 |
| BBa_K801012 | ADH1 yeast terminator | | 349 |
| BBa_Y1015 | CycE1 | | 252 |
| BBa_J52016 | eukaryotic -- derived from SV40 early poly A signal sequence | Forward | 238 |
| BBa_J63002 | ADH1 terminator from *S. cerevisiae* | Forward | 225 |
| BBa_K110012 | STE2 terminator | Forward | 123 |
| BBa_K1159307 | 35S Terminator of Cauliflower Mosaic Virus (CaMV) | | 217 |
| BBa_K1462070 | cyc1 | | 250 |
| BBa_K1484215 | nopaline synthase terminator | | 293 |
| BBa_K1486025 | ADH1 Terminator | Forward | 188 |
| BBa_K392003 | yeast ADH1 terminator | | 129 |
| BBa_K404108 | hGH terminator | | 481 |
| BBa_K404116 | hGH_[AAV2]-right-ITR | | 632 |
| BBa_K678012 | SV40 poly A, terminator for mammalian cells | | 139 |

TABLE 1.1-continued

Non-exhaustive list of termination sequences of the present disclosure.
Yeast and other Eukaryotes

| Name | Description | Direction | Length |
|---|---|---|---|
| BBa_K678018 | hGH poly A, terminator for mammalian cells | | 635 |
| BBa_K678019 | BGH poly A, mammalian terminator | | 233 |
| BBa_K678036 | trpC terminator for *Aspergillus nidulans* | | 759 |
| BBa_K678037 | T1-motni, terminator for *Aspergillus niger* | | 1006 |
| BBa_K678038 | T2-motni, terminator for *Aspergillus niger* | | 990 |
| BBa_K678039 | T3-motni, terminator for *Aspergillus niger* | | 889 |
| BBa_K801011 | TEF1 yeast terminator | | 507 |
| BBa_K801012 | ADH1 yeast terminator | | 349 |
| BBa_Y1015 | CycE1 | | 252 |

Hypothesis-Driven Diversity Pools and Hill Climbing

The present disclosure teaches that the HTP genomic engineering methods of the present disclosure do not require prior genetic knowledge in order to achieve significant gains in host cell performance. Indeed, the present disclosure teaches methods of generating diversity pools via several functionally agnostic approaches, including random mutagenesis, and identification of genetic diversity among pre-existing host cell variants (e.g., such as the comparison between a wild type host cell and an industrial variant).

In some embodiments however, the present disclosure also teaches hypothesis-driven methods of designing genetic diversity mutations that will be used for downstream HTP engineering. That is, in some embodiments, the present disclosure teaches the directed design of selected mutations. In some embodiments, the directed mutations are incorporated into the engineering libraries of the present disclosure (e.g., SNP swap, PRO swap, or STOP swap).

In some embodiments, the present disclosure teaches the creation of directed mutations based on gene annotation, hypothesized (or confirmed) gene function, or location within a genome. The diversity pools of the present disclosure may include mutations in genes hypothesized to be involved in a specific metabolic or genetic pathway associated in the literature with increased performance of a host cell. In other embodiments, the diversity pool of the present disclosure may also include mutations to genes associated with improved host performance. In yet other embodiments, the diversity pool of the present disclosure may also include mutations to genes based on algorithmic predicted function, or other gene annotation.

In some embodiments, the present disclosure teaches a "shell" based approach for prioritizing the targets of hypothesis-driven mutations. The shell metaphor for target prioritization is based on the hypothesis that only a handful of primary genes are responsible for most of a particular aspect of a host cell's performance (e.g., production of a single biomolecule). These primary genes are located at the core of the shell, followed by secondary effect genes in the second layer, tertiary effects in the third shell, and . . . etc. For example, in one embodiment the core of the shell might comprise genes encoding critical biosynthetic enzymes within a selected metabolic pathway (e.g., production of citric acid). Genes located on the second shell might comprise genes encoding for other enzymes within the biosynthetic pathway responsible for product diversion or feedback signaling. Third tier genes under this illustrative metaphor would likely comprise regulatory genes responsible for modulating expression of the biosynthetic pathway, or for regulating general carbon flux within the host cell.

The present disclosure also teaches "hill climb" methods for optimizing performance gains from every identified mutation. In some embodiments, the present disclosure teaches that random, natural, or hypothesis-driven mutations in HTP diversity libraries can result in the identification of genes associated with host cell performance. For example, the present methods may identify one or more beneficial SNPs located on, or near, a gene coding sequence. This gene might be associated with host cell performance, and its identification can be analogized to the discovery of a performance "hill" in the combinatorial genetic mutation space of an organism.

In some embodiments, the present disclosure teaches methods of exploring the combinatorial space around the identified hill embodied in the SNP mutation. That is, in some embodiments, the present disclosure teaches the perturbation of the identified gene and associated regulatory sequences in order to optimize performance gains obtained from that gene node (i.e., hill climbing). Thus, according to the methods of the present disclosure, a gene might first be identified in a diversity library sourced from random mutagenesis, but might be later improved for use in the strain improvement program through the directed mutation of another sequence within the same gene.

The concept of hill climbing can also be expanded beyond the exploration of the combinatorial space surrounding a single gene sequence. In some embodiments, a mutation in a specific gene might reveal the importance of a particular metabolic or genetic pathway to host cell performance. For example, in some embodiments, the discovery that a mutation in a single RNA degradation gene resulted in significant host performance gains could be used as a basis for mutating related RNA degradation genes as a means for extracting additional performance gains from the host organism. Persons having skill in the art will recognize variants of the above described shell and hill climb approaches to directed genetic design.

Morphology-Related Genes

The morphology related genes for use in the methods, strains and systems provided herein can be any gene known in the art that has been shown or is suspected to play a role in controlling or affecting the morphology of a filamentous eukaryotic microbe (e.g., filamentous fungal host cell or strain). The gene that regulates morphology of the host cell can be any such gene as provided herein. In one embodiment, the gene is an orthologue of the *S. cerevisiae* SLN1. In another embodiment, the morphology related gene can be any gene from the same pathway as the orthologue of the *S. cerevisiae* SLN1 gene. The genes that are part of the same pathway can be selected from orthologues of the *S. cerevisiae* Ypd1, Skn7, Ssk1 and Ssk2 genes or any combination thereof. In another embodiment, the gene is an orthologue of the *A. niger* gene with nucleic acid SEQ ID NO: 11 and/or any gene in the same biochemical pathway of said orthologue of the *A. niger* gene with nucleic acid SEQ ID NO: 11. In another embodiment, the gene is an orthologue of the *A. niger* gene with nucleic acid SEQ ID NO: 12 and/or any gene in the same biochemical pathway of said orthologue of the *A. niger* gene with nucleic acid SEQ ID NO: 12. In another embodiment, the gene is an orthologue of the *A. niger* gene with nucleic acid SEQ ID NO. 14 and/or any gene in the same biochemical pathway of said orthologue of the *A. niger* gene with nucleic acid SEQ ID NO: 14.

The morphology related genes for use in the methods, strains and systems provided herein can be any gene known in the art that has been shown or is suspected to play a role in controlling or affecting the morphology of *A. niger*. In one embodiment, the gene is a SNP containing gene with a nucleic acid sequence selected from SEQ ID NOs: 11, 12, 13 or 14 (see Table 4). In one embodiment, the gene is a plurality of genes. The plurality of genes can be any combination of the SNP containing genes with a nucleic acid sequence selected from SEQ ID NOs: 11, 12, 13 or 14. The plurality of genes can be any combination of the SNP containing genes with a nucleic acid sequence selected from SEQ ID NOs: 11 and any gene present within the same biochemical pathway. The plurality of genes can be any combination of the SNP containing genes with a nucleic acid sequence selected from SEQ ID NOs: 12 and any gene present within the same biochemical pathway. The plurality of genes can be any combination of the SNP containing genes with a nucleic acid sequence selected from SEQ ID NOs: 13 and any gene present within the same biochemical pathway. The plurality of genes can be any combination of the SNP containing genes with a nucleic acid sequence selected from SEQ ID NOs: 14 and any gene present within the same biochemical pathway. In one embodiment, the gene is a wild-type or non-SNP containing version of the gene with a nucleic acid sequence selected from SEQ ID NOs: 11, 12, 13 or 14 (see Table 4).

In one embodiment, the gene that regulates morphology of an *A. niger* host cell is an *A. niger* orthologue of the *S. cerevisiae* SLN1 gene. The *A. niger* ortholog of the *S. cerevisiae* SLN1 gene can be a wild-type form or a mutant form. The mutated form of the *A. niger* orthologue of the *S. cerevisiae* SLN1 gene can be FungiSNP_18 from Table 4 or with a nucleic acid sequence of SEQ ID NO: 13. In another embodiment, the morphology related gene can be any gene from the same pathway as the *A. niger* orthologue of the *S. cerevisiae* SLN1 gene. The genes that are part of the same pathway can be selected from *A. niger* orthologues of the *S. cerevisiae* Ypd1, Skn7, Ssk1 and Ssk2 genes or any combination thereof. The genes that are part of the same pathway can be selected from the nucleic acid sequences represented by SEQ ID NOs: 15, 16, 17, 18, 19 or any combination thereof.

The morphology-related genes can be any of the genes or orthologues thereof that are disclosed in Dai et al. ("Identification of Genes Associated with Morphology in *Aspergillus niger* by Using Suppression Subtractive Hybridization" Applied and Environmental Microbiology, April 2004, p. 2474-2485), the contents of which are incorporated by reference in its entirety. The morphology-related gene can be selected from the gas1 gene, the sfb3 gene, the seb1 gene, the mpg1 gene, the crz1 gene, and the tps2 gene. The expression of any of the morphology related genes can be increased or decreased depending on if the gene promotes a filamentous or mycelial morphology or pellet morphology.

As described herein, the expression of any of the morphology related genes or mutant thereof (e.g., FungiSNPs 9, 12, 18 or 40 from Table 4) provided herein can be controlled by replacing the native promoter of the gene with a heterologous promoter that confers expression at a level (e.g., higher or lower) different from the native promoter. The heterologous promoter can be selected from Table 1. Replacement of the native promoter can be performed using a PRO swap method as provided herein.

It is a further object of the present invention to provide a filamentous fungus host cell comprising a heterologous modification of the host cell's orthologue of a *S. cerevisiae* SLN1 gene, whereby the modified orthologue of the *S. cerevisiae* SLN1 gene has reduced activity and/or reduced expression relative to a parental filamentous fungal host cell lacking the heterologous modification. The filamentous fungal host can possess a non-mycelium, pellet forming phenotype. This pellet phenotype can be due to the filamentous fungal host cell possessing the heterologous modification in the orthologue of the *S. cerevisiae* SLN1 gene that causes cells of the filamentous host cell to produce a substantially reduced amount and/or substantially less active form of functional orthologue of a *S. cerevisiae* SLN1 gene as compared to cells of that do not possess said heterologous modification. The filamentous fungal host cell and any parental strain said filamentous fungal host cell is derived therefrom can be any filamentous fungus known in the art and/or provided herein such as, for example, *A. niger*. In one embodiment, the filamentous fungal host cell sporulates normally as compared to a parental strain when grown under non-submerged growth conditions such as, for example, on solid media. In another embodiment, the filamentous fungal host cell is sporulates normally as compared to the parental strain when grown under non-submerged growth conditions such as, for example, on solid media only when one, all or a combination of orthologoues of the SNP containing gene from Table 4 are also expressed in the filamentous fungal host cell. In one embodiment, the filamentous fungal host cell is *A. niger* and said *A. niger* host cell sporulates normally as compared to a parental strain when grown under non-submerged growth conditions such as, for example, on solid media only when one, all or a combination of the SNP containing genes from Table 4 are also expressed in said *A. niger* host cell. In yet another embodiment, the filamentous fungal host cell sporulates normally as compared to a parental strain when grown under non-submerged growth conditions such as, for example, on solid media only when one, all or a combination of orthologoues of the SNP containing genes from Table 4 are also expressed in the filamentous fungal host cell. The submerged culture conditions can comprise growing the variant strain in CAP medium. The CAP media can comprise manganese and be substantially free of chelating agents. The manganese can be present in amount that is at least 13 ppb or higher.

The genetic alteration to the orthologue of the *S. cerevisiae* SLN1 gene can be replacement of the wild-type form of the gene with a mutated orthologue of the *S. cerevisiae* SLN1 gene, replacement of the native promoter of the gene with a heterologous promoter that more weakly expresses the gene for the orthologue of the *S. cerevisiae* SLN1 protein as compared to the native promoter, or a combination thereof. Alternatively, the genetic alteration to the orthologue of the *S. cerevisiae* SLN1 gene can be the removal of the orthologue of the *S. cerevisiae* SLN1 gene and replacement with a selectable marker gene. The mutated form of the orthologue of the *S. cerevisiae* SLN1 gene can comprise a SNP, a non-sense mutation, a missense mutation, a deletion, an insertion or any combination thereof. In one embodiment, the filamentous fungal host cell is *A. niger* and the *A. niger* orthologue of the *S. cerevisiae* SLN1 protein can be encoded by SEQ ID NO: 13. The heterologous promoter can be selected from a promoter listed in Table 1. In one embodiment, the heterologous promoter is a manB or amyB promoter. Further to this embodiment, the heterologous promoter can be SEQ ID NO: 1 or SEQ ID NO: 2. The selectable marker can be selected from an auxotrophic marker gene, a colorimetric marker gene, antibiotic resistance gene, or a directional marker gene as provided herein.

The filamentous fungal host cell that possesses a substantially reduced amount and/or substantially less active form of functional orthologue of the *S. cerevisiae* SLN1 protein can further comprise a genetic disruption or alteration in one or more genes that are part of the same pathway as the orthologue of the *S. cerevisiae* SLN1 gene. The one or more genes that are part of the same pathway can be selected from orthologues of the *S. cerevisiae* Ypd1, Skn7, Ssk1 and Ssk2 genes or any combination thereof. In one embodiment, the filamentous fungal host cell is *A. niger* and the orthologues of the *S. cerevisiae* SLN1, Ypd1, Skn7, Ssk1 and Ssk2 genes are *A. niger* orthologues or mutants thereof. Further to this embodiment, the one or more genes that are part of the same pathway can be selected from the nucleic acid sequences represented by SEQ ID NOs: 15, 16, 17, 18, 19 or any combination thereof. The filamentous fungal host cell can further comprise a genetic disruption or alteration in one or more genes that are part of the different pathway that is known to play a role in controlling filamentous fungal morphology. The one or more genes that are part of the different pathway can be any of the genes provided herein. The one or more genes that are part of the different pathway can be selected from *A. niger* orthologues of genes with nucleic acid sequences represented by SEQ ID NOs: 11, 12, 14 or any combination thereof. In one embodiment, the filamentous fungal host cell is *A. niger* and the one or more genes that are part of the different pathway are the *A. niger* genes with nucleic acid sequences represented by SEQ ID NOs: 11, 12, 14 or any combination thereof. In another embodiment, the filamentous fungal host cell is *A. niger* and the one or more genes that are part of the different pathway are the non-SNP containing versions of the *A. niger* genes with nucleic acid sequences represented by SEQ ID NOs: 11, 12, 14 or any combination thereof.

The genetic disruption or alteration to the one or more genes that are part of the same pathway as the orthologue of the *S. cerevisiae* SLN1 gene or are part of the different pathway that is known to play a role in controlling filamentous fungal morphology can be replacement of the wild-type form of the gene with a mutated form of the gene, replacement of the native promoter of the gene with a heterologous promoter that alters the expression (e.g., higher or lower) of the gene as compared to the native promoter, or a combination thereof. The promoter can be a promoter listed in Table 1. Alternatively, the genetic disruption or alteration to the one or more genes that are part of the same pathway as the orthologue of the *S. cerevisiae* SLN1 gene or are part of the different pathway that is known to play a role in controlling filamentous fungal morphology can be the removal of the gene and replacement with a selectable marker gene. The selectable marker can be selected from an auxotrophic marker gene, a colorimetric marker gene, antibiotic resistance gene, or a directional marker gene as provided herein.

Also provided herein, are methods for generating the filamentous fungus host cell that possess a substantially reduced amount and/or substantially less active form of functional orthologue of the *S. cerevisiae* SLN1 protein. The methods can comprise performing a PRO swap method, a SNP Swap method or a combination of a PRO swap and SNP swap method as provided herein.

It is a further object of the present invention to provide a filamentous fungus host cell comprising a heterologous modification of the host cell's orthologue of an *A. niger* gene with a nucleic acid sequence selected from SEQ ID NO. 11, 12, 14 or any combination thereof, whereby the modified orthologue of the *A. niger* gene with a nucleic acid sequence selected from SEQ ID NO. 11, 12, 14 or any combination thereof has reduced activity and/or reduced expression relative to a parental filamentous fungal host cell lacking the heterologous modification(s). The filamentous fungal host can possess a non-mycelium, pellet forming phenotype as compared to the cells of the parental strain when grown in a submerged culture due to the filamentous host cell possessing a heterologous modification to the orthologue of an *A. niger* gene with nucleic acid sequence SEQ ID NO: 11, 12, 14 or any combination thereof. Possession of an orthologue of an *A. niger* gene with a nucleic acid sequence of SEQ ID NO: 11, 12, 14 or any combination thereof can cause cells of the host cell to produce a substantially reduced amount and/or substantially less active form of functional protein encoded by orthologues of the *A. niger* genes with said SEQ ID NOs as compared to cells of a parental host cell when grown under submerged culture conditions. The filamentous host cell and parental strain of said filamentous fungal host cell can be any filamentous fungus known in the art and/or provided herein such as, for example, *A. niger*. In one embodiment, the filamentous host cell strain sporulates normally as compared to a parental strain when grown under non-submerged growth conditions such as, for example, on solid media. In some cases, the orthologues of the *A. niger* genes with SEQ ID NOs; 11, 12 or 14 are further genetically altered. The further genetic alteration can be replacement of the native promoter of the gene with a heterologous promoter that more weakly expresses the gene as compared to the native promoter. Alternatively, the further genetic alteration can be the removal of the orthologues of the *A. niger* genes with SEQ ID NO: 11, 12 or 14 and replacement with a selectable marker gene. The selectable marker can be selected from an auxotrophic marker gene, a colorimetric marker gene, antibiotic resistance gene, or a directional marker gene as provided herein. The heterologous promoter can be selected from a promoter listed in Table 1. In one embodiment, the heterologous promoter is a manB or amyB promoter. Further to this embodiment, the heterologous promoter can have the nucleic acid sequence of SEQ ID NO: 1 or SEQ ID NO: 2. The submerged culture conditions can comprise growing the variant strain in CAP medium. The CAP media can comprise manganese and be substantially free of chelating agents. The manganese can be present in amount that is at least 13 ppb or higher. It should be understood that in embodiments where the filamentous fungal host cell is *A. niger*, the *A. niger* gene with a nucleic acid sequence selected from SEQ ID NO. 11, 12, 14 or wild-type versions thereof can comprise the heterologous modifications detailed herein.

The filamentous fungal host cell that possesses a substantially reduced amount and/or substantially less active form of functional protein encoded by orthologues of the *A. niger* genes with sequences selected from SEQ ID NOs: 11, 12 or 14 can further comprise a genetic disruption or alteration in one or more genes that are part of the same pathway. The filamentous fungal host cell can further comprise a genetic disruption or alteration in one or more genes that are part of the different pathway that is known to play a role in controlling filamentous fungal morphology. The one or more genes that are part of the different pathway can be any of the genes provided herein. The genetic disruption or alteration to the one or more genes that are part of the same pathway or are part of the different pathway that is known to play a role in controlling filamentous fungal morphology can be replacement of the wild-type form of the gene with a mutated form of the gene, replacement of the native promoter of the gene with a heterologous promoter that alters the expression (e.g., higher or lower) of the gene as compared to the native promoter, or a combination thereof. The promoter can be a promoter listed in Table 1. Alternatively, the genetic disruption or alteration to the one or more genes that are part of the same pathway or are part of the different pathway that is known to play a role in controlling filamentous fungal morphology can be the removal of the gene and replacement with a selectable marker gene. The selectable marker can be selected from an auxotrophic marker gene, a colorimetric marker gene, antibiotic resistance gene, or a directional marker gene as provided herein.

Also provided herein, are methods for generating the variant strain of filamentous fungus that possess a substantially reduced amount and/or substantially less active form of functional protein encoded by orthologues of the *A. niger* genes with SEQ ID NOs: 11, 12 or 14. The methods can comprise performing a PRO swap method, a SNP Swap method or a combination of a PRO swap and SNP swap method as provided herein.

It is yet another object of this invention to provide a filamentous fungal host cell comprising a promoter operably linked to a gene that regulates morphology of the host cell, wherein the promoter is heterologous to the gene, and wherein the promoter has a sequence selected from the group consisting of SEQ ID NOs. 1-4. The filamentous fungus host cell can be any filamentous fungus known in the art and/or provided herein such as, for example, *A. niger*. In some cases, the fungal host cell sporulates normally as compared to a parental strain of the host cell when grown under non-submerged growth conditions such as, for example, on solid media, but forms a non-mycelium, pellet morphology when grown under submerged culture conditions. In some cases, the host cell can comprise one or more genes that regulate morphology such that each of said one or more genes has a heterologous promoter linked thereto. The one or more genes that regulates morphology of the host cell can be any such gene as provided herein such as, for example, the SNP containing gene sequences represented by SEQ ID NOs: 11, 12, 13 or 14 or orthologues thereof from Table 4, either alone or in combination. In some cases, the SNP containing gene sequences represented by SEQ ID NOs: 11, 12, 13 or 14 or orthologues thereof from Table 4 can be in combination with one or more genes from the same pathway as the respective SNP containing gene sequence. In one embodiment, the one or more genes is a wild-type or non-SNP containing version of the gene with a nucleic acid sequence selected from SEQ ID NOs: 11, 12, 13 or 14 or orthologues thereof, either alone or in combination. In another embodiment, the wild-type or non-SNP containing version of the gene with a nucleic acid sequence selected from SEQ ID NOs: 11, 12, 13 or 14 or orthologues thereof can be in combination with one or more genes from the same pathway as the respective wild-type or non-SNP containing gene sequence. In one embodiment, the gene that regulates morphology of the host cell can be an orthologue of the *S. cerevisiae* SLN1 gene or a gene in the same signaling pathway. The one or more genes that are part of the same signaling pathway can be selected from orthologues of the *S. cerevisiae* Ypd1, Skn7, Ssk1 and Ssk2 genes or any combination thereof. In one embodiment, the filamentous fungal host cell is *A. niger* and the one or more genes that are part of the same signaling pathway can be selected from the nucleic acid sequences represented by SEQ ID NOs: 15, 16, 17, 18, 19 or any combination thereof. The orthologue of the *S. cerevisiae* SLN1 gene can be a wild-type or mutant form of the gene. In one embodiment, the filamentous fungal host cell is *A. niger* and the mutated *A. niger* orthologue of the *S. cerevisiae* SLN1 gene has the nucleic acid sequence of SEQ ID NO: 13. The submerged culture conditions can comprise growing the variant strain in CAP medium. The CAP media can comprise manganese and be substantially free of chelating agents. The manganese can be present in amount that is at least 13 ppb or higher.

Cell Culture and Fermentation

Cells of the present disclosure can be cultured in conventional nutrient media modified as appropriate for any desired biosynthetic reactions or selections. In some embodiments, the present disclosure teaches culture in inducing media for activating promoters. In some embodiments, the present disclosure teaches media with selection agents, including selection agents of transformants (e.g., antibiotics), or selection of organisms suited to grow under inhibiting conditions (e.g., high ethanol conditions). In some embodiments, the present disclosure teaches growing cell cultures in media optimized for cell growth. In other embodiments, the present disclosure teaches growing cell cultures in media optimized for product yield. In some embodiments, the present disclosure teaches growing cultures in media capable of inducing cell growth and also contains the necessary precursors for final product production (e.g., high levels of sugars for ethanol production).

Culture conditions, such as temperature, pH and the like, are those suitable for use with the host cell selected for expression, and will be apparent to those skilled in the art. As noted, many references are available for the culture and production of many cells, including cells of bacterial, plant, animal (including mammalian) and archaebacterial origin. See e.g., Sambrook, Ausubel (all supra), as well as Berger, *Guide to Molecular Cloning Techniques, Methods in Enzymology* volume 152 Academic Press, Inc., San Diego, Calif.; and Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelle et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture;* Fundamental Methods Springer Lab Manual, Springer-Verlag (Berlin Heidelberg N.Y.); Jones, ed. (1984) *Plant Gene Transfer and Expression Protocols*, Humana Press, Totowa, N.J. and Plant Molecular Biology (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* from Sigma-Aldrich, Inc (St Louis, Mo.) ("Sigma-LSRCCC") and, for example, *The Plant Culture Catalogue* and supplement also from Sigma-Aldrich, Inc (St Louis, Mo.) ("Sigma-PCCS"), all of which are incorporated herein by reference.

The culture medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981).

The present disclosure furthermore provides a process for fermentative preparation of a product of interest, comprising the steps of: a) culturing a microorganism according to the present disclosure in a suitable medium, resulting in a fermentation broth; and b) concentrating the product of interest in the fermentation broth of a) and/or in the cells of the microorganism.

In some embodiments, the present disclosure teaches that the microorganisms produced may be cultured continuously—as described, for example, in WO 05/021772—or discontinuously in a batch process (batch cultivation) or in a fed-batch or repeated fed-batch process for the purpose of producing the desired organic-chemical compound. A summary of a general nature about known cultivation methods is available in the textbook by Chmiel (Bioprozeßtechnik. 1: Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

In some embodiments, the cells of the present disclosure are grown under batch or continuous fermentations conditions.

Classical batch fermentation is a closed system, wherein the compositions of the medium is set at the beginning of the fermentation and is not subject to artificial alternations during the fermentation. A variation of the batch system is a fed-batch fermentation which also finds use in the present disclosure. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art.

Continuous fermentation is a system where a defined fermentation medium is added continuously to a bioreactor and an equal amount of conditioned medium is removed simultaneously for processing and harvesting of desired biomolecule products of interest. In some embodiments, continuous fermentation generally maintains the cultures at a constant high density where cells are primarily in log phase growth. In some embodiments, continuous fermentation generally maintains the cultures at a stationary or late log/stationary, phase growth. Continuous fermentation systems strive to maintain steady state growth conditions.

Methods for modulating nutrients and growth factors for continuous fermentation processes as well as techniques for maximizing the rate of product formation are well known in the art of industrial microbiology.

For example, a non-limiting list of carbon sources for the cultures of the present disclosure include, sugars and carbohydrates such as, for example, glucose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol; and organic acids such as, for example, acetic acid or lactic acid.

A non-limiting list of the nitrogen sources for the cultures of the present disclosure include, organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

A non-limiting list of the possible phosphorus sources for the cultures of the present disclosure include, phosphoric acid, potassium dihydrogen phosphate or dipotassium hydrogen phosphate or the corresponding sodium-containing salts.

The culture medium may additionally comprise salts, for example in the form of chlorides or sulfates of metals such as, for example, sodium, potassium, magnesium, calcium and iron, such as, for example, magnesium sulfate or iron sulfate, which are necessary for growth.

Finally, essential growth factors such as amino acids, for example homoserine and vitamins, for example thiamine, biotin or pantothenic acid, may be employed in addition to the abovementioned substances.

In some embodiments, the pH of the culture can be controlled by any acid or base, or buffer salt, including, but not limited to sodium hydroxide, potassium hydroxide, ammonia, or aqueous ammonia; or acidic compounds such as phosphoric acid or sulfuric acid in a suitable manner. In some embodiments, the pH is generally adjusted to a value of from 6.0 to 8.5, preferably 6.5 to 8.

In some embodiments, the cultures of the present disclosure may include an anti-foaming agent such as, for example, fatty acid polyglycol esters. In some embodiments the cultures of the present disclosure are modified to stabilize the plasmids of the cultures by adding suitable selective substances such as, for example, antibiotics.

In some embodiments, the culture is carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired product of interest (e.g. an organic-chemical compound) sufficient for being recovered has formed. This aim can normally be achieved within 10 hours to 160 hours. In continuous processes, longer cultivation times are possible. The activity of the microorganisms results in a concentration (accumulation) of the product of interest in the fermentation medium and/or in the cells of said microorganisms.

In some embodiments, the culture is carried out under anaerobic conditions.

Screening

In some embodiments, the present disclosure teaches high-throughput initial screenings. In other embodiments, the present disclosure also teaches robust tank-based validations of performance data (see FIG. 6B).

In some embodiments, the high-throughput screening process is designed to predict performance of strains in bioreactors. As previously described, culture conditions are selected to be suitable for the organism and reflective of bioreactor conditions. Individual colonies are picked and transferred into 96 well plates and incubated for a suitable amount of time. Cells are subsequently transferred to new 96 well plates for additional seed cultures, or to production cultures. Cultures are incubated for varying lengths of time, where multiple measurements may be made. These may include measurements of product, biomass or other characteristics that predict performance of strains in bioreactors. High-throughput culture results are used to predict bioreactor performance.

In some embodiments, the tank-based performance validation is used to confirm performance of strains isolated by high-throughput screening. Candidate strains are screened using bench scale fermentation reactors (e.g., reactors disclosed in Table 3 of the present disclosure) for relevant strain performance characteristics such as productivity or yield.

Product Recovery and Quantification

Methods for screening for the production of products of interest are known to those of skill in the art and are discussed throughout the present specification. Such methods may be employed when screening the strains of the disclosure.

In some embodiments, the present disclosure teaches methods of improving strains designed to produce non-secreted intracellular products. For example, the present disclosure teaches methods of improving the robustness, yield, efficiency, or overall desirability of cell cultures producing intracellular enzymes, oils, pharmaceuticals, or other valuable small molecules or peptides. The recovery or isolation of non-secreted intracellular products can be achieved by lysis and recovery techniques that are well known in the art, including those described herein.

For example, in some embodiments, cells of the present disclosure can be harvested by centrifugation, filtration, settling, or other method. Harvested cells are then disrupted by any convenient method, including freeze-thaw cycling, sonication, mechanical disruption, or use of cell lysing agents, or other methods, which are well known to those skilled in the art.

The resulting product of interest, e.g. a polypeptide, may be recovered/isolated and optionally purified by any of a number of methods known in the art. For example, a product polypeptide may be isolated from the nutrient medium by conventional procedures including, but not limited to: centrifugation, filtration, extraction, spray-drying, evaporation, chromatography (e.g., ion exchange, affinity, hydrophobic interaction, chromatofocusing, and size exclusion), or precipitation. Finally, high performance liquid chromatography (HPLC) can be employed in the final purification steps. (See for example Purification of intracellular protein as described in Parry el al., 2001, *Biochem. J.* 353:117, and Hong et al., 2007, *Appl. Microbiol. Biotechnol.* 73:1331, both incorporated herein by reference).

In addition to the references noted supra, a variety of purification methods are well known in the art, including, for example, those set forth in: Sandana (1997) *Bioseparation of Proteins*, Academic Press, Inc.; Bollag et al. (1996) *Protein Methods*, 2$^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* 3$^{rd}$ Edition, Springer Verlag, NY; Janson and Ryden (1998) *Protein Purification: Principles. High Resolution Methods and Applications*, Second Edition, Wiley-VCH, NY; and Walker (1998) *Protein Protocols on CD-ROM*, Humana Press, NJ, all of which are incorporated herein by reference.

In some embodiments, the present disclosure teaches the methods of improving strains designed to produce secreted products. For example, the present disclosure teaches methods of improving the robustness, yield, efficiency, or overall desirability of cell cultures producing valuable small molecules or peptides.

In some embodiments, immunological methods may be used to detect and/or purify secreted or non-secreted products produced by the cells of the present disclosure. In one example approach, antibody raised against a product molecule (e.g., against an insulin polypeptide or an immunogenic fragment thereof) using conventional methods is immobilized on beads, mixed with cell culture media under conditions in which the endoglucanase is bound, and precipitated. In some embodiments, the present disclosure teaches the use of enzyme-linked immunosorbent assays (ELISA).

In other related embodiments, immunochromatography is used, as disclosed in U.S. Pat. Nos. 5,591,645, 4,855,240, 4,435,504, 4,980,298, and Se-Hwan Paek, et al., "Development of rapid One-Step Immunochromatographic assay, Methods", 22, 53-60, 2000), each of which are incorporated by reference herein. A general immunochromatography detects a specimen by using two antibodies. A first antibody exists in a test solution or at a portion at an end of a test piece in an approximately rectangular shape made from a porous membrane, where the test solution is dropped. This antibody is labeled with latex particles or gold colloidal particles (this antibody will be called as a labeled antibody hereinafter). When the dropped test solution includes a specimen to be detected, the labeled antibody recognizes the specimen so as to be bonded with the specimen. A complex of the specimen and labeled antibody flows by capillarity toward an absorber, which is made from a filter paper and attached to an end opposite to the end having included the labeled antibody. During the flow, the complex of the specimen and labeled antibody is recognized and caught by a second antibody (it will be called as a tapping antibody hereinafter) existing at the middle of the porous membrane and, as a result of this, the complex appears at a detection part on the porous membrane as a visible signal and is detected.

In some embodiments, the screening methods of the present disclosure are based on photometric detection techniques (absorption, fluorescence). For example, in some embodiments, detection may be based on the presence of a fluorophore detector such as GFP bound to an antibody. In other embodiments, the photometric detection may be based on the accumulation on the desired product from the cell culture. In some embodiments, the product may be detectable via UV of the culture or extracts from said culture.

Persons having skill in the art will recognize that the methods of the present disclosure are compatible with host cells producing any desirable biomolecule product of interest. Table 2 below presents a non-limiting list of the product categories, biomolecules, and host cells, included within the scope of the present disclosure. These examples are provided for illustrative purposes, and are not meant to limit the applicability of the presently disclosed technology in any way.

TABLE 2

A non-limiting list of the host cells and products of interest of the present disclosure.

| Product category | Products | Host category | Hosts |
|---|---|---|---|
| Flavor & Fragrance | Agarwood | Yeast | Saccharomyces cerevisiae |
| Flavor & Fragrance | Ambrox | Yeast | Saccharomyces cerevisiae |
| Flavor & Fragrance | Nootkatone | Yeast | Saccharomyces cerevisiae |
| Flavor & Fragrance | Patchouli oil | Yeast | Saccharomyces cerevisiae |
| Flavor & Fragrance | Saffron | Yeast | Saccharomyces cerevisiae |
| Flavor & Fragrance | Sandalwood oil | Yeast | Saccharomyces cerevisiae |
| Flavor & Fragrance | Valencene | Yeast | Saccharomyces cerevisiae |
| Flavor & Fragrance | Vanillin | Yeast | Saccharomyces cerevisiae |
| Food | CoQ10/Ubiquinol | Yeast | Schizosaccharomyces pombe |
| Food | Omega 3 fatty acids | Microalgae | Schizochytrium |
| Food | Omega 6 fatty acids | Microalgae | Schizochytrium |
| Food | Vitamin B2 | Filamentous fungi | Ashbya gossypii |
| Food | Erythritol | Yeast-like fungi | Torula coralline |
| Food | Erythritol | Yeast-like fungi | Pseudozyma tsukubaensis |
| Food | Erythritol | Yeast-like fungi | Moniliella pollinis |
| Food | Steviol glycosides | Yeast | Saccharomyces cerevisiae |
| Organic acids | Citric acid | Filamentous fungi | Aspergillus niger |
| Organic acids | Citric Acid | Filamentous fungi | Aspergillus carbonarius |
| Organic acids | Citric Acid | Filamentous fungi | Aspergillus aculeatus |
| Organic acids | Citric acid | Yeast | Pichia guilliermondii |
| Organic acids | Gluconic acid | Filamentous fungi | Aspergillus niger |
| Organic acids | Itaconic acid | Filamentous fungi | Aspergillus terreus |
| Organic acids | Itaconic acid | Filamentous fungi | Aspergillus niger |
| Organic acids | LCDAs - DDDA | Yeast | Candida |
| Organic acids | Kojic Acid | Filamentous fungi | Aspergillus oryzae |
| Organic acids | Kojic Acid | Filamentous fungi | Aspergillus flavus |
| Organic acids | Kojic Acid | Filamentous fungi | Aspergillus tamarii |
| Organic acids | Malic Acid | Filamentous fungi | Aspergillus oryzae |
| Organic acids | Oxalic acid | Filamentous fungi | Aspergillus niger |
| Organic acids | Succinic acid | Filamentous fungi | Aspergillus saccarolyticus |
| Organic acids | Lactic acid | Filamentous fungi | Aspergillus niger |
| Organic acids | Lactic acid | Filamentous fungi | Aspergillus brasiliensis |
| Hypolipidemic agent | Lovastatin | Filamentous fungi | Aspergillus terreus |
| Melanogenesis inhibitor | Terrein | Filamentous fungi | Aspergillus terreus |
| Immunosuppresent drug | Cyclosporine A | Filamentous fungi | Aspergillus terreus |
| Antiproliferative agent | Asperfuranone | Filamentous fungi | Aspergillus terreus |
| Antiproliferative agent | Asperfuranone | Filamentous fungi | Aspergillus nidulans |
| Cholesterol-lowering agent | Pyripyropene | Filamentous fungi | Aspergillus fumigatus |
| Antibiotics | Penicillin | Filamentous fungi | Aspergillus oryzae |
| Antibiotics | Penicillin | Filamentous fungi | Aspergillus nidulans |
| Antimicrobial agent | Fumagillin | Filamentous fungi | Aspergillus fumigatus |

TABLE 2-continued

A non-limiting list of the host cells and products of interest of the present disclosure.

| Product category | Products | Host category | Hosts |
|---|---|---|---|
| Anticancer agent | Fumitremorgin C | Filamentous fungi | Aspergillus fumigatus |
| Anticancer agent | Spirotryprostatins | Filamentous fungi | Aspergillus fumigatus |
| Anticancer agent; Antimicrobial agent | Plinabulin | Filamentous fungi | Aspergillus ustus |
| Anticancer agent | Phenylahistin | Filamentous fungi | Aspergillus ustus |
| Anticancer agent | Stephacidin A & B | Filamentous fungi | Aspergillus ochraceus |
| Anti cancer agent | Asperphenamate | Filamentous fungi | Aspergillus flavus |
| Cholecystokinin antagonist | Asperlicin | Filamentous fungi | Aspergillus alliaceus |
| Industrial enzyme | Alpha-amylase | Filamentous fungi | Aspergillus niger |
| Industrial enzyme | Alpha-amylase | Filamentous fungi | Aspergillus oryzae |
| Industrial enzyme | Aminopeptidase | Filamentous fungi | Aspergillus niger |
| Industrial enzyme | Aminopeptidase | Filamentous fungi | Aspergillus oryzae |
| Industrial enzyme | Aminopeptidase | Filamentous fungi | Aspergillus sojae |
| Industrial enzyme | AMP deaminase | Filamentous fungi | Aspergillus melleus |
| Industrial enzyme | Catalase | Filamentous fungi | Aspergillus niger |
| Industrial enzyme | Cellulase | Filamentous fungi | Aspergillus niger |
| Industrial enzyme | Chymosin | Filamentous fungi | Aspergillus niger |
| Industrial enzyme | Esterase | Filamentous fungi | Aspergillus niger |
| Industrial enzyme | Alpha-galactosidase | Filamentous fungi | Aspergillus niger |
| Industrial enzyme | Beta-glucanase | Filamentous fungi | Aspergillus niger |
| Industrial enzyme | Beta-glucanase | Filamentous fungi | Aspergillus aculeatus |
| Industrial enzyme | Glucose oxidase | Filamentous fungi | Aspergillus niger |
| Industrial enzyme | Glutaminase | Filamentous fungi | Aspergillus oryzae |
| Industrial enzyme | Glutaminase | Filamentous fungi | Aspergillus sojae |
| Industrial enzyme | Beta-D-Glucosidase | Filamentous fungi | Aspergillus niger |
| Industrial enzyme | Inulinase | Filamentous fungi | Aspergillus niger |
| Industrial enzyme | Lactase | Filamentous fungi | Aspergillus niger |
| Industrial enzyme | Lipase | Filamentous fungi | Aspergillus niger |
| Industrial enzyme | Lipase | Filamentous fungi | Aspergillus oryzae |
| Industrial enzyme | Xylanase | Filamentous fungi | Aspergillus niger |

Selection Criteria and Goals

The selection criteria applied to the methods of the present disclosure will vary with the specific goals of the strain improvement program. The present disclosure may be adapted to meet any program goals. For example, in some embodiments, the program goal may be to maximize single batch yields of reactions with no immediate time limits. In other embodiments, the program goal may be to rebalance biosynthetic yields to produce a specific product, or to produce a particular ratio of products. In other embodiments, the program goal may be to modify the chemical structure of a product, such as lengthening the carbon chain of a polymer. In some embodiments, the program goal may be to improve performance characteristics such as yield, titer, productivity, by-product elimination, tolerance to process excursions, optimal growth temperature and growth rate. In some embodiments, the program goal is improved host performance as measured by volumetric productivity, specific productivity, yield or titre, of a product of interest produced by a microbe.

In other embodiments, the program goal may be to optimize synthesis efficiency of a commercial strain in terms of final product yield per quantity of inputs (e.g., total amount of ethanol produced per pound of sucrose). In other embodiments, the program goal may be to optimize synthesis speed, as measured for example in terms of batch completion rates, or yield rates in continuous culturing systems. In other embodiments, the program goal may be to increase strain resistance to a particular phage, or otherwise increase strain vigor/robustness under culture conditions.

In some embodiments, strain improvement projects may be subject to more than one goal. In some embodiments, the goal of the strain project may hinge on quality, reliability, or overall profitability. In some embodiments, the present disclosure teaches methods of associated selected mutations or groups of mutations with one or more of the strain properties described above.

Persons having ordinary skill in the art will recognize how to tailor strain selection criteria to meet the particular project goal. For example, selections of a strain's single batch max yield at reaction saturation may be appropriate for identifying strains with high single batch yields. Selection based on consistency in yield across a range of temperatures and conditions may be appropriate for identifying strains with increased robustness and reliability.

In some embodiments, the selection criteria for the initial high-throughput phase and the tank-based validation will be identical. In other embodiments, tank-based selection may operate under additional and/or different selection criteria. For example, in some embodiments, high-throughput strain selection might be based on single batch reaction completion yields, while tank-based selection may be expanded to include selections based on yields for reaction speed.

Sequencing

In some embodiments, the present disclosure teaches whole-genome sequencing of the organisms described herein. In other embodiments, the present disclosure also teaches sequencing of plasmids, PCR products, and other oligos as quality controls to the methods of the present disclosure. Sequencing methods for large and small projects are well known to those in the art.

In some embodiments, any high-throughput technique for sequencing nucleic acids can be used in the methods of the disclosure. In some embodiments, the present disclosure teaches whole genome sequencing. In other embodiments, the present disclosure teaches amplicon sequencing ultra deep sequencing to identify genetic variations. In some embodiments, the present disclosure also teaches novel methods for library preparation, including tagmentation (see WO/2016/073690). DNA sequencing techniques include classic dideoxy sequencing reactions (Sanger method) using labeled terminators or primers and gel separation in slab or capillary; sequencing by synthesis using reversibly terminated labeled nucleotides, pyrosequencing; 454 sequencing; allele specific hybridization to a library of labeled oligonucleotide probes; sequencing by synthesis using allele specific hybridization to a library of labeled clones that is followed by ligation; real time monitoring of the incorporation of labeled nucleotides during a polymerization step; polony sequencing; and SOLiD sequencing.

In one aspect of the disclosure, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)).

In another embodiment, the methods of the present disclosure comprise amplifying the isolated molecules either before or after they are spatially isolated on a solid surface. Prior amplification may comprise emulsion-based amplification, such as emulsion PCR, or rolling circle amplification. Also taught is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference.

In one embodiment, individual molecules disposed and amplified on a solid surface form clusters in a density of at least $10^5$ clusters per cm$^2$; or in a density of at least $5 \times 10^5$ per cm$^2$; or in a density of at least $10^6$ clusters per cm$^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

Computational Analysis and Prediction of Effects of Genome-Wide Genetic Design Criteria In some embodiments, the present disclosure teaches methods of predicting the effects of particular genetic alterations being incorporated into a given host strain. In further aspects, the disclosure provides methods for generating proposed genetic alterations that should be incorporated into a given host strain, in order for said host to possess a particular phenotypic trait or strain parameter. In given aspects, the disclosure provides predictive models that can be utilized to design novel host strains. The novel host strains can be filamentous fungal host strains such as for example *A. niger*.

In some embodiments, the present disclosure teaches methods of analyzing the performance results of each round of screening and methods for generating new proposed genome-wide sequence modifications predicted to enhance strain performance in the following round of screening.

In some embodiments, the present disclosure teaches that the system generates proposed sequence modifications to host strains based on previous screening results. In some embodiments, the recommendations of the present system are based on the results from the immediately preceding screening. In other embodiments, the recommendations of the present system are based on the cumulative results of one or more of the preceding screenings.

In some embodiments, the recommendations of the present system are based on previously developed HTP genetic design libraries. For example, in some embodiments, the present system is designed to save results from previous screenings, and apply those results to a different project, in the same or different host organisms.

In other embodiments, the recommendations of the present system are based on scientific insights. For example, in some embodiments, the recommendations are based on known properties of genes (from sources such as annotated gene databases and the relevant literature), codon optimization, transcriptional slippage, uORFs, or other hypothesis driven sequence and host optimizations.

In some embodiments, the proposed sequence modifications to a host strain recommended by the system, or predictive model, are carried out by the utilization of one or more of the disclosed molecular tools sets comprising: (1) Promoter swaps, (2) SNP swaps, (3) Start/Stop codon exchanges, (4) Sequence optimization, (5) Stop swaps, and (5) Epistasis mapping.

The HTP genetic engineering platform described herein is agnostic with respect to any particular microbe or phenotypic trait (e.g. production of a particular compound). That is, the platform and methods taught herein can be utilized with any host cell to engineer said host cell to have any desired phenotypic trait. Furthermore, the lessons learned from a given HTP genetic engineering process used to create one novel host cell, can be applied to any number of other host cells, as a result of the storage, characterization, and analysis of a myriad of process parameters that occurs during the taught methods. In particular aspects, the host cells can be any coenocytic organism known in the art. For example, the host cell can be a filamentous fungal host cell. An example of a filamentous fungal host cell for use herein can be *A. niger*.

As alluded to in the epistatic mapping section, it is possible to estimate the performance (a.k.a. score) of a hypothetical strain obtained by consolidating a collection of mutations from a HTP genetic design library into a particular background via some preferred predictive model. Given such a predictive model, it is possible to score and rank all hypothetical strains accessible to the mutation library via combinatorial consolidation. The below section outlines particular models utilized in the present HTP platform.

Predictive Strain Design

Described herein is an approach for predictive strain design, including: methods of describing genetic changes and strain performance, predicting strain performance based on the composition of changes in the strain, recommending candidate designs with high predicted performance, and filtering predictions to optimize for second-order considerations, e.g. similarity to existing strains, epistasis, or confidence in predictions.

Inputs to Strain Design Model

In one embodiment, for the sake of ease of illustration, input data may comprise two components: (1) sets of genetic changes and (2) relative strain performance. Those skilled in the art will recognize that this model can be readily extended to consider a wide variety of inputs, while keeping in mind the countervailing consideration of overfitting. In addition to genetic changes, some of the input parameters (independent variables) that can be adjusted are cell types (genus, species, strain, phylogenetic characterization, etc.) and process parameters (e.g., environmental conditions, handling equipment, modification techniques, etc.) under which fermentation is conducted with the cells.

The sets of genetic changes can come from the previously discussed collections of genetic perturbations termed HTP genetic design libraries. The relative strain performance can be assessed based upon any given parameter or phenotypic trait of interest (e.g. production of a compound, small molecule, or product of interest).

Cell types can be specified in general categories such as prokaryotic and eukaryotic systems, genus, species, strain, tissue cultures (vs. disperse cells), etc. Process parameters that can be adjusted include temperature, pressure, reactor configuration, and medium composition. Examples of reactor configuration include the volume of the reactor, whether the process is a batch or continuous, and, if continuous, the volumetric flow rate, etc. One can also specify the support structure, if any, on which the cells reside. Examples of medium composition include the concentrations of electrolytes, nutrients, waste products, acids, pH, and the like.

Sets of Genetic Changes from Selected HTP Genetic Design Libraries to be Utilized in the Initial Linear Regression Model that Subsequently is Used to Create the Predictive Strain Design Model To create a predictive strain design model, genetic changes in strains of the same microbial species are first selected. The history of each genetic change is also provided (e.g., showing the most recent modification in this strain lineage—"last change"). Thus, comparing this strain's performance to the performance of its parent represents a data point concerning the performance of the "last change" mutation.

Built Strain Performance Assessment

The goal of the taught model is to predict strain performance based on the composition of genetic changes introduced to the strain. To construct a standard for comparison, strain performance is computed relative to a common reference strain, by first calculating the median performance per strain, per assay plate. Relative performance is then computed as the difference in average performance between an engineered strain and the common reference strain within the same plate. Restricting the calculations to within-plate comparisons ensures that the samples under consideration all received the same experimental conditions.

Figure 41:
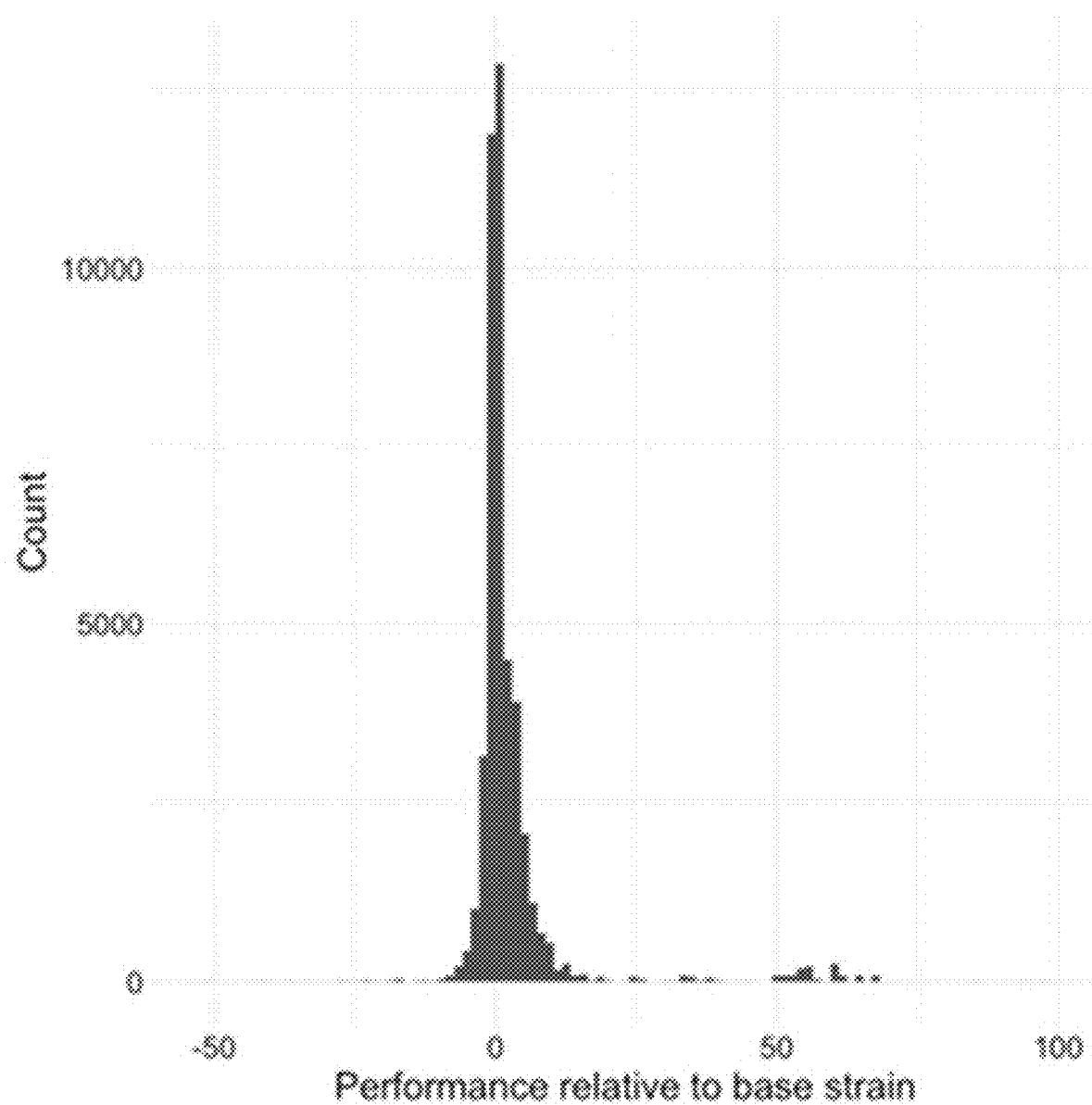
FIG. 41 illustrates an example of the distribution of relative strain performances for the input data under consideration done in *Corynebacterium* by using the method described in the present disclosure. A relative performance of zero indicates that the engineered strain performed equally well to the in-plate base strain. The processes described herein are designed to identify the strains that are likely to perform significantly above zero.

FIG. 41 shows a hypothetic example in which the distribution of relative strain performances for the input data is under consideration. A relative performance of zero indicates that the engineered strain performed equally well to the in-plate base or "reference" strain. Of interest is the ability of the predictive model to identify the strains that are likely to perform significantly above zero. Further, and more generally, of interest is whether any given strain outperforms its parent by some criteria. In practice, the criteria can be a product titer meeting or exceeding some threshold above the parent level, though having a statistically significant difference from the parent in the desired direction could also be used instead or in addition. The role of the base or "reference" strain is simply to serve as an added normalization factor for making comparisons within or between plates.

A concept to keep in mind is that of differences between: parent strain and reference strain. The parent strain is the background that was used for a current round of mutagenesis. The reference strain is a control strain run in every plate to facilitate comparisons, especially between plates, and is typically the "base strain" as referenced above. But since the base strain (e.g., the wild-type or industrial strain being used to benchmark overall performance) is not necessarily a "base" in the sense of being a mutagenesis target in a given round of strain improvement, a more descriptive term is "reference strain."

In summary, a base/reference strain is used to benchmark the performance of built strains, generally, while the parent strain is used to benchmark the performance of a specific genetic change in the relevant genetic background.

Ranking the Performance of Built Strains with Linear Regression

The goal of the disclosed model is to rank the performance of built strains, by describing relative strain performance, as a function of the composition of genetic changes introduced into the built strains. As discussed throughout the disclosure, the various HTP genetic design libraries provide the repertoire of possible genetic changes (e.g., genetic perturbations/alterations) that are introduced into the engineered strains. Linear regression is the basis for the currently described exemplary predictive model.

Genetic changes and their effect on relative performance is then input for regression-based modeling. The strain performances are ranked relative to a common base strain, as a function of the composition of the genetic changes contained in the strain.

Linear Regression to Characterize Built Strains

Linear regression is an attractive method for the described HTP genomic engineering platform, because of the ease of implementation and interpretation. The resulting regression coefficients can be interpreted as the average increase or decrease in relative strain performance attributable to the presence of each genetic change.

For example, in some embodiments, this technique allows us to conclude that changing the original promoter to another promoter improves relative strain performance by approximately 1, 2, 3, 4, 5, 6, 7, 8, 9, 10 or more units on average and is thus a potentially highly desirable change, in the absence of any negative epistatic interactions (note: the input is a unit-less normalized value).

The taught method therefore uses linear regression models to describe/characterize and rank built strains, which have various genetic perturbations introduced into their genomes from the various taught libraries.

Predictive Design Modeling

The linear regression model described above, which utilized data from constructed strains, can be used to make performance predictions for strains that haven't yet been built.

The procedure can be summarized as follows: generate in silico all possible configurations of genetic changes→use the regression model to predict relative strain performance→order the candidate strain designs by performance. Thus, by utilizing the regression model to predict the performance of as-yet-unbuilt strains, the method allows for the production of higher performing strains, while simultaneously conducting fewer experiments.

Generate Configurations

When constructing a model to predict performance of as-yet-unbuilt strains, the first step is to produce a sequence of design candidates. This is done by fixing the total number of genetic changes in the strain, and then defining all possible combinations of genetic changes. For example, one can set the total number of potential genetic changes/perturbations to 29 (e.g. 29 possible SNPs, or 29 different promoters, or any combination thereof as long as the universe of genetic perturbations is 29) and then decide to design all possible 3-member combinations of the 29 potential genetic changes, which will result in 3,654 candidate strain designs.

To provide context to the aforementioned 3,654 candidate strains, consider that one can calculate the number of non-redundant groupings of size r from n possible members using: $n!/((n-r)!*r!)$. If $r=3$, $n=29$ gives 3,654. Thus, if one designs all possible 3-member combinations of 29 potential changes the results is 3,654 candidate strains.

Predict Performance of New Strain Designs

Using the linear regression constructed above with the combinatorial configurations as input, one can then predict the expected relative performance of each candidate design. For example, the composition of changes for the top 100 predicted strain designs can be summarized in a 2-dimensional map, in which the x-axis lists the pool of potential genetic changes (29 possible genetic changes), and the y-axis shows the rank order.

Predictive accuracy should increase over time as new observations are used to iteratively retrain and refit the model. Results from a study by the inventors illustrate the methods by which the predictive model can be iteratively retrained and improved. The quality of model predictions can be assessed through several methods, including a correlation coefficient indicating the strength of association between the predicted and observed values, or the root-mean-square error, which is a measure of the average model error. Using a chosen metric for model evaluation, the system may define rules for when the model should be retrained.

A couple of unstated assumptions to the above model include: (1) there are no epistatic interactions; and (2) the genetic changes/perturbations utilized to build the predictive model were all made in the same background, as the proposed combinations of genetic changes.

Filtering for Second-Order Features

The above illustrative example focused on linear regression predictions based on predicted host cell performance. In some embodiments, the present linear regression methods can also be applied to non-biomolecule factors, such as saturation biomass, resistance, or other measurable host cell features. Thus, the methods of the present disclosure also teach considering other features outside of predicted performance when prioritizing the candidates to build. Assuming there is additional relevant data, nonlinear terms are also included in the regression model.

Closeness with Existing Strains

Predicted strains that are similar to ones that have already been built could result in time and cost savings despite not being a top predicted candidate Diversity of Changes When constructing the aforementioned models, one cannot be certain that genetic changes will truly be additive (as assumed by linear regression and mentioned as an assumption above) due to the presence of epistatic interactions. Therefore, knowledge of genetic change dissimilarity can be used to increase the likelihood of positive additivity. If one knows, for example, that the changes from the top ranked strain are on the same metabolic pathway and have similar performance characteristics, then that information could be used to select another top ranking strain with a dissimilar composition of changes. As described in the section above concerning epistasis mapping, the predicted best genetic changes may be filtered to restrict selection to mutations with sufficiently dissimilar response profiles. Alternatively, the linear regression may be a weighted least squares regression using the similarity matrix to weight predictions.

Diversity of Predicted Performance

Finally, one may choose to design strains with middling or poor predicted performance, in order to validate and subsequently improve the predictive models.

Iterative Strain Design Optimization

In embodiments, the order placement engine 208 places a factory order to the factory 210 to manufacture microbial strains incorporating the top candidate mutations. In feedback-loop fashion, the results may be analyzed by the analysis equipment 214 to determine which microbes exhibit desired phenotypic properties (314). During the analysis phase, the modified strain cultures are evaluated to determine their performance, i.e., their expression of desired phenotypic properties, including the ability to be produced at industrial scale. For example, the analysis phase uses, among other things, image data of plates to measure microbial colony growth as an indicator of colony health. The analysis equipment 214 is used to correlate genetic changes with phenotypic performance, and save the resulting genotype-phenotype correlation data in libraries, which may be stored in library 206, to inform future microbial production.

In particular, the candidate changes that actually result in sufficiently high measured performance may be added as rows in the database to tables. In this manner, the best performing mutations are added to the predictive strain design model in a supervised machine learning fashion.

LIMS iterates the design/build/test/analyze cycle based on the correlations developed from previous factory runs. During a subsequent cycle, the analysis equipment 214 alone, or in conjunction with human operators, may select the best candidates as base strains for input back into input interface 202, using the correlation data to fine tune genetic modifications to achieve better phenotypic performance with finer granularity. In this manner, the laboratory information management system of embodiments of the disclosure implements a quality improvement feedback loop.

Figure 16:
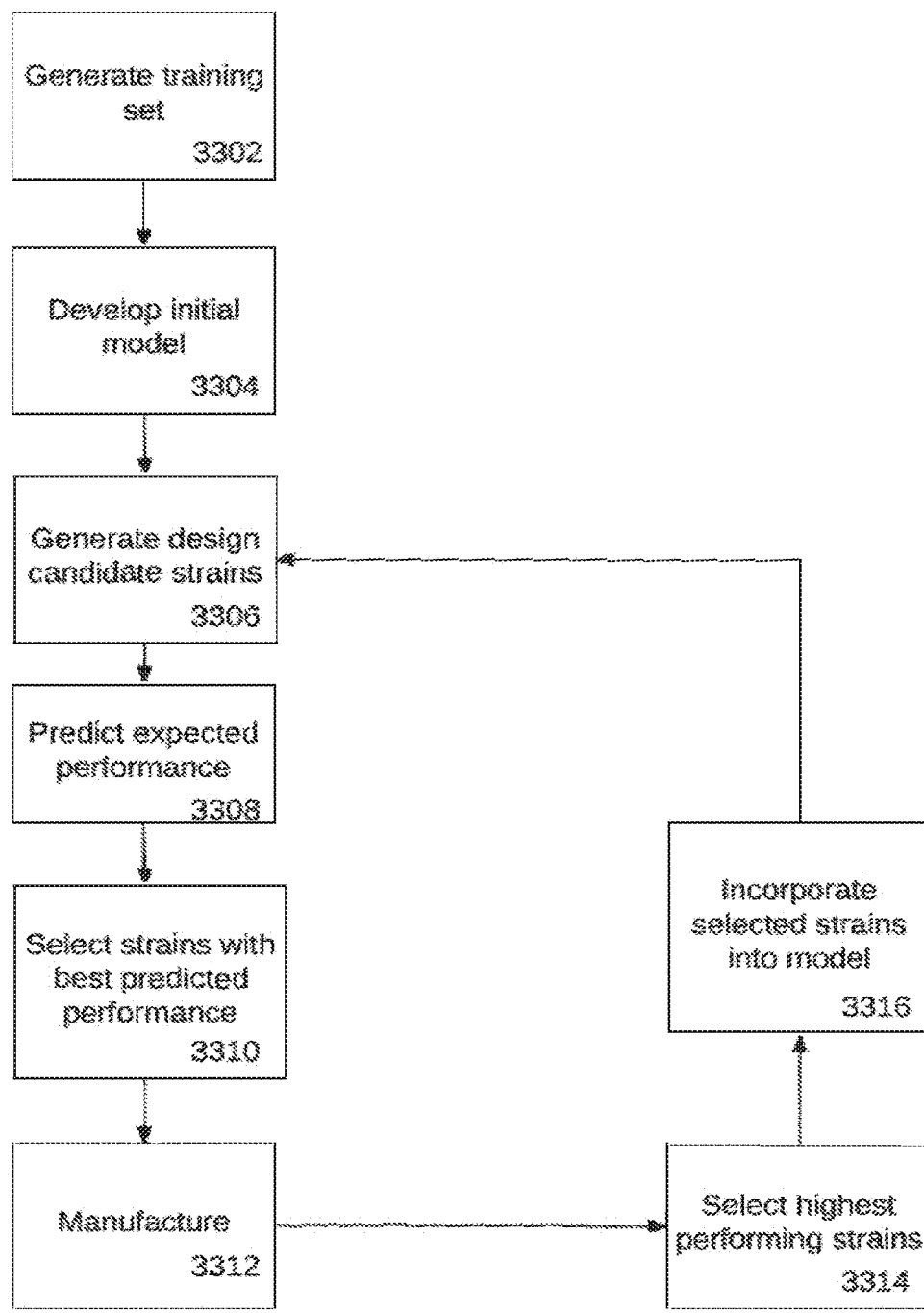
FIG. 16 depicts an embodiment of the iterative predictive strain design workflow of the present disclosure.

In sum, with reference to the flowchart of FIG. 16 the iterative predictive strain design workflow may be described as follows:

Generate a training set of input and output variables, e.g., genetic changes as inputs and performance features as outputs (3302). Generation may be performed by the analysis equipment 214 based upon previous genetic changes and the corresponding measured performance of the microbial strains incorporating those genetic changes.

Develop an initial model (e.g., linear regression model) based upon training set (3304). This may be performed by the analysis equipment 214.

Generate design candidate strains (3306)

In one embodiment, the analysis equipment 214 may fix the number of genetic changes to be made to a background strain, in the form of combinations of changes. To represent these changes, the analysis equipment 214 may provide to the interpreter 204 one or more DNA specification expressions representing those combinations of changes. (These genetic changes or the microbial strains incorporating those changes may be referred to as "test inputs.") The interpreter 204 interprets the one or more DNA specifications, and the execution engine 207 executes the DNA specifications to populate the DNA specification with resolved outputs representing the individual candidate design strains for those changes.

Based upon the model, the analysis equipment 214 predicts expected performance of each candidate design strain (3308).

The analysis equipment 214 selects a limited number of candidate designs, e.g., 100, with highest predicted performance (3310).

As described elsewhere herein with respect to epistasis mapping, the analysis equipment 214 may account for second-order effects such as epistasis, by, e.g., filtering top designs for epistatic effects, or factoring epistasis into the predictive model.

Build the filtered candidate strains (at the factory 210) based on the factory order generated by the order placement engine 208 (3312).

The analysis equipment 214 measures the actual performance of the selected strains, selects a limited number of those selected strains based upon their superior actual performance (3314), and adds the design changes and their resulting performance to the predictive model (3316). In the linear regression example, add the sets of design changes and their associated performance as new rows in a table.

The analysis equipment 214 then iterates back to generation of new design candidate strains (3306), and continues iterating until a stop condition is satisfied. The stop condition may comprise, for example, the measured performance of at least one microbial strain satisfying a performance metric, such as yield, growth rate, or titer.

In the example above, the iterative optimization of strain design employs feedback and linear regression to implement machine learning. In general, machine learning may be described as the optimization of performance criteria, e.g., parameters, techniques or other features, in the performance of an informational task (such as classification or regression) using a limited number of examples of labeled data, and then performing the same task on unknown data. In supervised machine learning such as that of the linear regression example above, the machine (e.g., a computing device) learns, for example, by identifying patterns, categories, statistical relationships, or other attributes, exhibited by training data. The result of the learning is then used to predict whether new data will exhibit the same patterns, categories, statistical relationships or other attributes.

Embodiments of the disclosure may employ other supervised machine learning techniques when training data is available. In the absence of training data, embodiments may employ unsupervised machine learning. Alternatively, embodiments may employ semi-supervised machine learning, using a small amount of labeled data and a large amount of unlabeled data. Embodiments may also employ feature selection to select the subset of the most relevant features to optimize performance of the machine learning model. Depending upon the type of machine learning approach selected, as alternatives or in addition to linear regression, embodiments may employ for example, logistic regression, neural networks, support vector machines (SVMs), decision trees, hidden Markov models, Bayesian networks, Gram Schmidt, reinforcement-based learning, cluster-based learning including hierarchical clustering, genetic algorithms, and any other suitable learning machines known in the art. In particular, embodiments may employ logistic regression to provide probabilities of classification (e.g., classification of genes into different functional groups) along with the classifications themselves. See, e.g., Shevade, A simple and efficient algorithm for gene selection using sparse logistic regression, Bioinformatics, Vol. 19, No. 17 2003, pp. 2246-2253, Leng, et al., Classification using functional data analysis for temporal gene expression data, Bioinformatics, Vol. 22, No. 1, Oxford University Press (2006), pp. 68-76, all of which are incorporated by reference in their entirety herein.

Embodiments may employ graphics processing unit (GPU) accelerated architectures that have found increasing popularity in performing machine learning tasks, particularly in the form known as deep neural networks (DNN). Embodiments of the disclosure may employ GPU-based machine learning, such as that described in GPU-Based Deep Learning Inference: A Performance and Power Analysis, NVidia Whitepaper, November 2015, Dahl, et al., Multi-task Neural Networks for QSAR Predictions, Dept. of Computer Science, Univ. of Toronto, June 2014 (arXiv: 1406.1231 [stat.ML]), all of which are incorporated by reference in their entirety herein. Machine learning techniques applicable to embodiments of the disclosure may also be found in, among other references, Libbrecht, et al., Machine learning applications in genetics and genomics, Nature Reviews: Genetics, Vol. 16, June 2015, Kashyap, et al., Big Data Analytics in Bioinformatics: A Machine Learning Perspective, Journal of Latex Class Files, Vol. 13, No. 9, September 2014, Prompramote, et al., Machine Learning in Bioinformatics, Chapter 5 of Bioinformatics Technologies, pp. 117-153, Springer Berlin Heidelberg 2005, all of which are incorporated by reference in their entirety herein.

Iterative Predictive Strain Design: Example

The following provides an example application of the iterative predictive strain design workflow outlined above.

An initial set of training inputs and output variables was prepared. This set comprised 1864 unique engineered strains with defined genetic composition. Each strain contained between 5 and 15 engineered changes. A total of 336 unique genetic changes were present in the training.

An initial predictive computer model was developed. The implementation used a generalized linear model (Kernel Ridge Regression with 4th order polynomial kernel). The implementation models two distinct phenotypes (yield and productivity). These phenotypes were combined as weighted sum to obtain a single score for ranking, as shown below. Various model parameters, e.g. regularization factor, were tuned via k-fold cross validation over the designated training data.

The implementation does not incorporate any explicit analysis of interaction effects as described in the Epistasis Mapping section above. However, as those skilled in the art would understand, the implemented generalized linear model may capture interaction effects implicitly through the second, third and fourth order terms of the kernel.

The model is trained against the training set After training, a significant quality fitting of the yield model to the training data can be demonstrated.

Candidate strains are then generated. This embodiments includes a serial build constraint associated with the introduction of new genetic changes to a parent strain. Here, candidates are not considered simply as a function of the desired number of changes. Instead, the analysis equipment 214 selects, as a starting point, a collection of previously designed strains known to have high performance metrics ("seed strains"). The analysis equipment 214 individually applies genetic changes to each of the seed strains. The introduced genetic changes do not include those already present in the seed strain. For various technical, biological or other reasons, certain mutations are explicitly required, or explicitly excluded Based upon the model, the analysis equipment 214 predicted the performance of candidate strain designs. The analysis equipment 214 ranks candidates from "best" to "worst" based on predicted performance with respect to two phenotypes of interest (yield and productivity). Specifically, the analysis equipment 214 used a weighted sum to score a candidate strain:

$$Score=0.8*yield/max(yields)+0.2*prod/max(prods),$$

where yield represents predicted yield for the candidate strain,
max(yields) represents the maximum yield over all candidate strains,
prod represents productivity for the candidate strain, and max(prods) represents the maximum yield over all candidate strains.

The analysis equipment 214 generates a final set of recommendations from the ranked list of candidates by imposing both capacity constraints and operational constraints. In some embodiments, the capacity limit can be set at a given number, such as 48 computer-generated candidate design strains.

The trained model (described above) can be used to predict the expected performance (for yield and productivity) of each candidate strain. The analysis equipment 214 can rank the candidate strains using the scoring function given above. Capacity and operational constraints can be then applied to yield a filtered set of 48 candidate strains. Filtered candidate strains are then built (at the factory 210) based on a factory order generated by the order placement engine 208 (3312). The order can be based upon DNA specifications corresponding to the candidate strains.

In practice, the build process has an expected failure rate whereby a random set of strains is not built.

The analysis equipment 214 can also be used to measure the actual yield and productivity performance of the selected strains. The analysis equipment 214 can evaluate the model and recommended strains based on three criteria: model accuracy; improvement in strain performance; and equivalence (or improvement) to human expert-generated designs.

The yield and productivity phenotypes can be measured for recommended strains and compared to the values predicted by the model.

Next, the analysis equipment 214 computes percentage performance change from the parent strain for each of the recommended strains.

Predictive accuracy can be assessed through several methods, including a correlation coefficient indicating the strength of association between the predicted and observed values, or the root-mean-square error, which is a measure of the average model error. Over many rounds of experimentation, model predictions may drift, and new genetic changes may be added to the training inputs to improve predictive accuracy. For this example, design changes and their resulting performance were added to the predictive model (3316).

Genomic Design and Engineering as a Service

Figure 15:
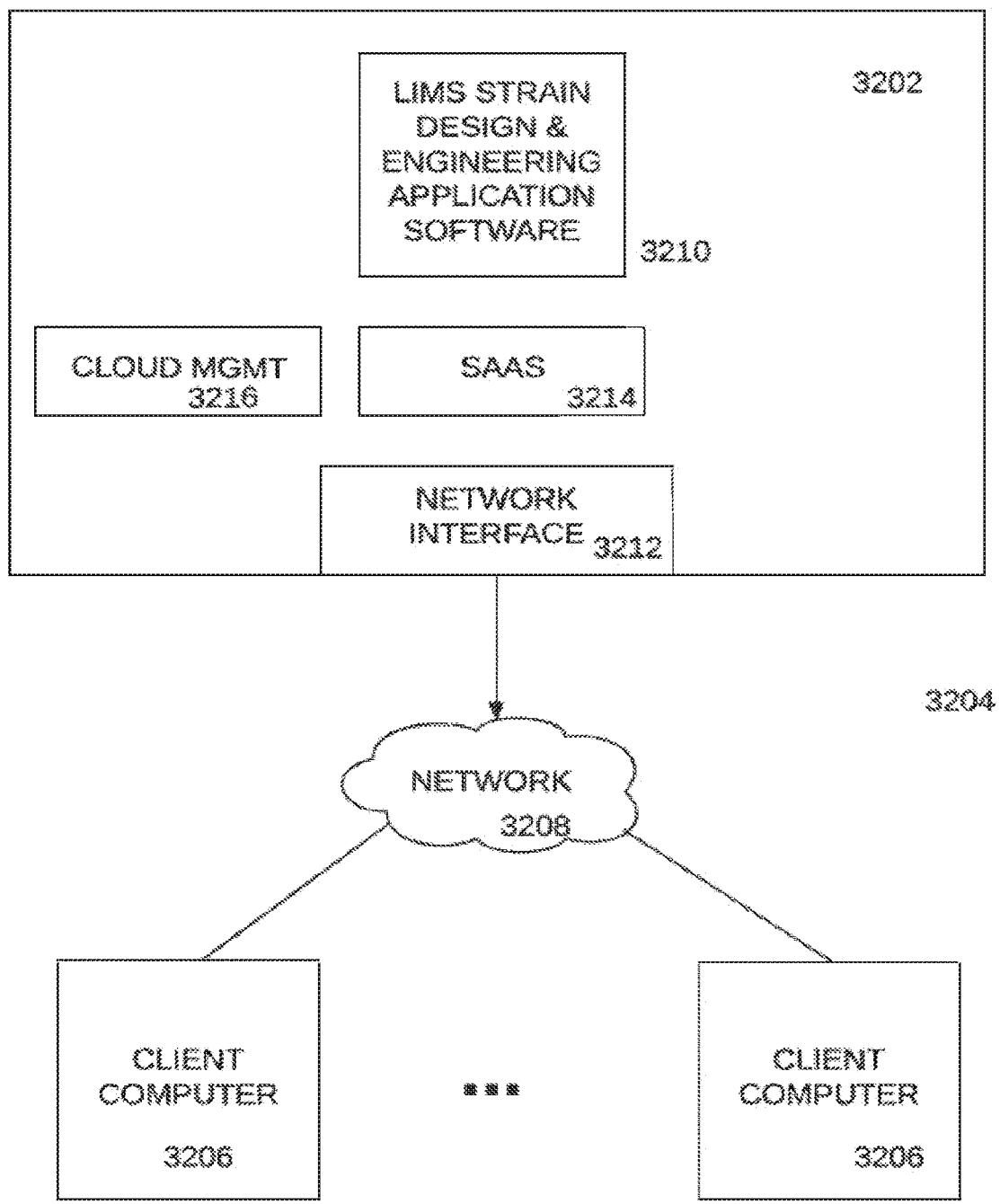
FIG. 15 diagrams a cloud computing implementation of embodiments of the LIMS system of the present disclosure.

In embodiments of the disclosure, the LIMS system software 3210 of FIG. 15 may be implemented in a cloud computing system 3202 of FIG. 15, to enable multiple users to design and build microbial strains according to embodiments of the present disclosure. FIG. 15 illustrates a cloud computing environment 3204 according to embodiments of the present disclosure. Client computers 3206, such as those illustrated in FIG. 15, access the LIMS system via a network 3208, such as the Internet. In embodiments, the LIMS system application software 3210 resides in the cloud computing system 3202. The LIMS system may employ one or more computing systems using one or more processors, of the type illustrated in FIG. 15. The cloud computing system itself includes a network interface 3212 to interface the LIMS system applications 3210 to the client computers 3206 via the network 3208. The network interface 3212 may include an application programming interface (API) to enable client applications at the client computers 3206 to access the LIMS system software 3210. In particular, through the API, client computers 3206 may access components of the LIMS system 200, including without limitation the software running the input interface 202, the interpreter 204, the execution engine 207, the order placement engine 208, the factory 210, as well as test equipment 212 and analysis equipment 214. A software as a service (SaaS) software module 3214 offers the LIMS system software 3210 as a service to the client computers 3206. A cloud management module 3216 manages access to the LIMS system 3210 by the client computers 3206. The cloud management module 3216 may enable a cloud architecture that employs multitenant applications, virtualization or other architectures known in the art to serve multiple users. FIG. 44 depicts a proof of principle of the utility of the LIMS system as applied to a filamentous fungal host cell system.

Genomic Automation

Automation of the methods of the present disclosure enables high-throughput phenotypic screening and identification of target products from multiple test strain variants simultaneously.

The aforementioned genomic engineering predictive modeling platform is premised upon the fact that hundreds and thousands of mutant strains are constructed in a high-throughput fashion. The robotic and computer systems described below are the structural mechanisms by which such a high-throughput process can be carried out.

In some embodiments, the present disclosure teaches methods of improving host cell productivities, or rehabilitating industrial strains. As part of this process, the present disclosure teaches methods of assembling DNA, building new strains, screening cultures in plates, and screening cultures in models for tank fermentation. In some embodiments, the present disclosure teaches that one or more of the aforementioned methods of creating and testing new host strains is aided by automated robotics.

Figure 6B:
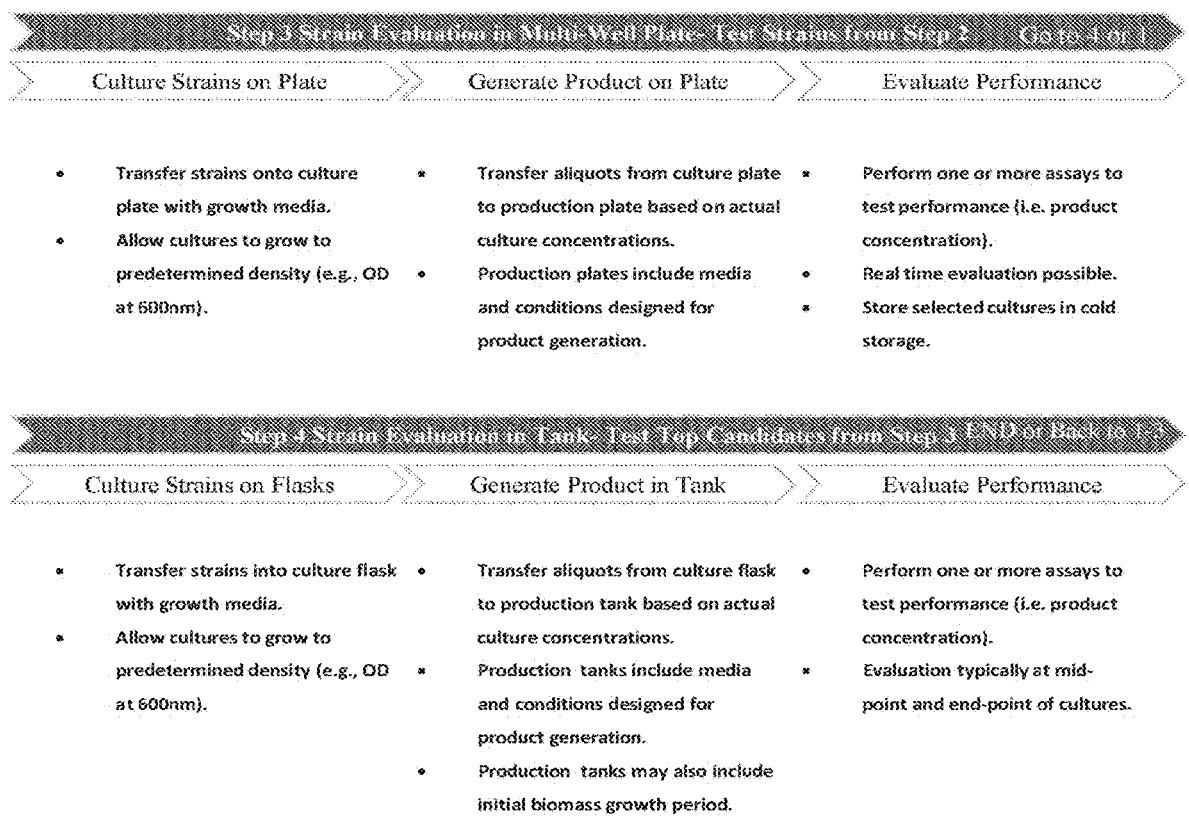

In some embodiments, the present disclosure teaches a high-throughput strain engineering platform as depicted in FIG. 6A-B.

HTP Robotic System

In some embodiments, the methods and systems provided herein comprise automated steps. For example, the generation of protoplasts, transformation of protoplasts, screening transformed protoplasts by NGS prior to purification, purifying homokaryotic protoplasts via selection/counterselection and screening transformed protoplasts by NGS after purification as described herein can be automated. As described herein, the methods and system can contain a further step of screening purified homokaryotic transformants for the production of a protein or metabolite of interest. The automated methods of the disclosure can comprise a robotic system. The systems outlined herein can be generally directed to the use of 96- or 384-well microtiter plates, but as will be appreciated by those in the art, any number of different plates or configurations may be used. In addition, any or all of the steps outlined herein may be automated; thus, for example, the systems may be completely or partially automated. The automated methods and systems can be high-throughput. For purposes of this disclosure, high-throughput screening can refers to any partially- or fully-automated method that is capable of evaluating about 1,000 or more transformants per day, and particularly to those methods capable of evaluating 5,000 or more transformants per day, and most particularly to methods capable of evaluating 10,000 or more transformants per day. The partially or fully-automated methods can entail the use of one or more liquid handling steps.

As described herein, the methods and system provided herein can comprise a screening step such that a transformant generated and purified as described herein is screened or tested for the production of a product of interest. The product of interest can be any product of interest provided herein such as, for example, an alcohol, pharmaceutical, metabolite, protein, enzyme, amino acid, or acid (e.g., citric acid). Accordingly, the methods and systems provided herein can further comprise culturing a clonal colony or culture purified according to the methods of the disclosure, under conditions permitting expression and secretion of the product of interest and recovering the subsequently produced product of interest. As described herein, the product of interest can an exogenous and/or heterologous protein or a metabolite produced as the result of the expression of an exogenous and or heterologous protein.

In some embodiments, the automated methods of the disclosure comprise a robotic system. The systems outlined herein are generally directed to the use of 96- or 384-well microtiter plates, but as will be appreciated by those in the art, any number of different plates or configurations may be used. In addition, any or all of the steps outlined herein may be automated; thus, for example, the systems may be completely or partially automated.

Figure 7:
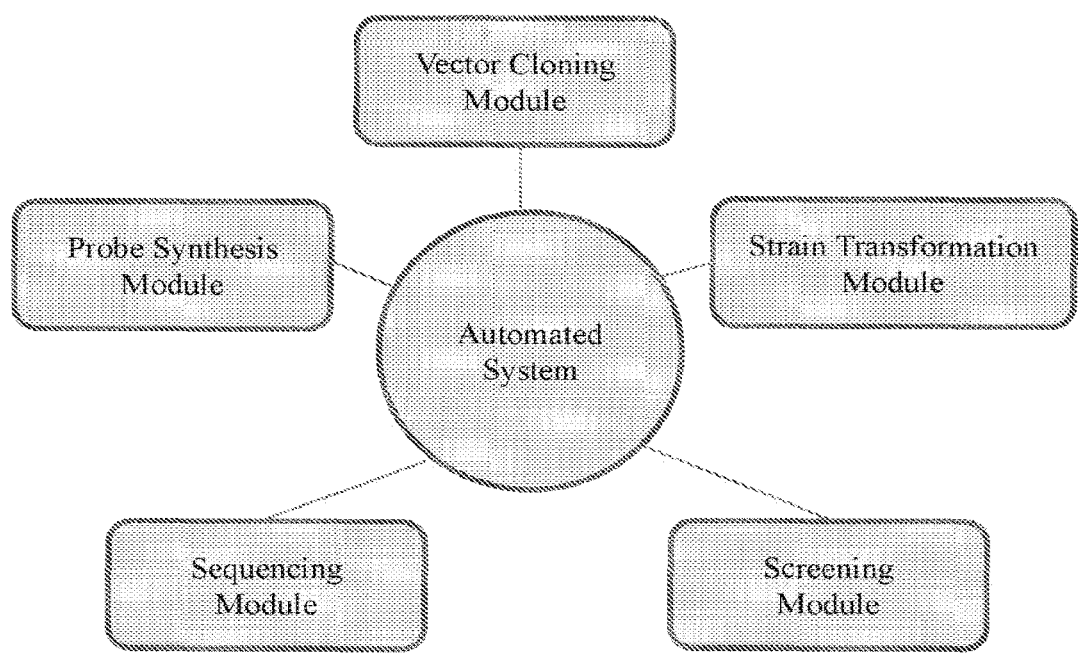
FIG. 7 depicts one embodiment of the automated system of the present disclosure. The present disclosure teaches use of automated robotic systems with various modules capable of cloning, transforming, culturing, screening and/or sequencing host filamentous fungus

In some embodiments, the automated systems of the present disclosure comprise one or more work modules. For example, in some embodiments, the automated system of the present disclosure comprises a DNA synthesis module, a vector cloning module, a strain transformation module, a screening module, and a sequencing module (see FIG. 7).

Figure 8:
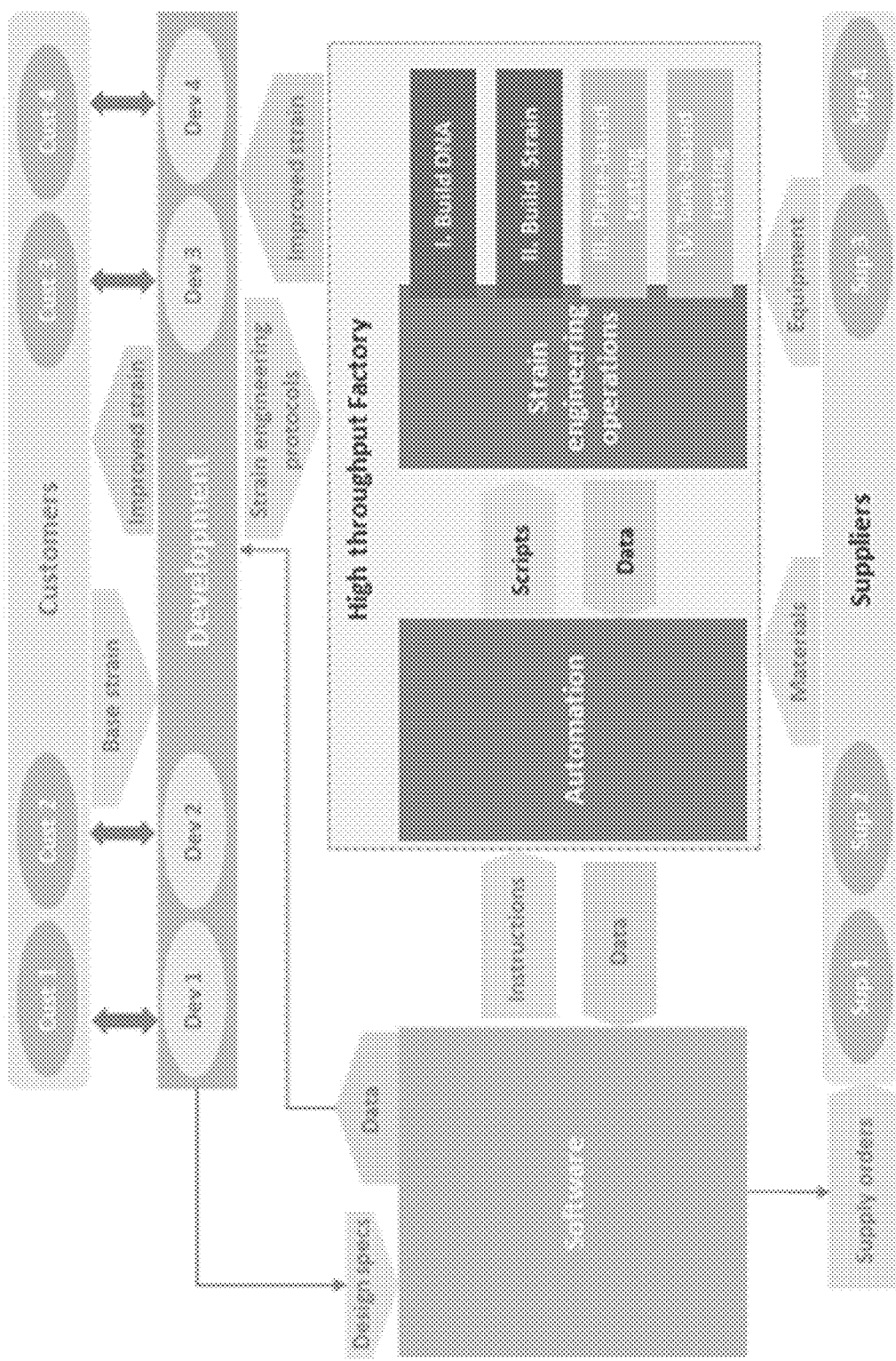
FIG. 8 depicts an overview of an embodiment of the filamentous fungal strain improvement program of the present disclosure.

As will be appreciated by those in the art, an automated system can include a wide variety of components, including, but not limited to: liquid handlers; one or more robotic arms; plate handlers for the positioning of microplates; plate sealers, plate piercers, automated lid handlers to remove and replace lids for wells on non-cross contamination plates; disposable tip assemblies for sample distribution with disposable tips; washable tip assemblies for sample distribution; 96 well loading blocks; integrated thermal cyclers; cooled reagent racks; microtiter plate pipette positions (optionally cooled); stacking towers for plates and tips; magnetic bead processing stations; filtrations systems; plate shakers; barcode readers and applicators; and computer systems. FIG. 8 depicts an overview of an integrated filamentous fungal strain improvement program of the present disclosure.

In some embodiments, the robotic systems of the present disclosure include automated liquid and particle handling enabling high-throughput pipetting to perform all the steps in the process of gene targeting and recombination applications. This includes liquid and particle manipulations such as aspiration, dispensing, mixing, diluting, washing, accurate volumetric transfers; retrieving and discarding of pipette tips; and repetitive pipetting of identical volumes for multiple deliveries from a single sample aspiration. These manipulations are cross-contamination-free liquid, particle, cell, and organism transfers. The instruments perform automated replication of microplate samples to filters, membranes, and/or daughter plates, high-density transfers, full-plate serial dilutions, and high capacity operation.

The automated system can be any known automated high-throughput system known in the art. For example, the automated system can be the automated microorganism handling tool is described in Japanese patent application publication number 11-304666. This device is capable of the transfer of microdroplets containing individual cells, and it is anticipated that the fungal strains of the present disclosure, by virtue of their morphology, will be amenable to micromanipulation of individual clones with this device. An additional example of an automated system for use in the methods and system of the present disclosure is the automated microbiological high-throughput screening system described in Beydon et al., J. Biomol. Screening 5:13 21 (2000). The automated system for use herein can be a customized automated liquid handling system. In some embodiments, the customized automated liquid handling system of the disclosure is a TECAN machine (e.g. a customized TECAN Freedom Evo).

In some embodiments, the automated systems of the present disclosure are compatible with platforms for multi-well plates, deep-well plates, square well plates, reagent troughs, test tubes, mini tubes, microfuge tubes, cryovials, filters, micro array chips, optic fibers, beads, agarose and acrylamide gels, and other solid-phase matrices or platforms are accommodated on an upgradeable modular deck. In some embodiments, the automated systems of the present disclosure contain at least one modular deck for multi-position work surfaces for placing source and output samples, reagents, sample and reagent dilution, assay plates, sample and reagent reservoirs, pipette tips, and an active tip-washing station.

In some embodiments, the automated systems of the present disclosure include high-throughput electroporation systems. In some embodiments, the high-throughput electroporation systems are capable of transforming cells in 96 or 384-well plates. In some embodiments, the high-throughput electroporation systems include VWR® High-throughput Electroporation Systems, BTX™, Bio-Rad® Gene Pulser MXcel™ or other multi-well electroporation system.

In some embodiments, the integrated thermal cycler and/or thermal regulators are used for stabilizing the temperature of heat exchangers such as controlled blocks or platforms to provide accurate temperature control of incubating samples from 0° C. to 100° C.

In some embodiments, the automated systems of the present disclosure are compatible with interchangeable machine-heads (single or multi-channel) with single or multiple magnetic probes, affinity probes, replicators or pipetters, capable of robotically manipulating liquid, particles, cells, and multi-cellular organisms. Multi-well or multi-tube magnetic separators and filtration stations manipulate liquid, particles, cells, and organisms in single or multiple sample formats.

In some embodiments, the automated systems of the present disclosure are compatible with camera vision and/or spectrometer systems. Thus, in some embodiments, the automated systems of the present disclosure are capable of detecting and logging color and absorption changes in ongoing cellular cultures.

In some embodiments, the automated system of the present disclosure is designed to be flexible and adaptable with multiple hardware add-ons to allow the system to carry out multiple applications. The software program modules allow creation, modification, and running of methods. The system's diagnostic modules allow setup, instrument alignment, and motor operations. The customized tools, labware, and liquid and particle transfer patterns allow different applications to be programmed and performed. The database allows method and parameter storage. Robotic and computer interfaces allow communication between instruments.

Figure 11:
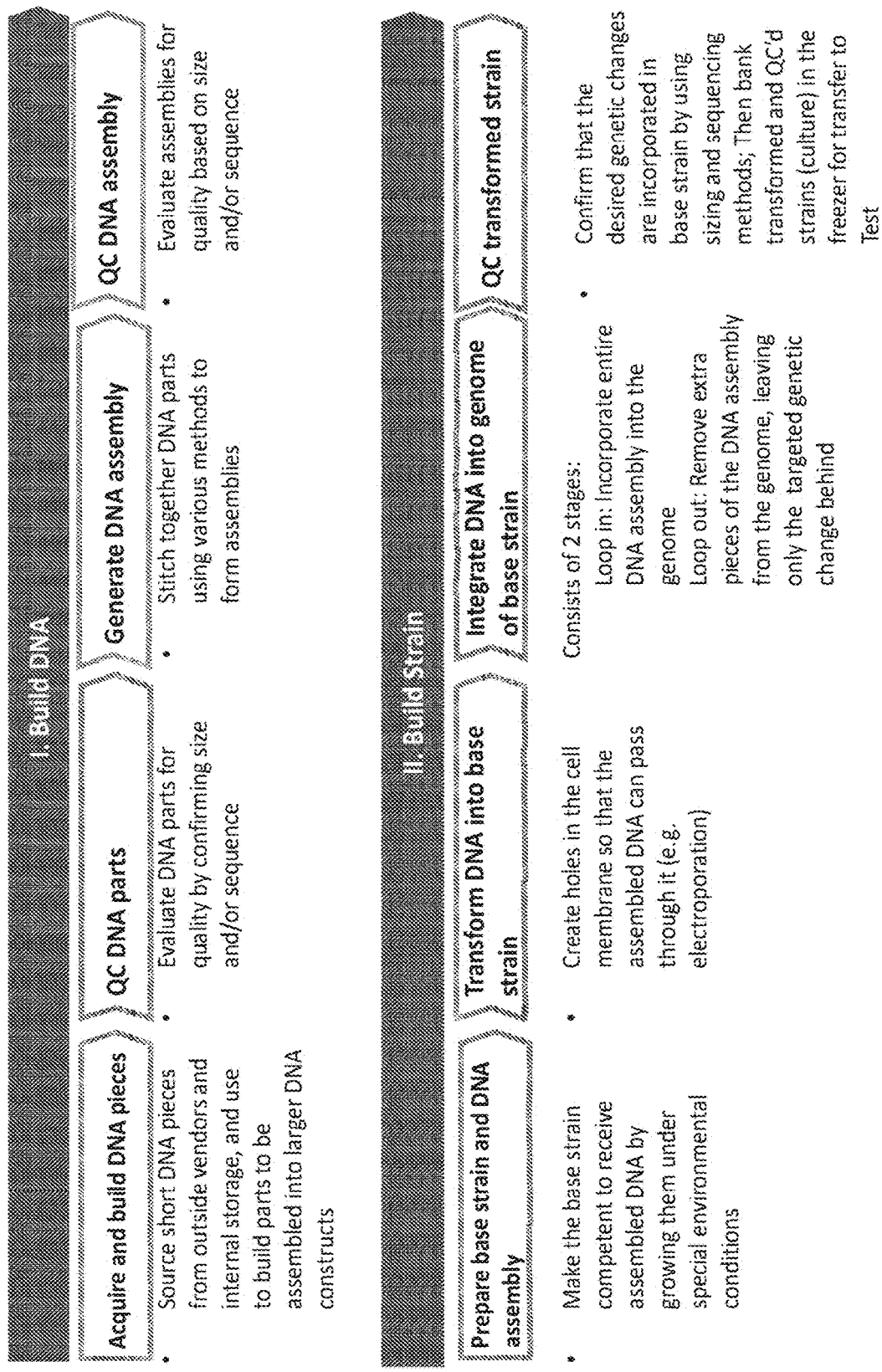
FIG. 11 depicts the DNA assembly and transformation steps of one of the embodiments of the present disclosure. The flow chart depicts the steps for building DNA fragments, cloning said DNA fragments, transforming said DNA fragments into host filamentous fungal strains, and looping out selection sequences through counter selection.
Figure 12:
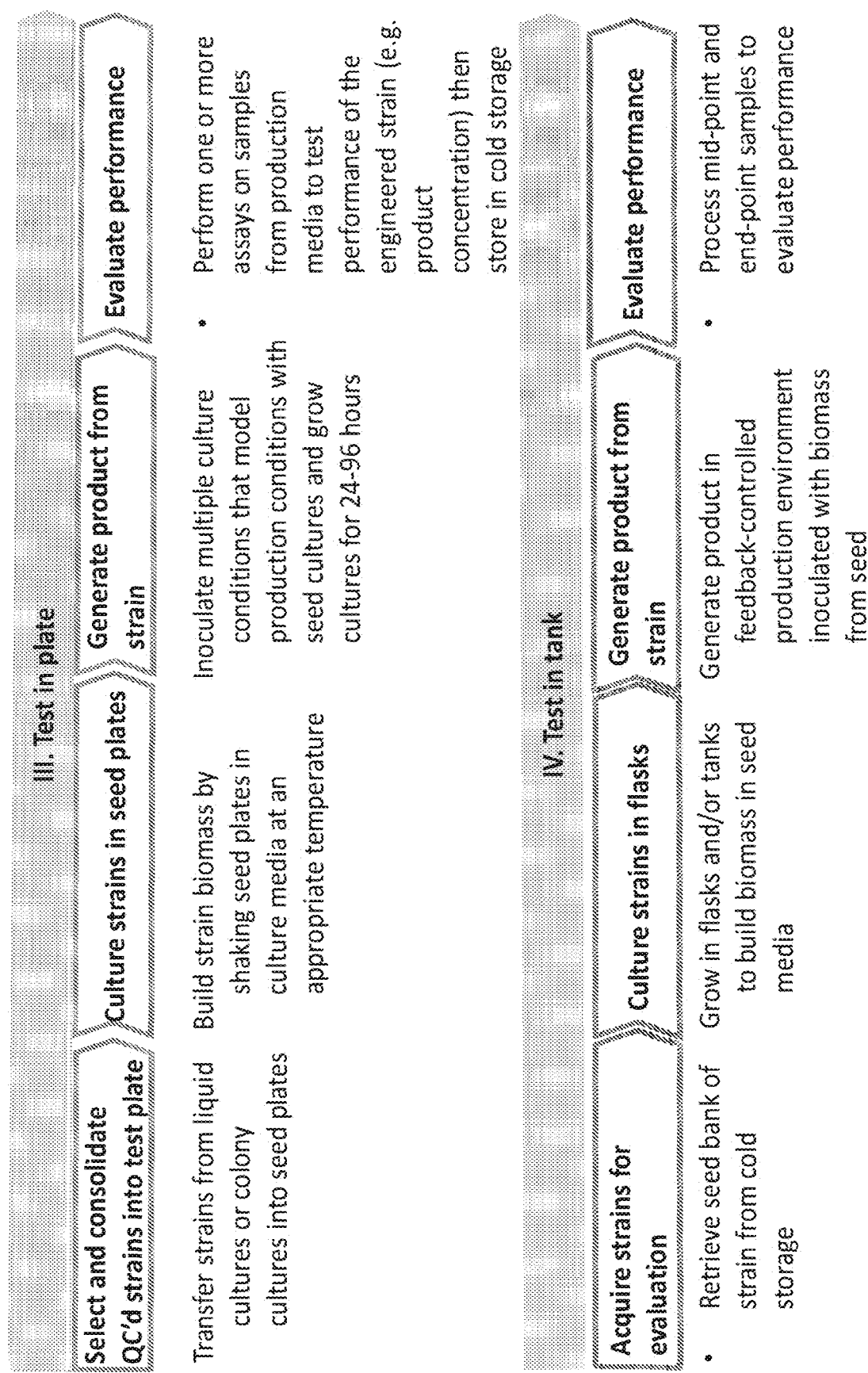
FIG. 12 depicts the steps for high-throughput culturing, screening, and evaluation of selected host filamentous fungal strains. This figure also depicts the optional steps of culturing, screening, and evaluating selected filamentous fungal strains in culture tanks.

Thus, in some embodiments, the present disclosure teaches a high-throughput strain engineering platform, as depicted in FIGS. 11 and 12.

Persons having skill in the art will recognize the various robotic platforms capable of carrying out the HTP engineering methods of the present disclosure. Table 3 below provides a non-exclusive list of scientific equipment capable of carrying out each step of the HTP engineering steps of the present disclosure as described in FIGS. 11 and 12.

TABLE 3

Non-exclusive list of Scientific Equipment Compatible with the HTP engineering methods of the present disclosure.

| Equipment Type | | Operation(s) performed | Compatible Equipment Make/Model/Configuration |
|---|---|---|---|
| Acquire and build DNA pieces | liquid handlers | Hitpicking (combining by transferring) primers/templates for PCR amplification of DNA parts | Hamilton Microlab STAR, Labcyte Echo 550, Tecan EVO 200, Beckman Coulter Biomek FX, BioFluidix GmbH BioSpot BT600 liquid handling workstation, or equivalents |
| | Thermal cyclers | PCR amplification of DNA parts | Inheco Cycler, ABI 2720, ABI Proflex 384, ABI Veriti, or equivalents |
| QC DNA parts | Fragment analyzers (capillary electrophoresis) | gel electrophoresis to confirm PCR products of appropriate size | Agilent Bioanalyzer, AATI Fragment Analyzer, or equivalents |
| | Sequencer (sanger: Beckman) | Verifying sequence of parts/templates | Beckman Ceq-8000, Beckman GenomeLab ™, or equivalents |
| | NGS (next generation sequencing) instrument | Verifying sequence of parts/templates | Illumina MiSeq series sequences, Illumina Hi-Seq, Ion torrent, pac bio or other equivalents |
| | nanodrop/plate reader | assessing concentration of DNA samples | Molecular Devices SpectraMax M5, Tecan M1000, or equivalents. |
| Generate DNA assembly | liquid handlers | Hitpicking (combining by transferring) DNA parts for assembly along with cloning vector, addition of reagents for assembly reaction/process | Hamilton Microlab STAR, Labcyte Echo 550, Tecan EVO 200, Beckman Coulter Biomek FX, BioFluidix GmbH BioSpot BT600 liquid handling workstation, or equivalents |
| QC DNA assembly | Colony pickers | for inoculating colonies in liquid media | Scirobotics Pickolo, Molecular Devices QPix 420 |
| | liquid handlers | Hitpicking primers/templates, diluting samples | Hamilton Microlab STAR, Labcyte Echo 550, Tecan EVO 200, Beckman Coulter Biomek FX, BioFluidix GmbH BioSpot BT600 liquid handling workstation, or equivalents |

TABLE 3-continued

Non-exclusive list of Scientific Equipment Compatible with the HTP engineering methods of the present disclosure.

| | Equipment Type | Operation(s) performed | Compatible Equipment Make/Model/Configuration |
|---|---|---|---|
| | Fragment analyzers (capillary electrophoresis) | gel electrophoresis to confirm assembled products of appropriate size | Agilent Bioanalyzer, AATI Fragment Analyzer |
| | Sequencer (sanger: Beckman) | Verifying sequence of assembled plasmids | ABI3730 Thermo Fisher, Beckman Ceq-8000, Beckman GenomeLab ™, or equivalents |
| | NGS (next generation sequencing) instrument | Verifying sequence of assembled plasmids | Illumina MiSeq series sequences, Illumina Hi-Seq, Ion torrent, pac bio or other equivalents |
| Prepare base strain and DNA assembly | centrifuge | spinning/pelleting cells | Beckman Avanti floor centrifuge, Hettich Centrifuge |
| Transform DNA into base strain | Electroporators | electroporative transformation of cells | BTX Gemini X2, BIO-RAD MicroPulser Electroporator |
| | Ballistic transformation | ballistic transformation of cells | BIO-RAD PDS1000 |
| | Incubators, thermal cyclers | for chemical transformation/heat shock | Inheco Cycler, ABI 2720, ABI Proflex 384, ABI Veriti, or equivalents |
| | Liquid handlers | for combining DNA, cells, buffer | Hamilton Microlab STAR, Labcyte Echo 550, Tecan EVO 200, Beckman Coulter Biomek FX, BioFluidix GmbH BioSpot BT600 liquid handling workstation, or equivalents |
| Integrate DNA into genome of base strain | Colony pickers | for inoculating colonies in liquid media or diluting spores | Scirobotics Pickolo, Molecular Devices QPix 420 |
| | Single cell/spore dispensers | for dispensing single cells/spores into wells on microtiter plate | Cellenion CellenONE, Berkeley Lights Beacon Instrument, FACS, or Cytena single cell printer |
| | Liquid handlers | For transferring cells onto Agar, transferring from culture plates to different culture plates (inoculation into other selective media) or dispensing diluted spore preparations into microtiter plates | Hamilton Microlab STAR, Labcyte Echo 550, Tecan EVO 200, Beckman Coulter Biomek FX, BioFluidix GmbH BioSpot BT600 liquid handling workstation or equivalents |
| | Platform shaker-incubators | incubation with shaking of microtiter plate cultures | Kuhner Shaker ISF4-X, Infors-ht Multitron Pro |
| QC transformed strain | Colony pickers | for inoculating colonies in liquid media | Scirobotics Pickolo, Molecular Devices QPix 420 |
| | liquid handlers | Hitpicking primers/templates, diluting samples | Hamilton Microlab STAR, Labcyte Echo 550, Tecan EVO 200, Beckman Coulter Biomek FX, BioFluidix GmbH BioSpot BT600 liquid handling workstation or equivalents |
| | Thermal cyclers | cPCR verification of strains | Inheco Cycler, ABI 2720, ABI Proflex 384, ABI Veriti, or equivalents |
| | Fragment analyzers (capillary electrophoresis) | gel electrophoresis to confirm cPCR products of appropriate size | Infors-ht Multitron Pro, Kuhner Shaker ISF4-X |
| | Sequencer (sanger: Beckman) | Sequence verification of introduced modification | Beckman Ceq-8000, Beckman GenomeLab ™, or equivalents |
| | NGS (next generation sequencing) instrument | Sequence verification of introduced modification | Illumina MiSeq series sequences, Illumina Hi-Seq, Ion torrent, pac bio or other equivalents |
| Select and consolidate QC'd strains into test plate | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |

TABLE 3-continued

Non-exclusive list of Scientific Equipment Compatible with the HTP engineering methods of the present disclosure.

| | Equipment Type | Operation(s) performed | Compatible Equipment Make/Model/Configuration |
|---|---|---|---|
| | Colony pickers | for inoculating colonies in liquid media | Scirobotics Pickolo, Molecular Devices QPix 420 |
| | Platform shaker-incubators | incubation with shaking of microtiter plate cultures | Kuhner Shaker ISF4-X, Infors-ht Multitron Pro |
| Culture strains in seed plates | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |
| | Platform shaker-incubators | incubation with shaking of microtiter plate cultures | Kuhner Shaker ISF4-X, Infors-ht Multitron Pro |
| | liquid dispensers | Dispense liquid culture media into microtiter plates | Well mate (Thermo), Benchcel2R (velocity 11), plateloc (velocity 11) |
| | microplate labeler | apply barcoders to plates | Microplate labeler (a2+ cab - agilent), benchcell 6R (velocity11) |
| Generate product from strain | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |
| | Platform shaker-incubators | incubation with shaking of microtiter plate cultures | Kuhner Shaker ISF4-X, Infors-ht Multitron Pro |
| | liquid dispensers | Dispense liquid culture media into multiple microtiter plates and seal plates | well mate (Thermo), Benchcel2R (velocity 11), plateloc (velocity 11) |
| | microplate labeler | Apply barcodes to plates | microplate labeler (a2+ cab - agilent), benchcell 6R (velocity11) |
| Evaluate performance | Liquid handlers | For processing culture broth for downstream analytical | Hamilton Microlab STAR, Labcyte Echo 550, Tecan EVO 200, Beckman Coulter Biomek FX, BioFluidix GmbH BioSpot BT600 liquid handling workstation or equivalents |
| | UHPLC, HPLC | quantitative analysis of precursor and target compounds | Agilent 1290 Series UHPLC and 1200 Series HPLC with UV and RI detectors, or equivalent; also any LC/MS |
| | LC/MS | highly specific analysis of precursor and target compounds as well as side and degradation products | Agilent 6490 QQQ and 6550 QTOF coupled to 1290 Series UHPLC |
| | Spectrophotometer | Quantification of different compounds using spectrophotometer based assays | Tecan M1000, spectramax M5, Genesys 10S |
| Culture strains in flasks | Fermenters: | incubation with shaking | Sartorius, DASGIPs (Eppendorf), BIO-FLOs (Sartorius-stedim). Applikon |
| | Platform shakers | | innova 4900, or any equivalent |
| Generate product from strain | Fermenters: DASGIPs (Eppendorf), BIO-FLOs (Sartorius-stedim) | | |
| Evaluate performance | Liquid handlers | For transferring from culture plates to different culture plates (inoculation into production media) | Hamilton Microlab STAR, Labcyte Echo 550, Tecan EVO 200, Beckman Coulter Biomek FX, BioFluidix GmbH BioSpot BT600 liquid handling workstation or equivalents |
| | UHPLC, HPLC | quantitative analysis of precursor and target compounds | Agilent 1290 Series UHPLC and 1200 Series HPLC with UV and RI detectors, or equivalent; also any LC/MS |

TABLE 3-continued

Non-exclusive list of Scientific Equipment Compatible with
the HTP engineering methods of the present disclosure.

| Equipment Type | Operation(s) performed | Compatible Equipment Make/Model/Configuration |
|---|---|---|
| LC/MS | highly specific analysis of precursor and target compounds as well as side and degradation products | Agilent 6490 QQQ and 6550 QTOF coupled to 1290 Series UHPLC |
| Flow cytometer | Characterize strain performance (measure viability) | BD Accuri, Millipore Guava |
| Spectrophotometer | Characterize strain performance (measure biomass) | Tecan M1000, Spectramax M5, or other equivalents |

Computer System Hardware

Figure 17:
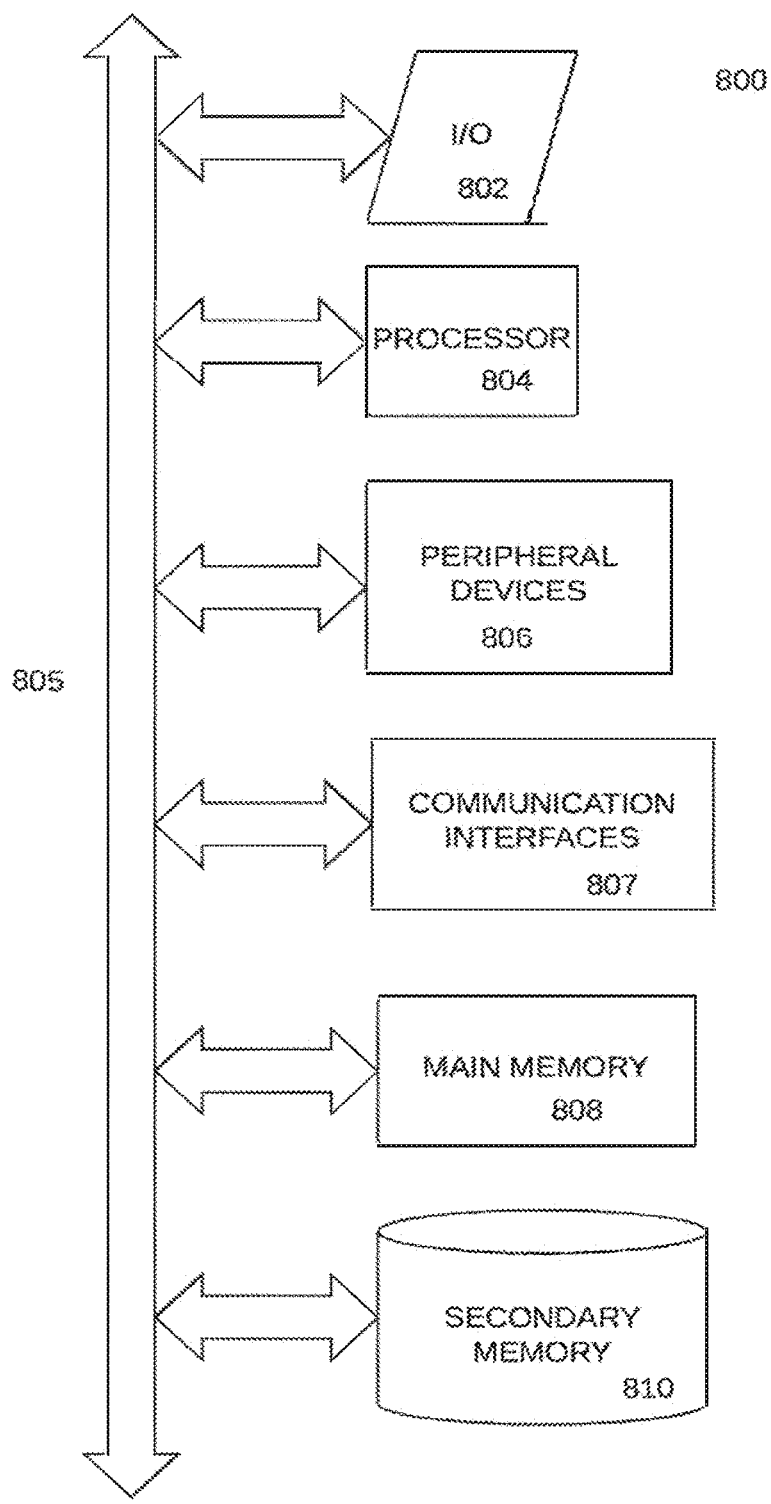
FIG. 17 diagrams an embodiment of a computer system, according to embodiments of the present disclosure.

FIG. 17 illustrates an example of a computer system 800 that may be used to execute program code stored in a non-transitory computer readable medium (e.g., memory) in accordance with embodiments of the disclosure. The computer system includes an input/output subsystem 802, which may be used to interface with human users and/or other computer systems depending upon the application. The I/O subsystem 802 may include, e.g., a keyboard, mouse, graphical user interface, touchscreen, or other interfaces for input, and, e.g., an LED or other flat screen display, or other interfaces for output, including application program interfaces (APIs). Other elements of embodiments of the disclosure, such as the components of the LIMS system, may be implemented with a computer system like that of computer system 800.

Program code may be stored in non-transitory media such as persistent storage in secondary memory 810 or main memory 808 or both. Main memory 808 may include volatile memory such as random access memory (RAM) or non-volatile memory such as read only memory (ROM), as well as different levels of cache memory for faster access to instructions and data. Secondary memory may include persistent storage such as solid state drives, hard disk drives or optical disks. One or more processors 804 reads program code from one or more non-transitory media and executes the code to enable the computer system to accomplish the methods performed by the embodiments herein. Those skilled in the art will understand that the processor(s) may ingest source code, and interpret or compile the source code into machine code that is understandable at the hardware gate level of the processor(s) 804. The processor(s) 804 may include graphics processing units (GPUs) for handling computationally intensive tasks. Particularly in machine learning, one or more CPUs 804 may offload the processing of large quantities of data to one or more GPUs 804.

The processor(s) 804 may communicate with external networks via one or more communications interfaces 807, such as a network interface card, WiFi transceiver, etc. A bus 805 communicatively couples the I/O subsystem 802, the processor(s) 804, peripheral devices 806, communications interfaces 807, memory 808, and persistent storage 810. Embodiments of the disclosure are not limited to this representative architecture. Alternative embodiments may employ different arrangements and types of components, e.g., separate buses for input-output components and memory subsystems.

Those skilled in the art will understand that some or all of the elements of embodiments of the disclosure, and their accompanying operations, may be implemented wholly or partially by one or more computer systems including one or more processors and one or more memory systems like those of computer system 800. In particular, the elements of the LIMS system 200 and any robotics and other automated systems or devices described herein may be computer-implemented. Some elements and functionality may be implemented locally and others may be implemented in a distributed fashion over a network through different servers, e.g., in client-server fashion, for example. In particular, server-side operations may be made available to multiple clients in a software as a service (SaaS) fashion, as shown in FIG. 15.

The term component in this context refers broadly to software, hardware, or firmware (or any combination thereof) component. Components are typically functional components that can generate useful data or other output using specified input(s). A component may or may not be self-contained. An application program (also called an "application") may include one or more components, or a component can include one or more application programs.

Some embodiments include some, all, or none of the components along with other modules or application components. Still yet, various embodiments may incorporate two or more of these components into a single module and/or associate a portion of the functionality of one or more of these components with a different component.

The term "memory" can be any device or mechanism used for storing information. In accordance with some embodiments of the present disclosure, memory is intended to encompass any type of, but is not limited to: volatile memory, nonvolatile memory, and dynamic memory. For example, memory can be random access memory, memory storage devices, optical memory devices, magnetic media, floppy disks, magnetic tapes, hard drives, SIMMs, SDRAM, DIMMs, RDRAM, DDR RAM, SODIMMS, erasable programmable read-only memories (EPROMs), electrically erasable programmable read-only memories (EEPROMs), compact disks, DVDs, and/or the like. In accordance with some embodiments, memory may include one or more disk drives, flash drives, databases, local cache memories, processor cache memories, relational databases, flat databases, servers, cloud based platforms, and/or the like. In addition, those of ordinary skill in the art will appreciate many additional devices and techniques for storing information can be used as memory.

Memory may be used to store instructions for running one or more applications or modules on a processor. For example, memory could be used in some embodiments to house all or some of the instructions needed to execute the functionality of one or more of the modules and/or applications disclosed in this application.

HTP Microbial Strain Engineering Based Upon Genetic Design Predictions: An Example Workflow In some embodiments, the present disclosure teaches the directed engineering of new host organisms based on the recommendations of the computational analysis systems of the present disclosure.

In some embodiments, the present disclosure is compatible with all genetic design and cloning methods. That is, in some embodiments, the present disclosure teaches the use of traditional cloning techniques such as polymerase chain reaction, restriction enzyme digestions, ligation, homologous recombination, RT PCR, and others generally known in the art and are disclosed in for example: Sambrook et al. (2001) Molecular Cloning: A Laboratory Manual ($3^{rd}$ ed., Cold Spring Harbor Laboratory Press, Plainview, N.Y.), incorporated herein by reference.

In some embodiments, the cloned sequences can include possibilities from any of the HTP genetic design libraries taught herein, for example: promoters from a promoter swap library, SNPs from a SNP swap library, start or stop codons from a start/stop codon exchange library, terminators from a STOP swap library, or sequence optimizations from a sequence optimization library.

Further, the exact sequence combinations that should be included in a particular construct can be informed by the epistatic mapping function.

In other embodiments, the cloned sequences can also include sequences based on rational design (hypothesis-driven) and/or sequences based on other sources, such as scientific publications.

Figure 2:
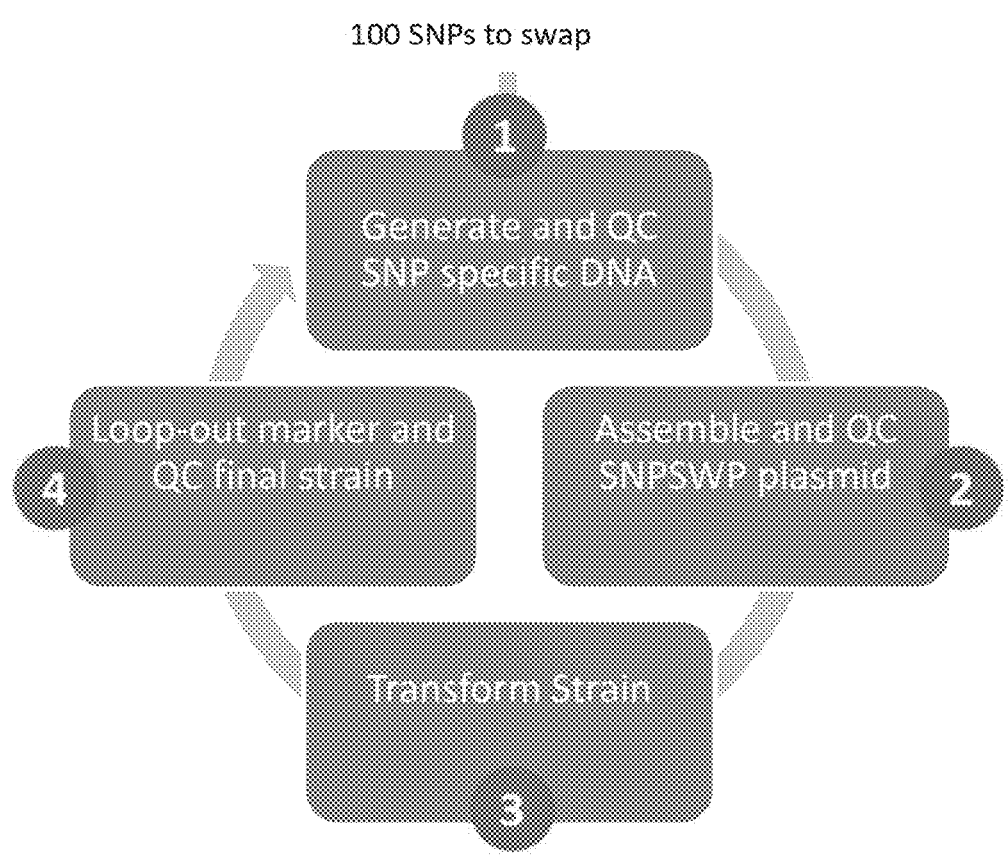
FIG. 2 outlines methods of the present disclosure for generating new host filamentous fungal strains with selected sequence modifications (e.g., 100 SNPs to swap). Briefly, the method comprises (1) desired DNA inserts are designed and generated using any of the methods provided herein, (2) DNA inserts are cloned into transformation constructs, (3) completed constructs are transferred into desired strains (e.g., base or production strains), where they are integrated into the host strain genome, and (4) selection markers and other unwanted DNA elements are looped out of the host strain. Each DNA assembly step may involve additional quality control (QC) steps, such as cloning constructs into filamentous fungal cells for amplification and sequencing. The transformation step can be preceded by a protoplasting step. The protoplasting can be performed using any protoplasting method known in the art. In one embodiment, protoplasting of the filamentous fungal host cells is performed using the method provided herein. In one embodiment, protoplasts are generated from the filamentous fungal host cells prior to transformation.

In some embodiments, the present disclosure teaches methods of directed engineering, including the steps of i) generating custom-made SNP-specific DNA, ii) assembling SNP-specific constructs, iii) transforming target host cells with SNP-specific DNA, and iv) looping out any selection markers (see FIG. 2).

FIG. 6A depicts the general workflow of the strain engineering methods of the present disclosure, including acquiring and assembling DNA, assembling any necessary vectors, transforming host cells and removing selection markers.

Build Specific DNA Oligonucleotides

In some embodiments, the present disclosure teaches inserting and/or replacing and/or altering and/or deleting a DNA segment of the host cell organism. In some aspects, the methods taught herein involve building an oligonucleotide of interest (i.e. a target DNA segment), that will be incorporated into the genome of a host organism. In some embodiments, the target DNA segments of the present disclosure can be obtained via any method known in the art, including: copying or cutting from a known template, mutation, or DNA synthesis. In some embodiments, the present disclosure is compatible with commercially available gene synthesis products for producing target DNA sequences (e.g., GeneArt™, GeneMaker™, GenScript™, Anagen™, Blue Heron™, Entelechon™, GeNOsys, Inc., or Qiagen™).

In some embodiments, the target DNA segment is designed to incorporate a SNP into a selected DNA region of the host organism (e.g., adding a beneficial SNP). In other embodiments, the DNA segment is designed to remove a SNP from the DNA of the host organisms (e.g., removing a detrimental or neutral SNP).

In some embodiments, the oligonucleotides used in the inventive methods can be synthesized using any of the methods of enzymatic or chemical synthesis known in the art. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian el al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648).

A great number of advances have been achieved in the traditional four-step phosphoramidite chemistry since it was first described in the 1980s (see for example, Sierzchala, et al. *J. Am. Chem. Soc.,* 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., *Nucleosides, Nucleotides, and Nucleic Acids,* 24 (5-7), 1037-1041 (2005) for improved synthesis of longer oligonucleotides through the use of large-pore CPG; and Damha et al., *NAR,* 18, 3813-3821 (1990) for improved derivatization).

Regardless of the type of synthesis, the resulting oligonucleotides may then form the smaller building blocks for longer oligonucleotides. In some embodiments, smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA, oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligonucleotides that are homologous to the forward strand at the 5' end of the gene and against the reverse strand at the 3' end of the gene.

Another method of synthesizing a larger double stranded DNA fragment is to combine smaller oligonucleotides through top-strand PCR (TSP). In this method, a plurality of oligonucleotides spans the entire length of a desired product and contain overlapping regions to the adjacent oligonucleotide(s). Amplification can be performed with universal forward and reverse primers, and through multiple cycles of amplification a full-length double stranded DNA product is formed. This product can then undergo optional error correction and further amplification that results in the desired double stranded DNA fragment end product.

In one method of TSP, the set of smaller oligonucleotides that will be combined to form the full-length desired product are between 40-200 bases long and overlap each other by at least about 15-20 bases. For practical purposes, the overlap region should be at a minimum long enough to ensure specific annealing of oligonucleotides and have a high enough melting temperature (Tm) to anneal at the reaction temperature employed. The overlap can extend to the point where a given oligonucleotide is completely overlapped by adjacent oligonucleotides. The amount of overlap does not seem to have any effect on the quality of the final product. The first and last oligonucleotide building block in the assembly should contain binding sites for forward and reverse amplification primers. In one embodiment, the terminal end sequence of the first and last oligonucleotide contain the same sequence of complementarity to allow for the use of universal primers.

Assembling DNA Fragments/Cloning Custom Plasmids

In some embodiments, the present disclosure teaches methods for constructing DNA fragments capable of inserting desired target DNA sections (e.g. containing a particular SNP) into the genome of host organisms. FIG. 1 depicts a DNA recombination method of the present disclosure for increasing variation in diversity pools. DNA sections, such as genome regions from related species, can be cut via physical or enzymatic/chemical means. The cut DNA regions are melted and allowed to reanneal, such that overlapping genetic regions prime polymerase extension reactions. Subsequent melting/extension reactions are carried out until products are reassembled into chimeric DNA, comprising elements from one or more starting sequences and a promoter. A general scheme for the entire design, generate, assemble, QC, transform, loop-out and QC process for a SNPswap is shown in FIG. 2. It should be noted that this scheme can be applied to other HTP tools as provided herein (e.g., PROswp, STOPswp). In some embodiments, the present disclosure teaches methods of generating linear DNA fragments comprising the target DNA, homology arms, and at least one selection marker (see FIGS. 45 and 46A).

In some embodiments, the present disclosure is compatible with any method suited for transformation of DNA fragments into the host organism (e.g., filamentous fungus such as A. niger). In some embodiments, the present disclosure teaches use of plasmids or assembly vectors for which a desired target DNA section can be cloned into and amplified therefrom. When used, the assembly vectors can further comprise any origins of replication that may be needed for propagation in a host cell (e.g., yeast and/or E. coli). In certain instances, the target DNA can be inserted into vectors, constructs or plasmids obtainable from any repository or catalogue product, such as a commercial vector (see e.g., DNA2.0 custom or GATEWAY® vectors). In certain instances, the target DNA can be inserted into vectors, constructs or plasmids obtainable from any repository or catalogue product, such as a commercial vector (see e.g., DNA2.0 custom or GATEWAY® vectors). The use of plasmids for generating linear DNA fragments for ultimately transforming a host cell such as a filamentous fungus host cell can entail synthesizing parts of a target DNA construct comprising a desired gene to be integrated into a host genome, transforming a yeast cell with the parts of the target DNA construct along with an assembly vector, isolating the assembled plasmids containing the target DNA construct from said transformed yeast cell, propagating the isolated plasmids in E. coli, and PCR amplifying the target DNA construct from E. coli to generate a linear DNA fragment comprising a desired gene to be integrated into a host genome prior to transformation of the filamentous fungal host cell.

Figure 45:
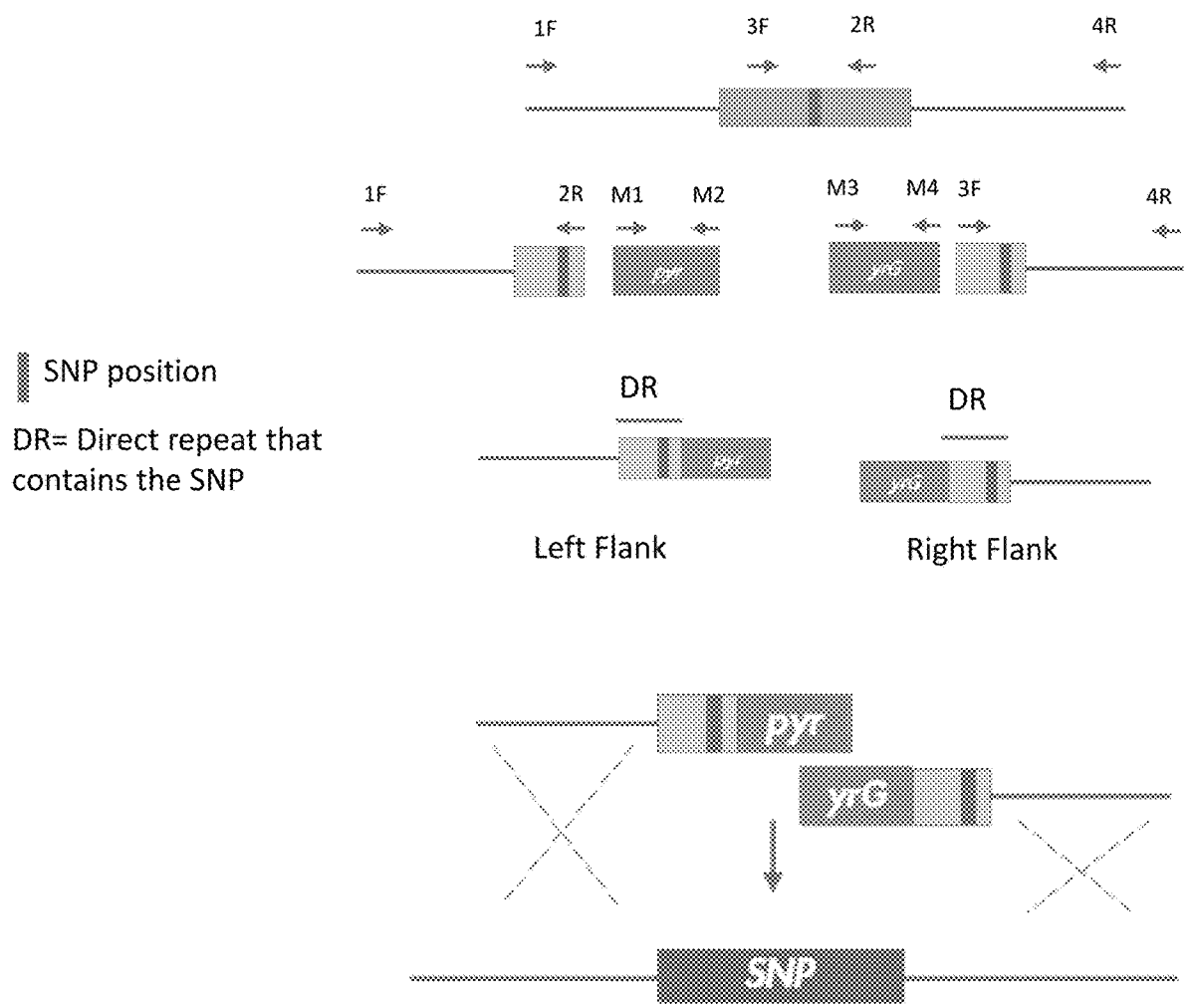
FIG. 45 illustrates the use of fusion PCR the generate split-marker constructs for use in the present invention.

In an alternative embodiment, assembly or generation of a linear DNA fragment(s) comprising a desired gene to be integrated into a host genome (e.g., filamentous fungal cell) can entail using fusion PCR. Fusion PCR can be performed using any fusion PCR method known in the art including, for example, the method described in Yu et al, Fungal Genetics and Biology, vol 41, pages 973-981 (2004), which is herein incorporated by reference in its entirety. FIG. 45 depicts a method of the use of fusion PCR to generate two linear DNA fragments that comprise a marker gene (i.e., pyrG) split between them. Conceptually, fusion PCR can be used to generate any of the constructs comprising target gene mutations and/or selectable markers genes provided herein.

The linear DNA fragments for use in the methods provided herein can comprise markers for selection and/or counter-selection as described herein. The markers can be any markers known in the art and/or provided herein. The linear DNA fragments can further comprise any regulatory sequence(s) provided herein. The regulatory sequence can be any regulatory sequence known in the art or provided herein such as, for example, a promoter, start, stop, signal, secretion and/or termination sequence used by the genetic machinery of the host cell (e.g., filamentous fungal cell).

In some embodiments, the assembly/cloning methods of the present disclosure may employ at least one of the following assembly strategies: i) type II conventional cloning, ii) type II S-mediated or "Golden Gate" cloning (see, e.g., Engler, C., R. Kandzia, and S. Marillonnet. 2008 "A one pot, one step, precision cloning method with high-throughput capability". PLos One 3:e3647; Kotera, I., and T. Nagai. 2008 "A high-throughput and single-tube recombination of crude PCR products using a DNA polymerase inhibitor and type IIS restriction enzyme." J Biotechnol 137:1-7.; Weber, E., R. Gruetzner, S. Werner, C. Engler, and S. Marillonnet. 2011 Assembly of Designer TAL Effectors by Golden Gate Cloning. PloS One 6:e19722), iii) GATEWAY® recombination, iv) TOPO® cloning, exonuclease-mediated assembly (Aslanidis and de Jong 1990. "Ligation-independent cloning of PCR products (LIC-PCR)." Nucleic Acids Research, Vol. 18, No. 20 6069), v) homologous recombination, vi) non-homologous end joining, vii) Gibson assembly (Gibson et al., 2009 "Enzymatic assembly of DNA molecules up to several hundred kilobases" Nature Methods 6, 343-345) or a combination thereof. Modular type IIS based assembly strategies are disclosed in PCT Publication WO 2011/154147, the disclosure of which is incorporated herein by reference.

In some embodiments, the present disclosure teaches cloning vectors with at least one selection marker. Various selection marker genes are known in the art often encoding antibiotic resistance function for selection in prokaryotic (e.g., against ampicillin, kanamycin, tetracycline, chloramphenicol, zeocin, spectinomycin/streptomycin) or eukaryotic cells (e.g. geneticin, neomycin, hygromycin, puromycin, blasticidin, zeocin) under selective pressure. Other marker systems allow for screening and identification of wanted or unwanted cells such as the well-known blue/white screening system used in bacteria to select positive clones in the presence of X-gal or fluorescent reporters such as green or red fluorescent proteins expressed in successfully transduced host cells. Another class of selection markers most of which are only functional in prokaryotic systems relates to counter selectable marker genes often also referred to as "death genes" which express toxic gene products that kill producer cells. Examples of such genes include sacB, rpsL (strA), tetAR, pheS, thyA, gata-1, or ccdB, the function of which is described in (Reyrat et al. 1998 "Counterselectable Markers: Untapped Tools for Bacterial Genetics and Pathogenesis." Infect Immun. 66(9): 4011-4017).

Figure 18:
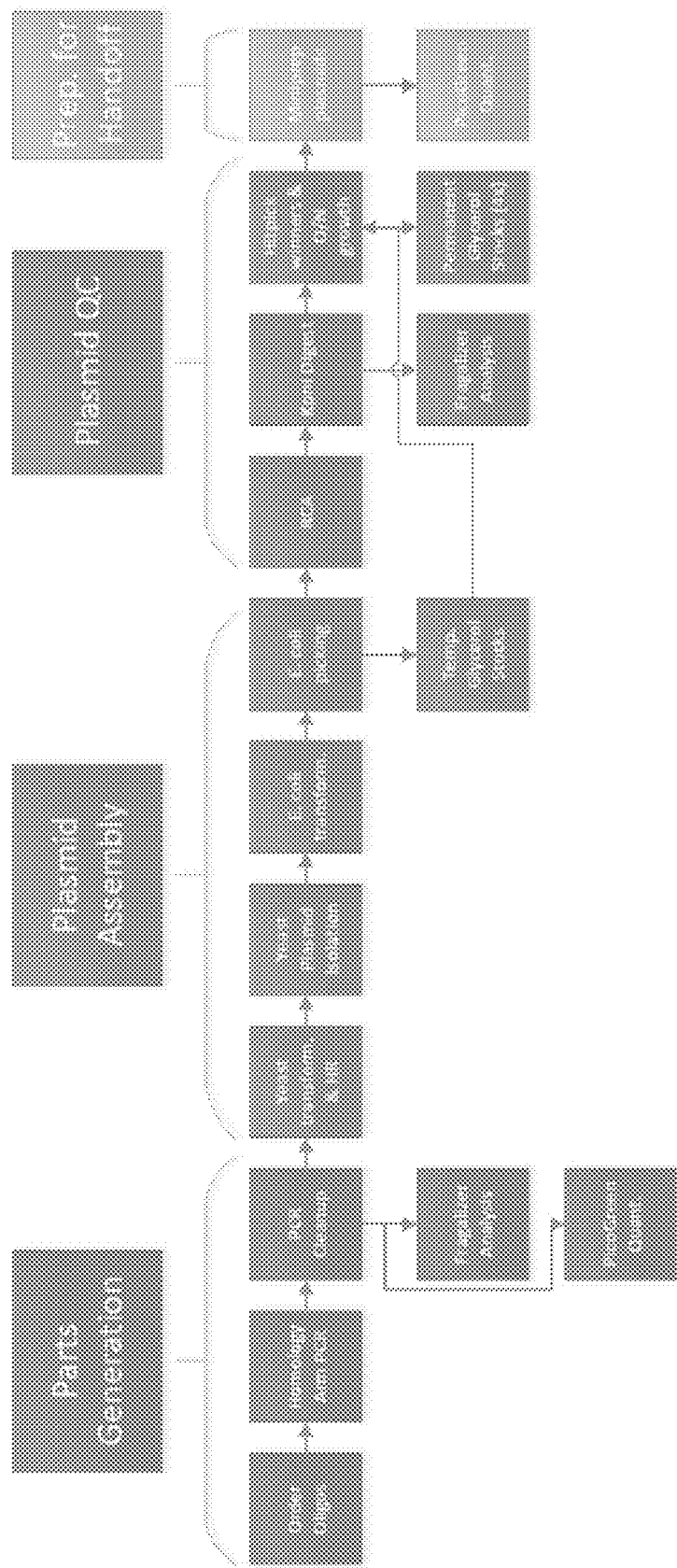
FIG. 18 depicts the workflow associated with the DNA assembly according to one embodiment of the present disclosure. This process is divided up into 4 stages: parts generation, plasmid/construct assembly, plasmid/construct QC, and plasmid/construct preparation for transformation. During parts generation, oligos designed by Laboratory Information Management System (LIMS) are ordered from an oligo sequencing vendor and used to amplify the target sequences from the host organism via PCR. These PCR parts are cleaned to remove contaminants and assessed for success by fragment analysis, in silico quality control comparison of observed to theoretical fragment sizes, and DNA quantification. The parts are transformed into yeast along with an assembly vector and assembled into plasmids via homologous recombination. Assembled plasmids are isolated from yeast and transformed into E. coli for subsequent assembly quality control and amplification. During plasmid assembly quality control, several replicates of each plasmid are isolated, amplified using Rolling Circle Amplification (RCA), and assessed for correct assembly by enzymatic digest and fragment analysis. Correctly assembled plasmids identified during the QC process are hit picked to generate permanent stocks and the specific gene construct including any flanking sequences necessary to facilitate genome integration are then PCR amplified from the plasmid to generate linear DNA fragments that are quantified prior to transformation into the target host organism (e.g., filamentous fungal host cell). As an alternative to generating plasmids as described above, fusion PCR can be used to generate specific gene constructs including any flanking sequences necessary to facilitate genome integration in a filamentous fungal host cell.

FIG. 18 depicts a workflow associated with DNA assembly according to one embodiment of the present disclosure. This process can be divided up into 4 stages: parts generation, plasmid/construct assembly, plasmid/construct QC, and plasmid/construct preparation for transformation. During parts generation, oligos designed by Laboratory Information Management System (LIMS) are ordered from an oligo sequencing vendor and used to amplify the target sequences from the host organism via PCR. These PCR parts are cleaned to remove contaminants and assessed for success by fragment analysis, in silico quality control comparison of observed to theoretical fragment sizes, and DNA quantification. As shown in FIG. 18, in one embodiment, the parts are transformed into yeast along with an assembly vector and assembled into plasmids via homologous recombination. Assembled plasmids are isolated from yeast and transformed into a separate yeast host cell for subsequent assembly quality control and amplification. During plasmid assembly quality control, several replicates of each plasmid are isolated, amplified using Rolling Circle Amplification (RCA), and assessed for correct assembly by enzymatic digest and fragment analysis. Correctly assembled plasmids identified during the QC process are hit picked to generate permanent stocks and the specific gene construct including any flanking sequences necessary to facilitate genome integration are then PCR amplified from the plasmid to generate linear DNA fragments that are quantified and QC'd via fragment analysis prior to transformation into the target host organism (e.g., filamentous fungal host cell). As also shown in FIG. 18, in a separate embodiment, the parts are subjected to fusion PCR (see FIGS. 45 and 46A-B for example) to generate linear DNA fragments, which are QC'd via fragment and sequence analysis prior to transformation into the target host organism (e.g., filamentous fungal host cell).

Protoplasting Methods

Figure 28:
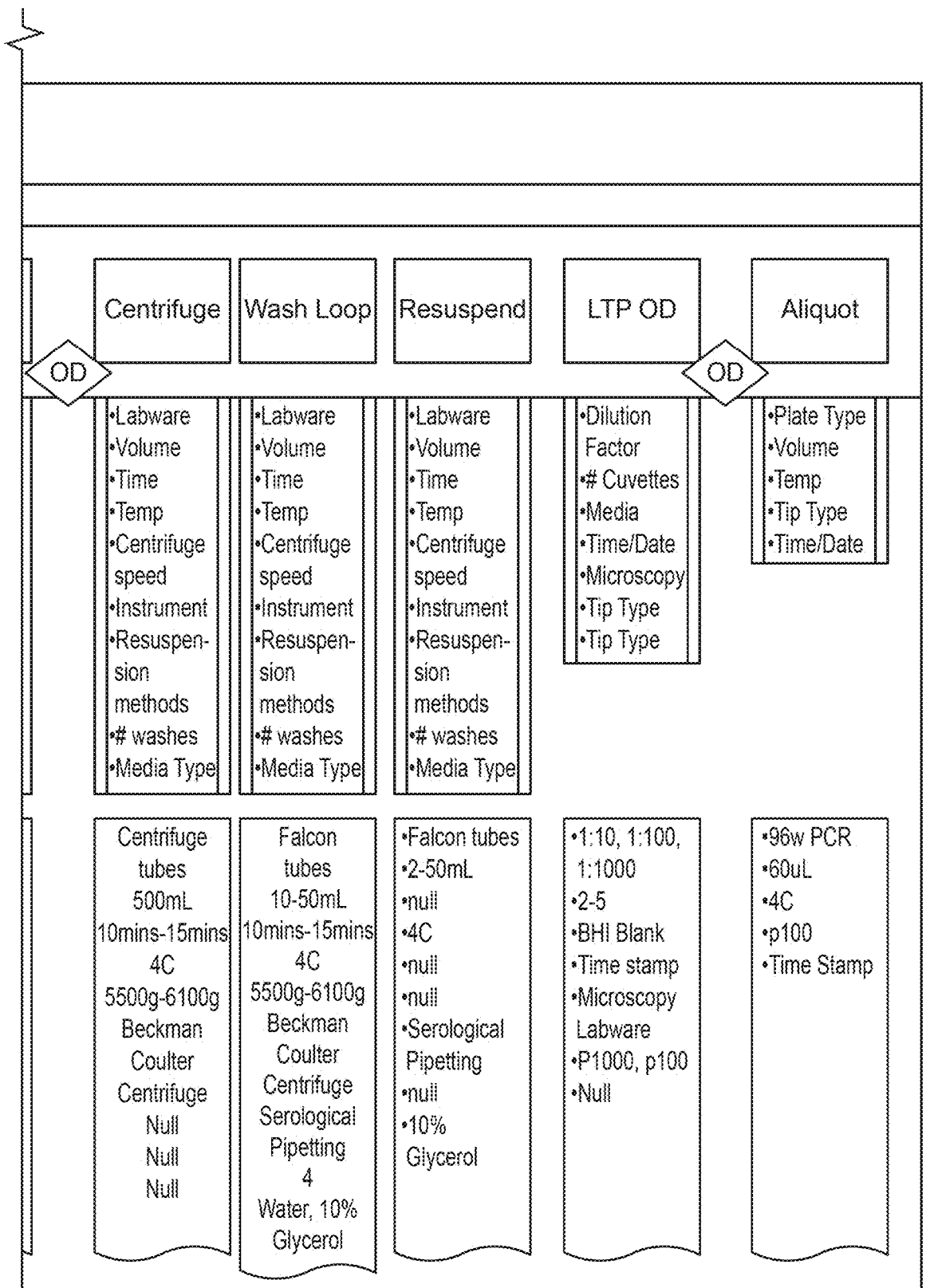
FIG. 28 depicts a protoplasting portion of a workflow for a high-throughput (HTP) system for building strains of coenocytic organisms (e.g., filamentous fungi)

In one embodiment, the methods and systems provided herein require the generation of protoplasts from coenocytic organisms (e.g., filamentous fungal cells) as provided herein. Suitable procedures for preparation of protoplasts can be any known in the art including, for example, those described in EP 238,023 and Yelton et al. (1984, Proc. Natl. Acad. Sci. USA 81:1470-1474). In one embodiment, protoplasts are generated by treating a pre-cultivated culture of filamentous fungal cells with one or more lytic enzymes or a mixture thereof. The lytic enzymes can be a beta-glucanase and/or a polygalacturonase. In one embodiment, the enzyme mixture for generating protoplasts is VinoTaste concentrate. Many of the parameters utilized to pre-cultivate cultures of coenocytic organisms (e.g., filamentous fungal cells) and subsequently generate and utilize protoplasts therefrom for use in the methods and compositions provided herein can be varied. For example, there can be variations of inoculum size, inoculum method, pre-cultivation media, pre-cultivation times, pre-cultivation temperatures, mixing conditions, washing buffer composition, dilution ratios, buffer composition during lytic enzyme treatment, the type and/or concentration of lytic enzyme used, the time of incubation with lytic enzyme, the protoplast washing procedures and/or buffers, the concentration of protoplasts and/or polynucleotide and/or transformation reagents during the actual transformation, the physical parameters during the transformation, the procedures following the transformation up to the obtained transformants. In some cases, these variations can be utilized to optimize the number of protoplasts and the transformation efficiency. In one embodiment, the coenocytic organism is a filamentous fungal cell as provided herein (e.g., *A. niger*). Further to this embodiment, the pre-cultivation media can be YPD or complete media. The volume of pre-cultivation media can be at least, at most or about 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml or 1000 ml. The volume of pre-cultivation media can be from about 50 ml to about 100 ml, about 100 ml to about 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to about 500 ml, about 500 ml to about 550 ml, about 550 ml to about 600 ml, about 600 ml to about 650 ml, about 650 ml to about 700 ml, about 700 ml to about 750 ml, about 750 ml to about 800 ml, about 800 ml to about 850 ml, about 850 ml to about 900 ml, about 900 ml to about 950 ml or about 950 ml to about 1000 ml. In some cases, a plurality of cultures are cultivated and subsequently subjected to protoplasting. The plurality of cultures can be 2, 3, 4, 5, 6, 7, 8, 9, 10, 12, 14, 16, 18, 20, 25, 50, 75, 100, 150, 200, 300, 400, 500 or more. In one embodiment, a pre-cultivation preparation is prepared by inoculating 100 ml of rich media (e.g., YPD or complete media) with $10^6$ spores/ml and incubating the pre-cultivation preparation between 14-18 hours at 30° C. In another embodiment, a pre-cultivation preparation is prepared by inoculating 500 ml of rich media (e.g., Yeast Mold Broth, YPD or complete media) with at least $10^6$ spores/ml and incubating the pre-cultivation preparation between 14-18 hours at 30° C. Prior to protoplasting, the coenocytic organism can be isolated by any method known in the art such as, for example centrifugation. In one embodiment, the coenocytic organism is filamentous fungus (e.g., *A. niger*). Further to this embodiment, Yeast Mold Broth (YMB) is inoculated with $10^6$ spores/ml of the filamentous fungal cells and grown for 16 hours at 30° C. Further still to this embodiment, the filamentous fungal cells grown in the precultivation preparation can be isolated by centrifugation. The pre-cultivation preparations provided herein for use in the methods and compositions provided herein can produce an amount of hyphae for subsequent protoplasting of about, at least or more than 0.5 g, 1 g, 1.5 g, 2 g, 2.5 g, 3 g, 3.5 g, 4 g or 5 g of wet weight. Pre-cultivation/cultivation of the coenocytic organism (e.g., filamentous fungus) can be part of a workflow in a high-throughput system (HTP) such as depicted in FIG. 28. The HTP system can be automated or semi-automated. As shown in FIG. 28, pre-cultivation of the organism can entail inoculating a small scale volume (e.g., 100 ml) of sporulation media (PDAmedia in FIG. 28) with $10^6$ spores/ml of the organism (e.g., *A. niger*) and growing for 14-16 hours at 30° C. As shown in FIG. 28, during pre-cultivation, the workflow can contain a step whereby an enzyme solution for generating protoplasts from the pre-cultivated organism (e.g., *A. niger*) is generated. The enzyme solution can consist of Vinotaste pro (Novozymes) enzyme mix in phosphate buffer comprising 1.2 M $MgSO_4$. Following pre-cultivation, hyphae can be collected following filtration through a Miracloth and a large-scale culture can be cultivated by inoculating about 500 ml of complete media in a 2.8 L flask with 10 ul to 20 ml of the collected hyphae. Inoculum size can be variable based on the OD of the culture obtained from the pre-cultivation step. The large scale culture can be grown for 6-18 hours at either 30° C. or 18° C. at 80% humidity with shaking at 200 rpms. Following cultivation, the culture(s) can be isolated by centrifugation following by one or more washes and resuspended. In one embodiment, the cultures are resuspended in a protoplasting buffer as described herein and subjected to protoplasting as described herein. Centrifugation can be performed in 500 ml centrifuge tubes at 4° C. for 10-15 minutes at 5500-6100×g. Each of the one or more washes can be performed in 10-50 ml of wash buffer (e.g., water with 10% glycerol) followed by centrifugation at 4° C. for 10-15 minutes at 5500-6100×g.

Following isolation as described above, the coenocytic organism (e.g., filamentous fungal cells such as *A. niger*) can be resuspended in protoplasting buffer such that the protoplasting buffer comprises one or enzymes as provided herein (e.g., VinoTaste pro concentrate (Novozymes)) for generating protoplasts. In one embodiment, the protoplasting buffer has a high concentration of osmolite (e.g., greater than or equal to 1 M of an osmolite such as $MgSO_4$). In embodiments utilizing a protoplasting buffer with a high osmolite concentration (e.g., 1.2 M $MgSO_4$), the incubation time for the enzymatic treatment (e.g., VinoTaste pro concentrate (Novozymes)) can be from about 14-16 hours at about 30° C. The volume of protoplasting buffer used for resuspension can be 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml or 1000 ml. The volume of protoplasting buffer used for resuspension can be can be from about 50 ml to about 100 ml, about 100 ml to about 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to about 500 ml, about 500 ml to about 550 ml, about 550 ml to about 600 ml, about 600 ml to about 650 ml, about 650 ml to about 700 ml, about 700 ml to about 750 ml, about 750 ml to about 800 ml, about 800 ml to about 850 ml, about 850 ml to about 900 ml, about 900 ml to about 950 ml or about 950 ml to about 1000 ml. In one embodiment, filamentous fungal cells are grown in 500 ml of rich media (e.g., YPD or complete media) as shown, for example, in FIG. 28, and hyphae (can be about 1 g wet mass as shown in FIG. 28) are isolated by filtration through a Miracloth, rinsing with 100 ml of wash buffer (e.g., 100 mM sodium phosphate buffer with 1.2 M $MgSO_4$, pH 5.5) and resuspended in about 500 ml of protoplasting buffer (e.g., 100 mM sodium phosphate buffer with 1.2 M $MgSO_4$ pH 5.5 in FIG. 28) comprising a protoplasting enzyme mixture (e.g., VinoTaste pro concentrate (Novozymes)) in a 1 L bottle. The hyphae in the enzyme solution can be incubated for 14-16 hours at 30° C. with shaking at 140 rpm with continued monitoring of protoplast formation via microscopic examination.

In one embodiment, one or more chemical inhibitors of the NHEJ pathway are added to a protoplasting buffer as provided. The one or more chemical inhibitors can be selected from W-7, chlorpromazine, vanillin, Nu7026, Nu7441, mirin, SCR7, AG14361 or any combination thereof. Addition of the one or more chemical inhibitors to the protoplasting buffer can occur at any point during the protoplasting procedure. In one embodiment, treatment with the one or more chemical inhibitors is for the entire protoplasting procedure. In a separate embodiment, treatment with the one or more chemical inhibitors is for less than the entire protoplasting procedure. Treatment with the one or more chemical inhibitors can be for about 1, 5, 10, 15, 20, 30, 45, 60, 90, 120, 150, 180, 210, 240, 270 or 300 minutes. In one embodiment, the co-enocytic cells (e.g., filamentous fungal cells) are treated with W-7. In another embodiment, the co-enocytic cells (e.g., filamentous fungal cells) are treated with SCR-7.

Following enzymatic treatment, the protoplasts can be isolated using methods known in the art. Prior to isolation of protoplasts, undigested hyphal fragments can be removed by filtering the mixture through a porous barrier (such as Miracloth) in which the pores range in size from 20-100 microns in order to produce a filtrate of filtered protoplasts.

Figure 27:
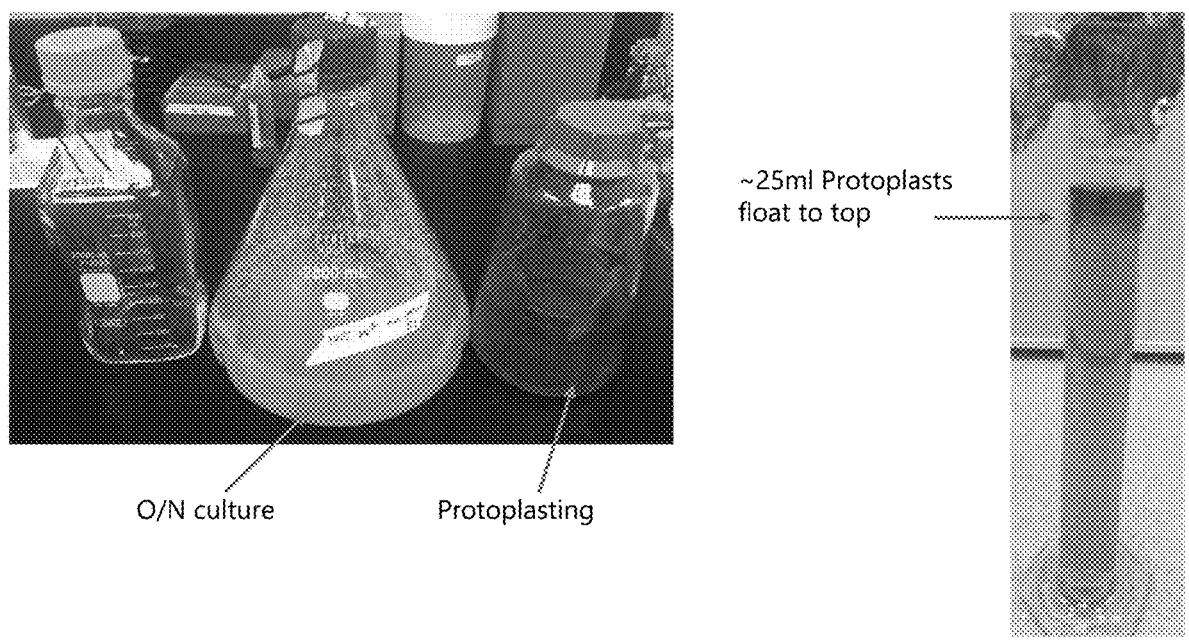
FIG. 27 depicts a large scale protoplasting method in which multiple batches of 500 ml cultures are subjected to protoplasting in 500 ml of protoplasting buffer followed by storing the generated protoplasts at −80 C. This is method is scaled up as compared to using 100 ml cultures in 50-100 ml protoplasting buffer.

In one embodiment, the filtered protoplasts are then centrifuged at moderate levels of centripetal force to cause the protoplasts to pellet to the bottom of the centrifuge tube. The centripetal force can be from about 500-1500×g. In a preferred embodiment, the centripetal force used is generally below 1000×g (e.g., 800×g for 5 minutes as shown in FIG. 28). In a separate embodiment, a buffer of substantially lower osmotic strength is gently applied to the surface of the protoplasts (e.g., filtered protoplasts) following generation of protoplasts in a protoplasting buffer comprising a high concentration of osmolite. Examples of buffers of substantially lower osmotic strength include buffers (e.g., Tris buffer) comprising 1M Sorbitol, 1M NaCl, 0.6M Ammonium Sulfate or 1M KCl. In one embodiment, as shown in FIG. 28, the lower osmotic strength buffer for use in the methods provided herein is a Sorbitol-Tris (ST) buffer that comprises 0.4 M sorbitol and has a pH of 8. This layered preparation can then be centrifuged, which can cause the protoplasts to accumulate at a layer in the tube in which they are neutrally buoyant. Protoplasts can then be isolated from this layer for further processing (e.g., storage and/or transformation). In yet another embodiment, the protoplasts (e.g., filtered protoplasts) generated in a protoplasting buffer comprising a high concentration of osmolite (e.g., 100 mM phosphate buffer comprising 1.2M $MgSO_4$, pH 5.5) are transferred to an elongated collection vessel (e.g., graduated cylinder) and a buffer of lower osmolarity as provided herein (e.g., 0.4M ST buffer, pH 8) is overlaid on the surface of the protoplasts (e.g., filtered protoplasts) to generate a layer at which the protoplasts are neutrally buoyant. The combination of the buffers of differing osmolarity in the elongated collection vessel (e.g., graduated cylinder) can facilitate the protoplasts 'floating' to the surface of the elongated collection vessel (e.g., graduated cylinder; FIG. 27). Once at the top of the collection vessel, the protoplasts can be isolated. In one embodiment, a 500 ml pre-cultivation preparation of coenocytic organisms (e.g., filamentous fungal cells such as *A. niger*) grown and subjected to protoplasting as provided herein yields about 25 ml of protoplasts.

Following protoplast isolation, the remaining enzyme containing buffer can be removed by resuspending the protoplasts in an osmotic buffer (e.g., 1M sorbitol buffered using 10 mM TRIS, pH 8) and recollected by centrifugation as shown in FIG. 28. This step can be repeated. After sufficient removal of the enzyme containing buffer, the protoplasts can be further washed in osmotically stabilized buffer also containing Calcium chloride (e.g., 1M sorbitol buffered using 10 mM TRIS, pH 8, 50 mM $CaCl_2$) one or more times (see, for example, FIG. 28).

Following isolation and washing, the protoplasts can be resuspended in an osmotic stabilizing buffer. The composition of such buffers can vary depending on the species, application and needs. However, typically these buffers contain either an organic component like sucrose, citrate, mannitol or sorbitol between 0.5 and 2 M. More preferably between 0.75 and 1.5 M; most preferred is 1 M. Otherwise these buffers contain an inorganic osmotic stabilizing component like KCl, $(NH_4)_2SO_4$, $MgSO_4$, NaCl or $MgCl_2$ in concentrations between 0.1 and 1.5 M. Preferably between 0.2 and 0.8 M; more preferably between 0.3 and 0.6 M, most preferably 0.4 M. The most preferred stabilizing buffers are STC (sorbitol, 0.8 M; $CaCl_2$, 25 mM; Tris, 25 mM; pH 8.0) or KCl-citrate (KCl, 0.3-0.6 M; citrate, 0.2% (w/v)). The protoplasts can be used in a concentration between $1×10^5$ and $1×10^{10}$ cells/ml or between $1$-$3×10^7$ protoplasts per ml. Preferably, the concentration is between $1×10^6$ and $1×10^9$; more preferably the concentration is between $1×10^7$ and $5\times10^8$; most preferably the concentration is $1\times10^8$ cells/ml. To increase the efficiency of transfection, carrier DNA (as salmon sperm DNA or non-coding vector DNA) may be added to the transformation mixture. DNA is used in a concentration between 0.01 and 10 ug; preferably between 0.1 and 5 ug, even more preferably between 0.25 and 2 ug; most preferably between 0.5 and 1 ug.

In one embodiment, following generation and subsequent isolation and washing, the protoplasts are mixed with one or more cryoprotectants. The cryoprotectants can be glycols, dimethyl sulfoxide (DMSO), polyols, sugars, 2-Methyl-2,4-pentanediol (MPD), polyvinylpyrrolidone (PVP), methylcellulose, C-linked antifreeze glycoproteins (C-AFGP) or combinations thereof. Glycols for use as cryoprotectants in the methods and systems provided herein can be selected from ethylene glycol, propylene glycol, polypropylene glycol (PEG), glycerol, or combinations thereof. Polyols for use as cryoprotectants in the methods and systems provided herein can be selected from propane-1,2-diol, propane-1,3-diol, 1,1,1-tris-(hydroxymethyl)ethane (THME), and 2-ethyl-2-(hydroxymethyl)-propane-1,3-diol (EHMP), or combinations thereof. Sugars for use as cryoprotectants in the methods and systems provided herein can be selected from trehalose, sucrose, glucose, raffinose, dextrose or combinations thereof. In one embodiment, the protoplasts are mixed with DMSO. DMSO can be mixed with the protoplasts at a final concentration of at least, at most, less than, greater than, equal to, or about 1%, 2%, 3%, 4%, 5%, 6%, 7%, 8%, 9%, 10%, 12.5%, 15%, 20%, 25%, 30%, 35%, 40%, 45%, 50%, 55%, 60%, 65%, 70%, or 75% w/v or v/v. The protoplasts/cryoprotectant (e.g., DMSO) mixture can be distributed to microtiter plates prior to storage. The protoplast/cryoprotectant (e.g., DMSO) mixture can be stored at any temperature provided herein for long-term storage (e.g., several hours, day(s), week(s), month(s), year(s)) as provided herein such as, for example −20° C. or −80° C. In one embodiment, an additional cryoprotectant (e.g., PEG) is added to the protoplasts/DMSO mixture. In yet another embodiment, the additional cryoprotectant (e.g., PEG) is added to the protoplast/DMSO mixture prior to storage. The PEG can be any PEG provided herein and can be added at any concentration (e.g., w/v or v/v) as provided herein. In one embodiment, the PEG solution is prepared as 40% w/v in STC buffer. 20% v/v of this 40% PEG-STC can then be added to the protoplasts. For example, 800 microliters of $1.25\times10^7$ protoplasts would have 200 microliters of 40% PEG-STC giving a final volume of 1 ml. Seventy microliters of DMSO can then be added to this 1 ml to bring this prep to 7% v/v DMSO.

Any pre-cultivation, cultivation and/or protoplasting protocol provided herein can be performed in a high-throughput manner. For example, pre-cultivation, cultivation and protoplasting can be performed as part of a workflow such that said workflow represents a portion of a high-throughput (HTP) protocol such as depicted in FIG. 28. The high-throughput protocol can utilized automated liquid handling for any and/or all steps.

Transformation of Host Cells

In some embodiments, the vectors or constructs of the present disclosure may be introduced into the host cells (e.g., filamentous fungal cells or protoplasts derived therefrom) using any of a variety of techniques, including transformation, transfection, transduction, viral infection, gene guns, or Ti-mediated gene transfer (see Christie, P. J., and Gordon, J. E., 2014 "The *Agrobacterium* Ti Plasmids" Microbiol SPectr. 2014; 2(6); 10.1128). Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include, for example, lithium acetate transformation and electroporation see, e.g., Gietz et al., Nucleic Acids Res. 27:69-74 (1992); Ito et al., J. Bacterol. 153:163-168 (1983); and Becker and Guarente, Methods in Enzymology 194:182-187 (1991). In some embodiments, transformed host cells are referred to as recombinant host strains.

In some embodiments, the present disclosure teaches high-throughput transformation of cells using the 96-well plate robotics platform and liquid handling machines of the present disclosure.

In one embodiment, the methods and systems provided herein require the transfer of nucleic acids to protoplasts derived from filamentous fungal cells as described herein. In another embodiment, the transformation utilized by the methods and systems provided herein is high-throughput in nature and/or is partially or fully automated as described herein. The partially or fully automated method can entail the use of automated liquid handling one or more liquid handling steps as provided herein. Further to this embodiment, the transformation is performed by adding constructs or expression constructs as described herein to the wells of a microtiter plate followed by aliquoting protoplasts generated by the methods provided herein to each well of the microtiter plate. Suitable procedures for transformation/transfection of protoplasts can be any known in the art including, for example, those described in international patent applications PCT/NL99/00618, PCT/EP99/202516, Finkelstein and Ball (eds.), Biotechnology of filamentous fungi, technology and products, Butterworth-Heinemann (1992), Bennett and Lasure (eds.) More Gene Manipulations in fungi, Academic Press (1991), Turner, in: Puhler (ed), Biotechnology, second completely revised edition, VHC (1992) protoplast fusion, and the Ca-PEG mediated protoplast transformation as described in EP635574B. Alternatively, transformation of the filamentous fungal host cells or protoplasts derived therefrom can also be performed by electroporation such as, for example, the electroporation described by Chakraborty and Kapoor, Nucleic Acids Res. 18:6737 (1990), *Agrobacterium tumefaciens*-mediated transformation, biolistic introduction of DNA such as, for example, as described in Christiansen et al., Curr. Genet. 29:100 102 (1995); Durand et al., Curr. Genet. 31:158 161 (1997); and Barcellos et al., Can. J. Microbiol. 44:1137 1141 (1998) or "magneto-biolistic" transfection of cells such as, for example, described in U.S. Pat. Nos. 5,516,670 and 5,753,477. In one embodiment, the transformation procedure used in the methods and systems provided herein is one amendable to being high-throughput and/or automated as provided herein such as, for example, PEG mediated transformation.

Transformation of the protoplasts generated using the methods described herein can be facilitated through the use of any transformation reagent known in the art. Suitable transformation reagents can be selected from Polyethylene Glycol (PEG), FUGENE® HD (from Roche), Lipofectamine® or OLIGOFECTAMINE® (from Invitrogen), TRANSPASS® D1 (from New England Biolabs), LYPOVEC® or LIPOGEN® (from Invivogen). In one embodiment, PEG is the most preferred transformation/transfection reagent. PEG is available at different molecular weights and can be used at different concentrations. Preferably, PEG 4000 is used between 10% and 60%, more preferably between 20% and 50%, most preferably at 40%.

In one embodiment, the PEG is added to the protoplasts prior to storage as described herein.

Looping Out of Selected Sequences

In some embodiments, the present disclosure teaches methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. In some embodiments, the present disclosure teaches looping out selection markers from positive transformants. Looping out deletion techniques are known in the art, and are described in (Tear et al. 2014 "Excision of Unstable Artificial Gene-Specific inverted Repeats Mediates Scar-Free Gene Deletions in *Escherichia coli*." Appl. Biochem. Biotech. 175:1858-1867). The looping out methods used in the methods provided herein can be performed using single-crossover homologous recombination or double-crossover homologous recombination. In one embodiment, looping out of selected regions as described herein can entail using single-crossover homologous recombination as described herein.

Figure 3:
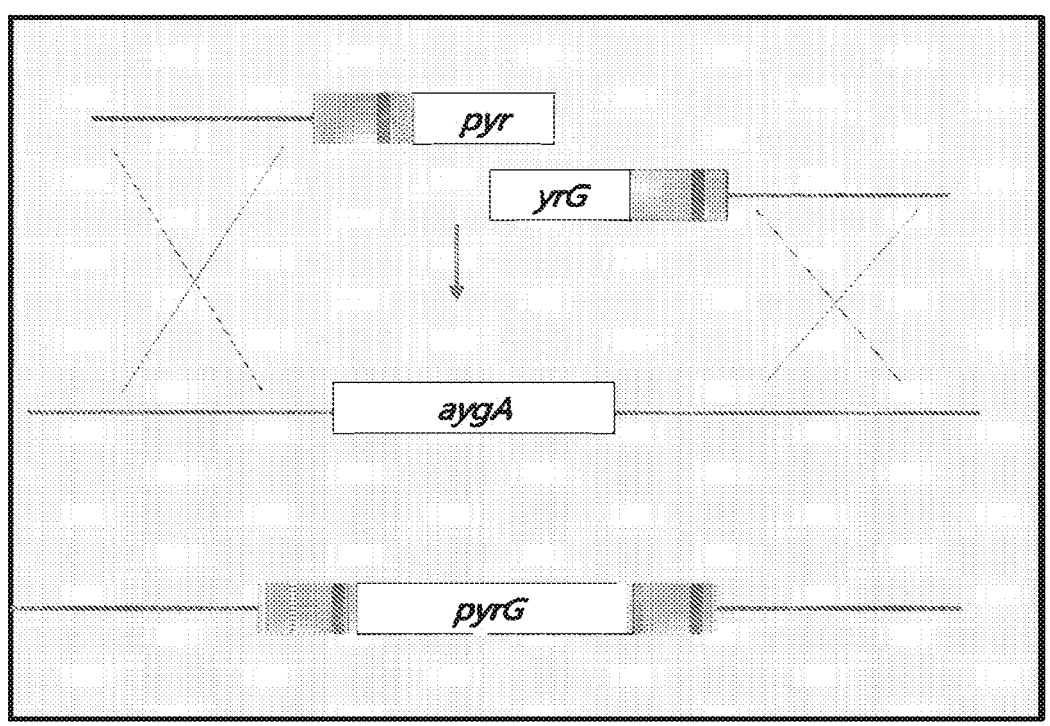
FIG. 3 is a representation of how SNPs are targeted to a specific locus in filamentous fungi using a split marker system. The marker gene (pyrG in this example) is amplified into two components that are unable to complement the mutation in the target strain without homologous recombination, which restores gene function. Flanking these fragments is a direct repeat of DNA that each of which contains the SNPs to be targeted to the locus. Non-repeat DNA sequence on each construct facilitates proper integration through native homologous recombination pathways. These constructs are placed into the target strains during step 2 of FIG. 20B.
Figure 36:
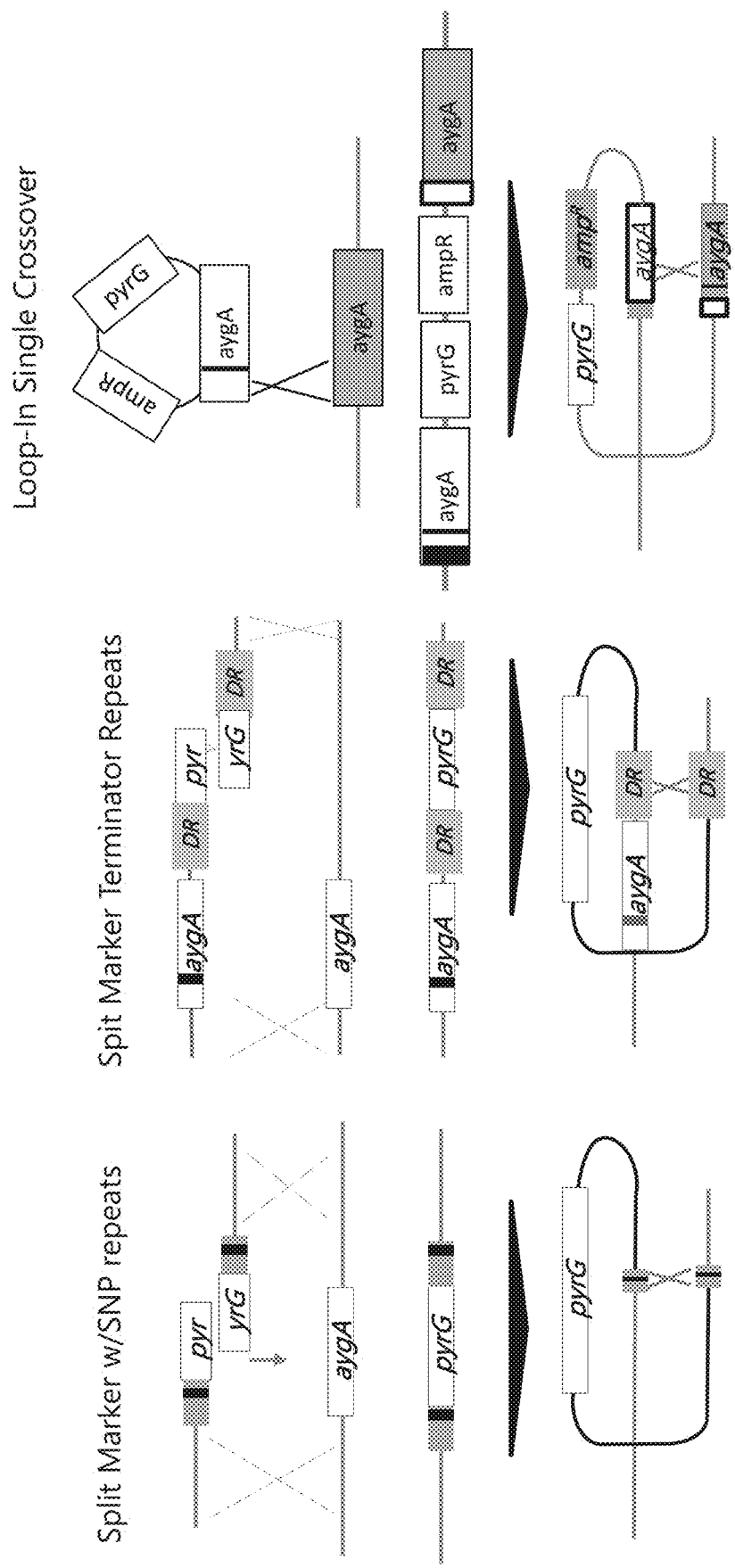
FIG. 36 depicts three approaches (Spilt marker with SNP repeats; Spilt Marker Terminator Repeats; Loop-in Single Crossover) for performing SNP integration. The split marker with SNP repeats can be used to generate an insertional null as described in the present disclosure. The split marker terminator repeats has the advantage that it may facilitate the desired phenotype from a primary integrant. In contrast, the loop-in single crossover requires plasmid cloning cloning and preparation, ectopic integration may be high and Concatemers may occur.

First, loop out constructs are inserted into selected target regions within the genome of the host organism (e.g., via homologous recombination, CRISPR, or other gene editing technique). In one embodiment, double-crossover homologous recombination is used between a construct or constructs and the host cell genome in order to integrate the construct or constructs such as depicted in FIG. 3. The inserted construct or constructs can be designed with a sequence which is a direct repeat of an existing or introduced nearby host sequence, such that the direct repeats flank the region of DNA slated for looping-out and deletion. Once inserted, cells containing the loop out construct or constructs can be counter selected for deletion of the selection region (e.g., see FIG. 4; lack of resistance to the selection gene). Further illustrations of the loop-in and loop-out process are depicted in FIGS. 36-37.

Persons having skill in the art will recognize that the description of the loopout procedure represents but one illustrative method for deleting unwanted regions from a genome. Indeed the methods of the present disclosure are compatible with any method for genome deletions, including but not limited to gene editing via CRISPR, TALENS, FOK, or other endonucleases. Persons skilled in the art will also recognize the ability to replace unwanted regions of the genome via homologous recombination techniques Constructs for Transformation In one embodiment, the methods and systems provided herein entail the transformation or transfection of filamentous fungal cells or protoplasts derived therefrom with at least one nucleic acid. The transformation or transfection can be using of the methods and reagents described herein. The generation of the protoplasts can be performed using any of the methods provided herein. The protoplast generation and/or transformation can be high-throughput and/or automated as provided herein. The nucleic acid can be DNA, RNA or cDNA. The nucleic acid can be a polynucleotide. The nucleic acid or polynucleotide for use in transforming a filamentous fungal cell or protoplast derived therefrom using the methods and systems provided herein can be an endogenous gene or a heterologous gene relative to the variant strain and/or the parental strain. The endogenous gene or heterologous gene can encode a product or protein of interest as described herein. As described herein, the protein of interest can refer to a polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be expressed intracellularly or as a secreted protein. The endogenous gene or heterologous gene can comprise a mutation and/or be under the control of or operably linked to one or more genetic control or regulatory elements. The mutation can be any mutation provided herein such as, for example, an insertion, deletion, substitution and/or single nucleotide polymorphism. The one or more genetic control or regulatory elements can be a promoter sequence and/or a terminator sequence. The endogenous gene or heterologous gene can be present on one expression construct or split across multiple expression constructs such as shown in FIGS. 36-38. When split across multiple expression constructs, each portion of the endogenous gene or heterologous gene can comprise a mutation and/or be under the control of or operably linked to one or more genetic control or regulatory elements. In one embodiment, an endogenous gene or heterologous gene is bipartite, wherein said endogenous gene or heterologous gene is split into two portions such that each of said two portions is present on a separate construct. In one embodiment, the gene is FungiSNP_9 (SEQ ID NO: 11), FungiSNP_12 (SEQ ID NO: 12), FungiSNP_18 (SEQ ID NO: 13) or FungiSNP_40 (SEQ ID NO: 14). In another embodiment, the gene is FungiSNP_9 (SEQ ID NO: 11), FungiSNP_12 (SEQ ID NO: 12), FungiSNP_18 (SEQ ID NO: 13) or FungiSNP_40 (SEQ ID NO: 14) fused to or operably linked to any of the promoters from Table 1. In one embodiment, the gene is FungiSNP_18 (SEQ ID NO: 13). In another embodiment, the gene is FungiSNP_18 (SEQ ID NO: 13) fused to or operably linked to the man8p or amy8p promoter from Table 1.

The promoter sequence and/or terminator sequence can be endogenous or heterologous relative to the variant strain and/or the parental strain. Promoter sequences can be operably linked to the 5' termini of the sequences to be expressed. A variety of known fungal promoters are likely to be functional in the host strains of the disclosure such as, for example, the promoter sequences of C1 endoglucanases, the 55 kDa cellobiohydrolase (CBH1), glyceraldehyde-3-phosphate dehydrogenase A, *C. lucknowense* GARG 27K and the 30 kDa xylanase (Xy1F) promoters from *Chrysosporium*, as well as the *Aspergillus* promoters described in, e.g. U.S. Pat. Nos. 4,935,349; 5,198,345; 5,252,726; 5,705,358; and 5,965,384; and PCT application WO 93/07277. In one embodiment, the promoters for use in the methods and systems provided herein are inducible promoters. The inducible promoters can be any promoter whose transcriptional activity is regulated by the presence or absence of a chemical such as for example, alcohol, tetracycline, steroids, metal or other compounds known in the art. The inducible promoters can be any promoter whose transcriptional activity is regulated by the presence or absence of light or low or high temperatures. In one embodiment, the inducible promoter is catabolite repressed by glucose (see FIG. 37 for example) such as, for example, the promoter for the *A. niger* amylase B gene. In one embodiment, the inducible promoters are selected from filamentous fungal genes such as the srpB gene, the amyB gene, the manB gene or the mbfA gene. In one embodiment, the inducible promoter is selected form the promoters listed in Table 1.

Terminator sequences can be operably linked to the 3' termini of the sequences to be expressed. A variety of known fungal terminators are likely to be functional in the host strains of the disclosure. Examples are the *A. nidulans* trpC terminator, *A. niger* alpha-glucosidase terminator, *A. niger* glucoamylase terminator, *Mucor miehei* carboxyl protease terminator (see U.S. Pat. No. 5,578,463), *Chrysosporium* terminator sequences, e.g. the EG6 terminator, and the *Trichoderma reesei* cellobiohydrolase terminator. In one embodiment, the terminator sequences are direct repeats (DRs). In one embodiment, a transcriptional terminator sequence of the present disclosure can be selected from a terminator sequence listed in Table 1.1 or an orthologue of a termination sequence provided in Table 1.1. For example, if the host cell is an *Aspergillus*, the termination sequence can be an orthologue of a non-*Aspergillus* termination sequence selected from Table 1.1.

In one embodiment, a protoplast generated from a filamentous fungal cell is co-transformed with two or more nucleic acids or polynucleotides. Further to this embodiment, at least one of the two or more polynucleotides is an endogenous gene or a heterologous gene relative to the filamentous fungal strain from which the protoplast was generated and at least one of the two or more polynucleotides is a gene for a selectable marker. The selectable marker gene can be any selectable marker as provided herein. As described herein, each of the two or more nucleic acids or polynucleotides can be split into separate portions such that each separate portion is present on a separate construct (see FIGS. 36-38).

In one embodiment, each nucleic acid or polynucleotide for use in transforming or transfecting a filamentous fungal cell or protoplast derived therefrom comprises sequence homologous to DNA sequence present in a pre-determined target locus of the genome of the filamentous fungal cell or protoplast derived therefrom that is to be transformed on either a 5', a 3' or both a 5' and a 3' end of the nucleic acid or polynucleotide. The nucleic acid or polynucleotide can be an endogenous gene or heterologous gene relative to the filamentous fungal cell used for transformation or a selectable marker gene such that sequence homologous to a pre-determined locus in the filamentous fungal host cell genome flanks the endogenous, heterologous, or selectable marker gene. In one embodiment, each nucleic acid or polynucleotide is cloned into a cloning vector using any method known in the art such as, for example, pBLUE-SCRIPT® (Stratagene). Suitable cloning vectors can be the ones that are able to integrate at the pre-determined target locus in the chromosomes of the filamentous fungal host cell used. Preferred integrative cloning vectors can comprise a DNA fragment, which is homologous to the DNA sequence to be deleted or replaced for targeting the integration of the cloning vector to this pre-determined locus. In order to promote targeted integration, the cloning vector can be linearized prior to transformation of the host cell or protoplasts derived therefrom. Preferably, linearization is performed such that at least one but preferably either end of the cloning vector is flanked by sequences homologous to the DNA sequence to be deleted or replaced. In some cases, short homologous stretches of DNA may be added for example via PCR on both sides of the nucleic acid or polynucleotide to be integrated. The length of the homologous sequences flanking the nucleic acid or polynucleotide sequence to be integrated is preferably less than 2 kb, even preferably less, than 1 kb, even more preferably less than 0.5 kb, even more preferably less than 0.2 kb, even more preferably less than 0.1 kb, even more preferably less than 50 bp and most preferably less than 30 bp. The length of the homologous sequences flanking the nucleic acid or polynucleotide sequence to be integrated can vary from about 30 bp to about 1000 bp, from about 30 bp to about 700 bp, from about 30 bp to about 500 bp, from about 30 bp to about 300 bp, from about 30 bp to about 200 bp, and from about 30 bp to about 100 bp. The nucleic acids or polynucleotides for use in transforming filamentous fungal cells or protoplasts derived therefrom can be present as expression cassettes. In one embodiment, the cloning vector is pUC19. Further to this embodiment, a cloning vector containing a marker sequence as provided herein can be associated with targeting sequence by building the construct through using a Gibson assembly as known in the art. Alternatively, the targeting sequence can be added by fusion PCR. Targeting sequence for co-transformation that is not linked to a marker may be amplified from genomic DNA.

In theory, all loci in the filamentous fungi genome could be chosen for targeted integration of the expression cassettes comprising nucleic acids or polynucleotides provided herein. Preferably, the locus wherein targeting will take place is such that when the wild type gene present at this locus has been replaced by the gene comprised in the expression cassette, the obtained mutant will display a change detectable by a given assay such as, for example a selection/counterselection scheme as described herein. In one embodiment, the protoplasts generated from filamentous fungal cells as described herein are co-transformed with a first construct or expression cassette and a second construct or expression cassette such that the first construct or expression cassette is designed to integrate into a first locus of the protoplast genome, while the second construct or expression cassette is designed to integrate into a second locus of the protoplast genome. To facilitate integration into the first locus and second locus, the first construct or expression cassette is flanked by sequence homologous to the first locus, while the second construct or expression cassette is flanked by sequence homologous to the second locus. In one embodiment, the first construct or expression cassette comprises sequence for an endogenous gene, while the second construct comprises sequence for a selectable marker gene. Further to this embodiment, the second locus contains sequence for an additional selectable marker gene present in the protoplast genome used in the methods and systems provided herein, while the first locus contains sequence for the endogenous target gene present in the protoplast genome used in the methods and systems provided herein. In a separate embodiment, the first construct or expression cassette comprises sequence for an endogenous gene or a heterologous gene, while the second construct comprises sequence for a first selectable marker gene. Further to this separate embodiment, the second locus contains sequence for a second selectable marker gene that is present in the protoplast genome used in the methods and systems provided herein, while the first locus contains sequence for a third selectable marker gene that is present in the protoplast genome used in the methods and systems provided herein. In each of the above embodiments, the endogenous gene and/or heterologous gene can comprise a mutation (e.g., SNP) and/or a genetic control or regulatory element as provided herein.

Purification of Homokaryotic Protoplasts

As will be appreciated by those skilled in the art, protoplasts derived from filamentous fungal can often contain more than one nucleus such that subsequent transformation with a construct (e.g., insert DNA fragment) as provided herein can produce protoplasts that are heterokaryotic such that the construct (e.g., insert DNA fragment) is incorporated into only a subset of the multiple nuclei present in the protoplast. In order to reduce the number or percentage of heterokaryotic protoplasts following transformation, strategies can be employed to increase the percentage of mononuclear protoplasts in a population of protoplasts derived from filamentous fungal host cells prior to transformation such as, for example, using the method described in Roncero et al., 1984, Mutat. Res. 125:195, the contents of which are herein incorporated by reference in its entirety.

In another embodiment, provided herein is a method for isolating clonal populations derived from individual spores. In some cases, the individual fungal spores are sporulated from protoplasts derived from fungal strains following genetic perturbation of said protoplasts. The methods for isolating the clonal populations derived from the individual spores can facilitates or aid in the isolation of homokaryotic fungal strains following genetic perturbation using any of the methods provided herein. Further to this embodiment, a plurality of spores (e.g., spores ultimately derived from filamentous fungal cells or strains) can be resuspended to generate a liquid suspension and individual spores in discrete volumes of the liquid suspension can be placed or distributed into the wells or reaction areas of a substrate such as, for example, a microtiter plate. The microtiter plate can be a 96 well, 384 well or 1536 well plate.

In order to achieve a high statistical probability that each reaction area or well in the microtiter plate contains either a single individual fungal spore or no fungal spore, the resuspended plurality of spores can be diluted. In one embodiment, the dilution is such that the suspension of spores is at a concentration whereby the probability that a dispensed or discrete volume of the suspension contains either one or no spore follows a Poisson Distribution. Further to this embodiment, greater than 90% of the wells will contain no spores and thus be empty. Of the remaining wells, greater than 90%, 91%, 92%, 93%, 94%, 95%, 96%, 97%, 98%, 99% or 99.5% will have a single cell, and less than 2%, 1%, 0.5% or 0% will have 2 or more cells. Dispensing of the suspension of spores can be accomplished using any of the liquid handling devices provided herein (see Table 3) and/or known in the art.

In another embodiment, following resuspension and dilution of the plurality of spores, discrete volumes of the suspension are screened for the presence or absence of single individual fungal spores in the discrete volume. Further to this embodiment, if a discrete volume of the suspension contains only a single individual fungal spore, said discrete volume is distributed, placed or dispensed into a well or reaction area. The screening can be performed using any of the single cell/spore dispensing devices provided herein (see Table 3) and/or known in the art. In one embodiment, the device optically identifies single cells or spores. The device can be a FACS device, a CellenONE device, a Cytena Single Cell Printer or a Berkeley Lights Beacon device. Prior to resuspension and dilution, the plurality of individual fungal spores can be picked or isolated using any of the devices provided herein (see Table 3) and/or known in the art. The resuspension and dilution of the spores can be accomplished using any of the devices provided herein (see Table 3) and/or known in the art.

Following the screening for the presence or absence of single individual fungal spores in the discrete volume, the methods described hereinfor distributing or dispensing individual spores to the wells or reaction areas of a substrate comprising wells or reaction areas can result in at least 70%, 75%, 80%, 85%, 90%, 95%, 99 or 99.5% of the wells or reaction areas in the substrate containing a single individual viable spore from a plurality of spores. Using the methods described herein for distributing individual spores to the wells or reaction areas of a substrate comprising wells or reaction areas can result in greater than 70%, 75%, 80%, 85%, 90%, 95%, 99 or 99.5% of the wells or reaction areas in the substrate containing a single individual viable spore from a plurality of spores. Using the methods described herein for distributing individual spores to the wells or reaction areas of a substrate comprising wells or reaction areas can result in substantially all of the wells or reaction areas in the substrate containing a single individual viable spore from a plurality of spores. Using the methods described herein for distributing individual spores to the wells or reaction areas of a substrate comprising wells or reaction areas can result in all or 100% of the wells or reaction areas in the substrate containing a single individual viable spore from a plurality of spores. Using the methods described herein for distributing individual spores to the wells or reaction areas of a substrate comprising wells or reaction areas can result in a statistical probability that greater than or at least 70%, 75%, 80%, 85%, 90%, 95%, 99 or 99.5% of the wells in the microtiter plate contain a single individual viable spore. Using the methods described herein for distributing individual spores to the wells or reaction areas of a substrate comprising wells or reaction areas can result in a statistical probability that all or substantially all of the wells in the microtiter plate contain a single individual viable spore. The substrate can be a microtiter plate. The microtiter plate can be a 96 well, 384 well or 1536 well plate.

The plurality of individual fungal spores can be derived from a filamentous fungal strain. The filamentous fungal strain can be selected from Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora (e.g., Myceliophthora thermophila), Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella species or teleomorphs, or anamorphs, and synonyms or taxonomic equivalents thereof. In one embodiment, the filamentous fungal strain is Aspergillus niger. In another embodiment, the filamentous fungal strain possess a non-mycelium forming phenotype. In yet another embodiment, the filamentous fungal strain possesses a non-functional non-homologous end joining (NHEJ) pathway. The NHEJ pathway can be made non-functional by exposing the cell to an antibody, a chemical inhibitor, a protein inhibitor, a physical inhibitor, a peptide inhibitor, or an anti-sense or RNAi molecule directed against a component of the NHEJ pathway.

The liquid used for resuspending the plurality of individual spores can be culture media or a buffer. Further, the wells or reaction areas can comprise selective media that can serve to select spores containing a specific genetic perturbation such that culturing the distributed individual fungal spores in the reaction areas or wells comprising media selective for the genetic variation facilitates identification and selection of colonies derived from an individual spore that contained the desired genetic perturbation.

Aside from or in addition to employing strategies to increase the number or percentage of mononuclear protoplasts prior to transformation, strategies can be employed to drive protoplasts (and the colonies derived therefrom following regeneration of said protoplasts) to being homokaryotic post-transformation regardless of whether they are mono- or multi-nucleate. As provided herein, increasing the number or percentage of protoplasts (and the colonies derived therefrom) that are homokaryotic for a desired or target gene of interest can entail subjecting the colonies derived from the transformed protoplast or population of transformed protoplasts to selection and/or counter-selection based on the presence and/or absence of one or more selectable markers. The one or more selectable markers can be any selectable marker or combination of selectable markers as provided herein and the selection and/or counter-selection scheme can any such scheme as provided herein.

Identification of Homokaryotic Transformants

Homokaryotic transformants produced by the methods provided herein can be identified through the use of phenotypic screening, sequence-based screening or a combination thereof. In other words, phenotypic screening, sequence-based screening or a combination thereof can be used to detect the presence or absence of a parental genotype in a colony derived from a protoplast following transformation of said protoplast with a construct (e.g., insert DNA fragment). Identification or detection of homokaryotic transformants can occur before and/or following subjecting said transformants to a selection and/or counter-selection scheme as provided herein in keeping with the introduction and/or loss of one or more selectable marker genes. Phenotypic screening can be used to identify a transformant with a discernable phenotype (change in growth and/or colorimetric change), while sequence-based screening can be used to identify transformants with or without a discernable phenotype following transformation and integration of a construct or constructs as provided herein.

Sequence-Based Screening

As described herein, sequence-based screening can be used to determine the presence or absence of a desired or target construct in a transformant. In this manner, sequence-based sequencing can be used to assess whether or not integration of a desired gene or construct has occurred in a specific transformant. Sequence-based screening can be used to determine the percentage of nuclei in a multinucleate cell or population of multinucleate cells that contain a desired gene, mutation or construct. Further, sequence-based screening can be used to determine the percentage of a population of transformants that has experienced a desired target integration. The construct can be any construct or a plurality of constructs as described herein. In some cases, the results of sequence-based screening can be used to select purification schemes (e.g., homokaryotic purification) if the percentage or ratio of nuclei comprising a desired gene, mutation or construct vs. nuclei lacking said desired gene, mutation or construct is below a certain threshold.

In general, sequence-based screening can entail isolating transformants that may contain a desired mutation or construct. Each transformant may contain one or a plurality of nuclei such that the one or each of the plurality of the nuclei contain fragments of nucleic acid (e.g., one or more constructs or genes comprising a mutation) introduced during transformation. The transformation can be targeted transformations of protoplasts with specific fragments of DNA (e.g., one or more constructs or genes comprising a mutation) as provided herein.

In some cases, following isolation, sequence-based screening entails propagating the transformants that contain a mixture of nuclei with both the target gene (introduced construct) and the wild-type or parental gene on media that impacts the purity of the target gene (i.e., selective media) or may be completely non-selective for any particular phenotype or trait, thereby generating colonies derived from the transformants. In one embodiment, each isolated transformant or a portion of a colony derived therefrom is transferred to or placed in a well of a microtiter plate such as, for example, an Omnitray (see FIG. 30 and seed plate in FIG. 31) comprising agar wherein the transformant or a portion of a colony derived therefrom sporulate. The microtiter plate can be a 96 well, 384 well or 1536 well microtiter plate.

Figure 30:
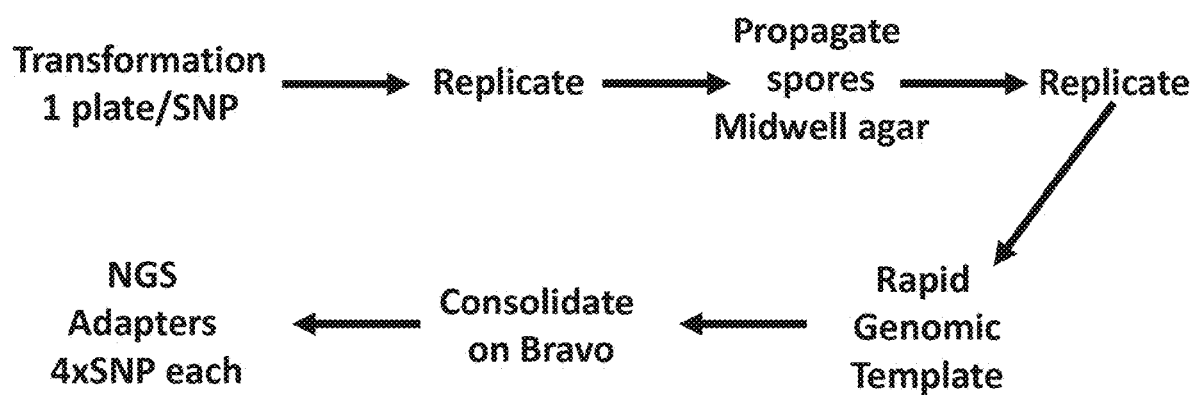
FIG. 30 depicts steps to rapidly isolate genomic DNA and prepare amplicons that contain identifying sequences that associate specific amplicons with the well that they came from which contains the organism that was isolated following genetic alteration. The method allows for isolation and screening of 96 transformants/transformations. Transformants are plated to Omnitrays, allowed to sporulate and a sterile 96 pin replicator used to rapidly isolate.
Figure 31:
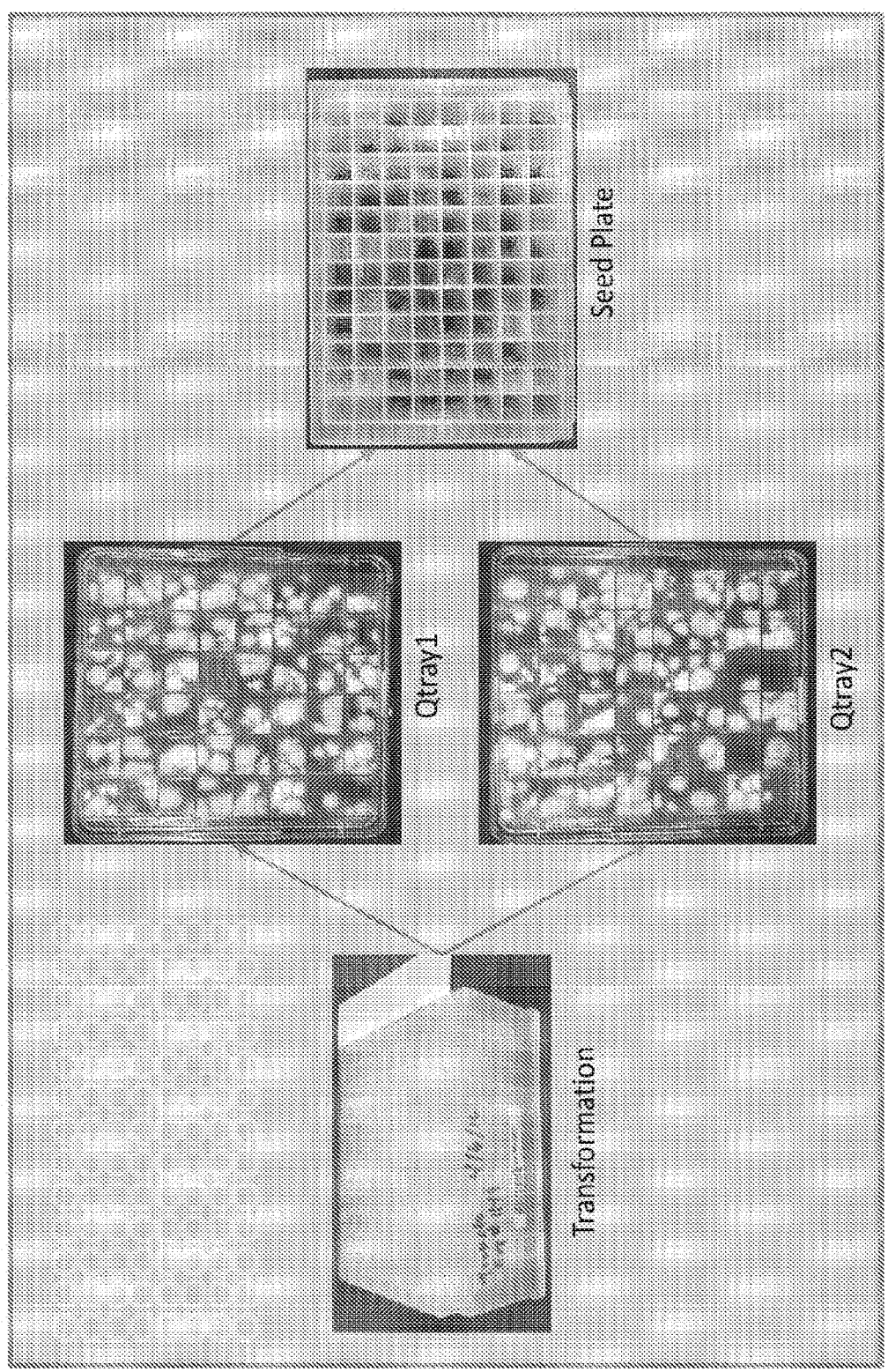
FIG. 31 depicts picking of transformants and their subsequent transfer to and sporulation in 96-well microtiter seed plates. The colonies are picked with toothpicks (K-picks). The seed plate contains 400 µl agar media. Spore suspensions made from the seed plate are used to make Spore plate, and stamping/screening are done from Spore plate.
Figure 32:
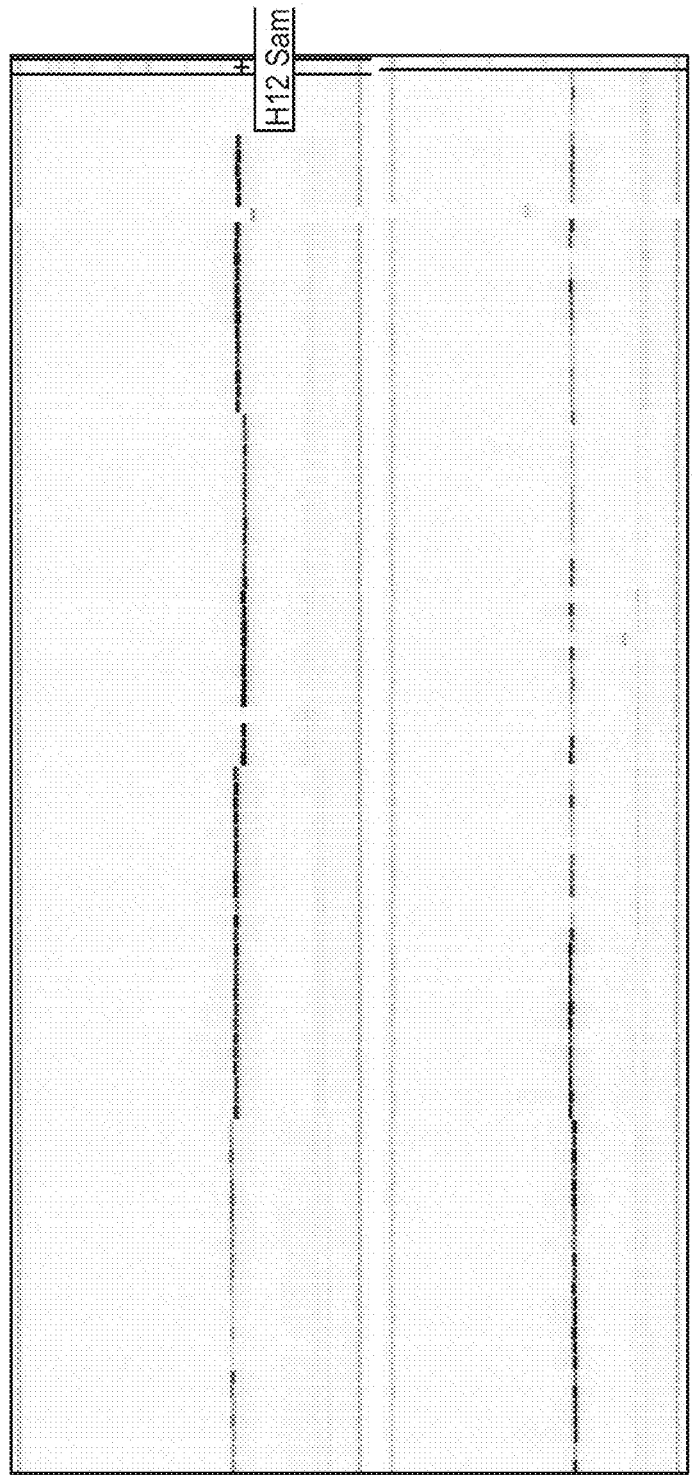
FIG. 32 depicts a fragment analyzer run following amplification of nucleic acid fragments following extraction of DNA from fungal transformants using a boil prep method as provided herein. Preparing genomic template from multiple samples in fungi can be challenging since the cell wall makes grinding often necessary, obtaining DNA from spores can be difficult and spore PCR does not work well with most fungi. As shown, short length PCRs for NGS was performed successfully. The boil prep method showed that PrepMan can be used as an effective method for genomic DNA purification, and can be automated.

Following isolation alone or in combination with propagation, nucleic acid (e.g., DNA) can be extracted from the transformant or colonies or spores derived therefrom. As shown in FIG. 30, nucleic acid isolation can be from spores derived from transformants and can be performed in a microtiter plate format, and can utilize automated liquid handling. Extraction of the nucleic acid can be performed using any known nucleic acid extraction method known in the art and/or commercially available kit such as for example Prepman™ (ThermoFischer Scientific). In one embodiment, nucleic acid extracted from spores derived from transformants is performed using a boil prep method that allows for amplification of DNA (see FIG. 32). The boil prep method can include the inoculation of spores into a small amount of growth media. In one embodiment, the spores are separated into 96 wells in a plate suitable for PCR wherein each well comprises the small amount of growth media. The spores can be allowed to grow for between 10 and 16 hours, which can help the spores discard pigments that may inhibit PCR. Additionally, the growth can also facilitate several rounds of nuclear division which can serve to increase the genomic DNA content of each well. Subsequently, the overnight "mini cultures" can then be supplemented with a buffer that assists in cell lysis as well as stabilizes the DNA that will be released during lysis. One example of a suitable buffer can be PrepMan Ultra (Thermo Fisher). Other examples of suitable buffers can include Tris buffered solutions that contain a small amount of ionic detergent. The min-culture-buffer mixtures can then be heated in a thermocycler to 99 degrees C. for any of a range of incubation times of between 15 minutes and 1 hour.

Following nucleic acid extraction, sequence-based screening can be performed to assess the percentage or ratio of target or mutant nuclei comprising an introduced target gene or construct to parent nuclei (i.e., non-transformed nuclei). The sequence-based screening can be any method known in the art that can be used to determine or detect the sequence of a nucleic acid. The method used to perform sequence-based screening can be selected from nucleic acid sequencing methods or hybridization based assays oe methods. The nucleic acid sequencing assay or technique utilized by the methods provided herein can be a next generation sequencing (NGS) system or assay. The hybridization based assay for detecting a particular nucleic acid sequence can entail the use of microarrays or the nCounter system (Nanostring). Prior to conducting sequence-based screening, the extracted nucleic acid can be amplified using PCR with primer pair(s) directed to the target gene.

Figure 33:
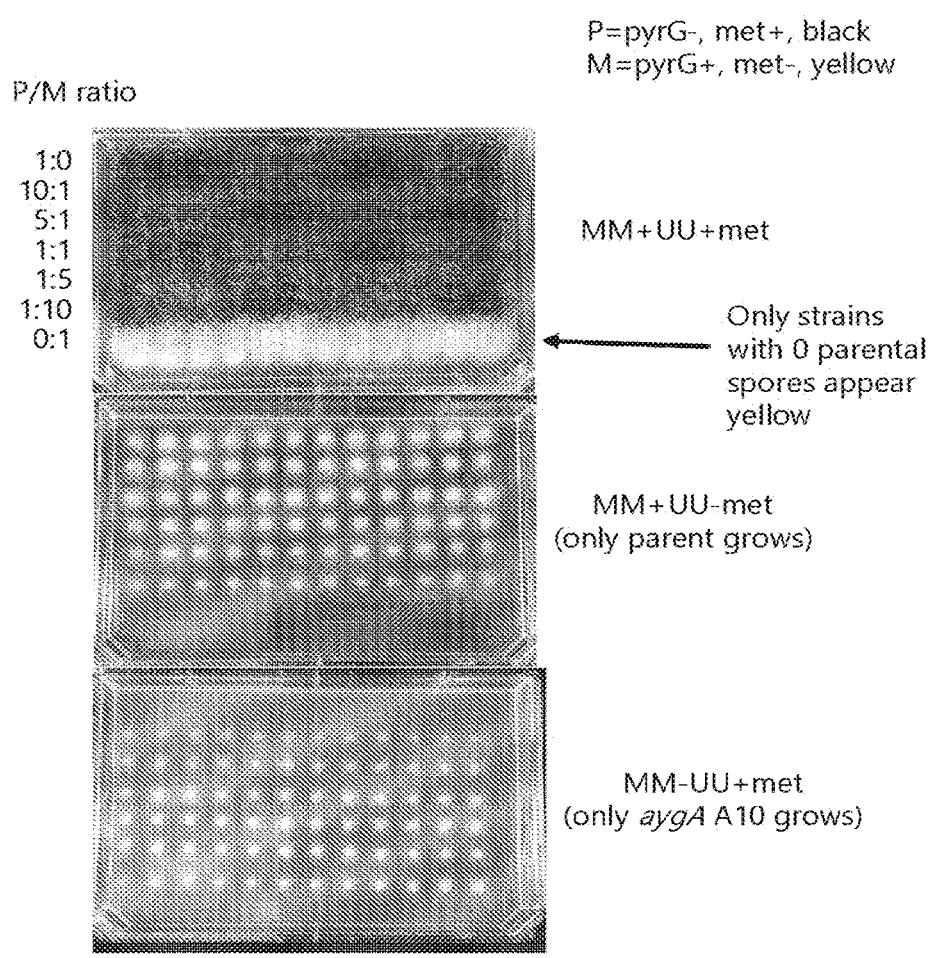
FIG. 33 depicts colorimetric differences in strains containing a mixture of spores of difference genetic background (i.e., mutant (m) vs. parental (p)) at different ratios. As shown, only strains with no parental spores (0:1 p/m ratio) appear yellow in the tested selection scheme. There two ways to determine if a transformant is a heterokaryon: 1.) phenotype and 2.) Sequencing. In this figure, the transformants were scored by yellow phenotype and NGS. Testing the sensitivity of these two methods is important for adapting transformant scoring to a workflow. If 1/10 of the nucleic are black, the colony may appear black and thus NGS can be used before and after counterselection.

In embodiments utilizing nucleic acid sequencing methologies, the primer pairs utilized in the PCR can comprise adapter sequences that can be subsequently used in a secondary amplification using coded indexing primers. Amplicons generated by the secondary amplification reaction can then be sequenced using multiplex sequencing with sequencing primers directed to the coded indexed primers. The sequencing can be performed using any type of sequencing known in the art. In one embodiment, the sequencing is next generation sequencing (NGS). The NGS can be any known NGS method known in the art such as, for example, Illumina NGS. FIG. 30 depicts an embodiment of a workflow whereby transformation, sporulation, nucleic acid extraction and NGS based sequence-based screening is performed in an automated or semi-automated manner. As shown in FIGS. 25, 26, 34 and 35, data from the multiplex sequencing reactions can then be used to determine the presence or absence of the target nuclei. In some cases, the data from the multiplex sequencing reactions can also be used to determine the ratio of parental nuclei to mutant nuclei for a transformant within the target well (see FIGS. 34 and 35). Further to this embodiment, a standard curve can be generated in order to quantify the percentage or ratio of parent to mutant nuclei. The standard curve can be generated by amplifying and sequencing nucleic acid isolated from strains containing known ratios of a parent to mutant nuclei such as shown in FIG. 33 and subsequently using the ratio of parent to mutant amplicons that appear in the known ratio to determine an approximation of the purity of a test sample. The strains used to generate the standard curve can be processed (e.g., isolated, propagated and extracted) in the same set of plates as the test sample.

In one embodiment, sequence-based sequencing is used following selection and/or counter-selection in order to assess or determine the homokaryotic status of each transformant. Sequence-based sequencing post selection and/or counter-selection can use multiplex sequencing as described herein and can be automated or semi-automated. Sequence-based sequencing post selection and/or counter-selection can also utilize generation of a standard curve as described herein as means of determining the presence and/or amount (e.g., ratio) a transformant is heterokaryotic.

Use of Sequence-Based Screening to Determine Purity of Transformants

Figure 34:
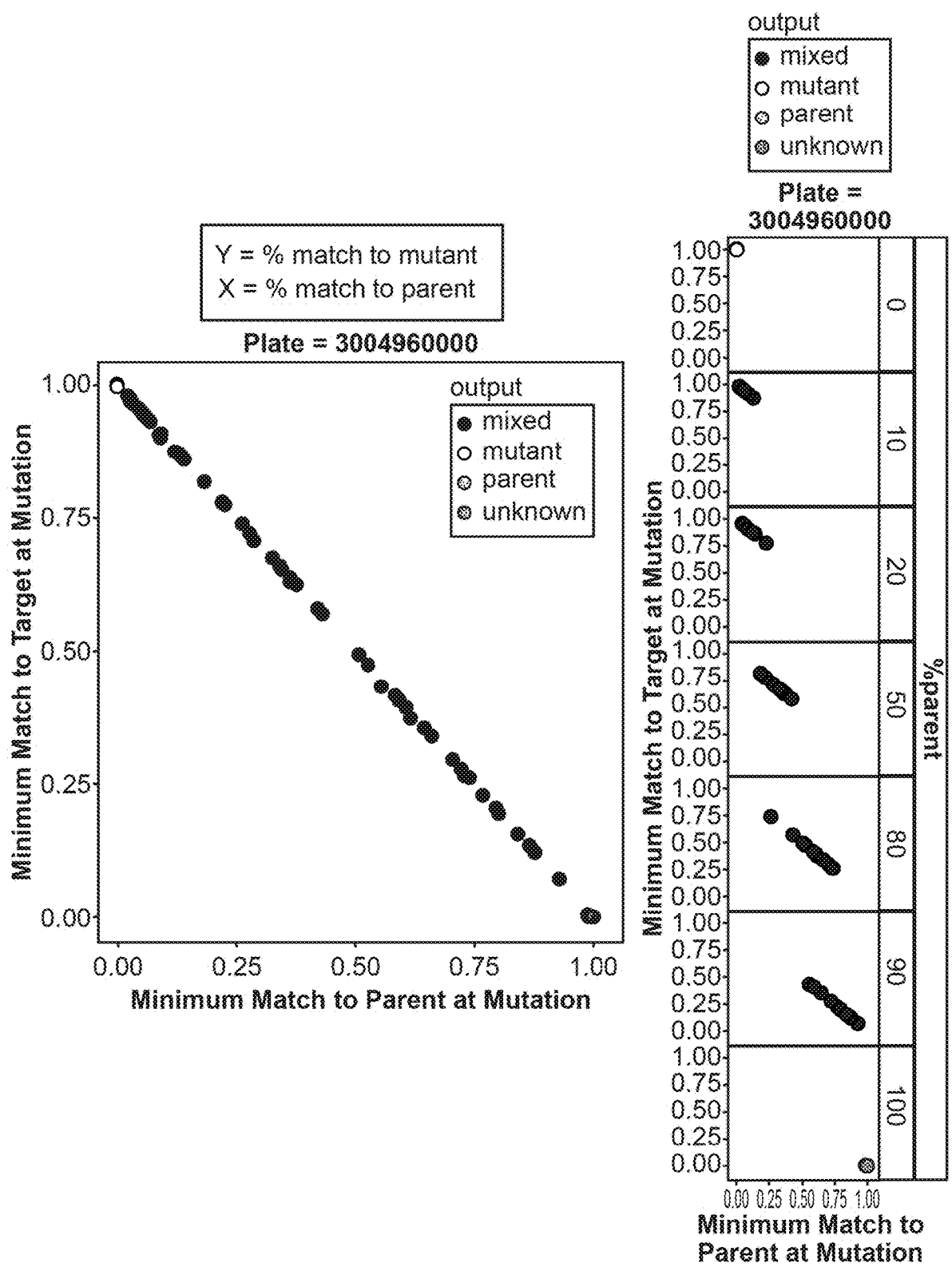
FIG. 34 depicts a plot of the amplicon sequences from the mixed spore plate shown in FIG. 33 and the plate at the top of FIG. 35. The percentage of amplicons that contained the targeted mutation is on the Y axis and the percentage that still contain the parent is on the X axis. The large plot contains data from the entire plate demonstrating a complete range of mixed spores within the plate. The graphs on the right are of the individual rows from the plate. These graphs of the rows define the range of amplicon distribution that is observed in NGS when a defined mixture of nuclei are tested. This analyses can then be used to predict the distribution of SNPs within a data set from a SNPSWP strain build. This prediction can be used to QC steps in a strain build process.
Figure 35:
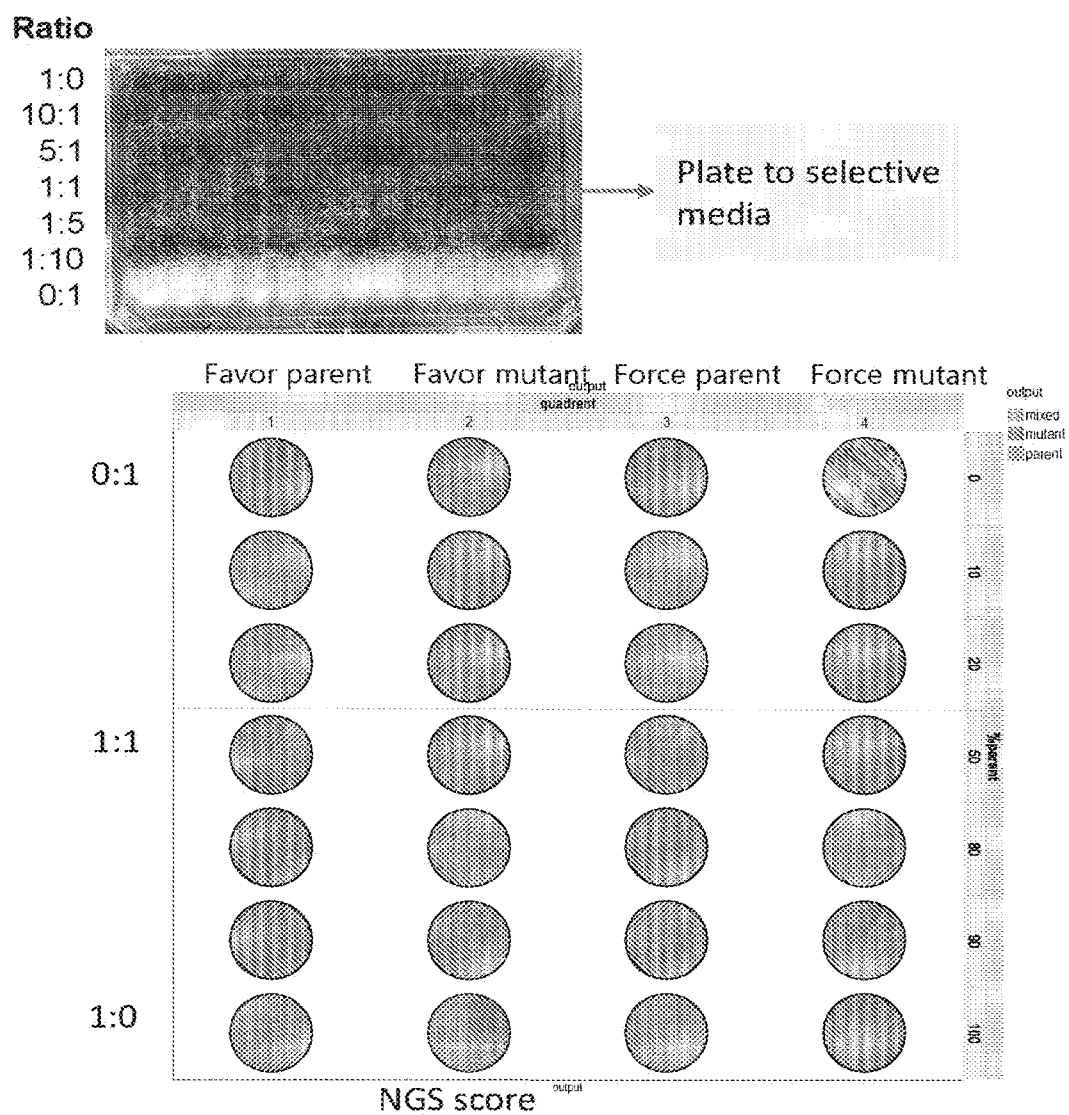
FIG. 35 depicts a test of the ability of NGS to detect SNPS in a mixture of spores from filamentous fungi with different genetic backgrounds that give rise to strains with either a pyrG-background (black) or met3-background (light colored). The met3-strains require growth media with methionine and are resistant to selenite. The plate containing spores at the top demonstrates that phenotypes can be masked in mixed cultures and can be difficult to score visually. The row that contains 10 fold more mutant (yellow) nuclei still appears black. NGS can detect the mutation where visual phenotype cannot. The pie charts are an example of how the population can shift under different growth conditions. In particular, NGS showed that selective media can force mixed populations of nuclei to homokaryon. This can be utilized for strain purification but it also demonstrates that growth and propagation during the process of strain building must be monitored at the individual SNP level.

As discussed herein, protoplasts generated from coenocytic host cells (e.g., filamentous fungal host cells) in the methods, systems and workflows provided herein can be multinucleate. Subsequently, protoplasts transformed with one or more constructs such as those provided herein can contain only a portion or percentage of their multiple nuclei with a particular construct or constructs integrated into their genome. Depending on the nature of the transformed constructs, colonies derived from the transformed protoplast may not produce a discernable phenotype due to the presence of the mixed population of nuclei present in the colony. Accordingly, the use of sequence-based screening can be essential for determining the percentage of the nuclei in a mixed population of nuclei that contain a desired construct or constructs vs. those that do not contain a desired construct or constructs. FIGS. 33-35 show the utility of NGS based screening for detecting parental vs. mutant nuclei in colonies containing cells with a mixed population of nuclei. In one embodiment, NGS based screening is used to identify transformants or strains derived therefrom that contain a desired percentage of nuclei with an introduced construct or constructs. The desired percentage can be a threshold percentage, whereby transformants or strains derived therefrom at or above said threshold percentage produce a desired product of interest or level thereof. The product of interest can be selected from a product listed in Table 2. The desired percentage can be 50%, 55%, 60%, 65%, 70%, 75%, 80%, 85%, 90%, 95%, 99% or 100%. The percentage can be determined by utilizing a standard curve as described herein.

Phenotypic Screening

As described herein, phenotypic screening can be used in combination with sequence-based screening or transformants. In some cases, the results of sequence-based screening can be used to determine purification schemes in order to ensure the isolation of homokaryotic transformants. Further, sequence-based screening can be utilized following phenotypic screening/purification in order to assess if the isolates obtained by phenotypic screening/purification are homokaryotic.

Phenotypic screening of transformants generated using the methods, compositions or systems provided herein can employ the use of one or more selectable markers. A selectable marker can often encode a gene product providing a specific type of resistance foreign to the non-transformed strain. This can be resistance to heavy metals, antibiotics or biocides in general. Prototrophy can also be a useful selectable marker of the non-antibiotic variety. Auxotrophic markers can generate nutritional deficiencies in the host cells, and genes correcting those deficiencies can be used for selection.

There is a wide range of selection markers in use in the art and any or all of these can be applied to the methods and systems provided herein. The selectable marker genes for use herein can be auxotrophic markers, prototrophic markers, dominant markers, recessive markers, antibiotic resistance markers, catabolic markers, enzymatic markers, fluorescent markers, luminescent markers or combinations thereof. Examples of these include, but are not limited to: amdS (acetamide/fluoroacetamide), ble (belomycin-phleomycin resistance), hg (hygromycinR), nat (nourseotricin R), pyrG (uracil/5FOA), niaD (nitrate/chlorate), sutB (sulphate/selenate), eGFP (Green Fluorescent Protein) and all the different color variants, aygA (colorimetric marker), met3 (methionine/selenate), pyrE (orotate P-ribosyl transferase), trpC (anthranilate synthase), argB (ornithine carbamoyl-transferase), bar (phosphinothricin acetyltransferase), mutant acetolactate synthase (sulfonylurea resistance), and neomycin phosphotransferase (aminoglycoside resistance).

Figure 39:
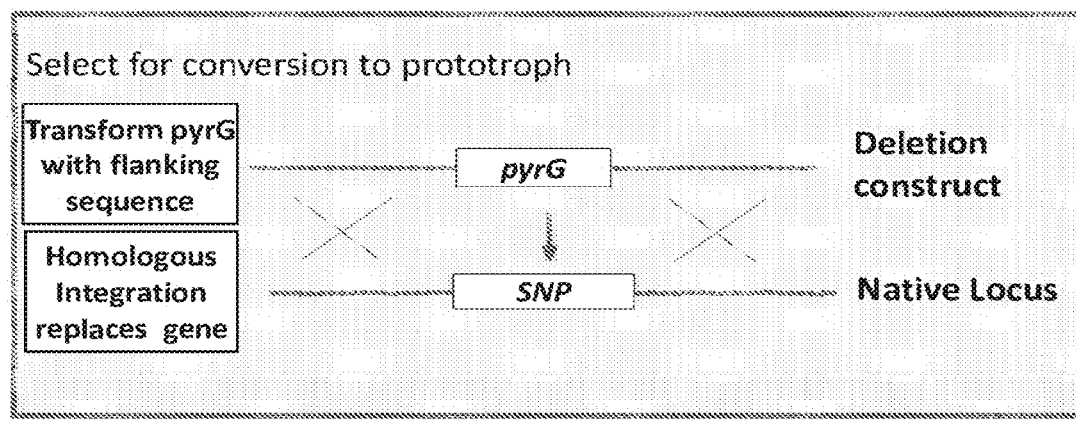
FIG. 39 depicts performing SNPSWP by generating gene deletions.

In one embodiment, a single selection marker is used for examining the phenotypic effects of a specific mutation of a target gene in the genome of a coenocytic organism. The coenocytic organism can be a filamentous fungi such as *A. niger*. The target gene can be a gene involved in a biosynthetic pathway such as, for example, a gene involved in citric acid production. An example of this type of embodiment can be seen in FIG. 39. At the top of FIG. 39, a deletion construct comprising a pyrG gene flanked by sequence homologous to a gene involved in citric acid production in *A. niger* is introduced into a host protoplast comprising a version of the citric acid production gene comprising a mutation (e.g., SNP) and lacking a native pyrG gene. Homologous recombination of the pyrG construct generates transformants that can be selected for based on the presence of pyrG gene as described herein. Further, transformants can have a deletion phenotype that can be used to inform about the role said mutation plays in the pathway. Alternatively, the bottom of FIG. 39, depicts an embodiment where a construct comprising a gene involved in citric acid production with a specific mutation (e.g., SNP) flanked by sequence homologous to the native pyrG locus in the host protoplast is introduced into the host protoplast. Homologous recombination between the construct and the native pyrG locus can generate transformants that can be selected for by growing said transformants on media comprising FOA. The phenotypic effects of the introduced SNP can then be assessed as described herein.

Another embodiment of the present disclosure entails the use of two or more selection markers active in filamentous fungi. There is a wide range of combinations of selection markers that can be used and all of these can be applied in the selection/counterselection scheme provided herein. For example, the selection/counterselection scheme can utilize a combination of auxotrophic markers, prototrophic markers, dominant markers, recessive markers, antibiotic resistance markers, catabolic markers, enzymatic markers, fluorescent markers, and luminescent markers. A first marker can be used to select in the forward mode (i.e., if active integration has occurred), while additional markers can be used to select in the reverse mode (i.e., if active integration at the right locus has occurred). Selection/counterselection can be carried out by cotransformation such that a selection marker can be on a separate vector or can be in the same nucleic acid fragment or vector as the endogenous or heterologous gene as described herein.

In one embodiment, the homokaryotic protoplast purification scheme of the present disclosure entails co-transforming protoplasts generated form filamentous fungal host cells with a first construct comprising sequence for an endogenous gene or heterologous gene and a second construct comprising sequence for a first selectable marker gene such that the first construct is directed to a first locus of the protoplast genome that comprises sequence for a target gene to be removed or inactivated, while the second construct is directed to a second locus of the protoplast genome that comprises sequence for a second selectable marker gene. In one embodiment, the first construct comprises sequence for an endogenous gene or heterologous gene and the target gene to be removed or inactivated is for a third selectable marker gene. In a separate embodiment, the first construct comprises a sequence for an endogenous gene and the target gene to be removed or inactivated is the copy of the endogenous gene present in the genome of the protoplast prior to transformation. As described herein, the endogenous gene or heterologous gene of the first construct can comprise a mutation (e.g., SNP) and/or a genetic regulatory or control element (e.g., promoter and/or terminator). The first, second and/or third selectable marker can be any auxotrophic markers, prototrophic markers, dominant markers, recessive markers, antibiotic resistance markers, catabolic markers, enzymatic markers, fluorescent markers, luminescent markers known in the art and/or described herein. To be directed to a specific locus each of the constructs is flanked by nucleotides homologous to the desired locus in the protoplast genome as described herein.

An example of the embodiment where the first construct comprises sequence for an endogenous gene or heterologous gene and the target gene to be removed or inactivated is for a third selectable marker gene is shown in FIG. 23A. In this example, the first construct comprises sequence for an endogenous gene involved in citric acid production in filamentous fungus that comprises a SNP that is integrated into the locus for the colorimetric selectable marker gene aygA, while the second construct comprises sequence for the auxotrophic marker gene pyrG that is integrated into the locus for the auxotrophic marker gene met3. In this example, the filamentous fungal host cell is pyrG negative or uracil auxotrophic. Accordingly, purification of homokaryotic protoplast transformants entails growing said transformants on minimal media lacking uracil. As shown in FIG. 23A, homokaryotic transformants will not only be uracil prototrophs, but will also be pure yellow in color, indicting incorporation of the pyrG gene and removal of the aygA gene. Counterselection and removal of any residual heterokaryotic colonies can be accomplished by subsequently plating the transformants on minimal media (with or without uracil) that contains selenate, whereby transformants with met3+ nucleic will die in the presence of selenate. Another marker that operates similarly to the met3 gene can be, for example, the niaA gene encoding nitrate reductase, which can be used in the selection/counterselection scheme described in this embodiment. For the niaA gene, the filamentous fungal host cells can be niaA+, whereby correct integration of the second construct generates niaA-progeny which are resistant to chlorate used during counterselection. In one embodiment, confirmation of correct integration of the first and/or second construct into the protoplast genome is confirmed by sequencing the genome of the protoplast using such as, for example next generation sequencing (NGS).

Figure 24:
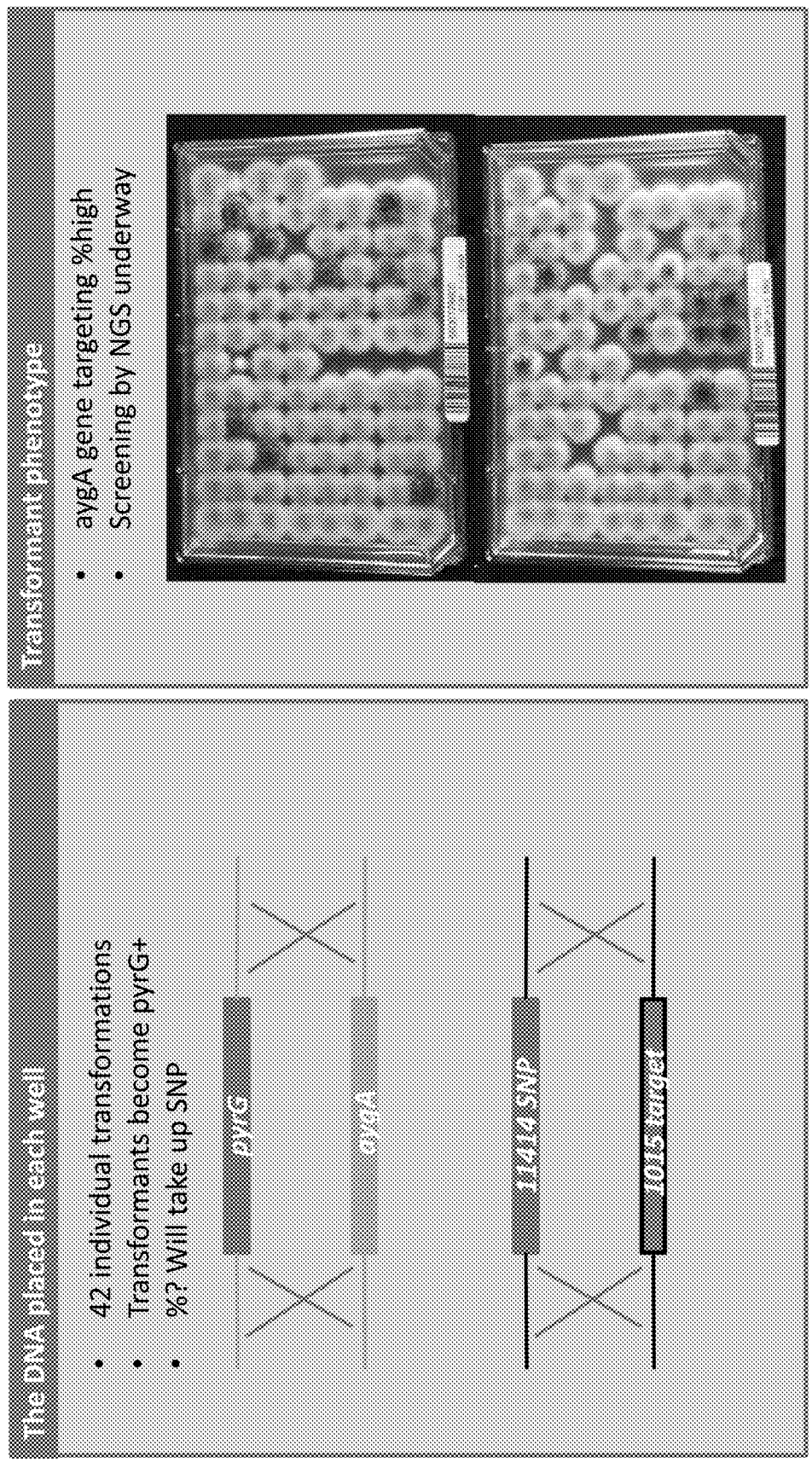
FIG. 24 depicts a SNP swap implementation in *A. niger*. The left side of FIG. 24 illustrates the designed genetic edits for each SNP of the SNP swap. The FIG. 24 further illustrates the cotransformation in which the pyrG gene is introduced into the locus for the aygA wild type gene. The right side of FIG. 24 shows two pictures of the 96-well media plates for screening the *A. niger* transformants. Light yellow colonies represent transformants in which the aygA gene has been successfully disrupted. The *A. niger* strain used to build the mutant strains depicted within FIG. 24 were strains with reduced NHEJ pathway activity.

An example of the embodiment where the first construct comprises a sequence for an endogenous gene and the target gene to be removed or inactivated is the copy of the endogenous gene present in the genome of the protoplast prior to transformation is shown in FIG. 24. In this example, the first construct comprises sequence for an endogenous gene involved in citric acid production in filamentous fungus that comprises a SNP that is integrated into the locus for said endogenous gene lacking said SNP, while the second construct comprises sequence for the auxotrophic marker gene pyrG that is integrated into the locus for the colorimetric marker gene aygA. In this example, the filamentous fungal host cell is pyrG negative or uracil auxotrophic. Accordingly, purification of homokaryotic protoplast transformants entails growing said transformants on minimal media lacking uracil. As shown in FIG. 24, homokaryotic transformants will not only be uracil prototrophs, but will also be pure yellow in color, indicting incorporation of the pyrG gene and removal of the aygA gene. In one embodiment, confirmation of correct integration of the first and/or second construct into the protoplast genome is confirmed by sequencing the genome of the protoplast using such as, for example next generation sequencing (NGS). The NGS system or method used can be any NGS system or method known in the art such as for example Illumina NGS.

In one embodiment, the second construct comprises an expression cassette that encodes a recyclable or reversible marker. The recyclable or reversible marker can be a disruption neo-pyrG-neo expression cassette. The neo-pyrG-neo construct can be co-transformed with the first construct as described in the above embodiments in a ura-strain of filamentous fungal host cell (e.g., *A. niger*) and homokaryotic transformants can be selected by plating on uracil deficient medium and selecting pure yellow uracil prototrophs as described above. Subsequently, use of pyrG selection can be regenerated by plating said homokaryotic transformants on 5-FOA containing medium and selecting transformants that grow on said 5-FOA medium, which indicates that said transformants have undergone an intrachromosomal recombination between the neo repeats that results in excision of the pyrG gene.

In a further embodiment, instead of using co-transformation as provided herein, the homokaryotic protoplast purification scheme of the present disclosure entails transforming protoplasts generated form filamentous fungal host cells with a deletion construct comprising sequence for a specific gene such that the construct is directed to a desired locus of the protoplast genome that comprises sequence for a target gene to be removed or inactivated. To be directed to a specific locus the constructs is flanked by nucleotides homologous to the desired locus in the protoplast genome as described herein. Use of this type of construct/transformation can be used to provide information on the role a particular gene plays in a particular biochemical pathway. In one embodiment, confirmation of correct integration of the deletion construct into the protoplast genome is confirmed by sequencing the genome of the protoplast using such as, for example next generation sequencing (NGS). The NGS system or method used can be any NGS system or method known in the art such as for example Illumina NGS.

Examples of this embodiment are shown in FIG. 39. In one case, the filamentous fungal host cell is pyrG negative and the deletion construct comprises a selectable marker gene (e.g., pyrG gene in FIG. 39), while the target gene is a SNP. Accordingly, purification of homokaryotic protoplast transformants entails growing said transformants on minimal media lacking uracil. In another case, the filamentous fungal host cell is pyrG positive and the deletion construct comprises a SNP, while the target gene is a selectable marker gene (e.g., pyrG gene in FIG. 39). Accordingly, purification of homokaryotic protoplast transformants entails growing said transformants on minimal media comprising FOA.

In yet another embodiment, a mutated gene (e.g., a SNP) is integrated into a target locus in the genome of a coenocytic organism (e.g., filamentous fungi such as *A. niger*) via transformation and integration of multiple portions of the mutated gene such that each of the multiple portions of the mutated gene are present on a separate construct. Each of the multiple constructs can comprise a unique portion of the mutated gene plus an overlapping portion of the mutated gene that is also present on one of the other multiple constructs in order to facilitate recombination of the multiple constructs to produce a functional copy of the mutated gene in the organism's genome. To facilitate integration of each portion of the mutated gene into the desired locus of the organism, each of the multiple constructs can further comprise nucleotides homologous to the desired locus in the organism's genome that flank the portion of the mutated gene in the construct. In some cases, the mutated gene is split across two constructs and is introduced into the organism via bipartite transformation of the two constructs. One example of this concept is depicted in FIG. 36. As shown in the left hand column of FIG. 36, the pyrG marker gene is split into two constructs such that each of the constructs comprises a unique portion of the pyrG and a portion that overlaps with the other construct. Further, each construct further comprises sequence homologous to the aygA marker gene in the host organism genome such that each of the portion of homologous sequence in the two construct also contains a SNP. Recombination of the two constructs following transformation using any of the methods provided herein results in insertion of a the whole pyrG marker gene comprising the two SNPs. Transformants containing the wholly integrated pyrG marker gene and transformants who have lost the pyrG marker gene via loop-out can be detected via selection/counterselection as described herein. In particular, loop-outs can be selected by growing the transformants on media with FOA.

A further example of bipartite transformation is illustrated in FIG. 37. FIG. 37 depicts an example of a combinatorial SNPSWP in fungi (e.g., *A. niger*) whereby multiple mutations of a target gene (i.e., aygA gene) are introduced into a protoplast genome by the integration into the parental aygA gene of two separate constructs each comprising a mutation and a portion of a split marker gene (divergent pyrG genes) in a single transformation. As shown in FIG. 37, upon successful recombination between the overlapping portions of the respective pyrG gene containing constructs and between the homologous portions of the aygA gene in the constructs and host genome, expression of each of the whole pyrG genes can be controlled via catabolite repression by glucose. Accordingly, transformants can be selected by growing the transformants on glucose such that the growth of transformants in which the desired recombination and integration events have occurred will be favored. Further, loop-outs can be facilitated by growing the transformants on media with FOA. As can be understood by one skilled in the art, the concepts depicted in FIG. 37 can be used to introduce combinations of mutations (e.g., SNPs) into a target gene and subsequently test the phenotypic effects of said combination. The phenotypic effect can be generation of a desired property or activity of an exogenous protein. The property or activity of interest can mean any physical, physicochemical, chemical, biological, or catalytic property, or any improvement, increase, or decrease in such a property, associated with the exogenous protein. The phenotypic effect can also be the production or lack of production of one or more metabolites. The phenotypic effect can also be increased or decreased quantities of a protein or metabolite. Further, it is contemplated that further mutations can be introduced using a similar technique in order to build strains containing specific combinations of mutations.

The middle and right hand columns of FIG. 36 illustrate additional approaches that can be used in the methods and systems provided herein for generating transformants with targeted integration of mutations in a target gene. In one embodiment, co-transformation of a coenocytic organism (e.g., filamentous fungi) is performed using a first construct comprising sequence homologous to a desired locus in the host organism genome, a target gene with a mutation (e.g., SNP) and a portion of marker gene (e.g., pyrG) flanked by a terminator repeat (e.g., direct repeat (DR)) and a second construct comprising an overlapping portion of the marker gene on the first construct as well as the remainder of the marker gene flanked by a second terminator repeat (DR) and sequence homologous to the desired locus in the host organism genome. Transformants comprising successful recombination of the constructs and integration into the desired locus can be isolated using any of the selection/counterselection schemes provided herein (e.g., aygA based selection and loss of pyrG counterselection in FIG. 36). The right hand column of FIG. 36 depicts an example of integration of a mutation (e.g., SNP) in a target gene (e.g., aygA) using a loop-in single crossover event with a construct comprising a copy of the target gene with a mutation and one or more selectable markers (e.g., antibiotic resistance gene ($amp^R$) and auxotrophic marker gene (pyrG)).

Library Generation

Figure 5:
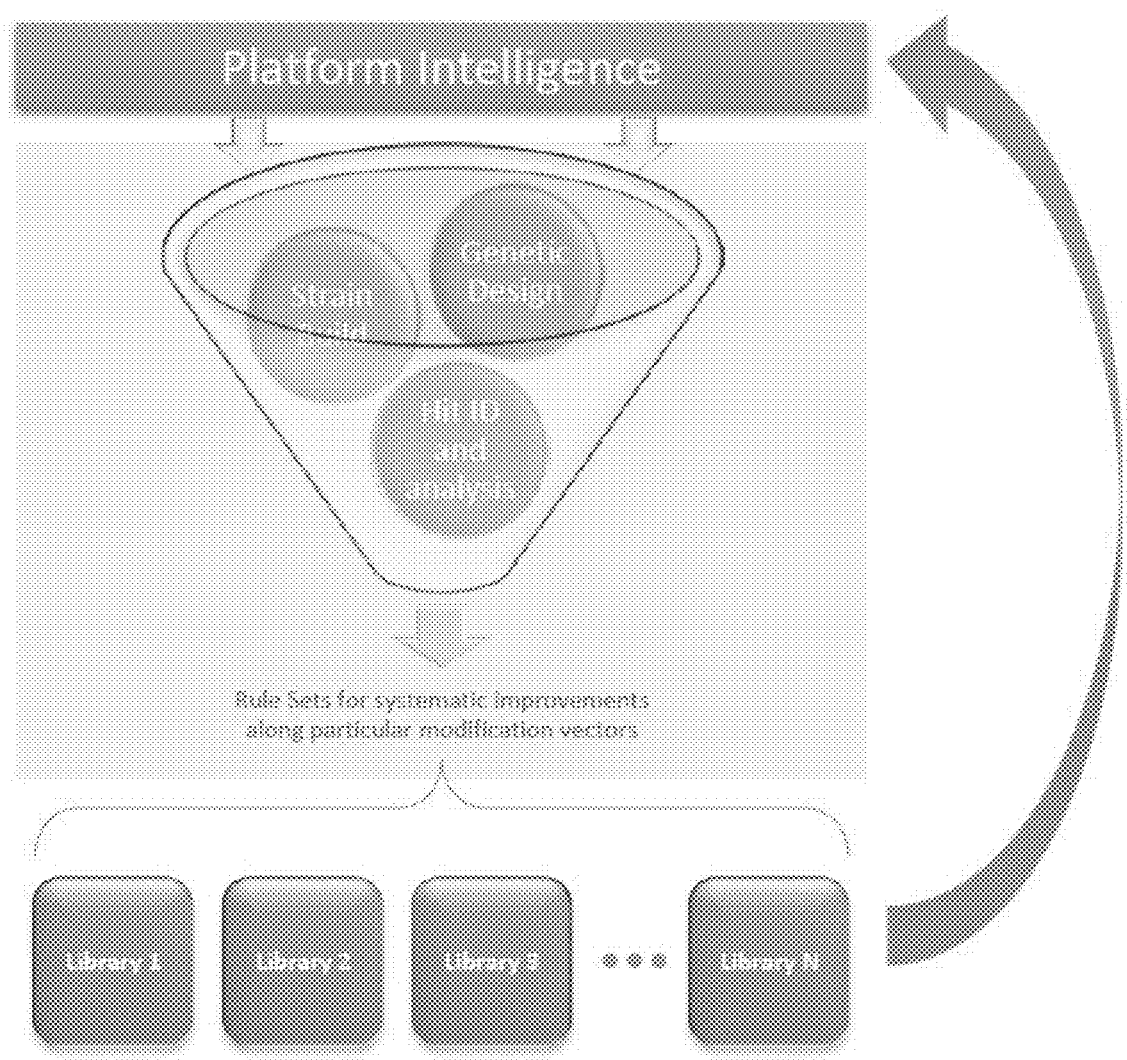
FIG. 5 depicts an embodiment of the filamentous fungal strain improvement process of the present disclosure. Host strain sequences containing genetic modifications (Genetic Design) are tested for strain performance improvements in various strain backgrounds (Strain Build). Strains exhibiting beneficial mutations are analyzed (Hit ID and Analysis) and the data is stored in libraries for further analysis (e.g., SNP swap libraries, PRO swap libraries, and combinations thereof, among others). Selection rules of the present disclosure generate new proposed filamentous fungal host strain sequences based on the predicted effect of combining elements from one or more libraries for additional iterative analysis.

A further aspect of the disclosure can include the construction and screening of fungal mutant libraries, and fungal mutant libraries prepared by the methods disclosed herein. As shown in FIG. 5, the fungal libraries can be incorporated into platform for building fungal strains. The libraries may be obtained by transformation of the fungal hosts according to this disclosure with any means of integrative transformation, using methods known to those skilled in the art. A library of fungi based on the preferred host strains generated using the methods and systems provided herein may be handled and screened for desired properties or activities of exogenous proteins in miniaturized and/or high-throughput format screening methods. Property or activity of interest can mean any physical, physicochemical, chemical, biological, or catalytic property, or any improvement, increase, or decrease in such a property, associated with an exogenous protein of a library member. The library may also be screened for metabolites, or for a property or activity associated with a metabolite, produced as a result of the presence of exogenous and/or endogenous proteins. The library may also be screened for fungi producing increased or decreased quantities of such protein or metabolites.

In one embodiment, the methods and systems provided herein generate a plurality of protoplasts such that each protoplast from the plurality of protoplasts is transformed with a single first construct from a plurality of first constructs and a single second construct from a plurality of second constructs. Further to this embodiment, a first polynucleotide in each first construct from the plurality of first constructs comprises a different mutation and/or genetic control or regulatory element while a second polynucleotide in each second construct from the plurality of second constructs is identical. The method further comprises transforming and purifying homokaryotic transformants using selection/counterselection as described herein two or more times in order to generate a library of filamentous fungal cells such that each filamentous fungal cell in the library comprises a first polynucleotide with a different mutation and/or genetic control or regulatory element. In one embodiment, the first polynucleotide comprises sequence for a target filamentous fungal gene or a heterologous gene comprising a mutation such that the iterative process generates a library of filamentous fungal cells upon regeneration of the protoplasts such that each member of the library comprises a target filamentous fungal gene or a heterologous gene with a distinct mutation. As described herein, the first polynucleotide can be split between more than one construct such that each construct can comprise an overlapping portion of the first polynucleotide in order to facilitate homologous recombination between the constructs when introduced into a host organism. Further, each construct comprising an overlapping portion of the first polynucleotide can further comprise sequence homologous to a desired locus in the host genome in order to facilitate integration of the recombined first polynucleotide into the desired locus. In one embodiment, the mutation is a SNP and the methods thereby produces a SNPSwap library. In one embodiment, the target filamentous fungal gene is a gene involved in citric acid production and the plurality of first constructs is the library of SNPs provided in Table 4. In another embodiment, the first polynucleotide comprises sequence for a target filamentous fungal gene or a heterologous gene operably linked to a genetic control or regulatory element such that the iterative process described herein generates a library of filamentous fungal cells upon regeneration of the protoplasts such that each member of the library comprises a target filamentous fungal gene or a heterologous gene operably linked to a distinct genetic control or regulatory element. In one embodiment, the genetic control or regulatory element is a promoter and the methods thereby produces a Promoter or PRO library. In one embodiment, the genetic control or regulatory element is a terminator and the methods thereby produces a Terminator or STOP library. The promoter and/or terminator sequence can be a promoter or terminator sequence provided herein and/or known in the art for expression in a filamentous fungal host cells used in the methods and systems provided herein. In one embodiment, the promoter is an inducible promoter.

TABLE 4

SNPs potentially involved in citric acid production in A. niger.

| Mutation name | Location | Sequence change | Orientation | Contig | Description | SNP in Coding Domain | Morphological Phenotype |
|---|---|---|---|---|---|---|---|
| FungiSNP_01 | 50669-680224 | ~>~ | 680224 | chr_1_1 | | | |
| FungiSNP_02 | 1172974 | G > A | + | chr_1_1 | Aromatic amino acid aminotransferase and related protein | X | |
| FungiSNP_03 | 367948 | C > T | + | chr_1_2 | | | |
| FungiSNP_04 | 549014 | C > G | − | chr_1_2 | | | |
| FungiSNP_05 | 1330718 | G > A | + | chr_1_2 | | | |
| FungiSNP_06 | 662258 | G> | + | chr_2_1 | Taurine catabolism dioxygenase TauD/TfdA | X | |
| FungiSNP_07 | 673547 | G > A | − | chr_2_1 | alpha/beta hydrolase | X | |
| FungiSNP_08 | 946654 | T> | + | chr_2_1 | | | |
| FungiSNP_09 | 641661 | T > A | − | chr_2_2 | pseudouridylate synthase activity | X | X |
| FungiSNP_10 | 2316591 | G > A | + | chr_2_2 | | | |
| FungiSNP_11 | 935908 | A > G | − | chr_3_1 | Serine/threonine protein kinase | X | |
| FungiSNP_12 | 205638 | T > A | + | chr_3_2 | Transcription factor | X | X |
| FungiSNP_13 | 268107 | T > C | + | chr_3_3 | | | |
| FungiSNP_14 | 186943 | A > T | + | chr_3_4 | | | |
| FungiSNP_15 | 276232 | C > T | + | chr_3_4 | | | |
| FungiSNP_16 | 1287891 | T > C | − | chr_4_1 | Serine/threonine protein kinase | X | |
| FungiSNP_17 | 1639965 | A > T | + | chr_4_1 | | | |
| FungiSNP_18 | 1826343 | G > A | − | chr_4_1 | Sensory transduction histidine kinase | X | X |
| FungiSNP_19 | 1358794 | C > A | + | chr_4_2 | | | |
| FungiSNP_20 | 1466380 | CTA> | + | chr_4_2 | mannitol-1-phosphate 5-dehydrogenase | X | |

TABLE 4-continued

SNPs potentially involved in citric acid production in *A. niger*.

| Mutation name | Location | Sequence change | Orientation | Contig | Description | SNP in Coding Domain | Morphological Phenotype |
|---|---|---|---|---|---|---|---|
| FungiSNP_21 | 1700330 | C > A | − | chr_4_2 | Tomosyn and related SNARE-interacting protein | X | |
| FungiSNP_22 | 2873296 | A > G | + | chr_4_2 | | | |
| FungiSNP_23 | 815022 | G > A | + | chr_5_2 | unknown function | X | |
| FungiSNP_24 | 831672 | G > A | − | chr_5_2 | Cytochrome c heme-binding site | X | |
| FungiSNP_25 | 1507652 | >A | + | chr_5_2 | | | |
| FungiSNP_26 | 442488 | T > C | + | chr_6_1 | | | |
| FungiSNP_27 | 93202-103239 | ~>~ | + | chr_6_2 | | | |
| FungiSNP_28 | 972833 | A > T | + | chr_6_2 | | | |
| FungiSNP_29 | 972932 | A> | + | chr_6_2 | | | |
| FungiSNP_30 | 1183094 | G> | + | chr_6_2 | Monooxygenase involved in coenzyme Q (ubiquinone) biosynthesis | X | |
| FungiSNP_31 | 1701762 | T > G | + | chr_6_2 | | | |
| FungiSNP_32 | 236406 | G > A | − | chr_7_1 | extracellular unknown protein | X | |
| FungiSNP_33 | 2350056 | A> | + | chr_7_1 | | | |
| FungiSNP_34 | 375013 | C > T | + | chr_8_1 | | | |
| FungiSNP_35 | 1272037 | C > T | + | chr_8_1 | | | |
| FungiSNP_36 | 281612 | T > C | + | chr_8_2 | unknown function | X | |
| FungiSNP_37 | 565087 | A > G | + | chr_8_2 | | | |
| FungiSNP_38 | 865958 | A> | + | chr_8_2 | | | |
| FungiSNP_39 | 947633 | A> | + | chr_8_2 | | | |
| FungiSNP_40 | 2482267 | G > A | | chr_8_2 | Uncharacterized conserved coiled-coil protein | X | X |
| FungiSNP_41 | 2486601 | G> | + | chr_8_2 | Magnesium-dependent phosphatase | X | |
| FungiSNP_42 | 2709491 | T > C | + | chr_8_2 | | | |
| FunuiSNP_43 | 2708043 | >A | ~ | chr_8_2 | GTPase-activating protein | X | |

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

A brief table of contents (i.e., Table 5) is provided below solely for the purpose of assisting the reader. Nothing in this table of contents is meant to limit the scope of the examples or disclosure of the application.

TABLE 5

Table of Contents For Example Section

| Example # | Title | Brief Description |
|---|---|---|
| 1 | HTP Genomic Engineering of filamentous fungi: Generation & Storage of Filamentous Fungal Protoplasts | Describes methods for generating and storing protoplasts for use in HTP genomic engineering methods |
| 2 | HTP Genomic Engineering of filamentous fungi: Alternative Method for Generating Protoplasts | Describes an alternative method for generating protoplasts for use in HTP genomic engineering methods |
| 3 | HTP Genomic Engineering of filamentous fungi: Demonstration of Co-transformation of Filamentous Fungal Protoplasts-Proof of Principle | Describes proof-of-principle for HTP co-transformation of filamentous fungi |

TABLE 5-continued

Table of Contents For Example Section

| Example # | Title | Brief Description |
| --- | --- | --- |
| 4 | HTP Genomic Engineering of filamentous fungi: Demonstration of Co-transformation of Filamentous Fungal Protoplasts- Proof of Principle using colorimetric selection/counterselection | Describes HTP method for proof-of-principle for using selection/counter-selection in filamentous fungal protoplasts |
| 5 | HTP Genomic Engineering of filamentous fungi: Implementation of an HTP SNP Library Strain Improvement Program to Improve Citric Acid production in Eukaryote Aspergillus niger ATCC 11414 | Describes HTP method for SNP library strain improvement program in A. niger |
| 6 | HTP Genomic Engineering of filamentous fungi: Demonstration of the ability of next-generation sequencing (NGS) to detect SNPs in filamentous fungi with different genetic backgrounds | Describes using NGS to detect SNPs in filamentous fungi |
| 7 | HTP Genomic Engineering of filamentous fungi: Demonstration of the ability of next-generation sequencing (NGS) to detect SNPSWP in filamentous fungi | Describes using NGS to detect SNPSWPs in filamentous fungi |
| 8 | HTP Genomic Engineering of filamentous fungi: Demonstration of Co-transformation of Filamentous Fungal Protoplasts-Additional Proof of Principle | Describes HTP co-transformation of filamentous fungi with marker and desired gene mutation split across multiple constructs |
| 9 | Non-homologous end joining (NHEJ) and HR-mediated genomic editing of filamentous fungi using Cas9 ribonucleic acid protein (RNP) transformations enable SNPs, insertions, and indels without direct selection for the desired edits | Describes utilization of an RNA guided endonuclease to edit a filamentous fungi, e.g. A. niger |
| 10 | HR-mediated genomic editing of filamentous fungi using Cas9 ribonucleic acid protein (RNP) transformation to introduce single SNP without scrambling PAM site | Describes utilization of a nucleic acid guided nuclease to edit a filamentous fungi, e.g. A. niger |
| 11 | Purification of Transformed Fungal Strains into Clonal Populations at Scale | Describes a HTP method for fungal purification to a uniform genotype through automated separation of spores following transformation |
| 12 | HTP Genomic Engineering of filamentous fungi: identification of genes that affect filamentous fungal morphology | Describes SNP swap method for generating filamentous fungal strains with non-mycelium, pellet phenotype in submerged CAP culture |
| 13 | HTP Genomic Engineering of filamentous fungi: confirmation of role the identified genes play in filamentous fungal morphology | Describes confirmation genes that play a role in morphology of filamentous fungal strains in submerged CAP culture by knocking out putative morphologically related genes |
| 14 | HTP Genomic Engineering of filamentous fungi: Demonstration of PROSWP in filamentous fungi by altering filamentous fungal cell morphology by altering gene expression | Describes a PROSWP library being utilized in filamentous fungi to control expression of a putative morphologically related gene |

Figure 20A:
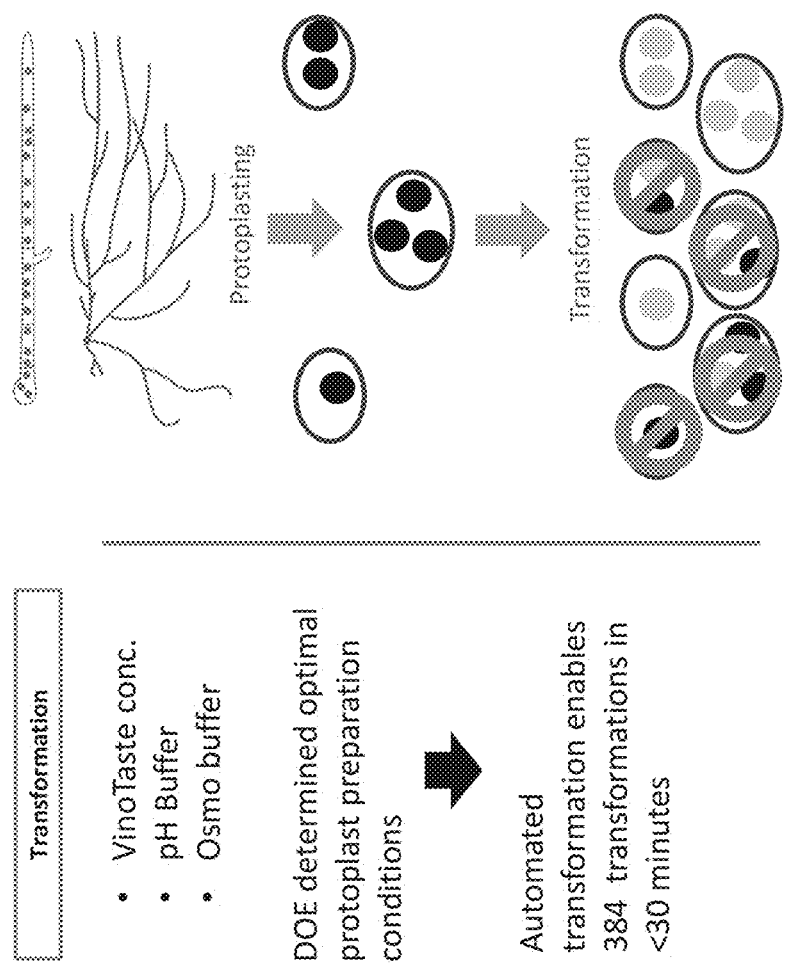
FIG. 20A depicts a general outline for the automated transformation, screening and purification of homokaryotic protoplasts provided herein and described in Example 1.
Figure 43:
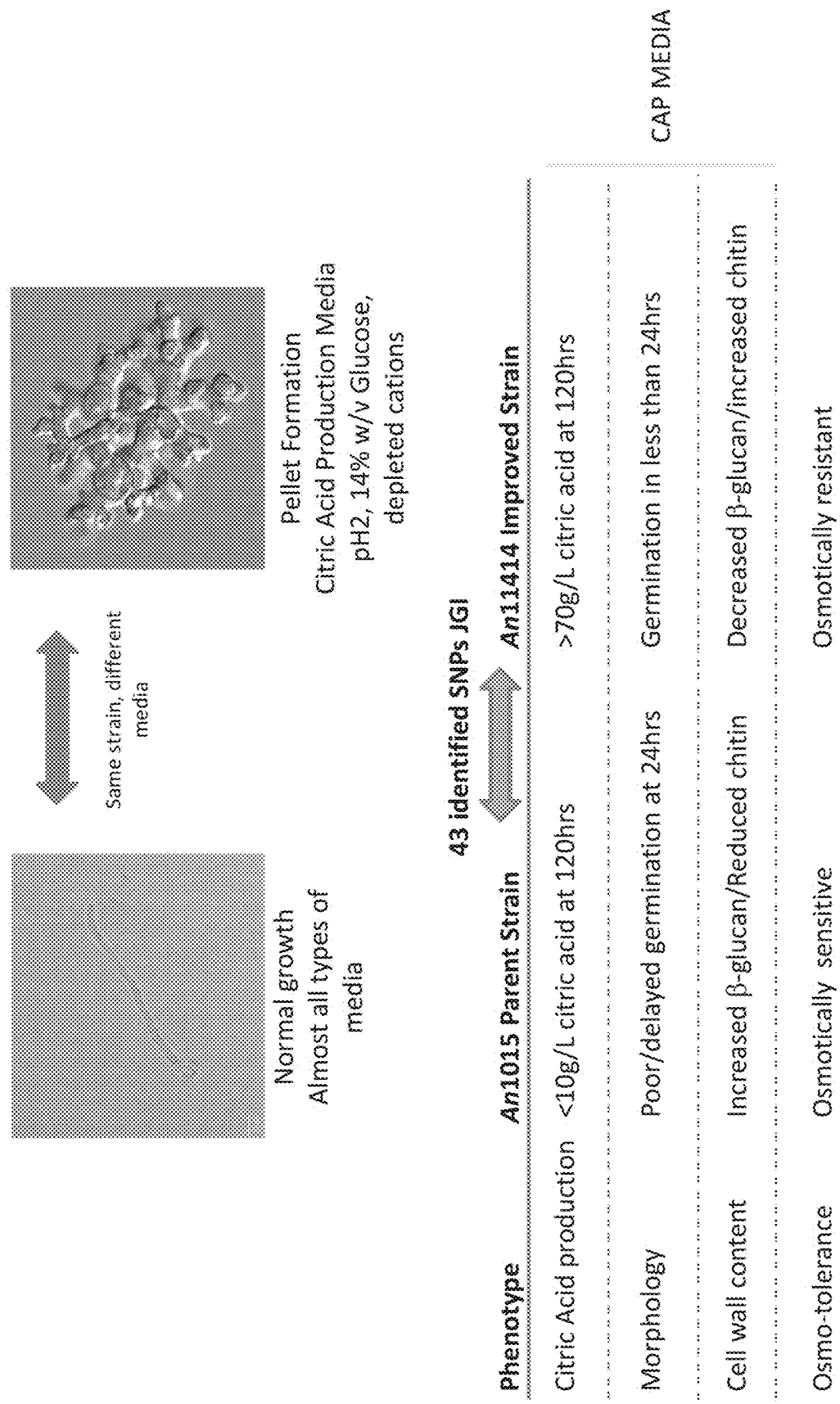
FIG. 43 illustrates how a strain and its improved descendants differ in their response to Citric Acid production media.

Example 1: HTP Genomic Engineering of Filamentous Fungi: Generation & Storage of Filamentous Fungal Protoplasts Generation of Protoplasts As shown in FIG. 20A, 100 milliliters of complete media was inoculated with $10^6$ conidia/ml of Aspergillus niger and grown overnight at 150 rpm at 30° ~C. Following the overnight growth. the mycelia were harvested by filtering the culture through Miracloth. Subsequently, the mycelia were rinsed thoroughly with sterile water. For the experiments described in the following examples, two strains of A. niger were used, A. niger strain 1015 and A. niger strain 11414. Harvested and washed mycelia were then subjected to enzymatic digestion by with a VinoTaste Pro (VTP) enzymatic cocktail. Features of each strain are depicted in FIG. 43.

For A. niger strain 1015, enzymatic digestion was performed by first making 50 ml of 60 mg/ml of VTP in protoplasting buffer (1.2M magnesium sulfate, 50 mM phosphate buffer, pH 5). After dissolving the VTP, the buffer was placed in clean Oakridge tubes and spun at 15,000×g for 15 minutes. The solution was then filter sterilized after centrifugation. Once made, some of the harvested mycelia was added to the VTP solution and the mycelia was digested at 30° C. at 80 rpm for 2~4 hours. At various intervals during VTP digestion, small samples were examined under 400× magnification for the presence of protoplasts (i.e., large round cells that are larger than conidia and are sensitive to osmotic lysis). When most or all of the mycelia were digested, the culture was filtered through sterile Miracloth such that 25 ml of the flow through containing the protoplasts were separated into 1 of 2 50 ml Falcon tubes. To each of the 25 ml samples, 5 ml of 0.4M ST buffer (0.4M Sorbitol, 100 mM Tris, pH 8) was gently overlaid. The overlaid samples were then spun at 800×g for 15 minutes at 4° C. in order to form a visible layer between the ST and digestion buffers. The protoplasts were then removed with a pipette and mixed gently with 25 ml of ST solution (1.0 M sorbitol, 50 mM Tris, Ph 8.0) and respun at 800×g for 10 minutes. The protoplasts should pellet at the bottom of the tube. The protoplasts were then resuspended in 25 ml of ST solution and collected by centrifugation at 800×g for 10 minutes.

For *A. niger* strain 11414, enzymatic digestion was performed by first making 40 ml of 30 mg/ml of VTP in protoplasting buffer (0.6M ammonium sulfate, 50 mM Maleic Acid, pH 5.5). All of the harvested mycelia were added to the VTP solution and the mycelia were digested at 30° C. at 70 rpm for 3-4 hours. At various intervals during VTP digestion, small samples were examined under 400× magnification for the presence of protoplasts. When most or all of the mycelia were digested, the culture was filtered through sterile Miracloth. The filtrate was then spun at 800×g for 10 min at 4° C. to pellet the cells. 25 ml of ST solution (1.0M sorbitol, 50 mM Tris, pH 8.0) was added and the cells were resuspended and respun. The cells were then washed in 10 ml of STC buffer (1.0M sorbitol, 50 mM Tris, pH 8.0, 50 mM $CaCl_2$) and collected by centrifugation at 800×g for 10 min. The protoplasts (~$10^8$/ml) were counted and adjusted to be at $1.2 \times 10^7$/ml.

For protoplasts generated from either *A. niger* strain (i.e., 1015 or 11414), following enzymatic digestion, 20% v/v of a 40% PEG solution (40% PEG-4000 in STC buffer)) was added to the protoplasts and mixed gently followed by adding 7% v/v of dimethyl sulfoxide (DMSO) to make a 8% PEG/7% DMSO solution. Following resuspension, the protoplasts were distributed to 96 well (25-50 microliters) microtiter plates using an automated liquid handler as depicted in FIG. 20A, followed by storage at at least −80° C. prior to transformation.

Example 2: HTP Genomic Engineering of Filamentous Fungi: Alternative Method for Generating Protoplasts As shown in FIG. 27, 500 milliliters of complete media was inoculated with $10^6$ conidia/ml of *Aspergillus niger* and grown overnight at 150 rpm at 30° C. Following the overnight growth, the mycelia were harvested by filtering the culture through Miracloth. Subsequently, the mycelia were rinsed thoroughly with sterile water. Harvested and washed mycelia were then subjected to enzymatic digestion by with a VinoTaste Pro (VTP) enzymatic cocktail.

Enzymatic digestion was performed by first making 50 ml of 60 mg/ml of VTP in protoplasting buffer (1.2M magnesium sulfate, 50 mM phosphate buffer, pH 5). After dissolving the VTP, the buffer was placed in clean Oakridge tubes and spun at 15,000×g for 15 minutes. The solution was then filter sterilized after centrifugation. Once made, some of the harvested mycelia was added to the VTP solution and the mycelia was digested at 30° C. at 80 rpm for 2-4 hours. At various intervals during VTP digestion, small samples were examined under 400× magnification for the presence of protoplasts (i.e., large round cells that are larger than conidia and are sensitive to osmotic lysis). When most or all of the mycelia were digested, the culture was filtered through sterile Miracloth and the filtrate was collected in a graduated cylinder. The filtered protoplasts were transferred to a graduated cylinder and a buffer of lower osmolite concentration (5 ml of 0.4M ST buffer (0.4M Sorbitol, 100 mM Tris, pH 8) was gently overlaid. The overlaid samples were then spun at 800×g for 15 minutes at 4° C. and protoplasts were then removed with a pipette and mixed gently with 25 ml of ST solution (1.0 M sorbitol, 50 mM Tris, Ph 8.0) and respun at 800×g for 10 minutes. The protoplasts should pellet at the bottom of the tube. The protoplasts were then resuspended in 25 ml of ST solution and collected by centrifugation at 800×g for 10 minutes.

Example 3: HTP Genomic Engineering of Filamentous Fungi: Demonstration of Co-Transformation of Filamentous Fungal Protoplasts-Proof of Principle Preparation of Targeting DNA In an effort to provide proof of concept (POC) for the automated filamentous fungal transformation and screening method depicted in FIGS. 20A-C, the DNA sequence of the *Aspergillus niger* argB gene was obtained and the proper reading frame was determined. A set of SNPs were then designed such that integration of any of said SNPs into the argB locus of the *A. niger* genome would result in null mutation of the argB gene. The designs were generated as in silico constructs that predicted a set of oligomers that were used to build the constructs using Gibson assembly.

Automated Transformation of Protoplasts

Protoplasts derived from *A. niger* strain 1015 generated and stored in 96 well plates (100 microliters protoplast/well) as described in Example 1 were then subjected to traditional PEG Calcium mediated transformations using automated liquid handlers to combine the SNP DNA constructs with the protoplast-PEG/DMSO mixtures in the 96 well plates. More specifically, to 100 microliters of protoplasts, 1-10 micrograms of the SNP DNA constructs (in a volume of 10 microliters or less) were added and the mixture was incubated on ice for 15 minutes. To this mixture, 1 ml of 40% PEG was added and incubated for 15 minutes for room temperature. Subsequently, 10 ml of minimum medium plus 1M sorbitol was added and shaken at 80 rpm for 1 hour at 30° C. Following this incubation, the protoplasts were spun down at 800×g for 5 minutes and then resuspended in 12 ml of minimal medium containing 1M sorbitol and 0.8% agar. The following day, using an additional automated liquid handling step, the protoplasts were plated on to selective media (i.e., minimal media+arginine) and non-selective media (i.e., minimal media). Successful transformation of the protoplasts generated with the automated transformation protocol would be expected to be auxotrophic for arginine and thus not grow on minimal media lacking arginine due to targeting of the argB gene by the SNP constructs.

As shown in FIG. 21, about 3% of the transformants displayed integration of the targeting DNA constructs at the correct (i.e., argB) locus as evidenced by lack of growth in the minimal media lacking arginine. Confirmation of integration of the SNP containing constructs at the correct locus will be confirmed via next generation sequencing.

Example 4: HTP Genomic Engineering of Filamentous Fungi: Demonstration of Co-Transformation of Filamentous Fungal Protoplasts—Proof of Principle Using Colorimetric Selection/Counterselection This example demonstrates an additional proof of principle for the automated, HTP co-transformation of filamentous fungal cells and further demonstrates the use of selection/counterselection for the isolation of desired transformants.

*Aspergillus Niger* Protoplast Formation and Transformation

A large volume (500 ml) of protoplasts of a eukaryotic fungal strain of *Aspergillus niger*, ATCC 1015, was generated using a commercially available enzyme mixture which contains beta-glucanase activity as described in Example 1. The protoplasts were isolated from the enzyme mixture by centrifugation and were ultimately re-suspended in a buffer containing calcium chloride by the method described in Example 1.

The protoplasts were aliquoted and frozen at negative 80 degrees Celsius in containers containing a suspension of dimethyl sulfoxide and polyethylene glycol (PEG) as described in Example 1. In some embodiments, the present disclosure teaches that a stock of 96-well microtiter plates containing 25-50 microliters of protoplasts in each well can be prepared and frozen in large batches for large scale genome editing campaigns using this technique.

Traditional PEG Calcium mediated transformations were carried out by automated liquid handlers, which combined the DNA with the protoplast-PEG mixtures in the 96 wells. An additional automated liquid handling step was used to plate the transformation on to selective media after transformation.

Automated Screening of Transformants

Figure 23B:
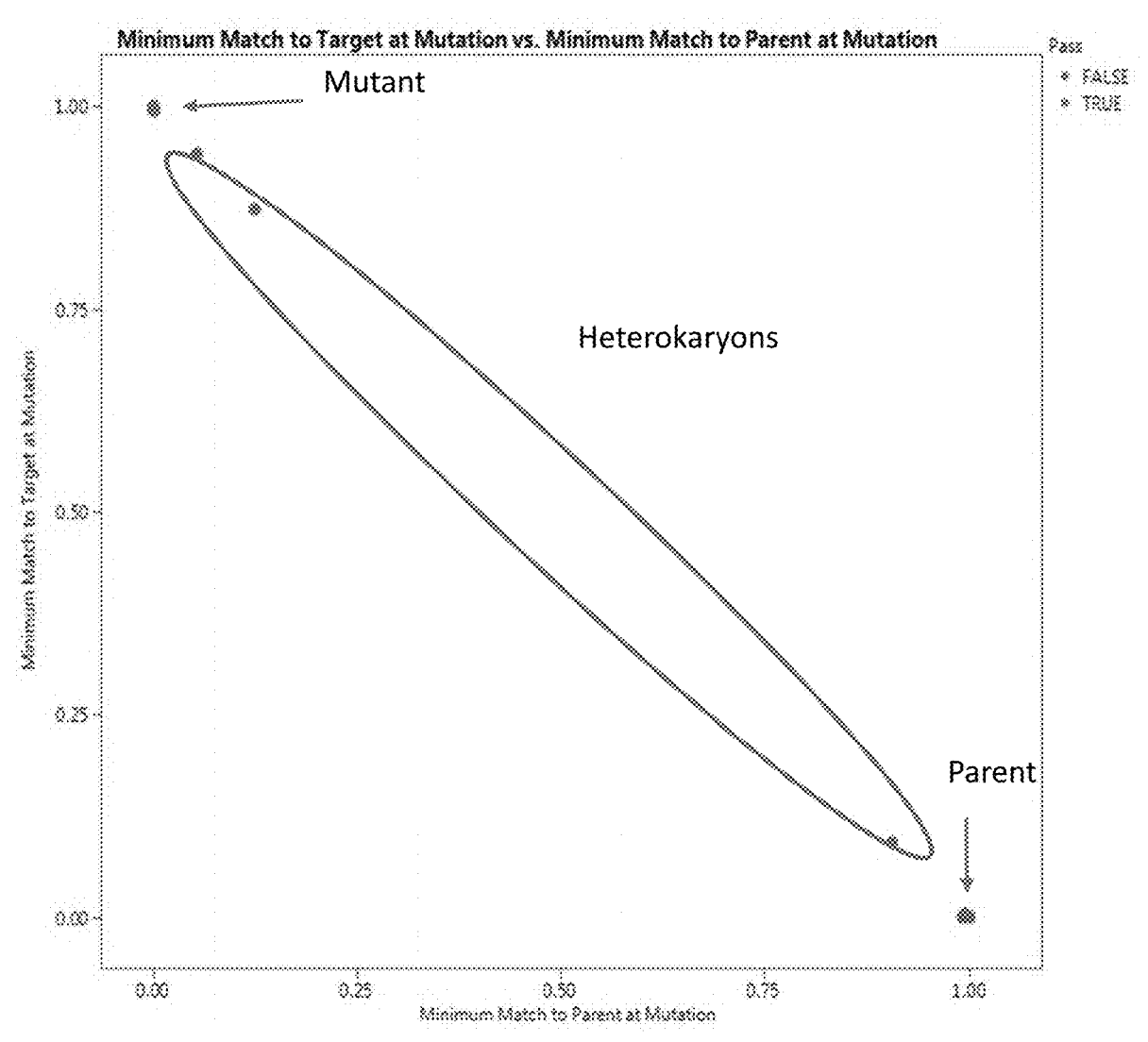

As discussed in more detail below, the *A. niger* cells used in this example lacked a functional pyrG gene (i.e., pyrG−) were transformed with a functional pyrG gene, which permitted transformed cells to grow in the absence of Uracil. As shown in FIG. 23A-B, the pyrG gene of this example was further designed to incorporate into the location of *A. niger*'s wild type met3 gene, thus incorporating a disruption to the naturally occurring met3 gene. Disruption of the met3 gene further results in the transformants being methionine auxotrophs, providing a secondary screening method for identifying transformants.

Transformants grown on the selective media without Uracil were isolated and placed into individual wells of a second microtiter plate. The transformants in the second microtiter plate were allowed to grow and sporulate for 2-3 days, before being resuspended in a liquid consisting of water and a small amount of detergent to generate a spore stock suitable for storage and downstream automated screening.

A small aliquot of each of the aforementioned spore stocks was then used to inoculate liquid media in a third 96 well PCR plate. These small cultures are allowed to grow over night in a stationary incubator so that the yellow-pigment containing spores germinate and form hyphae that are more amenable to selection, and downstream steps.

Following the culturing step, the hyphae of the third PCR plate were lysed by adding a commercially available buffer and heating the cultures to 99 degrees Celsius for 20 minutes. The plates were then centrifuged to separate the DNA suspension supernatant from the cell/organelle pellets. The DNA extractions were then used for PCR analysis to identify cell lines comprising the desired DNA modifications.

Co-Transformation for Integration of SNPs-Design of SNPs

The DNA sequence of the *Aspergillus niger* gene aygA was obtained and the proper reading frame was determined. Four distinct types of mutations were designed, which if integrated would result in a null mutation.

The mutations included a single base pair change that incorporates an in-frame stop codon, a small two base pair deletion, a three-base pair integration, and a larger 100 base pair deletion all of which if properly integrated will eliminate aygA activity. Strains lacking aygA activity have a yellow spore phenotype. The designs were generated as in silico constructs that predicted a set of oligomers that were used to build the constructs using Gibson assembly.

Integration of SNPs by Co-Transformation

Figure 22:
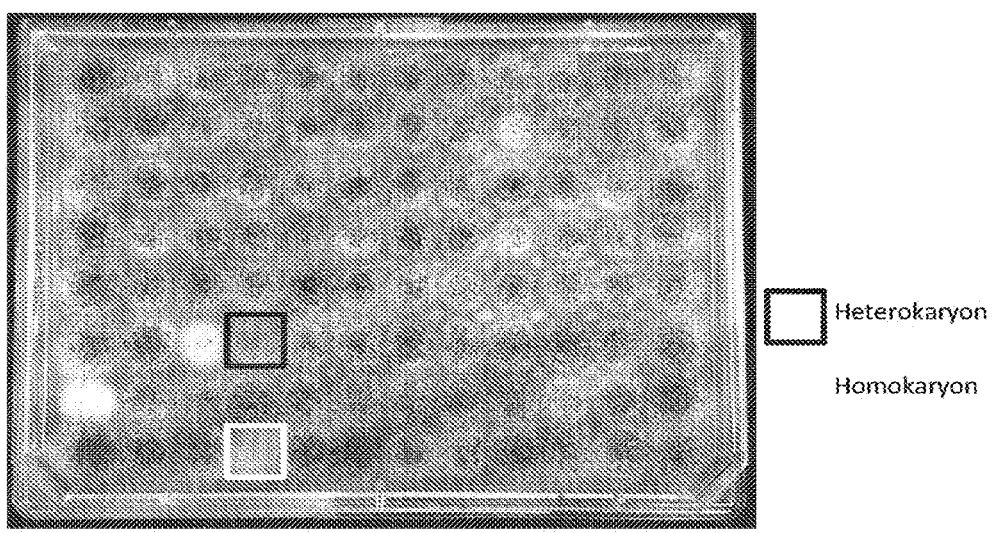
FIG. 22 depicts characterization of heterokaryons/homokaryons. In particular, this figure illustrates screening of A. niger mutant strains utilizing the aygA colorimetric gene marker by observing growth of A. niger mutant strains on minimal media following automated transformation and screening as described in Example 3. Colonies derived from homokaryotic protoplasts were pure yellow in color and lacked black spores.

Using the transformation approach described above, amplicons containing the small changes were incorporated into the genome of an *Aspergillus niger* strain 1015. As previously discussed, this strain of *Aspergillus niger* comprised a non-functional pyrG gene, and was therefore unable to grow in the absence of exogenous uracil. Cells that had successfully integrated the pyrG gene were now capable of growth in the absence of uracil. Of these pyrG+ transformants, isolates that also integrated the small mutations in the aygA gene exhibited the yellow spore phenotype. (see FIGS. 22 and 23A). The presence of the mutation was also detected through sequencing of small amplicons that contain the region targeted for the SNP exchange (FIG. 23B).

Example 5: HTP Genomic Engineering of Filamentous Fungi: Implementation of an HTP SNP Library Strain Improvement Program to Improve Citric Acid Production in Eukaryote *Aspergillus niger* ATCC 11414

Example 3 above described the techniques for automating the genetic engineering techniques of the present disclosure in a high throughput manner. This example applies the techniques described above to the specific HTP strain improvement of *Aspergillus niger* strain ATCC11414.

*Aspergillus niger* is a species of filamentous fungi used for the large scale production of citric acid through fermentation. Multiple strains of this species have been isolated and shown to have varying capacity for production of citric and other organic acids. The HTP strain engineering methods of the present disclosure can be used to combine causative alleles and eliminate detrimental alleles to improve citric acid production.

Identification of a Genetic Design Library for SNPs from Natural *A. niger* Strain Variants.

*A. niger* strain ATCC 1015 was identified as a producer of citric acid in the early twentieth century. An isolate of this strain named ATCC 11414, was later found to exhibit increased citric acid yield over its parent (see FIG. 43). For example, *A. niger* strain ATCC 1015 on average produces 7 grams of citric acid from 140 grams of glucose in media containing ammonium nitrate, but lacking both iron and manganese cations. Isolate strain ATCC 11414 on the other hand, exhibits a 10-fold yield increase (70 grams of citric acid) under the same conditions. Moreover, strain ATCC 11414 spores germinate and grow better in citric acid production media than do spores of strain 1015.

In order to identify potential genetic sources for these phenotypic differences, the genomes of both the ATCC 1015 and ATCC 11414 strains were sequenced and analyzed. The resulting analysis identified 43 SNPs distinguishing the 1015 and 11414 strains (i.e., Table 4).

Exchanging Causative Alleles

Protoplasts were prepared from strain ATCC 1015 ("base strain") for transformation as described in Example 1. Each of the above-identified 43 SNPs were then individually introduced into the base strain via the gene editing techniques of the present disclosure (see FIG. 24). Each SNP was co-transformed with the functional pyrG and aygA gene mutation as described above. Transformants that had successful gene targeting to the aygA locus produced yellow spores (FIG. 24).

Screening for Successful Integration

Transformants containing putative SNPs were isolated and a spore stock was propagated as stated above. Amplicons that contain the region of DNA containing the putative SNP were analyzed by next generation sequencing. Using this approach it is possible to determine successful integration events within each transformant even in the presence of the parental DNA. This capability is essential to determine targeting in fungi which can grow as heterokaryons which contain nuclei with differing genotype in the same cell.

Figure 25:
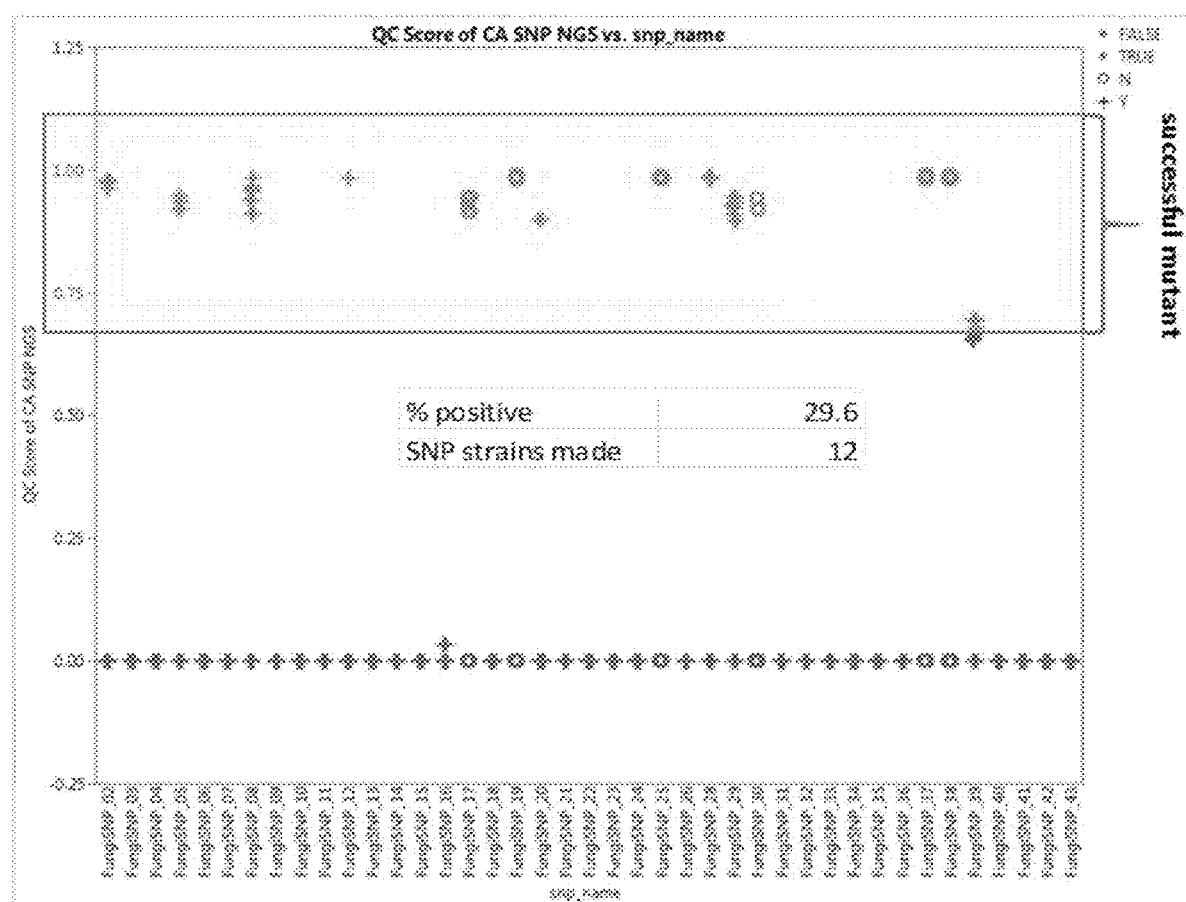
FIG. 25 depicts a quality control (QC) chart identifying successful *A. niger* mutant transformants (top box) based on next generation sequencing results. Overall 29.2% of yellow colonies selected from the culture plates exhibit the expected SNP genetic change.
Figure 26:
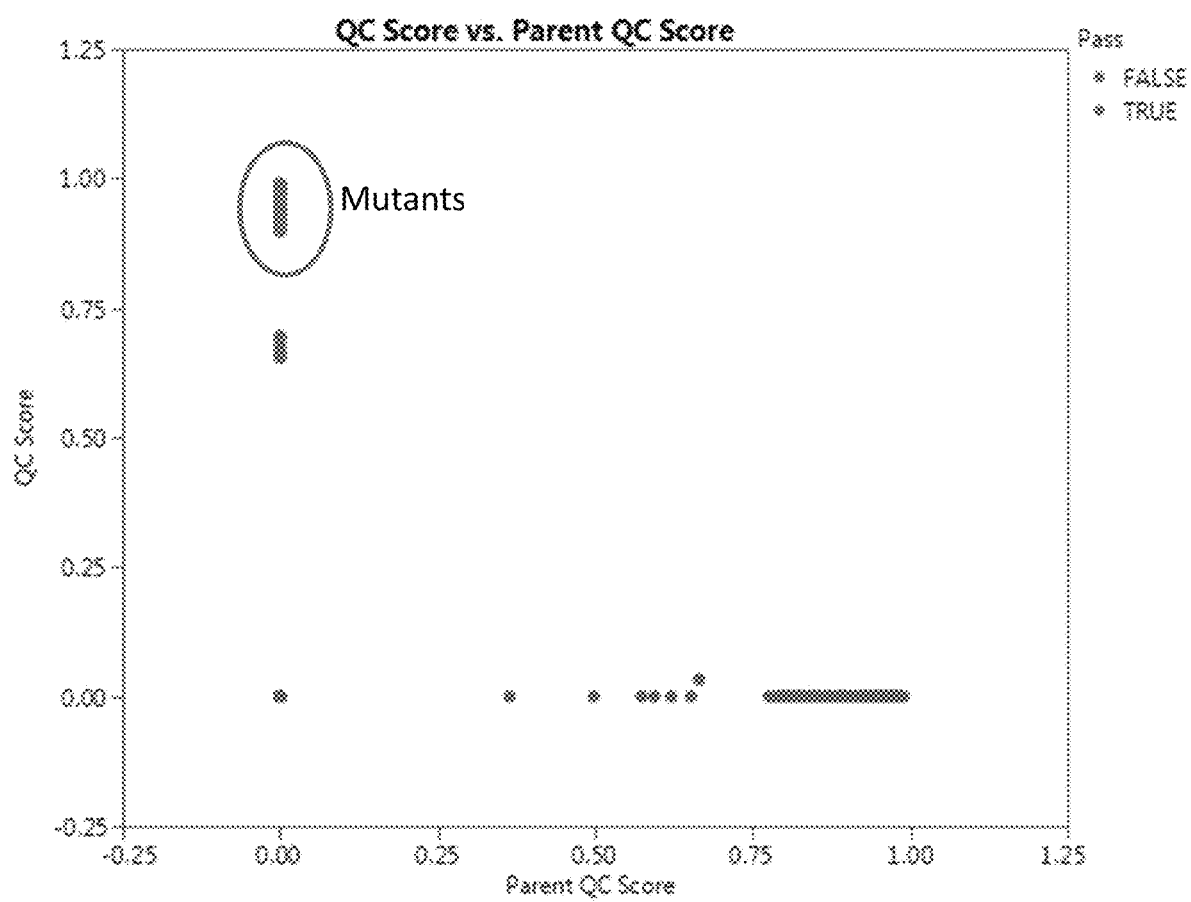
FIG. 26 depicts the results of next generation sequencing of transformed *A. niger* mutants. The X-axis represents the target DNA's sequence identity with the untransformed parent strain. The Y-axis represents the target DNA's sequence identity with the expected mutation. Data points towards the bottom right of the chart exhibit high similarity with the parent strain, and low similarity with the expected transformed sequences. Data points towards the top left of the chart exhibit high similarity to expected transformed sequences and low identity with parent strain. Data points in the middle likely represent heterokaryons with multiple nuclei.

Transformants were further validated for presence of the desired SNP change. The cotransformants that had the yellow spore phenotype also contained proper integration of the citric acid SNP in approximately 30% of the isolates (FIGS. 25 and 26).

Next, the created SNP swap microbial strain library will be phenotypically screened in order to identify SNPs beneficial to the production of citric acid. The information will be utilized in the context of the HTP methods of genomic engineering described herein, to derive an *A. niger* strain with increased citric acid production.

Example 6: HTP Genomic Engineering of Filamentous Fungi: Demonstration of the Ability of Next-Generation Sequencing (NGS) to Detect SNPs in Filamentous Fungi with Different Genetic Backgrounds This example demonstrates an example of how NGS can be used to detect target gene mutations in a specific background of the target gene parental strain.

In order to test the sensitivity of sequence based screening vs. phenotypic screening, a pair of strains that differ by a single SNP in a target gene (or test domain) were mixed at known ratios and grown in 96-well microtiter plates. The strains used were the parental strain (pyrG−, met+, (P)) and the mutant strain (pyrG+, met−, (M)). The parental strain spores appear black or dark in color when grown on minimal media (MM), while the mutant strain spores appear yellow or light in color when grown on MM. The ratios of P:M tested were 1:0, 10:1, 5:1, 1:1, 1:5, 1:10, and 0:1). As shown in FIG. 33, when plated on MM supplemented with uracil (+UU) and devoid of methionine (−met), only parental spores (P) grow, whereas only mutant spores (M) grow on MM with met (+met) and devoid of uracil (−UU). As seen in FIG. 33 and the plate at the top of FIG. 35, when plated on MM that is +UU and +met, both P and M spores grow such that even the lowest ratio (1:10) of P/M spores produced black colonies that were visually identical to the highest ratio (10:1) of P/M spores. In other words, a single base pair mutation in the avgA gene (M spores) results in the presence of yellow spores; however, the presence of just a few nuclei containing the parental avgA gene (P spores) resulted in colonies that contain black spores. Accordingly, it was difficult to score colonies with small amounts of parental spores on non-selective media as harboring the mutant gene via phenotypic screening. In other words, the presence of the mutation was masked by even a small number of copies of the parental gene therefore highlighting the limitations of phenotypic screening in filamentous fungal hosts.

In order to address the limitations of phenotypic screening, the presence of a target gene mutation was assessed using NGS sequencing in each of the wells in the 96 well plate from FIG. 33. Here, the nucleic acid from the pairs of strains that differed by a single SNP in the test domain used in FIG. 33 were using the boil preparation method described herein. DNA extraction was performed in a 96-well microtiter plate format whereby a replicate plate was created from the plate in FIG. 33 such that DNA extraction was performed in each well of the replicate plate and the isolated DNA was subsequently transferred to an additional microtiter plate using automated liquid handling system (e.g., Agilent Bravo system) in which Illumina based sequencing (NGS sequencing) was performed in each well. As can be seen in FIG. 34, NGS sequencing was able to detect the presence of parental and mutant DNA as well as mixtures thereof, whereby the NGS data clearly showed mixtures of single base pair changes in the same sample. Given that the experiments performed in both FIGS. 33 and 34 were performed using growth conditions that did not force homokaryon status, the data showed that NGS sequencing can be utilized as a quality control step during a strain building process in order to assess the efficiency or frequency of transformation/cotransformation for a particular construct(s) in a particular strain under particular growth conditions. In other words, NGS can be used to assess or determine the purity of a particular transformant. In some cases, NGS can be used to determine if selection/counterselection is necessary for a particular transformant.

In order to assess the ability for NGS to detect the presence, absence or percentage of mutant vs. parental target genes following a selection scheme, the parental, mutant and mixed mutant/parental spores from the experiment depicted in FIG. 33 were grown under conditions that forced the presence of colonies that were homokaryotic for either the mutant or parental genotype. More specifically, some of the mixed populations were grown on media that favored the parental genotype or nuclei (i.e., minimal media supplemented with uracil and devoid of methionine), while some of the mixed populations were grown on media that favored the mutant genotype or nuclei (i.e., minimal media supplemented with uracil and devoid of methionine). As can be seen in FIG. 35, selective media forced mixed populations of nuclei to homokaryon status for either parental nucleic when grown on minimal media supplemented with uracil and devoid of methionine or mutant nuclei when grown on minimal media supplemented with uracil and devoid of methionine). Further, this forcing of homokaryon status by selection was easily detected by NGS. NGS readily detected populations that were entirely homokaryotic for a specific type of nuclei as well as mixtures thereof. Accordingly, NGS can be used during a strain build process as provided herein in order to assess the efficacy of a particular selection/counterselection scheme. This can be particularly useful when the introduction of specific mutations does not generate a discernable phenotype or a phenotype that can be masked by even low percentages of nuclei containing the parent genotype. This example also illustrates the utility of NGS as a method for screening transformants either alone or in combination with phenotypic screening in order to isolate transformants homokaryotic for an introduced DNA insert or transformants with a threshold percentage of nucleic harboring the introduce DNA insert. The threshold percentage can be a percentage whereby said transformant produces a desired level of a product. The product can be any product known in the art. The product can be selected from a product in Table 2. The threshold percentage can be 50%, 55%, 60%, 65%, 70%, 75%, 80%, 85%, 90%, 95%, 99% or 100%.

Example 7: HTP Genomic Engineering of Filamentous Fungi: Demonstration of the Ability of Next-Generation Sequencing (NGS) to Detect SNPSWP in Filamentous Fungi This example demonstrates an example of how NGS can be used to detect target gene mutations in a specific background of the target gene parental strain. A general scheme of the entire process for the SNP swapping and screening methods can be found in FIGS. 20B-C.

Figure 38A:
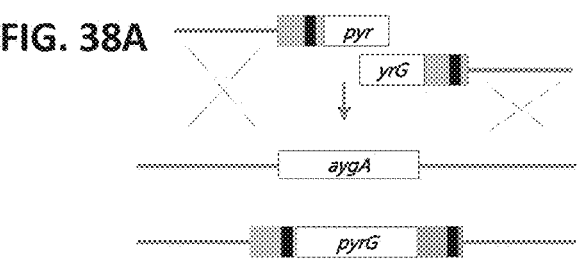
FIGS. 38A-C depicts use of NGS sequencing to detect multiple integrations, ectopic integration or the presence of SNPs and non-SNPs in the same nuclei.
Figure 38B:
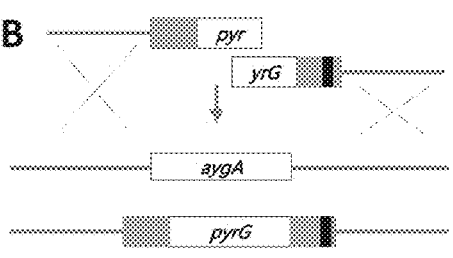
Figure 38C:
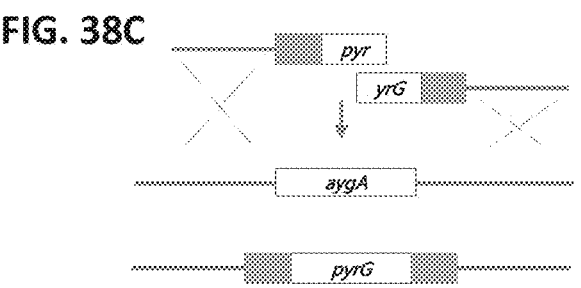

As shown in FIGS. 38A-C, in order to test the ability of sequencing based screening using NGS to detect multiple integration, ectopic integrations and/or the presence of SNPs and non-SNPs in the same nuclei, three different scenarios where specific constructs will be introduced into the aygA locus of a host A. niger genome via homologous recombination will be examined. In the first scenario, a pyrG marker gene is split between two constructs such that an overlapping portion of the pyrG gene is present on both constructs. The first construct further comprises sequence homologous to the aygA gene present in the host genome is present 5' to the pyrG gene, while the second construct further comprises 3' to the portion of the pyrG gene, sequence homologous to a second portion of the host aygA gene. In both constructs, the sequence homologous to the aygA gene further comprises a mutation (i.e., SNP). The second scenario utilizes two constructs similar to those in the first scenario but only the second construct comprises a mutation (i.e., SNP) in the sequence homologous to the aygA gene. Finally, the third scenario utilizes two constructs similar to those used in the second scenario but neither the first or second construct comprise a mutation (i.e., SNP) in the sequence homologous to the aygA gene.

The A. niger host will be cultivated, protoplasts of A. niger will be generated and each of the constructs will be transformed into the protoplasts using the methods described in Example 4. Following transformation, transformants will be phenotypically screened for the presence of the intact aygA gene (black spores) or loss of the intact aygA gene (yellow spores). Additionally, each of the transformants will be replicate plated and the DNA from the replicate plate will be extracted and screened using NGS as described in Example 6. The expected results for both the phenotypic and sequence-based screening are outlined in FIGS. 38A-C.

Figure 4:
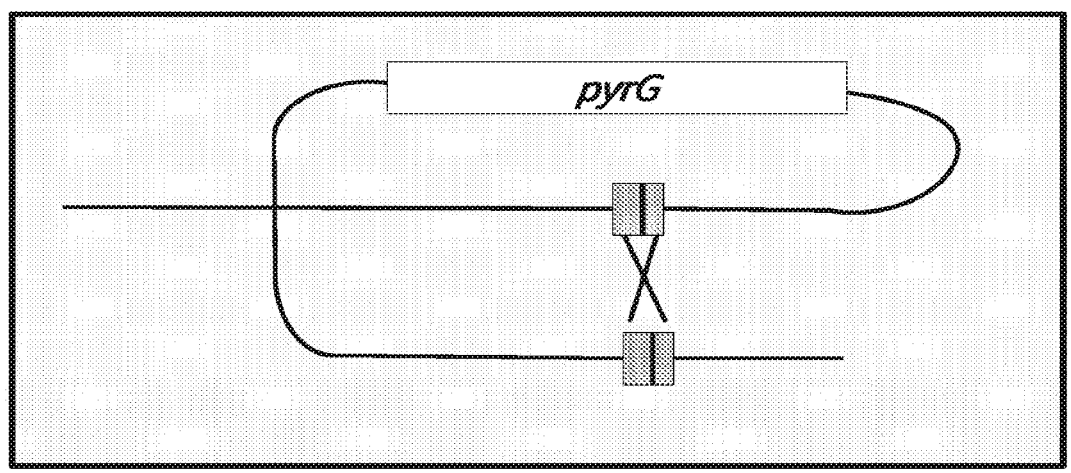
FIG. 4 illustrates that the direct repeats flanking the marker gene are unstable and will result in marker removal through homologous recombination between the direct repeats. Essentially, the loop-out is facilitated by direct repeats that were incorporated into the transforming DNA. Cells counter selected for the selection marker contain deletions of the loop DNA flanked by the direct repeat regions.

Example 8: HTP Genomic Engineering of Filamentous Fungi: Demonstration of SNPSWP in Filamentous Fungi Using Split-Marker Loop-Out This example demonstrates a proof of principle for a SNP SWP method in filamentous fungal cells using a split-marker loop-out procedure as shown in FIGS. 3-4. A general scheme of the entire process for the SNP swapping and screening methods can be found in FIGS. 20B-C.

In Examples 4 and 5, targeted SNPSWP in filamentous fungi was performed by transformation of the host using two linear fragments of DNA. One of the fragments contained a selectable marker that allows for the isolation of cells that have taken up the DNA. The second independent fragment contained the single base pair change that was to be tested for influence on the desired phenotype. In this Example, two fragments are used; however, these fragments both contain the SNP within a direct repeat of DNA that flanks the marker gene. Each fragment only contains one half of the selectable marker. If the fragments integrate independently they will not reconstitute the marker gene and no transformants will arise. When the marker recombines to form a functional gene, it will do so through non-homologous end joining. When this occurs it will be much more likely that the flanking sequences will also properly integrate at the targeted locus. Once the marker has integrated at the locus the direct repeats will provide an unstable integration that can result in the loss of the marker sequence. Strains that have lost the marker will leave behind the desired SNP in the proper position and context relative to the gene. Ultimately, the approach described in Examples 4 and 5 can be used when the SNP is within an essential gene and disruption of the gene may be lethal. In the approach of Examples 4 and 5, the targeting efficiency of the cotransformation can vary between 5-15%. In contrast, the method of this Example can be desirable because the marker is linked to the SNP and targeting efficiency is near 100%.

Figure 20B:
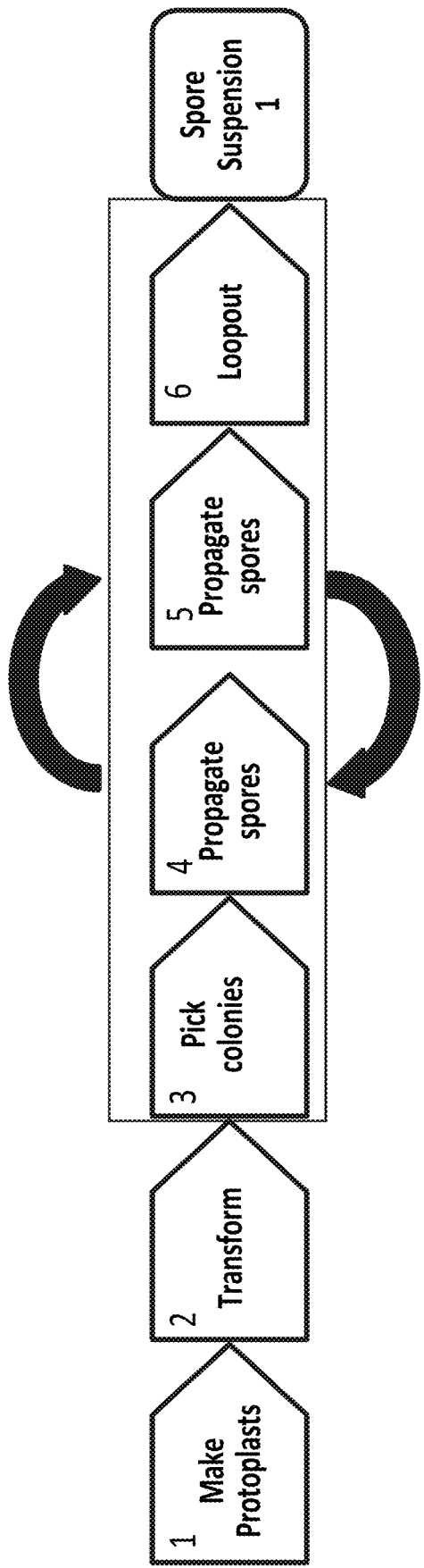
FIG. 20B illustrates steps in the process of SNP/PRO/STOP swapping in filamentous fungi.
Figure 20C:
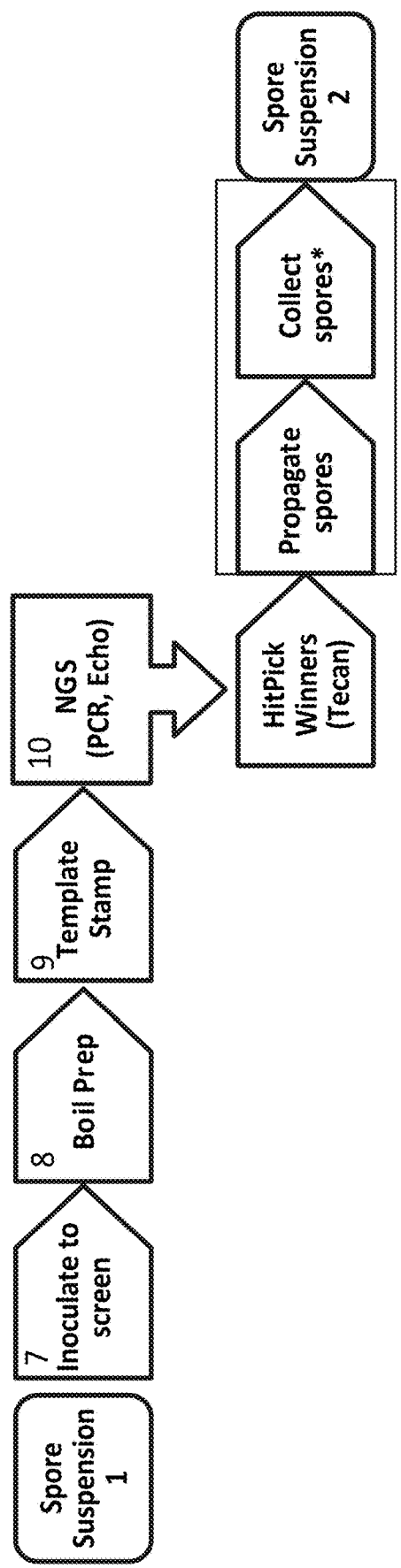
FIG. 20C illustrates steps in the process of screening the transformants for proper integration using any of the swapping methods provided throughout this disclosure.
Figure 46A:
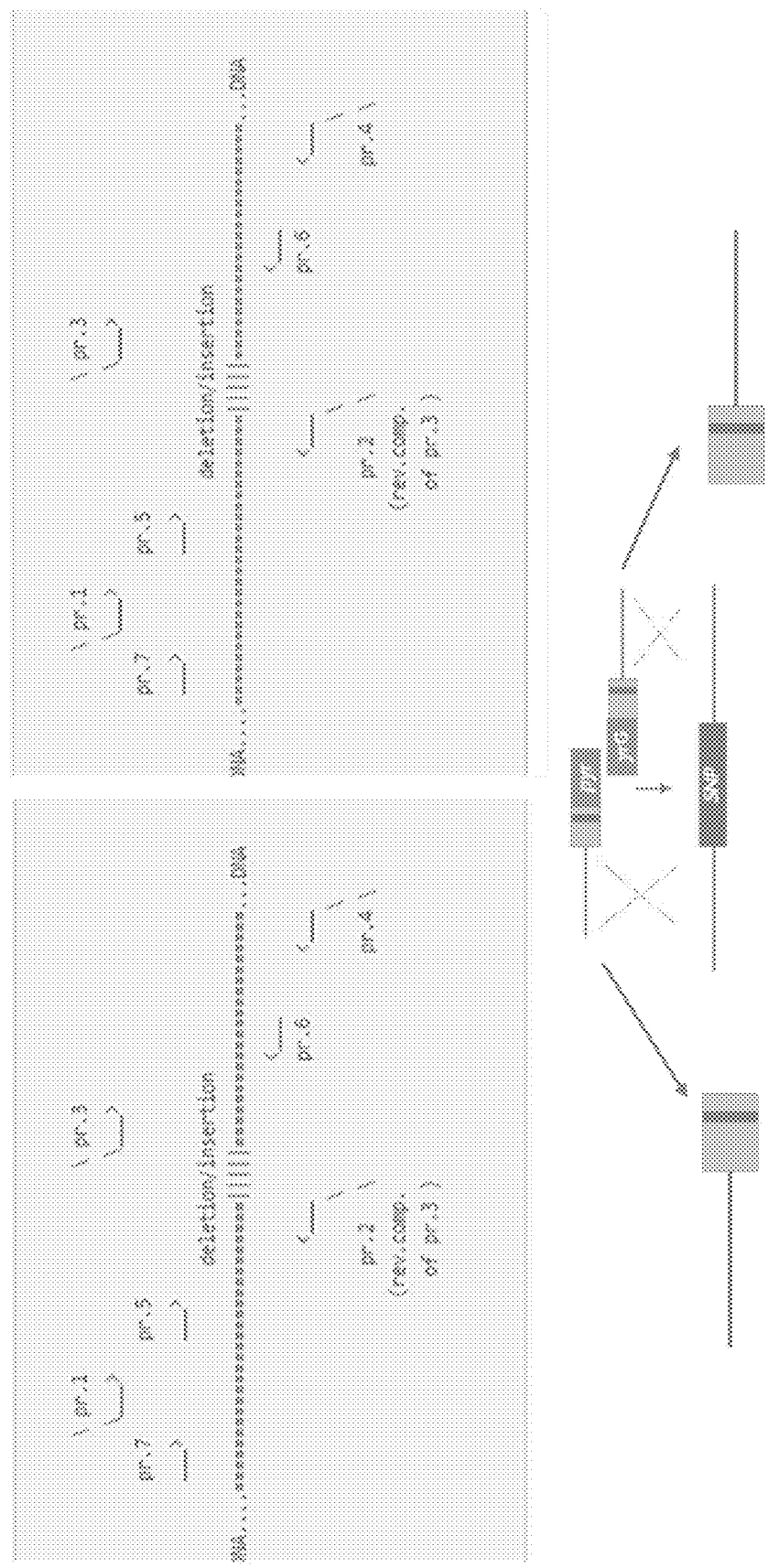
FIG. 46A-B illustrates design and generation (see FIG. 46A) as well as quality control analysis using a fragment analyzer (see FIG. 46B) of split-marker constructs generated as depicted in FIG. 45.
Figure 46B:
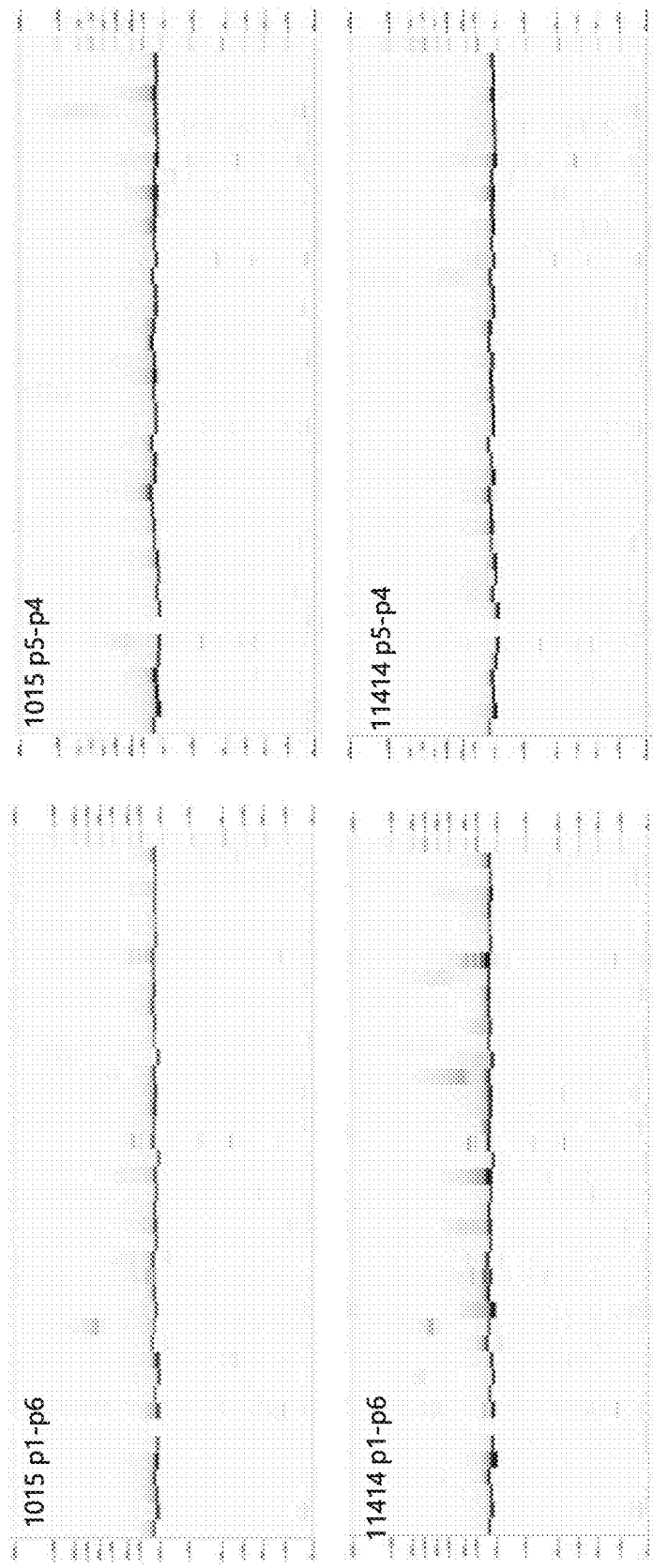

To perform the method of this Example, A. niger host cells from a 1015 parental strain and a 11414 parental strains were cultivated, converted to protoplasts, and transformed as described in Example 4 above and shown in the scheme depicted in FIG. 20B-C. In this Example, as shown in FIG. 46A, the protoplasts from each parental strain were co-transformed with two constructs ("split-marker constructs"), wherein each of the two constructs contained an overlapping portion of a selectable marker (i.e., pyrG in FIGS. 45 and 46A) and were flanked by direct repeat sequence comprising a target SNP. The split-marker constructs were generated using fusion PCR as depicted in FIGS. 45 and 46A and were quality controlled (QC'd) using a fragment analyzer as shown in FIG. 46B. Moreover, each of these constructs contained sequence flanking the direct repeat portions of each construct in order to direct integration into a target SNP in the host cell genome. Correct integration was assessed by screening the transformants using sequence-based screening as described herein.

Genetic Engineering Using a Split-Marker Approach

Figure 60:
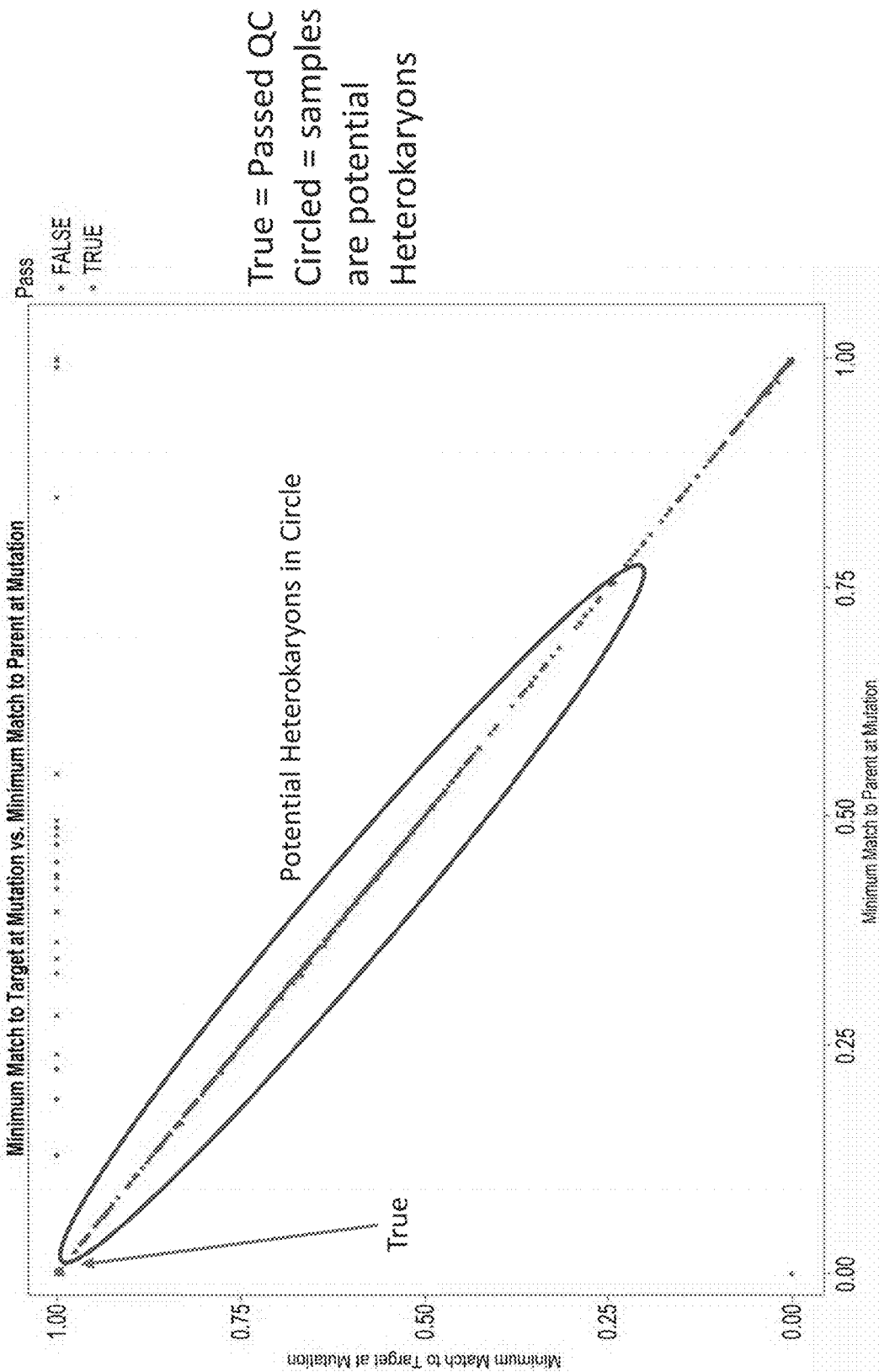
FIG. 60 illustrates the results of *A. niger* split marker design transformation and validation according to the methods of the present disclosure. The data was generated using NGS of transformed (via split marker) *A. niger* mutants and is a distribution of the match to the mutation at the target vs. match to parent at the target. Every sample in the top left corner of this graph are correct and have passed QC. The samples within the circle contain both the mutant and parent at the locus and may be processed again through steps 4 and 5 of FIG. 20B in order to generate isolates that may pass QC.

The initial steps of the split marker mediated SNP exchange were as shown in FIG. 20B as steps 1 and 2. In step 2, the transforming DNA consists of two separate linear fragments that contain non-complementary halves of the marker fused to homologous DNA for targeting the SNP to the proper locus. The transformations were placed onto selective media and allowed to grow. Properly complemented strains that have stable integration of the DNA formed colonies. These colonies were picked either by hand or by an automated platform to individual wells in a microtiter plate which contains 100-200 microliters of selective agar media. The picked transformants were allowed to grow and propagate spores as indicated in step 4. The spores of A. niger are uninucleate and are inherently clonal. The transformed strains were purified to homokaryon (all nuclei in the cell are of identical genotype) by taking small numbers of spores and plating them again onto selective media. This process is represented by arrows in FIG. 20B. Repeated reduction of the population to small numbers of clonal spores resulted in a homokaryon in each well. These purified strains in wells were then plated to media containing a counterselection agent that was toxic to strains that contain the selectable marker. Strains that took up the marker that is flanked by the direct repeats containing the SNP lost the markers at a frequency that directly correlated to the size of the direct repeats. For example, a 1,000 base pair direct repeat is less stable than a 100 base pair direct repeat. This loop out phase is step 6 in FIG. 60. FIG. 60 contains data from a SNPSWP campaign that was performed utilizing spilt marker integration and loop out.

Results

Figure 61:
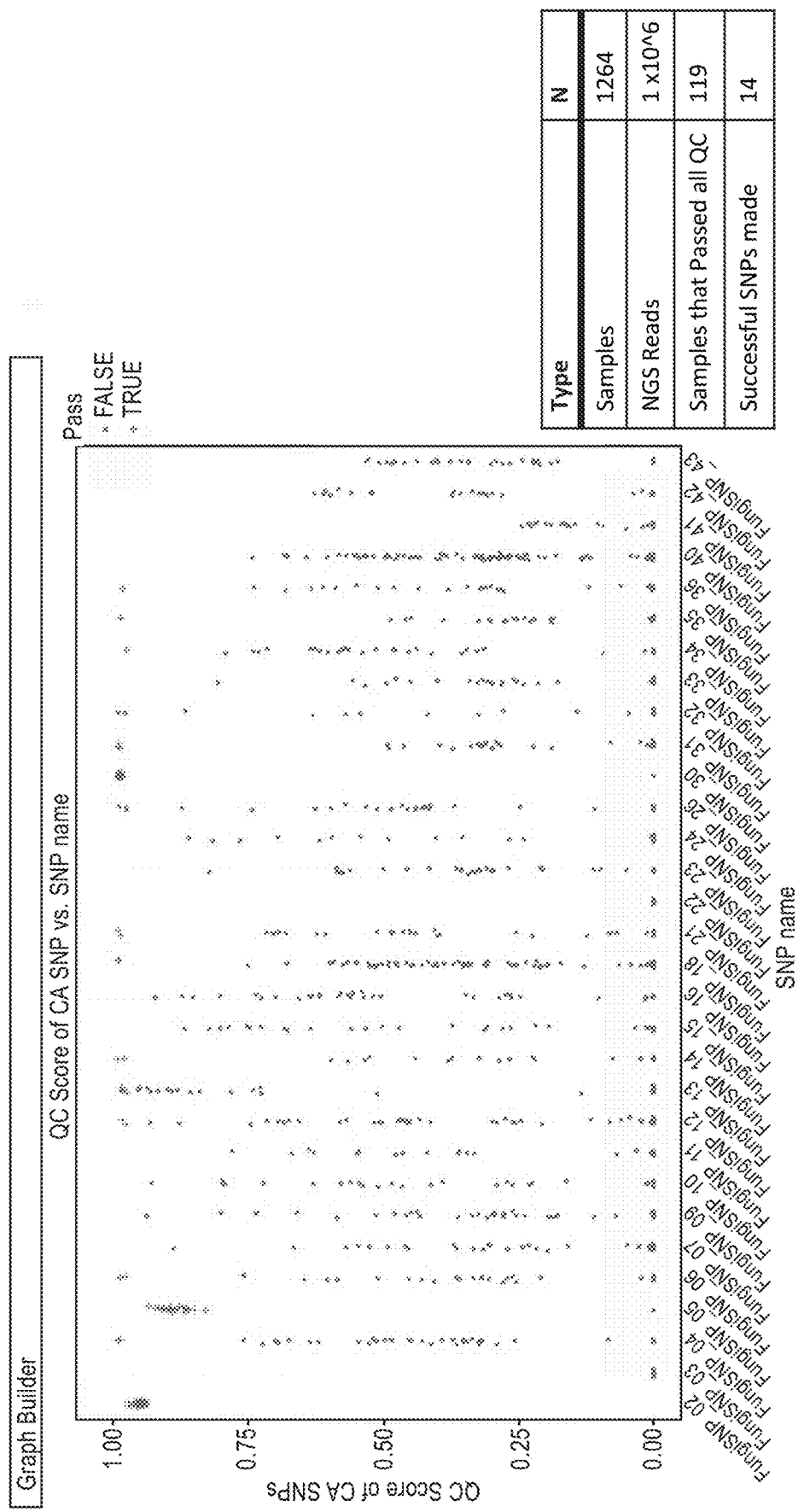
FIG. 61 is a graphic representation of the NGS data from a SNPSWP campaign. In this example, 31 loci were targeted using constructs designed as presented in FIG. 45. Here 1264 total isolates were screened by sequencing each amplicon populations from all individual samples. This data set contained over one million sequenced amplicons. There were 119 samples that passed all QC requirements. Quality control includes checking for the presence of parental mutation at the loci and all of the amplicons from the well must match the target DNA across the entire amplicon. Samples with the + symbol are correct, samples that have the dot symbol may contain both the parent and the mutation.

In this example over 1200 individual looped out samples were screened using NGS. From this set, 119 successful strains were generated and appeared as dots in the upper left corner of FIG. 60 because 100% of the amplicons from that well contained the SNP from the production strain. The samples designated in the circled area contained both amplicons with the desired SNP and the native base pair at this locus. These strains may be made homokaryotic using the spore propagation and passing represented in steps 4 and 5 in FIG. 20B. The 119 samples that have passed QC can be analyzed for their impact on desired strain improvement traits. The success rate of SNP introduction across various SNP positions is shown in FIG. 61.

Example 9: Non-Homologous End Joining (NHEJ) and HR-Mediated Genomic Editing of Filamentous Fungi Using Cas9 Ribonucleic Acid Protein (RNP) Transformations Enable SNPs, Insertions, and Indels without Direct Selection for the Desired Edits This example demonstrates an additional means of facile genomic editing in an NHEJ proficient background, without direct selection for the desired edit. Such a method may be useful for high throughput genomic editing by enabling rapid creation of genomic edits without selecting for the edit or looping out a selectable marker.

Two crRNA sequences were designed targeting the AygA gene. Disruption of this gene results in a null mutation, creating strains that generate yellow-pigment containing spores, rather than black wildtype spores. Disruption could be enabled by NHEJ-mediated error-prone repair or by providing a homologous recombination donor that disrupts the gene's translation.

Figure 47:
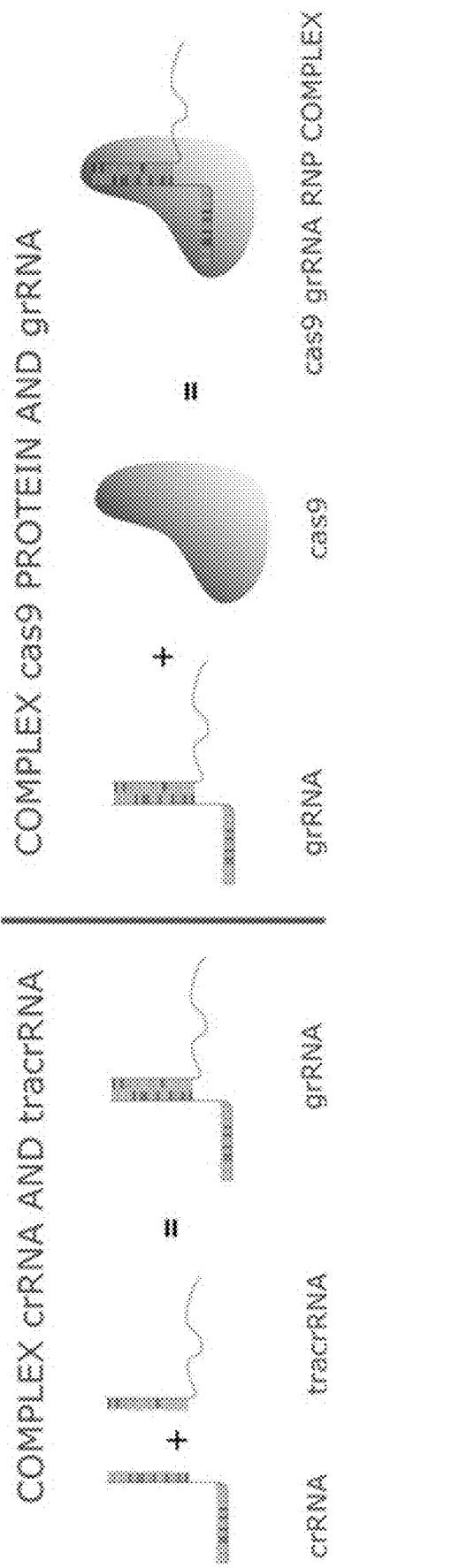
FIG. 47 illustrates the annealing of crRNA to tracrRNA and complexed to Cas9 protein, thereby creating an RNP capable of crRNA-directed DNA cleavage.

Assembly of Cas9 RNPs (FIG. 47). Chemically modified crRNA (see Table 6) and tracrRNA (obtained from Synthego) were brought to 250 pmol/μL in nuclease free TE buffer. 5 μL of crRNA (250 μM) and 10 μL tracrRNA (250 μM) were mixed with 10 μL of 5× annealing buffer (Synthego) and brought to 50 μL of H₂O. Samples were annealed by bringing the mixture to 78° C. for 10 minutes and then 37° C. for 30 minutes. Samples were then allowed to come to room temperature over 15 minutes. Cas9 RNPs were made by mixing 1 μL of 3.22 μg/IL EnGen Cas9 (obtained from New England Biolabs) with 1.5 μL of crRNA/tracrRNA complex (25 μM) in 0.7 uL STC buffer (1.0M sorbitol, 50 mM Tris, pH 8.0, 50 mM CaCl₂). This was a ratio of 1.875 mol of RNA complex/1 mol Cas9 and a total concentration of Cas9 of 1 μg/μL. Complexes were formed by incubation at room temperature for 10 minutes.

Figure 48:
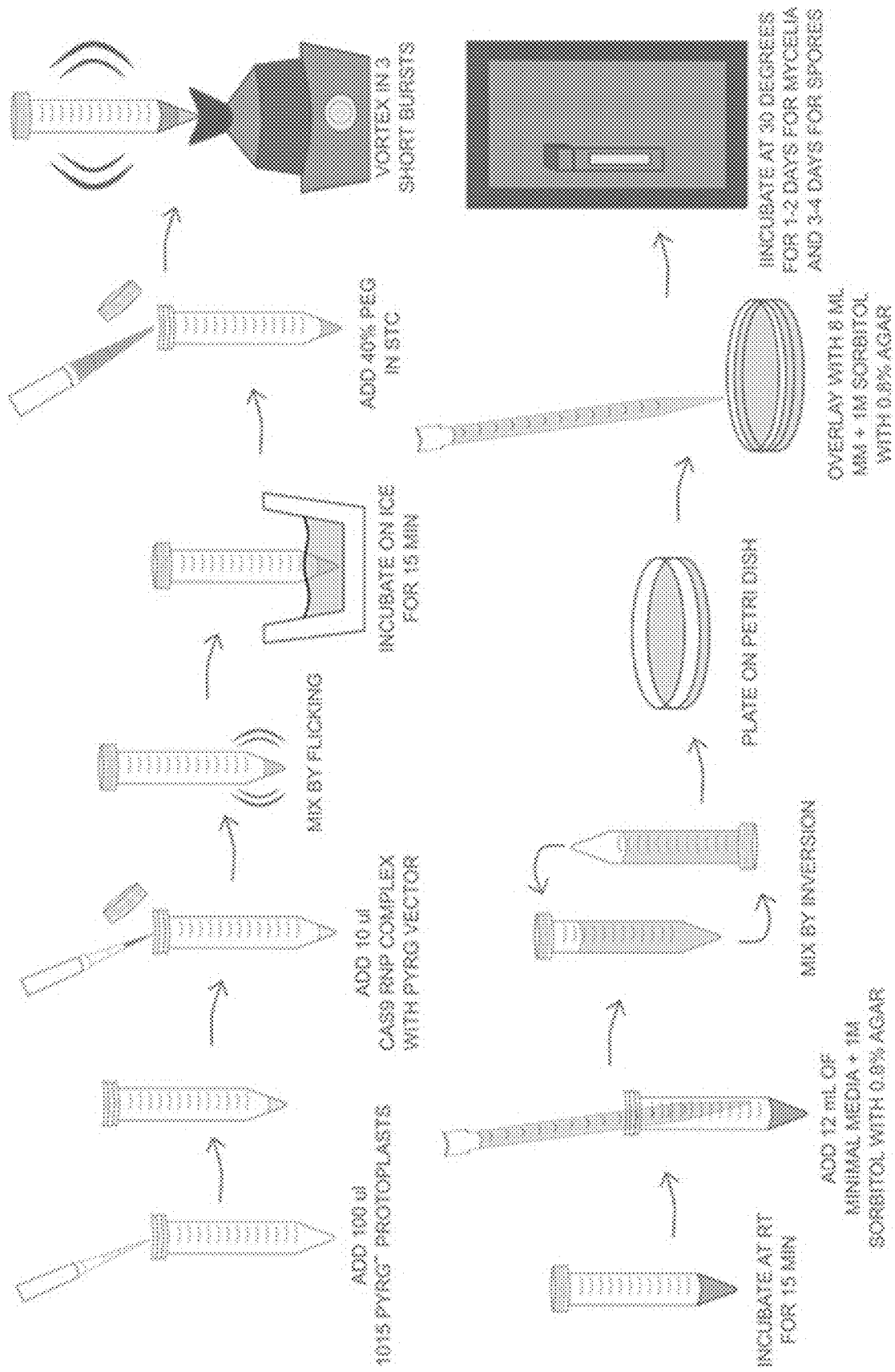
FIG. 48 illustrates the method for transforming RNP into *Aspergillus niger* protoplasts. 100 uL or 10^6 protoplasts (PyrG−) are transformed with RNP and a plasmid containing a PyrG marker in 10 ul of STC buffer. These are mixed and incubated on ice for fifteen minutes. The cells are then mixed with 40% PEG in STC and placed at room temperature for 15 minutes. Transformants are mixed in osmotically stabilized minimal media with +0.8% agarose and overlayed with additional agar. Colonies are then counted and scored for changes in phenotype caused by RNP-mediated genome editing (not shown).

Transformations were performed by first making a 2 fold dilution of the RNP complex in STC. Then, 1 μL of this complex (containing 0.5 ug Cas9) was mixed with 500 ng of vector containing the AMA1 origin and pyrG from *A. fumigatus* up to a total of 10 μL in STC. This RNP mixture was added and mixed to 100 μL of thawed protoplasts of 1015 (PyrG−) (i.e. 1015 *Aspergillus niger* strain) prepared and frozen as described as in Example 1. After the incubation on ice, 1 mL of room temperature 40% PEG 4000 made in STC was then added to the protoplast RNP mixture, which was vortexed and incubated at room temperature for 15 minutes. Protoplasts were then mixed with 12 mL melted minimal media+1M sorbitol and 0.8% agar and plated on 10 cm petri dishes. After solidifying, transformations were overlayed with an additional 8 mL of the melted minimal media+1M sorbitol and 0.8% agar. A 10× dilution of transformants were also plated as above (FIG. 48).

TABLE 6 crRNA protospacer sequences

| SEQ ID NO: | crRNA name | crRNA protospacer sequence |
|---|---|---|
| 6 | aygA.1 | UCAGUCUAUCCGUUUCACGA |
| 7 | aygA.3 | UUCCCACGAAGCGAUCACGG |
| 8 | control | AUGUGUCAGAGACAACUCAA |

For cotransformations with two crRNA/tracrRNA/Cas9 complexes, crRNA and tracrRNA pairs were annealed separately and complexed to Cas9 separately. After complexation, equal amounts of Cas9 complexed to crRNA/tracrRNA were mixed together before transformation.

For homologous recombination experiments, donor was created by amplifying gBlocks via PCR and purification. Purified product (800 ng) was added to the RNP and plasmid and transformed as above. RNP cleavage upregulated DNA repair mechanisms, stimulating HR with the exogenously provided donor. The homologous recombination donor sequences were designed to contain a mutated region flanked by 400-500 bp of homology to the AygA gene around the ayg.1 crRNA protospacer cut site. Sequences show the two homologous donors used in this experiment. DJV_03_pyrG_insertion_in_AygA shows pyrG with promoter and terminator (lowercase) flanked by 5' and 3' regions of homology (uppercase) to the AygA gene (FIG. 51, SEQ ID NO:9). Regions of homology flank the predicted cut site of crRNA protospacer AygA.1. DJV_07_4 bp_insertion_in_AygA contains a 4 bp insertion (lowercase) flanked by 5' and 3' regions of homology (uppercase) to the AygA gene (FIG. 52, SEQ ID NO:10).

Phenotypes were determined by: (1) counting colonies and later scoring the color of conidiating colonies, (2) Picking colonies prior to conidiation and then scoring individual isolated colonies after conidiation, or (3) isolating individual spores 5-7 days after transformation and allowing these spores to germinate and conidiate. FIG. 49A-F shows the results of colony counting and scoring of phenotypic color changes in conidia; using method 1, it was estimated that 35-40% of transformed colonies produced yellow conidia. Genotypes were determined by inoculating 20 μL yeast mold media with spores from one of these three methods in a static incubator at 37° C. overnight in a wet chamber. Cultures were lysed by mixing 50 μL prepman ultra sample preparation reagent and incubating mixtures at 98° C. for 30 minutes followed by centrifugation to pellet lysate.

Figure 49E:
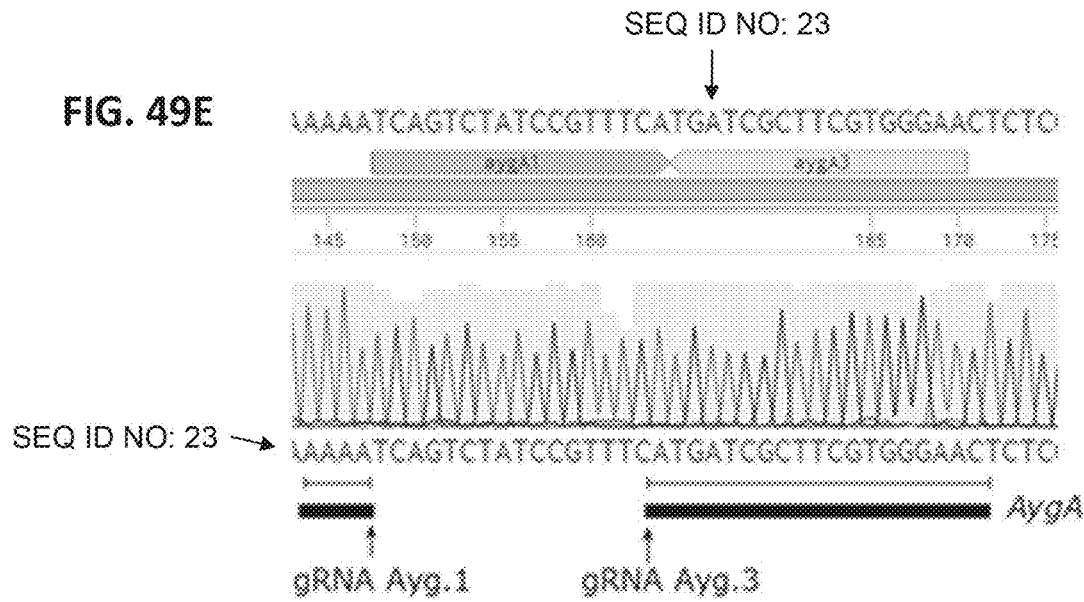
Figure 49F:
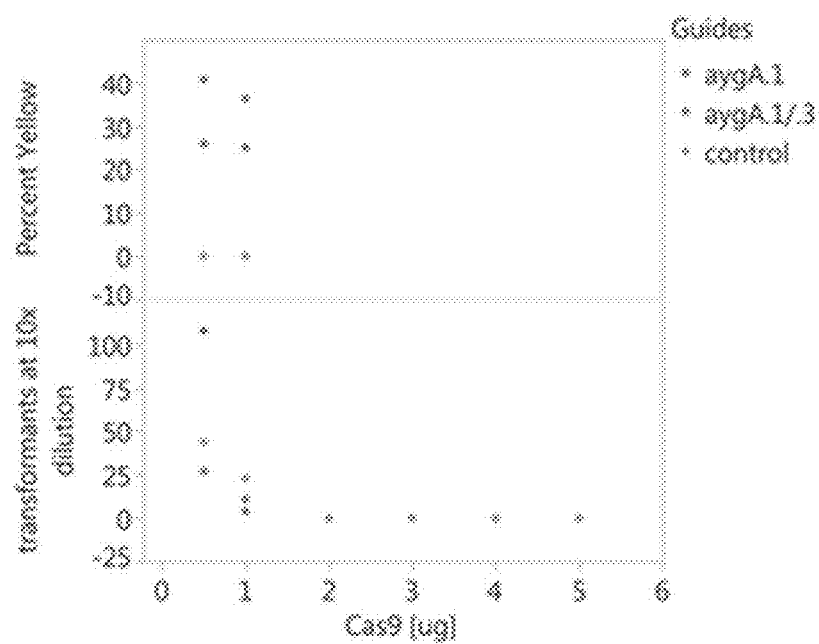
Figure 50A:
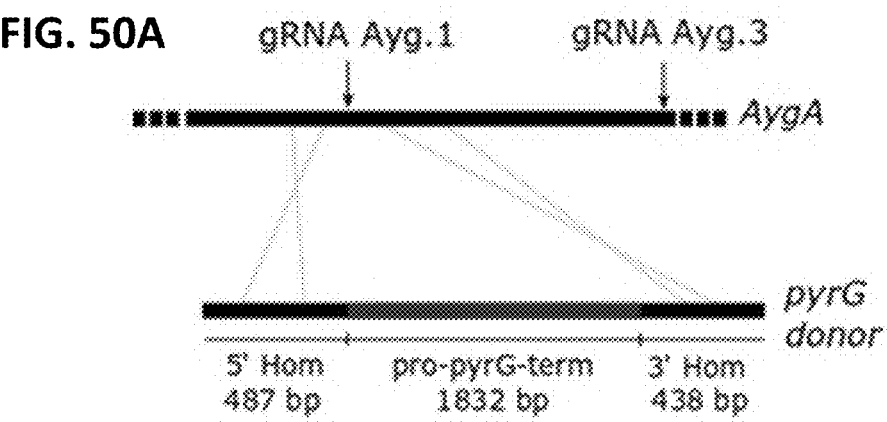
FIG. 50A-50C illustrates the measurement of the efficiency of HR mediated by linear donors and an RNP targeting the genome. Protoplasts are co-transformed Cas9 complexed to one (Ayg.1) or two (Ayg.1+Ayg.3) cr/tracrRNAs targeting the AygA gene as well as a linear donor and a plasmid containing pyrG. The donor is flanked with 487 or 438 bp of homology around the Ayg.1 cut site. The donor contains (FIG. 50A) a pyrG gene with a promoter and terminator or (FIG. 50B) a 4 bp insertion. The AygA locus was PCR amplified from single germinated spores (FIG. 50C). Results demonstrate that contransforming RNPs, plasmid and a donor mediates insertion of the pyrG gene in the presence of targeted crRNA but not control crRNAs. This experiment also shows that an RNP co-transformation with donor from (FIG. 50B) enables an 86% HR editing rate.
Figure 50B:
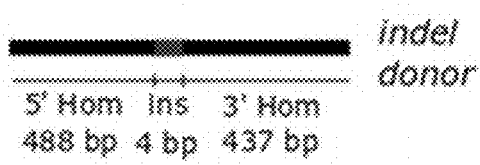
Figure 50C:
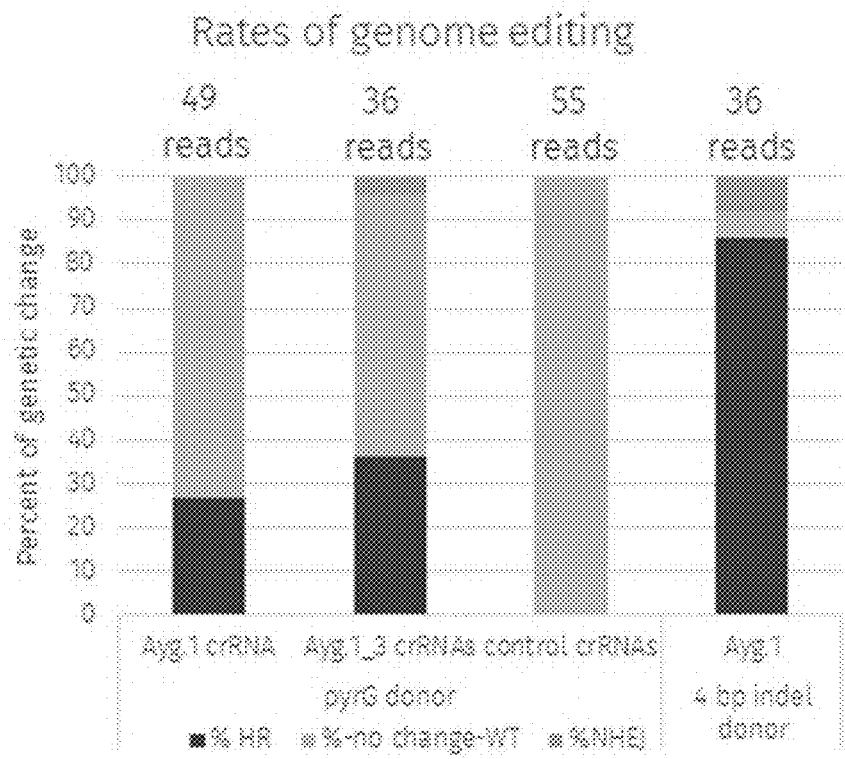

Regions flanking a cut site or cut sites were amplified and sequenced by Sanger chemistry (FIG. 49D and FIG. 49E). The resulting sequenced amplicons were used to confirm the presence of NHEJ-mediated indels in yellow conidia. To test for homologous recombination, PCR primers were designed such that the forward primer annealed upstream of the genomic region that is homologous to the repair fragment, while the reverse primer annealed within the region homologous to the repair fragment. This PCR scheme ensures that only genomic DNA and not an unintegrated donor could result in a PCR amplicon at the AygA locus. For homologous recombination assays, spores, sorted via the CellenONE, were phenotyped and subsequently genotyped; pyrG payloads were inserted at an efficiency of 26-36%, 4 bp payloads were inserted with an efficiency of 86% (FIG. 50A-C).

Example 10: HR-Mediated Genomic Editing of Filamentous Fungi Using Cas9 Ribonucleic Acid Protein (RNP) Transformation to Introduce Single SNP without Scrambling PAM Site This example demonstrates an additional means of facile genomic editing in an NHEJ proficient background using Cas9 RNP-complex transformation to introduce a single SNP without scrambling or altering the PAM site and without direct selection for the desired edit. Such a method may be useful for high throughput genomic editing by enabling rapid creation of genomic edits without selecting for the edit or looping out a selectable marker.

Transformations were performed by mixing 0.2 µg EnGen Cas9 (complexed to an annealed Ayg.1 cr/tracRNA) to 350 ng of a double stranded DNA donor and 200 ng of vector containing the AMA1 origin and pyrG from *A. fumigatus*, brought to 4 µL in STC buffer. This was added to 40 µL of protoplasts and transformed as in Example 9. Double stranded donor DNA encoded for a single nonsense mutation flanked on the 5' and 3' side by 50 bp of homology to the AygA gene (see FIG. 56A, SEQ ID NO: 24); the donor was made by annealing two complementary oligos. Individual colonies were picked, and spores from colonies were used to grow, isolate and PCR amplify genomic DNA. Of 24 colonies isolated, 2 contained mixtures of black and yellow spores, 2 contained only yellow spores and only 20 contained black spores. Eight of twenty-four sequences were successfully PCR amplified and were sequenced. Of these, three of eight sequences examined contained the desired mutation without additional mutations (see example wildtype (SEQ ID NO: 25) and mutant (SEQ ID NO: 26) traces in FIG. 56B). The remainder of the sequences were wildtype AygA genes. As a result, this Example demonstrates that two annealed oligos can create a SNP without altering the PAM or seed region of the protospacer site.

Example 11: Purification of Transformed Fungal Strains into Clonal Populations at Scale Many filamentous fungi have a stage in their life cycle in which vegetative growth includes a state in which multiple nuclei are present in individual cells. This has a consequence on the ability to genetically manipulate these organisms. Any genetic changes in one nucleus must be made clonal by purification away from nuclei that do not contain the desired mutation. One method for separating these nuclei is to allow the organism to go through a stage of asexual reproduction in which the resulting spores contain few nuclei, all of the same genotype. By separating individual spores, the strains that are propagated from these spores will contain the desired production traits. This example describes a method of isolating single spores, and therefore, clonal fungal strains, containing targeted mutations with high fidelity and high throughput. The method allows for the rapid generation and purification of improved fungal production strains.

Traditionally, spore purification can be performed by streaking spores onto individual petri plates containing selective media. In this method, a spore suspension can be made from each transformed colony which contains a mixture of nuclei within the same mycelia. The spore suspension can be gathered using a sterile loop and then spread as quadrants on the agar plate so that the spores become dilute with each streak. The resulting plate should contain some number of spores that are separated from all of the others and can then be isolated as clonal individuals.

The method set forth herein eliminates the need to use individual petri plates/dishes for each transformation and facilitates the use of microtiter plates for building strains. Petri dishes are large and not compatible with automation, therefore limiting to the ability to scale to high throughput. Most importantly, the present method can yield clonal populations in >97% of wells, whereas traditional methods known in the art method may never necessarily result in a clonal population, even after successive passaging (repeated application of the selection process, which can be very inefficient). In the approach detailed herein, individual clonal strains are placed into wells of a microtiter plate for further screening that can facilitate simple integration to high-throughput automation. The method can also facilitate the isolation of transformants without the need for colony growth on petri dishes such that the entirety of the strain build can occur in a microtiter format. See FIGS. 54A and 54B for the work flow comparisons between the traditional method known in the art and the method described in this example.

*Aspergillus niger* or a related fungal microbe can produce one or more metabolites, chemicals, or biologics of interest. Transformation protocols call for the transformation of *A. niger* spores with donor DNA. The spores are clonally isolated/deposited into a microtiter plate via the Poisson distribution or optically based upon single cell dispensing.

Upon transformation, *Aspergillus niger* is plated and grown to sporulation. The resulting spores are suspended in liquid and diluted. The dilution is performed in one of two ways.

In the first type of dilution, the spores are diluted to a concentration where there is a statistical probability according to a Poisson distribution of only one or no spores existing in the volume dispensed. The spores are then dispensed using an ECHO, BIOSPOT, or other liquid handling device, into microtiter plates where they can germinate. Generally this approach may generate many empty wells for each well that contains a single spore, and ideally very few wells that contain two spores.

In the second type of dilution, the spores are diluted to a concentration where they can be optically distinguished as single cells. The concentration can be different depending on the instrument used for dispensing. After optical verification that a single cell exists in a droplet, that droplet is dispensed into a microtiter plate. If multiple spores, or none, are in the dispensed volume, they can be put into waste collection or re-aspirated. Compared to the Poisson distribution approach (first type of dilution above), it can be expected that each well of the output data will have a single cell in it, with far fewer empty or double spore wells.

Figure 55A:
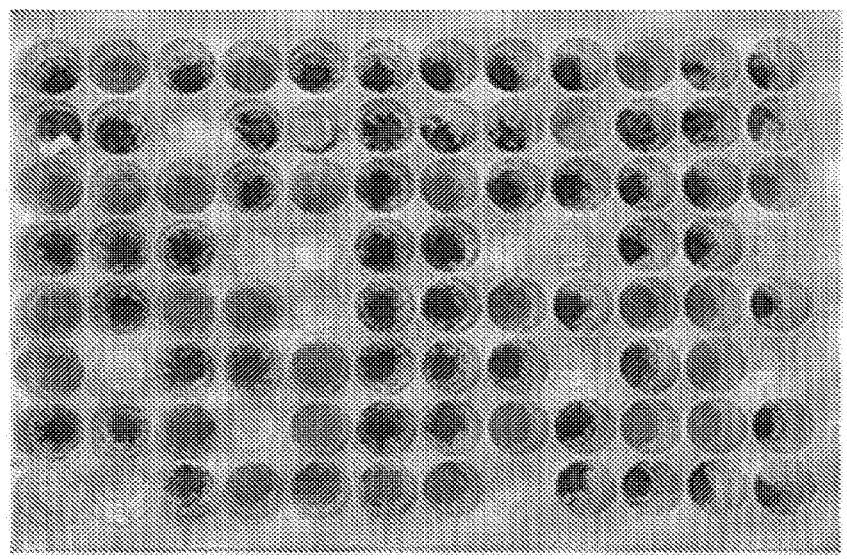
FIG. 55A, FIG. 55B, and FIG. 55C depict one print single spores with high fidelity, dispensed by the CellenONE (Cellenion, Lyon, FR). Yellow and black spores were mixed 1:1 in water at a final concentration of 2×10$^6$ and dispensed by the CellenONE (Cellenion, Lyon, FR) into three×96 well and one×384 well microtiter plates containing agar. After 4 days, wells were visually counted (FIG. 55A). Image of a 96 well plate printed with back and yellow spores (FIG. 55B). Percentage of wells that did not contain a germinating spore. This could be due to a misprint (dispensing nothing) or to printing of a non-viable spore (FIG. 55C). Percentage of wells showing both black and yellow spores, indicating that two spores were printed in the same droplet.
Figure 55B:
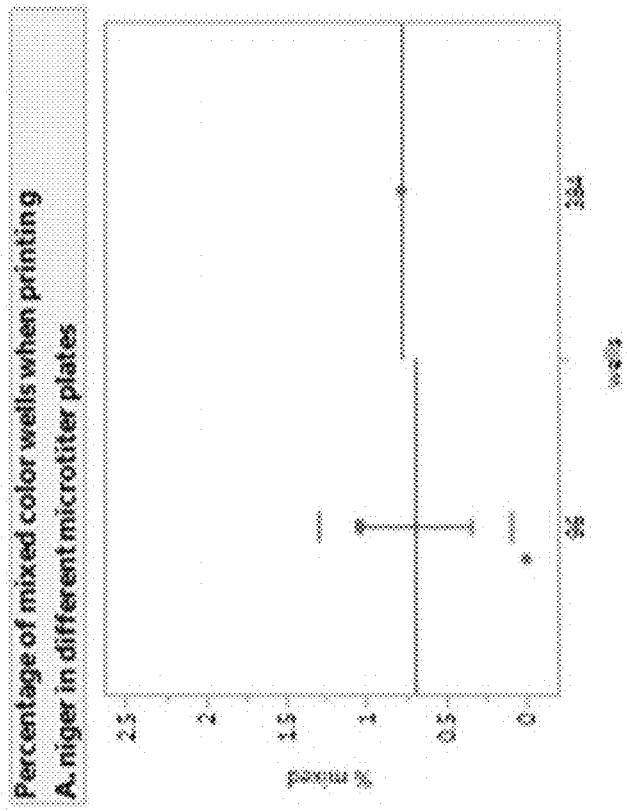
Figure 55C:
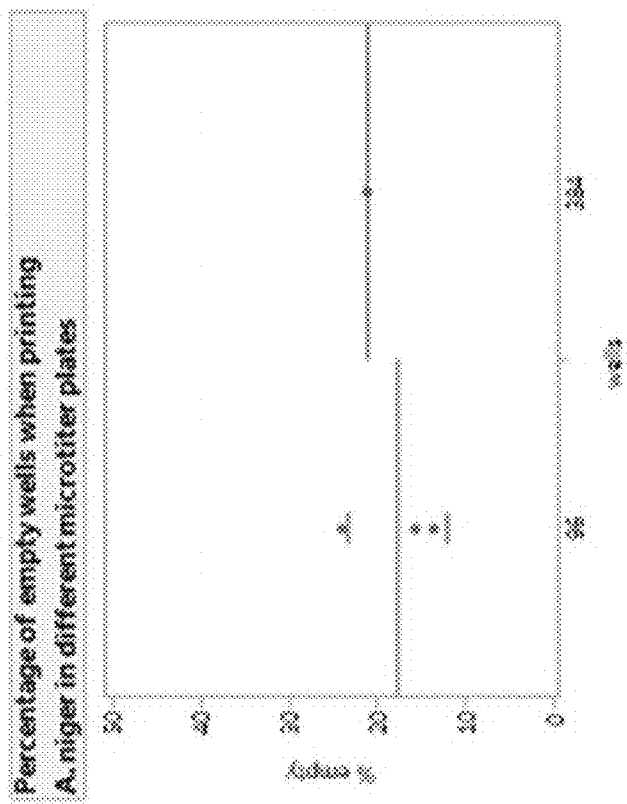

Instruments for the second type of dilution can include (1) the CellenONE instrument, which uses microfluidics combined with optics to visually verify that only a single spore are dispensed into a microtiter plate, where they can germinate; (2) the Berkeley Lights Beacon instrument, which operates by flushing cells or spores into a microchannel, and then uses a laser to push individual cells or spores into micro-holding pens where they can grown and replicate; (3) a FACS instrument, which uses a microfluidic flow channel to move individual cells past a optical sensor that can detect fluorescence, and can sort cells to output wells based on their fluorescence signal. Unfortunately, currently the only FACS machines on the market are limited to either sorting cells from a single source to multiple destinations, or are designed to select from many sources and sort to a single destination. Should a machine be developed that can easily sort cells from many sources to many destinations, it would be appropriate for the high-throughput use case described in this example, with the final requirement that the cells being sorted need to be fluorescently active (either naturally, or through genetic engineering); (4) a Cytena instrument, which operates using similar optical and microfluidic technology as the CellenONE instrument, but it is not compatible with high-throughput/plate-based inputs. It uses a disposable cartridge to hold source liquid, which must be manually bolted to the machine, giving it similar throughput limitations as a FACS machine. The CellenONE can print single spores with high fidelity, see FIG. 55A-55C.

Example 12: HTP Genomic Engineering of Filamentous Fungi: Identification of Genes that Affect Filamentous Fungal Morphology This example demonstrates the use of SNP Swap libraries in a SNPSWAP method in the filamentous fungi, *Aspergillus niger*, in order to identify genes that play a role in controlling fungal cell morphology. In particular, this example describes the identification of a group of genes that confer a non-mycelium forming, pellet-like morphological phenotype in *A. niger* mutant strains, where the cells maintain a tighter, less elongated phenotype with each cell having multiple tips when grown in submerged cultures. This type of growth can be favorable to stirred tank fermentation.

*Aspergillus niger* is a species of filamentous fungi used for the large scale production of citric acid through fermentation. Multiple strains of this species have been isolated and shown to have varying capacity for production of citric acid and other organic acids. The *A. niger* strain ATCC 1015 was identified as a producer of citric acid in the early twentieth century. An isolate of this strain named ATCC 11414, was later found to exhibit increased citric acid yield over its parent. For example, *A. niger* strain ATCC 1015 on average produces 7 grams of citric acid from 140 grams of glucose in media containing ammonium nitrate, but lacking both iron and manganese cations. Isolate strain ATCC 11414 on the other hand, exhibits a 10-fold yield increase (70 grams of citric acid) under the same conditions. Moreover, strain ATCC 11414 spores germinate and grow better in citric acid production media than do spores of strain 1015.

In order to identify potential genetic sources for these phenotypic differences, the genomes of both the ATCC 1015 and ATCC 11414 strains were sequenced and analyzed. The resulting analysis identified 43 SNPs distinguishing the 1015 and 11414 strains (see Table 4). Of these 43 SNPs, 18 were found to be in the coding domains of their respective genes (see Table 4).

In order to identify genes that play a potential role in controlling the morphology/growth of filamentous fungi under different culture conditions, the 43 SNPs from Table 4 were used in a SNP swap process as described herein in order to systematically introduce each individual SNP from Table 4 into the base 1015 strain and examine phenotype differences from a morphological standpoint between resulting parent and mutant strains. Conversely, the same type of process was performed in the 11414 production strain, whereby each of the SNPs from Table 4 already present in the genome of 11414 was systemically replaced with wild-type versions of each gene and any resulting difference in morphology between the parent and mutant strains were noted.

Constructs for Transforming Protoplasts

In this Example, each strain (i.e., 1015 and 11414) was co-transformed with two constructs ("split-marker constructs"), wherein each of the two constructs contained an overlapping portion of a selectable marker (i.e., pyrG in FIGS. 45 and 46A) and were flanked by direct repeat sequence as shown in FIGS. 45 and 46A. The split-marker constructs were generated using fusion PCR and were quality controlled (QC'd) using a fragment analyzer as shown in FIG. 46B. Moreover, each of these constructs further comprised sequence flanking the direct repeat portions of each construct in order to direct integration in the host cell genome at the respective target gene for each SNP from Table 4. For the 1015 base strain protoplasts, the direct repeats in the split constructs comprised one of the SNPs from Table 4 (see FIG. 3). In contrast, for the 11414 production strain protoplasts, the direct repeats did not comprise a SNP from Table 4.

The *A. niger* base strain 1015 and production strain 11414 were cultivated, converted to protoplasts, transformed and screened as described herein. In summary, each of these steps were as follows:

Generation of Protoplasts 500 milliliters of complete media was inoculated with $10^6$ conidia/ml and grown overnight at 150 rpm at 30° C. for both the *A. niger* 1015 base strain and *A. niger* 11414 production strain. Following the overnight growth, the mycelia were harvested by filtering each culture through Miracloth. Subsequently, the mycelia were rinsed thoroughly with sterile water. Harvested and washed mycelia from both strains were then each separately subjected to enzymatic digestion with a VinoTaste Pro (VTP) enzymatic cocktail.

Enzymatic digestion of the mycelia for both strains was performed by first making 50 ml of 60 mg/ml of VTP in protoplasting buffer (1.2M magnesium sulfate, 50 mM phosphate buffer, pH 5). After dissolving the VTP, the buffer was placed in clean Oakridge tubes and spun at 15,000×g for 15 minutes. The solution was then filter sterilized after centrifugation. Once made, some of the harvested mycelia was added to the VTP solution and the mycelia was digested at 30° C. at 80 rpm for ~2-4 hours. At various intervals during VTP digestion, small samples were examined under 400× magnification for the presence of protoplasts (i.e., large round cells that are larger than conidia and are sensitive to osmotic lysis). When most or all of the mycelia for each strain were digested, the culture from each strain was filtered through sterile Miracloth and the filtrates were collected in a graduated cylinder. The filtered protoplasts were transferred to a graduated cylinder and a buffer of lower osmolite concentration (5 ml of 0.4M ST buffer (0.4M Sorbitol, 100 mM Tris, pH 8) was gently overlaid. The overlaid samples were then spun at 800×g for 15 minutes at 4° C. and protoplasts were then removed with a pipette and mixed gently with 25 ml of ST solution (1.0 M sorbitol, 50 mM Tris, Ph 8.0) and respun at 800×g for 10 minutes. The protoplasts should pellet at the bottom of the tube. The protoplasts from each strain were then each separately resuspended in 25 ml of ST solution and collected by centrifugation at 800×g for 10 minutes.

Transformation of Protoplasts

Following centrifugation, the protoplasts from both strains were ultimately re-suspended in a buffer containing calcium chloride. Subsequently, protoplasts from both strains were subjected to traditional PEG Calcium mediated transformations using automated liquid handlers, which combined the DNA from the split constructs described above with the protoplast-PEG mixtures in the 96 wells.

Screening for Transformants

As described above, the split marker constructs utilized in this Example contained direct repeats flanking the pyrG marker gene, which were subsequently used for looping out the marker gene. As a result, strains containing the loop out construct were counter selected for deletion of the selection region (e.g., see FIG. 45 and FIG. 4; absence of pyrG gene). Correct integration was further assessed by sequence-based screening as described herein. Further, the mutant strains were screened using NGS in order to assess the homokaryotic nature of the transformants as provided herein. Homokaryotic or substantially homokaryotic mutant strains were plated on minimal media with (see FIGS. 62 and 63) or without (see FIG. 64) various supplements in order to assess said strains ability to grow under low pH (FIG. 62) or osmotic stress (FIG. 63) or sporulate (FIG. 64). In addition, the mutant strains were grown as submerged cultures in CAP media in order to assess their phenotype in submerged production media.

Results

Individual integration of 4 of the SNPs shared between Table 4 into the base *A. niger* strain 1015, generated a morphological phenotype. In particular, integration of FungiSNP_9 (SEQ ID NO: 11), FungiSNP_12 (SEQ ID NO: 12), FungiSNP_18 (SEQ ID NO: 13) or FungiSNP_40 (SEQ ID NO: 14) into the 1015 genome generated mutant strains produced a non-mycelium, pellet morphology when grown as a submerged culture in CAP media.

The role of the genes containing the 4 SNPs in affecting fungal morphology was further demonstrated in the wave down experiments, whereby removal of each of these 4 SNPs rescued the observed morphological phenotypes. The sequences of the 4 SNPs can be found in the attached sequence listing, while their putative or known protein function can be found in Table 4.

As shown in FIG. 62, strains that contain the Base SNP18 grow faster on low pH media. The presence of FungiSNP_18 from the production strain (11414) in the base strain (i.e., Base snp18$^{prod}$ in FIG. 62) reduced radial growth of the resultant colony on pH2 media as compared to the base (i.e., Base from FIG. 62). In contrast, the presence of the wild-type version of FungiSNP_18 from the base strain in the production strain (i.e., Production SNP18Ba in FIG. 62) allowed for radial growth in said strain as compared to the Base and Production strains from FIG. 62. Further, it seems that other SNPs present in the production strain also contribute to lower radial growth (see Production in smaller than snp18$^{prod}$ in FIG. 62).

Figure 63:
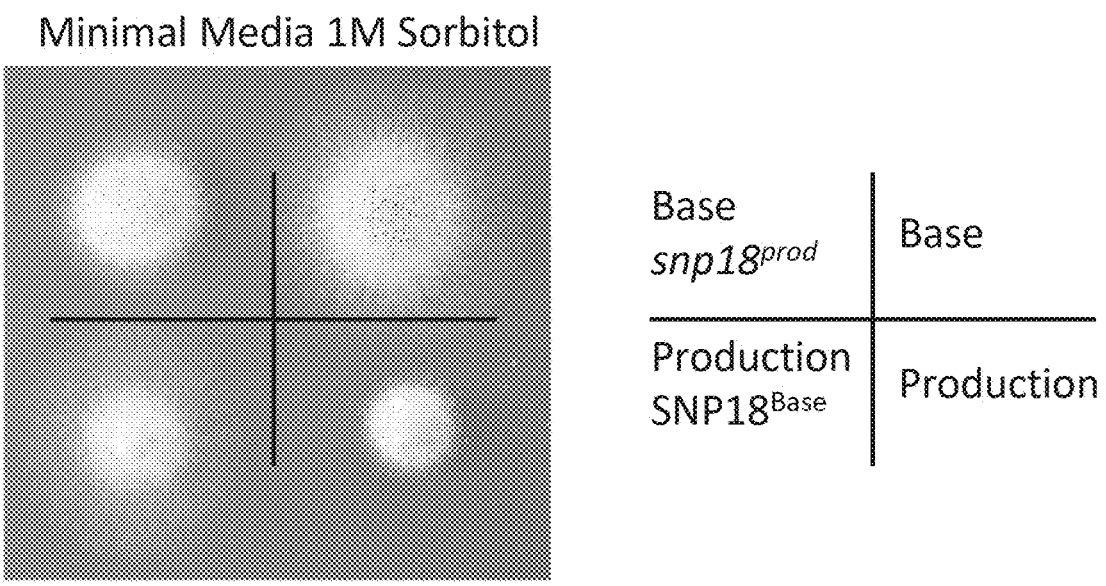
FIG. 63 illustrates that strains that contain the Base SNP18 grow faster on media which provide osmotic stress.

As shown in FIG. 63, strains that contain the base SNP18 (i.e., wild-type version of FungiSNP_18) grow faster on media which provide osmotic stress. The presence of FungiSNP_18 from the production strain (11414) in the base strain (i.e., Base snp18$^{prod}$ in FIG. 63) reduced radial growth of the resultant colony under osmotic stress as compared to the base (i.e., Base from FIG. 63). In contrast, the presence of the wild-type version of FungiSNP_18 from the base strain in the production strain (i.e., Production SNP18$^{Base}$ in FIG. 63) allowed for radial growth in said strain as compared to the Base and Production strains from FIG. 63. Further, it seems that other SNPs present in the production strain also contribute to lower radial growth (see Production in smaller than Base snp18$^{prod}$ in FIG. 63).

Interestingly, base strains containing each of FungiSNP_9, FungiSNP_12, or FungiSNP_40 grew normally and sporulated normally when not grown in submerged cultures (e.g., on plates). Expressing FungiSNP_18 in the base strain (i.e., 1015) did show an effect on radial growth rate (reduced) and sporulation as shown in FIG. 64.

Example 13: HTP Genomic Engineering of Filamentous Fungi: Confirmation of Role the Identified Genes Play in Filamentous Fungal Morphology-Deletion of the Identified Morphological Control Genes This example demonstrates confirmation of the role of the 4 genes identified in Example 12 as playing a role in fungal morphology. In particular, this example describes knocking out or deleting each of the 4 genes using HTP methods as described herein in *A. niger* strains 1015 and 11414.

The *A. niger* base strain 1015 and production strain 11414 were cultivated, converted to protoplasts, transformed and screened as described in Example 12.

Constructs for Transforming Protoplasts

In this Example, protoplasts from each strain (i.e., 1015 and 11414) were transformed with a series of single constructs whereby each construct in the series contained a selectable marker gene (i.e., pyrG) flanked by sequence complementary to genomic sequence flanking one of the 4 genes of interest identified in Example 12 in order to direct integration of the marker gene into the host cell genome. As shown in FIG. 39, integration of the marker gene into the locus of one of the 4 genes (one of the 4 wild-type genes in the 1015 strain and one the of 4 SNPs in the 11414 strain) essentially served to remove said wildtype gene or SNP containing gene from the locus of the respective strain.

Following growth, the mutant strains were screened using NGS in order to assess the homokaryotic nature of the transformants as provided herein. Homokaryotic or substantially homokaryotic mutant strains were plated on media in order to assess said strains ability to sporulate or grown as submerged cultures in CAP media in order to assess their phenotype in submerged production media.

Results

Figure 65:
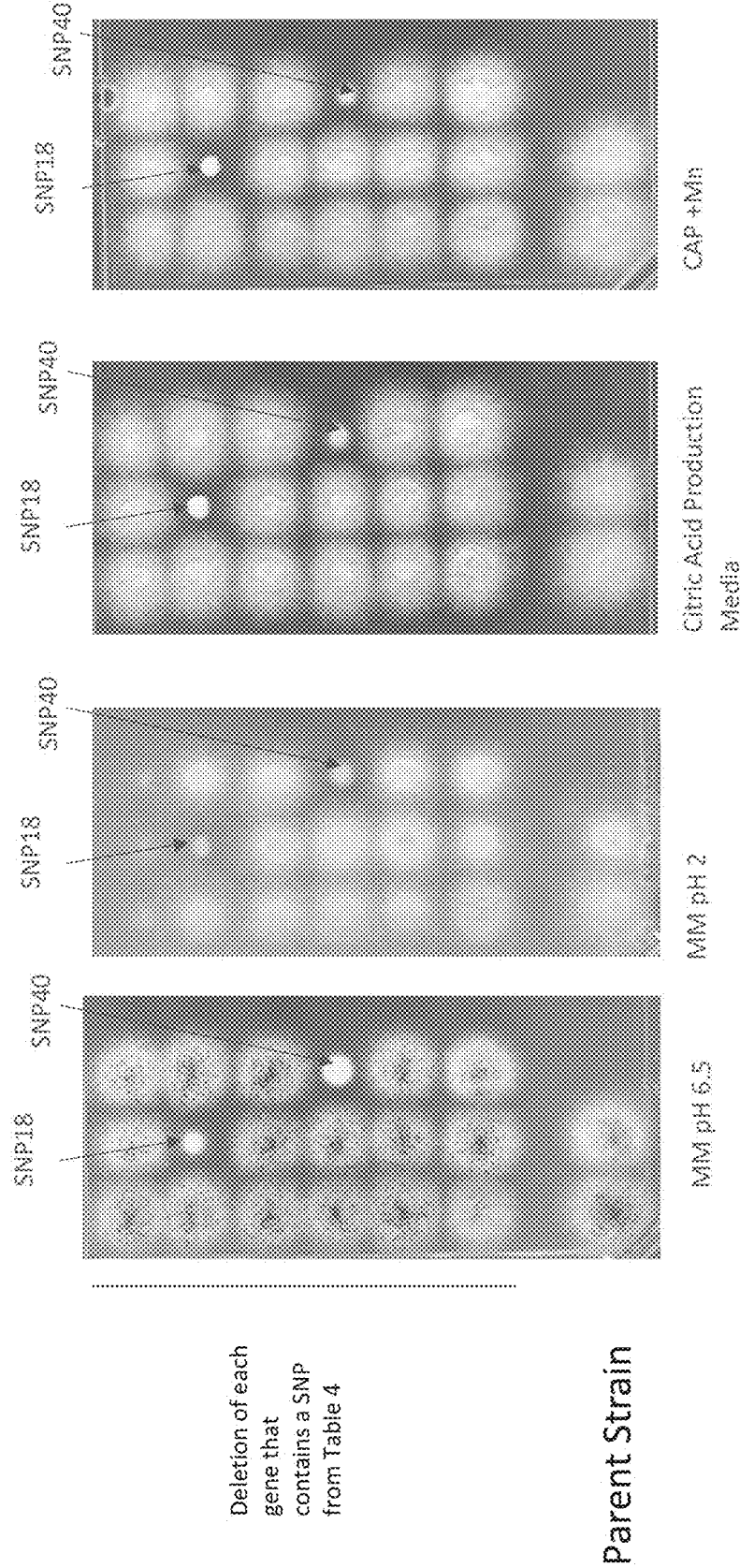
FIG. 65 illustrates deletion in the base strain of all coding sequences that contain SNPs (i.e., the FungiSNPs from Table 4) in the production strain.

Removal of each of the 4 genes from the base 1015 strain as well as the 11414 production strain confirmed the results from Example 12 in that each of said 4 genes clearly play a role in affecting fungal morphology. In particular, as in Example 12, removal of the non-SNP containing version of the gene containing FungiSNP_18 in the 1015 strain or the gene containing FungiSNP_18 in the 11414 strain, produced the most striking phenotype whereby under submerged culture conditions, said strains had a pellet like morphology. Further, as shown in FIG. 65, deletion of FungiSNP18 and FungiSNP40 genes resulted in a tight morphology under all conditions. This data may indicate that the SNPs are not loss of function mutations given that the deletion phenotypes are more pronounced (stronger impact on morphology) than the SNPs themselves. Thus, it seems that altering the expression of these genes may impact morphology in a manner that is desirable for growth in fermenters.

Figure 66:
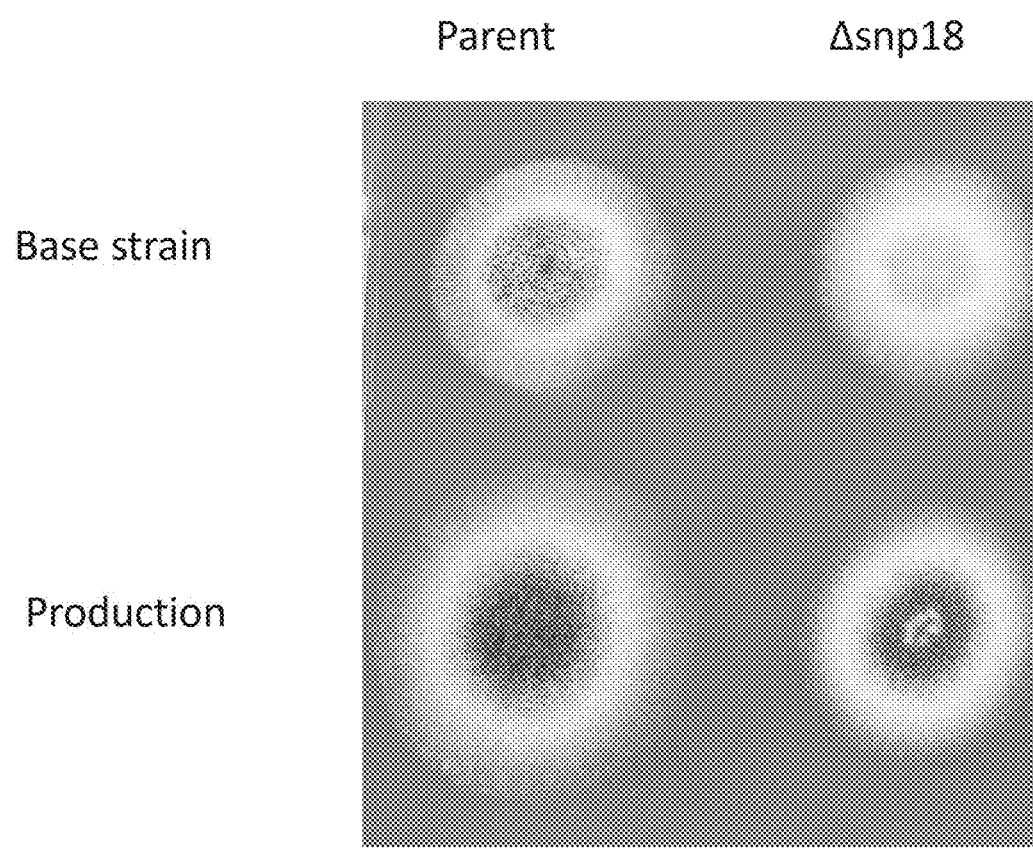
FIG. 66 illustrates that the gene that contains FungiSNP18 is dispensible for sporulation in the production strain but not in the base strain.

Interestingly, deletion of the non-SNP containing version of the gene containing FungiSNP_18 in the 1015 strain produced a negative sporulation phenotype in the resultant variant 1015 strain such that said variant 1015 strain lost the ability to sporulate (see FIG. 66). This loss of sporulation was not observed in the 11414 strain in which the FungiSNP_18 gene was removed. Given that the genetic backgrounds of the 11414 and 1015 strains are identical aside from the SNPs present in Table 4, this suggested that the presence of one, all or some combination of the SNPs from Table 4 in the 11414 genetic background is enough to rescue the negative sporulation phenotype produced when FungiSNP_18 is removed. Put another way, there are other mutations (SNPs) that act epistatically to maintain sporulation in the production strain in the absence of SNP18 activity.

It should be noted that the loss of sporulation was not observed in either the variant 11414 or 1015 strains produced by removing FungiSNP_9, FungiSNP_12 or FungiSNP_40 or their non-SNP containing versions, respectively.

It should be further noted that the observed morphological phenotypes under submerged culture conditions in this Example were more striking than in Example 12 for each of the 4 genes, which could be due to the experimental design whereby successful transformants essentially displayed a deletion phenotype. Moreover, the phenotypes in the 11414 strain were also more pronounced which could be due to contributions to the phenotype by one or more of the other SNPs present in this strain vs. the 1015 base strain Example 14: HTP Genomic Engineering of Filamentous Fungi: Altering Filamentous Fungal Cell Morphology by Altering Gene Expression This example serves as a proof of principle for the automated, HTP PROSWP method in filamentous fungal cells by showing the use of an automated, HTP PROSWP method in filamentous fungal cells in order to test the effects of modulating the expression of the FungiSNP_9, FungiSNP_12, FungiSNP_18 and FungiSNP_40 genes identified from Examples 1 and 2 that are thought to play a role in controlling filamentous fungal morphology.

Figure 67:
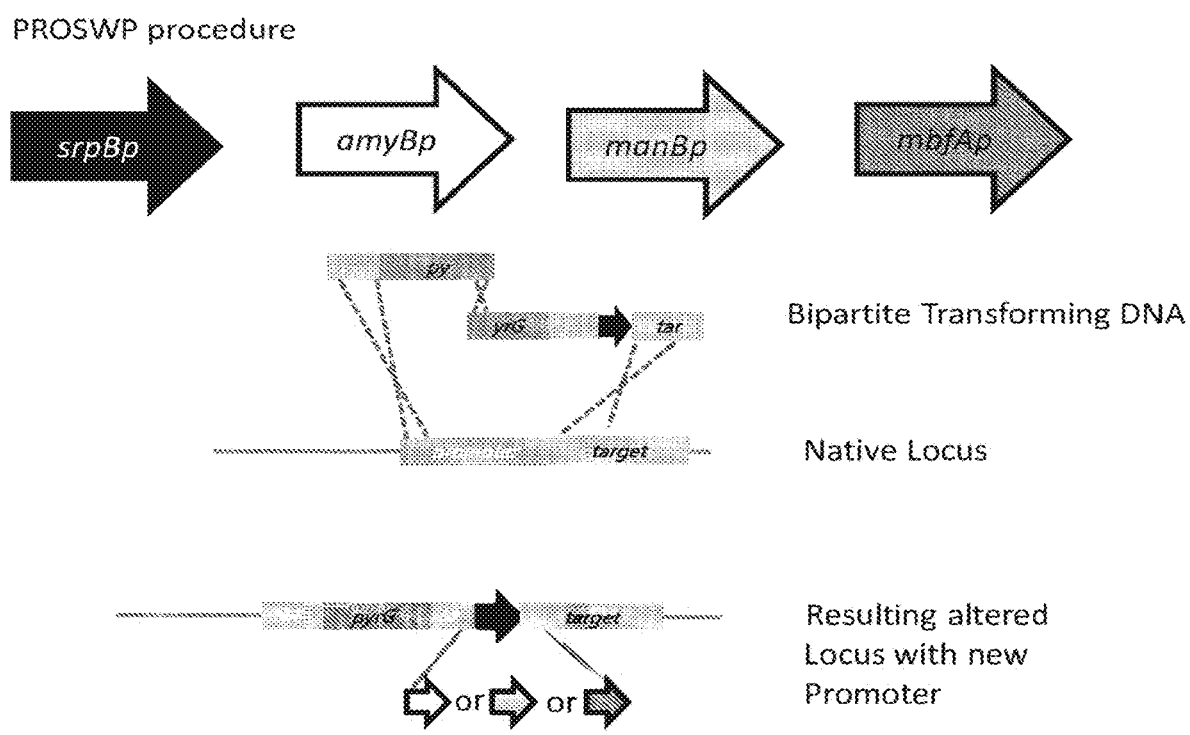
FIG. 67 illustrates the design of the bipartite constructs and general scheme employed for conducting the PROSWP experiments described in Example 3.

In this Example, the expression of the FungiSNP_18 gene (i.e., SEQ ID NO: 13) identified in Examples 12 and 13 was modulated in both the *A. niger* 1015 base strain and the *A. niger* 11414 production strain by replacing the annotated native promoter with one of the four promoters from Table 1 using the PROSWP method described herein. More specifically, for each of the strains (i.e., the 1015 parent strain or the 11414 parent strain) for each FungiSNP, a set of (4) variant or mutant strains were generated, where a 1st variant strain expresses a first construct comprising said candidate FungiSNP (FungiSNP_9 (SEQ ID NO: 11); _12 (SEQ ID NO: 12); _18 (SEQ ID NO: 13); 40 (SEQ ID NO: 14)) gene under the control of the srp8p promoter described in Table 1, a 2nd variant strain had said candidate FungiSNP gene under the control of the amy8p promoter described in Table 1, a 3rd variant strain had said candidate FungiSNP gene under the control of the man8p promoter described in Table 1 and a 4th variant strain had said candidate FungiSNP gene under the control of the mbfAp promoter described in Table 1. Each of the constructs used to generate the variants further comprised sequence flanking the candidate FungiSNP gene and promoter that served to direct integration of the construct into the locus of the respective candidate FungiSNP. A general description of the bipartite construct design and integration scheme used in this Example is shown in FIG. 67.

Figure 40:
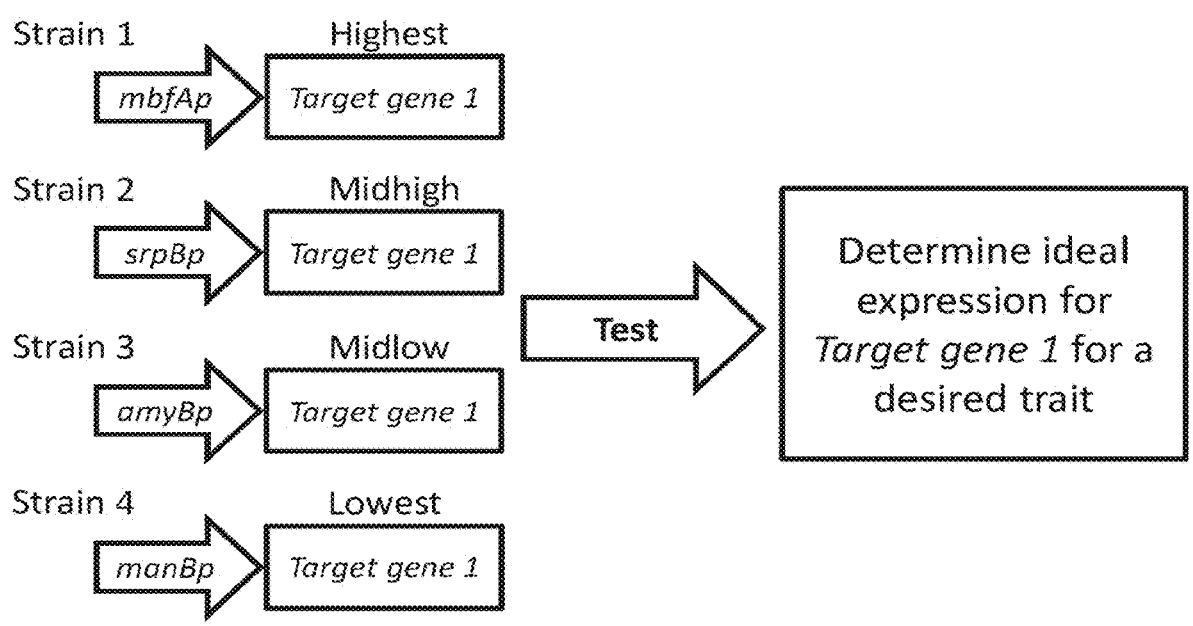
FIG. 40 depicts four different promoters being placed in front of a target gene to generate 4 different strains. These strains can the be compared in a test for a desired trait and an ideal level of expression can be determined.
Figure 68:
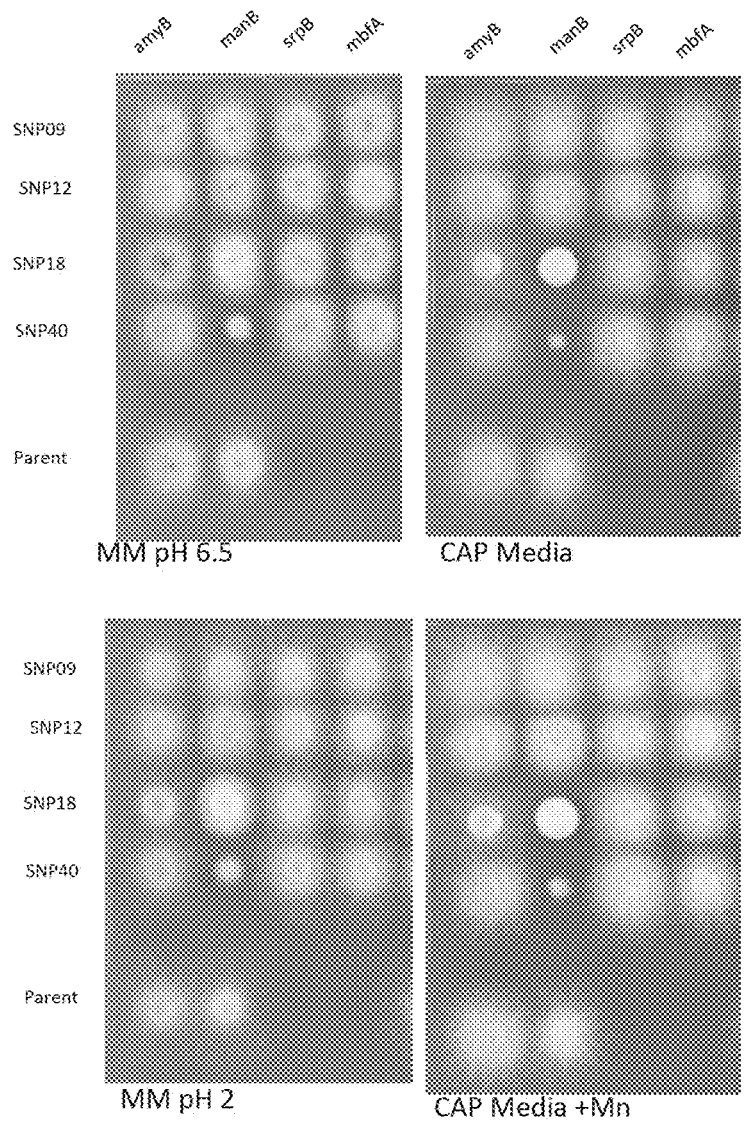
FIG. 68 illustrates that weaker promoters used in Example 3 impact morphology. The strain containing FungiSNP_18 (SNP18) under the weak manB promoter has tighter colony morphology than strains containing other promoter combinations. The impact of SNP18 control is more pronounced under osmotic stress than under low pH.

Following their generation, each construct for each candidate FungiSNP used to generate the (4) variant strains was individually transformed into protoplasts generated for both the *A. niger* 1015 base strain as well as the *A. niger* 11414 production strain. The protoplasts for both strains were cultivated, converted to protoplasts, transformed and screened to select for substantially homokaryotic protoplasts using phenotypic and/or sequence-based screening as described in the Examples above. Accordingly, the transformation of each individual construct led to the generation of the 4 variant or mutant strains for each of the parental strains for each candidate FungiSNP as generally depicted in FIG. 40. The morphological phenotype of each of these strains was then observed and compared with the morphological phenotype of a mutant strain comprising the identified gene under the control of the native promoter for said gene. An ideal level of expression was then determined for each of the identified genes Results Overall, promoter swapping for each morphology control gene target (i.e., FungiSNP_9, _12, _18 and 40) with the different promoters from Table 1 revealed that controlling expression of these genes impacted morphology (see FIG. 68). The strain containing SNP18 under the weak manB promoter had tighter colony morphology than strains containing other promoter combinations. The impact of SNP18 control was more pronounced under osmotic stress than under low pH. Further, the strain containing SNP40 under the weak manB promoter had a drastic effect on colony morphology than strains containing other promoter combinations under all growth conditions tested.

Figure 69:
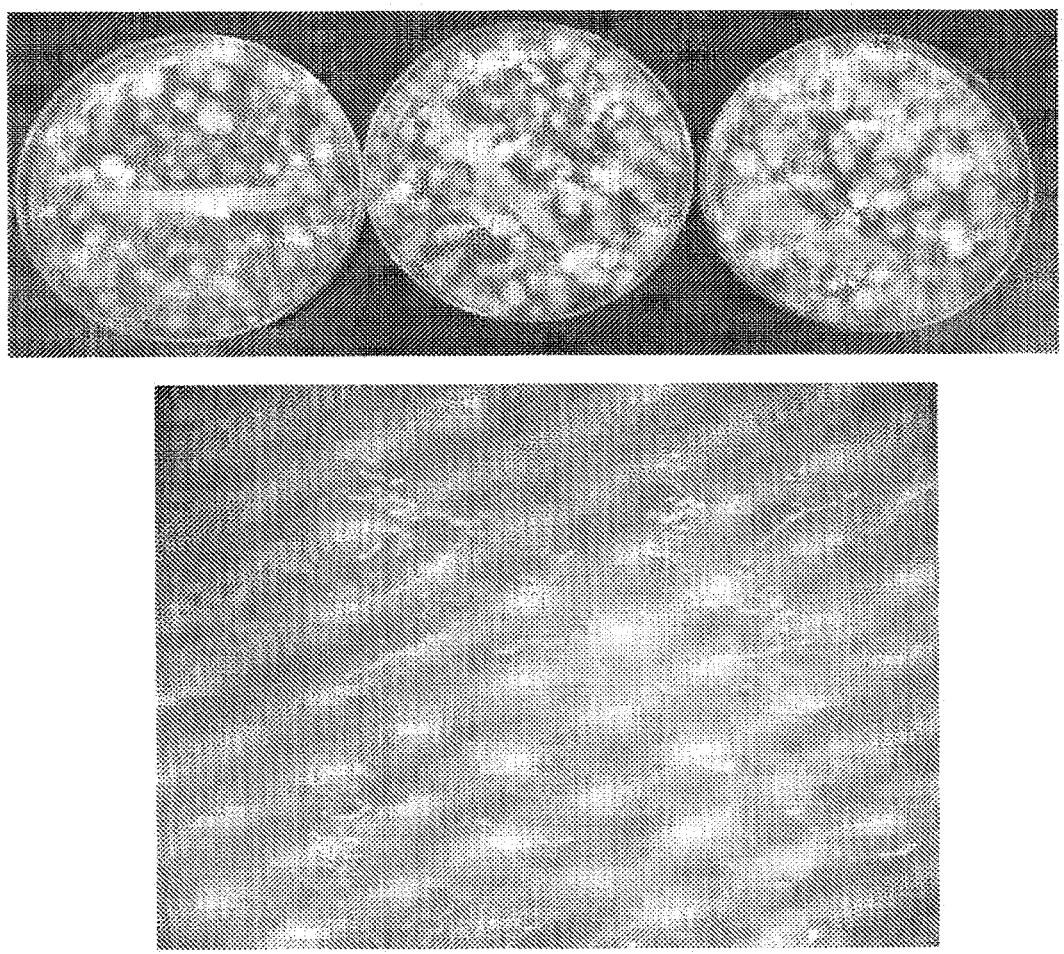
FIG. 69 illustrates the PROSWP of FungiSNP_12 (snp_12), Lower strength promoters operably linked to snp_12 and result in yellow pigment in hyphae and some altered morphology (observed at the edge of colonies). This yellow pigment is common in a variety of mutants and is thought of as a sign of metabolic stress.

As shown in FIG. 69, promoter swapping of morphology control gene target 12 (FungiSNP_12; SEQ ID NO: 12) with the different promoters from Table 1 revealed that lower strength promoters resulted in yellow pigment in hyphae and some altered morphology observed at the edge of colonies. The presence of the yellow pigment indicated that the variant or mutant strains were experiencing metabolic stress.

Figure 58:
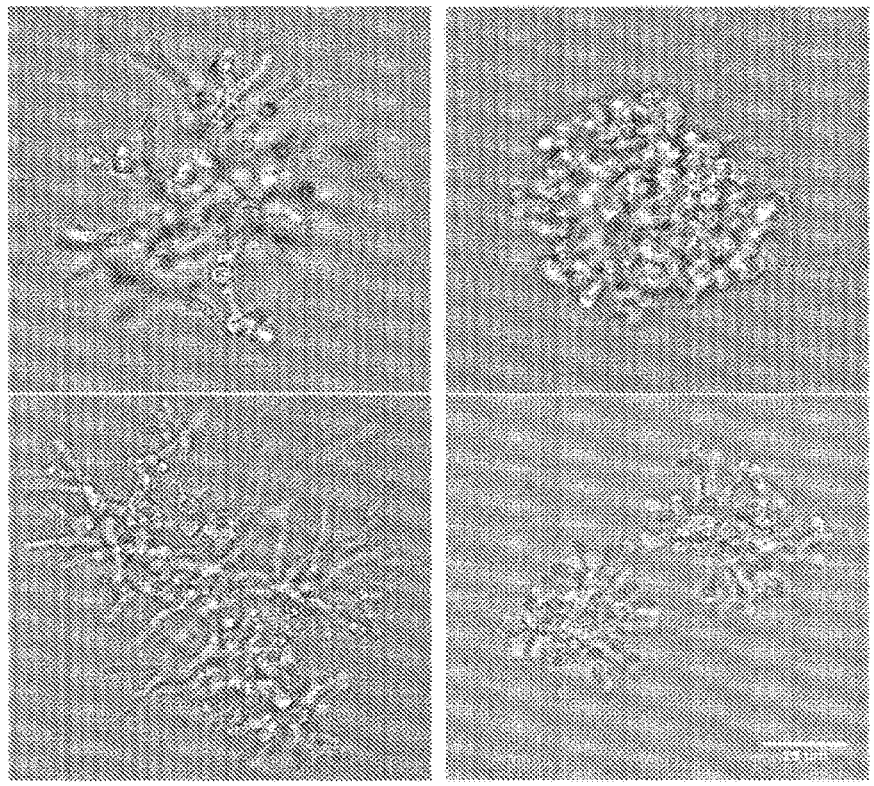
FIG. 58 illustrates promoter swapping of morphology gene target 18 in the base 1015 strain and 11414 production strain. The gene product associated with FungiSNP_18 is a signaling kinase that responds to osmotic stress (i.e., *A. niger* ortholog of *S. cerevisiae* SLN1). This figure shows that when the gene expression of said gene is reduced by replacing the native promoter with a weaker promoter, the cells maintain a tighter, less elongated phenotype, which is referred to herein as a 'pellet' phenotype (see right hand panels for the cells expressing the manB(p)snp18 gene in the base 1015 strain and 11414 production strain). The strains were grown in citric acid production media (14% w/v Glucose, pH 2, depleted Mn++) at 30° C. for 24 hours. This type of growth can be favorable to stirred tank fermentation.

Moreover, promoter swapping of morphology control gene target 18 (FungiSNP_18; SEQ ID NO: 13) with the different promoters from Table 1 revealed that controlling expression of this gene with the two weaker promoters impacted morphology (see FIGS. 57, 58 and 70). For example, the strains containing the manB fusion and the amyB fusion retained a multiple tip phenotype, whereas those with higher expression srpB and mbfA lacked the multiple tip phenotype and instead showed abnormal swelling (see FIG. 57). The images in FIG. 58 are of strains grown in citric acid production media at 30° C. for 24 hours. The images in FIG. 57 are of parent 11414 strains as well as 11414 strains expressing various non-native promoter-FungiSNP_18 fusions grown in citric acid production media at 30° C. for 48 hours. When allowed to incubate for 168 hours, the strains with higher expression promoters as well as the parent strain control all contained long filamentous hyphae. The strains with the lower level of expression from the promoter fusion, amyB and manB, remained pelleted. It should be noted that, as shown in FIG. 70, when driven by weaker promoters, SNP_18 has more severe morphological phenotype in the base strain than in the production strain.

Figure 59:
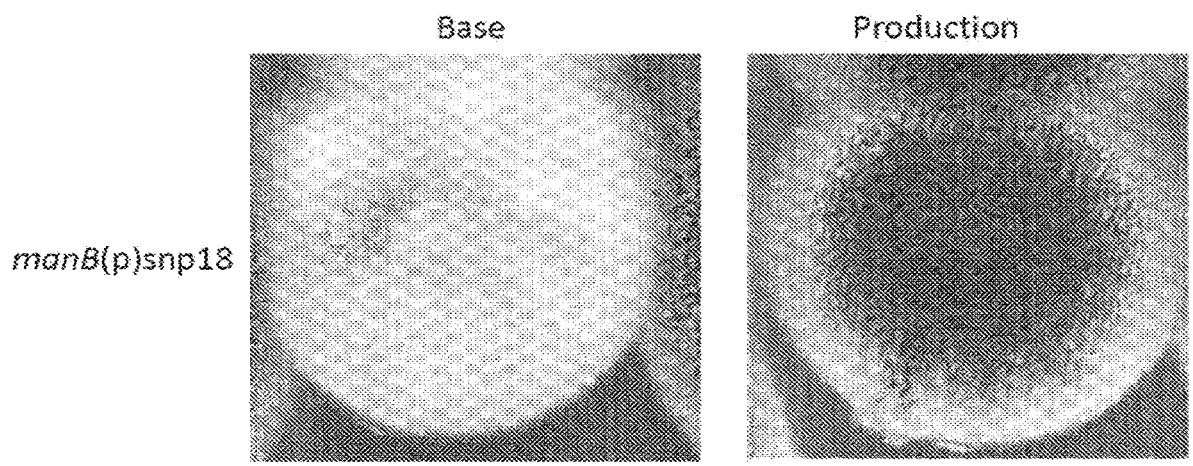
FIG. 59 illustrates that reduced levels of the FungiSNP_18 gene product in the base strain (i.e., *A. niger* 1015) by introducing the FungiSNP_18 gene (SEQ ID NO: 13) under the control of the manB(p) promoter (SEQ ID NO: 1) results in inability to sporulate in the base strain genetic background. This phenotype was not observed when the same construct was introduced to the production strain (i.e., *A. niger* 11414).

Similar to the results of the deletion experiments from Example 13, reduction of the expression of the FungiSNP_18 gene in the 1015 strain resulted in cells that experienced a loss of sporulation as shown in FIG. 59. This loss of sporulation was not observed in the 11414 mutant strains. Again, given that the genetic backgrounds of the 11414 and 1015 strains are identical aside from the SNPs present in Table 4, this suggested that the presence of one, all or some combination of the SNPs from Table 4 in the 11414 genetic background is enough to rescue the negative sporulation phenotype produced when expression of the FungiSNP_18 is reduced.

TABLE 7

SEQUENCES OF THE DISCLOSURE WITH SEQ ID NO IDENTIFIERS
GENE HOMOLOGUES, ORTHOLOGUES OR PARALOGS

Figures 56A, 56B:
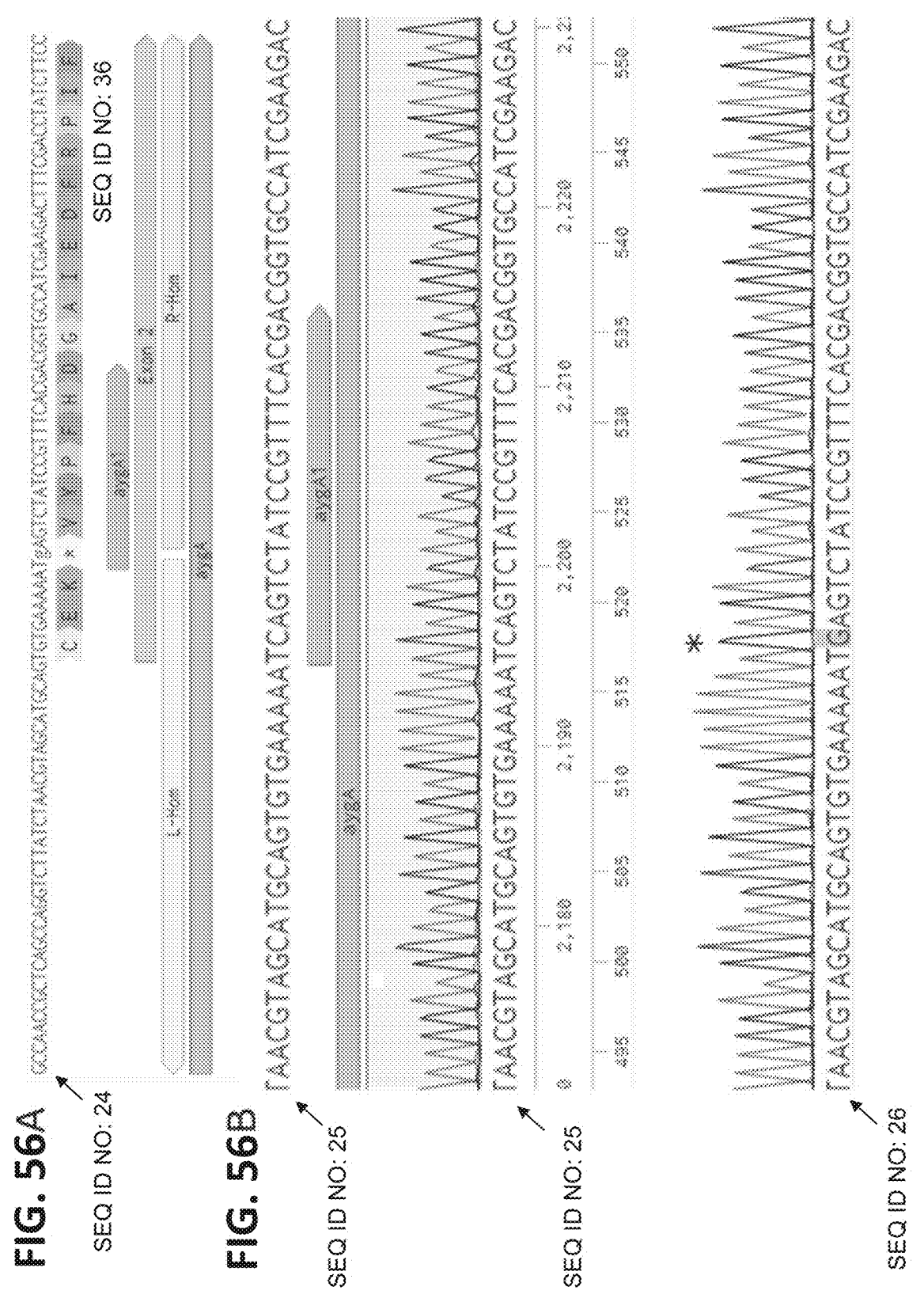

| NAME | SOURCE | SEQ ID NO: | COMMENTS |
| --- | --- | --- | --- |
| manBp | A. niger | 1 | Native promoter of manB gene |
| amyBp | A. oryzae | 2 | Native promoter of amyB gene |
| srpBp | A. niger | 3 | Native promoter of srpB gene |
| mbfAp | A. niger | 4 | Native promoter of mbfA gene |
| pyrG | A. niger | 5 | Native pyrG gene |
| aygA.1 crRNA protospacer sequence | Artificial | 6 | |
| avgA.3 crRNA protospacer sequence | Artificial | 7 | |
| Control crRNA protospacer sequence | Artificial | 8 | |
| DJV_03_pyrG_insertion_in_AygA | Artificial | 9 | pyrG with promoter and terminator (lowercase) flanked by 5' and 3' regions of homology (uppercase) to the AygA gene |
| DJV_07_4bp_insertion_in_AygA | Artificial | 10 | 4 bp insertion (lowercase) flanked by 5' and 3' regions of homology (uppercase) to the AygA gene |
| FungiSNP_9 | A. niger | 11 | |
| FungiSNP_12 | A. niger | 12 | |
| FungiSNP_18 | A. niger | 13 | A. niger orthologue of S. cerevisiae SLN1 |
| FungiSNP_40 | A. niger | 14 | |
| Ypd1 orthologue | A. niger | 15 | A. niger orthologue of S. cerevisiae Ypd1 |
| Ssk1 orthologue | A. niger | 16 | A. niger orthologue of S. cerevisiae Ssk1 |
| Skn7 orthologue #1 | A. niger | 17 | A. niger orthologue of S. cerevisiae Skn7 |
| Skn7 orthologue #2 | A. niger | 18 | A. niger orthologue of S. cerevisiae Skn7 |
| Ssk2 orthologue | A. niger | 19 | A. niger orthologue of S. cerevisiae Ssk2 |
| | Aspergillus | 20 | sequenced portion of genome with BamHI site created by mutating EcoRV from FIG. 42 |
| aygA | A. niger | 21 | sequenced portion of aygA gene from FIG. 49D |
| aygA | A. niger | 22 | sequenced portion of aygA gene with indel mutation from FIG. 49D |
| aygA | A. niger | 23 | sequenced portion of aygA gene from FIG. 49E |
| aygA | A. niger | 24 | portion of aygA gene containing a nonsense mutation from FIG. 56A |
| aygA | A. niger | 25 | sequenced portion of aygA gene from 56B |
| aygA | A. niger | 26 | sequenced portion of aygA gene containing a nonsense mutation from 56B |
| argB | A. niger | 27 | argB gene containing a mutation from FIG. 44 |
| argB | A. niger | 28 | sequenced portion of argB gene from FIG. 44 |

TABLE 7-continued

SEQUENCES OF THE DISCLOSURE WITH SEQ ID NO IDENTIFIERS
GENE HOMOLOGUES, ORTHOLOGUES OR PARALOGS

| NAME | SOURCE | SEQ ID NO: | COMMENTS |
| --- | --- | --- | --- |
| ARGB | A. niger | 29 | sequenced portion of ARGB protein from FIG. 44 |
| argB | A. niger | 30 | sequenced portion of argB gene containing a mutation from FIG. 44 |
| ARGB | A. niger | 31 | sequenced portion of ARGB protein from FIG. 44 |
| ARGB | A. niger | 32 | sequenced portion of ARGB protein from FIG. 44 |
| argB | A. niger | 33 | sequenced portion of argB gene containing a mutation from FIG. 44 |
| argB | A. niger | 34 | sequenced portion of argB gene containing a mutation from FIG. 44 |
| ARGB | A. niger | 35 | sequenced portion of ARGB protein from FIG. 44 |
| AYGA | A. niger | 36 | sequenced portion of AYGA protein from FIG. 56A |

NUMBERED EMBODIMENTS OF THE DISCLOSURE

Other subject matter contemplated by the present disclosure is set out in the following numbered embodiments:

1. A method for producing a filamentous fungal strain, the method comprising:
a.) providing a plurality of protoplasts, wherein the protoplasts were prepared from a culture of filamentous fungal cells;
b.) transforming the plurality of protoplasts with a first construct and a second construct, wherein the first construct comprises a first polynucleotide flanked on both sides by nucleotides homologous to a first locus in the genome of the protoplast and the second construct comprises a second polynucleotide flanked on both sides by nucleotides homologous to a second locus in the genome of the protoplast, wherein transformation results in integration of the first construct into the first locus and the second construct into the second locus by homologous recombination, wherein at least the second locus is a first selectable marker gene in the protoplast genome, and wherein the first polynucleotide comprises a mutation and/or a genetic control element;
c.) purifying homokaryotic transformants by performing selection and counter-selection; and
d.) growing the purified transformants in media conducive to regeneration of the filamentous fungal cells.

2. The method of embodiment 1, wherein the first construct is split into construct A and construct B, wherein construct A comprises a first portion of the first polynucleotide and nucleotides homologous to the first locus 5' to the first portion of the first polynucleotide, and wherein construct B comprises a second portion of the first polynucleotide and nucleotides homologous to the first locus 3' to the second portion of the first polynucleotide, wherein the first portion and the second portion of the first polynucleotide comprises overlapping complementary sequence.

3. The method of embodiment 1 or 2, wherein the second construct is split into construct A and construct B, wherein construct A comprises a first portion of the second polynucleotide and nucleotides homologous to the first locus 5' to the first portion of the second polynucleotide, and wherein construct B comprises a second portion of the second polynucleotide and nucleotides homologous to the first locus 3' to the second portion of the second polynucleotide, wherein the first portion and the second portion of the second polynucleotide comprises overlapping complementary sequence.

4. The method of any one of the above embodiments, wherein each protoplast from the plurality of protoplasts is transformed with a single first construct from a plurality of first constructs and a single second construct from a plurality of second constructs, wherein the first polynucleotide in each first construct from the plurality of first constructs comprises a different mutation and/or genetic control element; and wherein the second polynucleotide in each second construct from the plurality of second constructs is identical.

5. The method of embodiment 4, further comprising repeating steps a-d to generate a library of filamentous fungal cells, wherein each filamentous fungal cell in the library comprises a first polynucleotide with a different mutation and/or genetic control element.

6. The method of any one of the above embodiments, wherein the first polynucleotide encodes a target filamentous fungal gene or a heterologous gene.

7. The method of any one of the above embodiments, wherein the mutation is a single nucleotide polymorphism.

8. The method of any one of the above embodiments, wherein the genetic control is a promoter sequence and/or a terminator sequence.

9. The method of any one of the above embodiments, wherein the genetic control element is a promoter sequence, wherein the promoter sequence is selected from the promoter sequences listed in Table 1.

10. The method of any one of the above embodiments, wherein the plurality of protoplasts are distributed in wells of a microtiter plate.

11. The method of any one of the above embodiments, wherein steps a-d are performed in wells of a microtiter plate.

12. The method of embodiment 10 or 11, wherein the microtiter plate is a 96 well, 384 well or 1536 well microtiter plate.

13. The method of any one of the above embodiments, wherein the filamentous fungal cells are from an *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, anamorphs, synonyms or taxonomic equivalents thereof.

14. The method of any one of the above embodiments, wherein the filamentous fungal cells are from *Aspergillus niger*.

15. The method of any one of the above embodiments, wherein the filamentous fungal cells possess a non-mycelium forming phenotype.

16. The method of any one of the above embodiments, wherein the fungal cells possess a non-functional non-homologous end joining (NHEJ) pathway.

17. The method of embodiment 16, wherein the non-functional NHEJ pathway is due to exposure of the cell to an antibody, a chemical inhibitor, a protein inhibitor, a physical inhibitor, a peptide inhibitor, or an anti-sense or RNAi molecule directed against a component of the NHEJ pathway.

18. The method of embodiment 17, wherein the chemical inhibitor is W-7.

19. The method of any one of embodiments 6-18, wherein the first locus is for the target filamentous fungal gene.

20. The method of any one of embodiments 1-18, wherein the first locus is for a second selectable marker gene in the protoplast genome.

21. The method of embodiment 20, wherein the second selectable marker gene is an auxotrophic marker gene, a colorimetric marker gene, or a directional marker gene.

22. The method of any one of the above embodiments, wherein the first selectable marker gene is an auxotrophic marker gene, a colorimetric marker gene, or a directional marker gene.

23. The method of any one of the above embodiments, wherein the second polynucleotide is an auxotrophic marker gene, a directional marker gene, or an antibiotic resistance gene.

24. The method of embodiment 21 or 22, wherein the colorimetric marker gene is an aygA gene.

25. The method of any one of embodiments 21-23, wherein the auxotrophic marker gene is an argB gene, a trpC gene, a pyrG gene, or a met3 gene.

26. The method of any one of embodiments 21-23, wherein the directional marker gene is an acetamidase (amdS) gene, a nitrate reductase gene (niaD), or a sulphate permease (SutB) gene.

27. The method of embodiment 23, wherein the antibiotic resistance gene is a ble gene, wherein the ble gene confers resistance to pheomycin.

28. The method of embodiment 19, wherein the first selectable marker gene is an aygA gene and the second polynucleotide is a pyrG gene.

29. The method of any one of embodiments 20-27, wherein the first selectable marker gene is a met3 gene, the second selectable marker gene is an aygA gene and the second polynucleotide is a pyrG gene.

30. The method of any one of the above embodiments, wherein the plurality of protoplasts are prepared by removing cell walls from the filamentous fungal cells in the culture of filamentous fungal cells; isolating the plurality of protoplasts; and resuspending the isolated plurality of protoplasts in a mixture comprising dimethyl sulfoxide (DMSO), wherein the final concentration of DMSO is 7% v/v or less.

31. The method of embodiment 30, wherein the mixture is stored at at least −20° C. or −80° C. prior to performing steps a-d.

32. The method of any one of embodiments 30-31, wherein the culture is at least 1 liter in volume.

33. The method of any one of embodiments 30-31, wherein the culture is grown for at least 12 hours prior to preparation of the protoplasts.

34. The method of any one of embodiments 30-33, wherein the fungal culture is grown under conditions whereby at least 70% of the protoplasts are smaller and contain fewer nuclei.

35. The method of any one of embodiments 30-34, wherein removing the cell walls is performed by enzymatic digestion.

36. The method of embodiment 35, wherein the enzymatic digestion is performed with a mixture of enzymes comprising a beta-glucanase and a polygalacturonase.

37. The method of any one of embodiments 30-36, further comprising adding 40% v/v polyethylene glycol (PEG) to the mixture comprising DMSO prior to storing the protoplasts.

38. The method of embodiment 37, wherein the PEG is added to a final concentration of 8% v/v or less.

39. The method of any one of the above embodiments, wherein steps a-d are automated.

40. A method for preparing filamentous fungal cells for storage, the method comprising: preparing protoplasts from a fungal culture comprising filamentous fungal cells, wherein the preparing the protoplasts comprises removing cell walls from the filamentous fungal cells in the fungal culture;
isolating the protoplasts; and
resuspending the isolated protoplasts in a mixture comprising dimethyl sulfoxide (DMSO) at a final concentration of 7% v/v or less.

41. The method of embodiment 40, wherein the mixture is stored at at least −20° C. or −80° C.

42. The method of any one of embodiments 40-41, wherein the fungal culture is at least 1 liter in volume.

43. The method of any of embodiments 40-42, wherein the fungal culture is grown for at least 12 hours prior to preparation of the protoplasts.

44. The method of any one of embodiments 40-43, wherein the fungal culture is grown under conditions whereby at least 70% of the protoplasts are smaller and have fewer nuclei.

45. The method of any one of embodiments 40-44, wherein removing the cell walls is performed by enzymatic digestion.

46. The method of embodiment 45, wherein the enzymatic digestion is performed with mixture of enzymes comprising a beta-glucanase and a polygalacturonase.

47. The method of any one of embodiments 40-46, further comprising adding 40% v/v polyethylene glycol (PEG) to the mixture comprising DMSO prior to storing the protoplasts.

48. The method of embodiment 47, wherein the PEG is added to a final concentration of 8% v/v or less.

49. The method of any one of embodiments 40-48, further comprising distributing the protoplasts into microtiter plates prior to storing the protoplasts.

50. The method of any one of embodiments 40-49, wherein the filamentous fungal cells in the fungal culture possess a non-mycelium forming phenotype.

51. The method of any one of embodiments 40-50, wherein the filamentous fungal cells in the fungal culture are selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

52. The method of embodiment 50, wherein the filamentous fungal cells in the fungal culture are *Aspergillus niger* or teleomorphs or anamorphs thereof.

53. A system for generating a fungal production strain, the system comprising:
one or more processors; and
one or more memories operatively coupled to at least one of the one or more processors and
having instructions stored thereon that, when executed by at least one of the one or more processors, cause the system to:
a.) transform a plurality of protoplasts derived from culture of filamentous fungal cells with a first construct and a second construct, wherein the first construct comprises a first polynucleotide flanked on both sides by nucleotides homologous to a first locus in the genome of the protoplast and the second construct comprises a second polynucleotide flanked on both sides by nucleotides homologous to a second locus in the genome of the protoplast, wherein transformation results in integration of the first construct into the first locus and the second construct into the second locus by homologous recombination, wherein at least the second locus is a first selectable marker gene in the protoplast genome, and wherein the first polynucleotide comprises a mutation and/or a genetic control element;
b.) purify homokaryotic transformants by performing selection and counter-selection; and
c.) grow the purified transformants in media conducive to regeneration of the filamentous fungal cells.

54. The method of embodiment 53, wherein the first construct is split into construct A and construct B, wherein construct A comprises a first portion of the first polynucleotide and nucleotides homologous to the first locus 5' to the first portion of the first polynucleotide, and wherein construct B comprises a second portion of the first polynucleotide and nucleotides homologous to the first locus 3' to the second portion of the first polynucleotide, wherein the first portion and the second portion of the first polynucleotide comprises overlapping complementary sequence.

55. The method of embodiment 53 or 54, wherein the second construct is split into construct A and construct B, wherein construct A comprises a first portion of the second polynucleotide and nucleotides homologous to the first locus 5' to the first portion of the second polynucleotide, and wherein construct B comprises a second portion of the second polynucleotide and nucleotides homologous to the first locus 3' to the second portion of the second polynucleotide, wherein the first portion and the second portion of the second polynucleotide comprises overlapping complementary sequence.

56. The system of any one of embodiments 53-55, wherein each protoplast from the plurality of protoplasts is transformed with a single first construct from a plurality of first constructs and a single second construct from a plurality of second constructs, wherein the first polynucleotide in each first construct from the plurality of first constructs comprises a different mutation and/or genetic control element; and wherein the second polynucleotide in each second construct from the plurality of second constructs is identical.

57. The system of any one of embodiments 53-56, further comprising instructions to repeat steps a-c to generate a library of filamentous fungal cells, wherein each filamentous fungal cell in the library comprises a first polynucleotide with a different mutation and/or genetic control element.

58. The system of any one of embodiments 53-57, wherein the mutation is a single nucleotide polymorphism.

59. The system of any one of embodiments 53-58, wherein the genetic control element is a promoter sequence and/or a terminator sequence.

60. The system of any one of embodiments 53-58, wherein the genetic control element is a promoter sequence, wherein the promoter sequence is selected from the promoter sequences listed in Table 1.

61. The system of any one of embodiments 53-60, wherein steps a-c are performed in wells of a microtiter plate.

62. The system of embodiment 61, wherein the microtiter plate is a 96 well, 384 well or 1536 well microtiter plate.

63. The system of embodiments 53-62, wherein the filamentous fungal cells are selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

64. The system of embodiments 53-62, wherein the filamentous fungal cells are *Aspergillus niger*.

65. The system of any one of embodiments 53-64, wherein the filamentous fungal cells possess a non-mycelium forming phenotype.

66. The system of any one of embodiments 53-65, wherein the fungal cell possesses a non-functional non-homologous end joining pathway.

67. The system of embodiment 66, wherein the NHEJ pathway is made non-functional by exposing the cell to an antibody, a chemical inhibitor, a protein inhibitor, a physical inhibitor, a peptide inhibitor, or an anti-sense or RNAi molecule directed against a component of the NHEJ pathway.

68. The system of embodiment 67, wherein the chemical inhibitor is W-7.

69. The system of any of any one of embodiments 53-68, wherein the first locus is for the target filamentous fungal gene.

70. The system of embodiments 53-68, wherein the first locus is for a second selectable marker gene in the protoplast genome.

71. The system of embodiment 70, wherein the second selectable marker gene is selected from an auxotrophic marker gene, a colorimetric marker gene or a directional marker gene.

72. The system of any of embodiments 53-71, wherein the first selectable marker gene is selected from an auxotrophic marker gene, a colorimetric marker gene or a directional marker gene.

73. The system of any one of embodiments 53-72, wherein the second polynucleotide is selected from an auxotrophic marker gene, a directional marker gene or an antibiotic resistance gene.

74. The system of embodiment 71 or 72, wherein the colorimetric marker gene is an aygA gene.

75. The system of any one of embodiments 71-73, wherein the auxotrophic marker gene is selected from an argB gene, a trpC gene, a pyrG gene, or a met3 gene.

76. The system of any one of embodiments 71-73, wherein the directional marker gene is selected from an acetamidase (amdS) gene, a nitrate reductase gene (niaD), or a sulphate permease (Sut B) gene.

77. The system of embodiment 73, wherein the antibiotic resistance gene is a ble gene, wherein the ble gene confers resistance to pheomycin.

78. The system of embodiment 69, wherein the first selectable marker gene is an aygA gene and the second polynucleotide is a pyrG gene.

79. The system of any one of embodiments 53-68, wherein the first selectable marker gene is a met3 gene, the second selectable marker gene is an aygA gene and the second polynucleotide is a pyrG gene.

80. The system of any one of embodiments 53-79, wherein the plurality of protoplasts are prepared by removing cell walls from the filamentous fungal cells in the culture of filamentous fungal cells; isolating the plurality of protoplasts; and resuspending the isolated plurality of protoplasts in a mixture comprising dimethyl sulfoxide (DMSO) at a final concentration of 7% v/v or less.

81. The system of embodiment 80, wherein the mixture is stored at at least −20° C. or −80° C. prior to performing steps a-c.

82. The system of any one of embodiments 80-81, wherein the culture is at least 1 liter in volume.

83. The system of any one of embodiments 80-82, wherein the culture is grown for at least 12 hours prior to preparation of the protoplasts.

84. The system of any one of embodiments 80-83, wherein the fungal culture is grown under conditions whereby at least 70% of the protoplasts are smaller and have fewer nuclei.

85. The system of any one of embodiments 80-83, wherein removing the cell walls is performed by enzymatic digestion.

86. The system of embodiment 85, wherein the enzymatic digestion is performed with mixture of enzymes comprising a beta-glucanase and a polygalacturonase.

87. The system of any one of embodiments 53-86, further comprising adding 40% v/v polyethylene glycol (PEG) to the mixture comprising DMSO prior to storing the protoplasts.

88. The system of embodiment 87, wherein the PEG is added to a final concentration of 8% v/v or less.

89. A high-throughput (HTP) method of genomic engineering to evolve a filamentous fungus to acquire a desired phenotype, comprising:
a. perturbing the genomes of an initial plurality of filamentous fungal microbes having the same genomic strain background, to thereby create an initial HTP genetic design filamentous fungal strain library comprising individual filamentous fungal strains with unique genetic variations;
b. screening and selecting individual strains of the initial HTP genetic design filamentous fungal strain library for the desired phenotype;
c. providing a subsequent plurality of filamentous fungal microbes that each comprise a unique combination of genetic variation, said genetic variation selected from the genetic variation present in at least two individual filamentous fungal strains screened in the preceding step, to thereby create a subsequent HTP genetic design filamentous fungal strain library;
d. screening and selecting individual filamentous fungal strains of the subsequent HTP genetic design filamentous fungal strain library for the desired phenotype; and
e. repeating steps c)-d) one or more times, in a linear or non-linear fashion, until an filamentous fungal microbe has acquired the desired phenotype, wherein each subsequent iteration creates a new HTP genetic design filamentous fungal strain library comprising individual filamentous fungal strains harboring unique genetic variations that are a combination of genetic variation selected from amongst at least two individual filamentous fungal strains of a preceding HTP genetic design filamentous fungal strain library.

90. The HTP method of genomic engineering according to embodiment 89, wherein the initial HTP genetic design filamentous fungal strain library comprises at least one library selected from the group consisting of: a promoter swap microbial strain library, SNP swap microbial strain library, start/stop codon microbial strain library, optimized sequence microbial strain library, a terminator swap microbial strain library, and any combination thereof.

91. The HTP method of genomic engineering according to embodiment 89, wherein the initial HTP genetic design filamentous fungal strain library comprises a promoter swap microbial strain library.

92. The HTP method of genomic engineering according to embodiment 89, wherein the initial HTP genetic design filamentous fungal strain library comprises a promoter swap microbial strain library that contains at least one bicistronic design (BCD) regulatory sequence.

93. The HTP method of genomic engineering according to embodiment 89, wherein the initial HTP genetic design filamentous fungal strain library comprises a SNP swap microbial strain library.

94. The HTP method of genomic engineering according to embodiment 89, wherein the initial HTP genetic design filamentous fungal strain library comprises a microbial strain library that comprises:
a. at least one polynucleotide encoding for a chimeric biosynthetic enzyme, wherein said chimeric biosynthetic enzyme comprises:
i. an enzyme involved in a regulatory pathway in filamentous fungal;

ii. translationally fused to a DNA binding domain capable of binding a DNA binding site; and b. at least one DNA scaffold sequence that comprises the DNA binding site corresponding to the DNA binding domain of the chimeric biosynthetic enzyme.

95. The HTP method of genomic engineering according to embodiment 89, wherein the subsequent HTP genetic design filamentous fungal strain library is a full combinatorial strain library derived from the genetic variations in the initial HTP genetic design filamentous fungal strain library.

96. The HTP method of genomic engineering according to embodiment 89, wherein the subsequent HTP genetic design filamentous fungal strain library is a subset of a full combinatorial strain library derived from the genetic variations in the initial HTP genetic design filamentous fungal strain library.

97. The HTP method of genomic engineering according to embodiment 89, wherein the subsequent HTP genetic design filamentous fungus strain library is a full combinatorial strain library derived from the genetic variations in a preceding HTP genetic design filamentous fungal strain library.

98. The HTP method of genomic engineering according to embodiment 89, wherein the subsequent HTP genetic design filamentous fungal strain library is a subset of a full combinatorial strain library derived from the genetic variations in a preceding HTP genetic design filamentous fungal strain library.

99. The HTP method of genomic engineering according to embodiment 89, wherein perturbing the genome comprises utilizing at least one method selected from the group consisting of: random mutagenesis, targeted sequence insertions, targeted sequence deletions, targeted sequence replacements, and any combination thereof.

100. The HTP method of genomic engineering according to embodiment 89, wherein the initial plurality of filamentous fungal microbes comprise unique genetic variations derived from an industrial production filamentous fungal strain.

101. The HTP method of genomic engineering according to embodiment 89, wherein the initial plurality of filamentous fungal microbes comprise industrial production strain microbes denoted S1Gen1 and any number of subsequent microbial generations derived therefrom denoted SnGenn.

102. The HTP method according to embodiment 89, wherein the filamentous fungus is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

103. The HTP method according to embodiment 89, wherein the filamentous fungus is *Aspergillus niger.*

104. A method for generating a SNP swap filamentous fungal strain library, comprising the steps of:

a. providing a reference filamentous fungal strain and a second filamentous fungal strain, wherein the second filamentous fungal strain comprises a plurality of identified genetic variations selected from single nucleotide polymorphisms, DNA insertions, and DNA deletions, which are not present in the reference filamentous fungal strain; and b. perturbing the genome of either the reference filamentous fungal strain, or the second filamentous fungal strain, to thereby create an initial SNP swap filamentous fungal strain library comprising a plurality of individual filamentous fungal strains with unique genetic variations found within each strain of said plurality of individual strains, wherein each of said unique genetic variations corresponds to a single genetic variation selected from the plurality of identified genetic variations between the reference filamentous fungal strain and the second filamentous fungal strain.

105. The method for generating a SNP swap filamentous fungal strain library according to embodiment 104, wherein the genome of the reference filamentous fungal strain is perturbed to add one or more of the identified single nucleotide polymorphisms, DNA insertions, or DNA deletions, which are found in the second filamentous fungal strain.

106. The method for generating a SNP swap filamentous fungal strain library according to embodiment 104, wherein the genome of the second filamentous fungal strain is perturbed to remove one or more of the identified single nucleotide polymorphisms, DNA insertions, or DNA deletions, which are not found in the reference filamentous fungal strain.

107. The method for generating a SNP swap filamentous fungal strain library according to embodiment 104, wherein the resultant plurality of individual filamentous fungal strains with unique genetic variations, together comprise a full combinatorial library of all the identified genetic variations between the reference filamentous fungal strain and the second filamentous fungal strain.

108. The method for generating a SNP swap filamentous fungal strain library according to embodiment 104, wherein the resultant plurality of individual filamentous fungal strains with unique genetic variations, together comprise a subset of a full combinatorial library of all the identified genetic variations between the reference filamentous fungal strain and the second filamentous fungal strain.

109. The method for generating a SNP swap filamentous fungal strain library according to embodiment 104, wherein the filamentous fungus is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

110. The method for generating a SNP swap filamentous fungal strain library according to embodiment 104, wherein the filamentous fungus is *Aspergillus niger.*

111. A method for rehabilitating and improving the phenotypic performance of a production filamentous fungal strain, comprising the steps of:

a. providing a parental lineage filamentous fungal strain and a production filamentous fungal strain derived therefrom, wherein the production filamentous fungal strain comprises a plurality of identified genetic variations selected from single nucleotide polymorphisms, DNA insertions, and DNA deletions, not present in the parental lineage strain;

b. perturbing the genome of either the parental lineage filamentous fungal strain, or the production filamentous fungal strain, to create an initial library of filamentous fungal strains, wherein each strain in the initial library comprises a unique genetic variation from the plurality of identified genetic variations between the parental lineage filamentous fungal strain and the production filamentous fungal strain;

c. screening and selecting individual strains of the initial library for phenotypic performance improvements over a reference filamentous fungal strain, thereby identifying unique genetic variations that confer phenotypic performance improvements;

d. providing a subsequent plurality of filamentous fungal microbes that each comprise a combination of unique genetic variations from the genetic variations present in at least two individual filamentous fungal strains screened in the preceding step, to thereby create a subsequent library of filamentous fungal strains;

e. screening and selecting individual strains of the subsequent library for phenotypic performance improvements over the reference filamentous fungal strain, thereby identifying unique combinations of genetic variation that confer additional phenotypic performance improvements; and f. repeating steps d)-e) one or more times, in a linear or non-linear fashion, until an filamentous fungal strain exhibits a desired level of improved phenotypic performance compared to the phenotypic performance of the production filamentous fungal strain, wherein each subsequent iteration creates a new library of microbial strains, where each strain in the new library comprises genetic variations that are a combination of genetic variations selected from amongst at least two individual filamentous fungal strains of a preceding library.

112. The method for rehabilitating and improving the phenotypic performance of a production filamentous fungal strain according to embodiment 111, wherein the initial library of filamentous fungal strains is a full combinatorial library comprising all of the identified genetic variations between the parental lineage filamentous fungal strain and the production filamentous fungal strain.

113. The method for rehabilitating and improving the phenotypic performance of a production filamentous fungal strain according to embodiment 111, wherein the initial library of filamentous fungal strains is a subset of a full combinatorial library comprising a subset of the identified genetic variations between the parental lineage filamentous fungal strain and the production filamentous fungal strain.

114. The method for rehabilitating and improving the phenotypic performance of a production filamentous fungal strain according to embodiment 111, wherein the subsequent library of filamentous fungal strains is a full combinatorial library of the initial library.

115. The method for rehabilitating and improving the phenotypic performance of a production filamentous fungal strain according to embodiment 111, wherein the subsequent library of filamentous fungal strains is a subset of a full combinatorial library of the initial library.

116. The method for rehabilitating and improving the phenotypic performance of a production filamentous fungal strain according to embodiment 111, wherein the subsequent library of filamentous fungal strains is a full combinatorial library of a preceding library.

117. The method for rehabilitating and improving the phenotypic performance of a production filamentous fungal strain according to embodiment 111, wherein the subsequent library of filamentous fungal strains is a subset of a full combinatorial library of a preceding library.

118. The method for rehabilitating and improving the phenotypic performance of a production filamentous fungal strain according to embodiment 111, wherein the genome of the parental lineage filamentous fungal strain is perturbed to add one or more of the identified single nucleotide polymorphisms, DNA insertions, or DNA deletions, which are found in the production filamentous fungal strain.

119. The method for rehabilitating and improving the phenotypic performance of a production filamentous fungal strain according to embodiment 111, wherein the genome of the production filamentous fungal strain is perturbed to remove one or more of the identified single nucleotide polymorphisms, DNA insertions, or DNA deletions, which are not found in the parental lineage filamentous fungal strain.

120. The method for rehabilitating and improving the phenotypic performance of a production filamentous fungal strain according to embodiment 111, wherein perturbing the genome comprises utilizing at least one method selected from the group consisting of: random mutagenesis, targeted sequence insertions, targeted sequence deletions, targeted sequence replacements, and combinations thereof.

121. The method for rehabilitating and improving the phenotypic performance of a production filamentous fungal strain according to embodiment 111, wherein steps d)-e) are repeated until the phenotypic performance of an filamentous fungal strain of a subsequent library exhibits at least a 10% increase in a measured phenotypic variable compared to the phenotypic performance of the production filamentous fungal strain.

122. The method for rehabilitating and improving the phenotypic performance of a production filamentous fungal strain according to embodiment 111, wherein steps d)-e) are repeated until the phenotypic performance of an filamentous fungal strain of a subsequent library exhibits at least a one-fold increase in a measured phenotypic variable compared to the phenotypic performance of the production filamentous fungal strain.

123. The method for rehabilitating and improving the phenotypic performance of a production filamentous fungal strain according to embodiment 111, wherein the improved phenotypic performance of step f) is selected from the group consisting of: volumetric productivity of a product of interest, specific productivity of a product of interest, yield of a product of interest, titer of a product of interest, and combinations thereof.

124. The method for rehabilitating and improving the phenotypic performance of a production filamentous fungal strain according to embodiment 111, wherein the improved phenotypic performance of step f) is: increased or more efficient production of a product of interest, said product of interest selected from the group consisting of: a small molecule, enzyme, peptide, amino acid, organic acid, synthetic compound, fuel, alcohol, primary extracellular metabolite, secondary extracellular metabolite, intracellular component molecule, and combinations thereof.

125. The method for rehabilitating and improving the phenotypic performance of a production filamentous fungal strain according to embodiment 111, wherein the identified genetic variations further comprise artificial promoter swap genetic variations from a promoter swap library.

126. The method for rehabilitating and improving the phenotypic performance of a production filamentous fungal strain according to embodiment 111, further comprising:
engineering the genome of at least one microbial strain of either:
the initial library of filamentous fungal strains, or
a subsequent library of filamentous fungal strains, to comprise one or more promoters from a promoter ladder operably linked to an endogenous ilamentous fungal target gene.

127. The method for rehabilitating and improving the phenotypic performance of a production filamentous fungal strain according to embodiment 111, wherein the filamentous fungus is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*)*, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

128. The method for rehabilitating and improving the phenotypic performance of a production filamentous fungal strain according to embodiment 111, wherein the filamentous fungus is *Aspergillus niger*.

129. A method for generating a promoter swap filamentous fungal strain library, comprising the steps of:
a. providing a plurality of target genes endogenous to a base filamentous fungal strain, and a promoter ladder, wherein said promoter ladder comprises a plurality of promoters exhibiting different expression profiles in the base filamentous fungal strain; and
b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the target genes endogenous to the base filamentous fungal strain.

130. The method according to embodiment 129, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*)*, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

131. The method according to embodiment 129, wherein the filamentous fungal strain is an *Aspergillus niger* strain.

132. A promoter swap method for improving the phenotypic performance of a production filamentous fungal strain, comprising the steps of:
a. providing a plurality of target genes endogenous to a base filamentous fungal strain, and a promoter ladder, wherein said promoter ladder comprises a plurality of promoters exhibiting different expression profiles in the base filamentous fungal strain;
b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the target genes endogenous to the base filamentous fungal strain;
c. screening and selecting individual filamentous fungal strains of the initial promoter swap filamentous fungal strain library for phenotypic performance improvements over a reference filamentous fungal strain, thereby identifying unique genetic variations that confer phenotypic performance improvements;
d. providing a subsequent plurality of filamentous fungal microbes that each comprise a combination of unique genetic variations from the genetic variations present in at least two individual filamentous fungal strains screened in the preceding step, to thereby create a subsequent promoter swap filamentous fungal strain library;
e. screening and selecting individual filamentous fungal strains of the subsequent promoter swap filamentous fungal strain library for phenotypic performance improvements over the reference filamentous fungal strain, thereby identifying unique combinations of genetic variation that confer additional phenotypic performance improvements; and
f. repeating steps d)-e) one or more times, in a linear or non-linear fashion, until an filamentous fungal strain exhibits a desired level of improved phenotypic performance compared to the phenotypic performance of the production filamentous fungal strain, wherein each subsequent iteration creates a new promoter swap filamentous fungal strain library of microbial strains, where each strain in the new library comprises genetic variations that are a combination of genetic variations selected from amongst at least two individual filamentous fungal strains of a preceding library.

133. The promoter swap method for improving the phenotypic performance of a production filamentous fungal strain according to embodiment 132, wherein the subsequent promoter swap filamentous fungal strain library is a full combinatorial library of the initial promoter swap filamentous fungal strain library.

134. The promoter swap method for improving the phenotypic performance of a production filamentous fungal strain according to embodiment 132, wherein the subsequent promoter swap filamentous fungal strain library is a subset of a full combinatorial library of the initial promoter swap filamentous fungal strain library.

135. The promoter swap method for improving the phenotypic performance of a production filamentous fungal strain according to embodiment 132, wherein the subsequent promoter swap filamentous fungal strain library is a full combinatorial library of a preceding promoter swap filamentous fungal strain library.

136. The promoter swap method for improving the phenotypic performance of a production filamentous fungal strain according to embodiment 132, wherein the subsequent promoter swap filamentous fungal strain library is a subset of a full combinatorial library of a preceding promoter swap filamentous fungal strain library.

137. The promoter swap method for improving the phenotypic performance of a production filamentous fungal strain according to embodiment 132, wherein steps d)-e) are repeated until the phenotypic performance of an filamentous fungal strain of a subsequent promoter swap filamentous fungal strain library exhibits at least a 10% increase in a measured phenotypic variable compared to the phenotypic performance of the production filamentous fungal strain.

138. The promoter swap method for improving the phenotypic performance of a production filamentous fungal strain according to embodiment 132, wherein steps d)-e) are repeated until the phenotypic performance of an filamentous fungal strain of a subsequent promoter swap filamentous fungal strain library exhibits at least a one-fold increase in a measured phenotypic variable compared to the phenotypic performance of the production filamentous fungal strain.

139. The promoter swap method for improving the phenotypic performance of a production filamentous fungal strain according to embodiment 132, wherein the improved phenotypic performance of step f) is selected from the group consisting of: volumetric productivity of a product of interest, specific productivity of a product of interest, yield of a product of interest, titer of a product of interest, and combinations thereof.

140. The promoter swap method for improving the phenotypic performance of a production filamentous fungal strain according to embodiment 132, wherein the improved phenotypic performance of step f) is: increased or more efficient production of a product of interest, said product of interest selected from the group consisting of: a small molecule, enzyme, peptide, amino acid, organic acid, synthetic compound, fuel, alcohol, primary extracellular metabolite, secondary extracellular metabolite, intracellular component molecule, and combinations thereof.

141. The promoter swap method for improving the phenotypic performance of a production filamentous fungal strain according to embodiment 132, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

142. The promoter swap method for improving the phenotypic performance of a production filamentous fungal strain according to embodiment 132, wherein the filamentous fungal strain is an *Aspergillus niger* strain.

143. A method for generating a terminator swap filamentous fungal strain library, comprising the steps of:
a. providing a plurality of target genes endogenous to a base filamentous fungal strain, and a terminator ladder, wherein said terminator ladder comprises a plurality of terminators exhibiting different expression profiles in the base filamentous fungal strain; and
b. engineering the genome of the base filamentous fungal strain, to thereby create an initial terminator swap filamentous fungal strain library comprising a plurality of individual filamentous fungal strains with unique genetic variations found within each strain of said plurality of individual filamentous fungal strains, wherein each of said unique genetic variations comprises one or more of the terminators from the terminator ladder operably linked to one of the target genes endogenous to the base filamentous fungal strain.

144. The method according to embodiment 143, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

145. The method according to embodiment 143, wherein the filamentous fungal strain is an *Aspergillus niger* strain.

146. A terminator swap method for improving the phenotypic performance of a production filamentous fungal strain, comprising the steps of:
a. providing a plurality of target genes endogenous to a base filamentous fungal strain, and a terminator ladder, wherein said terminator ladder comprises a plurality of terminators exhibiting different expression profiles in the base filamentous fungal strain;
b. engineering the genome of the base filamentous fungal strain, to thereby create an initial terminator swap filamentous fungal strain library comprising a plurality of individual filamentous fungal strains with unique genetic variations found within each strain of said plurality of individual filamentous fungal strains, wherein each of said unique genetic variations comprises one or more of the terminators from the terminator ladder operably linked to one of the target genes endogenous to the base filamentous fungal strain;
c. screening and selecting individual filamentous fungal strains of the initial terminator swap filamentous fungal strain library for phenotypic performance improvements over a reference filamentous fungal strain, thereby identifying unique genetic variations that confer phenotypic performance improvements;
d. providing a subsequent plurality of filamentous fungal microbes that each comprise a combination of unique genetic variations from the genetic variations present in at least two individual filamentous fungal strains screened in the preceding step, to thereby create a subsequent terminator swap filamentous fungal strain library;
e. screening and selecting individual filamentous fungal strains of the subsequent terminator swap filamentous fungal strain library for phenotypic performance improvements over the reference filamentous fungal strain, thereby identifying unique combinations of genetic variation that confer additional phenotypic performance improvements; and
f. repeating steps d)-e) one or more times, in a linear or non-linear fashion, until an filamentous fungal strain exhibits a desired level of improved phenotypic performance compared to the phenotypic performance of the production filamentous fungal strain, wherein each subsequent iteration creates a new terminator swap filamentous fungal strain library of microbial strains, where each strain in the new library comprises genetic variations that are a combination of genetic variations selected from amongst at least two individual filamentous fungal strains of a preceding library.

147. The terminator swap method for improving the phenotypic performance of a production filamentous fungal strain according to embodiment 146, wherein the subsequent terminator swap filamentous fungal strain library is a full combinatorial library of the initial terminator swap filamentous fungal strain library.

148. The terminator swap method for improving the phenotypic performance of a production filamentous fungal strain according to embodiment 146, wherein the subsequent terminator swap filamentous fungal strain library is a subset of a full combinatorial library of the initial terminator swap filamentous fungal strain library.

149. The terminator swap method for improving the phenotypic performance of a production filamentous fungal strain according to embodiment 146, wherein the subsequent terminator swap filamentous fungal strain library is a full combinatorial library of a preceding terminator swap filamentous fungal strain library.

150. The terminator swap method for improving the phenotypic performance of a production filamentous fungal strain according to embodiment 146, wherein the subsequent terminator swap filamentous fungal strain library is a subset of a full combinatorial library of a preceding terminator swap filamentous fungal strain library.

151. The terminator swap method for improving the phenotypic performance of a production filamentous fungal strain according to embodiment 146, wherein steps d)-e) are repeated until the phenotypic performance of an filamentous fungal strain of a subsequent terminator swap filamentous fungal strain library exhibits at least a 10% increase in a measured phenotypic variable compared to the phenotypic performance of the production filamentous fungal strain.

152. The terminator swap method for improving the phenotypic performance of a production filamentous fungal strain according to embodiment 146, wherein steps d)-e) are repeated until the phenotypic performance of an filamentous fungal strain of a subsequent terminator swap filamentous fungal strain library exhibits at least a one-fold increase in a measured phenotypic variable compared to the phenotypic performance of the production filamentous fungal strain.

153. The terminator swap method for improving the phenotypic performance of a production filamentous fungal strain according to embodiment 146, wherein the improved phenotypic performance of step f) is selected from the group consisting of: volumetric productivity of a product of interest, specific productivity of a product of interest, yield of a product of interest, titer of a product of interest, and combinations thereof.

154. The terminator swap method for improving the phenotypic performance of a production filamentous fungal strain according to embodiment 146, wherein the improved phenotypic performance of step f) is: increased or more efficient production of a product of interest, said product of interest selected from the group consisting of: a small molecule, enzyme, peptide, amino acid, organic acid, synthetic compound, fuel, alcohol, primary extracellular metabolite, secondary extracellular metabolite, intracellular component molecule, and combinations thereof.

155. The terminator swap method for improving the phenotypic performance of a production filamentous fungal strain according to embodiment 146, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

156. The terminator swap method for improving the phenotypic performance of a production filamentous fungal strain according to embodiment 146, wherein the filamentous fungal strain is an *Aspergillus niger* strain.

157. A filamentous fungal host cell comprising a promoter operably linked to an endogenous gene of the host cell, wherein the promoter is heterologous to the endogenous gene, wherein the promoter has a sequence selected from the group consisting of SEQ ID Nos. 1-4.

158. The filamentous fungal host cell of embodiment 157, wherein filamentous fungal host cell has a desired level of improved phenotypic performance compared to the phenotypic performance of a reference filamentous fungal strain without the promoter operably linked to the endogenous gene.

159. The filamentous fungal host cell according to embodiment 157, wherein the filamentous fungal host cell is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

160. The filamentous fungal host cell according to embodiment 157, wherein the filamentous fungal host cell is *Aspergillus niger*.

161. A filamentous fungal strain library, wherein each filamentous fungal strain in the library comprises a promoter operably linked to an endogenous gene of the host cell, wherein the promoter is heterologous to the endogenous gene, wherein the promoter has a sequence selected from the group consisting of SEQ ID Nos. 1-4.

162. The filamentous fungal strain library according to embodiment 161, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

163. The filamentous fungal strain library according to embodiment 161, wherein the filamentous fungal strain is *Aspergillus niger*.

164. A method for isolating clonal populations derived from single fungal spores, the method comprising:

(a) providing a plurality of fungal spores in a liquid suspension, wherein the plurality of fungal spores were derived from a fungal strain:

(b) dispensing a discrete volume of the liquid suspension to an individual reaction area in a substrate comprising a plurality of reaction areas, wherein each reaction area in the plurality of reaction areas comprises growth media, wherein the dispensing results in a probability that at least 75% of the individual reaction areas contain no more than a single viable fungal spore from the plurality of fungal spores;

(c) culturing the dispensed single viable fungal spores in the reaction areas comprising growth media; and (d) selecting clonal populations growing in the reaction areas, thereby isolating clonal populations derived from single fungal spores.

165. The method of embodiment 164, further comprising screening the discrete volumes for the presence or absence of a single fungal spore in the discrete volumes, wherein only the discrete volumes containing a single fungal spore are selected for step (b).

166. The method of embodiment 165, wherein the dispensing results in a probability that at least 80% of the individual reaction areas contain no more than a single viable fungal spore from the plurality of fungal spores.

167. The method of embodiment 165, wherein the dispensing results in a probability that at least 90% of the individual reaction areas contain no more than a single viable fungal spore from the plurality of fungal spores.

168. The method of embodiment 165, wherein the dispensing results in a probability that at least 95% of the individual reaction areas contain no more than a single viable fungal spore from the plurality of fungal spores.

169. The method of embodiment 165, wherein the dispensing results in a probability that at least 99% of the individual reaction areas contain no more than a single viable fungal spore from the plurality of fungal spores.

170. The method of embodiment 165, wherein the dispensing results in a probability that substantially all of the individual reaction areas contain no more than a single viable fungal spore from the plurality of fungal spores.

171. The method of any one of embodiments 165-170, wherein the screening the discrete volumes entails optically distinguishing the presence or absence of a single fungal spore in the discrete volumes.

172. The method of embodiment 171, wherein the screening is performed using a microfluidic device capable of optically distinguishing the presence or absence of a single fungal spore in the discrete volumes.

173. A method for isolating clonal populations derived from single fungal spores, the method comprising:
(a) providing a plurality of fungal spores in a liquid suspension, wherein the plurality of fungal spores were derived from a fungal strain;
(b) diluting the liquid suspension, wherein the dilution is a limiting dilution;
(c) dispensing a discrete volume of the dilution to an individual reaction area in a substrate comprising a plurality of reaction areas, wherein each reaction area in the plurality of reaction areas comprises growth media, wherein the limiting dilution results in a probability that the discrete volume of the dilution dispensed to each reaction area contains either one or no viable spore follows a Poisson Distribution, whereby greater than 90% of the reaction areas in the plurality of reaction areas contain no viable spores and greater than 90% of reaction areas that contain one or more viable spores contain only a single viable spore;
(d) culturing the dispensed single viable fungal spores in the reaction areas comprising growth media; and
(e) selecting clonal populations growing in the reaction areas, thereby isolating clonal populations derived from single fungal spores.

174. The method of any of embodiments 164-173, wherein the reaction areas are present in a microtiter plate.

175. The method of embodiment 174, wherein the microtiter plate contains 96 wells, 384 wells or 1536 wells.

176. The method of any of embodiments 164-175, wherein the fungal strain is a filamentous fungal strain.

177. The method of embodiment 176, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

178. The method of embodiment 177, wherein the filamentous fungal strain is *Aspergillus niger* or teleomorphs or anamorphs thereof.

179. The method of embodiment 178, wherein the filamentous fungal strain possess a non-mycelium, pellet morphology.

180. The method of embodiment 179, wherein the filamentous fungal strain expresses a mutant form of an *A. niger* ortholog of the *S. cerevisiae* SLN1 gene.

181. The method of embodiment 180, wherein a nucleic sequence of the mutant form of the *A. niger* ortholog of the *S. cerevisiae* SLN1 gene is SEQ ID NO: 13.

182. The method of embodiment 179 or 180, wherein the mutant form of the *A. niger* ortholog of the *S. cerevisiae* SLN1 gene is operably linked to a promoter sequence selected from SEQ ID NO: 1 or 2.

183. The method of any of embodiments 164-182, wherein the fungal strain possesses a genetic perturbation.

184. The method of embodiment 183, wherein the genetic perturbation is selected from single nucleotide polymorphisms, DNA insertions, DNA deletions or any combination thereof.

185. The method of embodiment 183 or 184, wherein the genetic perturbation is introduced into protoplasts derived from the fungal strain via transforming the protoplasts with a ribonucleoprotein complex (RNP-complex).

186. The method of embodiment 185, wherein the RNP-complex comprises an RNA guided endonuclease complexed with a guide RNA (gRNA).

187. The method of embodiment 186, wherein the RNA guided endonuclease is a Class 2 CRISPR-Cas System RNA guided endonuclease.

188. The method of embodiment 187, wherein the Class 2 CRISPR-Cas system RNA guided endonuclease is a Type II, Type V or Type VI RNA guided endonuclease.

189. The method of embodiment 187, wherein the Class 2 CRISPR-Cas system RNA guided endonuclease is selected from Cas9, Cas12a, Cas12b, Cas12c, Cas12d, Cas12e, Cas13a, Cas13b, Cas13c or homologs, orthologs, mutants, variants or modified versions thereof.

190. The method of embodiment 189, wherein the Class 2 CRISPR-Cas system RNA guided endonuclease is Cas9 or homologs, orthologs or paralogs thereof.

191. The method of embodiment 186, wherein the gRNA is a CRISPR RNA (crRNA) alone or annealed to a transactivating CRISPR RNA (tracrRNA).

192. The method of embodiment 186, wherein the gRNA is a single guide RNA (sgRNA) comprising a tracrRNA and a crRNA.

193. The method of embodiment 191 or 192, wherein the crRNA comprises a guide sequence complementary to a target gene within the genome of the fungal strain, wherein introduction of the RNP-complex into the protoplasts facilitates introduction of the genetic perturbation into the target gene.

194. The method of embodiment 193, wherein the genetic perturbation of the target gene is facilitated by cleavage of the target gene by the RNP-complex to generate DNA ends in the target gene followed by non-homologous end joining of the DNA ends in the target gene by the non-homologous end joining (NHEJ) pathway.

195. The method of embodiment 193, further comprising co-transforming a donor DNA comprising a mutated version of the target gene, wherein the mutated version of the target gene is flanked on both sides by nucleotides homologous to the target gene locus.

196. The method of embodiment 195, wherein the genetic perturbation of the target gene is facilitated by cleavage of the target gene by the RNP-complex to generate DNA ends in the target gene followed by replacement of the target gene with the donor DNA via homologous recombination.

197. The method of any of embodiments 185-196, wherein step (b) further comprises co-transforming a vector comprising a selectable marker.

198. The method of embodiment 197, wherein the selectable marker is used during step (d) to select clonal populations derived from transformation competent fungal strains.

199. The method of embodiment 183 or 184, wherein the genetic perturbation is introduced into protoplasts derived from the fungal strain by transforming the plurality of protoplasts with a first construct and a second construct, wherein the first construct comprises a first polynucleotide flanked on both sides by nucleotides homologous to a first locus in the genome of the protoplast and the second construct comprises a second polynucleotide flanked on both sides by nucleotides homologous to a second locus in the genome of the protoplast, wherein the transformation results in integration of the first construct into the first locus and the second construct into the second locus by homologous recombination, wherein at least the second locus is a first selectable marker gene in the protoplast genome, and wherein the first polynucleotide comprises the genetic perturbation.

200. The method of embodiment 199, wherein the selectable marker gene is used during step (d) to facilitate selection of clonal populations derived from fungal strains comprising the genetic perturbation.

201. The method of any of embodiments 195-200, wherein the fungal strain possesses a non-functional non-homologous end joining (NHEJ) pathway.

202. The method of embodiment 201, wherein the NHEJ pathway is made non-functional by exposing the fungal strain to an antibody, a chemical inhibitor, a protein inhibitor, a physical inhibitor, a peptide inhibitor, or an anti-sense or RNAi molecule directed against a component of the NHEJ pathway.

203. The method of embodiment 202, wherein the chemical inhibitor is W-7.

204. A method for producing a filamentous fungal strain, the method comprising:
a.) providing a plurality of protoplasts, wherein the plurality of protoplasts were prepared from a culture of a parent filamentous fungal strain;
b.) transforming each protoplast from the plurality of protoplasts with a ribonucleoprotein complex (RNP-complex); and
c.) selecting and screening individual filamentous fungal strains derived from the transformed protoplasts for phenotypic performance improvements over the parent filamentous fungal strain, thereby identifying genetic perturbations in the genome of the selected individual filamentous fungal strains that confer phenotypic performance improvements.

205. The method of embodiment 204, wherein the genetic perturbations are selected from single nucleotide polymorphisms, DNA insertions, DNA deletions or any combination thereof.

206. The method of embodiment 204 or 205, wherein the RNP-complex comprises an RNA guided endonuclease complexed with a guide RNA (gRNA).

207. The method of embodiment 206, wherein the RNA guided endonuclease is a Class 2 CRISPR-Cas System RNA guided endonuclease.

208. The method of embodiment 207, wherein the Class 2 CRISPR-Cas system RNA guided endonuclease is a Type II, Type V or Type VI RNA guided endonuclease.

209. The method of embodiment 207, wherein the Class 2 CRISPR-Cas system RNA guided endonuclease is selected from Cas9, Cas12a, Cas12b, Cas12c, Cas12d, Cas12e, Cas13a, Cas13b, Cas13c or homologs, orthologs, mutants, variants or modified versions thereof.

210. The method of embodiment 209, wherein the Class 2 CRISPR-Cas system RNA guided endonuclease is Cas9 or homologs, orthologs or paralogs thereof.

211. The method of embodiment 206, wherein the gRNA is a CRISPR RNA (crRNA) alone or annealed to a transactivating CRISPR RNA (tracrRNA).

212. The method of embodiment 206, wherein the gRNA is a single guide RNA (sgRNA) comprising a tracrRNA and a crRNA.

213. The method of embodiment 211 or 212, wherein the crRNA comprises a guide sequence that is complementary to a target gene within the genome of the parent filamentous fungal strain, wherein introduction of the RNP-complex perturbs the target gene in the protoplasts.

214. The method of embodiment 213, wherein the perturbation of the target gene is facilitated by cleavage of the target gene by the RNP-complex to generate DNA ends in the target gene followed by non-homologous end joining of the DNA ends in the target gene by the non-homologous end joining (NHEJ) pathway.

215. The method of embodiment 213, wherein step (b) further comprises co-transforming a donor DNA comprising a mutated version of the target gene, wherein the mutated version of the target gene is flanked on both sides by nucleotides homologous to the target gene locus.

216. The method of embodiment 215, wherein the perturbation of the target gene is facilitated by cleavage of the target gene by the RNP-complex to generate DNA ends in the target gene followed by replacement of the target gene with the donor DNA via homologous recombination.

217. The method of any of embodiments 204-216, wherein step (b) further comprises co-transforming a vector comprising a selectable marker.

218. The method of embodiment 217, wherein the selectable marker is used during step (c) to select transformation competent individual filamentous fungal strains for subsequent screening for phenotypic performance improvements over the parent filamentous fungal strain.

219. The method of any of one of embodiments 215-218, wherein the parent filamentous fungal strain possesses a non-functional non-homologous end joining (NHEJ) pathway.

220. The method of embodiment 219, wherein the NHEJ pathway is made non-functional by exposing the cell to an antibody, a chemical inhibitor, a protein inhibitor, a physical inhibitor, a peptide inhibitor, or an anti-sense or RNAi molecule directed against a component of the NHEJ pathway.

221. The method of embodiment 220, wherein the chemical inhibitor is W-7.

222. The method of any of embodiments 204-221, wherein the phenotypic performance improvement of the filamentous fungal strain comprises at least a 10% increase in a measured phenotypic variable for a product of interest compared to the phenotypic performance of the parent filamentous fungal strain.

223. The method of any of embodiments 204-221, wherein the phenotypic performance improvement of the filamentous fungal strain comprises at least a one-fold increase in a measured phenotypic variable for a product of interest compared to the phenotypic performance of the parent filamentous fungal strain.

224. The method of embodiment 222 or 223, wherein the measured phenotypic variable is selected from the group consisting of: volumetric productivity of the product of interest, specific productivity of the product of interest, yield of the product of interest, titer of the product of interest, and combinations thereof.

225. The method of embodiment 222 or 223, wherein the measured phenotypic variable is increased or more efficient production of the product of interest, 226. The method of embodiment 222 or 223, wherein the product of interest is selected from the group consisting of: a small molecule, enzyme, peptide, amino acid, organic acid, synthetic compound, fuel, alcohol, primary extracellular metabolite, secondary extracellular metabolite, intracellular component molecule, and combinations thereof.

227. The method of any of embodiments 204-226, wherein the parent filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

228. The method of embodiment 227, wherein the filamentous fungal strain is *Aspergillus niger* or teleomorphs or anamorphs thereof.

229. The method of embodiment 228, wherein the filamentous fungal strain possess a non-mycelium, pellet morphology.

230. The method of embodiment 229, wherein the filamentous fungal strain expresses a mutant form of an *A. niger* ortholog of the *S. cerevisiae* SLN1 gene.

231. The method of embodiment 230, wherein a nucleic sequence of the mutant form of the *A. niger* ortholog of the *S. cerevisiae* SLN1 gene is SEQ ID NO: 13.

232. The method of embodiment 230 or 231, wherein the mutant form of the *A. niger* ortholog of the *S. cerevisiae* SLN1 gene is operably linked to a promoter sequence selected from SEQ ID NO: 1 or 2.

233. The method of any of embodiment 204-232, further comprising generating isolated clonal populations derived from the individual filamentous fungal strains prior to step (c).

234. The method of embodiment 233, wherein the isolating comprises:
(i) inducing the transformed protoplasts to produce a plurality of fungal spores, wherein each fungal spore form the plurality is derived from a single transformed protoplast;
(ii) resuspending the plurality of fungal spores derived from a single transformed protoplast in a liquid to generate a liquid suspension;
(iii) dispensing a discrete volume of the liquid suspension to an individual reaction area in a substrate comprising a plurality of reaction areas, wherein each reaction area in the plurality of reaction areas comprises growth media, wherein the dispensing results in a probability that at least 75% of the individual reaction areas contain no more than a single viable fungal spore from the plurality of fungal spores; and
(iv) culturing the dispensed single viable fungal spores in the reaction areas comprising growth media, thereby generating isolated clonal populations derived from the individual filamentous fungal strains.

235. The method of embodiments 234, further comprising screening the discrete volumes for the presence or absence of a single fungal spore in the discrete volumes, wherein only the discrete volumes containing a single fungal spore are selected for step (iii).

236. The method of embodiment 235, wherein the dispensing results in a probability that at least 80% of the individual reaction areas contain no more than an single viable fungal spore from the plurality of fungal spores.

237. The method of embodiment 235, wherein the dispensing results in a probability that at least 90% of the individual reaction areas contain no more than a single viable fungal spore from the plurality of fungal spores.

238. The method of embodiment 234, wherein the dispensing results in a probability that at least 95% of the individual reaction areas contain no more than a single viable fungal spore from the plurality of fungal spores.

239. The method of embodiment 234, wherein the dispensing results in a probability that at least 99% of the individual reaction areas contain no more than a single viable fungal spore from the plurality of fungal spores.

240. The method of embodiment 234, wherein the dispensing results in a probability that substantially all of the individual reaction areas contain no more than a single viable fungal spore from the plurality of fungal spores.

241. The method of embodiment 235, wherein the screening the discrete volumes entails optically distinguishing the presence or absence of a single fungal spore in the discrete volumes.

242. The method of embodiment 241, wherein the screening is performed using a microfluidic device capable of optically distinguishing the presence or absence of a single fungal spore in the discrete volumes.

243. The method of embodiment 233, wherein the isolating comprises. (i) inducing the transformed protoplasts to produce a plurality of fungal spores, wherein each fungal spore form the plurality is derived from a single transformed protoplast; (ii) resuspending the plurality of fungal spores derived from a single transformed protoplast in a liquid to generate a liquid suspension; (iii) diluting the liquid suspension, wherein the dilution is a limiting dilution; (iv) dispensing a discrete volume of the dilution to an individual reaction area in a substrate comprising a plurality of reaction areas, wherein each reaction area in the plurality of reaction areas comprises growth media, wherein the limiting dilution results in a probability that the discrete volume of the dilution dispensed to each reaction area contains either one or no viable spore follows a Poisson Distribution, whereby greater than 90% of the reaction areas in the plurality of reaction areas contain no viable spores and greater than 90% of reaction areas that contain one or more viable spores contain only a single viable spore; (v) culturing the dispensed single viable fungal spores in the reaction areas comprising growth media; and (vi) selecting clonal populations growing in the reaction areas, thereby isolating clonal populations derived from single fungal spores.

244. The method of any of embodiments 234-243, wherein the reaction areas are present in a microtiter plate.

245. The method of embodiment 244, wherein the microtiter plate contains 96 wells, 384 wells or 1536 wells.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

In addition, the following particular applications are incorporated herein by reference: U.S. application Ser. No. 15/396,230 (U.S. Pub. No. US 2017/0159045 A1) filed on Dec. 30, 20016; PCT/US2016/065465 (WO 2017/100377 A1) filed on Dec. 7, 2016; U.S. application Ser. No. 15/140,296 (US 2017/0316353 A1) filed on Apr. 27, 2016; PCT/US2017/029725 (WO 2017/189784 A1) filed on Apr. 26, 2017; PCT/US2016/065464 (WO 2017/100376 A2) filed on Dec. 7, 2016; U.S. Prov. App. No. 62/431,409 filed on Dec. 7, 2016; U.S. Prov. App. No. 62/264,232 filed on Dec. 7, 2015; and U.S. Prov. App. No. 62/368,786 filed on Jul. 29, 2016. In addition, the following particular applications are incorporated herein by reference: PCT/US2017/069086, filed on Dec. 29, 2017; and U.S. Prov. App. No. 62/441,040, filed on Dec. 30, 2016.

What is claimed is:

1. A method for isolating clonal populations from single fungal spores, the method comprising:
   (a) dispensing discrete volumes of a liquid suspension comprising a plurality of fungal spores from a fungal strain to individual reaction areas in a substrate comprising a plurality of reaction areas, wherein each reaction area in the plurality of reaction areas comprises growth media, wherein the dispensing results in a probability that at least 90% of the individual reaction areas contain either no viable spores or no more than a single viable fungal spore from the plurality of fungal spores;
   (b) culturing the dispensed single viable fungal spores in the reaction areas comprising growth media; and
   (c) selecting clonal populations growing in the reaction areas, thereby isolating clonal populations from single fungal spores.

2. The method of claim 1, further comprising screening the discrete volumes for the presence or absence of a single fungal spore in the discrete volumes, wherein only the discrete volumes containing a single fungal spore are selected for step (a).

3. The method of claim 2, wherein the dispensing results in a probability that at least 90%, at least 95%, at least 99% or all of the individual reaction areas contain no more than a single viable fungal spore from the plurality of fungal spores.

4. The method of claim 2, wherein the screening the discrete volumes comprises optically distinguishing the presence or absence of a single fungal spore in the discrete volumes.

5. The method of claim 4, wherein the screening is performed using a microfluidic device capable of optically distinguishing the presence or absence of a single fungal spore in the discrete volumes.

6. The method of claim 1, wherein the liquid suspension comprising a plurality of fungal spores from a fungal strain is a limiting dilution, wherein the dispensing of the limiting dilution results in a probability that the discrete volume of the dilution dispensed to each reaction area contains either one or no viable spore follows a Poisson Distribution, whereby greater than 90% of the reaction areas in the plurality of reaction areas contain no viable spores and greater than 90% of reaction areas that contain one or more viable spores contain only a single viable spore.

7. The method of claim 1, wherein the reaction areas are present in a microtiter plate, wherein the microtiter plate contains 96 wells, 384 wells or 1536 wells.

8. The method of claim 1, wherein the fungal strain is a filamentous fungal strain.

9. The method of claim 8, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species, teleomorphs, anamorphs, and synonyms and taxonomic equivalents thereof.

10. The method of claim 9, wherein the filamentous fungal strain is *Aspergillus niger* or teleomorphs or anamorphs thereof.

11. The method of claim 10, wherein the filamentous fungal strain possesses a non-mycelium, pellet morphology.

12. The method of claim 11, wherein the filamentous fungal strain expresses a mutant form of an *A. niger* ortholog of the *S. cerevisiae* sln1 gene.

13. The method of claim 12, wherein a nucleic sequence of the mutant form of the *A. niger* ortholog of the *S. cerevisiae* sln1 gene is SEQ ID NO: 13.

14. The method of claim 11, wherein the mutant form of the *A. niger* ortholog of the *S. cerevisiae* sln1 gene is operably linked to a promoter sequence selected from SEQ ID NO: 1 and 2.

15. The method of claim 1, wherein steps (a)-(c) are automated.

16. The method of claim 1, wherein steps (a)-(c) are performed using automated robotics.

17. The method of claim 16, wherein the automated robotics are in communication with one or more processors in a system, wherein the one or more processors are each in communication with one or more memories.

18. The method of claim 17, wherein the one or more processors comprise instructions stored thereon that when executed by the one or more processors cause the system to perform steps (a)-(c).

* * * * *

SEQUENCE LISTING

```
<160> NUMBER OF SEQ ID NOS: 36

<210> SEQ ID NO 1
<211> LENGTH: 504
<212> TYPE: DNA
<213> ORGANISM: Aspergillus niger

<400> SEQUENCE: 1
ctgtctccat ccgtattccc cccttcactc tcgtttactc tccgttcctg ctggtcagtc      60
tcttccttga ccgtgtccct cgcttccaac actcgtttcc ttcaatttcc tccccctttt    120
tctctcgttg ccccccctcct cccgctccct cccgccatgc gtctcgttcg agattgcctg    180
tatggggggt tattccttaa cacggcgctc ttctcccagc tctcccacgc catcgatatc    240
gatatcagca gtaccagtat gccttcccccc cacttcttca atctctttcc cattatatac    300
accactgtct cggcccttgc tttattccgt catccttctc ctctcctaca tacttggacg    360
cagttgcgcc actatatcta agactccatg ccttccattc caacgacata cataaatacc    420
atgaattgac aactgataca catttttatt gtccgtatag gttcaattaa agatgccgcc    480
agtaagacgg cctacgggtc catg                                            504

<210> SEQ ID NO 2
<211> LENGTH: 620
<212> TYPE: DNA
<213> ORGANISM: Aspergillus oryzae

<400> SEQUENCE: 2
gaattcatgg tgttttgatc attttaaatt tttatatggc gggtggtggg caactcgctt      60
gcgcgggcaa ctcgcttacc gattacgtta gggctgatat ttacgtaaaa atcgtcaagg    120
gatgcaagac caaagtagta aaaccccgga gtcaacagca tccaagccca agtccttcac    180
ggagaaaccc cagcgtccac atcacgagcg aaggaccacc tctaggcatc ggacgcacca    240
tccaattaga agcagcaaag cgaaacagcc caagaaaaag gtcggcccgt cggccttttc    300
tgcaacgctg atcacgggca gcgatccaac caacaccctc cagagtgact aggggcgaa    360 atttaaaggg attaatttcc actcaaccac aaatcacagt cgtcccggt attgtcctgc    420 agaatgcaat ttaaactctt ctgcgaatcg cttggattcc ccgccctgg ccgtagagct    480 taaagtatgt cccttgtcga tgcgatgtat cacaacatat aaatactagc aagggatgcc    540
```

```
atgcttggag datagcaacc gacaacatca catcaagctc tcccttctct gaacaataaa    600
ccccacagaa ggcatttatg                                                 620

<210> SEQ ID NO 3
<211> LENGTH: 1503
<212> TYPE: DNA
<213> ORGANISM: Aspergillus niger

<400> SEQUENCE: 3
gcttccatgg ttggcagggt cacgtagccg taattatttt cggggaaggt tggaatgcaa     60
tggaaggaga tttccgtagc tagggctttg atcgatgcgg ggagcactgc cggtaggagg    120
tctggggtga atggggtgat atgcaggcgc ttcgtatcgg acggtgtggt cgtcatttgc    180
ccaatagata gttagataga tacctgagta cggtagcagt gcaggtgacg gctaagaagt    240
cggagggaaa aaggtgcagt cacaagcgca ttcagcctaa caagtgtctt tgatactcgg    300
tgagaaacaa acttgagtag aataagacag aaagttcttg tgaatggtca caatgggctt    360
ccaacgaagc atcaagcaga ccctgttgca atagatattc caagaccgaa aaattaatga    420
taggatcagt tattggccga gggattttcc gggccgccaa gaccgggtta tggagatgtg    480
gcgcaggcat gccatcctca gccacaggtt tctgtgacat cccaaaagca ttgatcgaag    540
ttggtataag tttcattcta tctaccatgg tgacaaggaa gtacgggtgt agaaaagaaa    600
aatctggtag gaatagctca gcaacaaatg gcggaatgat tgatgtaaga ctcgatgtat    660
ccactggaac gagatgcaag ttgcaacagc aataaatgga tttcagcctc cattacaatg    720
taacagtcgg gccgatactc agccggagca ggatttggcg ggtgaatagt ggatccggag    780
agaaacgatc aggtaatctt tcgtacggga ccagacccga cccggcctgc ttttagtta    840 ccagctgtta cttgtgtaat cccgtaaaa cgatcagtaa ctgccattga tcttcctgct    900
ctttcccctt attccctttt cccctttga aacttatttt cttcttcctc ttcatcgctt    960
aactacttaa gtactaggat tctcactcgc cactcttccc caatatctaa aagtagtctc   1020
gctacgaaga tcccttcccc ctacattact cctcctcctt caacacaccc accccccct   1080 gatccggccc cataccagtc ttcccgcggc taactaaagc ccgcacgtct gatctcatcg   1140
ccgcttccag cttcgacctc agtcgctcac atggccactc ggattcctta gcatcatctc   1200
tttttttccc atccctccc cgccctacca actgagggtc ctctgaagtg tgctccacat   1260
ttccttccct tcacttattt tggatcctca ttttctttct tcctctgttt cggggcgttc   1320
ttcaacatcg ctacttagtc acttctctcc tctcattacc ggacgggaac ttcgctccct   1380
tctccgcttt cttatccgga ccgcctcttg ccaatctcac catcgatcct aacccgtcat   1440
aatccagtca ctcaacccta ctattgtcga catacacgtc ggttcccatt ctcgttcgag   1500
atg                                                                 1503

<210> SEQ ID NO 4
<211> LENGTH: 1503
<212> TYPE: DNA
<213> ORGANISM: Aspergillus niger

<400> SEQUENCE: 4
acagtggcca tgaaatccaa tcatttcctt ctggccgccc tcgggcaaga gatagtgccg     60
cagaggtctc tcacagcatc tacatctgcg accgcaacag ccaccaagcg aggcgcacat    120
gagcttgtcc tcctcccatg ccaaagtttg gccctcttcg tttctgtgat gctgaaggaa    180
gtcaaactcg tcgatgatag gaccagatgg tttgtcaagg gtcaacgctt ccatgccctt    240
```

-continued

```
ctggcaccgg tagtaatgct cttctgcaag ggagacttga cgtttcggat ccgcgggccc      300
cgggacatgc tggaagggat tttctggctc aataccacgt ctgtatttga ccctttccag      360
acagttaatc cgctgcagga gggcgaactg tagctcctcg ttctccttgt agcgcttgat      420
ccagtctttt tggatgttgc acttgcttgg cctatgcttc tcatataatc ttgccctgtc      480
atagagacga cgtctgagat tgtagcgttc gtctttgatc acccggagcc agataggcct      540
gagtatatct gacattagat caaagggtct gtggatagtc tccttcagca tcagcgacgc      600
atgtgactcg catgtcggag agagcttgtg ggtggtcatc tttgatggcg tcctctgctt      660
tcccttgatt ttcgttgatt gttttcgaa  agttaagtct ggaagtcaag agaatccttc      720
tgccagacat tatatttacg tatactgacg tagtagaaac agcgtcagga tgaggacatg      780
gtgtgtgctg gaccacggaa tcatagttca tcagtatatt gggttggaca ataacgctg       840 agcatgtata tgtctttaca cactataaaa gccagcgaac gccaataaaa tagggcatat      900
tgatgtgaaa atatgacacc agttaaaagc agtgtattga ttttatctct cttcacctcg      960
gacctatact accgtataca agactcaact tacttccaga tatagtaata tacaccctat     1020
ggacgaacca gcacaataat tacagccaaa caacaccacc caaatggcat attcctaatc     1080
agcactaagc acaaatacca ctgtcatcac agcataatca ataagaatcc cagacaaccg     1140
actcactctg actcacctta cacaaacccc caagcaaagc gcagcccaga acctcagcca     1200
acaatcgggc aacgtacggg gaaagattgg ccgatccatg atgtcagcag ccctaaccca     1260
aagcggacta gcgcataccg cccctctgac tccgccatcc cagggctcga gaagcttccg     1320
tggcgtcgat ataaattcag cgggccttga acatccctcc ttacgacaca cctcacgcga     1380
tcgattttga cactcacaca ccgccaccct cacatcctcc acccacacca cacccttaa      1440 tcaacccacc atcaccgcta gaacgtctat ctcatcaccg acttctcatc catcttcaaa     1500
atg                                                                  1503
```

<210> SEQ ID NO 5
<211> LENGTH: 318
<212> TYPE: DNA
<213> ORGANISM: Aspergillus niger

<400> SEQUENCE: 5

```
taatactata aaaggaggat cgaagttctg atggttatga atgatataga aatgcaactt       60
gccgcaacgg atacggaagc ggaaacggac caatgtcgag cacgggtagt cagactgcgg      120
catcggatgt ccaaacggta ttgatcctgc aggctactat ggtgtggcac aaggatcaat      180
gcggtacgac gatttgatgc agataagcag gctgcgaagt agtaactctt gcgtagagaa      240
aatggcgacg ggtggctgat aagggcggtg ataagcttaa ttgtcatcgc agataagcac      300
tgctgtctca agaccccta                                                  318
```

<210> SEQ ID NO 6
<211> LENGTH: 20
<212> TYPE: RNA
<213> ORGANISM: Artificial Sequence
<220> FEATURE:
<223> OTHER INFORMATION: aygA.1 crRNA protospacer sequence

<400> SEQUENCE: 6

```
ucagucuauc cguuucacga                                                  20
```

<210> SEQ ID NO 7

```
<211> LENGTH: 20
<212> TYPE: RNA
<213> ORGANISM: Artificial Sequence
<220> FEATURE:
<223> OTHER INFORMATION: aygA.3 crRNA protospacer sequence

<400> SEQUENCE: 7
uucccacgaa gcgaucacgg                                             20

<210> SEQ ID NO 8
<211> LENGTH: 20
<212> TYPE: RNA
<213> ORGANISM: Artificial Sequence
<220> FEATURE:
<223> OTHER INFORMATION: Control crRNA protospacer sequence

<400> SEQUENCE: 8
augugucaga gacaacucaa                                             20

<210> SEQ ID NO 9
<211> LENGTH: 2757
<212> TYPE: DNA
<213> ORGANISM: Artificial Sequence
<220> FEATURE:
<223> OTHER INFORMATION: DJV_03_pyrG_insertion_in_AygA

<400> SEQUENCE: 9
gagacccgag acagacagtg acgccccttg ttccctcagc ggccgtggat tggtcagccc     60
ccctgcgttt gtagccctaa gtactctcaa tggtggttgt gatgtcacaa ggtttggagg    120
agagttcatg tgcaacccag tcggcaagtt tcgccgtgag taccttacat tgaatgggct    180
acgtttaaaa agggtccttc aatgctgtct cccgcctgaa ctgtaaatct tcacattgtc    240
tactcacaga ctggacgacg cgaacaagca agcaaacaca atggctcctt ggatcctcgg    300
cgagaagttc aacaccgttt accccacaa gggctctatc aaagctctct gggaaacgaa    360
gtggaagttt gcagtaagtt ttcactggtg gtcggcatca ccacccttg ctcagtggtt     420 ggccaaccgc tcagccaggt cttatctaac gtagcatgca gtgtgaaaaa tcagtctatc    480
cgtttcaggg tcgcggtcgt ttgtacggca gcttctactt gcttgcacag ggagctctct    540
ggggcttgac gtcttttgga gttgcgaggg agttgatttc ctacttctaa gtttggactg    600
aatccgtggt gtgattgagg tgattggcga tgttggcta taccagctat atgtaataat    660
ctctactgta tactactatt caacgcattt tactatgcgt gctgctaggg tcggcaatga    720
caatggcaat ctgactgacg tggtctattt ctccatgtgc agcagggaat acgagctcca    780
atggacctcg ggagtggcac agtcaatggc aaggaaactc cgcctttgca ggtgtggctg    840
aaccccacgg gtcggaggcg gagcaatcca ccccgatgt ggctggtgcg tggagggggct    900 cgcgatgatt ttactgagct tgcttttctt gtcgacattg aacattgtcc ttggtcttcc    960
ttcagattta agggtcagtc actgctacat ttctcagtag tatccgcgca cgtctctgga   1020
tttacgaatc agggtccacc agtcgaaact tcgaactact ctcattatac aatcctcttt   1080
ccattcccgc attaacccct ccatcaacac catgtcctcc aagtcgcaat gacctacac    1140 tgcccgtgcc agcaagcatc ccaatgtctc ggcgaagagg ctgttcgaga ttgccgaggc   1200
caagaagacc aatgtgactg tctcggctga cgttaccacc actaaggagc tactagatct   1260
tgctgaccgt aggccgaccc gctactctgc ctgattatgc tgcatgcaaa cttattaacg   1320
gtgataccgg actgcaggtc tcggtcccta cattgccgtg atcaaaaccc acaactagtt   1380
cctctctgat ttcagcaacg agaccattga gggacttaag gctctcgcgc agaagcacaa   1440
```

```
ctttctcatc ttcgaggacc gcaagttcat tgacatcggc aacacggtcc agaagcaata    1500
ccacggcggt accctccgta tctcggaatg ggcccacatc atcaactgca gcattctccc    1560
tggtgagggt atcgtcgagg ctctcgctca gacggcgtct gcaccggact tcgcctacgg    1620
ccccgaacgc ggtctgttga tcttggcaga gatgacctct aagggctcct ggctaccgg     1680 ccagtacact acttcctcgg tcgattatgc ccggaaatac aagaacttcg ttatgggatt    1740
cgtgtcgacg cgcgcgttgg gtgaggtgca gtcggaagtc agctctcctt cggatgagga    1800
ggactttgtg gtcttcacga ctggtgtgaa catttcttcc aagggagata agcttggtca    1860
gcagtaccag acgcccggat cggctatcgg ccggggtgct gacttcatta tcgcgggtcg    1920
cggtatctac gccgcgccgg atccggtgca ggctgcgcaa cagtatcaga aggaggggtg    1980
ggaagcctac ctggcccgtg tcggcggaaa ctaatactat aaaaggagga tcgaagttct    2040
gatggttatg aatgatatag aaatgcaact tgccgcaacg gatacggaag cggaaacgga    2100
ccaatgtcga gcacgggtag tcagactgcg gcatcggatg tccaaacggt attgatcctg    2160
caggctacta tggtgtggca caaggatcaa tgcggtacga cgatttgatg cagataagca    2220
ggctgcgaag tagtaactct tgcgtagaga aaatggcgac gggtggctga taagggcggt    2280
gataagctta attgtcatcg cagataagca ctgctgtctc gacggtgcca tcgaagactt    2340
tcgacctatc ttccaaaagc ttatcgatgt aggttatcat aatcttgcca tgtgcgcctt    2400
acgagcgcaa gggtaaaata ctcacttcta gataggaaaa tatcaacgat gcctacaccg    2460
atgcctacac gcaggctttc ttcccggttg ctgaggcact cgaaaataag gcgtcagctg    2520 cttttgaacaa caacaatgtg gagatggcat ctgacttgct ccgaagagct gctgtggtct    2580
accgtatctc ccgcttccca tatgtcgacc cgaccagaga agacatcaaa aagaggcct    2640 tcaaccgcca gaagaaggtc tatctgaagg cagcatcctt ctggaagccc accatccagg    2700
aggtcatcat cccgcacaag cataagtcgg ccaccgacgg agcctatgtt ccccttt       2757
```

<210> SEQ ID NO 10
<211> LENGTH: 929
<212> TYPE: DNA
<213> ORGANISM: Artificial Sequence
<220> FEATURE:
<223> OTHER INFORMATION: DJV_07_4bp_insertion_in_AygA

<400> SEQUENCE: 10

```
gagacccgag acagacagtg acgccccttg ttccctcagc ggccgtggat tggtcagccc     60
ccctgcgttt gtagccctaa gtactctcaa tggtggttgt gatgtcacaa ggtttggagg    120
agagttcatg tgcaacccag tcggcaagtt tcgccgtgag taccttacat tgaatgggct    180
acgtttaaaa agggtcctte aatgctgtct cccgcctgaa ctgtaaatct tcacattgtc    240
tactcacaga ctggacgacg cgaacaagca agcaaacaca atggctcctt ggatcctcgg    300
cgagaagttc aacaccgttt accccacaa gggctctatc aaagctctct gggaaacgaa     360
gtggaagttt gcagtaagtt ttcactggtg gtcggcatca ccacccctttg ctcagtggtt    420 ggccaaccgc tcagccaggt cttatctaac gtagcatgca gtgtgaaaaa tcagtctatc    480
cgtttcacta gtgacggtgc catcgaagac tttcgaccta tcttccaaaa gcttatcgat    540
gtaggttatc ataatcttgc catgtgcgcc ttacgagcgc aagggtaaaa tactcacttc    600
tagataggaa aatatcaacg atgcctacac cgatgcctac acgcaggctt tcttcccggt    660
tgctgaggca ctcgaaaata aggcgtcagc tgcttttgaac aacaacaatg tggagatggc   720
```

```
atctgacttg ctccgaagag ctgctgtggt ctaccgtatc tcccgcttcc catatgtcga      780
cccgaccaga gaagacatca aaaagaggc cttcaaccgc cagaagaagg tctatctgaa       840
ggcagcatcc ttctggaagc ccaccatcca ggaggtcatc atcccgcaca agcataagtc     900
ggccaccgac ggagcctatg ttccccttt                                         929
```

<210> SEQ ID NO 11
<211> LENGTH: 1273
<212> TYPE: DNA
<213> ORGANISM: Aspergillus niger

<400> SEQUENCE: 11

```
atgagcttcc gtcaagccct cagacccttc cgtcgcacca tgtccggtga aaagatctac     60
gaaggcgtat tcggtatacc tcactcctag catttctgct ttgatttacc tccaagctaa    120
tactatggaa tgataaatag ccgtccacaa accccaaggc gtctcctccg ccgacgtcgt    180
ccgcaccctc caaacgcact tcaacccctc cacgctcttc gcccctggc tcgctgacga    240 gcgcgcccgt cgcgcccgcg aaagcaccta ccagcgcaag cgccgccgca cccagcgtct    300
cgacgtgaag atcggccacg gaggcaccct cgaccccctc gcgaccggca ttctcgtcgc    360
gggagtcggc aagggcacga aacacctgaa cgagttccta ggatgcacga agcaatatga    420
gaccgttgtg ctgttcggcg ccgagacaga tacctatgat cggctgggga aggtggtgcg    480
caaggcgccc tacgagcatg tgacaaggga gatggtggag aaggcactgg agcagttccg    540
tgggaagatt atgcagaggc cgccaatttt ctcggcgctg aaggtgaatg caagaagct     600 ttatgagtat gcccgcgagg caaggagcc gccgattgag atccagaaga ggccggtcga    660
ggtgacggat ttgaggattg tcgagtggta cgagcctgga acgcatgagt ttaagtggcc    720
tgaggttgag gcagacgggg aggagaaggc tgttgcggga aagttgttgg cgaaggagga    780
tgagttgccg attgtggaga gggaggcgga tggtgaagga gaggcctctg cgaagagaaa    840
gtccccgcct gcgcgaggatg ctaaggagga gaaggtagag ggtggtgata ctgagtctgc    900
tccctcggct aagaagcaga aggttgctga tggcgaggct gcgctgttg cgccggccga    960 gcaggaggcg tcggatgctc ccaatgctga agccgtggaa tcctcggaat ccaagcccca   1020
gtcccagccc cagccggctg cggtgaagat caccatgacg gtgtcatctg gcttctatgt   1080
gcgctccttg gcgcacgatc tgggcaaggc ggtcggaagc tgcgggctga tgtcctcgct   1140
gatccggtct cgtcaggctc agttcgagct tcacccggac aaggtgctcg agtataagga   1200
cctcgaggcc ggcgaggagg tctggggccc caaggtccag cgattcctcg aggactggga   1260
ggagaagcga ctg                                                       1273
```

<210> SEQ ID NO 12
<211> LENGTH: 3670
<212> TYPE: DNA
<213> ORGANISM: Aspergillus niger

<400> SEQUENCE: 12

```
atgactatcc cactgagtcg actatccacc gtggatccgc ggcaaccagg aattagtggc     60
cataatcggg gcctcttgaa cgccgacgtc gtcccgatca acgacaagca gaaagtcttt   120
cttgccggtt ctggccctcc gtcgccaatg catcgcgtac aacctctgga cggatcgcat    180
ggtccgccca gtgctccagc agtctacgag cagccatggc gccctccgta ctcgtcttct    240
tatgacggac atcccgcgga ccagcgtcgc acatcgaatg ctcctcagcc tgcgctccca    300
ccccacggat acccgatgaa cccaaaccgt gagctgccgc agctcccacc agaagtccca    360
```

```
tatggccgac agggcagttt gcctggcccc gtgcataccc ctccagaagc ccccactcct      420
catcccagct ttcgtcctat gaatggaact ccccatgagg ccgcccctca ttcagcaccc      480
cccgactatc gctcacggat gtcttttaca cctcaggagc ctcacagcaa tggggacgct      540
ccgctccccg cccacacgtt accccgact cagtatccca ctccggttcc gcatttgtcg       600
catactccta cgccgtacga ttcaggtctt tacggaaacc aggcgtacgg gatacgccag      660
cagcgaaagg ccgctcgggc gcaacaggtg aattgtctcc ttgcagcgaa gttagctgag      720
atattgatcg ggaaaccctg actaactcgt gagcttttgc tgtctttgaa ggcctgcgat      780
cagtgccgaa cgaaaaggc caagtgcgat gaaggccggc ctgcttgtag ccattgcaag      840
gagaacaact tgatatgtgt ttataaagaa gttccccctc acaagtccgt ggcccggcaa      900
ttgccactct aatagttcga tggacatgtg ctgacgacga atccaggcaa gaaaggcaa      960 cacagcttct tctggaccgt atctctcagt tggaagacgg tctcatcgaa aaaatcgatc    1020
gcattaatgc actccaggtc gagcacacga atcaactcac tcagctgtat cctcggttga    1080 agaggctaa agcgataagc accaaggaga cgacagagaa gcaagccatt cctcggatat     1140
cgaaagcgga tacctgat atcttacaaa aaacggaaac caagaagaa gacatgaacg       1200 cgatcgtcgg acaggagctt gaaagagccg aaggggaagt gattccacag ggtgaagacg    1260 gtgatcttc aattcccgtt gagcatacca ctgcagccca caagttgctt tcgtggccgt     1320
ctatcaaggc tcttctcgaa ccgagagagt acgatgaaga ttatgttatg aagctggaag    1380
aggagcgagg attgattctc gtttacggcc gcggtgaagg acacgatact agtgaaagcc    1440
cagcaatgac attctcatca tcatcgtccc ggtccaactg ggatcaaagt tacagcaatg    1500
gtgctcctgc tagcggccag tggaacccag gcgctgtcca aaatggcact catctcaaac    1560
cactcggacc cagtattgat gatttcggga tattcagcac tgatgccaaa accgttcgtc    1620
gttatcatca aagctacctg aaccacatgc ataagcttca tccatttatc aacctgaccg    1680
aattgagcgc aagcatcgaa tcattcattc agaaatactg ctcacctgac gtttctgttc    1740
cggtaaacat cctgaacagc catacgcccg cgacattcc acgcggtgcg aaaaggaagc    1800
gttcttgcga tacgctacat ggtggcggat gcgacatcca gttttctcct ggtgccaaac    1860
acgaaggctc tagcggacgt cgcgtggaga agtcactgga aaatgctatt gttctcttgg    1920
ttcttgcact tggcagtatt tgtgaagttc cgggagccat ccctggtcca gttactgaca    1980
cgcccgtgga ctttcaaaag gagcggattc ctggaccctc tacacgcagc atgctatcat    2040
cggcagatac agaactagtt atgcagtccc agggaagttt cttctcgcag acaagtaacc    2100
attcattttc atctgctacc gggggggcaga aggctgcttc cgatcggtcg ccatacccgg    2160
ataatagtca cttaaggaac gtggatgtca ttcctggctt ggcatattat gcgtacgccg    2220
cacagatctt ggggagtttg caaggcgcga acgggctgta ccatgttcaa gcagccttac    2280
tagcaggact ttatgcggga caattagcac atcctttcca gagccatgga tggatctacc    2340
aggcggccag agcatgccaa gtgcttgtcc gatcgtatgt atttccctat tttactcttc    2400
tttctctttt tcaccctgaa caccaggagt ttgcaagaaa atcccgtgc taaccagtct     2460 caggaaacgg tatgaacaaa tgaatgacgg cccgctgaaa gacctatata ctttgcgta    2520 ctggacctgc ctgcagctcg agaggtaagc acgttgctct cattatgcga tccatgagta    2580
ctaataagtc attcatatag cgacatcctt gccgaactag atcttccggc tagtggtata    2640
tctcgcgcgg aagcacggat tgagttgcca aagggccgaa ctctctctct acctaacgac    2700
```

| | |
|---|---:|
| cctgctgctc cgaacaccat gatgatgttt ttctactctg cccagatcca tttgagaaag | 2760 |
| gttctgaacc gtgttcacac cgatctatac aaagtcgaaa gtaagttgat cttaggcagg | 2820 |
| caggagccct tggctgtact aacgcttctc tgcagaacag aatgagaaca ggtggtctgc | 2880 |
| taacgtacag gagattctga gcatgaacct tgaactgtgg agaagcagct tacctgacat | 2940 |
| aatgagatgg aaggacacgg accctccaca tgaggatatt aatgtggctc ggatgcgagc | 3000 |
| taagtactac ggtgcacgat acattatcca tcgtccactc ctttactggg ctctgcatca | 3060 |
| ttcacatccc accgaaaacg gtcgatcggc atcagtggat tcccctacag gatcagcgat | 3120 |
| gtcgggagcc aagtcgcagc aggtttcgcc ctcaatggcg cacagccaac gtgctatcaa | 3180 |
| tatggcacga ttgtctagtg atgttggccc tatgggtcga tcggcaccga cgccaacccc | 3240 |
| cgctccgaca ggatcgcgac cagcactcgc atatcgcgac ctcaatccga agttacgaag | 3300 |
| agcgtgcaaa gtatgcatag actccgccat attgagtacc gaggcctttg atggcatcac | 3360 |
| aggccggccg gtagtaacta atatcttcgg cacagctcat gcgtaagtgg agcccaaaag | 3420 |
| ggagtgtgaa gccggatagt ggacgtcgct gaccttgctg atgctgtgct agtcaattcg | 3480 |
| gtaacatgct ggtattgtcg gccacgtata tgtcaagtct ctcagagctg gttgatcgga | 3540 |
| acgacctcga tcggttattt aagcgaacca tacgctttct cctccaaagc cgcgagatat | 3600 |
| cgccaaccct acgagccgat gcaaagattc tcagcgagat atacgagaag atctttgggg | 3660 |
| agccagctga | 3670 |

<210> SEQ ID NO 13
<211> LENGTH: 4038
<212> TYPE: DNA
<213> ORGANISM: Aspergillus niger

<400> SEQUENCE: 13

| | |
|---|---:|
| atggctggcg cggacgaaac gctcgcggcc gctgctgcca ttttgagagg tcttgcgaaa | 60 |
| gaaactcctt cctccagcgc tcctcccttc gacttcgaat ctcccatcc tcccgccaat | 120 |
| ggctacgaca caaaactcgc aaaattaccc ggggaaacga gttcagcaaa ggcggctttt | 180 |
| gaacaggagt tggaagcttt ggtccgacga gtccgtcatc tggaattcca aaatgtcagt | 240 |
| caccaccagt caaccccaa atcctcccag tcttctctca ctcccggcga aaggacgct | 300 |
| gatttcctct ggtcctttgg tctctctcgt gtttcgtccc gtgacggttc tgactcttgc | 360 |
| ctctcacagc atcaaaagac aacacaacaa caacaacaac aacaacccca tggatccaga | 420 |
| cgatcggcca tcgaaccgga agaccacgaa gtggaggaag catcgacga tgaggagagt | 480 |
| gacgaagatg aggaactgaa ttcaaggaca cgtttggtac gcgaggagga catcagctac | 540 |
| ctacggaatc atgttcaaaa acaagcggag gaaataagtt tccagaagga tatcattgct | 600 |
| caggtccgtg acgaattaca acaacaggag gagcaaacac gacgggcttt gaccaaggtc | 660 |
| gaaaacgaag atgtggtctt gctggagcgg gagctacgca agcaccagca ggccaacgaa | 720 |
| gcgttccaaa aggcactacg ggaaatcggc ggcatcatta cccaggtcgc aaacggtgac | 780 |
| ctgtccatga aggtgcagat tcacccgttg agatggacc ccgaaattgc cactttcaag | 840 |
| cgtacgatca acaccatgat ggaccaacta caagtcttcg gtagcgaggt gtcgcgagtc | 900 |
| gcacgagagg tcggaacaga gggcatactc ggtggtcagg ctcagatcac cggggtgcat | 960 |
| ggtatctgga aggagttgac ggagaacgtc aacataatgg ccaagaatct caccgatcag | 1020 |
| gtccgtgaga tcgctgcagt cacgacagcg gtcgcccacg tgacctgag ccagaagatt | 1080 |
| gaaagtcggg cccagggtga atcttggaa ctgcaacaga ctatcaacac catggtggac | 1140 |

```
caactaagga catttgcaac ggaagtcacc cgcgtcgcgc gtgatgtcgg tacggaaggt    1200
gtgcttggtg gacaggccca aattgaaggg gtgcaaggca tgtggaacga actcacggtg    1260
aatgtcaacg ccatggcgaa caatcttacg acgcaagtgc gtgatatcgc cacggttacc    1320
aaggctgtgg cgaagggtga cttgacgcag aaggttcagg cgaactgcaa gggagagatc    1380
gcagagttga agaatatcat caattccatg gttgaccaac taaggcagtt tgcacaagaa    1440
gtcaccaaga tcgccaagga ggtcggtacg gatggtgtcc ttggtggtca agccaccgtc    1500
aacgatgtgg agggcacatg gaaggatctg accgaaaacg tcaaccgtat ggccaacaat    1560
ctgaccaccc aggtcaggga gatcgccgac gtgaccaccg ccgtcgccaa gggtgatttg    1620
acaaagaagg tgacggctaa tgttcaaggt gaaatactgg acttgaagag cacgatcaac    1680
ggcatggtgg accggctaaa tacctttgcc tttgaagtca gcaaggtcgc gcgtgaagtc    1740
ggcacggatg gtacactggg tggtcaagcc aaggttgata atgtggaagg aaaatggaag    1800
gatctaaccg acaatgtgaa caccatggcc cagaatctga cgtcccaggt gcggagtata    1860
tcggacgtta cgcaagcaat tgcaaagggt gaccttagca agaagatcga ggtccatgca    1920
caaggagaga tactcaccct gaaggtcacc atcaaccaca tggttgaccg actagccaaa    1980
ttcgcgactg aactgaagaa ggtggcgcgc gatgttgggg ttgatggcaa gatgggtggt    2040
caggctaacg tcgaagggat cgctggaaca tggaaggaaa tcacggagga cgtgaatacg    2100
atggccgaga acctgacgtc tcaggtgcgc gcattcggtg agattacgga tgccgccacg    2160
gacggtgatt tcaccaagct catcacggtc aacgcatccg cgaaatgga tgagttgaag    2220 cggaagatca acaagatggt ttccaacctc cgagacagta tccaacgtaa cacggccgcc    2280
agggaagctg cagaattggc gaaccgcacc aaatccgagt tcctcgcaaa catgagtcac    2340
gagatccgga cgcccatgaa cggtatcatt ggtatgacgc agttgacctt ggacacggat    2400
gatctcaagc cctatacccg agagatgttg aatgtcgtgc acaacctggc caacagcttg    2460
ctcaccatca ttgatgacat actcgatatc tccaagatcg aagcgaaccg tatggtgatt    2520
gagagcatcc cgttcaccgt gaggggaacc gtcttcaacg ccctgaagac gttagccgtc    2580
aaggccaacg agaagttcct gagtttgacg taccaggtgg acaacaccgt tcctgactat    2640
gtcatcggtg atcccttccg tctgcggcag attatcctta accttgtcgg caatgccatc    2700
aagttcaccg agcatggcga agtcaaactt actatctgca aatccgaccg agagcagtgc    2760
gcagcagacg aatatgcgtt tgaattctcc gtctcggata caggtattgg tattgaggaa    2820
gacaagctag atctcatctt cgacaccttc cagcaggcgg acggatcgac cacgcggagg    2880
tttggtggaa ctggtcttgg tctgtccatt ccaagcgcc tcgtgaacct gatgggtggt    2940
gatgtctggg tcacttcgga atacggccat ggcagtacct tccacttcac ttgcgttgtt    3000
aaactggcgg accagtcttt gagcgtcatc gcctcgcagc tgttgccgta caagaaccac    3060
cgtgtcctct ttatcgacaa gggcgagaat ggtggccagg ccgagaatgt gatgaagatg    3120
ctcaagcaaa tcgacctgga accgttagtg gtgcggaacg aggatcatgt cccgccgcct    3180
gagattcagg acccgtcggg caaggagtcc ggccatgcct atgatgtgat aatcgtggac    3240
tcggtggcca ctgctcggct gctgcggacg ttcgatgact tcaagtacgt tcctattgtc    3300
ttggtgtgcc cgctggtctg cgtcagcttg aagtctgccc ttgacctcgg tatcagctcc    3360
tatatgacca cgccatgcca gccaattgat ctcggtaacg gtatgctgcc tgctcttgaa    3420
ggacggtcta cgcccatcac cacggaccac tcccggtcgt tcgacatcct tctggcggag    3480
```

-continued

```
gataacgacg tcaatcagaa gttggctgtg aagatacttg agaaacacaa ccacaacgtt    3540
tccgtcgtca gtaacggtct cgaagccgta gaagccgtaa agcaacgcg ctacgatgtc     3600 attctgatgg atgttcagat gccagtcatg ggtggtttcg aagccacagg caagatccgc    3660
gagtatgaga gggaaagtgg tctcagccgg acaccgatca tcgcgctaac tgcacacgcc    3720
atgctgggcg atcgagagaa gtgtattcaa gcccagatgg atgagtactt gtcgaaaccc    3780
ctgaagcaga accagatgat gcagaccatt ctcaaatgtg ctacattagg tggttctctt    3840
ttggagaaga gcaggagtcg cgaatctcaa gtagtggtga aatgcacccg gtccatcaca    3900
gtgggcctga tggcaagagc caacagcgtc cggggttgga acctcgatcc gtcaccgcaa    3960
ccagcactat taaccgtggt ggtggcctcg caagcccaaa cgttgaccga gcggatgagc    4020
ttgccgtcga aagggtga                                                  4038
```

<210> SEQ ID NO 14
<211> LENGTH: 6133
<212> TYPE: DNA
<213> ORGANISM: Aspergillus niger

<400> SEQUENCE: 14

```
atggctgctg ctacgattga gttaccgttt atttcgtcgc actacgccat tgccgagtcg      60
acattgagca ccctcaccac agctcctacg gtcgagctag tcaaccagct cttggaagct     120
atcactacga agcacgcga gcatgacgag ctcaagtctg acaagatacg cctcgaggtg      180
gaactcgata tgccgttcg ctccagagac aacaaaatca aggttctgaa gagctcggtc      240
gagaaaggtc atgccgaagt cgaggaaaca aggaagaaac ttcacgagtc cggttagttc     300
ctatgcggac ccgccaatac gcgtctactt acgctctgca gaaaacactc gttctaccct     360
ggaatccgag atcgctacac tcaagtcgtc ctccacgtca aacgagtctg aagccagctc     420
attgaagtct cgtatctcgt cgctcgaagc ttctaacaga gacactctct cactcctcga     480
atccaagtcc gcagcatatg acaagcttgc cgaggagctc tcaacacaac acaagaagac     540
aatcgaattg agacgcgaac tttccaccgc cgagcagaac ctccaagccg ccaactctgc     600
ttccgccagc gctaagttcc gtgagcagag tctccagcag gatttggaat tgacaaagaa     660
aaacaacgag tggttcgaga cggaattgaa gaccaagtcc gccgaatatc tgaaatttcg     720
caaggagaag agcgcccgga tttcggagct tcagcgtgaa aacgaggaga tcagtgcaaa     780
cgttgactcc ttgagacgaa gcgagaatgc ccttaagagc cgcctggatg aggtggaaca     840
gcgttatgaa gaggctcttt ccagcatcaa ccagctcaga aagacgcta tcaaggcgac      900 cgagtcgttc agaatcgaat tggacagtgc aagtagacta gccgagttgc agtcgaatgc     960
tgcagagact tcgaagcagc gtgccaagga atgtcaactc gctctggata aagcaaggga    1020
agatgctgcg gagcagattt cccgactccg agtggagatt gaaaccgaac atgccgacaa    1080
agaagctgct gaacgccgcg ttgctgagct tgagctcacg gtcagccagc tcgaatccga    1140
tggttttgct ggaagaagat ccatgagccc tgcactgaat ggcgcagggc ccagcacccc    1200
aatgcgtccc agtaccccag ttggcgcgtt ttcacctaga gcgtcgcgcg aaagggagg     1260 actcacactg acgcagatgt ataccgagta cgacaagatg agaatttcgc tggccatgga    1320
gcaaaaaaca aaccaagaac ttcgagcaac tctagacgag atggtccaag atctcgaggc    1380
cagcaagcct gaaatcgatg agctgcgtgc ggaccacggt agacttgaaa atgctgttgt    1440
tgagatgtct aacatactgg aaactgctgg gaaggaacga gacgatgcaa ctaaggaggc    1500
aagaaagtgg caaggccagg tggagggatt ggcccgggag ggagacattt tgcgccagca    1560
```

```
actcagagac ctgagctccc agattaaggt cttggttttg gaaaatgcaa ttctgaagga    1620
aggcgaaaca acgtacgata gagaggaact cgagaagatt gcgcgccagg agatcgatga    1680
ctcctctgct gatctcaacc caaccggacg gttcatcagt cgcaatctga tgacgttcaa    1740
ggatctccac gagctccaag agcagaatgt cactctccgt cgtatgctga gagagcttgg    1800
ggataagatg gagggtgcag aagctcgcga gcaggatgcc atccgtcaac aagagcaaga    1860
agagttgaag gacctgagaa tccgggtgca gacttaccgt gacgagatcg ctaacctcgt    1920
cgctcaaaca aagagctatg ttaaggagag agatacgttc cggagcatgc ttacccgccg    1980
ccgtcagact gttggcgatg cttctgtctt ctcccaatct cttcctctgg gcgcagctcc    2040
tcccgcttct gaagagccag ccaaggatgt tccagactac gctgatctgt tgcgcaaggt    2100
gcaggcacac ttcgacagct ccgcgagga gtccgccacc gaccatgcag ctttgaagca    2160
acaggtcaat gagttgtcca ggaagaacag tgaattgatg agcgaaatta gccgctctag    2220
cagtcagctt gttgccgcca cacagagagc ggagcttctt cagggtaact tcgatatgct    2280
caagaacgaa aacgcagaaa tgcagaaacg ctacgctacc ctcctggaga acgctaaccg    2340
gcaggatatc aggactcagc aagctgccga agatctggtg gagacgaagg gcctcgttga    2400
gagccttcaa cgggaaaatg ccaacctcaa ggcagaaaag gatctctgga gaatatcga    2460 gaagagactc atcgaggata acgagacact acgtaacgag agaggtcgac ttgattctct    2520
taacgcgaac ctccaaacca ttctcaatga gcgggaacat accgatgctg agagtcgccg    2580
tcgtttgcaa agcagtgtgg agtctctcga atcggagctt caatccacca agcggaagct    2640
taacgatgag gttgaggaag gaaagaaggc atcgctgcgt agggaatacg aacatgagca    2700
aagtcagaag cgaattgacg acttggtgac gagcttgggc gcagctcggg aggagttagt    2760
ggctgcgaag acgacaagag atcacttgca atcgagagtc gatgaactca ctgtcgagct    2820
gcgtagcgcc gaagagcgcc tccaggtcgt gcagactaag cccagtgtgt ctgctgctcc    2880
tactgaagcg cctgcggttc cggaggaagg ccaggagagt ggcctgacac gcgagcagga    2940
acttggtatt gaagtttccg agctccgtcg tgatttggag ttgacaaaga atgagcttca    3000
gcacgctgaa gagcgggtgg aggattataa ggctatcagt cagcagagcg aagagcgtct    3060
gcagtctgtc actgagaccc aggaacagta tcgggaggaa acggagcgtc tcatcgaaga    3120
gaaggataag aagattcagg acctcgaaaa gcgcatcgaa gaaatttccg ccgagctttc    3180
gactacgaac ggcgaactta ccaaattgcg tgacgagcaa ggggaggcta gccgacattt    3240
ggaggagcag aaggccgcgc tggaagcaga gatcacaagg ctgaaggacg agaatgaaag    3300
gcagatcgct tctgcccaat tccaccagga agatctcaag gcacaagctg aaatcgcgca    3360
gcatgcccag cagaactatg agagcgaact gctcaagcat gctgaagccg cgaagaatct    3420
acaattggtc cggtccgaag ctaaccagtt gaagctggaa gttgtcgaac tgcggacaca    3480
ggccgacact ttcaagaagg accttgctca aaggaggaa agctggaccg agatcaagga    3540
taggtatgag agcgagctta cggaactgca aaagcgccgc gaggaagttc tccaccagaa    3600
ctctttgttg cataccccaac tcgagaatat tacaaaccag atcgcagccc tccagcgtga    3660
ccgggctaac attcctgagg gagatgagga cggagaggcc ggcgcgccca acctcgaagg    3720
cctccagggg gtgatcaagt tcctgcgtcg ggagaaggag atcgttgatg tgcagtacca    3780
tctgtcaacc caggaaagca agcgtcttcg tcagcaactc gactacactc agacccagct    3840
tgacgaggcc cggcttaagc tcgagcagca gcgtcgcgcg gctgccgaca gtgaacatag    3900
```

|  |  |
|---|---|
| cgccctcagc cacaacaagc tgatggagac cctgaacgaa ctgaatctgt tccgcgagag | 3960 |
| tagtgttacg ctgcgtaacc aggttaagca ggcggaaacc tcacttgcgg agaagtcctc | 4020 |
| tcgcatcgaa gaacttgttc agcaaataca gccgctagag actagaatca gggaactgga | 4080 |
| gaacactgta gagacaaagg atggagagct gaagttgcta caggatgata gggaccggtg | 4140 |
| gcagcaacgt acgcagaata tcctgcagaa gtacgaccgg gtagatcccg cggaaatgga | 4200 |
| aggtctgaag gagaagctcg agactttgga aaaggagcgg gatgaggcca ttgctgcccg | 4260 |
| ggacactcta cagacccagg ctgctgcttt cccagaacag ctgaagcatg cggaggatcg | 4320 |
| cgtgcaagaa ctgcgcacga agctcacgga ccaattcaag gctcggtcca aggagttgac | 4380 |
| tggccgtata aacgctaaac aggtggagct caacacggtt atgcaggaga aggaagtcat | 4440 |
| tcaagaagaa ctcaagacga ctcgggagga attgaatgag ctgaagacga agatggccga | 4500 |
| gcaacccgca gctcctgctg ccccagctgt tgaaggagct actggtgttg actcaacgcc | 4560 |
| tgcctctcag ttccctgcgc caacaacgca gccgcctgcc gcttctgacg atcaacgcgt | 4620 |
| gaaggctctg gaagagaagg tgcagcgcct cgaggcagct cttgcggaga aggagacggc | 4680 |
| gttgaccgcg aaggaaacgg agcacgaggc gaagatcaag gagcggtccg acaagctgaa | 4740 |
| ggagatgttc aacagtaagc tggctgagat tcgagctgcg caccggcaag aagttgagcg | 4800 |
| gttgaaatcc agtcaaccag ccgctcctca agaacctgga accccagctc ccaaacccga | 4860 |
| gcaggtgcca gcaacgccgg cgactcctgc ggctgctcct gcgacaccct ccaaggacac | 4920 |
| tgggctgcct gaactgacag atgcgcaagc cagggagctc gttgccaaga acgagacgat | 4980 |
| tcgtaacatc attcggagca acatccgcac ccaggtggct aagcaaaagg aatccgacaa | 5040 |
| gcaggaaagc caggccaacc aggaggctat gagcacactg gagcagaagt taacgaaga | 5100 |
| gagagaagcg ttgaagaagg cccacgaaga gggtgtggag gagaagatca aggctgctgt | 5160 |
| cgagttgtcg gacaagaaat cactggcgaa actaagcatg ctggacaccc ggtaccggac | 5220 |
| agcccaggcc aagatcgatg tggttcagaa ggctgctacg gagacgcctc agaagcctgt | 5280 |
| tgtcgaagtc tgggaggtcg caaagaccac tagagcgcct ccagcggcgc aggccaagcc | 5340 |
| cgcccaggtg gcatctcctg cgcctgcacc gtctcccgcg cccgctgcgg cccaggcaac | 5400 |
| accggtggtg ccatcgccgt cgcctgcccc aacggctact cctgcggcca caccgcagc | 5460 |
| tacgcctgca gctgcacccc aggcccagcc tgtggagcct gcagcagcat ccacagccga | 5520 |
| gccagcttct gctgaatcta cgccgcagac aggtgcccca gcgcagcagc aaccgcagca | 5580 |
| acaacctgcg cctgaacagg ccgcacaaca acaagctgca cctgcgacgg ctcagccagc | 5640 |
| taccaatgct cctccaaacc cattcggtca gagccagaac aagcagccct cgtcgttgcc | 5700 |
| cagcaagccc ccagccggta atgcttctgg ccttatgcga gcactgacgt ccggactgcc | 5760 |
| cgtcgcgcga ggcggcaggg ccggcggccg cggtgggtcg caagcgaata ctttcggtca | 5820 |
| gcaacaggga caacagcaac aggcgcaagg tcaggctcaa gcccagcagc aagctcctag | 5880 |
| ccagcgcggc tctggtctac cccggggtcg tggcggacgc ggaggccatg gacgcggcgg | 5940 |
| aaaccaaaat gtacagccca cgaatgccgc tcagcaagga caggctagcc caggtcgctc | 6000 |
| gctgaatgcc ggtgctcgcc agttcgtccc tcagggcaac aagcgtgctc gcaggatgg | 6060 |
| agaagctgga ggcgaaggag caaccagtgg aggaaagcgc atgaggggag gaggtcatac | 6120 |
| ccgggggtca tag | 6133 |

<210> SEQ ID NO 15
<211> LENGTH: 543

<212> TYPE: DNA
<213> ORGANISM: Aspergillus niger

<400> SEQUENCE: 15

| | | | | | | |
|---|---|---|---|---|---|---|
| atggcgccca | ccactactac | aaagaccgtg | gaggagcctg | taggtgtcgc | gaagccgcac | 60 |
| actgaagcca | aggttgaagc | tgacctcccc | aagcccaagg | agactaagga | gatccctct | 120 |
| acattggcgg | agatgagtgg | gagtatcgac | cagagcacat | tcgagcagat | tttggagatg | 180 |
| gacgacgacg | acagtgatag | agatttcagc | aagggtatcg | tgtttgggtt | cttcgaccag | 240 |
| gctgagagca | cattcatcaa | gatggaggat | gctttgaagg | cggaagatct | gaatgatctg | 300 |
| tcttctctgg | gacactacct | gaaaggttca | tcagccacgc | tcggactcac | caaggtcaag | 360 |
| gatgcatgcg | agaagattca | acactacggc | gccggcaagg | atgagaccgg | tacgacggac | 420 |
| gagccggaca | gaagacctc | cctttcgcgc | attgagaaga | ccctgaccca | ggtgaaaaag | 480 |
| gattacaagg | aagtagaggc | cttcctgcgc | aagtattatg | gcgaagagga | ggaatcctct | 540 |
| taa | | | | | | 543 |

<210> SEQ ID NO 16
<211> LENGTH: 2685
<212> TYPE: DNA
<213> ORGANISM: Aspergillus niger

<400> SEQUENCE: 16

| | | | | | | |
|---|---|---|---|---|---|---|
| atgccagacc | gtcgctgggc | caagctcaag | gcaaagctgt | tattgcgacg | atcgtcgtcg | 60 |
| acctcgtccg | ctcccgccgc | caccagcgac | attattgccg | agaacaatcc | ccatgatgtc | 120 |
| cacgcccagc | aaagctgcgc | ccccgaacaa | ttggacgagt | cgatcgcgaa | ttttcccca | 180 |
| gcgcgaccca | tcagttccaa | tcggcgcgcg | atatcattgc | aggccgtgcc | ccaagccttg | 240 |
| aagctgagga | aggaggagga | cgaggaggag | gaggagaggc | aggaagagga | cgatcgggcg | 300 |
| agtgcagctg | aagggacgcg | gacatcggtg | attggcccga | aggcggggcg | gtcgagggga | 360 |
| tcattggagg | aggaagagaa | gttcgagaag | ttggagaact | gcaacttcaa | atcgaaatcc | 420 |
| tcctctcgcc | ccgaaccggt | cgcagaacaa | cgtgagggac | aacggcactc | gctcctcgtt | 480 |
| cctccaggtg | ccggtgccgg | tgctggtccc | agtgcttccc | gccagcgtca | gcatcagcaa | 540 |
| ttggacgcga | caacttcttg | cgatcgtgtt | cgccccgcgc | cctgcaggcg | tcacagtcac | 600 |
| ggtcccttt | ccgagcacgt | cctttcccca | ccccgacaa | ctctatcgcc | agatctgctc | 660 |
| ccttcgcctt | ctccgacccc | tcctccccct | gtctctgatc | gtggtgttgt | ctcgccgtct | 720 |
| ttccaatttg | gccacactca | aggccttgat | cgcctggggc | ctacggtcgg | ggagccgcag | 780 |
| ttgcccgtgt | tggatgtcgt | tgcggagaat | ccgacggtcg | aaccagaatt | tcagtcctcc | 840 |
| tccaaccata | ccccgctgc | ttccttccca | aagcgtccca | gtttaggctc | ccgtcgtcag | 900 |
| tcgctgctgg | ccccgtctca | tcaacacctg | atcaacagct | tgttggaccc | cggtgtgact | 960 |
| gcagagcctg | aaaccaacgg | taacggtcgc | tccgccacct | acagcacagg | catgtctcgc | 1020 |
| aagatctggg | tcaagcggcc | aggcgggtcg | gccaccttgg | tccccatctc | gctcgattct | 1080 |
| ttggtggacg | agctacggga | ccaggtgatt | ttgaagtact | cgaactcgct | tggcagaacc | 1140 |
| ttcgatgccc | ccgatattgt | cattcgcatt | actccgcgag | atggttcgaa | caggcaggcc | 1200 |
| actcccgatc | ggatgcttag | ccccgaagag | ccgctggcaa | gcgtggtgga | cacatattac | 1260 |
| ccggagggtc | aagctatcga | ggaggctcta | ataatcgata | tcccttcgcg | tcgcactccc | 1320 |
| aaaccctctc | cacgccattc | agtatactac | aaccaccatc | attccgaacc | gggcgagcat | 1380 |

| | |
|---|---|
| ggcgagtact tcccgctcat gccggcgaat cccagcgttc ccacgccgcc gacgcatccg | 1440 |
| tcaaactcgt ctgccagtgt taatgctcat cccgccccat caatatcgat cctgacgaca | 1500 |
| ggaatggccc ctccgctacc atctccaggg agtcgcggga ctcgacatcc ccgtcggccg | 1560 |
| cccttgactc gtcatgccac aaactcaccc accatcctca atcaggcgcc aacagcgaaa | 1620 |
| gaccccggaa tcgtccccag tagtatccct ccgcagcctg ctccgtccat ccctactccg | 1680 |
| ccaggcccgc cgccagaatc ccctcaggcc aaatccctga ctcctccagc acgcggggca | 1740 |
| tcaccgcgtc cacgtccctc cacatcctcc gcgaagccga agaagaccag cgcagcacaa | 1800 |
| tcattgagcg gggtctttgg aggcctcatc gagggcacgg taccgcccat caacgtcttg | 1860 |
| atcgtggagg acaataacat caaccaacgt ctcttggaag cttttatgaa acgtctcagc | 1920 |
| gttcgctgga agtgtgcggc caatggtgaa gaggcggtga acaaatggcg ccagggtggt | 1980 |
| ttccatctcg tcttgatgga tatccagttg cccgtcatga acggtctgga tgcgacgaaa | 2040 |
| gagatccgca ggctcgaacg cctgaacggc gtcggtgtgt ttcccaagac cgctgacggg | 2100 |
| cggtcgagcg ctgcaactgc caatgcggca tcgcctcgg caattgtggg cagtcgggaa | 2160 |
| cccctgaagg cagaggatac attacacgat ctgtctctgt tcaaaagtcc cgttattatt | 2220 |
| gtagccctga ccgcgagcag tctgcagagc gatcgtcacg aggctctggc agctggctgc | 2280 |
| aacgactttt tgaccaagcc ggttcgcttt gaatggctgg agcagaaagt gacagaatgg | 2340 |
| ggctgcatgc aagccttgat cgattttgaa ggctggcgca atggcgcgg ttacgccgat | 2400 |
| gacactcagc cttcgcccac gtctgatggt catacgagtc ccatgcaaac tggcggggac | 2460 |
| ggaacttcgc ggaaacagtc tcctgttatt ccgctctcac catcctctac cttgagtcaa | 2520 |
| ggagccacca aaaaggaccg caaaaccccc agcttcccta aacccatcga cgttacaccc | 2580 |
| gaagactctt ccggcagtgg tagcggcgag ggcttggact cacctgccag tccggtgaca | 2640 |
| tcagtccctg ttccagatgg gcctgcagat cctgatgcac tctga | 2685 |

<210> SEQ ID NO 17
<211> LENGTH: 2379
<212> TYPE: DNA
<213> ORGANISM: Aspergillus niger

<400> SEQUENCE: 17

| | |
|---|---|
| atggatctca acaaacgcct gttccatctc gatatcgaga ataagaccca agcgcaacct | 60 |
| ctcaacttct ctatggtaac cacaccaccg gatgatgagg atgatgacga ggtgaaccat | 120 |
| ctaaagctca aggtcgagtt gaaacaatct ccctcacgat catgacaagcc gcatcaccgt | 180 |
| caaaagaaga tgcccgatac cgatgcgcag caacctccag cggctctagg tcgaatatat | 240 |
| cgctataccc ccactcccag cgtcattctt gatccttcgt tacatgtcgt ggaggtatcg | 300 |
| gattcccacg tggcatttgc cgggctgtca agggcgctgt tgctcggccg gttcatctgt | 360 |
| gacatctgtc cacgcatcct gccggctcta gatgttgcta ttcttttttgg cgcattgcgc | 420 |
| gccgccatca cgacgcagga cgtccagtcg attgacaaaa tctgtataga tgacgctagc | 480 |
| acttgctata ctcttcgcat cacccccatc tttgaaaact ctaacctgtt atacattgtc | 540 |
| ctggaggcac ttgatatcac caagcgtcag gctacatcgg tgtccaagcc ccatgagtct | 600 |
| tactccaatg agacttacaa agtcctactg gacacggtca aggactatgc catcttcatg | 660 |
| ctcgacacac atggccatat tgtaacttgg aacacgggag cggccctgct gaaagggtac | 720 |
| tcggccaagg agatcatcgg acgtcacttt tccaccttct atagcctgga ggatcgcatg | 780 |
| gcggataagc ccggcaaaga actggaggta tgtctccggg agggcaaagt ggaggacgaa | 840 |

```
ggctggcggt accgcaagga cggttcgcgg ttctgggcca acgtgctgat cactcccatg    900
tacgccctgg gtcgccatat tggcttcacc aaggtcactc gcgatttaac ggaacgcaat    960
gcagccgaaa cccgcatgat cgcagccttt gaagaatcgt cgagattaaa gacagacttc   1020
ttggccaaca tgagccatga gattcgcacg ccaatgaacg gcatgctctt agcccttaca   1080
tcactgctgg ccacggactt gaacgaacag cagcgcgaat attcctctat catcgaagat   1140
tcgaccaatg ttttgctcca agtcatcaat gacgtcctcg actattcgaa attgtcatcc   1200
gggtctttta ctctgcatcc tgatactttc agtgtcgaca gtattaccaa cgccgtcgtg   1260
cgcaactgca agggcgctct gaaaaccggt gtccaactga ctagctctat ctcatccaac   1320
ttcccatccc aggtcgaggg tgatccgttg cggtaccgtc aggtccttca gaatcttgtc   1380
ggcaatgcag tcaagttcac cgaggagggc tacgtcaaga tcaacaccac cttctcggaa   1440
gatgcggagg atcctagtgt atattacatc cggacggagg ttgccgatac gggcgttggc   1500
gttcccgaag atgctcttgg ctcattgttc acaccgttca cacgcttcgc cgagactggt   1560
tcgaagagat accaaggcac gggccttggc ttatcgatct gcaaaagctt ggccgaactc   1620
atggacggaa gtgtcggata ccgacctaat cctgagagac atggcagtgt cttctgggtc   1680
acagccaaga tgcatcgggt gcgtgtgacg ccgcccgcta gaacgactgg gacagggaca   1740
cccgttgaag acgtcggtga cattgaacga aatatccacg acatcgctcc tcacaaacac   1800
gttctcctgg ttgaggacaa cctggttaac cagatgatga tgctcaagct tctccagaac   1860
atgggcttcg cgcggattga tactgcatgg gatggggcag aggcggttcg actggtgaag   1920
cagcagcctt tatcctacaa tacaattctt atggatatcg gcatgccggt gctggatggc   1980
gtacaggcga cacgcacagat ccggcaaatg ggactagaga tgcctatcat tgcgcttacg   2040
gggaacgtca tgccgggaga tatagaggat tatacgaagc agggaatgag cgatcatatt   2100
gggaaaccaa tccaccagaa acagttaatg cgtttgctct ggaatccgac tccgcataag   2160
aaactgagcg ttactgacac cgctttcgcg ttgaaccaac cctgcccatt acactgcaaa   2220
gcagtacgct ctagggcaat cgccatgatg agctcaggtg ctcaagaaca cagaaccatt   2280
cctgtaaagt ggacaggttc cgaagattac aatatgcaag actcacgatc ttctcttctc   2340
atgaagttta cgatgggaac atactacctc gatttatga                          2379
```

<210> SEQ ID NO 18
<211> LENGTH: 2022
<212> TYPE: DNA
<213> ORGANISM: Aspergillus niger

<400> SEQUENCE: 18

```
atgttcctcg acggccattt ggccgctctt tccctcgagg agaagtccgc gacaacacac     60
agtgtacgtg tgcccgacga tgactcccca gcggtgtctc cctctctggc atgcatctat    120
cgccatactc cgactcccac gatcgtcctc gattcatcta tgaccatcgt cgaggtctct    180
gatagtcatc tcgctttatc cggcaagacg cgccaatcca tgctgcatgc gaccgttcgt    240
gatctcgacc ctgctgccgt acccgcccct aatatcgcta tcctctgtgg cgcattgcgt    300
gcagcctgct cgacgaagga aattcagata gtcgagagaa ttgtgtctag cgataaatct    360
ttgtacaacc tccgagttac tccgatttttc aacgacttta ccctgcttta cattgtgttg    420
gaggcgcaca agctatcggt ggagaccgcc agcattaacc atgcctatac gaacgaaacc    480
tacaagatcc tcgtggatac tgtcaaagag tacgccattt tcatgctgga tacacagggc    540
```

```
aatatcacca cctggaaccc gggcgctgcc atcatgaagg gatggccagc agaggagatc    600
cttggcagac atttctctgt cttttacagc ccggaggatc gcctggcagg aaagcctcta    660
agaggtcttg ctgtgtgctt gcgagaaggc cgtatggagg atgaggggtg gaggtatcgg    720
cgcgatggct cgcggttttg ggccaacgta cttatcaccc ccatctacca gtttggacag    780
catgttggtt ttgttaaagt gacccgagat ctcagcgagc gcaagaaagc agaggcgcgc    840
ataattgctg ccttcgaaga gtcatcacgc ctcaaaacag actttctcgc taatattagc    900
catgaaattc gaactccgat gaatgggatg aaacttgcca tgaccatgct ggccgacaca    960
ggtctgtctg cgacacagct cgagcatgcc gcaatcatcc aagactctat gtcactctta   1020
cttgagactg tgaacgatgt tctcgactac tcgaaacttt catctggctc tttctcgtta   1080
cattccgacg tcgtcgatgt caacgatgtg gtcggagcgg tcatacgaaa ttgtcgcccc   1140
tcattgaaga acggggtgga actgactacg gacattgcac ccgactttcc caggaatctt   1200
cgaggagatc ccctacgata tcgccagatt ctgcagaatt tggtcggcaa tgccgtcaag   1260
tttaccgaga gcggccatat tcgggtctcc acagtgtgtt ctccggatga acaagaggag   1320
ggctgctgcc tagtgcgtac agaggtcata gacaccggca ttggcgttcc tgacaatgca   1380
atgaataccc tattcacccc gttcacacgc tttgccaact cgagcactcg acaataccag   1440
gggactggat taggcctttc catttgcaaa agcctggccg aactcatgga cggagaagtg   1500
ggatattcgc caaatcccga aggccgaggc agtgtcttct ggtttactgc caaattagga   1560
gaacgatcca ttactacgtc gctaaagccc cgcagtcctg tattaacacc cgtgggtgat   1620
gatctctgcg ataaaatgcg ggccattgca ccccacaaac atgtcttgtt ggttgaggac   1680
aacatggtca accataccat gatgctgaaa cttcttcgca gcatcggctt cacgcgagtg   1740
gatgggcct  ggaatggtgc tgaggcactt tccaagataa agaagaagcc tttatcgtac   1800
aacgtcgttt tgatggatgt ctccatgccc atcatggacg gccttgtcgc caccgggcat   1860
atccgcgaca tggggttaca aatgccgatt atcgcagtca cgggtaatgc tatgcagggc   1920
gatgccgaaa gctacattgc caagggcatg agcgattgca tcggtaagcc ggttcaccga   1980
gatcaactac tgagtatttt atggaagtgg attggatctt ga                      2022
```

<210> SEQ ID NO 19
<211> LENGTH: 4110
<212> TYPE: DNA
<213> ORGANISM: Aspergillus niger

<400> SEQUENCE: 19

```
atggaatctc agcaggaccg cgggtttccg atcatggagc atcctgattt aaacaaccat    60
gattcggatg gctccgggtc ctccgatgag cttctgcagc agccatatgc tgtaagagcc   120
aactccagtt tcccggagaa tttcgacacc caggtccaaa cccggcgac gaccatttcc   180
tcgtcccctc cccatccat tgcgtctgcc ctgccatcat gggcaaccgg cacgcccaca   240
cgcgcccgcg gggccagtat aggtgcttct gctgctcttg agaaagctcc gccgatggat   300
ggccatccgg tgaccgatcg tgacttgagg ccgcaacgtc cgtccggccc cgctcggacg   360
ccctccaata cctacgcgcc caacgacgc ccacctcagt atatcagctt ccaaaatgac   420
cgccaacgga gctcatcaac gaaacgaact tctagacgcg atcccaatgc acagtaccga   480
gctcaggaga aggcgtatgt ccagcgcatt cgtgcggacc ctcaggcctg gtacagtcat   540
ttcgatgagg ctcaaaacat gagcatgacg gtcgggggact cggacctaga gaaccctca   600
ccatcctcgg aggttccttt cgaagacgat gcctacgatc cggatattca actcttcctg   660
```

| | |
|---|---|
| accgacgaca atcagccgac gatcgaggaa ctcaagaacc caagaaacca agagaggctg | 720 |
| gagtggcatt ctatgctttc gtctgtgtta aagggagacg tggtgaagca agagaaacag | 780 |
| cgattactcg gctctacaga atcaaaacga tcgtcggccc agaacaacgc aatatggttg | 840 |
| ggtgtcagag ccaggacctg tggaaggagt gttgcactgc agaggaaact cattgaagaa | 900 |
| gcgagggctg gccttggccc catcatcgaa gaaattatca agttcgagat caaaggtgaa | 960 |
| acagagatcg ggaagccacc catcaagcag gttgaggata ttgtcgcaca gatagaacgt | 1020 |
| tgtgaaagcc tctactctac tcacaaggag ctggagactg cccacccag agtcgcttca | 1080 |
| gaggagtatc actcgagtcg cgatgctgtt tttgcctggc acaacacgac catcttgatc | 1140 |
| aacaccgagc tcgctatcct gcagaaatgg gttggaaacg atgagttgga tttcagcaaa | 1200 |
| tcgagaacga aatcaatcaa tagcgacctt tccgacgaaa catccttcct tgaccgcatc | 1260 |
| atgaaggagg atggcctcaa aacgctgcaa ggaaaacata acatgctcca cggcattgga | 1320 |
| gaagtcatcc aaaaagcaaa gaatacatta attgagaatg ccggttcctt cgccaaacgc | 1380 |
| cacttacctc cctatatcga agaacttctt actcttatca atttcccgtc tcgtctcata | 1440 |
| caggaaatta tacgggttcg actatcttac gctaagaata tgaaagaccc agcttcgcaa | 1500 |
| tccgccatct tagtcgatca aatgatatcg cagttccaga ttttgatgaa ggtggcggtc | 1560 |
| gatatcaaac ggcattattt ggatatcgcc agacccgagc ctgggtggga cctgcccct | 1620 |
| tgcattgatg acggtttcga cgcagtcgtc ttggatgcga tgaagtatta cttccggctt | 1680 |
| ctgaactgga agctgactgc aaataagaac acattcaaag aagcggagat tctagaacag | 1740 |
| gattgggaat tttccaacga ggtcggccga caacttgagg gcggagatat cgaggtcgcg | 1800 |
| gagcagttta gtgcactgac tgccaagtcg atccaacgct tgatgtacca cttcgagcgg | 1860 |
| gagttgcagc ctcgccatga cgaggatcct gccgacatgg acaagcgtta taaaagcgta | 1920 |
| ttggactcaa ctcggatccg gcaacggaag ctttaccgat tttcccgatt cttgcgccag | 1980 |
| ctgttcgaaa atgcaacgga atacaatttg ccggctgaca ttgcatacga cttttttggag | 2040 |
| tcgttgcttg tgtcggatca tttatgatc aaatcaaacg tctctgttgg tcaaaagggc | 2100 |
| gtctatctct ttgcgcaccc tgcattgtgg gatcgccctg cagatatcca agctatccta | 2160 |
| ggcacatcat ttcgtgagga tgacaccagc aaggatacac cccatgcacc gtatatactc | 2220 |
| gtggttcgtc cggaaaagcc cctttcctgg gctggcaaag aaatgcagct gggcatcatg | 2280 |
| gaacagccta cggacttgcg attgggcaaa ttgcgacttg tggttgaagg gacgcagcag | 2340 |
| cggctgtcta atgcgagaca tgagctgact catctcactg gtattcagct cgatatggcc | 2400 |
| atcgagcaac gtgccaatct tggtcgggtc aacgtggagc taaacaagat caagaagacg | 2460 |
| tcatttaagc tatcaatgac tatcatggat agtgttgccc ggatacggga gcaactcaag | 2520 |
| gatagagacg tggagaacca cgatctagtc caagcatgct atgcttttgc gaccgagttc | 2580 |
| gggaagcgtt cttcaaacgt tgatcccaat agacgcgcaa tgaacagtaa tagacttgtc | 2640 |
| gagttgtccc tcgactgggt ttcgttcatc tgtgatgatt gtgatgctgc tgacaggaaa | 2700 |
| accttcaagt gggccgttgc tgctctggaa tttgcaatgg ctatcacctc cagcaggcac | 2760 |
| ctcctgtcta tggatgatgc tcagtatagt cgactgagcg agaaggttgc cgggtgcatg | 2820 |
| tcgctcctta tatctcactt tgatatcatg ggtgctcgat cgtctcgtgc ggctcaagca | 2880 |
| gagaagcaac gcttggaaga gcgcggcggt tcgagacgaa tgggcgcagg gcgaatcctt | 2940 |
| acagatgaag aggcagccaa gcttgttcgg gagcagcgcg tggctcatct taccgagatc | 3000 |

```
gaggagagac gcgttgacga agatgctaaa cgccaagcat tgggaagggt tctagagggc    3060
tcaaacgaag cggacaggtc tcttacggtg ctttcatcct cggctacgaa cgttactctg    3120
cgatggcaac agggccagtt cattggtgga ggaacctttg ggtccgttta cgctggaatt    3180
aaccttgaca gcaactacct catggctgtc aaggagatcc gtttgcaaga ccccaacttt    3240
atccctaaaa ttgcccagca aatccgtgat gagatgggtg tgttggaagt cttggatcat    3300
cctaacatcg tctcttacca cggtattgaa gtgcaccgcg ataaggtcta catcttcatg    3360
gaatactgtt ctggtgggtc ccttgccagc ttgcttgagc acggacgtgt cgaggatgaa    3420
accgtcatta tggtctacgc tcttcagttg ctggagggat tagcgtacct gcaccaggct    3480
ggcattatcc atcgcgatat caagcctgaa aatatcctgc ttgatcataa cggtatcatc    3540
aaatacgtcg attttggagc tgcaaagatc atcgctcgtc agggcagaac cgttgtccct    3600
atggatgcct tcgctggcgc tggtcataag gacgctatag tgcccaagga cgcccagctg    3660
gctcacaaca attggggcaa gaaccagaaa acgatgaccg gcaccccaat gtacatgtca    3720
cccgaggtga ttcgcggcga taccacaaaa cttatccacc gccagggagc tgtcgacatc    3780
tggtcgttag gatgcgtgat cttagaaatg gccacgggtc gtcgcccttg gtccactctg    3840
gataacgaat gggccatcat gtacaacatt gcccagggca accaaccgca attgccatcc    3900
cgagaccagc tcagcgacct aggtatcgac ttcctccgac gatgcttcga gtgtgacccc    3960
aataaacggt ccactgcagc agaactcctc cagcatgaat ggatcgtctc catccgccag    4020
caagtcgtac tcgagccagc cacgcctggc agcgacaata gcggtggtag ttcccattca    4080
ggcagtcgcc agaactcagc gtatctatga                                    4110

<210> SEQ ID NO 20
<211> LENGTH: 53
<212> TYPE: DNA
<213> ORGANISM: Artificial Sequence
<220> FEATURE:
<223> OTHER INFORMATION: Aspergillus-sequenced portion of genome with
      BamHI site created by mutating EcoRV

<400> SEQUENCE: 20
gtcaatgcgg gtcgactact aagcgggatc ccgcgctttc catggacgca tac           53

<210> SEQ ID NO 21
<211> LENGTH: 32
<212> TYPE: DNA
<213> ORGANISM: Aspergillus niger

<400> SEQUENCE: 21
aatcagtcta tccgtttcac gacggtgcca tc                                  32

<210> SEQ ID NO 22
<211> LENGTH: 22
<212> TYPE: DNA
<213> ORGANISM: Artificial Sequence
<220> FEATURE:
<223> OTHER INFORMATION: Aspergillus niger-sequenced portion of aygA
      gene with indel mutation

<400> SEQUENCE: 22
aatcagtcta tccgtttcca tc                                             22

<210> SEQ ID NO 23
<211> LENGTH: 44
<212> TYPE: DNA
<213> ORGANISM: Asgerillus niger
```

```
<400> SEQUENCE: 23
aaaaatcagt ctatccgttt catgatcgct tcgtgggaac tctc                  44

<210> SEQ ID NO 24
<211> LENGTH: 100
<212> TYPE: DNA
<213> ORGANISM: Artificial Sequence
<220> FEATURE:
<223> OTHER INFORMATION: A. niger-portion of aygA gene containing a
      nonsense mutation (lower case)

<400> SEQUENCE: 24
gccaaccgct cagccaggtc ttatctaacg tagcatgcag tgtgaaaaat gagtctatcc   60
gtttcacgac ggtgccatcg aagactttcg acctatcttc                       100

<210> SEQ ID NO 25
<211> LENGTH: 60
<212> TYPE: DNA
<213> ORGANISM: Artificial Sequence
<220> FEATURE:
<223> OTHER INFORMATION: A. niger-sequenced portion of aygA gene

<400> SEQUENCE: 25
taacgtagca tgcagtgtga aaaatcagtc tatccgtttc acgacggtgc catcgaagac   60

<210> SEQ ID NO 26
<211> LENGTH: 60
<212> TYPE: DNA
<213> ORGANISM: Artificial Sequence
<220> FEATURE:
<223> OTHER INFORMATION: A. niger- sequenced portion of aygA gene
      containing a nonsense mutation

<400> SEQUENCE: 26
taacgtagca tgcagtgtga aaatgagtc tatccgtttc acgacggtgc catcgaagac    60

<210> SEQ ID NO 27
<211> LENGTH: 240
<212> TYPE: DNA
<213> ORGANISM: Artificial Sequence
<220> FEATURE:
<223> OTHER INFORMATION: argB gene containing a mutation from
      Aspergillus niger

<400> SEQUENCE: 27
gtataaatta tatattatta atattacata tatttttac ttctgaagag cttcattacc    60
tacttaatat tattattata ttttatattc tatctatgag actaagaatt agtttgagaa  120
actttactag attttcata taatttacta attttttct gaacaatctt ctgattatta   180
gttctctgtt taatgaaaca attagatatt attataaaaa ttttatataa aataaatcta  240

<210> SEQ ID NO 28
<211> LENGTH: 53
<212> TYPE: DNA
<213> ORGANISM: Aspergillus niger

<400> SEQUENCE: 28
caacccgcca cgaaatgcgc cgcctctact cttccaccag tcactccgcc gca          53

<210> SEQ ID NO 29
<211> LENGTH: 18
<212> TYPE: PRT
<213> ORGANISM: Aspergillus niger
```

<400> SEQUENCE: 29

Thr Thr Arg His Ala Leu Arg Arg Leu Tyr Ser Ser Thr Ser His Ser
1               5                   10                  15

Ala Ala

<210> SEQ ID NO 30
<211> LENGTH: 53
<212> TYPE: DNA
<213> ORGANISM: Artificial Sequence
<220> FEATURE:
<223> OTHER INFORMATION: argB gene containing a mutation from
      Aspergillus niger

<400> SEQUENCE: 30
caacccgcca cgaaatgcgc cgcctctaat cttccaccag tcactccgcc gca         53

<210> SEQ ID NO 31
<211> LENGTH: 9
<212> TYPE: PRT
<213> ORGANISM: Aspergillus niger

<400> SEQUENCE: 31

Thr Thr Arg His Ala Leu Arg Arg Leu
1               5

<210> SEQ ID NO 32
<211> LENGTH: 8
<212> TYPE: PRT
<213> ORGANISM: Aspergillus niger

<400> SEQUENCE: 32

Ser Ser Thr Ser His Ser Ala Ala
1               5

<210> SEQ ID NO 33
<211> LENGTH: 39
<212> TYPE: DNA
<213> ORGANISM: Artificial Sequence
<220> FEATURE:
<223> OTHER INFORMATION: argB gene containing a mutation from
      Aspergillus niger

<400> SEQUENCE: 33
caacccgcca cgaaatgcgc cgcctctaac tccgccgca                         39

<210> SEQ ID NO 34
<211> LENGTH: 50
<212> TYPE: DNA
<213> ORGANISM: Artificial Sequence
<220> FEATURE:
<223> OTHER INFORMATION: argB gene containing a mutation from
      Aspergillus niger

<400> SEQUENCE: 34
caacccgcca cgaaatgcgc cgcctctaaa gtagcctaaa ctccgccgca             50

<210> SEQ ID NO 35
<211> LENGTH: 7
<212> TYPE: PRT
<213> ORGANISM: Artificial Sequence
<220> FEATURE:
<223> OTHER INFORMATION: argB containing a mutation from Aspergillus
      niger

<400> SEQUENCE: 35

```
Ser Ser Leu Asn Ser Ala Ala
1               5
```

<210> SEQ ID NO 36
<211> LENGTH: 16
<212> TYPE: PRT
<213> ORGANISM: Artificial Sequence
<220> FEATURE:
<223> OTHER INFORMATION: A. niger truncated part of AygA protein

<400> SEQUENCE: 36

```
Val Tyr Pro Phe His Asp Gly Ala Ile Glu Asp Phe Arg Pro Ile Phe
1               5                   10                  15
```